US012221441B2

(12) United States Patent
Papaioannou et al.

(10) Patent No.: US 12,221,441 B2
(45) Date of Patent: Feb. 11, 2025

(54) PLASMA KALLIKREIN INHIBITORS AND USES THEREOF

(71) Applicant: Takeda Pharmaceutical Company Limited, Osaka (JP)

(72) Inventors: Nikolaos Papaioannou, Newton, MA (US); Jeremy Mark Travins, Southborough, MA (US); Sarah Jocelyn Fink, Arlington, MA (US); John Mark Ellard, Buntingford (GB); Alastair Rae, Saffron Walden (GB)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 18/234,608

(22) Filed: Aug. 16, 2023

(65) Prior Publication Data

US 2023/0391773 A1 Dec. 7, 2023

Related U.S. Application Data

(62) Division of application No. 17/024,437, filed on Sep. 17, 2020, now Pat. No. 11,787,796.

(60) Provisional application No. 62/902,353, filed on Sep. 18, 2019.

(51) Int. Cl.
*C07D 471/04* (2006.01)
*A61P 9/00* (2006.01)
*A61P 29/00* (2006.01)
*C07D 519/00* (2006.01)

(52) U.S. Cl.
CPC ......... *C07D 471/04* (2013.01); *C07D 519/00* (2013.01)

(58) Field of Classification Search
CPC ....... C07D 471/04; C07D 519/00; A61P 9/00; A61P 9/29
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,212,162 A | 5/1993 | Missel et al. | |
| 5,403,841 A | 4/1995 | Lang et al. | |
| 7,166,596 B2 | 1/2007 | Yu et al. | |
| 8,153,658 B2 | 4/2012 | Hachiya et al. | |
| 10,259,803 B2 | 4/2019 | McDonald et al. | |
| 10,301,284 B2 | 5/2019 | McDonald et al. | |
| 10,730,874 B2 | 8/2020 | Papaioannou et al. | |
| 11,352,356 B2 | 6/2022 | Papaioannou et al. | |
| 11,370,803 B2 | 6/2022 | Papaioannou et al. | |
| 11,787,796 B2 | 10/2023 | Papaioannou et al. | |
| 2008/0255025 A1 | 10/2008 | Ladner | |
| 2010/0039029 A1 | 2/2010 | Yang et al. | |
| 2010/0130563 A1 | 5/2010 | Sinha et al. | |
| 2012/0264798 A1 | 10/2012 | Sinha et al. | |
| 2014/0213611 A1 | 7/2014 | Evans et al. | |
| 2016/0106102 A1 | 4/2016 | Kuebbeler et al. | |
| 2016/0168123 A1 | 6/2016 | Edwards et al. | |
| 2016/0200704 A1 | 7/2016 | McDonald et al. | |
| 2017/0029406 A1 | 2/2017 | McDonald et al. | |
| 2017/0305863 A1 | 10/2017 | Evans et al. | |
| 2018/0155348 A1 | 6/2018 | Li et al. | |
| 2018/0282328 A1 | 10/2018 | Chan et al. | |
| 2018/0319782 A1 | 11/2018 | Davie et al. | |
| 2019/0127366 A1 | 5/2019 | McDonald et al. | |
| 2019/0169162 A1 | 6/2019 | Beaton et al. | |
| 2019/0284182 A1 | 9/2019 | Papaioannou et al. | |
| 2020/0239463 A1 | 7/2020 | Travins et al. | |
| 2020/0317667 A1 | 10/2020 | Papaioannou et al. | |
| 2021/0078999 A1 | 3/2021 | Papaioannou et al. | |
| 2021/0079022 A1 | 3/2021 | Papaioannou et al. | |
| 2022/0298176 A1 | 9/2022 | Papaioannou et al. | |
| 2023/0078513 A1 | 3/2023 | Papaioannou et al. | |

FOREIGN PATENT DOCUMENTS

| | | |
|---|---|---|
| CN | 105777632 A | 7/2016 |
| CN | 105849109 A | 8/2016 |
| CN | 106061480 A | 10/2016 |
| CN | 107072985 A | 8/2017 |
| CN | 110022875 A | 7/2019 |
| CN | 111848599 A | 10/2020 |
| CN | 112135825 A | 12/2020 |
| EP | 1908471 A1 | 4/2008 |
| EP | 1908762 A2 | 4/2008 |
| EP | 1963329 A2 | 9/2008 |
| JP | S62181284 A | 8/1987 |
| JP | 2000256286 A | 9/2000 |
| JP | 2012111731 A | 6/2012 |
| KR | 10-2017-0034902 A | 3/2017 |
| WO | WO-92/20350 A1 | 11/1992 |
| WO | WO-96/05309 A2 | 2/1996 |
| WO | WO-97/36876 A1 | 10/1997 |
| WO | WO-01/19829 A2 | 3/2001 |
| WO | WO-01/27107 A2 | 4/2001 |

(Continued)

OTHER PUBLICATIONS

RN1239205-88-9, registry database compound, 2010.*
Chemical Abstracts Service, Database Accession No. 1027012-72-1, 1 page, Jun. 10, 2008.
Chemical Abstracts Service, Database Accession No. 1212485-78-3, Mar. 21, 2010.
Chemical Abstracts Service, Database Accession No. 1252171-01-9, 1 page, Nov. 9, 2010.
Chemical Abstracts Service, Database Accession No. 1252171-06-4, 1 page, Nov. 9, 2010.
Chemical Abstracts Service, Database Accession No. 1281095-27-9, 1 page, Apr. 17, 2011.
Chemical Abstracts Service, Database Accession No. 1290603-18-7, 1 page, May 5, 2011.

(Continued)

*Primary Examiner* — Sun Jae Yoo
(74) *Attorney, Agent, or Firm* — Choate, Hall & Stewart LLP; Kristen C. Buteau; Alisha A. Contractor

(57) ABSTRACT

The present invention provides compounds and compositions thereof which are useful as inhibitors of plasma kallikrein and which exhibit desirable characteristics for the same.

19 Claims, No Drawings

(56) References Cited

FOREIGN PATENT DOCUMENTS

| | | |
|---|---|---|
| WO | WO-02/00651 A2 | 1/2002 |
| WO | WO-02/50065 A2 | 6/2002 |
| WO | WO-2002/051831 A1 | 7/2002 |
| WO | WO-2005/005443 A1 | 1/2005 |
| WO | WO-2005/115382 A1 | 12/2005 |
| WO | WO-2006/091898 A2 | 8/2006 |
| WO | WO-2007/009236 A1 | 1/2007 |
| WO | WO-2007/128460 A1 | 11/2007 |
| WO | WO-2008/059854 A1 | 5/2008 |
| WO | WO-2008/116665 A1 | 10/2008 |
| WO | WO-2008/154642 A2 | 12/2008 |
| WO | WO-2009/023179 A2 | 2/2009 |
| WO | WO-2010/065760 A1 | 6/2010 |
| WO | WO-2010/091409 A1 | 8/2010 |
| WO | WO-2010/124082 A1 | 10/2010 |
| WO | WO-2010/124086 A1 | 10/2010 |
| WO | WO-2010/124102 A1 | 10/2010 |
| WO | WO-2010/124108 A1 | 10/2010 |
| WO | WO-2010/124112 A1 | 10/2010 |
| WO | WO-2010/124114 A1 | 10/2010 |
| WO | WO-2010/124116 A1 | 10/2010 |
| WO | WO-2010/132598 A1 | 11/2010 |
| WO | WO-2010/137738 A1 | 12/2010 |
| WO | WO-2011/135303 A2 | 11/2011 |
| WO | WO-2012/016133 A1 | 2/2012 |
| WO | WO-2012/051036 A1 | 4/2012 |
| WO | WO-2012/051361 A1 | 4/2012 |
| WO | WO-2012/058645 A1 | 5/2012 |
| WO | WO-2012/082689 A1 | 6/2012 |
| WO | WO-2012/092471 A2 | 7/2012 |
| WO | WO-2012/116257 A1 | 8/2012 |
| WO | WO-2012/129562 A2 | 9/2012 |
| WO | WO-2012/139425 A1 | 10/2012 |
| WO | WO-2013/052526 A1 | 4/2013 |
| WO | WO-2013/081094 A1 | 6/2013 |
| WO | WO-2013/101974 A1 | 7/2013 |
| WO | WO-2013/127269 A1 | 9/2013 |
| WO | WO-2014/004376 A2 | 1/2014 |
| WO | WO-2014/187928 A1 | 11/2014 |
| WO | WO-2015/063093 A1 | 5/2015 |
| WO | WO-2015/095449 A1 | 6/2015 |
| WO | WO-2015/099196 A1 | 7/2015 |
| WO | WO-2015/103317 A1 | 7/2015 |
| WO | WO-2015/188051 A1 | 12/2015 |
| WO | WO-2016/011209 A1 | 1/2016 |
| WO | WO-2016/029146 A1 | 2/2016 |
| WO | WO-2016/083816 A1 | 6/2016 |
| WO | WO-2016/168059 A1 | 10/2016 |
| WO | WO-2017/001924 A1 | 1/2017 |
| WO | WO-2017/001926 A2 | 1/2017 |
| WO | WO-2017/001936 A2 | 1/2017 |
| WO | WO-2017/161028 A1 | 9/2017 |
| WO | WO-2017/207983 A1 | 12/2017 |
| WO | WO-2017/207985 A1 | 12/2017 |
| WO | WO-2017/208005 A1 | 12/2017 |
| WO | WO-2018/011628 A1 | 1/2018 |
| WO | WO-2018/015818 A2 | 1/2018 |
| WO | WO-2018/141002 A2 | 8/2018 |
| WO | WO-2018/161033 A1 | 9/2018 |
| WO | WO-2018/229543 A2 | 12/2018 |
| WO | WO-2018/234808 A1 | 12/2018 |
| WO | WO-2019/028362 A1 | 2/2019 |
| WO | WO-2019/106375 A1 | 6/2019 |
| WO | WO-2019/106377 A1 | 6/2019 |
| WO | WO-2019/178129 A1 | 9/2019 |
| WO | WO-2021/004535 A1 | 1/2021 |
| WO | WO-2021/055589 A1 | 3/2021 |
| WO | WO-2021/055621 A1 | 3/2021 |
| WO | WO-2022/056051 A1 | 3/2022 |
| WO | WO-2022/197755 A1 | 9/2022 |
| WO | WO-2022/197756 A1 | 9/2022 |
| WO | WO-2022/197758 A1 | 9/2022 |
| WO | WO-2022/197763 A1 | 9/2022 |
| WO | WO-2022/197789 A1 | 9/2022 |

OTHER PUBLICATIONS

Chemical Abstracts Service, Database Accession No. 1293616-34-8, 1 page, May 12, 2011.
Chemical Abstracts Service, Database Accession No. 1294658-40-4, 1 page, May 15, 2011.
Chemical Abstracts Service, Database Accession No. 1316344-05-4, 1 page, Aug. 12, 2011.
Chemical Abstracts Service, Database Accession No. 1318660-49-9, 1 page, Aug. 16, 2011.
Chemical Abstracts Service, Database Accession No. 1319066-26-6, 1 page, Aug. 17, 2011.
Chemical Abstracts Service, Database Accession No. 1347295-90-2, 1 page, Dec. 2, 2011.
Hampton, S. L. et al, KVD900 as a Single Dose, Rapid, Oral, Plasma Kallikrein Inhibitor for the On-Demand Treatment of Hereditary Angioedema Attacks: Pharmacokinetic and Pharmcodynamic results from a Phase 1 Single Ascending Dose Study, presented at AAAAI 2019, San Francisco, CA, Feb. 22-25, Poster (2019).
Heifetz, A. et al., Fragment Molecular Orbital Method Applied to Lead Optimization of Novel Interleukin-2 Inducible T-Cell Kinase (ITK) Inhibitors, J. Med. Chem., 59(9):4352-4363 (2016).
International Search Report for PCT/US2019/021897 (Substituted Imidazopyridines as Inhibitors of Plasma Kallikrein and Uses Thereof, filed Mar. 12, 2019), issued by ISA/EPO, 6 pages (May 9, 2019).
International Search Report for PCT/US2020/051249 filed Sep. 17, 2020, 5 pages, (Nov. 23, 2020).
International Search Report for PCT/US2020/051293, filed Sep. 17, 2020, 5 pages, (Nov. 10, 2020).
International Search Report for PCT/US2022/020474, filed Mar. 16, 2022, 5 pages, (mailed May 31, 2022).
International Search Report for PCT/US2022/020479, filed Mar. 16, 2022, 4 pages, (mailed May 27, 2022).
International Search Report for PCT/US2022/020482, filed Mar. 16, 2022, 4 pages, (mailed May 31, 2022).
International Search Report for PCT/US2022/020491, filed Mar. 16, 2022, 6 pages, (mailed May 30, 2022).
International Search Report for PCT/US2022/020527, filed Mar. 16, 2022, 7 pages, (mailed Jun. 7, 2022).
Li, Z. et al., Diversity-oriented synthesis of β-lactams and γ-lactams by post-Ugi nucleophilic cyclization: Lewis acids as regioselective switch, European Journal of Organic Chemistry, 18: 3957-3962 (2015).
Longhurst, H. et al, Oral Plasma Inhibitor BCX7353 is Safe and Effective as an On-Demand Treatment of Angioedema Attacks in Hereitary Angioedema (HAE) Patients: Results of the ZENITH-1 Trial, Presented at AAAAI 2019, San Francisco, CA, Feb. 22-25, Poster, (2019).
Nirogi, R. et al., Synthesis and SAR of Imidazo[1,5-a]pyridine derivatives as 5-HT4 receptor partial agonists for the treatment of cognitive disorders associated with Alzheimer's disease, European Journal of Medicinal Chemistry, 103: 289-301 (2015).
Registry Database Compound RN 1239205-88-9, 1 page, Aug. 26, 2010.
Roatsch, M. et al., Substituted 2-(2-aminopyrimidin-4-yl)pyridine-4-carboxylates as potent inhibitors of JumonjiC domain-containing histone demethylases, Future Med. Chem., 8(13):1553-1571 (2016).

* cited by examiner

PLASMA KALLIKREIN INHIBITORS AND USES THEREOF

I. CROSS REFERENCE TO RELATED APPLICATIONS

This application claims priority to and the benefit of U.S. Provisional Patent Application Ser. No. 62/902,353, filed on Sep. 18, 2019, entitled "PLASMA KALLIKREIN INHIBITORS AND USES THEREOF," the disclosure of which is incorporated herein by reference in its entirety.

II. BACKGROUND OF THE INVENTION

Plasma Kallikrein (pKal) is a serine protease zymogen in blood that is converted to its catalytically active form by coagulation factor XIIa, and contributes to the innate inflammatory response and intrinsic cascade of blood coagulation. The mechanisms that lead to the activation of this pathway in vivo include interactions with polyphosphates released from activated platelets and deficiency of C1 inhibitor (C1-INH), the primary physiological inhibitor of pKal. pKal-mediated cleavage of high-molecular weight kininogen generates the potent vasodilator and pro-inflammatory nonapeptide bradykinin (BK), which activates the bradykinin 2 receptor. Subsequent cleavage of BK by carboxypeptidases generates des-Arg9-BK, which activates the B1 receptor. Both B1 and B2 receptors are expressed by vascular, glial, and neuronal cell types, with the highest levels of retinal expression detected in the ganglion cell layer and inner and outer nuclear layers. Activation of B1 and B2 receptors causes vasodilation and increases vascular permeability.

pKal is also associated with a number of disorders, such as hereditary angioedema (HAE), an autosomal dominant disease characterized by painful, unpredictable, recurrent attacks of inflammation affecting the hands, feet, face, abdomen, urogenital tract, and the larynx. Prevalence for HAE is uncertain but is estimated to be approximately 1 case per 50,000 persons without known differences among ethnic groups. HAE is caused by deficient (Type I) or dysfunctional (Type II) levels of C1-INH, which inhibits pKal, bradykinin, and other serine proteases in the blood. Individuals with hereditary angioedema (HAE) are deficient in C1-INH and consequently undergo excessive bradykinin generation, which in turn cause painful, debilitating, and potentially fatal swelling attacks. If left untreated, HAE can result in a mortality rate as high as 40% primarily due to upper airway obstruction.

III. SUMMARY OF THE INVENTION

The present disclosure is based on, at least in part, the development of a number of compounds which bind to plasma kallikrein and effectively inhibit its activity. Accordingly, provided herein are compounds and uses thereof for targeting pKal and/or treating pKal-mediated diseases and disorders.

In some embodiments, the present invention provides a compound of Formula (I):

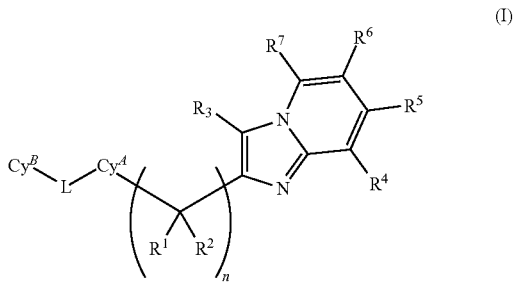

or a pharmaceutically acceptable salt thereof, wherein each of $Cy^A$, $Cy^B$, L, $R^1$, $R^2$, $R^3$, $R^4$, $R^5$, $R^6$, $R^7$, and n is defined and described in classes and subclasses herein. In certain embodiments, the present invention provides compounds of Formulae (I)-(IV), as defined and described in classes and subclasses herein.

In some embodiments, the present invention also provides methods of using compounds of Formulae (I)-(IV).

IV. DETAILED DESCRIPTION OF CERTAIN EMBODIMENTS

A. Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocyclyl," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocyclyl" or "cycloalkyl") refers to a monocyclic $C_3$-$C_7$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "halogen" means F, Cl, Br, or I.

The term "aryl" refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring." In some embodiments, an 8-10 membered bicyclic aryl group is an optionally substituted naphthyl ring. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-" refer to groups having 5 to 10 ring atoms, preferably 5, 6, or 9 ring atoms; having 6, 10, or 14 π C electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted.

As used herein, the terms "heterocyclyl," "heterocyclic radical," and "heterocyclic ring" are used interchangeably and refer to a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in this context in reference to a ring atom, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein and unless otherwise specified, the suffix "-ene" is used to describe a bivalent group. Thus, any of the terms above can be modified with the suffix "-ene" to describe a bivalent version of that moiety. For example, a bivalent carbocycle is "carbocyclene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", and so forth.

As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O(CH$_2$)$_{0-4}$C(O)OR°; —O(CH$_2$)$_{0-4}$OR°; —(CH$_2$)$_{0-4}$CH(OR°)$_2$, —(CH$_2$)$_{0-4}$SR°; —(CH$_2$)$_{0-4}$Ph, which may be substituted with R°; —(CH$_2$)$_{0-4}$O(CH$_2$)$_{0-4}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°2; —N(R°)C(S)NR°2; —(CH$_2$)$_{0-4}$N(R°)C(O)OR°; —N(R°)N(R°)C(O)R°; —N(R°)N(R°)C(O)NR°2; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, —SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$, —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$, —(CH$_2$)$_{0-4}$S(O)R°; —N(R°)S(O)$_2$NR°$_2$, —N(R°)S(O)$_2$R°; —N(OR°)R°; —C(NH)NR°$_2$; —P(O)$_2$R°; —P(O)R°$_2$; —OP(O)R°$_2$, —OP(O)(OR°)$_2$, SiR°$_3$; —(C$_{1-4}$ straight or branched alkylene)O—N(R°)$_2$, or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-4}$Ph, —CH$_2$-(5-6 membered heteroaryl ring), or a 5-6 membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12 membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•$2, —NO$_2$, —SiR$^•$$_3$, —OSiR$^•$$_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-4}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*)$_2$)$_{2-3}$O—, or —S(C(R*)$_2$)$_{2-3}$S—, wherein each independent occurrence of R* is selected from hydrogen, C$_{1-6}$ aliphatic which may be substituted as defined below, or an unsubstituted 5-6 membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(C(R*)$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —NH$_2$, —NHR$^•$, —N(R$^•$)$_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-4}$Ph, or a 5-6 membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†$$_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†$$_2$, —C(S)NR$^†$$_2$, —C(NH)NR$^†$$_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5- to 6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3- to 12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•$$_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-4}$Ph, or a 5- to 6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

In certain embodiments, the neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The term "oxo," as used herein, means an oxygen that is double bonded to a carbon atom, thereby forming a carbonyl.

The symbol "⤳", except when used as a bond to depict unknown or mixed stereochemistry, denotes the point of attachment of a chemical moiety to the remainder of a molecule or chemical formula.

The articles "a" and "an" are used herein to refer to one or to more than one (i.e., to at least one) of the grammatical object of the article. By way of example, "an element" means one element or more than one element.

A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

As will be understood from context, a "reference" sample or subject is one that is sufficiently similar to a particular sample or subject of interest to permit a relevant comparison.

In some embodiments, information about a reference sample is obtained simultaneously with information about a particular sample. In some embodiments, information about a reference sample is historical. In some embodiments, information about a reference sample is stored, for example in a computer-readable medium. In some embodiments, comparison of a particular sample of interest with a reference sample establishes identity with, similarity to, or difference of the particular sample of interest relative to the reference.

As used herein, the term "sample" refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample may be or comprise bone marrow; blood, e.g., whole blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from a subject. In some embodiments, obtained cells are or include cells from a subject from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood (e.g., whole blood), lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

As used herein, the phrase "therapeutic agent" refers to any agent that has a therapeutic effect and/or elicits a desired biological and/or pharmacological effect, when administered to a subject.

As used herein, the term "therapeutically effective amount" refers to an amount of a therapeutic agent that confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic agent effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder; the activity of the specific therapeutic agent employed; the specific composition employed; the age, body weight, general health, sex and diet of the subject; the time of administration, route of administration, and/or rate of excretion or metabolism of the specific therapeutic agent employed; the duration of the treatment; and like factors as is well known in the medical arts.

As used herein, the term "treatment" (also "treat" or "treating") refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

B. Compounds

In some embodiments, a provided compound is of Formula (I):

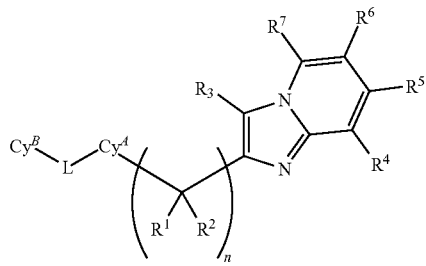

or a pharmaceutically acceptable salt thereof,
wherein:
- $Cy^A$ is selected from a 5-membered monocyclic heteroarylene having 1-4 heteroatoms independently selected from oxygen, nitrogen, and sulfur, and a 7- to 10-membered partially unsaturated bicyclic heterocyclylene having 1-4 heteroatoms selected from oxygen, nitrogen, and sulfur, wherein $Cy^A$ is substituted with 0-4 $R^A$ groups;
- each $R^A$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
- $Cy^B$ is selected from phenyl, a 5- to 6-membered monocyclic heteroaryl having 1-4 heteroatoms selected from oxygen, nitrogen, and sulfur, a 7- to 10-membered partially unsaturated bicyclic carbocyclyl, a 10-membered bicyclic aryl, a 7- to 10-membered bicyclic heterocyclyl having 1-4 heteroatoms selected from oxygen, nitrogen, and sulfur, a 7- to 10-membered bicyclic heteroaryl having 1-4 heteroatoms selected from oxygen, nitrogen, and sulfur, and a 12-membered tricyclic heterocyclyl having 1-4 heteroatoms selected from oxygen, nitrogen, and sulfur, wherein $Cy^B$ is substituted with 0-5 $R^B$ groups;
- each $R^B$ is independently selected from halogen, —CN, oxo, —C(R)=N(R), —C(O)R, —C(O)$_2$R, —C(O)N(R)$_2$, —C(=N(R))N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 7- to 10-membered bicyclic heteroaryl having 1-4 heteroatoms selected from oxygen, nitrogen, and sulfur, and 8- to 10-membered spirocyclic heterocyclyl having 1-3 heteroatoms selected from oxygen, nitrogen, or sulfur;
- L is an optionally substituted C$_{1-6}$ hydrocarbon chain, wherein 1 to 3 methylene units are independently replaced with -Cy-, —O—, —NR—, —C(O)—, —C(O)NR—, —NRC(O)—, —S(O)$_2$NR—, —NRS(O)$_2$—, or —S(O)$_2$—;
- -Cy- is 3- to 7-membered saturated or partially unsaturated monocyclic carbocyclylene, 3- to 7-membered saturated or partially unsaturated monocyclic heterocyclylene having 1-2 heteroatoms selected from oxygen, nitrogen, or sulfur, or 5- to 6-membered heteroarylene having 1-4 heteroatoms selected from oxygen, nitrogen, or sulfur;
- $R^1$ and $R^2$ are independently selected from hydrogen, halogen, —OR, —SR, —N(R)$_2$, and optionally substituted C$_{1-6}$ aliphatic; wherein $R^1$ may be taken together with a monocyclic $Cy^A$ to form an optionally substituted fused 7- to 10-membered saturated or partially unsaturated bicyclic heterocyclylene having 1-4 heteroatoms selected from oxygen, nitrogen, or sulfur;
- $R^3$, $R^4$, $R^5$, and $R^7$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
- $R^6$ is selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
- each R is independently hydrogen or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
- or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur; and
- n is 0 or 1;

with the proviso that:
(a) at least one of $R^3$, $R^4$, $R^5$, $R^6$ and $R^7$ is $C_{1-6}$ aliphatic or halogen; and
(b) the compound is other than N-[1-[(6-fluoroimidazo[1,2-a]pyridin-2-yl)methyl]-5-methyl-1H-pyrazol-3-yl]-3-pyridinecarboxamide, N-[1-[(6-chloroimidazo[1,2-a]pyridin-2-yl)methyl]-5-methyl-1H-pyrazol-3-yl]-3-pyridinecarboxamide, 3-chloro-4-[[5-[8-chloro-6-(trifluoromethyl)imidazo[1,2-a]pyridin-2-yl]-1,3,4-oxadiazol-2-yl]amino]-benzenepropanoic acid, 2-[(6,8-dichloroimidazo[1,2-a]pyridin-2-yl)methyl]-4-methyl-N-phenyl-5-thiazolecarboxamide, and N-(furan-2-ylmethyl)-N,3,5-trimethyl-1-((6-methylimidazo[1,2-a]pyridin-2-yl)methyl)-1H-pyrazole-4-sulfonamide.

In some embodiments, a provided compound, or a pharmaceutically acceptable salt thereof, has a structure of Formula (I), with the proviso that $Cy^B$ is a group other than

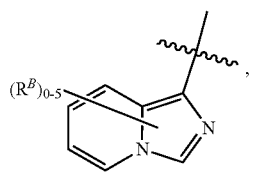

at least one of $R^3$, $R^4$, $R^5$, $R^6$ and $R^7$ is $C_{1-6}$ aliphatic or halogen, and the compound is other than N-[1-[(6-fluoroimidazo[1,2-a]pyridin-2-yl)methyl]-5-methyl-1H-pyrazol-3-yl]-3-pyridinecarboxamide, N-[1-[(6-chloroimidazo[1,2-a]pyridin-2-yl)methyl]-5-methyl-1H-pyrazol-3-yl]-3-pyridinecarboxamide, 3-chloro-4-[[5-[8-chloro-6-(trifluoromethyl)imidazo[1,2-a]pyridin-2-yl]-1,3,4-oxadiazol-2-yl]amino]-benzenepropanoic acid, 2-[(6,8-dichloroimidazo[1,2-a]pyridin-2-yl)methyl]-4-methyl-N-phenyl-5-thiazolecarboxamide, and N-(furan-2-ylmethyl)-N,3,5-trimethyl-1-((6-methylimidazo[1,2-a]pyridin-2-yl)methyl)-1H-pyrazole-4-sulfonamide.

In some embodiments, $Cy^A$ is selected from a 5-membered monocyclic heteroarylene having 1-4 heteroatoms independently selected from oxygen, nitrogen, and sulfur, and a 7- to 10-membered partially unsaturated bicyclic heterocyclylene having 1-4 heteroatoms selected from oxygen, nitrogen, and sulfur, wherein $Cy^A$ is substituted with 0-4 $R^A$ groups.

In some embodiments, $Cy^A$ is selected from a 5-membered monocyclic heteroarylene having 1-4 heteroatoms independently selected from oxygen, nitrogen, and sulfur, wherein $Cy^A$ is substituted with 0-3 $R^A$ groups. In some embodiments, $Cy^A$ is selected from a 5-membered monocyclic heteroarylene having 1-4 heteroatoms independently selected from oxygen, nitrogen, and sulfur, wherein $Cy^A$ is substituted with 0-2 $R^A$ groups. In some embodiments, $Cy^A$ is selected from a 5-membered monocyclic heteroarylene having 1-4 heteroatoms independently selected from oxygen, nitrogen, and sulfur, wherein $Cy^A$ is unsubstituted.

In some embodiments, $Cy^A$ is a 5-membered heteroarylene having 1-4 heteroatoms independently selected from oxygen and nitrogen, wherein $Cy^A$ is substituted with 0-3 $R^A$ groups. In some embodiments, $Cy^A$ is a 5-membered heteroarylene having 1-4 nitrogen atoms, wherein $Cy^A$ is substituted with 0-3 $R^A$ groups. In some embodiments, $Cy^A$ is a 5-membered heteroarylene having 2-3 nitrogen atoms, wherein $Cy^A$ is substituted with 0-2 $R^A$ groups. In some embodiments, $Cy^A$ is a 5-membered heteroarylene having 1 nitrogen atom, wherein $Cy^A$ is substituted with 0-3 $R^A$ groups. In some embodiments, $Cy^A$ is a 5-membered heteroarylene having 2 nitrogen atoms, wherein $Cy^A$ is substituted with 0-2 $R^A$ groups. In some embodiments, $Cy^A$ is a 5-membered heteroarylene having 3 nitrogen atoms, wherein $Cy^A$ is substituted with 0-1 $R^A$ groups. In some embodiments, $Cy^A$ is an unsubstituted 5-membered heteroarylene having 2 nitrogen atoms and 1 oxygen atom. In some embodiments, $Cy^A$ is an unsubstituted pyrrolediyl. In some embodiments, $Cy^A$ is a pyrazolediyl substituted with 0-2 $R^A$ groups. In some embodiments, $Cy^A$ is an unsubstituted imidazolediyl. In some embodiments, $Cy^A$ is an unsubstituted triazolediyl. In some embodiments, $Cy^A$ is an unsubstituted tetrazolediyl. In some embodiments, $Cy^A$ is an unsubstituted oxadiazolediyl.

In some embodiments, when n is 0, $Cy^A$ is a 7- to 10-membered saturated or partially unsaturated bicyclic heterocyclylene having 1-4 heteroatoms selected from oxygen, nitrogen, or sulfur.

In some embodiments, $Cy^A$ is a 7- to 10-membered partially unsaturated bicyclic heterocyclylene having 1-4 heteroatoms selected from oxygen, nitrogen, and sulfur. In some embodiments, $Cy^A$ is an 8-membered partially unsaturated bicyclic heterocyclylene having 1-4 heteroatoms selected from oxygen, nitrogen, and sulfur. In some embodiments, $Cy^A$ is an 8-membered partially unsaturated bicyclic heterocyclylene having 2-3 heteroatoms selected from oxygen, nitrogen, and sulfur. In some embodiments, $Cy^A$ is an 8-membered partially unsaturated bicyclic heterocyclylene having 2-3 heteroatoms selected from oxygen and nitrogen. In some embodiments, $Cy^A$ is an 8-membered partially unsaturated bicyclic heterocyclylene having 2 nitrogen atoms. In some embodiments, $Cy^A$ is an 8-membered partially unsaturated bicyclic heterocyclylene having 3 nitrogen atoms. In some embodiments, $Cy^A$ is an 8-membered partially unsaturated bicyclic heterocyclylene having 2 nitrogen atoms and 1 oxygen atom. In some embodiments, $Cy^A$ is an unsubstituted pyrrolopyrazolediyl. In some embodiments, $Cy^A$ is an unsubstituted pyrroloimidazolediyl. In some embodiments, $Cy^A$ is an unsubstituted pyrrolotriazolediyl. In some embodiments, $Cy^A$ is an unsubstituted dihydroimidazooxazolediyl.

In some embodiments, $Cy^A$ is selected from the group consisting of:

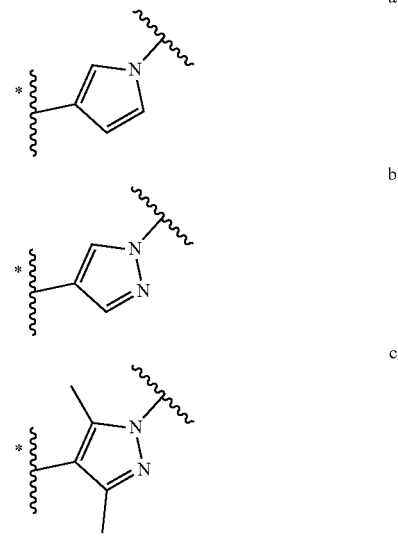

d 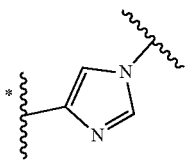

e 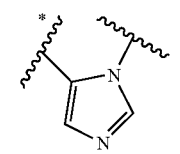

f 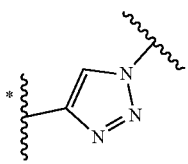

g 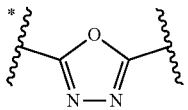

h 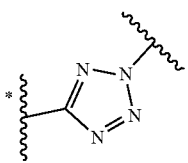

i 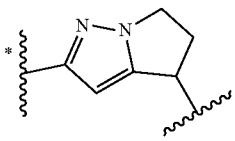

j 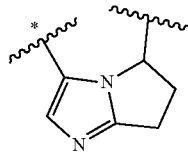

k 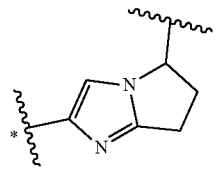

l 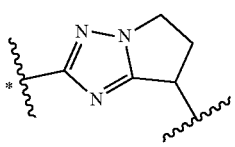

m 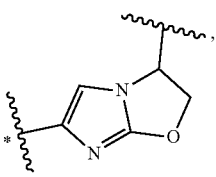

wherein * represents the point of attachment to L.

In some embodiments, each $R^A$ is independently selected from an optionally substituted group selected from $C_{1-6}$ aliphatic, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur.

In some embodiments, substituents on an optionally substituted $R^A$ group are independently halogen, $(CH_2)_{0-4}R°$, —$(CH_2)_{0-4}OR°$; and —$(CH_2)_{0-4}C(O)OR°$, wherein each $R°$ is independently hydrogen, $C_{1-6}$ aliphatic, or a 5- to 6-membered saturated, partially unsaturated, or aryl ring having 0-4 heteroatoms independently selected from nitrogen, oxygen, or sulfur.

In some embodiments, a single instance of $R^A$ is $C_{1-6}$ aliphatic substituted with halogen.

In some embodiments, a single instance of $R^A$ is $C_{1-6}$ aliphatic substituted with —$(CH_2)_{0-4}R°$, wherein $R°$ is hydrogen or $C_{1-6}$ aliphatic.

In some embodiments, a single instance of $R^A$ is $C_{1-6}$ aliphatic substituted with —$(CH_2)_{0-4}C(O)OR°$, wherein $R°$ is hydrogen or $C_{1-6}$ aliphatic.

In some embodiments, a single instance of $R^A$ is $C_{1-6}$ aliphatic is substituted with 5- to 6-membered saturated, partially unsaturated, or aryl ring having 0-4 heteroatoms independently selected from nitrogen, oxygen, or sulfur.

In some embodiments, a single instance of $R^A$ is optionally substituted 3- to 7-membered saturated or partially unsaturated monocyclic carbocyclyl. In some embodiments, a single instance of $R^A$ is optionally substituted cyclopropyl. In some embodiments, a single instance of $R^A$ is cyclopropyl substituted with —$(CH_2)_{0-4}C(O)OR°$ and $R°$ is hydrogen or $C_1$-6 aliphatic.

In some embodiments, each $R^A$ is independently selected from unsubstituted $C_{1-6}$ aliphatic. In some embodiments, each $R^A$ is independently selected from methyl, ethyl, n-propyl, iso-propyl, cyclopropyl, butyl, and cyclopentyl. In some embodiments, each $R^A$ is independently selected from methyl and ethyl.

In some embodiments, $Cy^B$ is selected from phenyl, a 5- to 6-membered monocyclic heteroaryl having 1-4 heteroatoms selected from oxygen, nitrogen, and sulfur, a 7- to 10-membered partially unsaturated bicyclic carbocyclyl, a 10-membered bicyclic aryl, a 7- to 10-membered bicyclic heterocyclyl having 1-4 heteroatoms selected from oxygen, nitrogen, and sulfur, a 7- to 10-membered bicyclic heteroaryl having 1-4 heteroatoms selected from oxygen, nitrogen, and sulfur, and a 12-membered tricyclic heterocyclyl having 1-4 heteroatoms selected from oxygen, nitrogen, and sulfur, wherein $Cy^B$ is substituted with 0-5 $R^B$ groups.

In some embodiments, $Cy^B$ is phenyl, wherein $Cy^B$ is substituted with 0-3 $R^B$ groups. In some embodiments, $Cy^B$ is phenyl, wherein $Cy^B$ is substituted with 3 $R^B$ groups. In some embodiments, $Cy^B$ is phenyl, wherein $Cy^B$ is substituted with 2 $R^B$ groups. In some embodiments, $Cy^B$ is phenyl, wherein $Cy^B$ is substituted with 1 $R^B$ group. In some embodiments, $Cy^B$ is unsubstituted phenyl.

In some embodiments, $Cy^B$ is a 5- to 6-membered monocyclic heteroaryl having 1-4 heteroatoms selected from oxygen, nitrogen, and sulfur, wherein $Cy^B$ is substituted with 0-3 $R^B$ groups.

In some embodiments, $Cy^B$ is a 5-membered monocyclic heteroaryl having 1-4 heteroatoms independently selected from oxygen, nitrogen, and sulfur, wherein $Cy^B$ is substituted with 0-3 $R^B$ groups. In some embodiments, $Cy^B$ is a 5-membered monocyclic heteroaryl having 2-3 heteroatoms independently selected from oxygen, nitrogen, and sulfur, wherein $Cy^B$ is substituted with 0-2 $R^B$ group. In some embodiments, $Cy^B$ is a 5-membered monocyclic heteroaryl having 2-3 heteroatoms independently selected from oxygen and nitrogen, wherein $Cy^B$ is substituted with 0-2 $R^B$ group. In some embodiments, $Cy^B$ is a 5-membered monocyclic heteroaryl having 2-3 heteroatoms independently selected from nitrogen and sulfur, wherein $Cy^B$ is substituted with 0-2 $R^B$ group. In some embodiments, $Cy^B$ is a 5-membered monocyclic heteroaryl having 2-3 nitrogen atoms, wherein $Cy^B$ is substituted with 0-2 $R^B$ group. In some embodiments, $Cy^B$ is an oxazolediyl substituted with 1 $R^B$ group. In some embodiments, $Cy^B$ is a thiazolediyl substituted with 1 $R^B$ group. In some embodiments, $Cy^B$ is a triazolediyl substituted with 1 $R^B$ group. In some embodiments, $Cy^B$ is an oxadiazolediyl substituted with 1 $R^B$ group. In some embodiments, $Cy^B$ is a thiadiazolediyl substituted with 1 $R^B$ group.

In some embodiments, $Cy^B$ is a 6-membered monocyclic heteroaryl having 1-4 heteroatoms selected from oxygen, nitrogen, and sulfur, wherein $Cy^B$ is substituted with 0-3 $R^B$ groups. In some embodiments, $Cy^B$ is a 6-membered monocyclic heteroaryl having 1-4 nitrogen atoms, wherein $Cy^B$ is substituted with 0-3 $R^B$ groups. In some embodiments, $Cy^B$ is a 6-membered monocyclic heteroaryl having 1-2 nitrogen atoms, wherein $Cy^B$ is substituted with 0-3 $R^B$ groups. In some embodiments, $Cy^B$ is a pyridinediyl substituted with 2-3 $R^B$ groups. In some embodiments, $Cy^B$ is a pyridinediyl substituted with 2 $R^B$ groups. In some embodiments, $Cy^B$ is a pyridinediyl substituted with 3 $R^B$ groups.

In some embodiments, $Cy^B$ is a 7- to 10-membered partially unsaturated bicyclic carbocyclyl, wherein $Cy^B$ is substituted with 0-1 $R^B$ groups. In some embodiments, $Cy^B$ is an indenediyl substituted with 0-1 $R^B$ groups.

In some embodiments, $Cy^B$ is a 10-membered bicyclic aryl, wherein $Cy^B$ is substituted with 0-1 $R^B$ groups. In some embodiments, $Cy^B$ is a naphthalenediyl substituted with 1 $R^B$ group.

In some embodiments, $Cy^B$ is a 7- to 10-membered bicyclic heterocyclyl having 1-4 heteroatoms selected from oxygen, nitrogen, and sulfur, wherein $Cy^B$ is substituted with 0-2 $R^B$ groups.

In some embodiments, $Cy^B$ is a 7- to 10-membered bicyclic heteroaryl having 1-4 heteroatoms selected from oxygen, nitrogen, and sulfur, wherein $Cy^B$ is substituted with 0-3 $R^B$ groups. In some embodiments, $Cy^B$ is a 9- to 10-membered bicyclic heteroaryl having 1-4 heteroatoms selected from oxygen, nitrogen, and sulfur, wherein $Cy^B$ is substituted with 0-3 $R^B$ groups. In some embodiments, $Cy^B$ is a 9- to 10-membered bicyclic heteroaryl having 1-3 heteroatoms selected from oxygen, nitrogen, and sulfur, wherein $Cy^B$ is substituted with 0-3 $R^B$ groups. In some embodiments, $Cy^B$ is a 9-membered bicyclic heteroaryl having 1-3 heteroatoms selected from oxygen, nitrogen, and sulfur, wherein $Cy^B$ is substituted with 0-3 $R^B$ groups. In some embodiments, $Cy^B$ is a 10-membered bicyclic heteroaryl having 1-2 heteroatoms selected from oxygen, nitrogen, and sulfur, wherein $Cy^B$ is substituted with 0-3 $R^B$ groups.

In some embodiments, $Cy^B$ is a 9-membered bicyclic heteroaryl having 1-3 heteroatoms selected from oxygen, nitrogen, and sulfur, wherein $Cy^B$ is substituted with 0-3 $R^B$ groups. In some embodiments, $Cy^B$ is an indolediyl substituted with 1-3 $R^B$ groups. In some embodiments, $Cy^B$ is a cyclopentapyridinediyl substituted with 1-2 $R^B$ groups. In some embodiments, $Cy^B$ is a benzothiophenediyl substituted with 0-1 $R^B$ groups. In some embodiments, $Cy^B$ is a benzoimidazolediyl substituted with 0-2 $R^B$ groups. In some embodiments, $Cy^B$ is an imidazopyridinediyl substituted with 1-2 $R^B$ groups. In some embodiments, $Cy^B$ is a benzoisoxazolediyl substituted with 3 $R^B$ groups. In some embodiments, $Cy^B$ is a benzoisothiazolediyl substituted with 1 $R^B$ group. In some embodiments, $Cy^B$ is a thienopyridinediyl substituted with 1 $R^B$ group. In some embodiments, $Cy^B$ is a triazolopyridinediyl substituted with 1 $R^B$ group.

In some embodiments, $Cy^B$ is a 10-membered bicyclic heteroaryl having 1-2 heteroatoms selected from oxygen, nitrogen, and sulfur, wherein $Cy^B$ is substituted with 0-3 $R^B$ groups. In some embodiments, $Cy^B$ is an isoquinolinediyl substituted with 1 $R^B$ groups. In some embodiments, $Cy^B$ is a napthyridinediyl substituted with 3 $R^B$ groups. In some embodiments, $Cy^B$ is a quinolinonediyl substituted with 0-1 $R^B$ groups.

In some embodiments, $Cy^B$ is a 12-membered tricyclic heterocyclyl having 1-4 heteroatoms selected from oxygen, nitrogen, and sulfur, wherein $Cy^B$ is substituted with 0-1 $R^B$ groups. In some embodiments, $Cy^B$ is a dihydroimidazoquinolinediyl substituted with 1 $R^B$ group.

In some embodiments, $Cy^B$ is selected from the group consisting of:

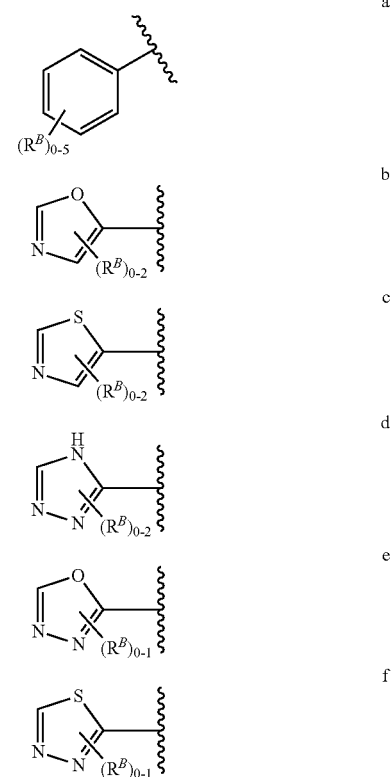

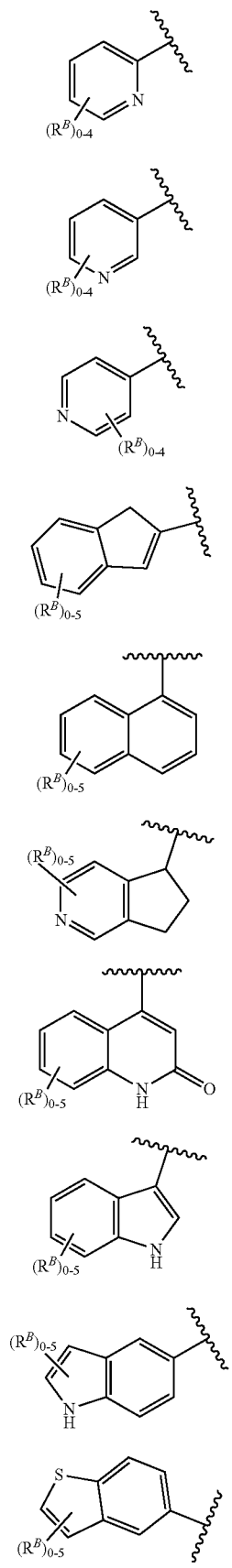
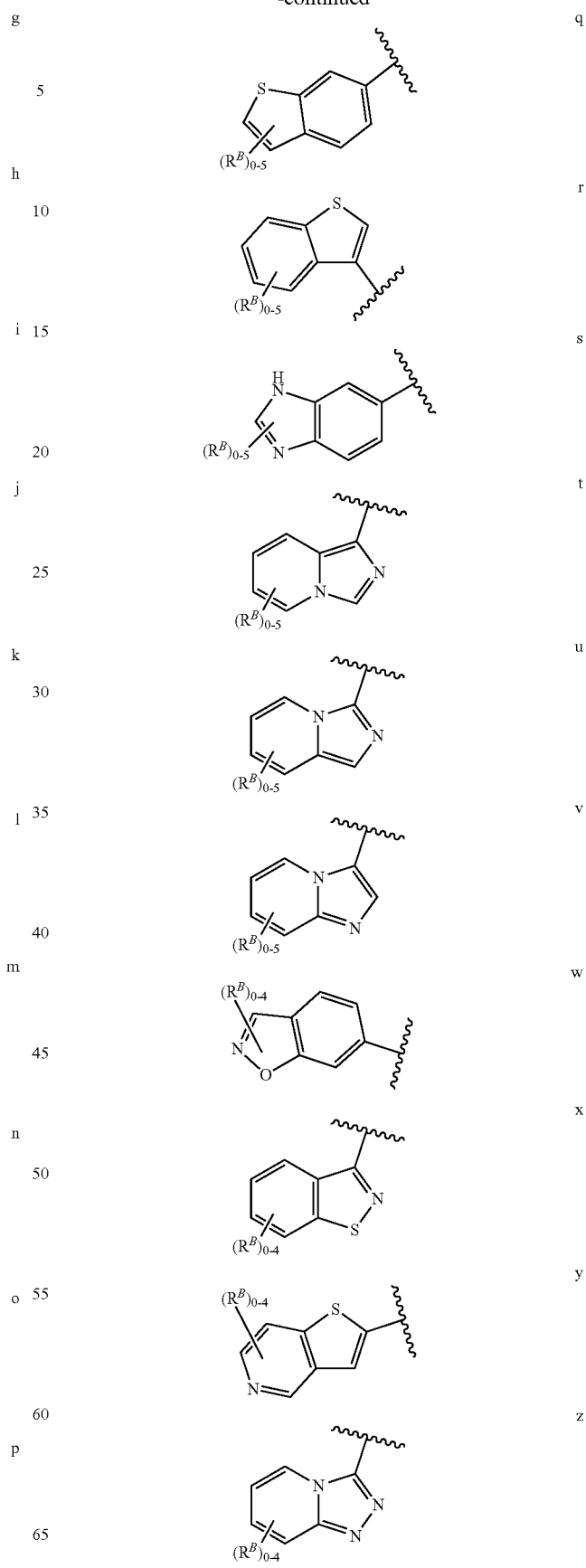

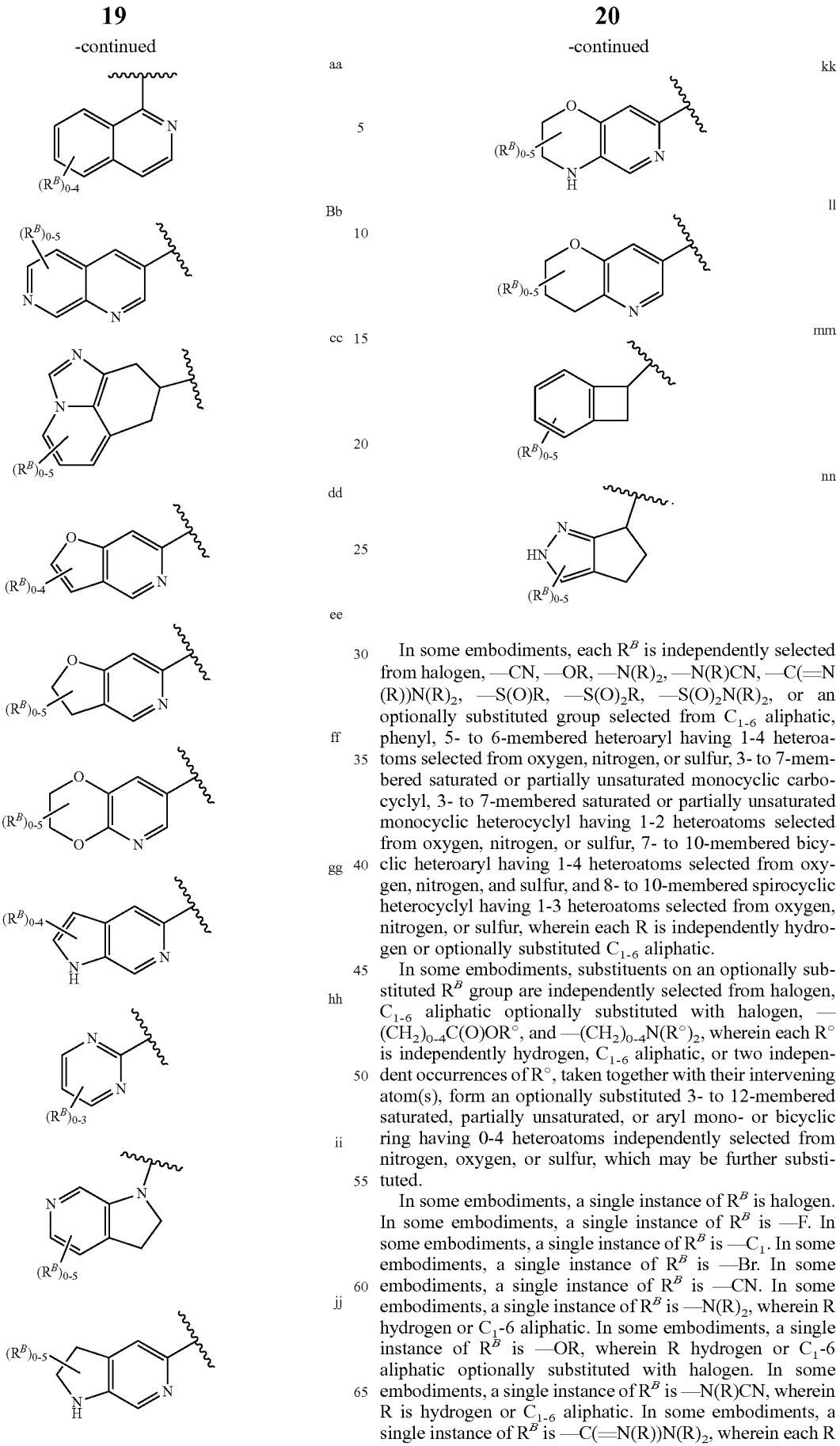

In some embodiments, each $R^B$ is independently selected from halogen, —CN, —OR, —N(R)$_2$, —N(R)CN, —C(=N(R))N(R)$_2$, —S(O)R, —S(O)$_2$R, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 7- to 10-membered bicyclic heteroaryl having 1-4 heteroatoms selected from oxygen, nitrogen, and sulfur, and 8- to 10-membered spirocyclic heterocyclyl having 1-3 heteroatoms selected from oxygen, nitrogen, or sulfur, wherein each R is independently hydrogen or optionally substituted $C_{1-6}$ aliphatic.

In some embodiments, substituents on an optionally substituted $R^B$ group are independently selected from halogen, $C_{1-6}$ aliphatic optionally substituted with halogen, —(CH$_2$)$_{0-4}$C(O)OR°, and —(CH$_2$)$_{0-4}$N(R°)$_2$, wherein each R° is independently hydrogen, $C_{1-6}$ aliphatic, or two independent occurrences of R°, taken together with their intervening atom(s), form an optionally substituted 3- to 12-membered saturated, partially unsaturated, or aryl mono- or bicyclic ring having 0-4 heteroatoms independently selected from nitrogen, oxygen, or sulfur, which may be further substituted.

In some embodiments, a single instance of $R^B$ is halogen. In some embodiments, a single instance of $R^B$ is —F. In some embodiments, a single instance of $R^B$ is —Cl. In some embodiments, a single instance of $R^B$ is —Br. In some embodiments, a single instance of $R^B$ is —CN. In some embodiments, a single instance of $R^B$ is —N(R)$_2$, wherein R hydrogen or $C_{1-6}$ aliphatic. In some embodiments, a single instance of $R^B$ is —OR, wherein R hydrogen or $C_{1-6}$ aliphatic optionally substituted with halogen. In some embodiments, a single instance of $R^B$ is —N(R)CN, wherein R is hydrogen or $C_{1-6}$ aliphatic. In some embodiments, a single instance of $R^B$ is —C(=N(R))N(R)$_2$, wherein each R is independently hydrogen or $C_{1-6}$ aliphatic. In some embodiments, a single instance of $R^B$ is —C(=N(R))N(R)$_2$, wherein R is hydrogen. In some embodiments, a single instance of $R^B$ is —S(O)R, wherein R is hydrogen or $C_{1-6}$ aliphatic. In some embodiments, a single instance of $R^B$ is —S(O)R, wherein R is $C_{1-6}$ aliphatic. In some embodiments, a single instance of $R^B$ is —S(O)R, wherein R is methyl. In some embodiments, a single instance of $R^B$ is —S(O)$_2$R, wherein R is hydrogen or $C_{1-6}$ aliphatic. In some embodiments, a single instance of $R^B$ is —S(O)$_2$R, wherein R is $C_{1-6}$ aliphatic. In some embodiments, a single instance of $R^B$ is —S(O)$_2$R, wherein R is methyl. In some embodiments, a single instance of $R^B$ is —S(O)$_2$N(R)$_2$, wherein R is hydrogen or $C_{1-6}$ aliphatic. In some embodiments, a single instance of $R^B$ is —S(O)$_2$N(R)$_2$, wherein R is $C_{1-6}$ aliphatic. In some embodiments, a single instance of $R^B$ is —S(O)$_2$N(R)$_2$, wherein R is methyl. In some embodiments, a single instance of $R^B$ is —S(O)$_2$N(R)$_2$, wherein two independent occurrences of R are taken together with their intervening atom(s), form an optionally substituted 3- to 12-membered saturated ring having 1-2 heteroatoms independently selected from nitrogen, oxygen, or sulfur. In some embodiments, a single instance of $R^B$ is —S(O)$_2$N(R)$_2$, wherein two independent occurrences of R are taken together with their intervening atom(s), form an optionally substituted 5- to 6-membered saturated ring having 1-2 heteroatoms independently selected from nitrogen, oxygen, or sulfur.

In some embodiments, a single instance of $R^B$ is $C_{1-6}$ aliphatic substituted with halogen.

In some embodiments, a single instance of $R^B$ is $C_{1-6}$ aliphatic substituted with —(CH$_2$)$_{0-4}$N(R°)$_2$, wherein R° is hydrogen or $C_{1-6}$ aliphatic. In some embodiments, a single instance of $R^B$ is C1 aliphatic substituted with —(CH$_2$)$_{0-4}$N(R°)$_2$, wherein R° is hydrogen or $C_1$-6 aliphatic. In some embodiments, a single instance of $R^B$ is C1 aliphatic substituted with —N(R°)$_2$, wherein R° is hydrogen or $C_{1-6}$ aliphatic. In some embodiments, a single instance of $R^B$ is —CH$_2$NH$_2$.

In some embodiments, a single instance of $R^B$ is $C_{1-6}$ aliphatic substituted with 7- to 10-membered bicyclic heteroaryl having 1-4 heteroatoms selected from oxygen, nitrogen, and sulfur, which may be further substituted. In some embodiments, a single instance of $R^B$ is $C_{1-6}$ aliphatic substituted with 9-membered bicyclic heteroaryl having 1-2 heteroatoms selected from oxygen, nitrogen, and sulfur, which may be further substituted. In some embodiments, a single instance of $R^B$ is $C_{1-6}$ aliphatic substituted with imidazopyridinediyl, which may be further substituted. In some embodiments, a single instance of $R^B$ is $C_{1-6}$ aliphatic substituted with imidazopyridinediyl, which may be further substituted with $C_{1-6}$ aliphatic. In some embodiments, a single instance of $R^B$ is $C_{1-6}$ aliphatic substituted with imidazopyridinediyl, which may be further substituted with cyclopropyl.

In some embodiments, a single instance of $R^B$ is optionally substituted phenyl. In some embodiments, a single instance of $R^B$ is phenyl is substituted with —(CH$_2$)$_{0-4}$C(O)OR° and R° is hydrogen or $C_{1-6}$ aliphatic.

In some embodiments, a single instance of $R^B$ is optionally substituted 5- to 6-membered heteroaryl having 1-4 heteroatoms selected from oxygen, nitrogen, or sulfur.

In some embodiments, a single instance of $R^B$ is optionally substituted 5-membered heteroaryl having 1-4 heteroatoms selected from oxygen, nitrogen, and sulfur. In some embodiments, a single instance of $R^B$ is optionally substituted 5-membered heteroaryl having 1-4 heteroatoms selected from oxygen and nitrogen. In some embodiments, a single instance of $R^B$ is optionally substituted 5-membered heteroaryl having 1-4 nitrogen atom. In some embodiments, a single instance of $R^B$ is optionally substituted pyrazolediyl. In some embodiments, a single instance of $R^B$ is pyrazolediyl substituted with $C_{1-6}$ aliphatic optionally substituted with halogen. In some embodiments, a single instance of $R^B$ is pyrazolediyl substituted with $C_{1-6}$ aliphatic. In some embodiments, a single instance of $R^B$ is unsubstituted pyrazolediyl. In some embodiments, a single instance of $R^B$ is optionally substituted imidazolediyl. In some embodiments, a single instance of $R^B$ is unsubstituted imidazolediyl. In some embodiments, a single instance of $R^B$ is optionally substituted triazolediyl. In some embodiments, a single instance of $R^B$ is triazolediyl substituted with halogen. In some embodiments, a single instance of $R^B$ is triazolediyl substituted with $C_{1-6}$ aliphatic optionally substituted with halogen. In some embodiments, a single instance of $R^B$ is unsubstituted triazolediyl. In some embodiments, a single instance of $R^B$ is optionally substituted tetrazolediyl. In some embodiments, a single instance of $R^B$ is unsubstituted tetrazolediyl. In some embodiments, a single instance of $R^B$ is optionally substituted oxadiazolediyl. In some embodiments, a single instance of $R^B$ is unsubstituted oxadiazolediyl.

In some embodiments, a single instance of $R^B$ is optionally substituted 6-membered heteroaryl having 1-4 heteroatoms selected from oxygen, nitrogen, or sulfur. In some embodiments, a single instance of $R^B$ is optionally substituted 6-membered heteroaryl having 1-2 heteroatoms selected from oxygen, nitrogen, or sulfur. In some embodiments, a single instance of $R^B$ is optionally substituted 6-membered heteroaryl having 1-2 nitrogen atoms. In some embodiments, a single instance of $R^B$ is optionally substituted pyridinediyl. In some embodiments, a single instance of $R^B$ is pyridinediyl substituted with halogen. In some embodiments, a single instance of $R^B$ is unsubstituted pyridinediyl. In some embodiments, a single instance of $R^B$ is optionally substituted pyridazinediyl. In some embodiments, a single instance of $R^B$ is unsubstituted pyridazinediyl. In some embodiments, a single instance of $R^B$ is optionally substituted pyrimidinediyl. In some embodiments, a single instance of $R^B$ is pyrimidinediyl substituted with —(CH$_2$)$_{0-4}$C(O)OR° and R° is hydrogen or $C_{1-6}$ aliphatic.

In some embodiments, a single instance of $R^B$ is optionally substituted 3- to 7-membered saturated or partially unsaturated monocyclic carbocyclyl. In some embodiments, a single instance of $R^B$ is optionally substituted cyclopropyl. In some embodiments, a single instance of $R^B$ is unsubstituted cyclopropyl.

In some embodiments, a single instance of $R^B$ is optionally substituted 3- to 7-membered saturated or partially unsaturated monocyclic heterocyclyl having 1-2 heteroatoms selected from oxygen, nitrogen, or sulfur.

In some embodiments, a single instance of $R^B$ is optionally substituted 7- to 10-membered bicyclic heteroaryl having 1-4 heteroatoms selected from oxygen, nitrogen, and sulfur. In some embodiments, a single instance of $R^B$ is optionally substituted 9-membered bicyclic heteroaryl having 1-4 heteroatoms selected from oxygen, nitrogen, and sulfur. In some embodiments, a single instance of $R^B$ is optionally substituted 9-membered bicyclic heteroaryl having 1-2 nitrogen atoms. In some embodiments, a single instance of $R^B$ is optionally substituted pyrazolopyridinediyl. In some embodiments, a single instance of $R^B$ is unsubstituted pyrazolopyridinediyl. In some embodiments, a single instance of $R^B$ is optionally substituted imidazopyridinediyl. In some embodiments, a single instance of $R^B$ is unsubstituted imidazopyridinediyl.

In some embodiments, a single instance of $R^B$ is optionally substituted 8- to 10-membered spirocyclic heterocyclyl having 1-3 heteroatoms independently selected from oxygen, nitrogen, and sulfur. In some embodiments, a single instance of $R^B$ is unsubstituted oxaazaspiroheptyl.

In some embodiments, L an optionally substituted $C_{1-6}$ hydrocarbon chain, wherein 1 to 3 methylene units are independently replaced with —O—, —NR—, —C(O)—, —C(O)NR—, —NRC(O)—, —S(O)$_2$NR—, —NRS(O)$_2$—, or —S(O)$_2$—, wherein each R is independently hydrogen or $C_{1-6}$ aliphatic optionally substituted with halogen. In some embodiments, L is selected from —(C(R)$_2$)$_m$NR(C(R)$_2$)$_m$-#, —(C(R)$_2$)$_m$NRC(O)(C(R)$_2$)$_m$-#, —(C(R)$_2$)$_m$C(O)NR(C(R)$_2$)$_m$-#, —NRC(O)NR-#, —(C(R)$_2$)$_m$OC(O)NR(C(R)$_2$)$_m$-#, —O(C(R)$_2$)$_m$NRC(O)-#, —O(C(R)$_2$)$_m$NRS(O)$_2$-#, —(C(R)$_2$)$_m$S(O)$_2$NR(C(R)$_2$)$_m$-#, and —(C(R)$_2$)$_m$NRS(O)$_2$(C(R)$_2$)$_m$-#, wherein each R is independently hydrogen or $C_{1-6}$ aliphatic, each m is independently 0, 1 or 2, and # represents the point of attachment to $Cy^4$. In some embodiments, L is selected from —NR-#, —C(R)$_2$NR-#, —C(R)$_2$NRC(R)$_2$-#, —NRC(O)-#, —C(R)$_2$NRC(O)-#, —C(R)$_2$C(R)$_2$NRC(O)-#, —C(O)NRC(R)$_2$-#, —C(R)$_2$C(O)NR-#, —C(R)$_2$C(O)NRC(R)$_2$-#, —NRC(O)NR-#, —C(R)$_2$OC(O)NR-#, —OC(R)$_2$C(R)$_2$NRC(O)-#, —OC(R)$_2$C(R)$_2$NRS(O)$_2$-#, —S(O)$_2$NRC(R)$_2$-#, —C(R)$_2$NRS(O)$_2$-#, and —C(R)$_2$C(R)$_2$NRS(O)$_2$-#, wherein each R is independently hydrogen or $C_{1-6}$ aliphatic and # represents the point of attachment to $Cy^4$. In some embodiments, L is selected from —NR-#, —C(R)$_2$NR-#, —C(R)$_2$NRC(R)$_2$-#, —NRC(O)-#, —C(R)$_2$NRC(O)-#, —C(R)$_2$C(R)$_2$NRC(O)-#, —C(O)NRC(R)$_2$-#, —C(R)$_2$C(O)NR-#, —C(R)$_2$C(O)NRC(R)$_2$-#, —NRC(O)NR-#, —C(R)$_2$OC(O)NR-#, —OC(R)$_2$C(R)$_2$NRC(O)-#, —OC(R)$_2$C(R)$_2$NRS(O)$_2$-#, —S(O)$_2$NRC(R)$_2$-#, —C(R)$_2$NRS(O)$_2$-#, and —C(R)$_2$C(R)$_2$NRS(O)$_2$-#, wherein each R is independently hydrogen or methyl and # represents the point of attachment to $Cy^4$.

In some embodiments, L is selected from the group consisting of: —NH-#, —CH$_2$NH-#, —CH$_2$NHCH$_2$-#, —C(CF$_3$)HNHCH$_2$-#, —NHC(O)-#, —CH$_2$NHC(O)-#, —CH(CH$_3$)NHC(O)-#, —CH$_2$N(CH$_3$)C(O)-#, CH$_2$CH$_2$NHC(O)-#, —CH$_2$C(O)NH-#, —C(CH$_3$)HC(O)NH-#, —C(O)NHCH$_2$-#, —CH$_2$C(O)NHCH$_2$-#, —NHC(O)NH-#, —CH$_2$OC(O)NH-#, —C(CH$_3$)HOC(O)NH-#, —S(O)$_2$NHCH$_2$-#, S(O)$_2$NHC(CH$_3$)H-#, —CH$_2$NHS(O)$_2$-#, —C(CH$_3$)HNHS(O)$_2$-#, —CH$_2$CH$_2$NHS(O)$_2$-#, —OCH$_2$CH$_2$NHC(O)-#, and —OCH$_2$CH$_2$NHS(O)$_2$-#, wherein # represents the point of attachment to $Cy^4$.

In some embodiments, L is selected from —NRC(O)-#, —C(R)$_2$NRC(O)-#, —C(R)$_2$NRC(R)$_2$-#, and —C(R)$_2$NRSO$_2$-#, wherein each R is independently selected from hydrogen and $C_{1-6}$ aliphatic and # represents the point of attachment to $Cy^4$. In some embodiments, L is selected from —NRC(O)-#, —C(R)$_2$NRC(O)-#, —C(R)$_2$NRC(R)$_2$-#, and —C(R)$_2$NRSO$_2$-#, wherein each R is independently selected from hydrogen and methyl and # represents the point of attachment to $Cy^4$. In some embodiments, L is selected from —NRC(O)-# and —C(R)$_2$NRC(O)-#, wherein each R is independently selected from hydrogen and $C_{1-6}$ aliphatic and # represents the point of attachment to $Cy^4$. In some embodiments, L is selected from —NRC(O)-# and —C(R)$_2$NRC(O)-#, wherein each R is independently selected from hydrogen and methyl and # represents the point of attachment to $Cy^4$.

In some embodiments, $R^1$ and $R^2$ are each hydrogen. In some embodiments, $R^2$ is hydrogen and $R^1$ is taken together with a monocyclic $Cy^4$ to form a fused 7- to 10-membered saturated or partially unsaturated bicyclic heterocyclylene having 1-4 heteroatoms selected from oxygen, nitrogen, or sulfur. In some embodiments, n is 1, $R^2$ is hydrogen and $R^1$ is taken together with a monocyclic $Cy^4$ to form a fused 7- to 10-membered saturated or partially unsaturated bicyclic heterocyclylene having 1-4 heteroatoms selected from oxygen, nitrogen, or sulfur. In some embodiments, n is 1, $R^2$ is hydrogen and $R^1$ is taken together with a monocyclic $Cy^4$ to form a fused 8-membered saturated or partially unsaturated bicyclic heterocyclylene having 1-4 heteroatoms selected from oxygen, nitrogen, or sulfur.

In some embodiments, $R^1$ and $R^2$ are independently selected from hydrogen, halogen, —OR, —SR, —N(R)$_2$, and optionally substituted $C_{1-6}$ aliphatic, wherein each R is independently selected from hydrogen and $C_{1-6}$ aliphatic. In some embodiments, $R^1$ and $R^2$ are independently selected from hydrogen, fluorine, —OH, —SH, —NH$_2$, and $C_{1-6}$ aliphatic substituted with —(CH$_2$)$_{0-4}$C(O)OR°, wherein R° is hydrogen or $C_{1-6}$ aliphatic. In some embodiments, $R^1$ and $R^2$ are independently selected from hydrogen, fluorine, —OH, and $C_{1-6}$ aliphatic substituted with —(CH$_2$)$_{0-4}$C(O)OR°, wherein R° is hydrogen, methyl or ethyl.

In some embodiments, $R^3$, $R^4$, $R^5$, and $R^7$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur. In some embodiments, $R^3$, $R^4$, $R^5$, and $R^7$ are independently selected from hydrogen, halogen, —CN, —C(O)$_2$R, or an optionally substituted group selected from $C_{1-6}$ aliphatic, 5- to 6-membered heteroaryl having 1-4 heteroatoms selected from oxygen, nitrogen, or sulfur, and 3- to 7-membered saturated or partially unsaturated monocyclic heterocyclyl having 1-2 heteroatoms selected from oxygen, nitrogen, or sulfur.

In some embodiments, substituents on an optionally substituted $R^3$, $R^4$, $R^5$, and $R^7$ are each independently halogen, —CN, (CH$_2$)$_{0-4}$R°, —(CH$_2$)$_{0-4}$OR°, —(CH$_2$)$_{0-4}$N(R°)$_2$, —(CH$_2$)$_{0-40}$(CH$_2$)$_{1}$-4N(R°)$_2$ and —(CH$_2$)$_{0-4}$C(O)OR°, wherein each R° is independently hydrogen, $C_1$-6 aliphatic, or a 3- to 5-membered saturated, partially unsaturated, or aryl ring having 1-2 heteroatoms independently selected from nitrogen, oxygen, or sulfur.

In some embodiments, substituents on an optionally substituted $R^3$, $R^4$, $R^5$, and $R^7$ are each independently —F, —CN, —R°, —OR°, —N(R°)$_2$, —COOR°, or -OC(R°)$_2$C(R°)$_2$N(R°)$_2$ wherein each R° is independently hydrogen, $C_{1-6}$ aliphatic, or a 4-membered saturated ring having 1-2 heteroatoms independently selected from nitrogen, oxygen, or sulfur. In some embodiments, substituents on an optionally substituted $R^3$, $R^4$, $R^5$, and $R^7$ are each independently selected from —F, —CN, —CH$_3$, —OH, —NH$_2$, —COOH, —COOCH$_2$CH$_2$, —OCH$_2$CH$_2$NH$_2$, —OCH$_2$CH$_2$N(CH$_3$)$_2$, and

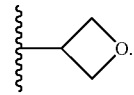 [SMILES: *C1COC1]

In some embodiments, $R^4$ is selected from hydrogen, halogen, —CN, —C(O)$_2$R, —C(O)N(R)$_2$, —N(R)$_2$, —OR, —SR, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur. In some embodiments, $R^4$ is selected from hydrogen, halogen, —CN, —C(O)$_2$R, or an optionally substituted group selected from C$_{1-6}$ aliphatic, 5- to 6-membered heteroaryl having 1-4 heteroatoms selected from oxygen, nitrogen, or sulfur, and 3- to 7-membered saturated or partially unsaturated monocyclic heterocyclyl having 1-2 heteroatoms selected from oxygen, nitrogen, or sulfur.

In some embodiments, a substituent on an optionally substituted $R^4$ is —F, —CN, —R°, —OR°, —N(R°)$_2$, —COOR°, or —OC(R°)$_2$C(R°)$_2$N(R°)$_2$ wherein each R° is independently hydrogen, C$_{1-6}$ aliphatic, or a 4-membered saturated ring having 1-2 heteroatoms independently selected from nitrogen, oxygen, or sulfur. In some embodiments, substituents on an optionally substituted $R^4$ is selected from —F, —CN, —CH$_3$, —OH, —NH$_2$, —COOH, —COOCH$_2$CH$_2$, —OCH$_2$CH$_2$NH$_2$, —OCH$_2$CH$_2$N(CH$_3$)$_2$, and

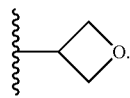 [SMILES: *C1COC1]

In some embodiments, each R is independently hydrogen or an optionally substituted C$_{1-6}$ aliphatic, or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur.

In some embodiments, n is 0. In some embodiments, n is 1.

In some embodiments, a provided compound is of Formula (II):

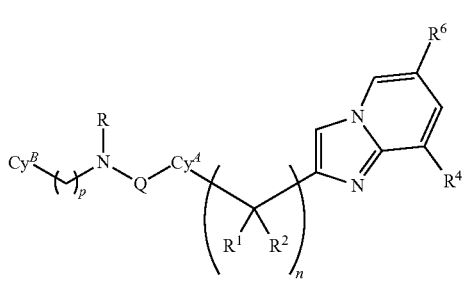

(II)

or a pharmaceutically acceptable salt thereof, wherein each of Cy$^A$, Cy$^B$, $R^1$, $R^2$, $R^4$, $R^6$, R, and n is defined and described in classes and subclasses herein;

Q is selected from —C(R)$_2$—, —C(O)—, and —S(O)$_2$—; and p is 0, 1, or 2;

with the proviso that the compound is other than N-(furan-2-ylmethyl)-N,3,5-trimethyl-1-((6-methylimidazo[1,2-a]pyridin-2-yl)methyl)-1H-pyrazole-4-sulfonamide and 2-[(6,8-dichloroimidazo[1,2-a]pyridin-2-yl)methyl]-4-methyl-N-phenyl-5-thiazolecarboxamide.

It will be understood that, unless otherwise specified or prohibited by the foregoing definition of Formula (II), embodiments of variables Cy$^A$, Cy$^B$, $R^1$, $R^2$, $R^4$, $R^6$, R, and n as defined above and described in classes and subclasses herein, also apply to compounds of Formula (II), both singly and in combination.

In some embodiments, Q is —C(R)$_2$— and p is 1. In some embodiments, Q is —C(O)— and p is 1. In some embodiments, —C(O)— and p is 0. In some embodiments, Q is —S(O)$_2$— and p is 1.

In some embodiments, a provided compound is of Formula (III):

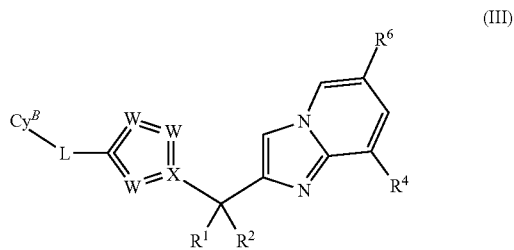

(III)

wherein ┈┈┈ represents a single or double bond;
X is selected from C and N;
each W is independently selected from CR$^A$, CH, N, and O; and
each of R$^A$, Cy$^B$, L, $R^1$, $R^2$, $R^4$, and $R^6$ is defined and described in classes and subclasses herein; with the proviso that the compound is other than N-(furan-2-ylmethyl)-N,3,5-trimethyl-1-((6-methylimidazo[1,2-a]pyridin-2-yl)methyl)-1H-pyrazole-4-sulfonamide.

In some embodiments, a provided compound, or a pharmaceutically acceptable salt thereof, has a structure of Formula (III-a), Formula (III-b), Formula (III-c), Formula (III-d), Formula (III-e), Formula (III-f), Formula (III-g),

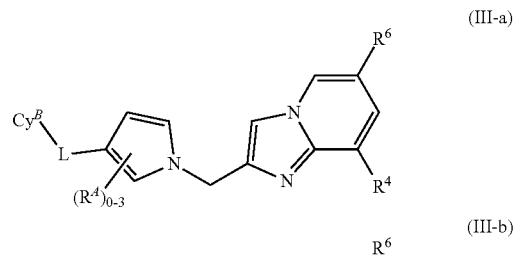

(III-a)

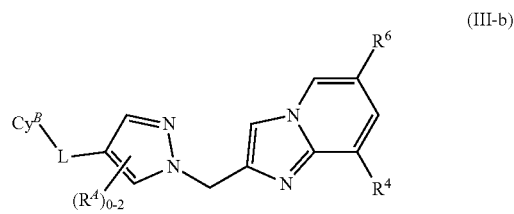

(III-b)

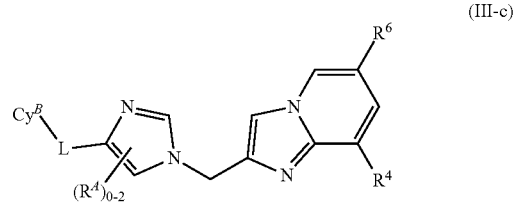

(III-c)

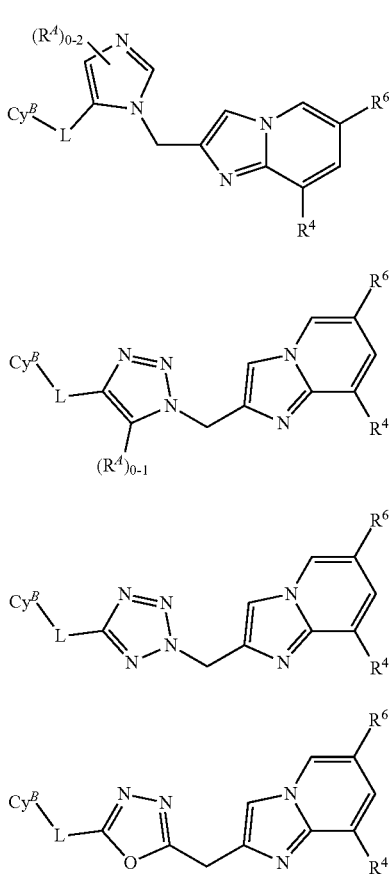
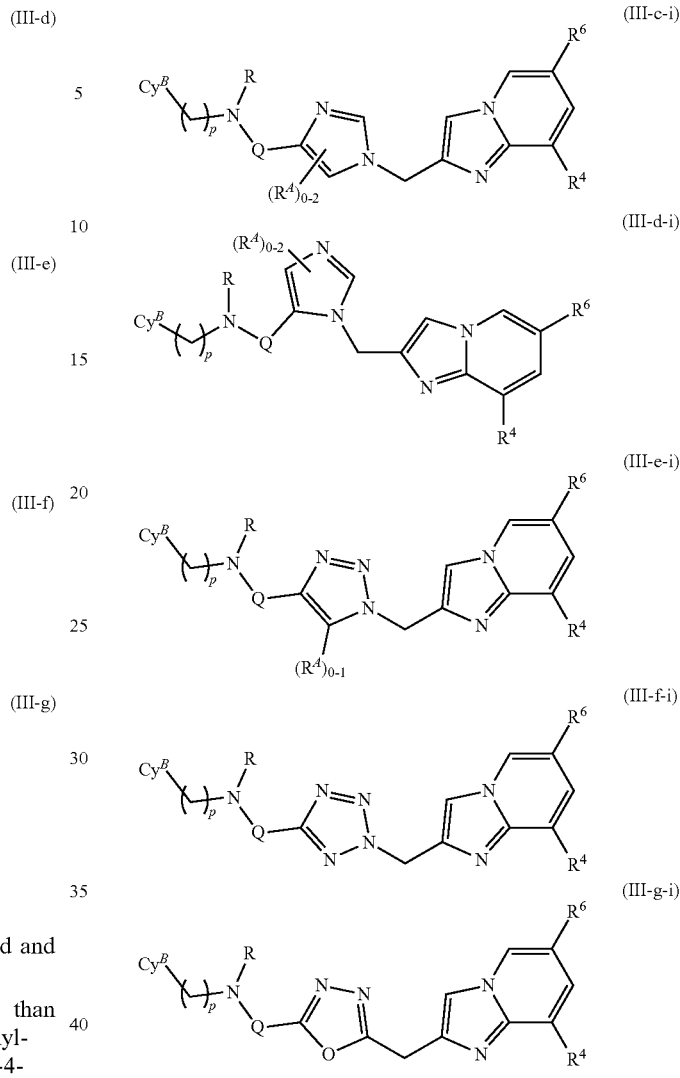

wherein each of $R^A$, $Cy^B$, L, $R^4$, and $R^6$ is defined and described in classes and subclasses herein;

with the proviso that the compound is other than N-(furan-2-ylmethyl)-N,3,5-trimethyl-1-((6-methylimidazo[1,2-a]pyridin-2-yl)methyl)-1H-pyrazole-4-sulfonamide.

In some embodiments, a provided compound, or a pharmaceutically acceptable salt thereof, has a structure of Formula (III-a-i), Formula (III-b-i), Formula (III-c-i), Formula (III-d-i), Formula (III-e-i), Formula (III-f-i), Formula (III-g-i),

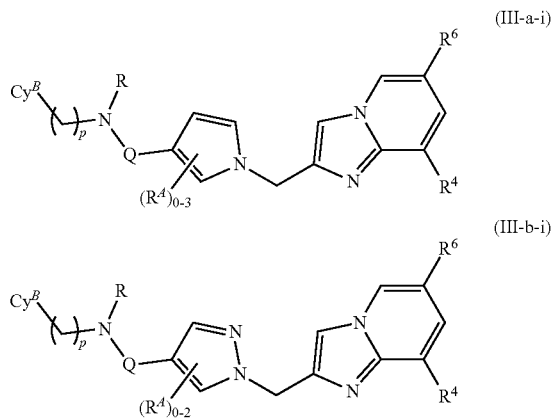

wherein Q is selected from —C(R)$_2$—, —C(O)—, and —S(O)$_2$—;

p is 0, 1, or 2; and each of $R^A$, $Cy^B$, L, $R^4$, $R^6$ and R is defined and described in classes and subclasses herein;

with the proviso that the compound is other than N-(furan-2-ylmethyl)-N,3,5-trimethyl-1-((6-methylimidazo[1,2-a]pyridin-2-yl)methyl)-1H-pyrazole-4-sulfonamide.

In some embodiments, Q is —C(R)$_2$— and p is 1. In some embodiments, Q is —C(O)— and p is 1. In some embodiments, —C(O)— and p is 0. In some embodiments, Q is —S(O)$_2$— and p is 1.

It will be understood that, unless otherwise specified or prohibited by the foregoing definition of Formula (III), embodiments of variables $R^A$, $Cy^B$, $R^1$, $R^2$, $R^6$, and $R^7$ as defined above and described in classes and subclasses herein, also apply to compounds of Formula (III-a), Formula (III-b), Formula (III-c), Formula (III-d), Formula (III-e), Formula (III-f), and Formula (III-g) and Formula (III-a-i), Formula (III-b-i), Formula (III-c-i), Formula (III-d i), Formula (III-e-i), Formula (III-f-i), and Formula (III-g-i) both singly and in combination.

In some embodiments, where $R^1$ is taken together with a monocyclic $Cy^A$ to form an optionally substituted fused ring, the compound is of Formula (IV):

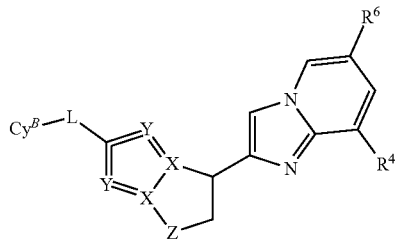
(IV)

wherein ═══ represents a single or double bond;
each X is independently N or C;
each Y is independently $CR^A$, CH, or N;
Z is $CH_2$ or O; and
each of $R^A$, $Cy^B$, L, $R^4$, and $R^6$ is defined and described in classes and subclasses herein.

In some embodiments, a provided compound, or a pharmaceutically acceptable salt thereof, has a structure of Formula (IV-a), Formula (IV-b), Formula (IV-c), and Formula (IV-d),

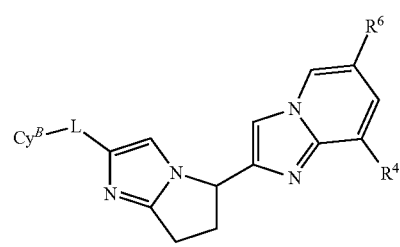
(IV-a)

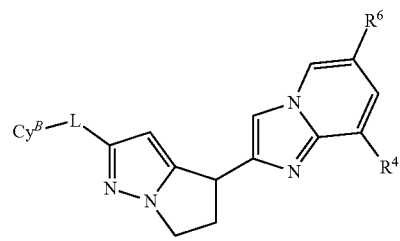
(IV-b)

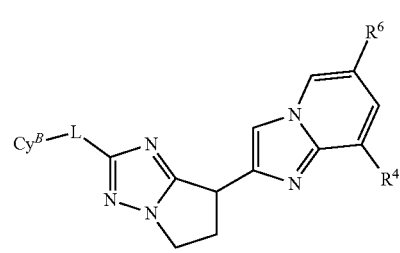
(IV-c)

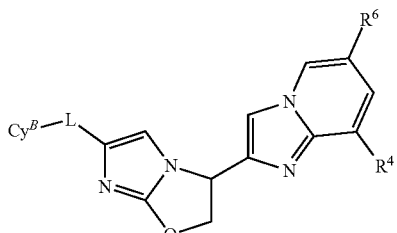
(IV-d)

wherein each of $Cy^B$, L, $R^4$, and $R^6$ is defined and described in classes and subclasses herein.

In some embodiments, a provided compound, or a pharmaceutically acceptable salt thereof, has a structure of Formula (IV-a-i), Formula (IV-b-i), Formula (IV-c-i), and Formula (IV-d-i),

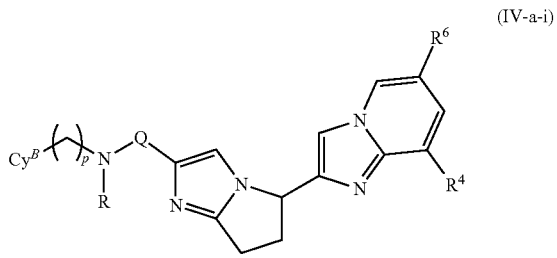
(IV-a-i)

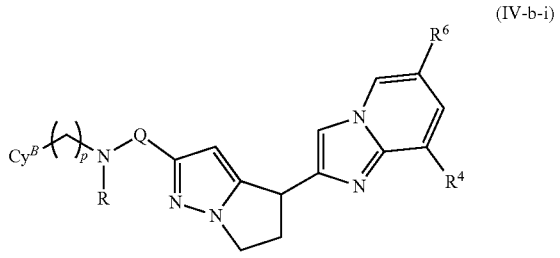
(IV-b-i)

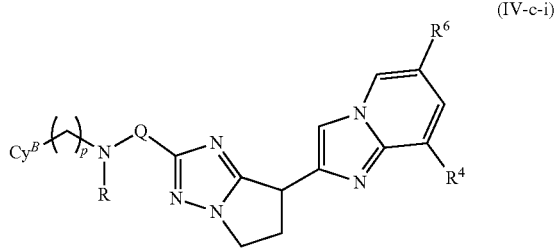
(IV-c-i)

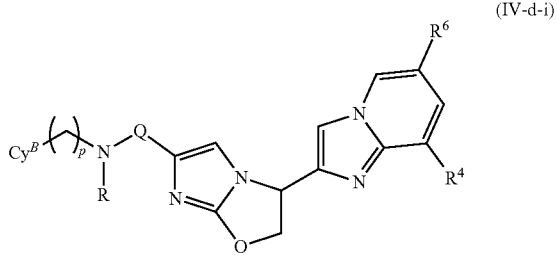
(IV-d-i)

wherein Q is selected from —C(R)$_2$—, —C(O)—, and —S(O)$_2$—;
p is 0, 1, or 2; and
each of $Cy^B$, $R^4$, $R^6$ and R is defined and described in classes and subclasses herein.

In some embodiments, Q is —C(R)$_2$— and p is 1. In some embodiments, Q is —C(O)— and p is 1. In some embodiments, —C(O)— and p is 0. In some embodiments, Q is —S(O)$_2$— and p is 1.

It will be understood that, unless otherwise specified or prohibited by the foregoing definition of Formula (IV), embodiments of variables $R^A$, L, $Cy^B$, $R^4$, $R^6$, and R as defined above and described in classes and subclasses herein, also apply to compounds of Formula (IV-a), Formula (IV-b), Formula (IV-c), and Formula (IV-d), and Formula (IV-a-i), Formula (IV-b-i), Formula (IV-c-i), and Formula (IV-d-i) both singly and in combination.

In some embodiments, a provided compound is any one of compounds I-1 through I-155 as shown in Table I:

TABLE I

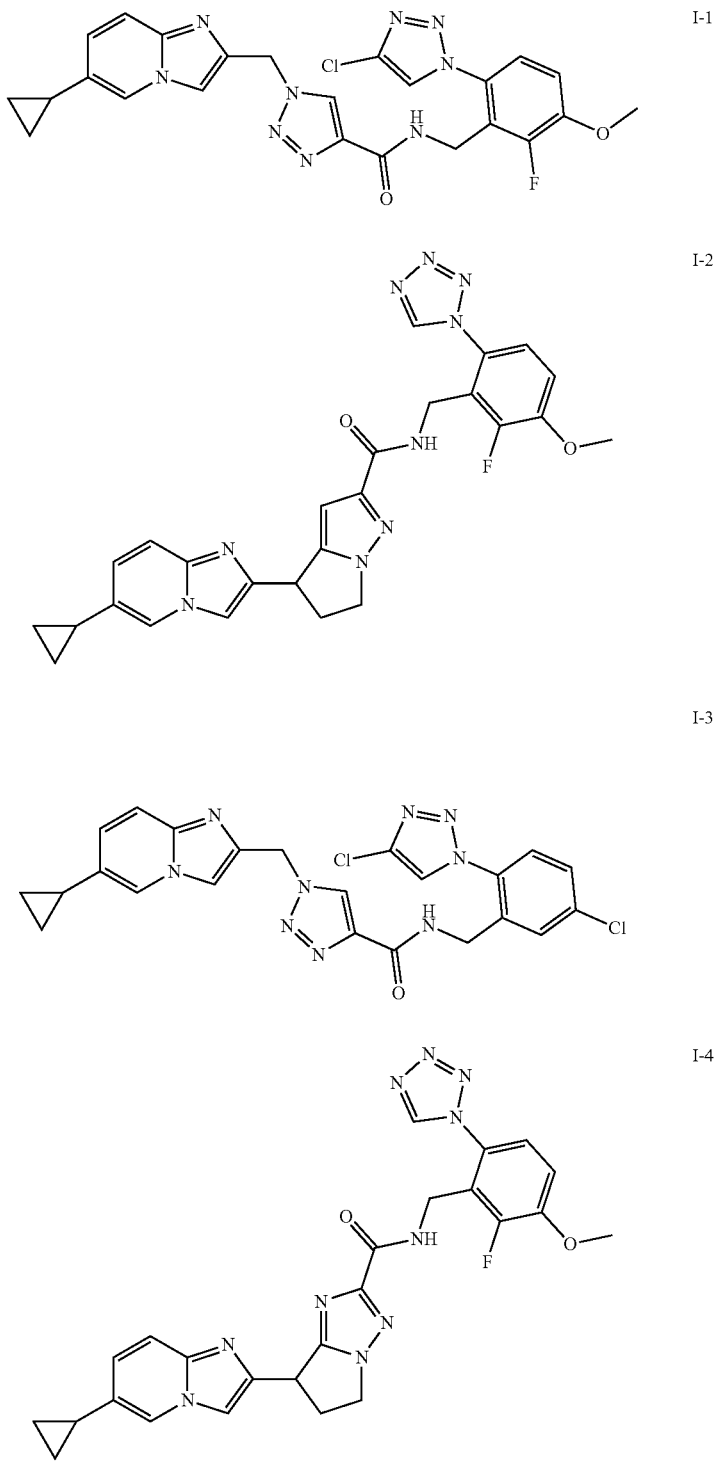

TABLE I-continued
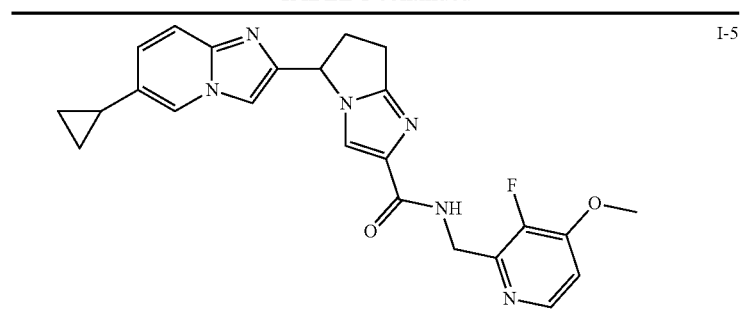 I-5
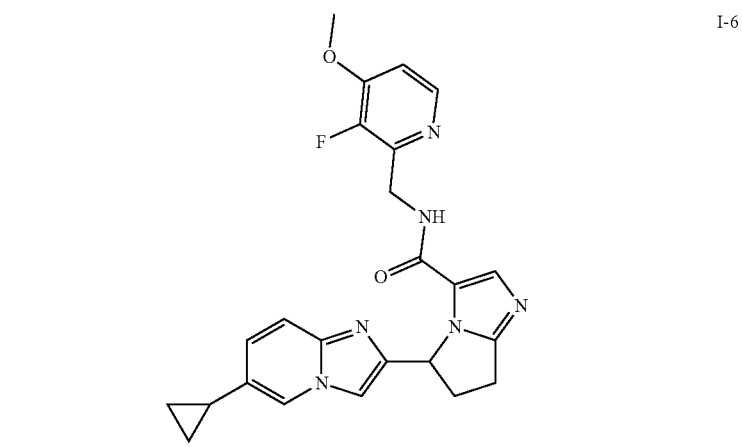 I-6
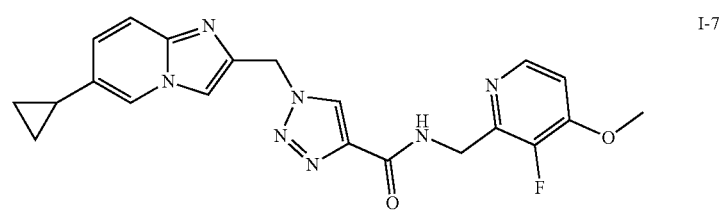 I-7
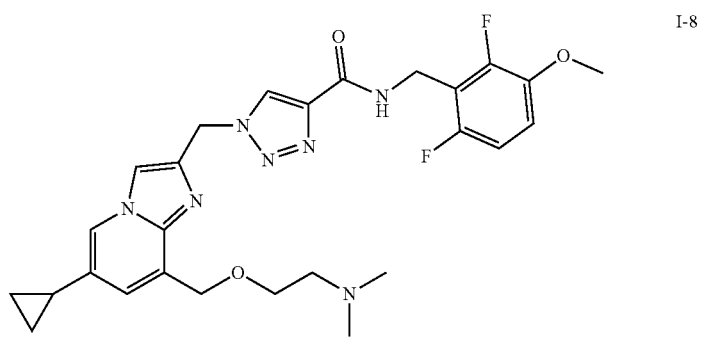 I-8
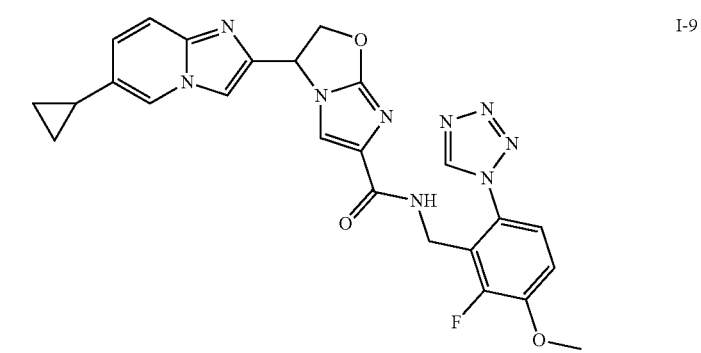 I-9

TABLE I-continued
I-10
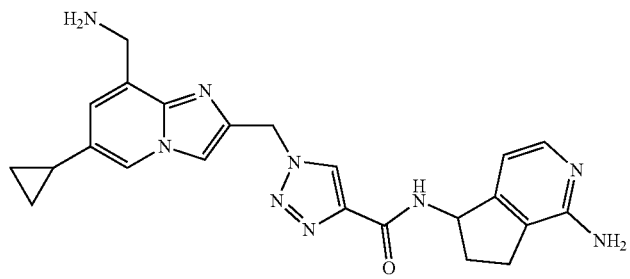 [SMILES: NCc1cc(C2CC2)cn2cc(Cn3cc(C(=O)NC4CCc5c4ccnc5N)nn3)nc12]
I-11
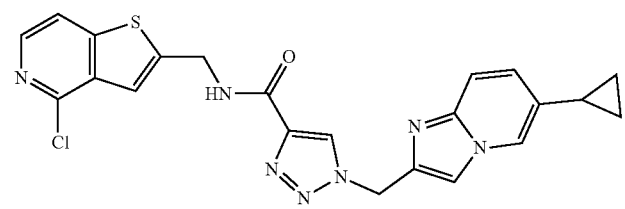 [SMILES: O=C(NCc1cc2c(Cl)nccc2s1)c1cn(Cc2cn3cc(C4CC4)ccc3n2)nn1]
I-12
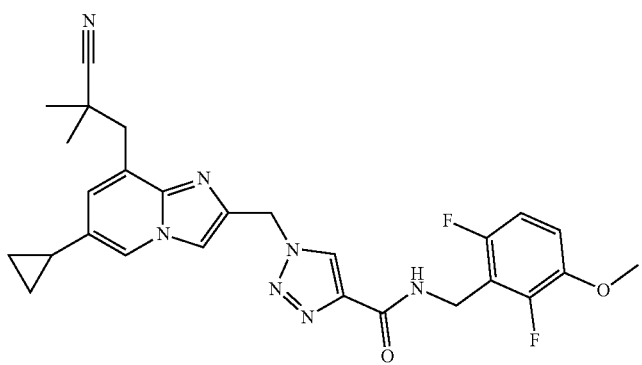 [SMILES: COc1ccc(F)c(CNC(=O)c2cn(Cc3cn4cc(C5CC5)cc(CC(C)(C)C#N)c4n3)nn2)c1F]
I-13
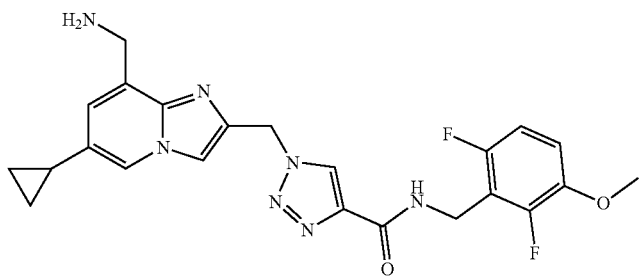 [SMILES: COc1ccc(F)c(CNC(=O)c2cn(Cc3cn4cc(C5CC5)cc(CN)c4n3)nn2)c1F]
I-14
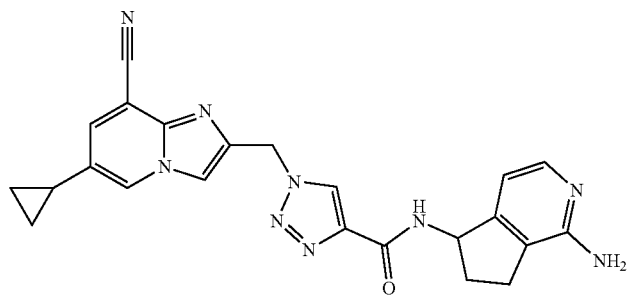 [SMILES: N#Cc1cc(C2CC2)cn2cc(Cn3cc(C(=O)NC4CCc5c4ccnc5N)nn3)nc12]

TABLE I-continued
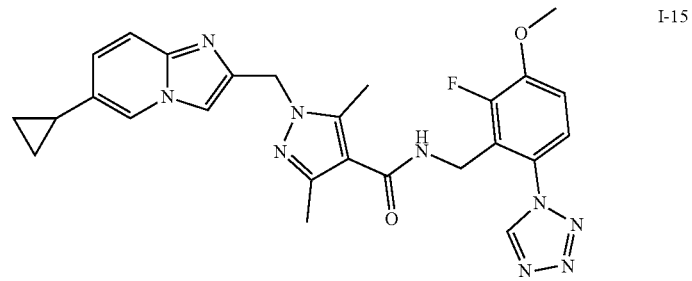 I-15
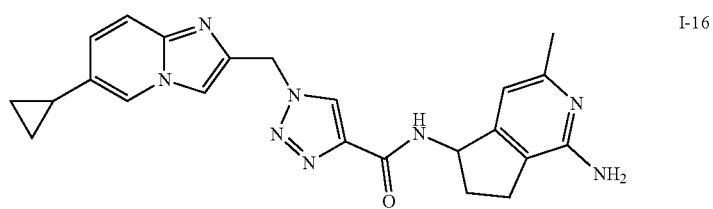 I-16
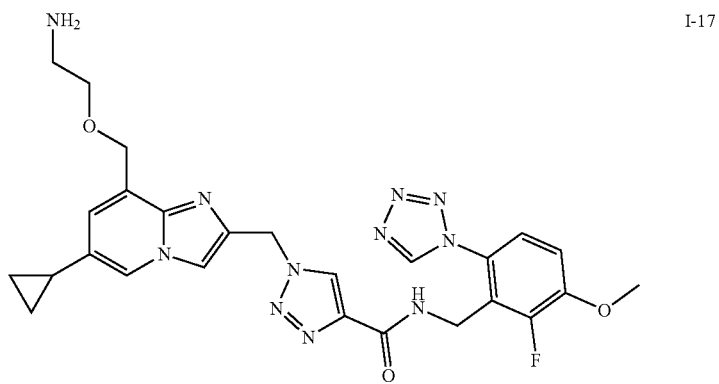 I-17
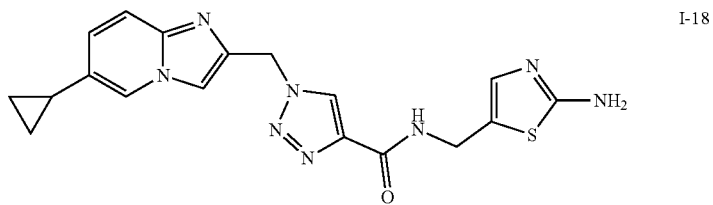 I-18
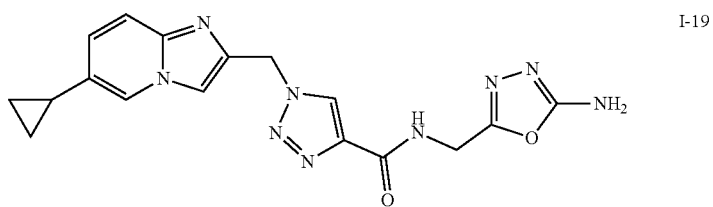 I-19
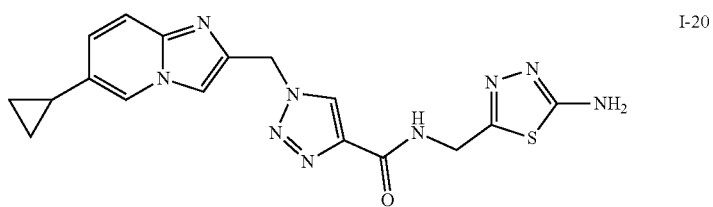 I-20

TABLE I-continued
I-21
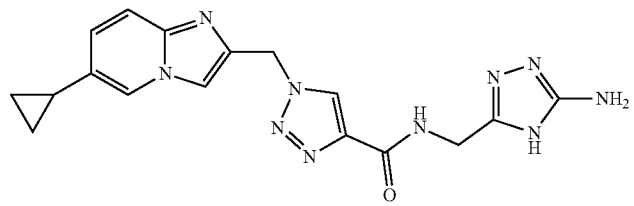 [SMILES: Nc1nnc(CNC(=O)c2cn(Cc3cn4cc(C5CC5)ccc4n3)nn2)[nH]1]
I-22
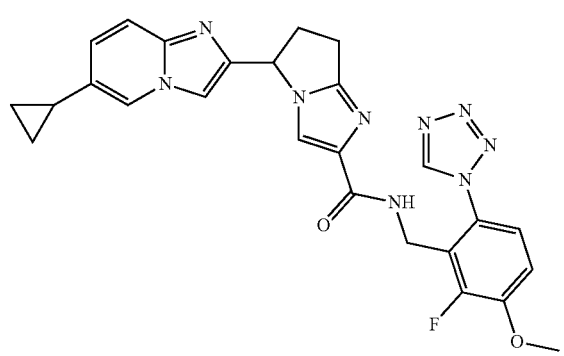 [SMILES: COc1ccc(-n2cnnn2)c(CNC(=O)c2cn3c(n2)CCC3c2cn3cc(C4CC4)ccc3n2)c1F]
I-23
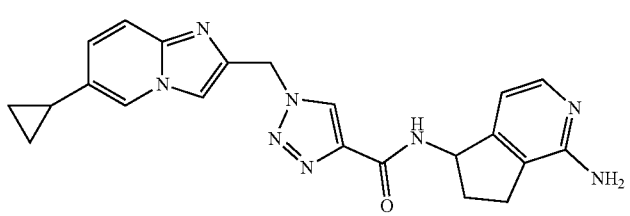 [SMILES: Nc1nccc2c1CCC2NC(=O)c1cn(Cc2cn3cc(C4CC4)ccc3n2)nn1]
I-24
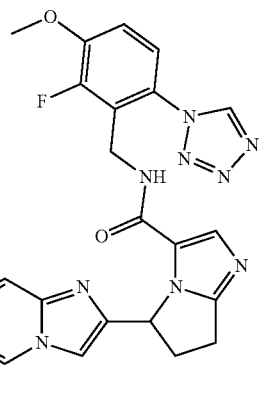
I-25
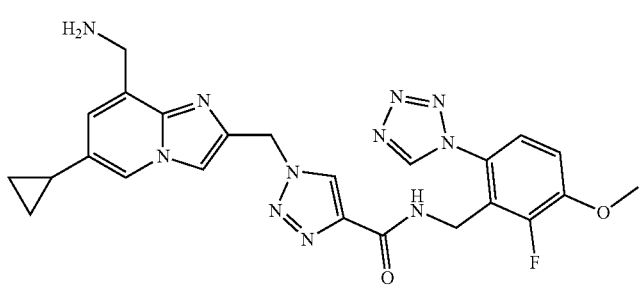 [SMILES: COc1ccc(-n2cnnn2)c(CNC(=O)c2cn(Cc3cn4cc(C5CC5)cc(CN)c4n3)nn2)c1F]

TABLE I-continued
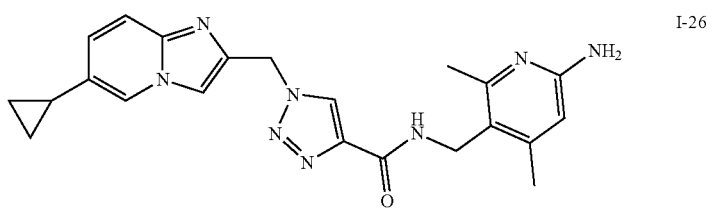 I-26
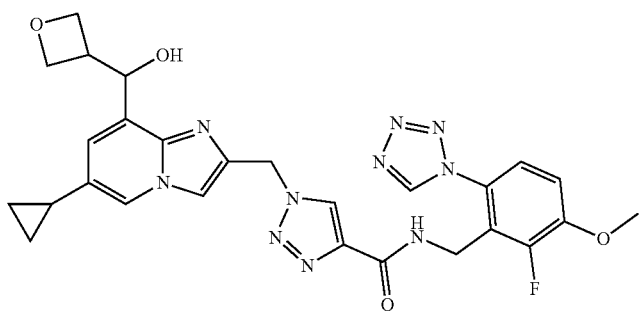 [SMILES: COc1ccc(-n2cnnn2)c(CNC(=O)c2cn(Cc3cn4cc(C5CC5)cc(C(O)C5COC5)c4n3)nn2)c1F] I-27
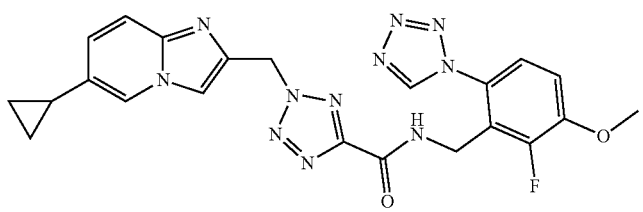 [SMILES: COc1ccc(-n2cnnn2)c(CNC(=O)c2nnn(Cc3cn4cc(C5CC5)ccc4n3)n2)c1F] I-28
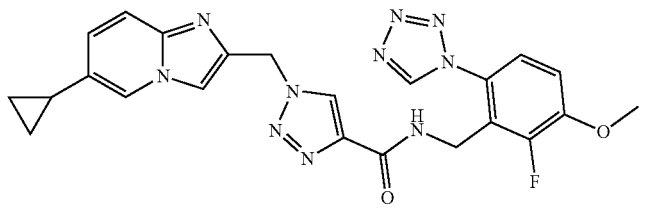 [SMILES: COc1ccc(-n2cnnn2)c(CNC(=O)c2cn(Cc3cn4cc(C5CC5)ccc4n3)nn2)c1F] I-29
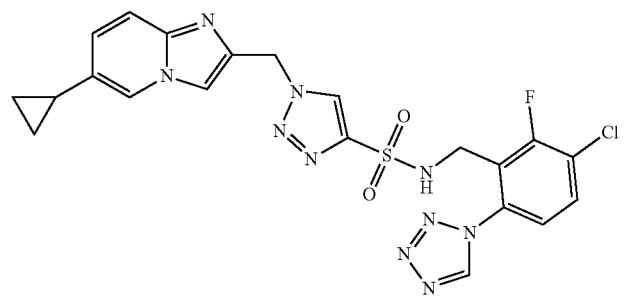 [SMILES: O=S(=O)(NCc1c(-n2cnnn2)ccc(Cl)c1F)c1cn(Cc2cn3cc(C4CC4)ccc3n2)nn1] I-30
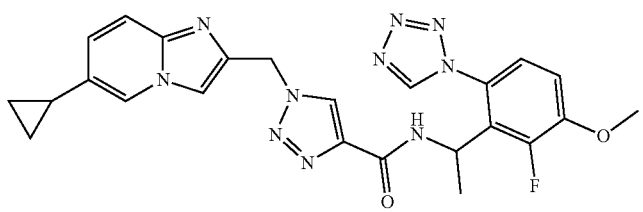 [SMILES: COc1ccc(-n2cnnn2)c(C(C)NC(=O)c2cn(Cc3cn4cc(C5CC5)ccc4n3)nn2)c1F] I-31

TABLE I-continued
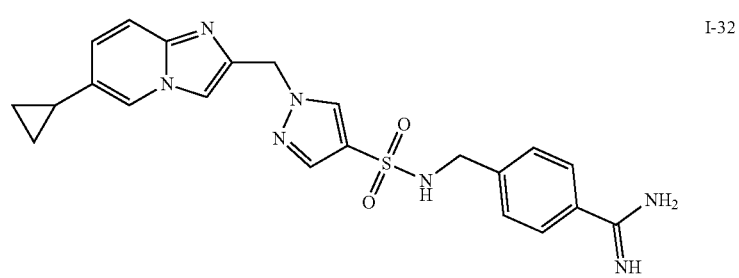 I-32
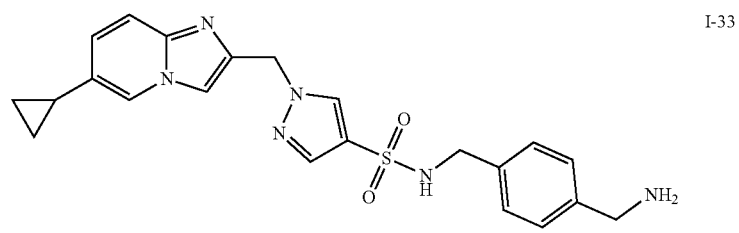 I-33
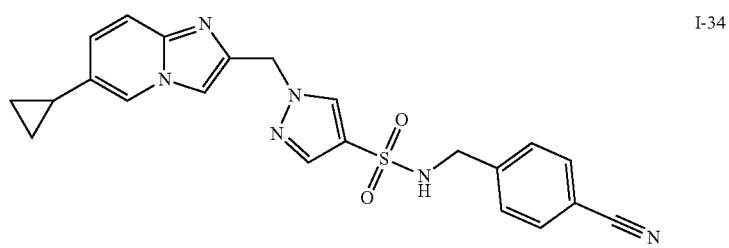 I-34
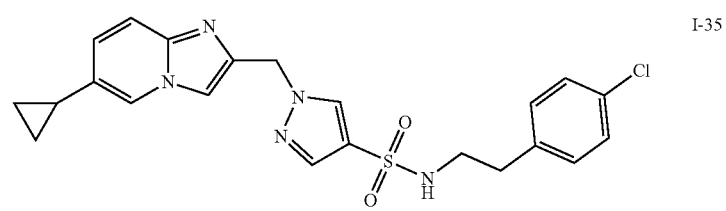 I-35
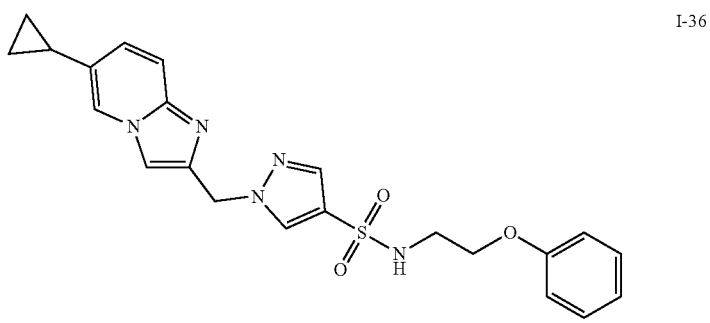 I-36
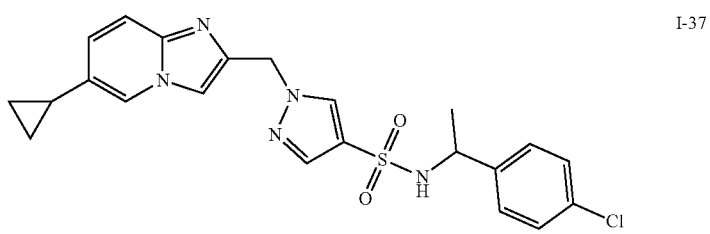 I-37

TABLE I-continued
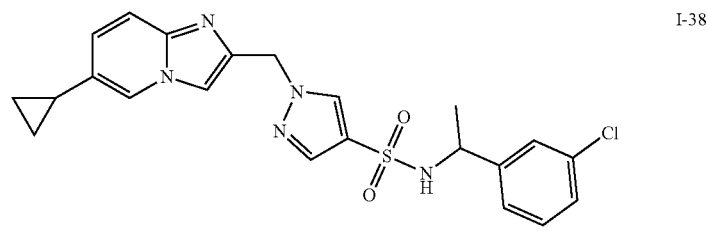
I-38
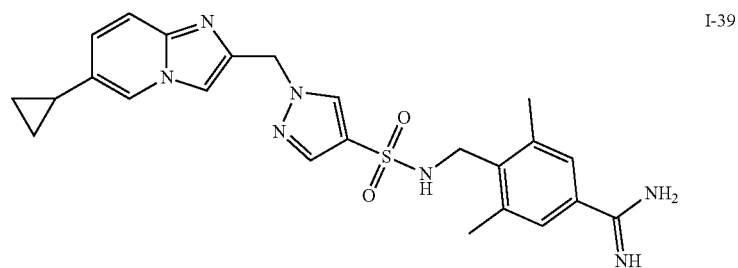
I-39
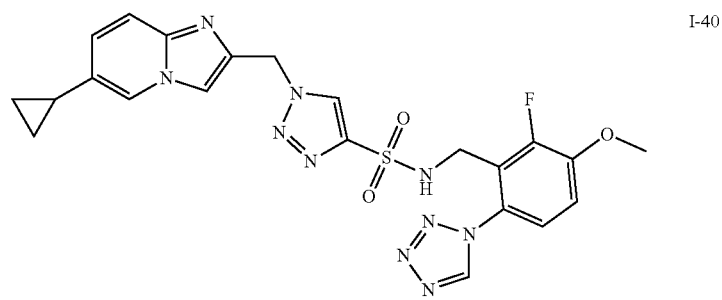
I-40
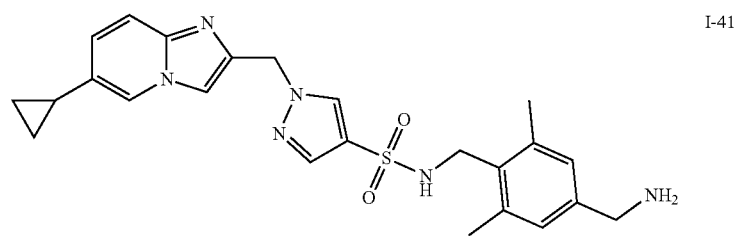
I-41
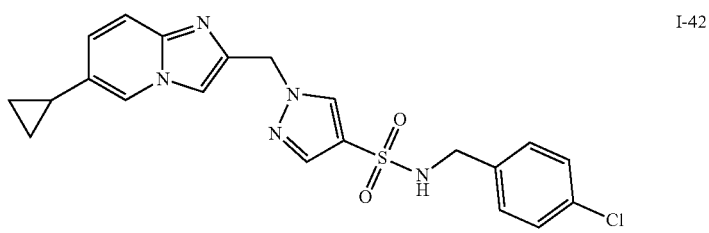
I-42
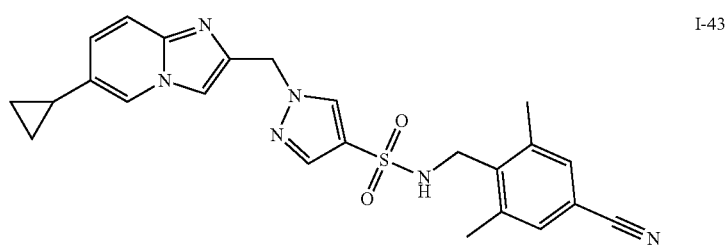
I-43

TABLE I-continued
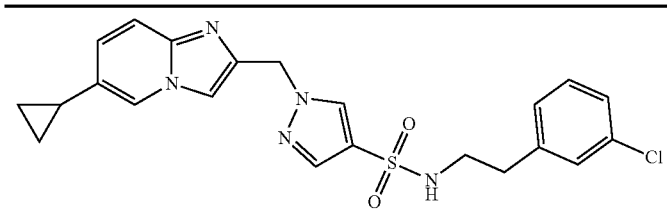
I-44
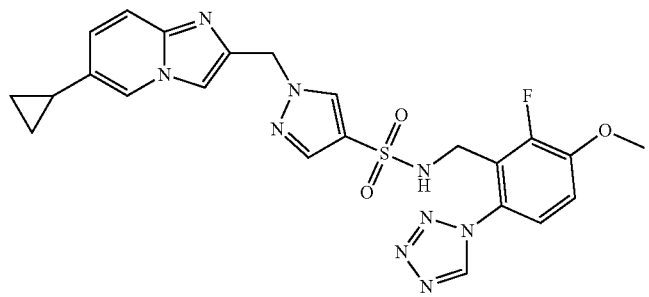 [SMILES: COc1ccc(-n2cnnn2)c(CNS(=O)(=O)c2cnn(Cc3cn4cc(C5CC5)ccc4n3)c2)c1F]
I-45
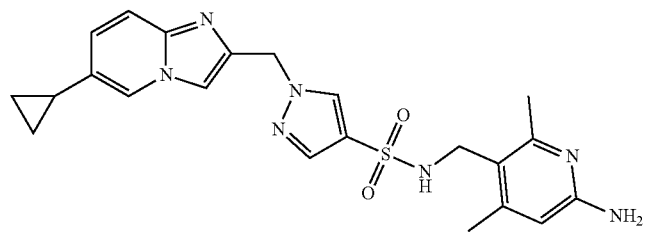 [SMILES: Cc1cc(N)nc(C)c1CNS(=O)(=O)c1cnn(Cc2cn3cc(C4CC4)ccc3n2)c1]
I-46
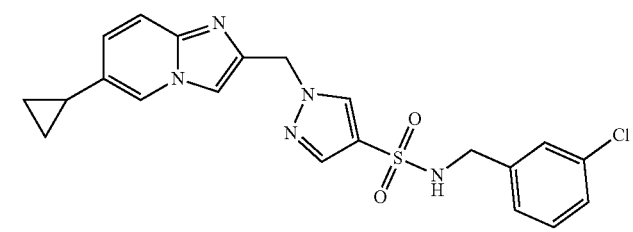 [SMILES: O=S(=O)(NCc1cccc(Cl)c1)c1cnn(Cc2cn3cc(C4CC4)ccc3n2)c1]
I-47
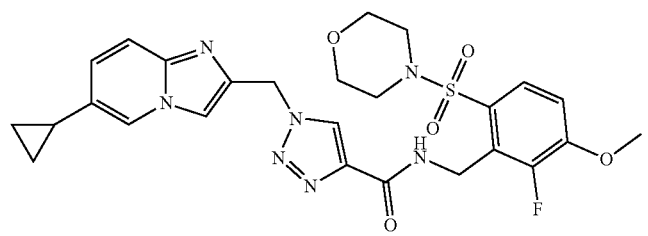 [SMILES: COc1ccc(S(=O)(=O)N2CCOCC2)c(CNC(=O)c2cn(Cc3cn4cc(C5CC5)ccc4n3)nn2)c1F]
I-48
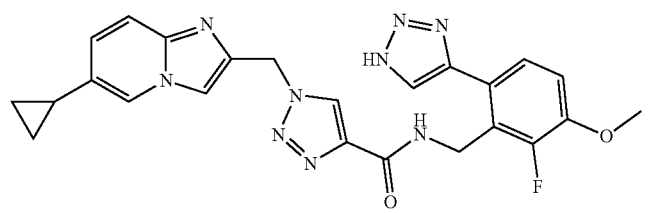 [SMILES: COc1ccc(-c2c[nH]nn2)c(CNC(=O)c2cn(Cc3cn4cc(C5CC5)ccc4n3)nn2)c1F]
I-49
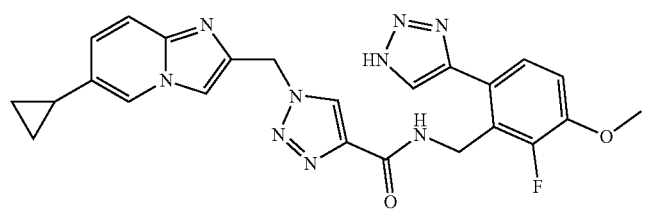 [SMILES: COc1ccc(-c2c[nH]nn2)c(CNC(=O)c2cn(Cc3cn4cc(C5CC5)ccc4n3)nn2)c1F]
I-50

TABLE I-continued
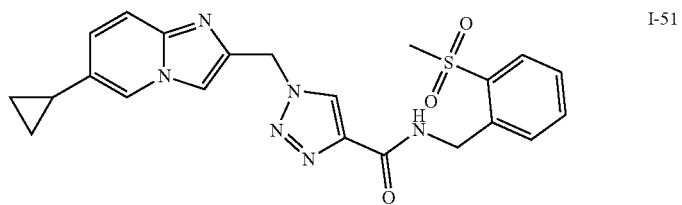 I-51
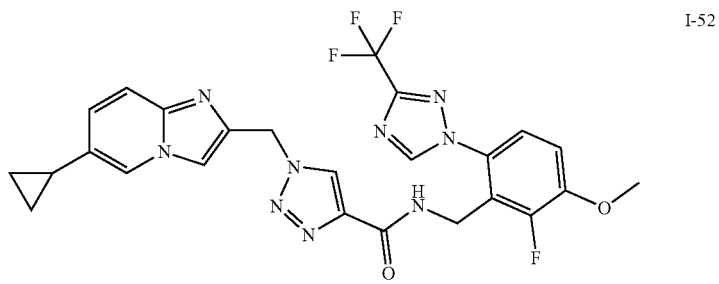 I-52
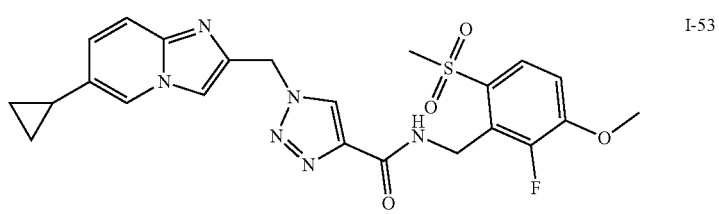 I-53
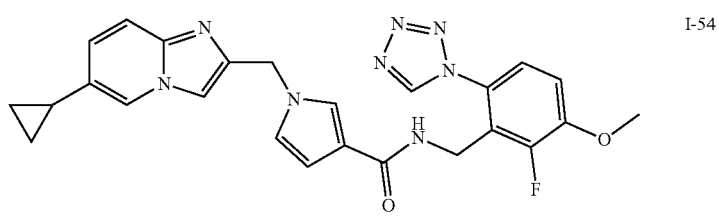 I-54
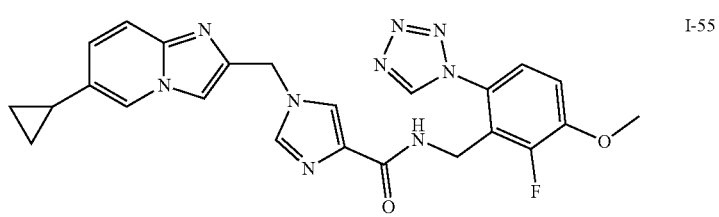 I-55
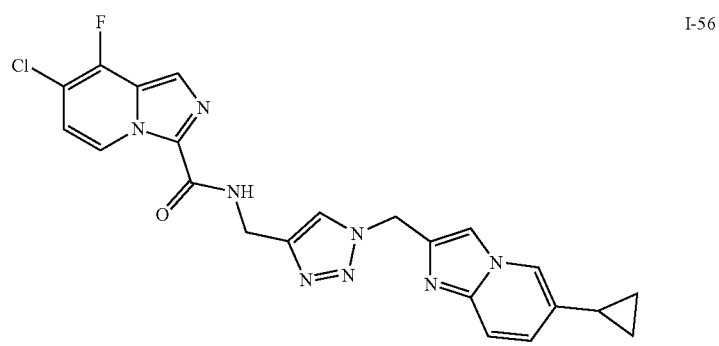 I-56

TABLE I-continued
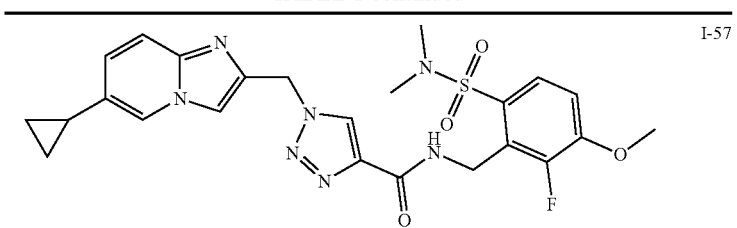 I-57
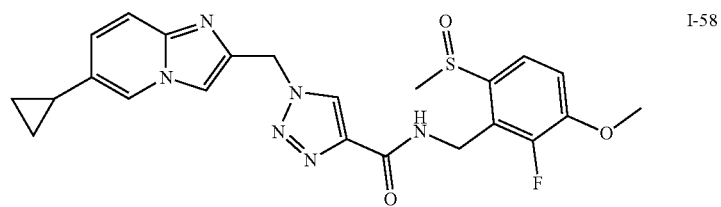 I-58
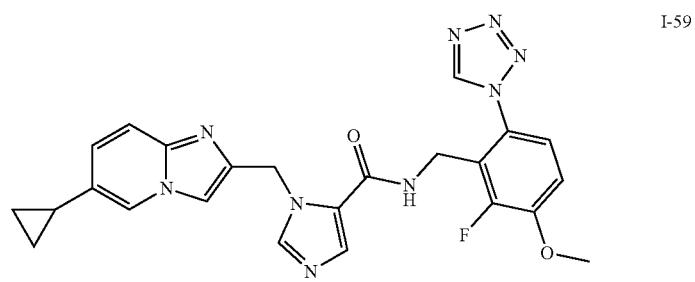 I-59
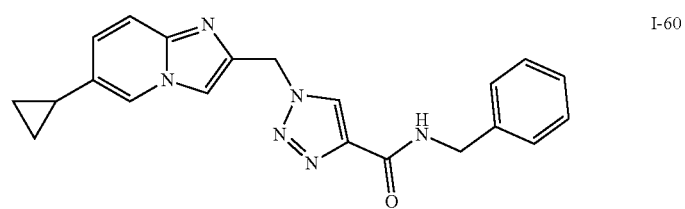 I-60
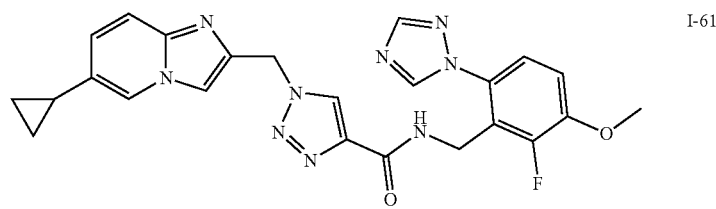 I-61
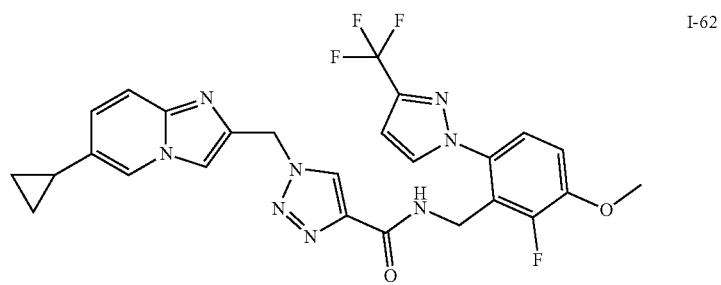 I-62
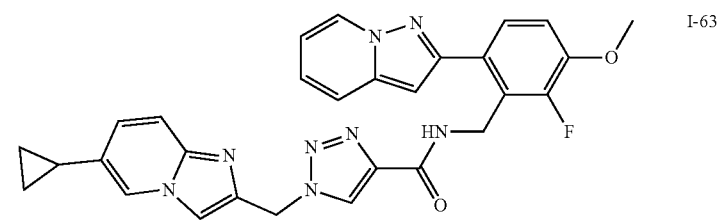 I-63

TABLE I-continued
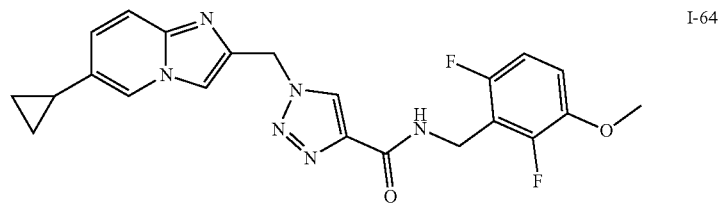
I-64
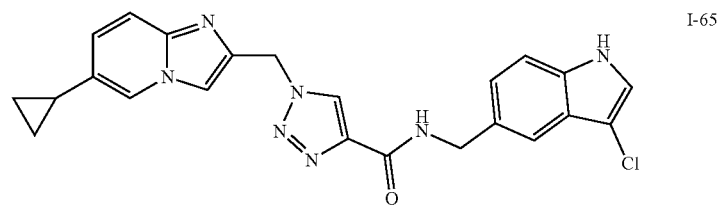
I-65
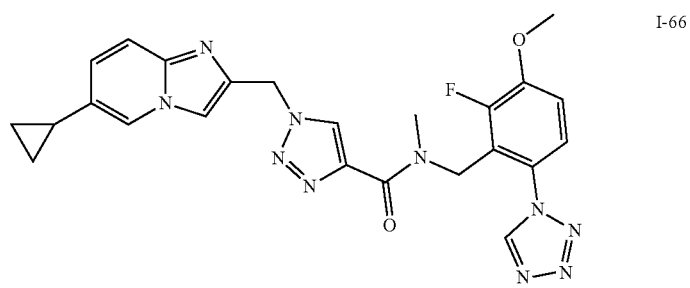
I-66
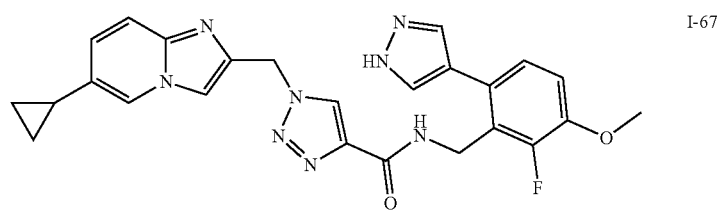
I-67
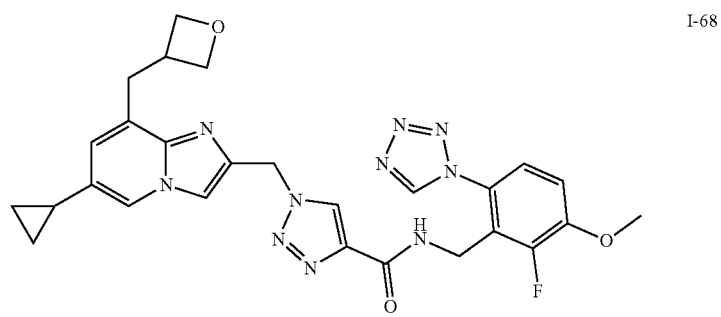
I-68
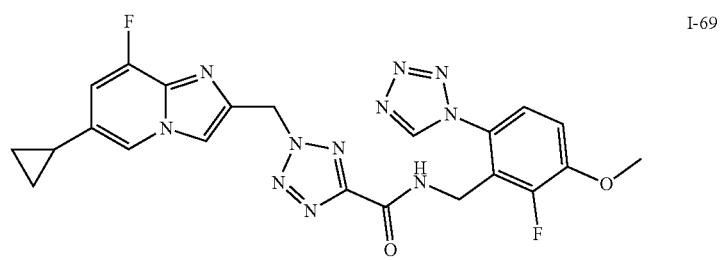
I-69

TABLE I-continued
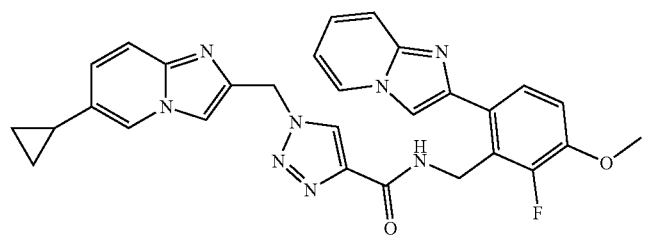 [SMILES: COc1ccc(-c2cn3ccccc3n2)c(CNC(=O)c2cn(Cc3cn4cc(C5CC5)ccc4n3)nn2)c1F]
I-70
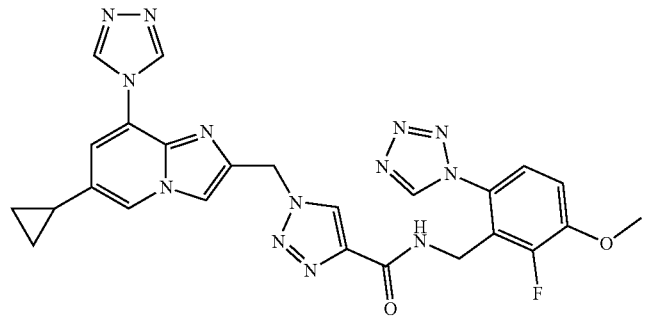 [SMILES: COc1ccc(-n2cnnn2)c(CNC(=O)c2cn(Cc3cn4cc(C5CC5)cc(-n5cnnc5)c4n3)nn2)c1F]
I-71
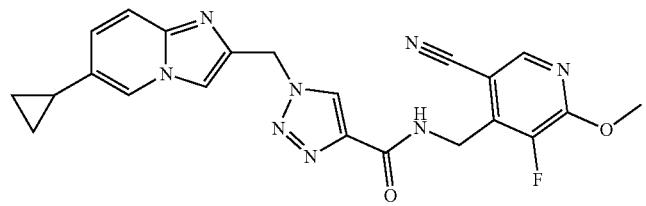 [SMILES: COc1ncc(C#N)c(CNC(=O)c2cn(Cc3cn4cc(C5CC5)ccc4n3)nn2)c1F]
I-72
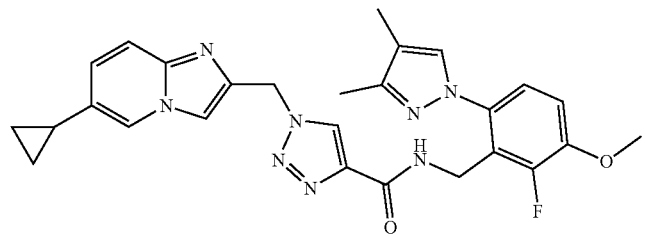 [SMILES: COc1ccc(-n2cc(C)c(C)n2)c(CNC(=O)c2cn(Cc3cn4cc(C5CC5)ccc4n3)nn2)c1F]
I-73
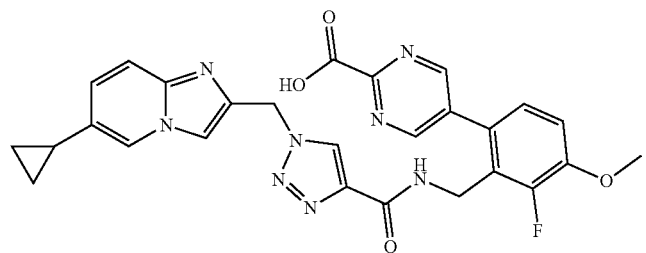 [SMILES: COc1ccc(-c2cnc(C(=O)O)nc2)c(CNC(=O)c2cn(Cc3cn4cc(C5CC5)ccc4n3)nn2)c1F]
I-74
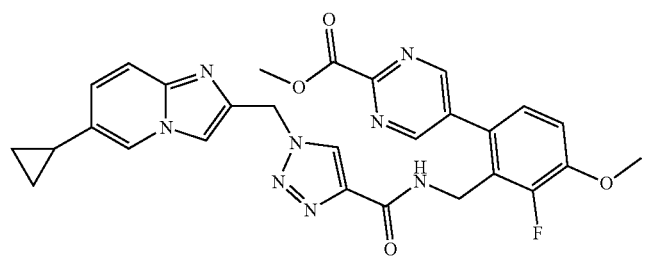 [SMILES: COC(=O)c1ncc(-c2ccc(OC)c(F)c2CNC(=O)c2cn(Cc3cn4cc(C5CC5)ccc4n3)nn2)cn1]
I-75

TABLE I-continued
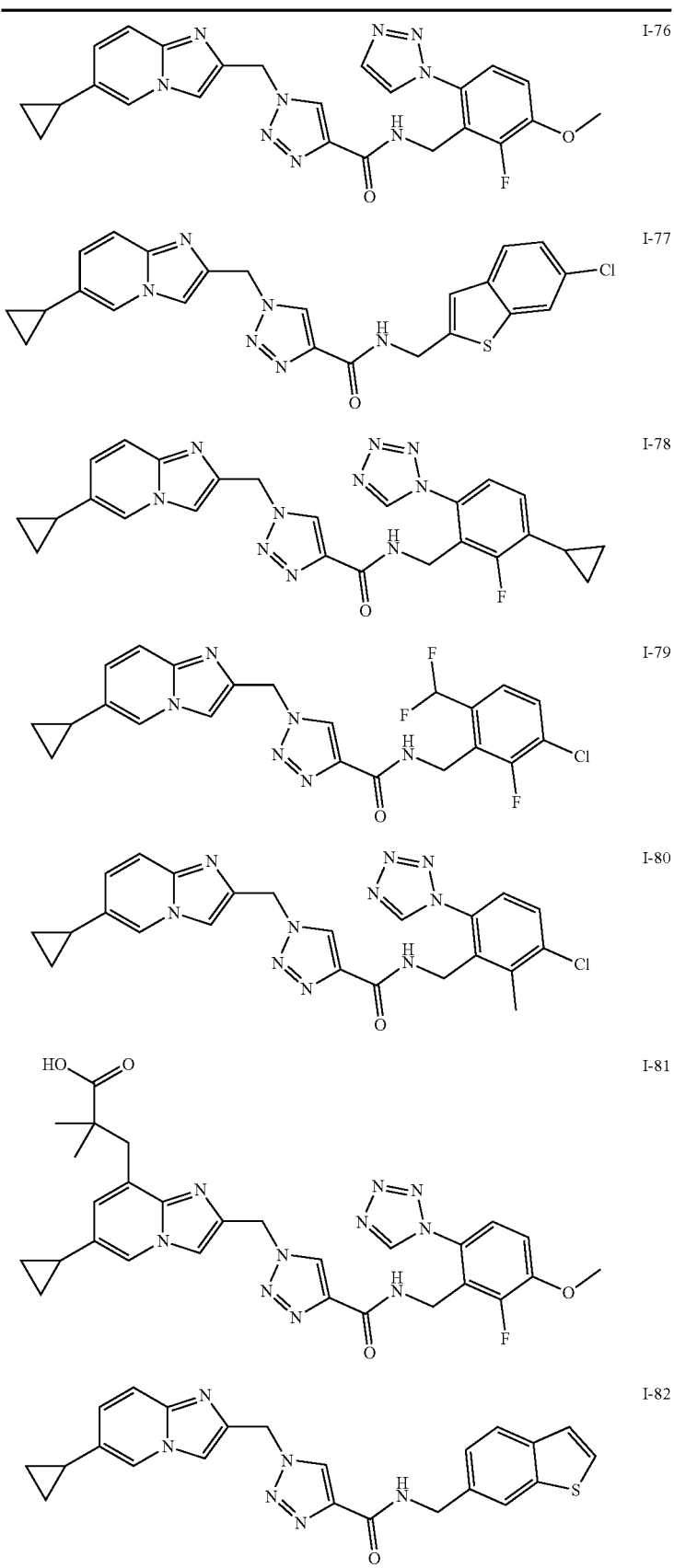

TABLE I-continued
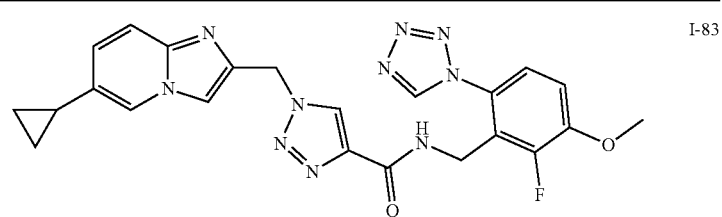
I-83
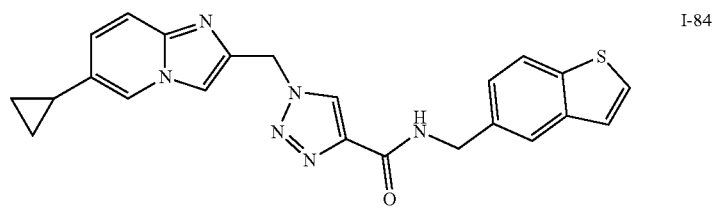
I-84
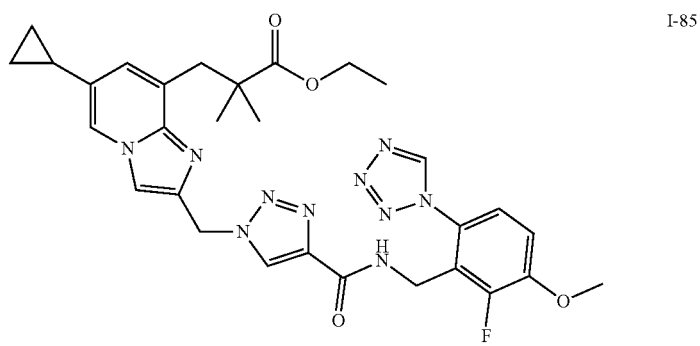
I-85
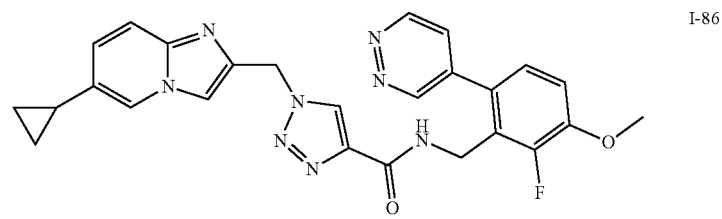
I-86
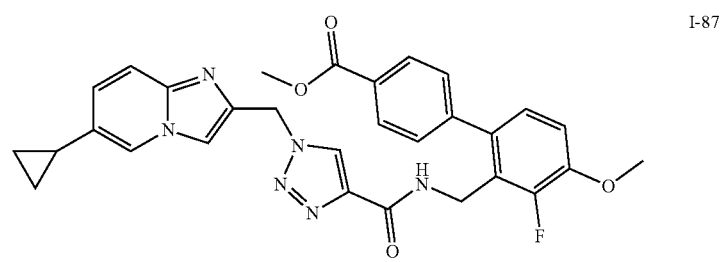
I-87
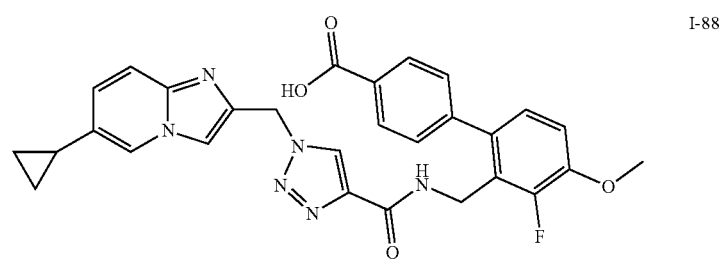
I-88

TABLE I-continued
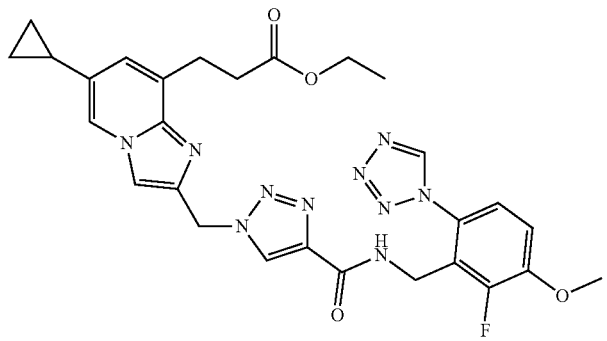 [SMILES: CCOC(=O)CCc1cc(C2CC2)cn2cc(Cn3cc(C(=O)NCc4c(-n5cnnn5)ccc(OC)c4F)nn3)nc12]
I-89
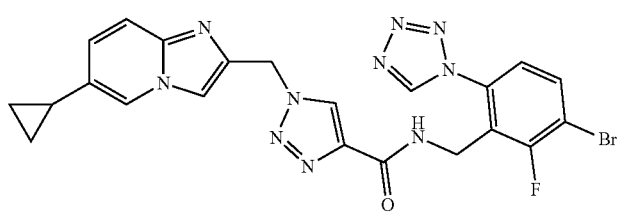 [SMILES: O=C(NCc1c(-n2cnnn2)ccc(Br)c1F)c1cn(Cc2cn3cc(C4CC4)ccc3n2)nn1]
I-90
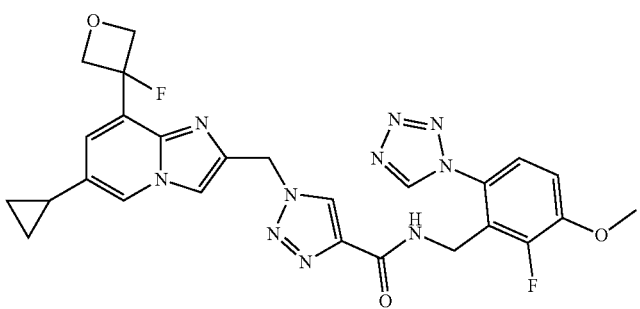 [SMILES: COc1ccc(-n2cnnn2)c(CNC(=O)c2cn(Cc3cn4cc(C5CC5)cc(C5(F)COC5)c4n3)nn2)c1F]
I-91
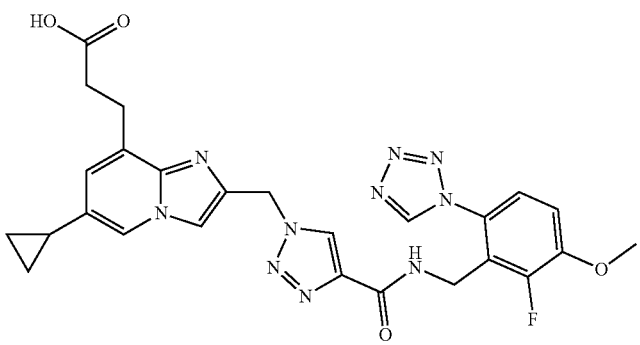 [SMILES: COc1ccc(-n2cnnn2)c(CNC(=O)c2cn(Cc3cn4cc(C5CC5)cc(CCC(=O)O)c4n3)nn2)c1F]
I-92
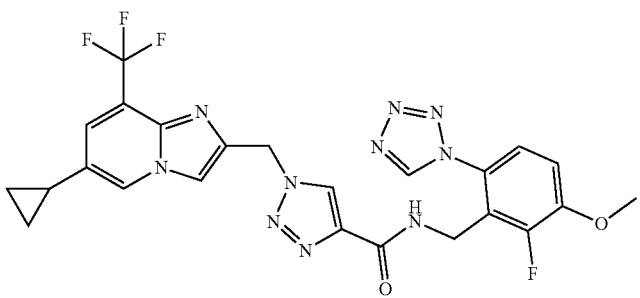 [SMILES: COc1ccc(-n2cnnn2)c(CNC(=O)c2cn(Cc3cn4cc(C5CC5)cc(C(F)(F)F)c4n3)nn2)c1F]
I-93

TABLE I-continued
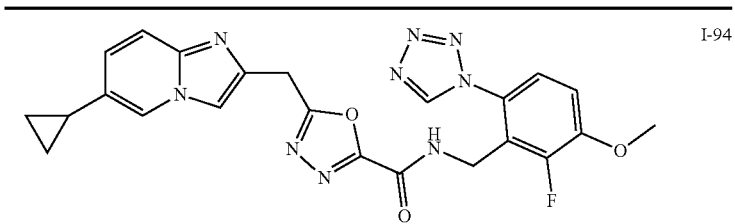
I-94
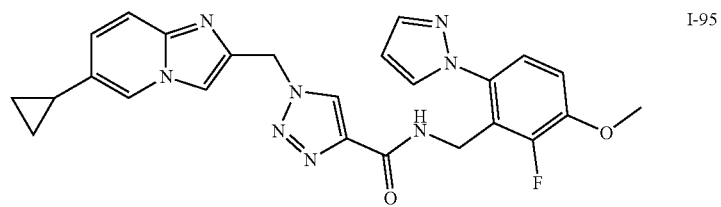
I-95
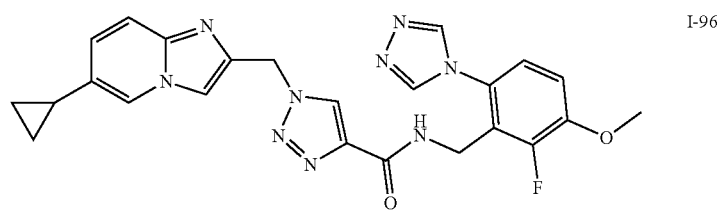
I-96
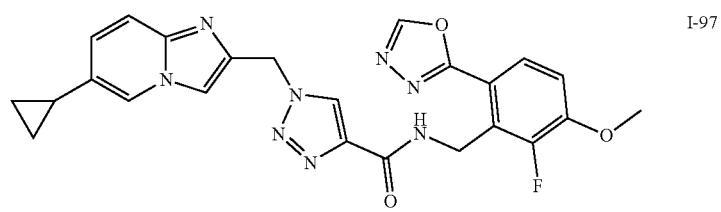
I-97
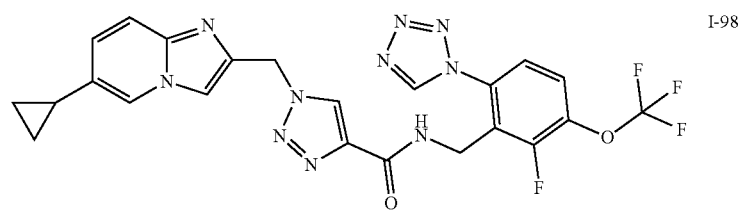
I-98
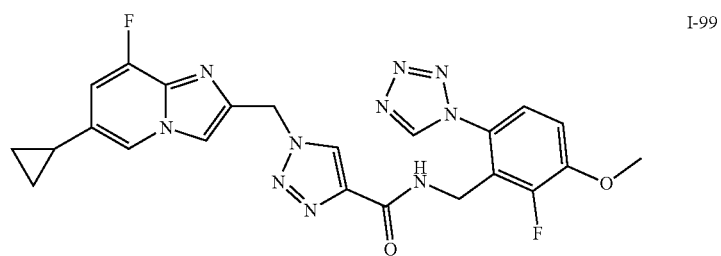
I-99
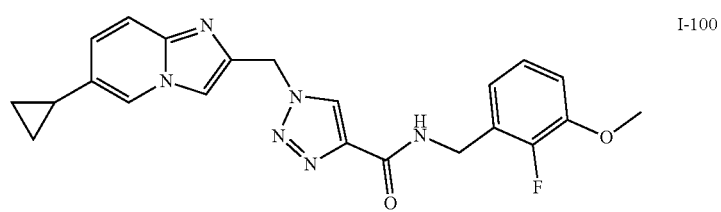
I-100

TABLE I-continued
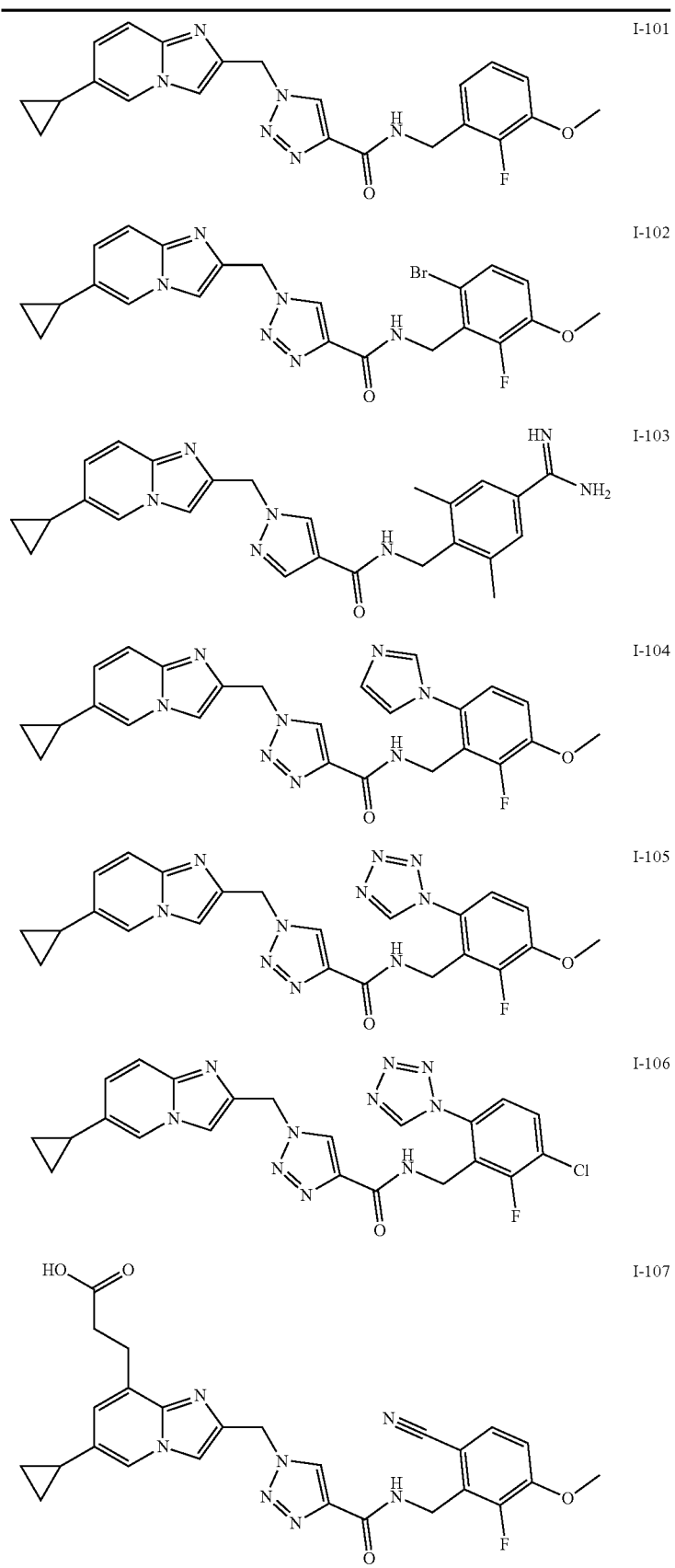

TABLE I-continued
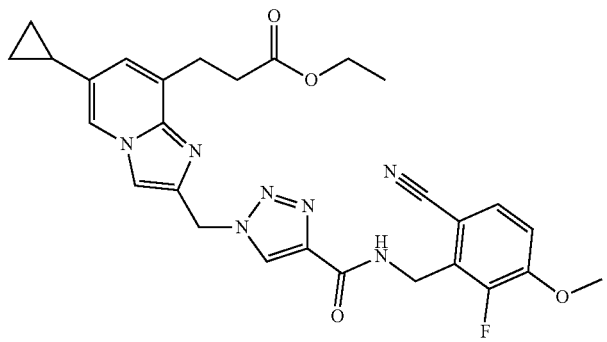 [SMILES: CCOC(=O)CCc1cc(C2CC2)cn2cc(Cn3cc(C(=O)NCc4c(C#N)ccc(OC)c4F)nn3)nc12]
I-108
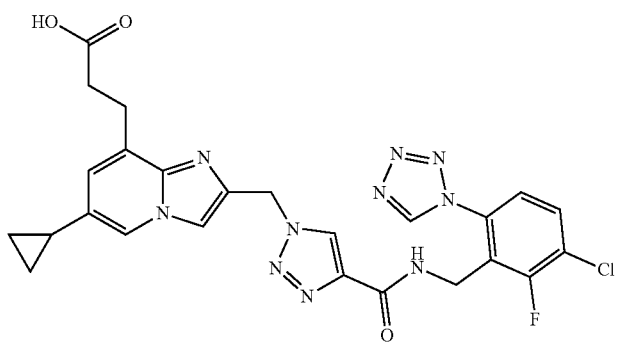 [SMILES: O=C(O)CCc1cc(C2CC2)cn2cc(Cn3cc(C(=O)NCc4c(-n5cnnn5)ccc(Cl)c4F)nn3)nc12]
I-109
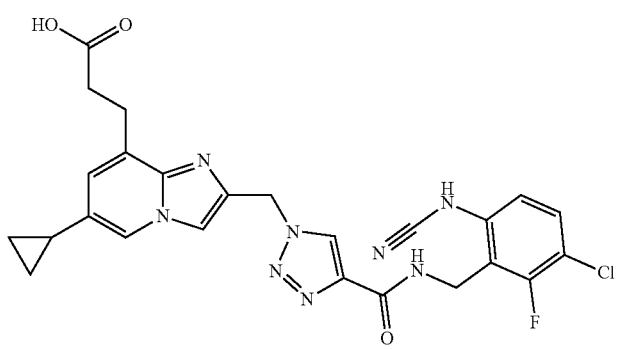 [SMILES: N#CNc1ccc(Cl)c(F)c1CNC(=O)c1cn(Cc2cn3cc(C4CC4)cc(CCC(=O)O)c3n2)nn1]
I-110
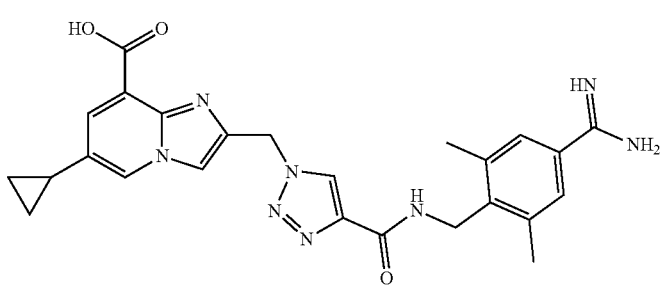 [SMILES: Cc1cc(C(=N)N)cc(C)c1CNC(=O)c1cn(Cc2cn3cc(C4CC4)cc(C(=O)O)c3n2)nn1]
I-111
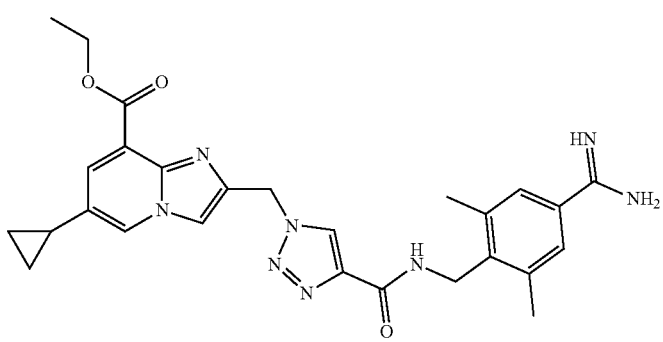 [SMILES: CCOC(=O)c1cc(C2CC2)cn2cc(Cn3cc(C(=O)NCc4c(C)cc(C(=N)N)cc4C)nn3)nc12]
I-112

TABLE I-continued
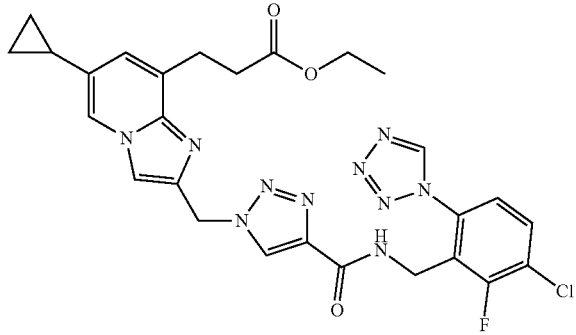 [SMILES: CCOC(=O)CCc1cc(C2CC2)cn2cc(Cn3cc(C(=O)NCc4c(-n5cnnn5)ccc(Cl)c4F)nn3)nc12]
I-113
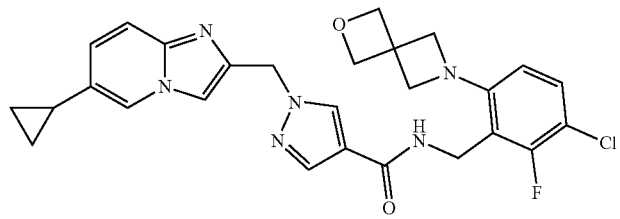 [SMILES: O=C(NCc1c(N2CC3(COC3)C2)ccc(Cl)c1F)c1cnn(Cc2cn3cc(C4CC4)ccc3n2)c1]
I-114
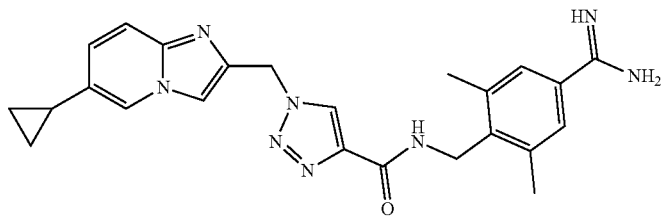 [SMILES: Cc1cc(C(=N)N)cc(C)c1CNC(=O)c1cn(Cc2cn3cc(C4CC4)ccc3n2)nn1]
I-115
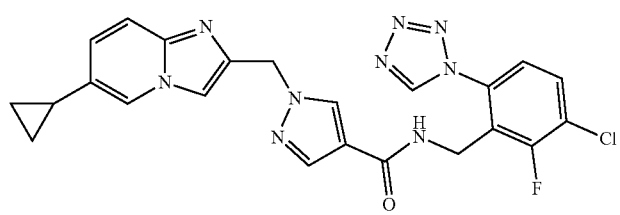 [SMILES: O=C(NCc1c(-n2cnnn2)ccc(Cl)c1F)c1cnn(Cc2cn3cc(C4CC4)ccc3n2)c1]
I-116
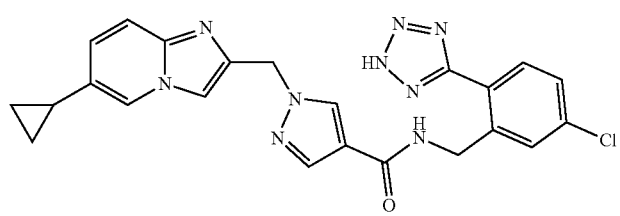 [SMILES: O=C(NCc1cc(Cl)ccc1-c1nn[nH]n1)c1cnn(Cc2cn3cc(C4CC4)ccc3n2)c1]
I-117
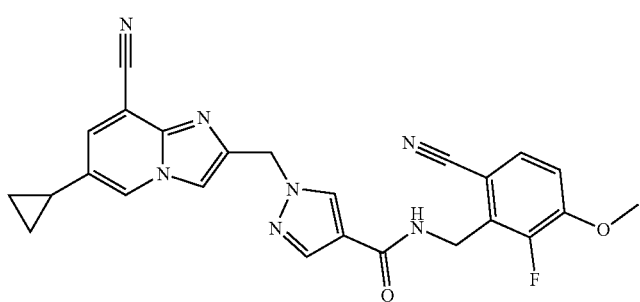 [SMILES: COc1ccc(C#N)c(CNC(=O)c2cnn(Cc3cn4cc(C5CC5)cc(C#N)c4n3)c2)c1F]
I-118

TABLE I-continued
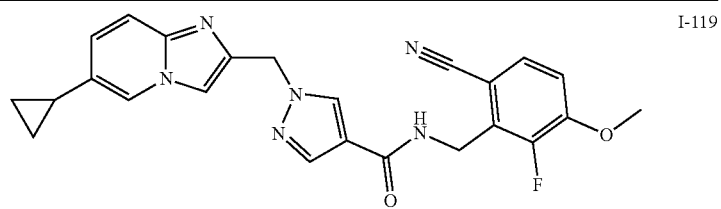
I-119
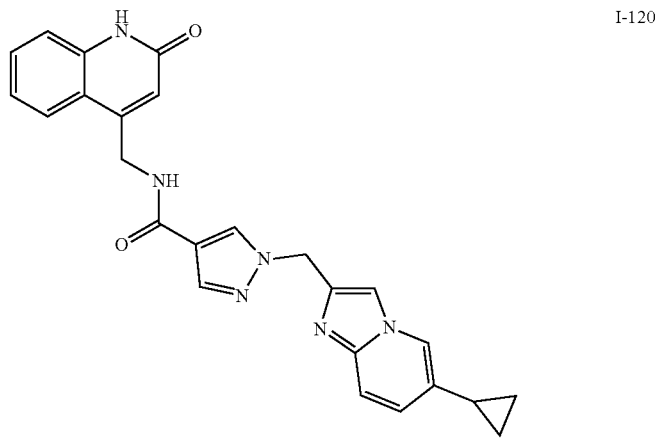
I-120
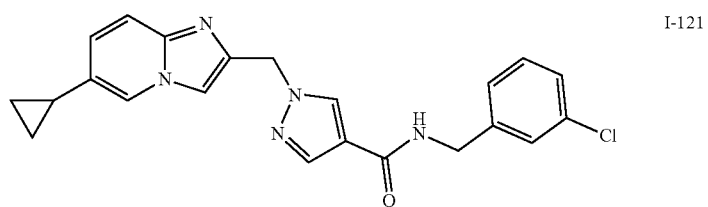
I-121
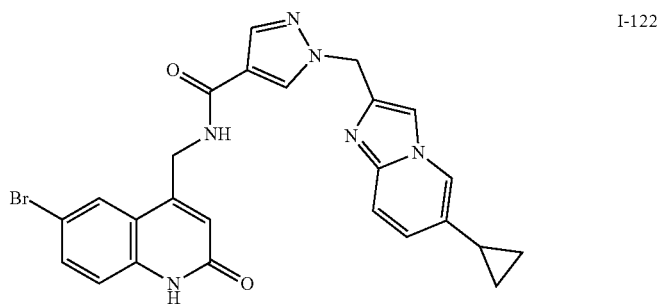
I-122
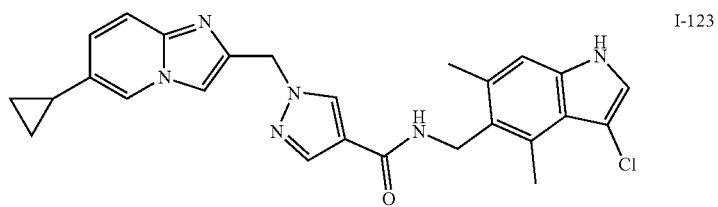
I-123
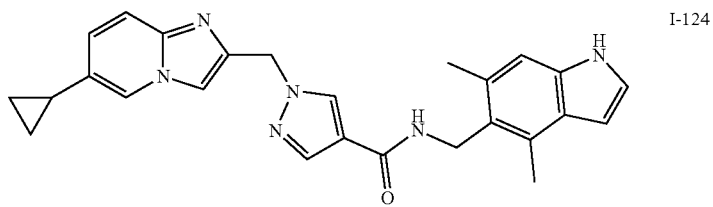
I-124

TABLE I-continued
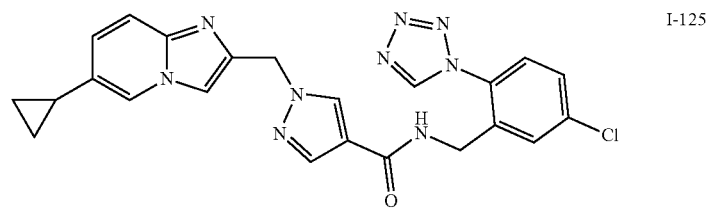 I-125
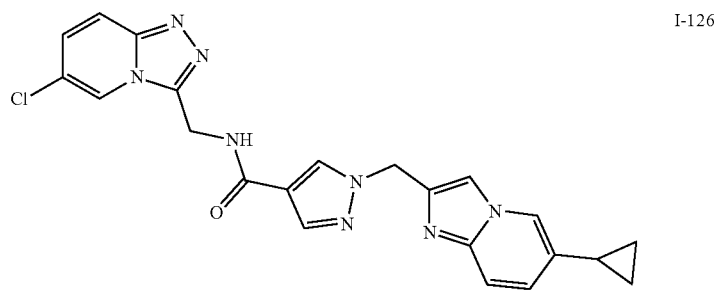 I-126
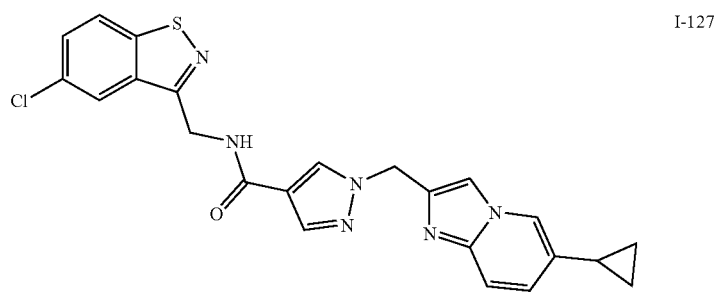 I-127
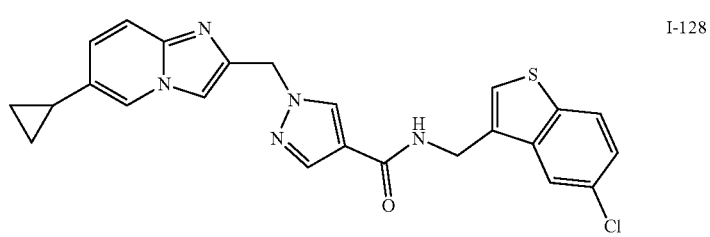 I-128
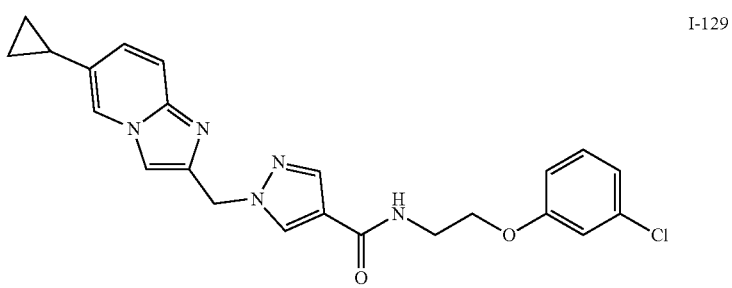 I-129
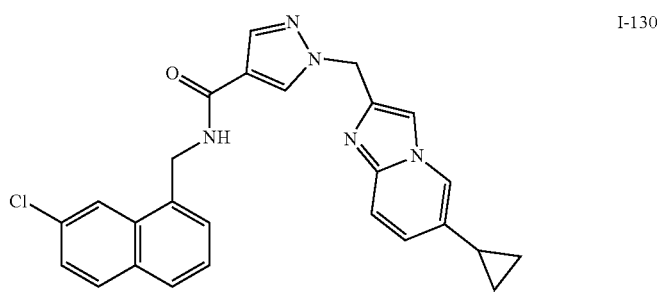 I-130

TABLE I-continued
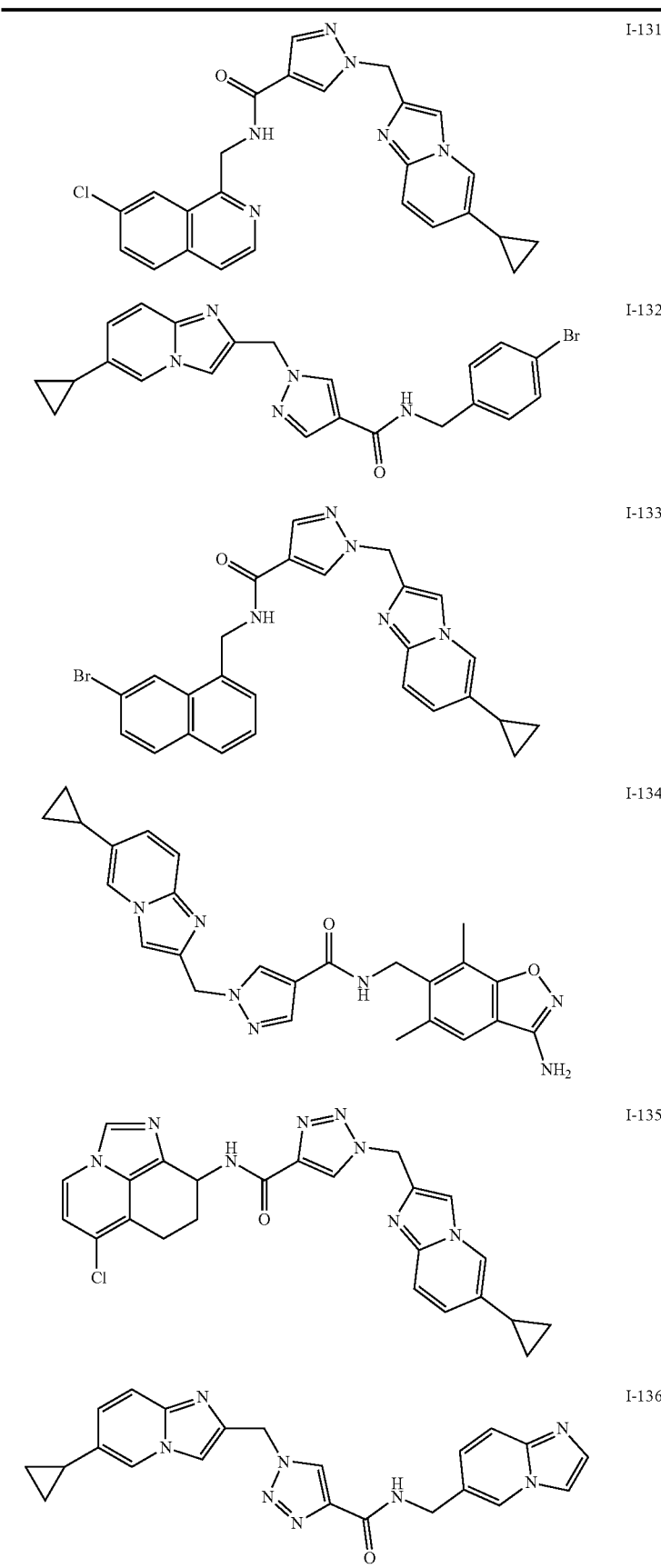

TABLE I-continued
I-137
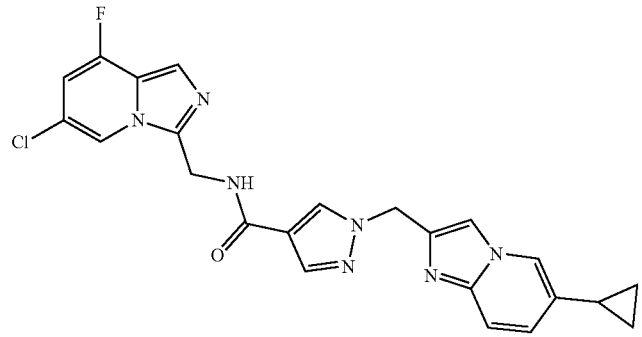 [SMILES: O=C(NCc1ncc2c(F)cc(Cl)cn12)c1cnn(Cc2cn3cc(C4CC4)ccc3n2)c1]
I-138
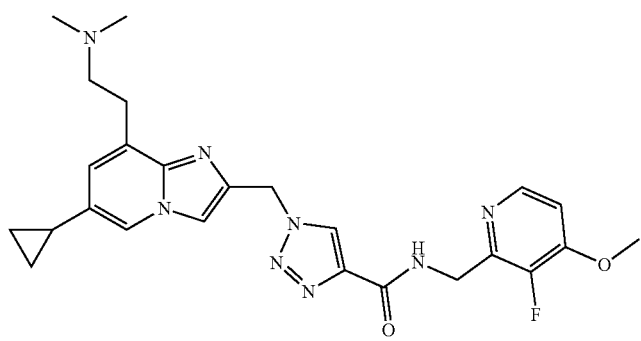 [SMILES: COc1ccnc(CNC(=O)c2cn(Cc3cn4cc(C5CC5)cc(CCN(C)C)c4n3)nn2)c1F]
I-139
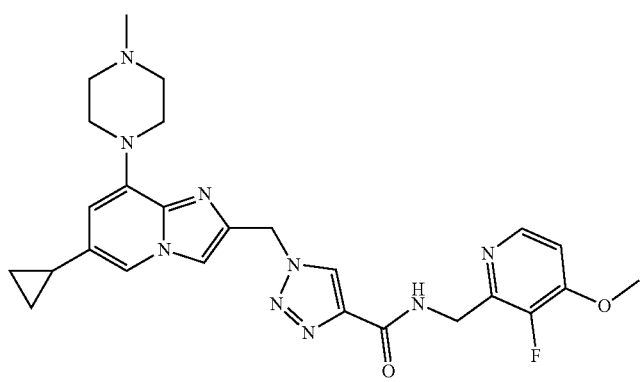 [SMILES: COc1ccnc(CNC(=O)c2cn(Cc3cn4cc(C5CC5)cc(N5CCN(C)CC5)c4n3)nn2)c1F]
I-140
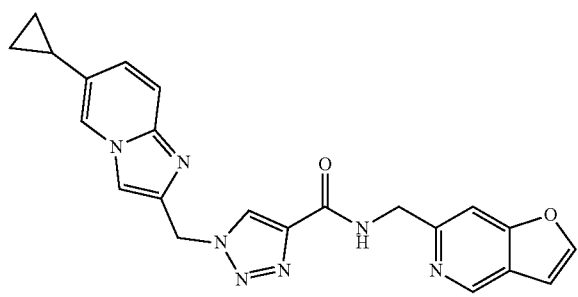 [SMILES: O=C(NCc1cc2occc2cn1)c1cn(Cc2cn3cc(C4CC4)ccc3n2)nn1]

TABLE I-continued
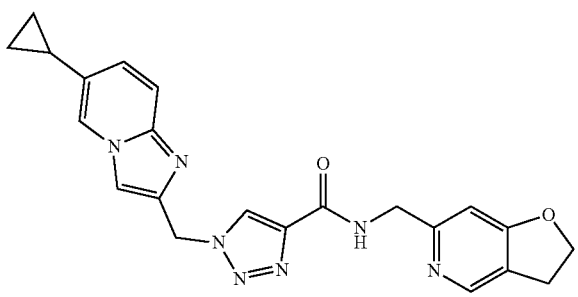 [SMILES: O=C(NCc1cc2c(cn1)CCO2)c1cn(Cc2cn3cc(C4CC4)ccc3n2)nn1]
I-141
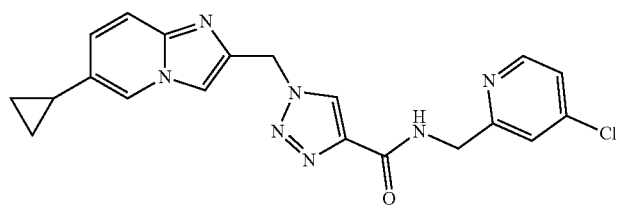 [SMILES: O=C(NCc1cc(Cl)ccn1)c1cn(Cc2cn3cc(C4CC4)ccc3n2)nn1]
I-142
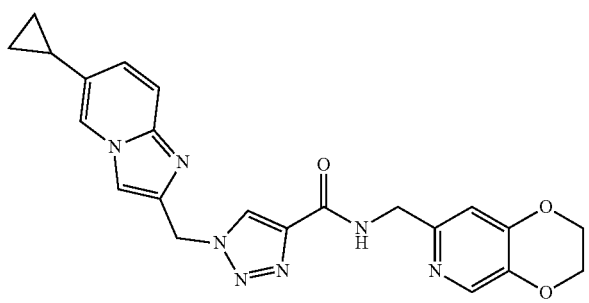 [SMILES: O=C(NCc1cc2c(cn1)OCCO2)c1cn(Cc2cn3cc(C4CC4)ccc3n2)nn1]
I-143
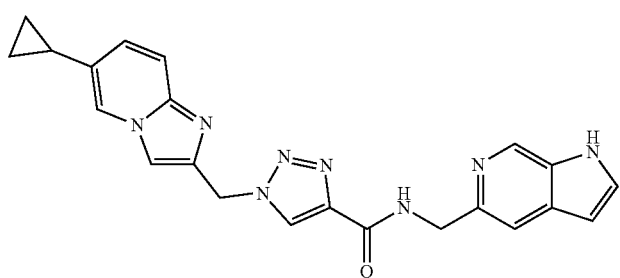 [SMILES: O=C(NCc1cc2cc[nH]c2cn1)c1cn(Cc2cn3cc(C4CC4)ccc3n2)nn1]
I-144
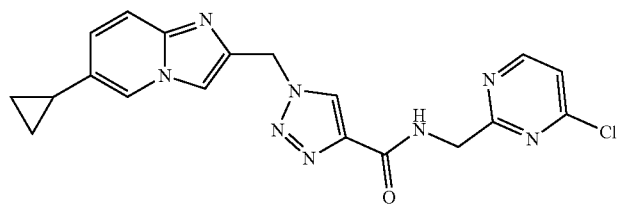 [SMILES: O=C(NCc1nccc(Cl)n1)c1cn(Cc2cn3cc(C4CC4)ccc3n2)nn1]
I-145
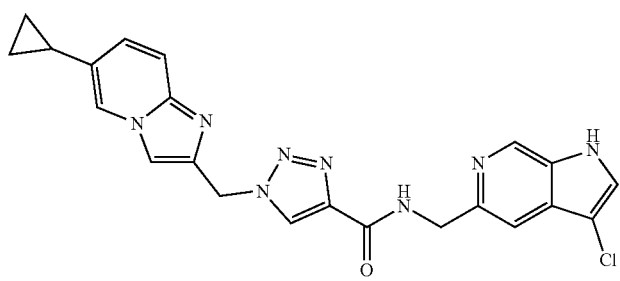 [SMILES: O=C(NCc1cc2c(Cl)c[nH]c2cn1)c1cn(Cc2cn3cc(C4CC4)ccc3n2)nn1]
I-146

TABLE I-continued
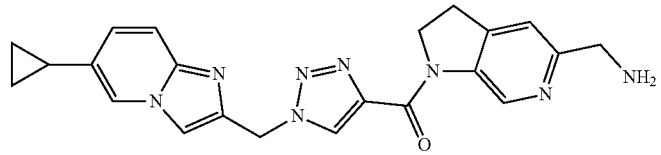 [SMILES: NCc1cc2c(cn1)N(C(=O)c1cn(Cc3cn4cc(C5CC5)ccc4n3)nn1)CC2]
I-147
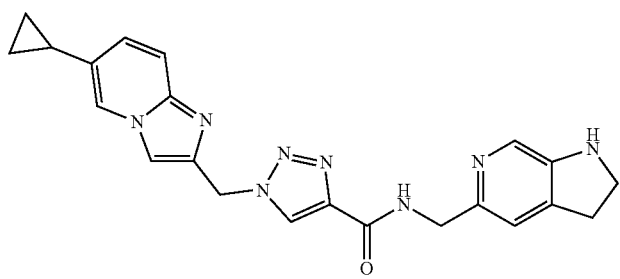 [SMILES: O=C(NCc1cc2c(cn1)NCC2)c1cn(Cc2cn3cc(C4CC4)ccc3n2)nn1]
I-148
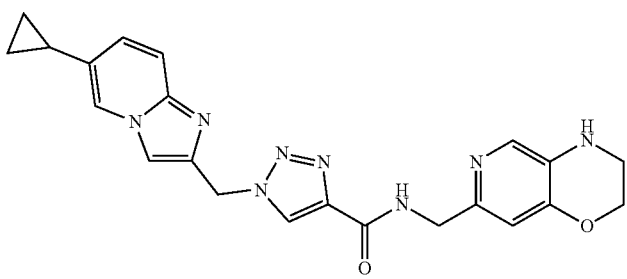 [SMILES: O=C(NCc1cc2c(cn1)NCCO2)c1cn(Cc2cn3cc(C4CC4)ccc3n2)nn1]
I-149
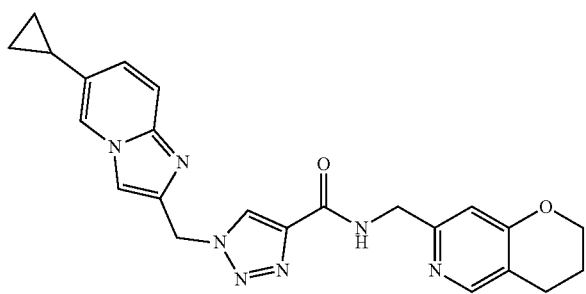 [SMILES: O=C(NCc1cc2c(cn1)CCCO2)c1cn(Cc2cn3cc(C4CC4)ccc3n2)nn1]
I-150
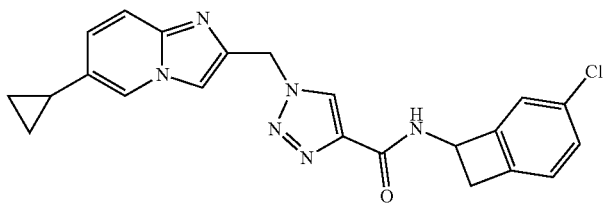 [SMILES: O=C(NC1Cc2ccc(Cl)cc21)c1cn(Cc2cn3cc(C4CC4)ccc3n2)nn1]
I-151

TABLE I-continued

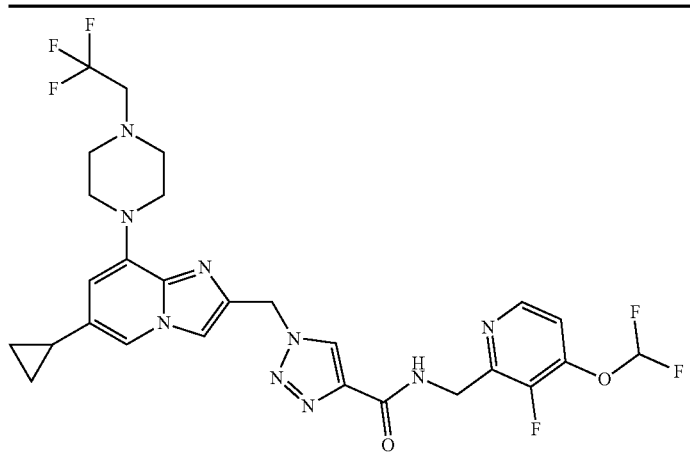

I-152

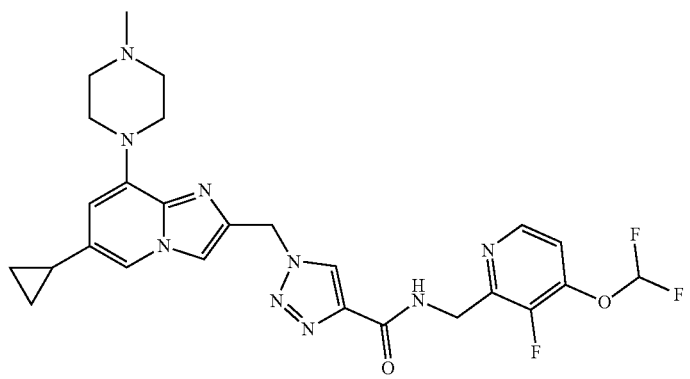 [SMILES: CN1CCN(c2cc(C3CC3)cn3cc(Cn4cc(C(=O)NCc5nccc(OC(F)F)c5F)nn4)nc23)CC1]

I-153

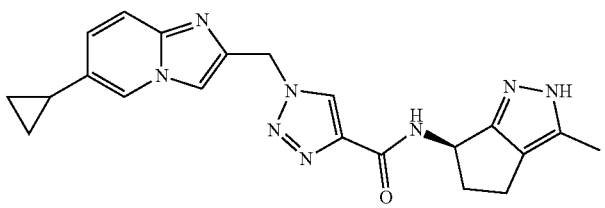 [SMILES: Cc1[nH]nc2c1CC[C@H]2NC(=O)c1cn(Cc2cn3cc(C4CC4)ccc3n2)nn1]

I-154

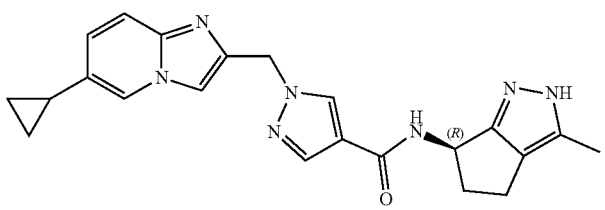

I-155 or a pharmaceutically acceptable salt thereof.

C₃. Pharmaceutical Compositions

In another aspect, the present invention provides pharmaceutical compositions comprising a compound of Formulae (I)-(IV) or a compound of Formulae (I)-(IV) in combination with a pharmaceutically acceptable excipient (e.g., carrier).

The pharmaceutical compositions include optical isomers, diastereomers, or pharmaceutically acceptable salts of the inhibitors disclosed herein. A compound of Formulae (I)-(IV) included in the pharmaceutical composition may be covalently attached to a carrier moiety, as described above. Alternatively, a compound of Formulae (I)-(IV) included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be co-administered to the subject. Co-administration is meant to include simultaneous or sequential administration of the compounds individually or in combination (more than one compound). The preparations can also be combined, when desired, with other active substances (e.g. to reduce metabolic degradation).

In some embodiments, a test agent as described herein can be incorporated into a pharmaceutical composition for administration by methods known to those skilled in the art and described herein for provided compounds.

D. Formulations

Compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, PA) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

E. Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat HAE, such compositions will contain an amount of active ingredient effective to achieve the desired result (e.g. inhibiting pKal and/or decreasing the amount of bradykinin in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to pKal inhibition); presence of other diseases or other health-related problems; kind of concurrent treatment; and complications from any disease or treatment regimen. Other therapeutic regimens or agents can be used in conjunction with the methods and compounds of the invention.

For any provided compound or test agent, the therapeutically effective amount can be initially determined from cell culture assays. Target concentrations will be those concentrations of active compound(s) that are capable of decreasing pKal enzymatic activity as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring pKal inhibition and adjusting the dosage upwards or downwards, as described above.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments, the dosage range is 0.001% to 10% (w/v). In some embodiments, the dosage range is 0.1% to 5% (w/v).

Dosage amounts and intervals can be adjusted individually to provide levels of the administered compound effective for the particular clinical indication being treated. This will provide a therapeutic regimen that is commensurate with the severity of the individual's disease state.

F. Methods of Treatment

The present disclosure provides compounds for use in medicine. The present disclosure further provides the use of any compounds described herein for inhibiting the activity of pKal, which would be beneficial to treatment of pKal-mediated diseases and conditions. Exemplary pKal-mediated disorders include edema, which refers to swelling in the whole body of a subject or a part thereof due to inflammation or injury when small blood vessels become leaky and releases fluid into nearby tissues. In some examples, the edema is HAE. In other examples, the edema occurs in eyes, e.g., diabetic macular edema (DME). The present disclosure provides methods of inhibiting the activity of pKal. In certain embodiments, the application provides a method of inhibiting the activity of pKal in vitro via contacting any of the compounds described herein with pKal molecules in a sample, such as a biological sample. In certain embodiments, the application provides a method of inhibiting the activity of pKal in vivo via delivering an effective amount of any of the compounds described herein to a subject in need of the treatment through a suitable route.

In certain embodiments, the methods comprise administering to a subject in need thereof (e.g., a subject such as a human patient with edema) any of the compounds described herein or a pharmaceutically acceptable salt thereof. In certain embodiments, the methods comprise administering a compound of Formulae (I)-(IV), or a pharmaceutically acceptable salt or composition thereof, to a subject in need thereof. In some embodiments, the method comprises administering a pharmaceutical composition comprising a compound of Formulae (I)-(IV), or a pharmaceutically acceptable salt to a subject in need thereof.

In certain embodiments, the subject to be treated by any of the methods described herein is a human patient having, suspected of having, or at risk for edema, for example, HAE or diabetic macular edema (DME). A subject having an edema can be identified by routine medical examination, e.g., laboratory tests. A subject suspected of having an edema might show one or more symptoms of the disease/disorder. A subject at risk for edema can be a subject having one or more of the risk factors associated with the disease, for example, deficiency in C1-INH as for HAE.

In certain embodiments, provided herein are methods of alleviating one or more symptoms of HAE in a human patient who is suffering from an HAE attack. Such a patient can be identified by routine medical procedures. An effective amount of one or more of the provided compounds can be given to the human patient via a suitable route, for example, those described herein. The compounds described herein may be used alone, or may be used in combination with other anti-HAE agents, for example, a C1 esterase inhibitor (e.g., Cinryze® or Berinert®), a pKal inhibitor (e.g., ecallantide or lanadelumab) or a bradykinin B2 receptor antagonist (e.g., Firazyr®).

In other embodiments, provided herein are methods or reducing the risk of HAE attack in a human HAE patient who is in quiescent stage. Such a patient can be identified based on various factors, including history of HAE attack. An effective amount of one or more of the compounds can be given to the human patient via a suitable route, for example, those described herein. The compounds described herein may be used alone, or may be used in combination with other anti-HAE agents, for example, a C1 esterase inhibitor (e.g., Cinryze® or Berinert®), a pKal inhibitor (e.g., ecallantide or lanadelumab) or a bradykinin B2 receptor antagonist (e.g., Firazyr®).

In yet other embodiments, provided herein are prophylactic treatment of HAE in human patients having risk to HAE attacks with one or more of the compounds described herein. Patients suitable for such prophylactic treatment may be human subjects having history of HAE attacks (e.g., human subjects experiencing more than 2 attacks per month). Alternatively, patients suitable for the prophylactic treatment may be human subjects having no HAE attack history but bearing one or more risk factors for HAE (e.g., family history, genetic defects in C1-INH gene, etc.) Such

89 prophylactic treatment may involve the compounds described herein as the sole active agent, or involve additional anti-HAE agents, such as those described herein.

In certain embodiments, provided herein are methods for preventing or reducing edema in an eye of a subject (e.g., a human patient). In some examples, the human patient is a diabetic having, suspected of having, or at risk for diabetic macular edema (DME). DME is the proliferative form of diabetic retinopathy characterized by swelling of the retinal layers, neovascularization, vascular leak, and retinal thickening in diabetes mellitus due to leaking of fluid from blood vessels within the macula. To practice this method, an effective amount of one or more of the compounds described herein, or pharmaceutically acceptable salts thereof, may be delivered into the eye of the subject where treatment is needed. For example, the compound may be delivered by intraocular injection, or intravitreal injection. A subject may be treated with the compound as described herein, either as the sole active agent, or in combination with another treatment for DME. Non-limiting examples of treatment for DME include laser photocoagulation, steroids, VEGF pathway targeting agents (e.g., Lucentis® (ranibizumab) or Eylea® (aflibercept)), and/or anti-PDGF agents.

In certain embodiments, the methods disclosed herein comprise administering to the subject an effective amount of a compound of Formulae (I)-(IV), or a pharmaceutically acceptable salt or composition thereof. In some embodiments, the effective amount is a therapeutically effective amount. In some embodiments, the effective amount is a prophylactically effective amount.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Certain methods described herein may comprise administering one or more additional pharmaceutical agent(s) in combination with the compounds described herein. The additional pharmaceutical agent(s) may be administered at the same time as the compound of Formulae (I)-(IV), or at different times than the compound of Formulae (I)-(IV). For example, the compound of Formulae (I)-(IV) and any additional pharmaceutical agent(s) may be on the same dosing schedule or different dosing schedules. All or some doses of the compound of Formulae (I)-(IV) may be administered before all or some doses of an additional pharmaceutical agent, after all or some does an additional pharmaceutical agent, within a dosing schedule of an additional pharmaceutical agent, or a combination thereof. The timing of administration of the compound of Formulae (I)-(IV) and additional pharmaceutical agents may be different for different additional pharmaceutical agents.

In certain embodiments, the additional pharmaceutical agent comprises an agent useful in the treatment of an edema, such as HAE or DME. Examples of such agents are provided herein.

90

V. EXEMPLARY EMBODIMENTS

The present disclosure contemplates, among other things, the following numbered embodiments:

1. A compound of Formula (I):

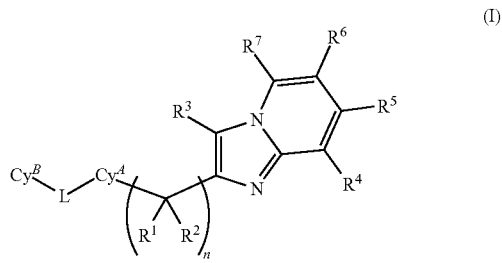

or a pharmaceutically acceptable salt thereof,
wherein:
$Cy^A$ is selected from a 5-membered monocyclic heteroarylene having 1-4 heteroatoms independently selected from oxygen, nitrogen, and sulfur, and a 7- to 10-membered partially unsaturated bicyclic heterocyclylene having 1-4 heteroatoms selected from oxygen, nitrogen, and sulfur, wherein $Cy^A$ is substituted with 0-4 $R^A$ groups;
each $R^A$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
$Cy^B$ is selected from phenyl, a 5- to 6-membered monocyclic heteroaryl having 1-4 heteroatoms selected from oxygen, nitrogen, and sulfur, a 7- to 10-membered partially unsaturated bicyclic carbocyclyl, a 10-membered bicyclic aryl, a 7- to 10-membered bicyclic heterocyclyl having 1-4 heteroatoms selected from oxygen, nitrogen, and sulfur, a 7- to 10-membered bicyclic heteroaryl having 1-4 heteroatoms selected from oxygen, nitrogen, and sulfur, and a 12-membered tricyclic heterocyclyl having 1-4 heteroatoms selected from oxygen, nitrogen, and sulfur, wherein $Cy^B$ is substituted with 0-5 $R^B$ groups;
each $R^B$ is independently selected from halogen, —CN, oxo, —C(R)=N(R), —C(O)R, —C(O)$_2$R, —C(O)N(R)$_2$, —C(=N(R))N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 7- to 10-membered bicyclic heteroaryl having 1-4 heteroatoms selected from oxygen, nitrogen, and sulfur, and 8- to 10-membered spirocyclic heterocyclyl having 1-3 heteroatoms selected from oxygen, nitrogen, or sulfur;

L is an optionally substituted $C_{1-6}$ hydrocarbon chain, wherein 1 to 3 methylene units are independently replaced with -Cy-, —O—, —NR—, —C(O)—, —C(O)NR—, —NRC(O)—, —S(O)$_2$NR—, —NRS(O)$_2$—, or —S(O)$_2$—;

-Cy- is 3- to 7-membered saturated or partially unsaturated monocyclic carbocyclylene, 3- to 7-membered saturated or partially unsaturated monocyclic heterocyclylene having 1-2 heteroatoms selected from oxygen, nitrogen, or sulfur, or 5- to 6-membered heteroarylene having 1-4 heteroatoms selected from oxygen, nitrogen, or sulfur;

$R^1$ and $R^2$ are independently selected from hydrogen, halogen, —OR, —SR, —N(R)$_2$, and optionally substituted $C_{1-6}$ aliphatic; wherein $R^1$ may be taken together with a monocyclic $Cy^4$ to form an optionally substituted fused 7- to 10-membered saturated or partially unsaturated bicyclic heterocyclylene having 1-4 heteroatoms selected from oxygen, nitrogen, or sulfur;

$R^3$, $R^4$, $R^5$, and $R^7$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

$R^6$ is selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

each R is independently hydrogen or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur; and n is 0 or 1;

with the proviso that:

(a) at least one of $R^3$, $R^4$, $R^5$, $R^6$ and $R^7$ is $C_{1-6}$ aliphatic or halogen; and (b) the compound is other than N-[1-[(6-fluoroimidazo[1,2-a]pyridin-2-yl)methyl]-5-methyl-1H-pyrazol-3-yl]-3-pyridinecarboxamide, N-[1-[(6-chloroimidazo[1,2-a]pyridin-2-yl)methyl]-5-methyl-1H-pyrazol-3-yl]-3-pyridinecarboxamide, 3-chloro-4-[[5-[8-chloro-6-(trifluoromethyl)imidazo[1,2-a]pyridin-2-yl]-1,3,4-oxadiazol-2-yl]amino]-benzenepropanoic acid, 2-[(6,8-dichloroimidazo[1,2-a]pyridin-2-yl)methyl]-4-methyl-N-phenyl-5-thiazolecarboxamide, and N-(furan-2-ylmethyl)-N,3,5-trimethyl-1-((6-methylimidazo[1,2-a]pyridin-2-yl)methyl)-1H-pyrazole-4-sulfonamide.

2. The compound of embodiment 1, wherein $Cy^A$ is selected from a 5-membered heteroarylene having 1-4 heteroatoms independently selected from oxygen and nitrogen and 8-membered partially unsaturated bicyclic heterocyclylene having 2-3 heteroatoms selected from oxygen and nitrogen, wherein $Cy^A$ is substituted with 0-3 $R^A$ groups.

3. The compound of embodiment 1, wherein $Cy^A$ is a 5-membered heteroarylene having 1 4 heteroatoms independently selected from oxygen and nitrogen, wherein $Cy^A$ is substituted with 0-3 $R^A$ groups.

4. The compound of embodiment 1, wherein $Cy^A$ is an 8-membered partially unsaturated bicyclic heterocyclylene having 2-3 heteroatoms selected from oxygen and nitrogen, wherein $Cy^A$ is substituted with 0-3 $R^A$ groups. 5. The compound of embodiment 1, wherein $Cy^A$ is selected from the group consisting of:

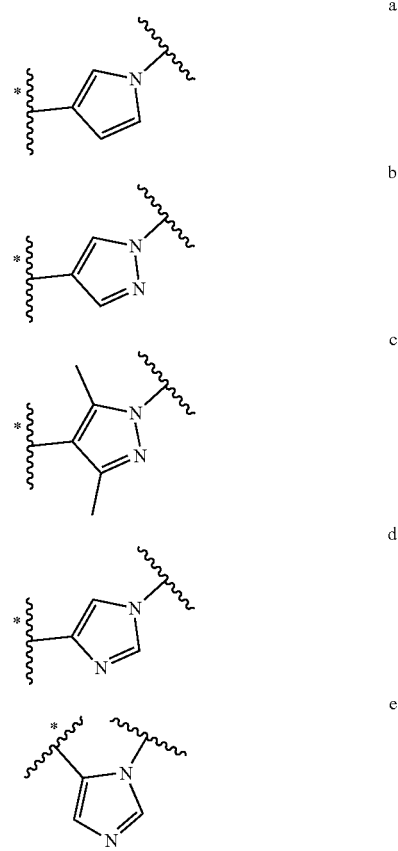

93
-continued

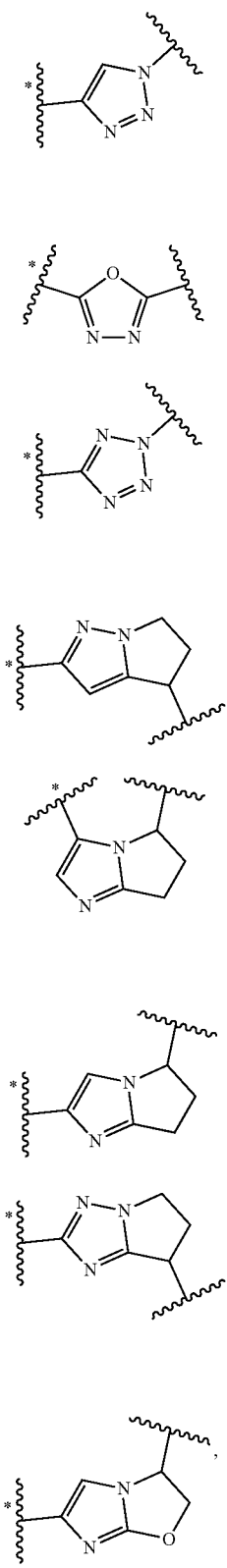

wherein * represents the point of attachment to L.

6. The compound of any one of the preceding embodiments, wherein R³, R⁵, and R⁷ are hydrogen.

7. The compound of embodiment 1, wherein the compound is of Formula (III):

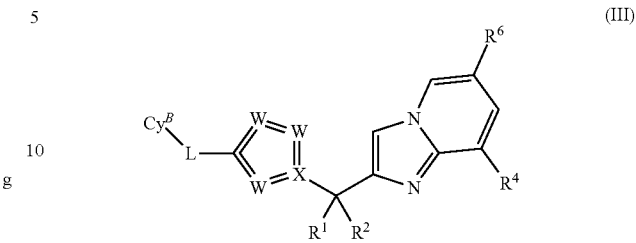

or a pharmaceutically acceptable salt thereof,
wherein:
- - - - - represents a single or double bond;
X is selected from C and N;
each W is independently selected from $CR^4$, CH, N, and O;
$R^4$ is selected from hydrogen, halogen, —CN, —C(O)OR, or an optionally substituted group selected from $C_{1-6}$ aliphatic, 5- to 6-membered heteroaryl having 1-4 heteroatoms selected from oxygen, nitrogen, or sulfur, and 3- to 7-membered saturated or partially unsaturated monocyclic heterocyclyl having 1-2 heteroatoms selected from oxygen, nitrogen, or sulfur;
$R^6$ is selected from $C_{1-6}$ aliphatic or halogen; and
each R is independently hydrogen or an optionally substituted group selected from $C_{1-6}$ aliphatic;
or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur;
with the proviso that the compound is other than N-(furan-2-ylmethyl)-N,3,5-trimethyl-1-((6-methylimidazo[1,2-a]pyridin-2-yl)methyl)-1H-pyrazole-4-sulfonamide.

8. The compound of embodiment 1, wherein $R^1$ is taken together with a monocyclic $Cy^A$ to form an optionally substituted fused 7- to 10-membered saturated or partially unsaturated bicyclic heterocyclylene having 1-4 heteroatoms selected from oxygen, nitrogen, or sulfur.

9. The compound of embodiment 1 or 8, wherein the compound is of Formula (IV):

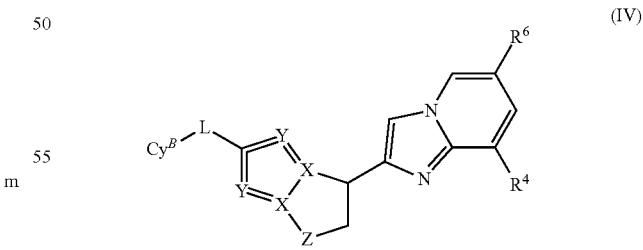

wherein - - - - - represents a single or double bond;
each X is independently N or C;
each Y is independently $CR^4$, CH, or N;
Z is $CH_2$ or O;
$R^4$ is selected from an optionally substituted group selected from $C_{1-6}$ aliphatic, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

$R^4$ is selected from hydrogen, halogen, —CN, —C(O)OR, or an optionally substituted group selected from $C_{1-6}$ aliphatic, 5- to 6-membered heteroaryl having 1-4 heteroatoms selected from oxygen, nitrogen, or sulfur, and 3- to 7-membered saturated or partially unsaturated monocyclic heterocyclyl having 1-2 heteroatoms selected from oxygen, nitrogen, or sulfur; and $R^6$ is selected from $C_{1-6}$ aliphatic or halogen.

10. The compound of embodiment 1 or 7, wherein the compound is of Formula (III-a), Formula (III-b), Formula (III-c), Formula (III-d), Formula (III-e), Formula (III-f), or Formula (III-g):

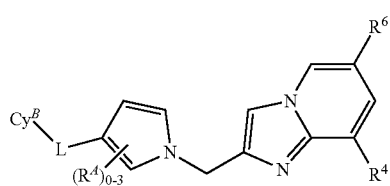
(III-a)

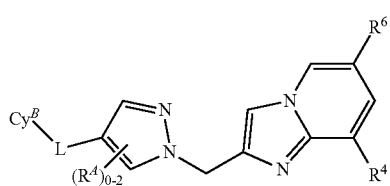
(III-b)

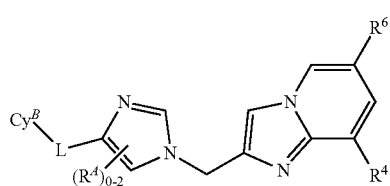
(III-c)

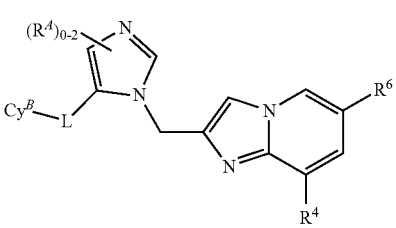
(III-d)

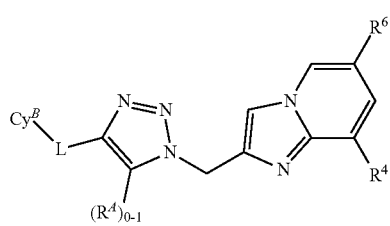
(III-e)

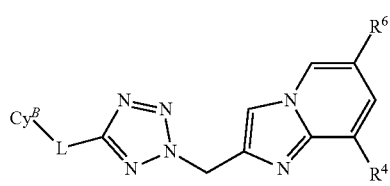
(III-f)

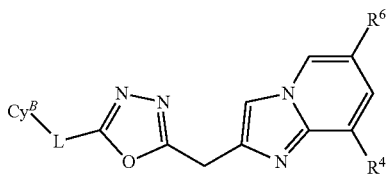
(III-g)

or a pharmaceutically acceptable salt thereof, wherein:

$R^A$ is selected from an optionally substituted group selected from $C_{1-6}$ aliphatic, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

$R^4$ is selected from hydrogen, halogen, —CN, —C(O)OR, or an optionally substituted group selected from $C_{1-6}$ aliphatic, 5- to 6-membered heteroaryl having 1-4 heteroatoms selected from oxygen, nitrogen, or sulfur, and 3- to 7-membered saturated or partially unsaturated monocyclic heterocyclyl having 1-2 heteroatoms selected from oxygen, nitrogen, or sulfur; and $R^6$ is selected from $C_{1-6}$ aliphatic or halogen;

with the proviso that the compound is other than N-(furan-2-ylmethyl)-N,3,5-trimethyl-1-((6-methylimidazo[1,2-a]pyridin-2-yl)methyl)-1H-pyrazole-4-sulfonamide.

11. The compound of embodiment 1 or 9, wherein the compound is of Formula (IV-a), Formula (IV-b), Formula (IV-c), or Formula (IV-d):

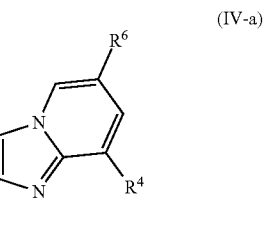
(IV-a)

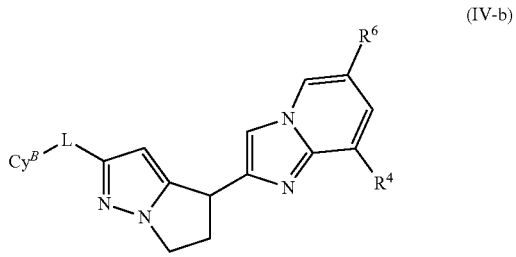
(IV-b)

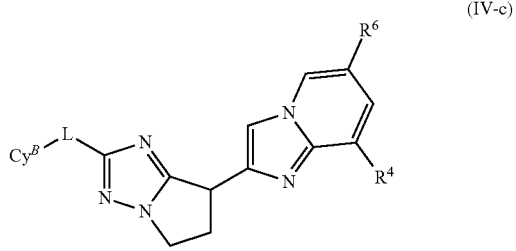
(IV-c)

-continued (IV-d)

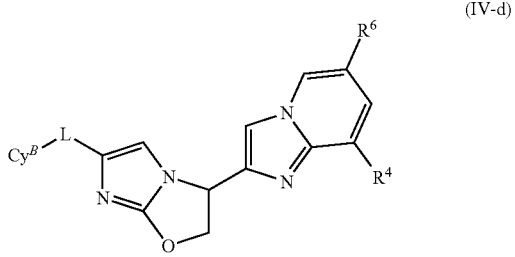

or a pharmaceutically acceptable salt thereof,
wherein:
R⁴ is selected from hydrogen, halogen, —CN, —C(O)OR, or an optionally substituted group selected from $C_{1-6}$ aliphatic, 5- to 6-membered heteroaryl having 1-4 heteroatoms selected from oxygen, nitrogen, or sulfur, and 3- to 7-membered saturated or partially unsaturated monocyclic heterocyclyl having 1-2 heteroatoms selected from oxygen, nitrogen, or sulfur; and
R⁶ is selected from $C_{1-6}$ aliphatic or halogen.

12. The compound of any one of the preceding embodiments, wherein L is selected from —$(C(R)_2)_m$NR$(C(R)_2)_m$-#, —$(C(R)_2)_m$NRC(O)$(C(R)_2)_m$-#, —$(C(R)_2)_m$C(O)NR$(C(R)_2)_m$-#, —NRC(O)NR-#, —$(C(R)_2)_m$OC(O)NR$(C(R)_2)_m$-#, -O$(C(R)_2)_m$NRC(O)-#, -O$(C(R)_2)_m$NRS(O)_2$— #, —$(C(R)_2)_m$S(O)_2$NR$(C(R)_2)_m$-#, and —$(C(R)_2)_m$NRS(O)_2$(C(R)_2)_m$-#, wherein each R is independently hydrogen or optionally substituted $C_{1-6}$ aliphatic, each m is independently 0, 1 or 2, and # represents the point of attachment to Cy$^A$.

13. The compound of any one of the preceding embodiments, wherein L is selected from —NR-#, —$C(R)_2$NR-#, —$C(R)_2$NRC(R)_2$-#, —NRC(O)-#, —$C(R)_2$NRC(O)-#, —$C(R)_2$C(R)_2$NRC(O)-#, —C(O)NRC(R)_2$-#, —$C(R)_2$C(O)NR-#, —$C(R)_2$C(O)NRC(R)_2$-#, —NRC(O)NR-#, —$C(R)_2$OC(O)NR-#, —OC(R)_2$C(R)_2$NRC(O)-#, —OC(R)_2$C(R)_2$NRS(O)_2$-#, —S(O)_2$NRC(R)_2$-#, —$C(R)_2$NRS(O)_2$-#, and —$C(R)_2$C(R)_2$NRS(O)_2$-#, each R is independently hydrogen or optionally substituted $C_{1-6}$ aliphatic and # represents the point of attachment to Cy$^A$.

14. The compound of any one of the preceding embodiments, wherein L is selected from —NRC(O)-#, —$C(R)_2$NRC(O)-#, —$C(R)_2$NRC(R)_2$-#, and —$C(R)_2$NRSO_2$-#, wherein each R is independently selected from hydrogen and optionally substituted $C_{1-6}$ aliphatic and # represents the point of attachment to Cy$^A$.

15. The compound of any one of the preceding embodiments, wherein L is selected from —NRC(O)-# and —$C(R)_2$NRC(O)-#, wherein each R is independently selected from hydrogen and optionally substituted $C_{1-6}$ aliphatic and # represents the point of attachment to Cy$^A$.

16. The compound of embodiment 1, wherein the compound is of Formula (II):

(II)

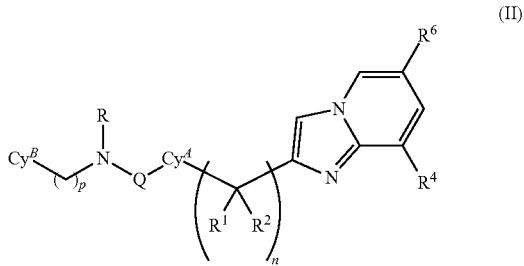

or a pharmaceutically acceptable salt thereof,
wherein:
Cy$^A$ is selected from a 5-membered monocyclic heteroarylene having 1-4 heteroatoms independently selected from oxygen, nitrogen, and sulfur, and a 7- to 10-membered partially unsaturated bicyclic heterocyclylene having 1-4 heteroatoms selected from oxygen, nitrogen, and sulfur, wherein Cy$^A$ is substituted with 0-4 R$^A$ groups;
R$^A$ is selected from an optionally substituted group selected from $C_{1-6}$ aliphatic, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
Q is selected from —$C(R)_2$—, —C(O)—, and —S(O)_2$—;
Cy$^B$ is selected from phenyl, a 5- to 6-membered monocyclic heteroaryl having 1-4 heteroatoms selected from oxygen, nitrogen, and sulfur, a 7- to 10-membered partially unsaturated bicyclic carbocyclyl, a 10-membered bicyclic aryl, a 7- to 10-membered bicyclic heterocyclyl having 1-4 heteroatoms selected from oxygen, nitrogen, and sulfur, a 7- to 10-membered bicyclic heteroaryl having 1-4 heteroatoms selected from oxygen, nitrogen, and sulfur, and a 12-membered tricyclic heterocyclyl having 1-4 heteroatoms selected from oxygen, nitrogen, and sulfur, wherein Cy$^B$ is substituted with 0-5 R$^B$ groups;
R$^B$ is selected from halogen, —CN, —OR, —N(R)_2$, —N(R)CN, —C(=N(R))N(R)_2$, —S(O)R, —S(O)_2$R, —S(O)_2$N(R)_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 7- to 10-membered bicyclic heteroaryl having 1-4 heteroatoms selected from oxygen, nitrogen, and sulfur, and 8- to 10-membered spirocyclic heterocyclyl having 1-3 heteroatoms selected from oxygen, nitrogen, or sulfur, wherein each R is independently hydrogen or optionally substituted $C_{1-6}$ aliphatic;
R¹ and R² are independently selected from hydrogen, halogen, —OR, —SR, —N(R)_2$, and optionally substituted $C_{1-6}$ aliphatic; wherein R¹ may be taken together with a monocyclic Cy$^A$ to form an optionally substituted fused 7- to 10-membered saturated or partially unsaturated bicyclic heterocyclylene having 1-4 heteroatoms selected from oxygen, nitrogen, or sulfur;
R⁴ is selected from hydrogen, halogen, —CN, —C(O)OR, or an optionally substituted group selected from $C_{1-6}$ aliphatic, 5- to 6-membered heteroaryl having 1-4 heteroatoms selected from oxygen, nitrogen, or sulfur, and 3- to 7-membered saturated or partially unsaturated monocyclic heterocyclyl having 1-2 heteroatoms selected from oxygen, nitrogen, or sulfur;
R⁶ is selected from $C_{1-6}$ aliphatic or halogen;
each R is independently hydrogen or an optionally substituted group selected from $C_{1-6}$ aliphatic;
or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur;
n is 0 or 1; and
p is 0, 1, or 2;
with the proviso that the compound is other than N-(furan-2-ylmethyl)-N,3,5-trimethyl-1-((6-methylimidazo[1,2-a]pyridin-2-yl)methyl)-1H-pyrazole-4-sulfonamide and 2-[(6,8-dichloroimidazo[1,2-a]pyridin-2-yl)methyl]-4-methyl-N-phenyl-5-thiazolecarboxamide.

17. A compound of embodiment 16, wherein $Cy^A$ is selected from a 5-membered heteroarylene having 1-4 heteroatoms independently selected from oxygen and nitrogen and 8-membered partially unsaturated bicyclic heterocyclylene having 2-3 heteroatoms selected from oxygen and nitrogen, wherein $Cy^A$ is substituted with 0-3 $R^A$ groups.

18. The compound of embodiment 16, wherein $Cy^A$ is a 5-membered heteroarylene having 1-4 heteroatoms independently selected from oxygen and nitrogen, wherein $Cy^A$ is substituted with 0-3 $R^A$ groups.

19. The compound of embodiment 16, wherein $Cy^A$ is an 8-membered partially unsaturated bicyclic heterocyclylene having 2-3 heteroatoms selected from oxygen and nitrogen, wherein $Cy^A$ is substituted with 0-3 $R^A$ groups.

20. The compound of embodiment 16, wherein $Cy^A$ is selected from the group consisting of:

wherein * represents the point of attachment to L.

21. The compound of embodiment 1, wherein the compound is of Formula (III-a-i), Formula (III-b-i), Formula (III-c-i), Formula (III-d-i), Formula (III-e-i), Formula (III-f-i), Formula (III-g-i):

-continued

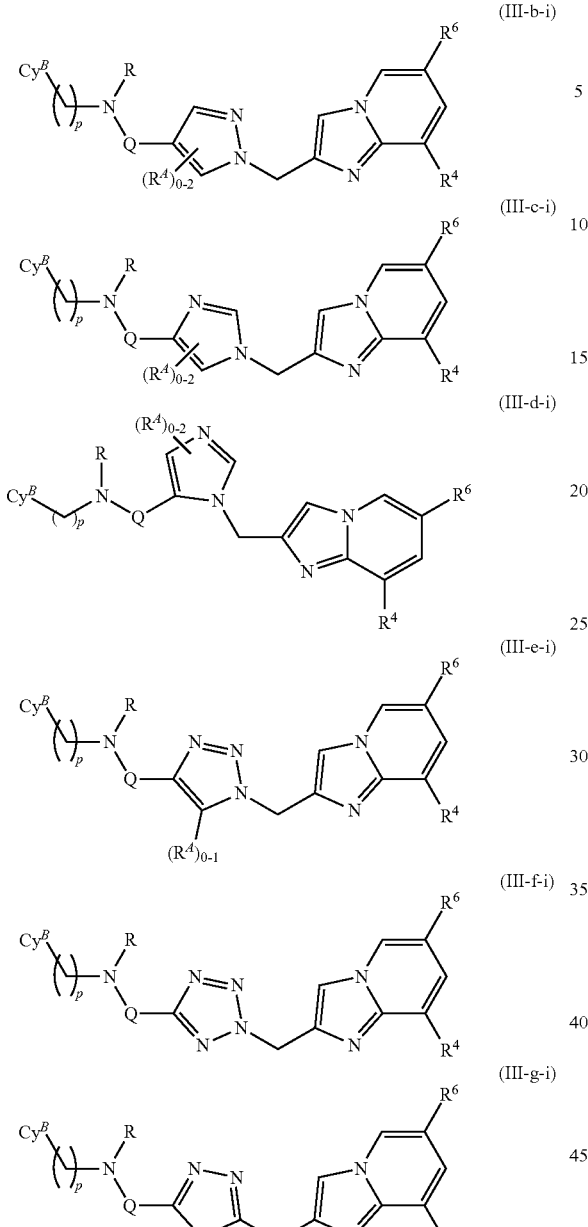

or a pharmaceutically acceptable salt thereof,
wherein:
Q is selected from —C(R)$_2$—, —C(O)—, and —S(O)$_2$—;
R$^A$ is selected from an optionally substituted group selected from C$_{1-6}$ aliphatic, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
R$^4$ is selected from hydrogen, halogen, —CN, —C(O)OR, or an optionally substituted group selected from C$_{1-6}$ aliphatic, 5- to 6-membered heteroaryl having 1-4 heteroatoms selected from oxygen, nitrogen, or sulfur, and 3- to 7-membered saturated or partially unsaturated monocyclic heterocyclyl having 1-2 heteroatoms selected from oxygen, nitrogen, or sulfur;
R$^6$ is selected from C$_{1-6}$ aliphatic or halogen; and p is 0, 1, or 2;

with the proviso that the compound is other than N-(furan-2-ylmethyl)-N,3,5-trimethyl-1-((6-methylimidazo[1,2-a]pyridin-2-yl)methyl)-1H-pyrazole-4-sulfonamide.

22. The compound of embodiment 8, wherein the compound is of Formula (IV-a-i), Formula (IV-b-i), Formula (IV-c-i), Formula (IV-d-i), Formula (IV-e-i), Formula (IV-f-i), Formula (IV-g-i):

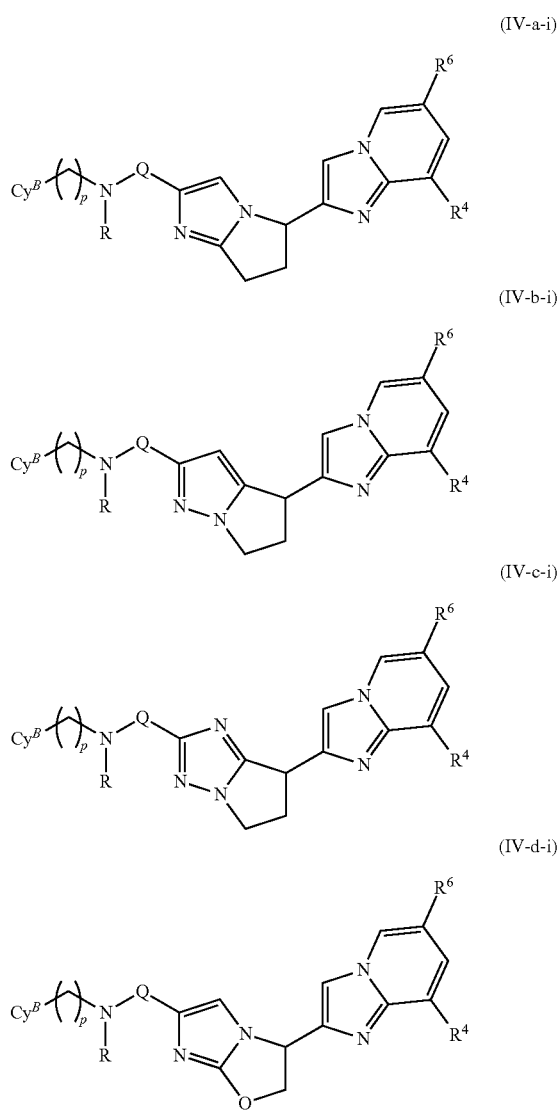

or a pharmaceutically acceptable salt thereof,
wherein:
Q is selected from —C(R)$_2$—, —C(O)—, and —S(O)$_2$—;
p is 0, 1, or 2;
R$^4$ is selected from hydrogen, halogen, —CN, —C(O)OR, or an optionally substituted group selected from C$_{1-6}$ aliphatic, 5- to 6-membered heteroaryl having 1-4 heteroatoms selected from oxygen, nitrogen, or sulfur, and 3- to 7-membered saturated or partially unsaturated monocyclic heterocyclyl having 1-2 heteroatoms selected from oxygen, nitrogen, or sulfur; and
R$^6$ is selected from C$_{1-6}$ aliphatic or halogen.

23. The compound of any one of embodiments 16 to 22, wherein Q is —C(R)$_2$— and p is 1.

24. The compound of any one of embodiments 16 to 22, wherein Q is —C(O)— and p is 1.

25. The compound of any one of embodiments 16 to 22, wherein —C(O)— and p is 0.

26. The compound of any one of embodiments 16 to 22, wherein Q is —S(O)$_2$— and p is 1.

27. The compound of any one of the preceding embodiments, wherein Cy$^B$ is selected from phenyl, a 5- to 6-membered monocyclic heteroaryl having 1-4 heteroatoms selected from oxygen, nitrogen, and sulfur, a 7- to 10-membered partially unsaturated bicyclic carbocyclyl, a 10-membered bicyclic aryl, a 7- to 10-membered bicyclic heterocyclyl having 1-4 heteroatoms selected from oxygen, nitrogen, and sulfur, a 7- to 10-membered bicyclic heteroaryl having 1-4 heteroatoms selected from oxygen, nitrogen, and sulfur, and a 12-membered tricyclic heterocyclyl having 1-4 heteroatoms selected from oxygen, nitrogen, and sulfur, wherein Cy$^B$ is substituted with 0-5 R$^B$ groups.

28. The compound of embodiment 27, wherein Cy$^B$ is phenyl substituted with 0-5 R$^B$ groups.

29. The compound of embodiment 27, wherein Cy$^B$ is a 5-membered monocyclic heteroaryl having 2-3 heteroatoms independently selected from oxygen, nitrogen, and sulfur, wherein Cy$^B$ is substituted with 0-2 R$^B$ group.

30. The compound of embodiment 27, wherein Cy$^B$ is a 6-membered monocyclic heteroaryl having 1-2 nitrogen atoms, wherein Cy$^B$ is substituted with 0-3 R$^B$ groups.

31. The compound of embodiment 27, wherein Cy$^B$ is a 9- to 10-membered bicyclic heteroaryl having 1-4 heteroatoms selected from oxygen, nitrogen, and sulfur, wherein Cy$^B$ is substituted with 0-3 R$^B$.

32. The compound of embodiment 27, wherein Cy$^B$ is selected from the group consisting of:

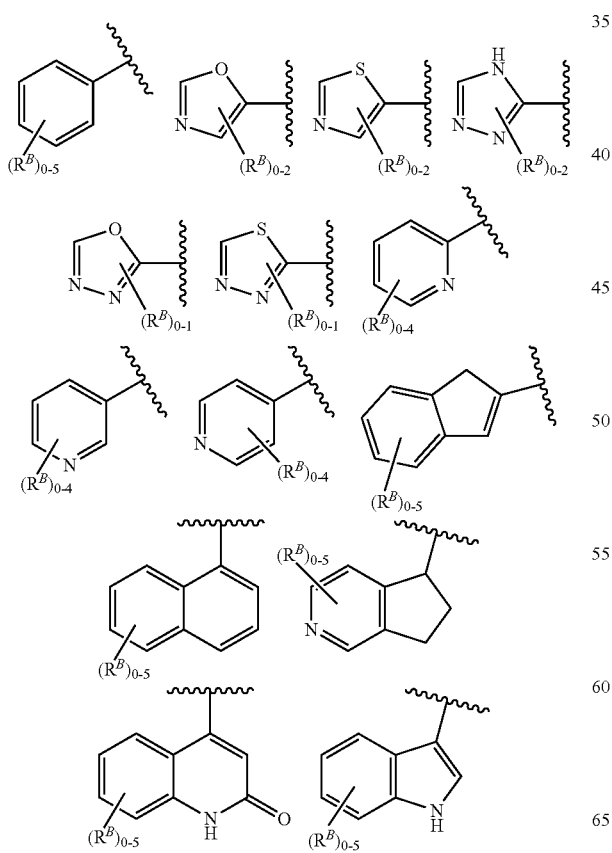

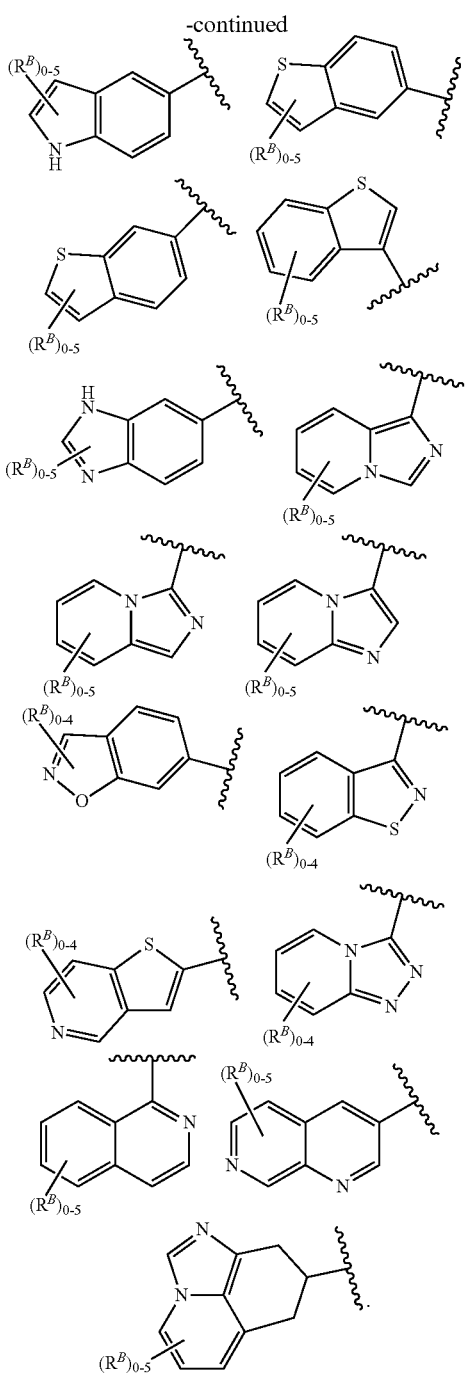

33. The compound of any one of the preceding embodiments, wherein Cy$^B$ is a group other than:

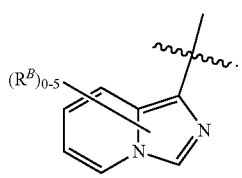

34. The compound of any one of the preceding embodiments, wherein R$^6$ is C$_{1-6}$ aliphatic.

35. The compound of any one of the preceding embodiments, wherein $R^6$ is $C_{1-6}$ cycloalkyl.

36. The compound of any one of the preceding embodiments, wherein $R^6$ is cyclopropyl.

37. The compound of any one of the preceding embodiments, wherein the compound is any one of compounds I-1 through I-137 as shown in Table I, or a pharmaceutically acceptable salt thereof.

38. The compound of any one of the preceding embodiments, wherein the compound is any one of compounds I-1 through I-125 and I-128 through I-137 as shown in Table I, or a pharmaceutically acceptable salt thereof.

39. A pharmaceutical composition comprising a compound of any one of the preceding embodiments, further comprising a pharmaceutically acceptable excipient.

40. A method of treating a plasma kallikrein-mediated disease or disorder using a compound or composition of any one of the preceding embodiments.

41. A method of treating hereditary angioedema or diabetic macular edema comprising administering to a patient in need thereof a compound of any one of the preceding embodiments.

VI. EXAMPLES

Example 1

General Procedure A for Amide Synthesis:

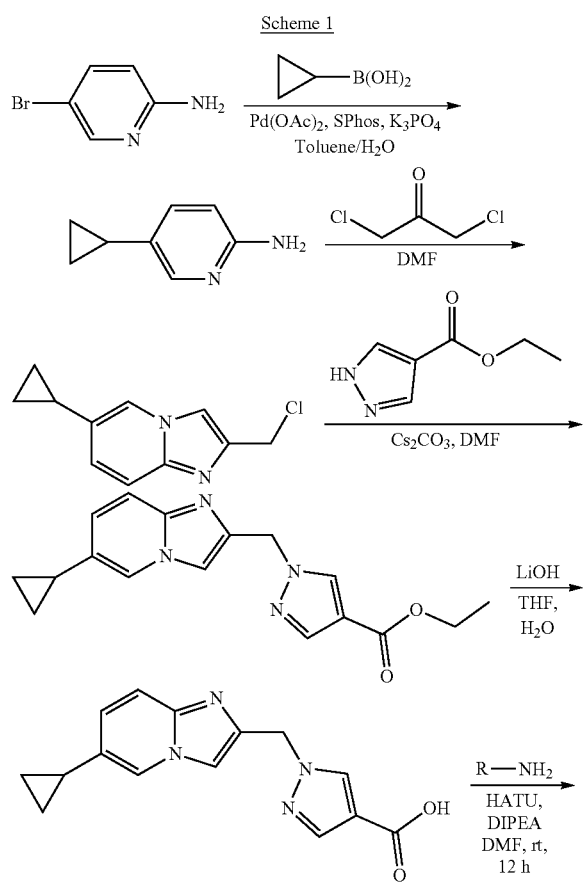

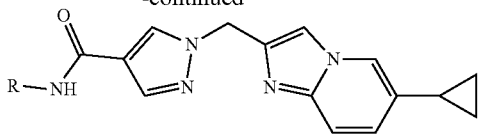

Synthesis of 5-cyclopropylpyridin-2-amine. A solution of 5-bromopyridin-2-amine (5 g, 29.1 mmol), cyclopropylboronic acid (3.75 g, 43.6 mmol), Pd(OAc)$_2$ (651 mg, 2.91 mmol), SPhos (1.19 g, 2.91 mmol) and K$_3$PO$_4$ (18.5 g, 87.3 mmol) in toluene/H$_2$O (100 mL/10 mL) was stirred at 95° C. for 12 h under nitrogen. Then the reaction mixture was quenched with H$_2$O (50 mL) and extracted with DCM (200 mL). The combined organic layers were dried over Na$_2$SO$_4$ and concentrated in vacuo to give the crude residue which was purified by silica gel chromatography (PE/EtOAc=1/1) to give the 5-cyclopropylpyridin-2-amine as yellow solid (3.8 g, 97.4% yield). ESI-MS [M+H]$^+$: 135.2.

Synthesis of 2-(chloromethyl)-6-cyclopropylimidazo[1,2-a]pyridine. To a solution 5-cyclopropyl-4-methylpyridin-2-amine (500 mg, 3.70 mmol) in DMF (10 mL) was added 1,3-dichloropropan-2-one (1409 mg, 11.1 mmol) at RT. The resulting reaction was stirred at 85° C. for 2 h. The solution was quenched with H$_2$O (60 mL), adjusted to pH 8 by adding saturated NaHCO$_3$ solution, and extracted with EtOAc (50 mL×3). The combined organic layers were washed with brine, dried over Na$_2$SO$_4$, and concentrated in vacuo to give the crude, which was purified with prep-TLC (PE/EtOAc=1/1) to give the 2-(chloromethyl)-6-cyclopropyl-7-methylimidazo[1,2-a]pyridine (300 mg, yield:39%) as a light yellow oil. ESI-MS [M+H]$^+$: 207.2.

Synthesis of ethyl 1-((6-cyclopropylimidazo[1,2-a]pyridin-2-yl)methyl)-1H-pyrazole-4-carboxylate. To a solution of 2-(chloromethyl)-6-cyclopropylimidazo[1,2-a]pyridine (2 g, 9.70 mmol) in DMF (20 mL) was added ethyl 1H-pyrazole-4-carboxylate (906 mg, 6.46 mmol) and Cs$_2$CO$_3$ (6.32 g, 19.38 mmol) at RT. The resulting reaction was stirred at RT for 12 h. H$_2$O (150 mL) was added to the reaction and then the mixture was extracted with EtOAc (100 mL×3). The combined organic layers were washed with brine, dried over Na$_2$SO$_4$, concentrated in vacuo to give the crude, which was purified with silica gel chromatography (DCM/MeOH=20/1) to give the ethyl 1-((6-cyclopropylimidazo[1,2-a]pyridin-2-yl)methyl)-1H-pyrazole-4-carboxylate (1.5 g, yield: 75%) as a white solid. ESI-MS [M+H]$^+$: 311.2.

Synthesis of 1-((6-cyclopropylimidazo[1,2-a]pyridin-2-yl)methyl)-1H-pyrazole-4-carboxylic acid. To a solution of ethyl 1-((6-cyclopropylimidazo[1,2-a]pyridin-2-yl)methyl)-1H-pyrazole-4-carboxylate (1.2 g, 3.87 mmol) in THF (20 mL) and H$_2$O (10 mL) was added LiOH (464 mg, 19.35 mmol). The mixture was stirred at RT for 16 h. Most of the THF was removed and the pH was adjusted to 4-5 by adding HCl (1 M). The resulting precipitate was collected and dried to give the 1-((6-cyclopropylimidazo[1,2-a]pyridin-2-yl)methyl)-1H-pyrazole-4-carboxylic acid as a white solid (1.0 g, yield: 91%). ESI-MS [M+H]$^+$: 283.2.

General Procedure A for Amide Coupling. To a solution of 1-((6-cyclopropylimidazo[1,2-a]pyridin-2-yl)methyl)-1H-pyrazole-4-carboxylic acid (60 mg, 0.21 mmol), amine (0.32 mmol) and HATU (120 mg, 0.31 mmol) in DMF (8 mL) was added DIPEA (81 mg, 0.63 mmol). The reaction mixture was stirred at room temperature for 12 h. Water (25 mL) was added and the mixture was extracted with EtOAc (30 mL×3). The combined organic layers were washed with brine, dried over Na$_2$SO$_4$, filtered, and concentrated in vacuo to give the crude product, which was purified by Prep-TLC, Prep-HPLC, or silica gel chromatography to give the desired product.

The following compounds were synthesized according to General Procedure A starting from 1-((6-cyclopropylimidazo[1,2-a]pyridin-2-yl)methyl)-1H-pyrazole-4-carboxylic acid and the indicated amine: N-((3-amino-5,7-dimethylbenzo[d]isoxazol-6-yl)methyl)-1-((6-cyclopropylimidazo[1,2-a]pyridin-2-yl)methyl)-1H-pyrazole-4-carboxamide (I-134), N-((7-bromonaphthalen-1-yl)methyl)-1-((6-cyclopropylimidazo[1,2-a]pyridin-2-yl)methyl)-1H-pyrazole-4-carboxamide (I-133), N-(3-bromophenethyl)-1-((6-cyclopropylimidazo[1,2-a]pyridin-2-yl)methyl)-1H-pyrazole-4-carboxamide (I-132), N-((7-chloroisoquinolin-1-yl)methyl)-1-((6-cyclopropylimidazo[1,2-a]pyridin-2-yl)methyl)-1H-pyrazole-4-carboxamide (I 131), N-(2-(3-chlorophenoxy)ethyl)-1-((6-cyclopropylimidazo[1,2-a]pyridin-2-yl)methyl)-1H-pyrazole-4-carboxamide (I-129), N-((5-chlorobenzo[b]thiophen-3-yl)methyl)-1-((6-cyclopropylimidazo[1,2-a]pyridin-2-yl)methyl)-1H-pyrazole-4-carboxamide (I-128), N-((5-chlorobenzo[d]isothiazol-3-yl)methyl)-1-((6-cyclopropylimidazo[1,2-a]pyridin-2-yl)methyl)-1H-pyrazole-4-carboxamide (I-127), N-((6-chloro-[1,2,4]triazolo[4,3-a]pyridin-3-yl)methyl)-1-((6-cyclopropylimidazo[1,2-a]pyridin-2-yl)methyl)-1H-pyrazole-4-carboxamide (I-126), N-(5-chloro-2-(1H-tetrazol-1-yl)benzyl)-1-((6-cyclopropylimidazo[1,2-a]pyridin-2-yl)methyl)-1H-pyrazole-4-carboxamide (I-125), 1-((6-cyclopropylimidazo[1,2-a]pyridin-2-yl)methyl)-N-((4,6-dimethyl-1H-indol-5-yl)methyl)-1H-pyrazole-4-carboxamide (I-124), N-((3-chloro-4,6-dimethyl-1H-indol-5-yl)methyl)-1-((6-cyclopropylimidazo[1,2-a]pyridin-2-yl)methyl)-1H-pyrazole-4-carboxamide (I-123), N-((6-bromo-2-oxo-1,2-dihydroquinolin-4-yl)methyl)-1-((6-cyclopropylimidazo[1,2-a]pyridin-2-yl)methyl)-1H-pyrazole-4-carboxamide (I-122), N-(3-chlorobenzyl)-1-((6-cyclopropylimidazo[1,2-a]pyridin-2-yl)methyl)-1H-pyrazole-4-carboxamide (I-121), N-((6-chloro-8-fluoroimidazo[1,5-a]pyridin-3-yl)methyl)-1-((6-cyclopropylimidazo[1,2-a]pyridin-2-yl)methyl)-1H-pyrazole-4-carboxamide (I-137), 1-((6-cyclopropylimidazo[1,2-a]pyridin-2-yl)methyl)-N-((2-oxo-1,2-dihydroquinolin-4-yl)methyl)-1H-pyrazole-4-carboxamide (I-120), N-(6-cyano-2-fluoro-3-methoxybenzyl)-1-((6-cyclopropylimidazo[1,2-a]pyridin-2-yl)methyl)-1H-pyrazole-4-carboxamide (I-119), and N-(3-chloro-2-fluoro-6-(1H-tetrazol-1-yl)benzyl)-1-((6-cyclopropylimidazo[1,2-a]pyridin-2-yl)methyl)-1H-pyrazole-4-carboxamide (I 116).

Example 2

N-((3-amino-5,7-dimethylbenzo[d]isoxazol-6-yl)methyl)-1-((6-cyclopropylimidazo[1,2-a]pyridin-2-yl)methyl)-1H-pyrazole-4-carboxamide (I-134)

Scheme 2

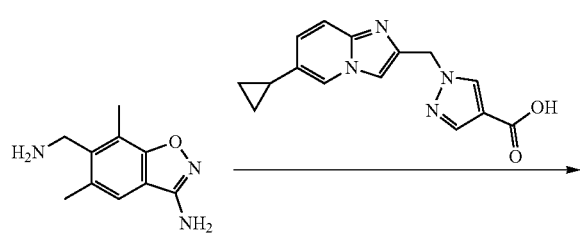

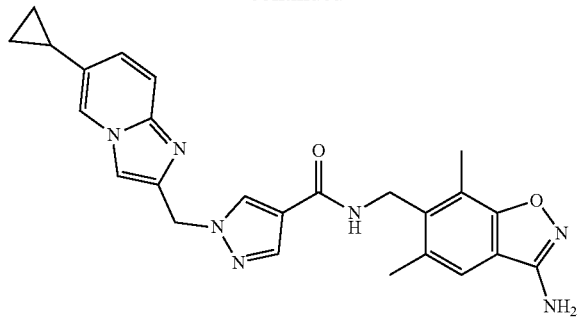

Synthesis of N-((3-amino-5,7-dimethylbenzo[d]isoxazol-6-yl)methyl)-1-((6-cyclopropylimidazo[1,2-a]pyridin-2-yl)methyl)-1H-pyrazole-4-carboxamide. N-((3-amino-5,7-dimethylbenzo[d]isoxazol-6-yl)methyl)-1-((6-cyclopropylimidazo[1,2-a]pyridin-2-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and 6-(aminomethyl)-5,7-dimethylbenzo[d]isoxazol-3-amine hydrochloride. The crude product was purified by prep-TLC (DCM/MeOH=10/1) to yield the product (17 mg, yield: 26.7%) as a white solid. ESI-MS [M+H]⁺: 456.2. ¹H NMR (400 MHz, DMSO) δ 8.49 (t, J=5.3 Hz, 1H), 8.34 (s, 1H), 8.23 (s, 1H), 7.88 (s, 1H), 7.75 (s, 1H), 7.40 (d, J=9.3 Hz, 1H), 7.00 (d, J=9.3 Hz, 1H), 6.87 (s, 1H), 5.85 (s, 2H), 5.40 (s, 2H), 4.43 (d, J=5.4 Hz, 2H), 2.50 (s, 3H), 2.32 (s, 3H), 1.95-1.89 (m, 1H), 0.92 (d, J=6.7 Hz, 2H), 0.67 (d, J=4.6 Hz, 2H).

Example 3

N-((7-bromonaphthalen-1-yl)methyl)-1-((6-cyclopropylimidazo[1,2-a]pyridin-2-yl)methyl)-1H-pyrazole-4-carboxamide (I-133)

Scheme 3

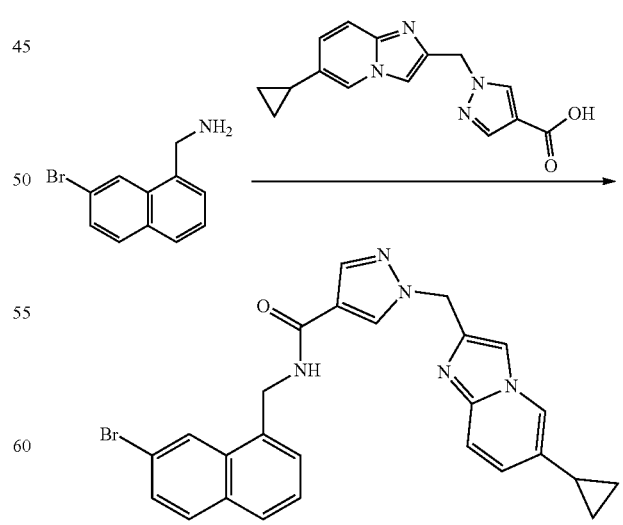

Synthesis of N-((7-bromonaphthalen-1-yl)methyl)-1-((6-cyclopropylimidazo[1,2-a]pyridin-2-yl)methyl)-1H-pyrazole-4-carboxamide. N-((7-bromonaphthalen-1-yl)methyl)-

1-((6-cyclopropylimidazo[1,2-a]pyridin-2-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and 6-(7-bromonaphthalen-1-yl)methanamine. The crude product was purified by prep-TLC (DCM/MeOH=10/1) to yield the product (6 mg, yield: 20%) as a white solid. ESI-MS [M+H]+: 500.1. ¹H NMR (400 MHz, MeOD) δ 8.32 (s, 1H), 8.16 (d, J=6.4 Hz, 2H), 7.95 (s, 1H), 7.81 (d, J=8.6 Hz, 2H), 7.70 (s, 1H), 7.62-7.51 (m, 2H), 7.50-7.43 (m, 1H), 7.37 (d, J=9.3 Hz, 1H), 7.12-7.06 (m, 1H), 5.44 (s, 2H), 4.92 (s, 2H), 1.98-1.88 (m, 1H), 1.00-0.94 (m, 2H), 0.73-0.67 (m, 2H).

Example 4

N-(3-bromophenethyl)-1-((6-cyclopropylimidazo[1,2-a]pyridin-2-yl)methyl)-1H-pyrazole-4-carboxamide (I-132)

Scheme 4

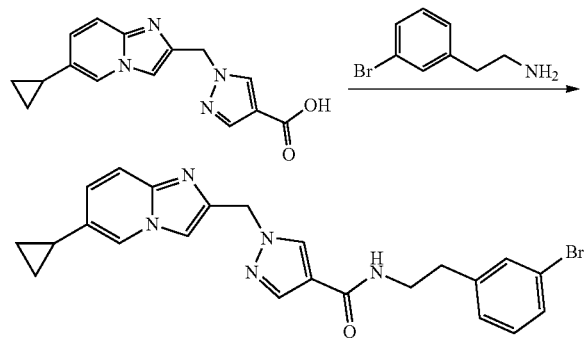

Synthesis of N-(3-bromophenethyl)-1-((6-cyclopropylimidazo[1,2-a]pyridin-2-yl)methyl)-1H-pyrazole-4-carboxamide. N-(3-bromophenethyl)-1-((6-cyclopropylimidazo[1,2-a]pyridin-2-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and 2-(3-bromophenyl)ethan-1-amine. The crude product was purified by prep-TLC (DCM/MeOH=10/1) to yield the product (35 mg, yield: 42.7%) as a pink solid. ESI-MS [M+H]+: 464.1. ¹H NMR (400 MHz, DMSO) δ 8.34 (s, 1H), 8.15 (s, 2H), 7.81 (s, 1H), 7.74 (s, 1H), 7.47-7.35 (m, 3H), 7.27-7.17 (m, 2H), 7.02-6.97 (m, 1H), 5.39 (s, 2H), 3.43-3.31 (m, 2H), 2.78 (t, J=7.2 Hz, 2H), 1.95-1.87 (m, 1H), 0.95-0.88 (m, 2H), 0.70-0.64 (m, 2H).

Example 5

N-((7-chloroisoquinolin-1-yl)methyl)-1-((6-cyclopropylimidazo[1,2-a]pyridin-2-yl)methyl)-1H-pyrazole-4-carboxamide (I-131)

Scheme 5

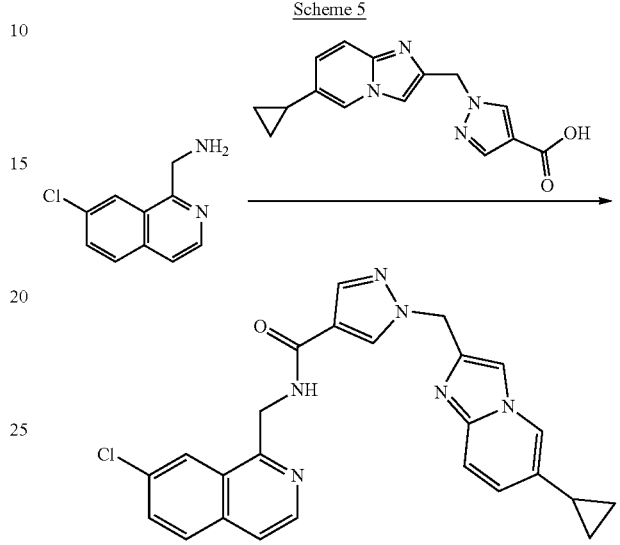

Synthesis of N-((7-chloroisoquinolin-1-yl)methyl)-1-((6-cyclopropylimidazo[1,2-a]pyridin-2-yl)methyl)-1H-pyrazole-4-carboxamide. N-((7-chloroisoquinolin-1-yl)methyl)-1-((6-cyclopropylimidazo[1,2-a]pyridin-2-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and (7-chloroisoquinolin-1-yl)methanamine. The crude product was purified by prep-TLC (DCM/MeOH=10/1) to yield the product (12 mg, yield:12.5%) as a white solid. ESI-MS [M+H]⁺: 457.2. ¹H NMR (400 MHz, DMSO) δ 8.71 (t, J=5.7 Hz, 1H), 8.47-8.46 (m, 2H), 8.33 (s, 1H), 8.26 (s, 1H), 8.05 (d, J=8.8 Hz, 1H), 7.90 (s, 1H), 7.82-7.79 (m, 2H), 7.74 (s, 1H), 7.40 (d, J=9.3 Hz, 1H), 7.02-6.97 (m, 1H), 5.40 (s, 2H), 5.01 (d, J=5.7 Hz, 2H), 1.93-1.59 (m, 1H), 0.94-0.90 (m, 2H), 0.68-0.64 (m, 2H).

Example 6

N-(2-(3-chlorophenoxy)ethyl)-1-((6-cyclopropylimidazo[1,2-a]pyridin-2-yl)methyl)-1H-pyrazole-4-carboxamide (I-129)

Scheme 6

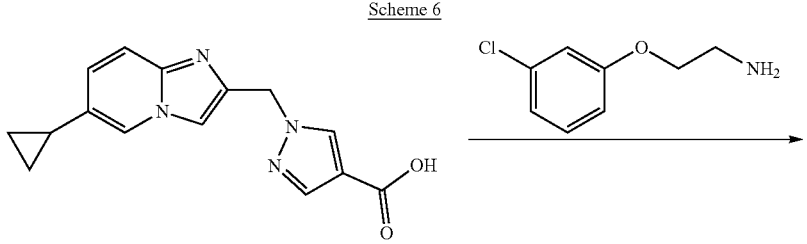

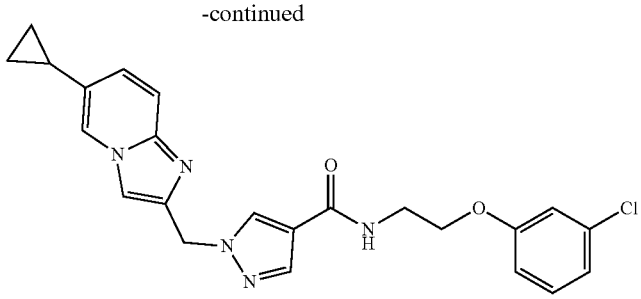

Synthesis of N-(2-(3-chlorophenoxy)ethyl)-1-((6-cyclopropylimidazo[1,2-a]pyridin-2-yl)methyl)-1H-pyrazole-4-carboxamide. N-(2-(3-chlorophenoxy)ethyl)-1-((6-cyclopropylimidazo[1,2-a]pyridin-2-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and 2-(3-chlorophenoxy)ethan-1-amine. The crude product was purified by prep-HPLC to yield the product (38 mg, yield: 25%) as a light yellow solid. ESI-MS [M+H]+: 436.2. $^1$H NMR (400 MHz, DMSO) δ 8.34 (s, 1H), 8.30 (t, J=5.5 Hz, 1H), 8.20 (s, 1H), 7.85 (s, 1H), 7.74 (s, 1H), 7.40 (d, J=9.3 Hz, 1H), 7.29 (t, J=8.2 Hz, 1H), 7.05-6.90 (m, 4H), 5.40 (s, 2H), 4.07 (t, J=5.8 Hz, 2H), 3.57-3.49 (m, 2H), 1.98-1.85 (m, 1H), 0.97-0.87 (m, 2H), 0.71-0.62 (m, 2H).

Example 7

N-((5-chlorobenzo[b]thiophen-3-yl)methyl)-1-((6-cyclopropylimidazo[1,2-a]pyridin-2-yl)methyl)-1H-pyrazole-4-carboxamide (I-128)

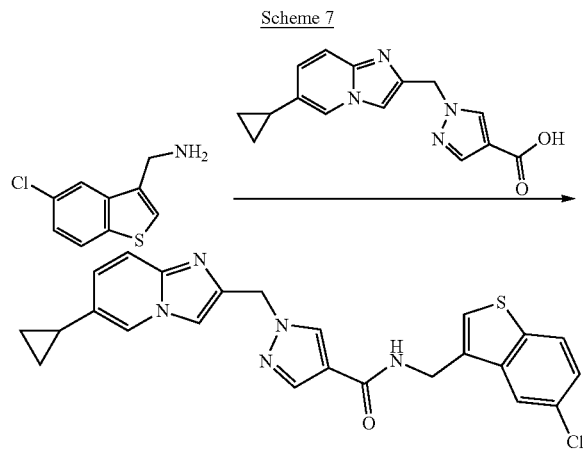

Synthesis of N-((5-chlorobenzo[b]thiophen-3-yl)methyl)-1-((6-cyclopropylimidazo[1,2-a]pyridin-2-yl)methyl)-1H-pyrazole-4-carboxamide. N-((5-chlorobenzo[b]thiophen-3-yl)methyl)-1-((6-cyclopropylimidazo[1,2-a]pyridin-2-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and (5-chlorobenzo[b]thiophen-3-yl)methanamine. The crude product was purified by Prep-TLC (DCM:MeOH=20:1) to yield the product (18.8 mg, yield: 27%) as a white solid. ESI-MS [M+H]+: 462.2. $^1$H NMR (400 MHz, DMSO) δ 8.63 (t, J=5.7 Hz, 1H), 8.32 (s, 1H), 8.23 (s, 1H), 8.03-7.99 (m, 2H), 7.88 (s, 1H), 7.73 (s, 1H), 7.65 (s, 1H), 7.41-7.37 (m, 2H), 7.01-6.96 (m, 1H), 5.40 (s, 2H), 4.60 (d, J=5.7 Hz, 2H), 1.94-1.88 (m, 1H), 0.94-0.86 (m, 2H), 0.70-0.62 (m, 2H).

Example 8

N-((7-chloronaphthalen-1-yl)methyl)-1-((6-cyclopropylimidazo[1,2-a]pyridin-2-yl)methyl)-1H-pyrazole-4-carboxamide (I-130)

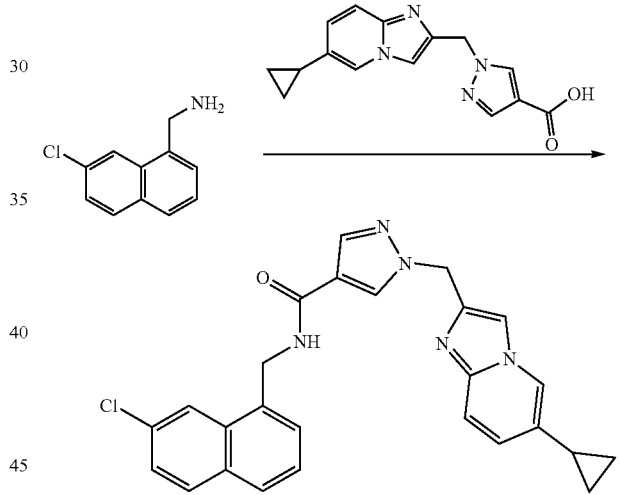

Synthesis of N-((7-chloronaphthalen-1-yl)methyl)-1-((6-cyclopropylimidazo[1,2-a]pyridin-2-yl)methyl)-1H-pyrazole-4-carboxamide. To a solution of methyl 1-((6-cyclopropylimidazo[1,2-a]pyridin-2-yl)methyl)-1H-pyrazole-4-carboxylic acid (100 mg, 0.354 mmol) in anhydrous DMF (5 mL) was added DIPEA (200 mg, 1.55 mmol). The mixture was stirred at RT for 1 h. Then (7-chloronaphthalen-1-yl)methanamine (1100 mg, 0.522 mmol) was added. The final mixture was stirred at RT for 16 h. Quenched with water (50 mL), extracted with EA (30 mL*3). The combined organic layers were washed with brine (30 mL), dried over Na2SO4 and concentrated. The residue was purified by Prep-TLC (DCM/MeOH=10/1) to give N-((7-chloronaphthalen-1-yl)methyl)-1-((6-cyclopropylimidazo[1,2-a]pyridin-2-yl)methyl)-1H-pyrazole-4-carboxamide (40 mg, yield: 24.8%) as an brown solid. ESI-MS [M+H]+: 456.2. Purity: 96.2 (214 nm), 97.0 (254 nm). $^1$H NMR (400 MHz, DMSO) δ 8.65 (t, J=5.8 Hz, 1H), 8.33 (s, 1H), 8.28-8.20 (m, 2H), 8.00 (d, J=8.8 Hz, 1H), 7.93-7.83 (m, 2H), 7.75 (s, 1H), 7.60-7.45 (m, 3H), 7.40 (d, J=9.3 Hz, 1H), 7.02-6.95 (m, 1H), 5.41 (d, J=4.8 Hz, 2H), 4.82 (d, J=5.8 Hz, 2H), 1.95-1.85 (m, 1H), 0.97-0.86 (m, 2H), 0.72-0.60 (m, 2H).

Example 9

N-((5-chlorobenzo[d]isothiazol-3-yl)methyl)-1-((6-cyclopropylimidazo[1,2-a]pyridin-2-yl)methyl)-1H-pyrazole-4-carboxamide (I-127)

Scheme 9

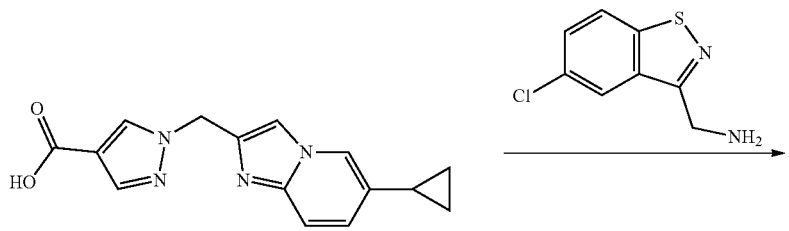

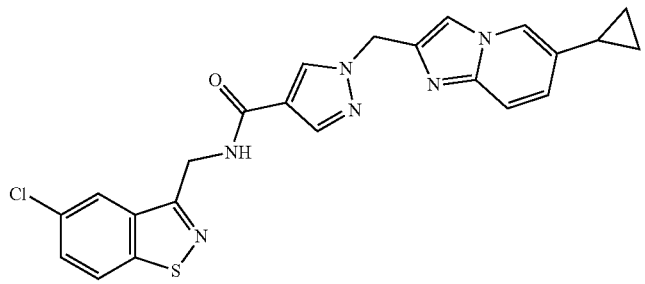

Synthesis of N-((5-chlorobenzo[d]isothiazol-3-yl)methyl)-1-((6-cyclopropylimidazo[1,2-a]pyridin-2-yl)methyl)-1H-pyrazole-4-carboxamide. N-((5-chlorobenzo[d]isothiazol-3-yl)methyl)-1-((6-cyclopropylimidazo[1,2-a]pyridin-2-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and (5-chlorobenzo[d]isothiazol-3-yl)methanamine. The crude product was purified by prep-TLC (DCM/MeOH=10/1) to yield the product (10 mg, yield: 18%) as a white solid. ESI-MS [M+H]+: 463.1. $^1$H NMR (400 MHz, DMSO) δ 8.82 (t, J=5.9 Hz, 1H), 8.38-8.30 (m, 2H), 8.26-8.22 (m, 2H), 7.89 (s, 1H), 7.74 (s, 1H), 7.66-7.62 (m, 1H), 7.40 (d, J=9.3 Hz, 1H), 7.01-6.98 (m, 1H), 5.41 (s, 2H), 4.85 (d, J=5.9 Hz, 2H), 1.95-1.87 (m, 1H), 0.96-0.87 (m, 2H), 0.69-0.62 (m, 2H).

Example 10

N-((6-chloro-[1,2,4]triazolo[4,3-a]pyridin-3-yl)methyl)-1-((6-cyclopropylimidazo[1,2-a]pyridin-2-yl)methyl)-1H-pyrazole-4-carboxamide (I-126)

Scheme 10

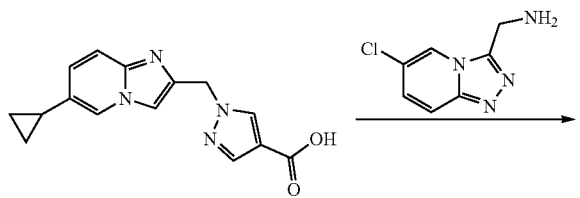

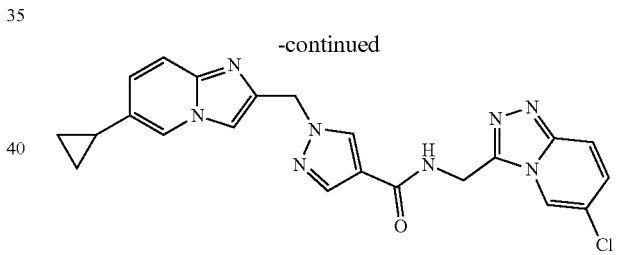

Synthesis of N-((6-chloro-[1,2,4]triazolo[4,3-a]pyridin-3-yl)methyl)-1-((6-cyclopropylimidazo[1,2-a]pyridin-2-yl)methyl)-1H-pyrazole-4-carboxamide. N-((6-chloro-[1,2,4]triazolo[4,3-a]pyridin-3-yl)methyl)-1-((6-cyclopropylimidazo[1,2-a]pyridin-2-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and (6-chloro-[1,2,4]triazolo[4,3-a]pyridin-3-yl)methanamine hydrobromide. The crude product was purified by prep-TLC (DCM/MeOH=10/1) to yield the product (15 mg, yield: 16%) as a white solid. ESI-MS [M+H]+: 447.1. $^1$H NMR (400 MHz, DMSO) δ 8.90 (t, J=5.8 Hz, 1H), 8.86-8.84 (m, 1H), 8.34 (s, 1H), 8.24 (s, 1H), 7.88 (s, 1H), 7.84-7.81 (m, 1H), 7.74 (s, 1H), 7.44-7.39 (m, 2H), 7.03-6.98 (m, 1H), 5.41 (s, 2H), 4.91 (d, J=5.8 Hz, 2H), 1.96-1.88 (m, 1H), 0.95-0.86 (m, 2H), 0.71-0.62 (m, 2H).

Example 11

1-((6-cyclopropylimidazo[1,2-a]pyridin-2-yl)methyl)-1H-pyrazole-4-carboxamide

Scheme 11

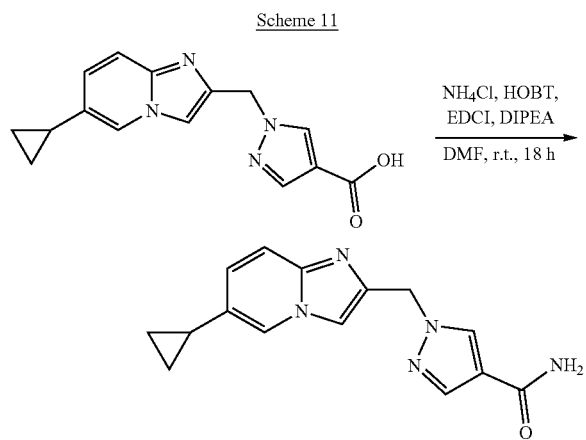

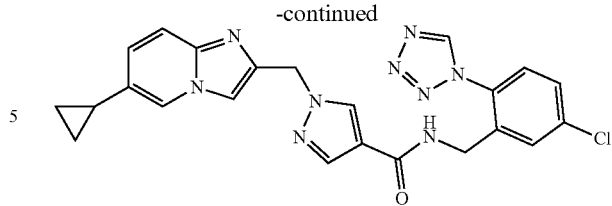

Synthesis of 1-((6-cyclopropylimidazo[1,2-a]pyridin-2-yl)methyl)-1H-pyrazole-4-carboxamide. To a mixture of 1-((6-cyclopropylimidazo[1,2-a]pyridin-2-yl)methyl)-1H-pyrazole-4-carboxylic acid (100 mg, 0.35 mmol), NH₄Cl (187 mg, 3.5 mmol), HOBT (94.5 mg, 0.7 mmol) and EDCI (134.4 mg, 0.7 mmol) in DMF (5 mL) was added DIPEA (225.8 mg, 1.76 mmol). The reaction mixture was stirred at room temperature for 18 h, then diluted with water (50 mL) and extracted with EtOAc (30 mL×5). The combined organic layers were washed with brine (50 mL), dried over Na₂SO₄ and concentrated in vacuo. The residue was purified by Prep-HPLC to give 1-((6-cyclopropylimidazo[1,2-a]pyridin-2-yl)methyl)-1H-pyrazole-4-carboxamide (15 mg, 15.2%) as a white solid. ESI-MS [M+H]+: 282.2. ¹H NMR (400 MHz, DMSO) δ 8.34 (s, 1H), 8.16 (S, 1H), 7.82 (s, 1H), 7.74 (s, 1H), 7.54 (s, 1H), 7.40 (d, J=9.3 Hz, 1H), 7.03-6.95 (m, 2H), 5.39 (s, 2H), 1.96-1.89 (m, 1H), 0.94-0.91 (m, 2H), 0.73-0.66 (m, 2H).

Example 12

N-(5-chloro-2-(1H-tetrazol-1-yl)benzyl)-1-((6-cyclopropylimidazo[1,2-a]pyridin-2-yl)methyl)-1H-pyrazole-4-carboxamide (I-125)

Scheme 12

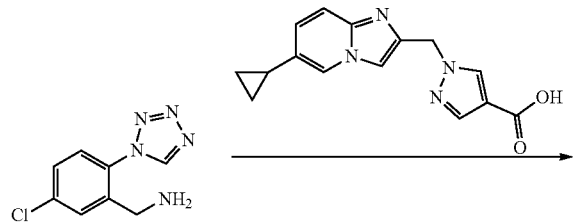

Synthesis of N-(5-chloro-2-(1H-tetrazol-1-yl)benzyl)-1-((6-cyclopropylimidazo[1,2-a]pyridin-2-yl)methyl)-1H-pyrazole-4-carboxamide. N-(5-chloro-2-(1H-tetrazol-1-yl)benzyl)-1-((6-cyclopropylimidazo[1,2-a]pyridin-2-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and (5-chloro-2-(1H-tetrazol-1-yl)phenyl)methanamine. The crude product was purified by prep-TLC (DCM/MeOH=10/1) to yield the product (10 mg, yield: 21%) as a yellow solid. ESI-MS [M+H]+: 474.2. ¹H NMR (400 MHz, DMSO) δ 9.87 (s, 1H), 8.59 (t, J=5.7 Hz, 1H), 8.34 (s, 1H), 8.19 (s, 1H), 7.82 (s, 1H), 7.76 (s, 1H), 7.63 (d, J=1.3 Hz, 2H), 7.58 (s, 1H), 7.40 (d, J=9.4 Hz, 1H), 7.00 (d, J=9.4 Hz, 1H), 5.41 (s, 2H), 4.22 (d, J=5.7 Hz, 2H), 1.96-1.89 (m, 1H), 0.93-0.89 (m, 2H), 0.69-0.65 (m, 2H).

Example 13

1-((6-cyclopropylimidazo[1,2-a]pyridin-2-yl)methyl)-N-((4,6-dimethyl-1H-indol-5-yl)methyl)-1H-pyrazole-4-carboxamide (I-124)

Scheme 13

Synthesis of 1-((6-cyclopropylimidazo[1,2-a]pyridin-2-yl)methyl)-N-((4,6-dimethyl-1H-indol-5-yl)methyl)-1H-pyrazole-4-carboxamide. 1-((6-cyclopropylimidazo[1,2-a]pyridin-2-yl)methyl)-N-((4,6-dimethyl-1H-indol-5-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and (4,6-dimethyl-1H-indol-5-yl)methanamine. The crude product was purified by prep-HPLC to yield the product (25 mg, yield: 25%) as a white solid. ESI-MS [M+H]+: 439.2. ¹H NMR (400 MHz, DMSO) δ 10.84 (s, 1H), 8.31 (s, 1H), 8.24 (s, 1H), 7.90-7.84 (m, 2H), 7.71 (s, 1H), 7.38 (d, J=9.3 Hz, 1H), 7.24-7.16 (m, 1H), 7.05 (s, 1H), 7.00-6.95 (m, 1H), 6.40 (s, 1H), 5.36 (s, 2H), 4.49

(d, J=4.4 Hz, 2H), 2.47 (s, 3H), 2.37 (s, 3H), 1.95-1.86 (m, 1H), 0.96-0.84 (m, 2H), 0.71-0.61 (m, 2H).

Example 14

N-((3-chloro-4,6-dimethyl-1H-indol-5-yl)methyl)-1-((6-cyclopropylimidazo[1,2-a]pyridin-2-yl)methyl)-1H-pyrazole-4-carboxamide (I-123)

Scheme 14

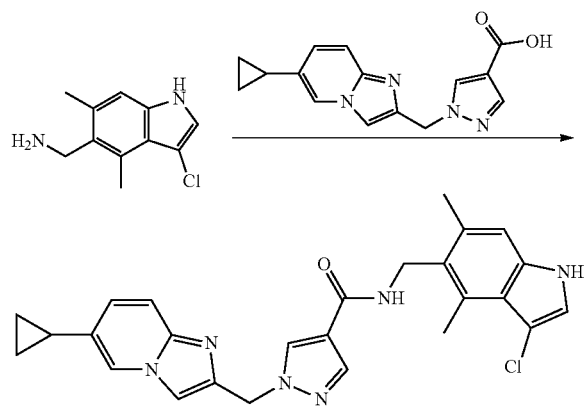

Synthesis of N-((3-chloro-4,6-dimethyl-1H-indol-5-yl)methyl)-1-((6-cyclopropylimidazo[1,2-a]pyridin-2-yl)methyl)-1H-pyrazole-4-carboxamide. N-((3-chloro-4,6-dimethyl-1H-indol-5-yl)methyl)-1-((6-cyclopropylimidazo[1,2-a]pyridin-2-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and (3-chloro-4,6-dimethyl-1H-indol-5-yl)methanamine. The crude product was purified by prep-HPLC to yield the product (15 mg, yield: 8.6%) as a white solid. ESI-MS [M+H]+: 473.2. $^1$H NMR (400 MHz, DMSO) δ 11.14 (s, 1H), 8.32 (s, 1H), 8.24 (s, 1H), 7.91-7.84 (m, 2H), 7.72 (s, 1H), 7.41-7.32 (m, 2H), 7.06 (s, 1H), 6.98 (d, J=9.1 Hz, 1H), 5.37 (s, 2H), 4.47 (d, J=4.0 Hz, 2H), 2.71 (s, 3H), 2.37 (s, 3H), 1.92-01.87 (m, 2H), 0.94-0.86 (m, 2H), 0.69-0.62 (m, 2H).

Example 15

N-((6-bromo-2-oxo-1,2-dihydroquinolin-4-yl)methyl)-1-((6-cyclopropylimidazo[1,2-a]pyridin-2-yl)methyl)-1H-pyrazole-4-carboxamide (I-122)

Scheme 15

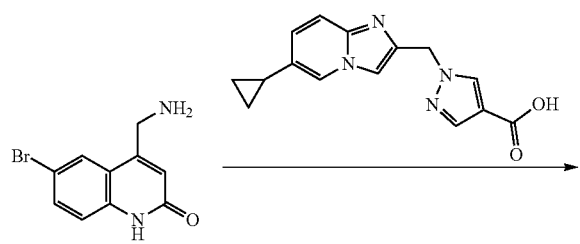

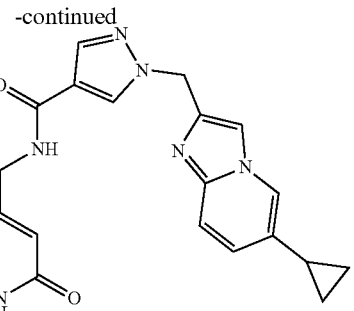

Synthesis of N-((6-bromo-2-oxo-1,2-dihydroquinolin-4-yl)methyl)-1-((6-cyclopropylimidazo[1,2-a]pyridin-2-yl)methyl)-1H-pyrazole-4-carboxamide. N-((6-bromo-2-oxo-1,2-dihydroquinolin-4-yl)methyl)-1-((6-cyclopropylimidazo[1,2-a]pyridin-2-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and 4-(aminomethyl)-6-bromoquinolin-2(1H)-one. The crude product was purified by Prep-TLC (MeOH/DCM=1/10) to yield the product (17.6 mg, yield: 16%) as a white solid. ESI-MS [M+H]+: 517.1. $^1$H NMR (400 MHz, DMSO) δ 11.82 (s, 1H), 8.66 (t, J=5.7 Hz, 1H), 8.34 (s, 1H), 8.27 (s, 1H), 8.01 (d, J=1.8 Hz, 1H), 7.91 (s, 1H), 7.76 (s, 1H), 7.69-7.65 (m, 1H), 7.41 (d, J=9.3 Hz, 1H), 7.27 (d, J=8.8 Hz, 1H), 7.02-6.97 (m, 1H), 6.36 (s, 1H), 5.42 (s, 2H), 4.59 (d, J=5.6 Hz, 2H), 1.95-1.89 (m, 1H), 0.94-0.88 (m, 2H), 0.71-0.63 (m, 2H).

Example 16

N-(3-chlorobenzyl)-1-((6-cyclopropylimidazo[1,2-a]pyridin-2-yl)methyl)-1H-pyrazole-4-carboxamide (I-121)

Scheme 16

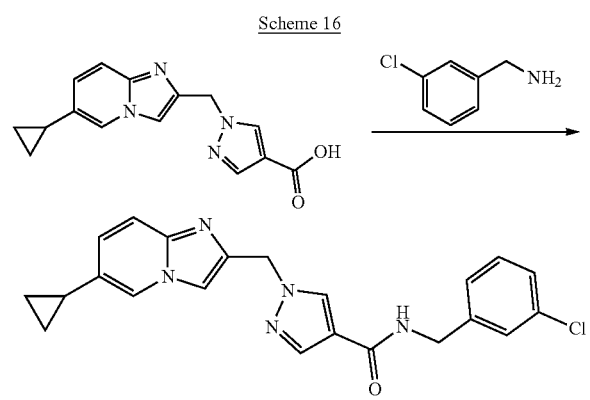

Synthesis of N-(3-chlorobenzyl)-1-((6-cyclopropylimidazo[1,2-a]pyridin-2-yl)methyl)-1H-pyrazole-4-carboxamide. N-(3-chlorobenzyl)-1-((6-cyclopropylimidazo[1,2-a]pyridin-2-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and (3-chlorophenyl)methanamine. The crude product was purified by Prep-HPLC to yield the product (55 mg, 27%) as a white solid. ESI-MS [M+H]+: 406.1. $^1$H NMR (400 MHz, DMSO) δ 8.66 (t, J=6.0 Hz, 1H), 8.34 (s, 1H), 8.23 (s, 1H), 7.88 (s, 1H), 7.75 (s, 1H), 7.49-7.13 (m, 5H), 7.00 (dd, J=9.4, 1.8 Hz, 1H), 5.41 (s, 2H), 4.39 (d, J=6.0 Hz, 2H), 2.05-1.78 (m, 1H), 1.05-0.80 (m, 2H), 0.82-0.37 (m, 2H).

Example 17

N-((6-chloro-8-fluoroimidazo[1,5-a]pyridin-3-yl)methyl)-1-((6-cyclopropylimidazo[1,2-a]pyridin-2-yl)methyl)-1H-pyrazole-4-carboxamide (I-137)

Scheme 17

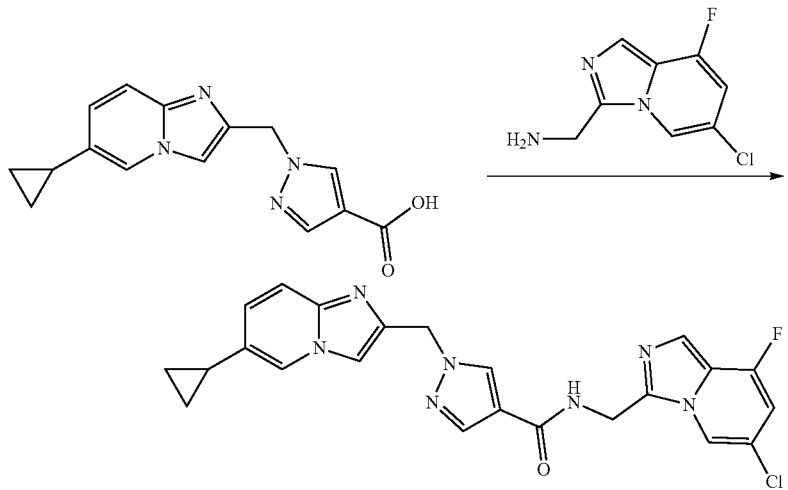

Synthesis of N-((6-chloro-8-fluoroimidazo[1,5-a]pyridin-3-yl)methyl)-1-((6-cyclopropylimidazo[1,2-a]pyridin-2-yl)methyl)-1H-pyrazole-4-carboxamide. N-((6-chloro-8-fluoroimidazo[1,5-a]pyridin-3-yl)methyl)-1-((6-cyclopropylimidazo[1,2-a]pyridin-2-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and (6-chloro-8-fluoroimidazo[1,5-a]pyridin-3-yl)methanamine hydrochloride. The crude product was purified by prep-TLC (DCM/MeOH=10/1) to yield the product (20 mg, yield: 21%) as a white solid. ESI-MS [M+H]+: 464.1. $^1$H NMR (400 MHz, DMSO) δ 8.81 (t, J=5.7 Hz, 1H), 8.55 (s, 1H), 8.33 (s, 1H), 8.23 (s, 1H), 7.87 (s, 1H), 7.73 (s, 1H), 7.57 (s, 1H), 7.39 (d, J=9.3 Hz, 1H), 7.01-6.98 (m, 1H), 6.94-6.90 (m, 1H), 5.39 (s, 2H), 4.80 (d, J=5.7 Hz, 2H), 1.95-1.87 (m, 1H), 0.95-0.86 (m, 2H), 0.71-0.62 (m, 2H).

Example 18

1-((6-cyclopropylimidazo[1,2-a]pyridin-2-yl)methyl)-N-((2-oxo-1,2-dihydroquinolin-4-yl)methyl)-1H-pyrazole-4-carboxamide (I-120)

Scheme 18

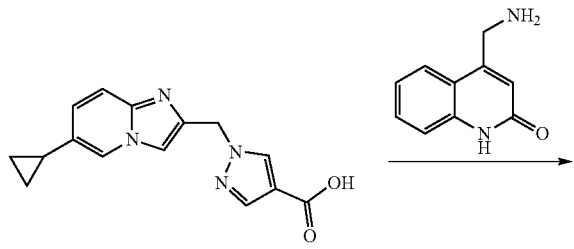

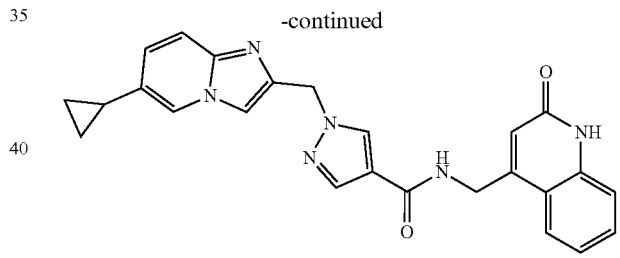

-continued

Synthesis of 1-((6-cyclopropylimidazo[1,2-a]pyridin-2-yl)methyl)-N-((2-oxo-1,2-dihydroquinolin-4-yl)methyl)-1H-pyrazole-4-carboxamide. 1-((6-cyclopropylimidazo[1,2-a]pyridin-2-yl)methyl)-N-((2-oxo-1,2-dihydroquinolin-4-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and 4-(aminomethyl)quinolin-2(1H)-one. The crude product was purified by prep-HPLC to yield the product (10 mg, yield: 10%) as a white solid. ESI-MS [M+H]+: 439.2. $^1$H NMR (400 MHz, DMSO) δ 11.68 (s, 1H), 8.65 (t, J=5.8 Hz, 1H), 8.35 (s, 1H), 8.28 (s, 1H), 7.92 (s, 1H), 7.82 (d, J=7.9 Hz, 1H), 7.76 (s, 1H), 7.55-7.48 (m, 1H), 7.41 (d, J=9.3 Hz, 1H), 7.33 (d, J=7.6 Hz, 1H), 7.19 (t, J=7.6 Hz, 1H), 7.03-6.98 (m, 1H), 6.33 (s, 1H), 5.43 (s, 2H), 4.63 (d, J=5.6 Hz, 2H), 1.97-1.88 (m, 1H), 0.95-0.88 (m, 2H), 0.74-0.63 (m, 2H).

Example 19

N-(6-cyano-2-fluoro-3-methoxybenzyl)-1-((6-cyclopropylimidazo[1,2-a]pyridin-2-yl)methyl)-1H-pyrazole-4-carboxamide (I-119)

Scheme 19

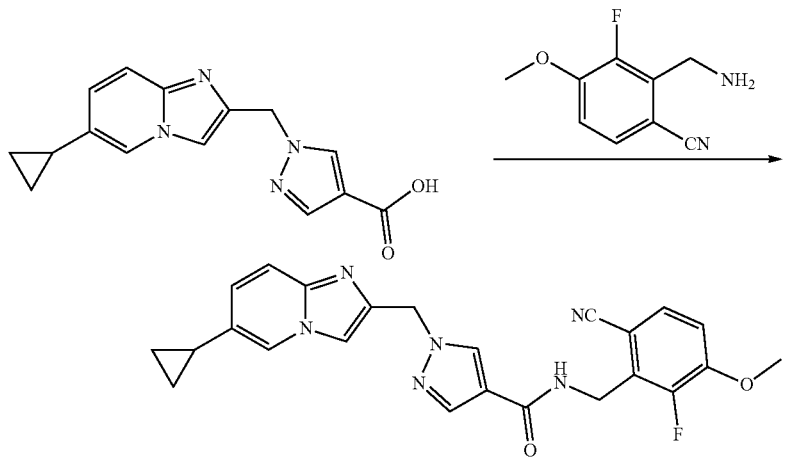

Synthesis of N-(6-cyano-2-fluoro-3-methoxybenzyl)-1-((6-cyclopropylimidazo[1,2-a]pyridin-2-yl)methyl)-1H-pyrazole-4-carboxamide. N-(6-cyano-2-fluoro-3-methoxybenzyl)-1-((6-cyclopropylimidazo[1,2-a]pyridin-2-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and 2-(aminomethyl)-3-fluoro-4-methoxybenzonitrile. The crude product was purified by silica gel column chromatography (DCM/MeOH=10/1) to yield the product (3.2 mg, yield: 0.5%) as a white solid. ESI-MS [M+H]+: 445.2. $^1$H NMR (400 MHz, DMSO) δ 8.56 (s, 1H), 8.33 (s, 1H), 8.19 (s, 1H), 7.83 (s, 1H), 7.73 (s, 1H), 7.66 (d, J=8.6 Hz, 1H), 7.40 (d, J=9.3 Hz, 1H), 7.27 (t, J=8.4 Hz, 1H), 6.99 (d, J=9.2 Hz, 1H), 5.39 (s, 2H), 4.50 (d, J=4.3 Hz, 2H), 3.91 (s, 3H), 1.93-1.83 (m, 1H), 0.91 (d, J=7.1 Hz, 2H), 0.66 (d, J=4.6 Hz, 2H).

Example 20

N-(5-chloro-2-(2H-tetrazol-5-yl)benzyl)-1-((6-cyclopropylimidazo[1,2-a]pyridin-2-yl)methyl)-1H-pyrazole-4-carboxamide (I-117)

Scheme 20

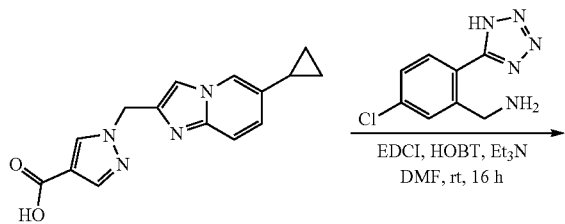

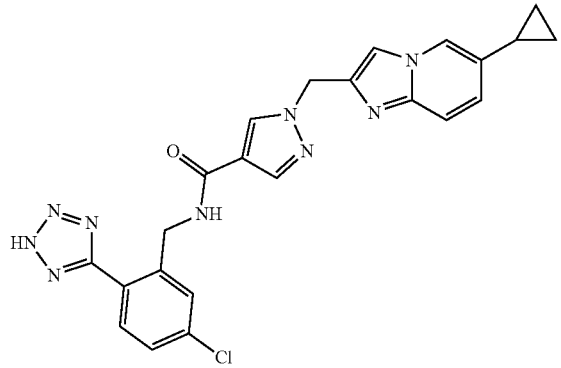

Synthesis of N-(5-chloro-2-(2H-tetrazol-5-yl)benzyl)-1-((6-cyclopropylimidazo[1,2-a]pyridin-2-yl)methyl)-1H-pyrazole-4-carboxamide. A mixture of 1-((6-cyclopropylimidazo[1,2-a]pyridin-2-yl)methyl)-1H-pyrazole-4-carboxylic acid (209 mg, 0.740 mmol), (5-chloro-2-(1H-tetrazol-5-yl)phenyl)methanamine (222 mg, 1.06 mmol), EDCI (203 mg, 1.06 mmol), HOBT (143 mg, 1.06 mmol) and Et3N (226 mg, 2.23 mmol) in DMF (6 mL) was stirred at room temperature for 16 h. The reaction mixture was concentrated and purified by Prep-HPLC to give N-(5-chloro-2-(2H-tetrazol-5-yl)benzyl)-1-((6-cyclopropylimidazo[1,2-a]pyridin-2-yl)methyl)-1H-pyrazole-4-carboxamide (38 mg, yield: 11%) as a white solid. ESI-MS [M+H]+: 474.2. $^1$H NMR (400 MHz, DMSO) δ 8.74 (t, J=5.8 Hz, 1H), 8.35 (s, 1H), 8.24 (s, 1H), 7.90-7.82 (m, 2H), 7.76 (s, 1H), 7.51 (dd, J=8.3, 1.9 Hz, 1H), 7.47-7.37 (m, 2H), 7.01 (d, J=9.4 Hz, 1H), 5.43 (s, 2H), 4.70 (d, J=5.8 Hz, 2H), 1.96-1.89 (m, 1H), 0.92 (m, 2H), 0.72-0.63 (m, 2H).

Example 21

N-(3-chloro-2-fluoro-6-(1H-tetrazol-1-yl)benzyl)-1-((6-cyclopropylimidazo[1,2-a]pyridin-2-yl)methyl)-1H-pyrazole-4-carboxamide (I-116)

Scheme 21

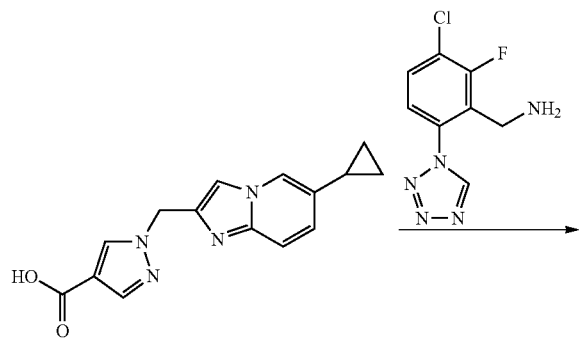

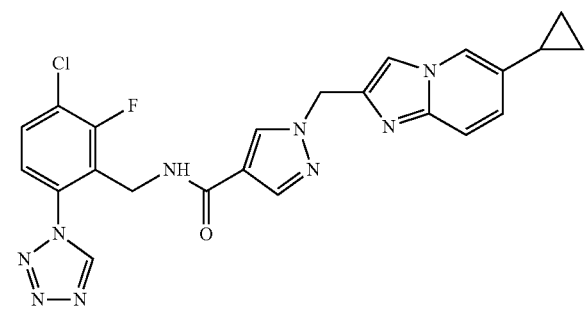

Synthesis of N-(3-chloro-2-fluoro-6-(1H-tetrazol-1-yl)benzyl)-1-((6-cyclopropylimidazo[1,2-a]pyridin-2-yl)methyl)-1H-pyrazole-4-carboxamide. N-(3-chloro-2-fluoro-6-(1H-tetrazol-1-yl)benzyl)-1-((6-cyclopropylimidazo[1,2-a]pyridin-2-yl)methyl)-1H-pyrazole-4-carboxamide was synthesized according to General Procedure A starting from 1-((6-cyclopropylimidazo[1,2-a]pyridin-2-yl)methyl)-1H-pyrazole-4-carboxylic acid and (3-chloro-2-fluoro-6-(1H-tetrazol-1-yl)phenyl)methanamine. The crude product was purified by flash chromatography (DCM/MeOH=10/1) to yield the product (14.5 mg, yield: 13.4%) as a white solid. ESI-MS [M+H]+: 491.9. $^1$H NMR (400 MHz, HDMSO) δ 9.84 (s, 1H), 8.47-8.45 (t, J=5.0 Hz, 1H), 8.33 (s, 1H), 8.10 (s, 1H), 7.86-7.82 (t, J=8.2 Hz, 1H), 7.72 (s, 2H), 7.50 (dd, J=8.7, 1.1 Hz, 1H), 7.39 (d, J=9.3 Hz, 1H), 6.99 (dd, J=9.4, 1.7 Hz, 1H), 5.37 (s, 2H), 4.26 (d, J=4.8 Hz, 2H), 1.94-1.88 (m, J=13.5, 8.4, 5.1 Hz, 2H), 0.94-0.89 (m, 2H), 0.68-0.64 (m, 2H).

Example 22

N-(3-chloro-2-fluoro-6-(2-oxa-6-azaspiro[3.3]heptan-6-yl)benzyl)-1-((6-cyclopropylimidazo[1,2-a]pyridin-2-yl)methyl)-1H-pyrazole-4-carboxamide (I-114)

Scheme 22

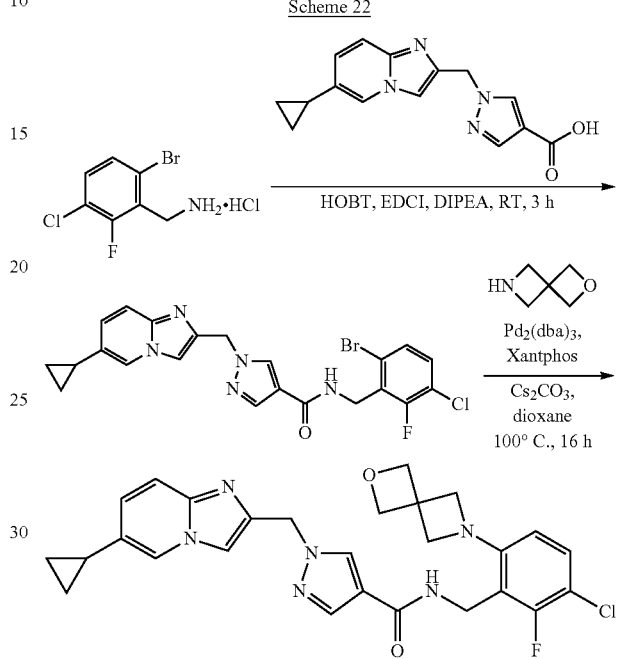

Synthesis of N-(6-bromo-3-chloro-2-fluorobenzyl)-1-((6-cyclopropylimidazo[1,2-a]pyridin-2-yl)methyl)-1H-1,2,3-triazole-4-carboxamide. To a solution of (6-bromo-3-chloro-2-fluorophenyl)methanamine hydrochloride (600 mg, 2.2 mmol) in DMF (5 mL) was added 1-((6-cyclopropylimidazo[1,2-a]pyridin-2-yl)methyl)-1H-pyrazole-4-carboxylic acid (568 mg, 2.0 mmol), HOBT (335 mg, 2.50 mmol), EDCI (483 mg, 2.52 mmol) and DIPEA (1.1 g, 8.4 mmol). The reaction mixture was stirred at RT for 3 h. Water (30 mL) was added and the mixture was extracted with EtOAc (30 mL×3). The combined organic layers were washed with brine, dried over Na2SO$_4$, and concentrated in vacuo to give the crude, which was purified by flash chromatography to give N-(6-bromo-3-chloro-2-fluorobenzyl)-1-((6-cyclopropylimidazo[1,2-a]pyridin-2-yl)methyl)-1H-pyrazole-4-carboxamide (362 mg, yield: 43%) as a white solid. ESI-MS [M+H]+: 502.2.

Synthesis of N-(3-chloro-2-fluoro-6-(2-oxa-6-azaspiro[3.3]heptan-6-yl)benzyl)-1-((6-cyclopropylimidazo[1,2-a]pyridin-2-yl)methyl)-1H-1,2,3-triazole-4-carboxamide. To a mixture of N-(6-bromo-3-chloro-2-fluorobenzyl)-1-((6-cyclopropylimidazo[1,2-a]pyridin-2-yl)methyl)-1H-1,2,3-triazole-4-carboxamide (50 mg, 0.099 mmol) in 1,4-dioxane (15 mL) was added 2-oxa-6-azaspiro[3.3]heptane (15 mg, 0.149 mmol), Pd$_2$(dba)$_3$ (20 mg, 0.022 mmol), Xantphos (20 mg, 0.035 mmol) and Cs$_2$CO$_3$ (0.5 mmol, 163 mmol). The reaction mixture was stirred at 100° C. for 3 h under N$_2$. The mixture was concentrated in vacuo and the residue was purified by Prep-HPLC to give N-(3-chloro-2-fluoro-6-(2-oxa-6-azaspiro[3.3]heptan-6-yl)benzyl)-1-((6-cyclopropylimidazo[1,2-a]pyridin-2-yl)methyl)-1H-1,2,3-triazole-4- carboxamide (22.9 mg, yield: 44%) as a yellow solid. ESI-MS [M+H]+: 520.9. Purity: 98.0 (214 nm), 98.1 (254 nm). ¹H NMR (400 MHz, DMSO) δ 8.33 (s, 1H), 8.26 (s, 1H), 8.12 (t, J=4.1 Hz, 1H), 7.88 (s, 1H), 7.75 (s, 1H), 7.40 (d, J=9.3 Hz, 1H), 7.31 (t, J=8.7 Hz, 1H), 6.99 (dd, J=9.4, 1.8 Hz, 1H), 6.33-6.27 (m, 1H), 5.39 (s, 2H), 4.66 (s, 4H), 4.30 (d, J=1.8 Hz, 2H), 4.12 (s, 4H), 1.96-1.86 (m, 1H), 0.93-0.85 (m, 2H), 0.71-0.62 (m, 2H).

Example 23

N-(4-carbamimidoyl-2,6-dimethylbenzyl)-1-((6-cyclopropylimidazo[1,2-a]pyridin-2-yl)methyl)-1H-pyrazole-4-carboxamide (I-103)

Scheme 23

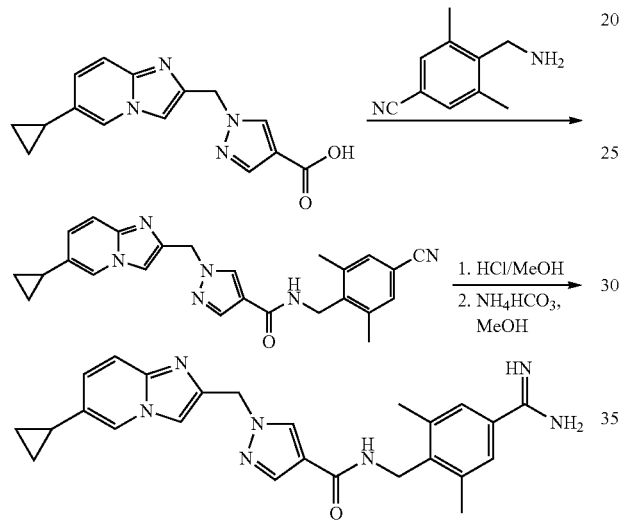

Synthesis of N-(4-cyano-2,6-dimethylbenzyl)-1-((6-cyclopropylimidazo[1,2-a]pyridin-2-yl)methyl)-1H-pyrazole-4-carboxamide. To a solution of 1-((6-cyclopropylimidazo[1,2-a]pyridin-2-yl)methyl)-1H-pyrazole-4-carboxylic acid (150.0 mg crude), 4-(aminomethyl)-3,5-dimethylbenzonitrile (82 mg, 0.51 mmol), 1-hydroxybenzotriazole (71 mg, 0.44 mmol) and EDCI (101 mg, 0.53 mmol) in DMF (10 mL) was added triethylamine (214 mg, 2.12 mmol). After stirring at room temperature for 2 hours, the reaction was quenched with saturated aqueous ammonium chloride solution (20 mL) and extracted with ethyl acetate (20×3). The combined organic layers were washed with brine (30 mL), dried over anhydrous sodium sulfate, filtered, and concentrated under reduced pressure to give the crude, which was purified by silica gel column chromatography (DCM/MeOH=20/1) to give N-(4-cyano-2,6-dimethylbenzyl)-1-((6-cyclopropylimidazo[1,2-a]pyridin-2-yl)methyl)-1H-pyrazole-4-carboxamide (50 mg, 22%). ESI-MS [M+H]+: 425.1.

Synthesis of N-(4-carbamimidoyl-2,6-dimethylbenzyl)-1-((6-cyclopropylimidazo[1,2-a]pyridin-2-yl)methyl)-1H-pyrazole-4-carboxamide. To a solution of N-(4-cyano-2,6-dimethylbenzyl)-1-((6-cyclopropylimidazo[1,2-a]pyridin-2-yl)methyl)-1H-pyrazole-4-carboxamide (50 mg, 0.11 mmol) in anhydrous MeOH (8 mL) was bubbled HCl (gas) for 1 h at 0° C. The reaction mixture was then stirred for 3 h at room temperature. The reaction was concentrated in vacuo, re-dissolved in MeOH (6 mL), and NH₄HCO₃ (220 mg, 2.78 mmol) was added slowly. The resulting mixture was stirred at room temperature for 16 h and then concentrated in vacuo to give the crude, which was purified by reverse-phase flash chromatography (Biotage SNAP C18, 12 g) eluting with a gradient of acetonitrile in water containing 0.1% formic acid (0-25% over 10 column volumes) to give N-(4-carbamimidoyl-2,6-dimethylbenzyl)-1-((6-cyclopropylimidazo[1,2-a]pyridin-2-yl)methyl)-1H-pyrazole-4-carboxamide (20 mg, 41%). ESI-MS [M+H]+: 442.1. ¹H NMR (400 MHz, DMSO, ppm) δ 11.49 (bs, 1H), 8.89 (bs, 0.7H), 8.44 (s, 1.62H), 8.33 (s, 1H), 8.22 (s, 1H), 8.18 (t, J=4.8 Hz, 1H), 7.83 (d, J=15.3 Hz, 1H), 7.74 (s, 1H), 7.49 (s, 2H), 7.38 (d, J=9.3 Hz, 1H), 6.99 (dd, J=9.4, 1.7 Hz, 1H), 5.40 (d, J=14.0 Hz, 2H), 4.45 (d, J=4.8 Hz, 2H), 2.41 (s, 6H), 1.99-1.84 (m, 1H), 0.97-0.87 (m, 2H), 0.71-0.62 (m, 2H).

Example 24

N-(6-cyano-2-fluoro-3-methoxybenzyl)-1-((8-cyano-6-cyclopropylimidazo[1,2-a]pyridin-2-yl)methyl)-1H-pyrazole-4-carboxamide (I-118)

Scheme 24

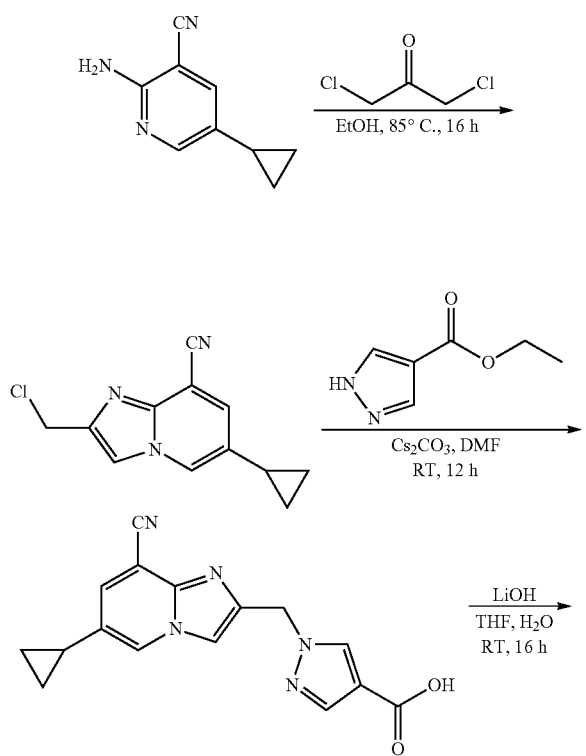

-continued

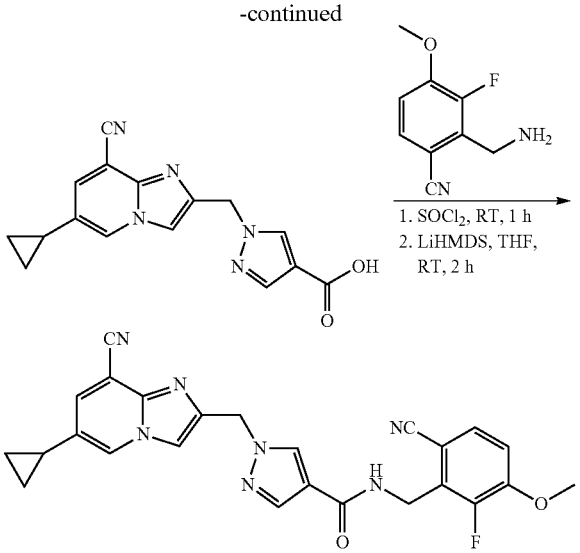

Synthesis of 2-amino-5-cyclopropylnicotinonitrile. To a mixture of 2-amino-5-bromonicotinonitrile (1 g, 5.1 mmol), cyclopropylboronic acid (647 mg, 7.6 mmol) and $K_3PO_4$ (3.78 g, 17.85 mmol) in toluene/$H_2O$ (20 mL/2 mL) was added Pd(OAc)$_2$ (114 mg, 0.51 mmol) and S-Phos (209 mg, 0.51 mmol). The mixture was stirred at 95° C. for 16 h. The reaction was cooled to room temperature, and the mixture was filtered. The filtrate was concentrated to give the crude product, which was purified by silica gel chromatography (EtOAc/PE=4/1) to give 2-amino-5-cyclopropylnicotinonitrile (570 mg, yield: 71%) as a yellow solid. ESI-MS [M+H]$^+$: 160.1

Synthesis of 2-(chloromethyl)-6-cyclopropylimidazo[1,2-a]pyridine-8-carbonitrile. To a solution of 2-amino-5-cyclopropylnicotinonitrile (570 mg, 3.58 mmol) in EtOH (20 mL) was added 1,3-dichloropropan-2-one (1.37 g, 10.75 mmol). The reaction mixture was stirred at 85° C. for 16 h. The reaction was concentrated and the residue was diluted with NaHCO$_3$(aq, 20 mL), extracted with EtOAc (50 mL×3). The combined organic layers were concentrated to give the crude, which was purified by silica gel chromatography (EtOAc/PE=2/1) to give 2-(chloromethyl)-6-cyclopropylimidazo[1,2-a]pyridine-8-carbonitrile (500 mg, yield: 58%) as a yellow solid. ESI-MS [M+H]$^+$: 232.1.

Synthesis of ethyl 1-((8-cyano-6-cyclopropylimidazo[1,2-a]pyridin-2-yl)methyl)-1H-pyrazole-4-carboxylate. To a solution 2-(chloromethyl)-6-cyclopropylimidazo[1,2-a]pyridine-8-carbonitrile (500 mg, 2.15 mmol) in DMF (10 mL) was added ethyl 1H-pyrazole-4-carboxylate (331 mg, 2.36 mmol) and Cs2CO3 (1.4 g, 4.3 mmol). The reaction mixture was stirred at RT for 12 h. Water (50 mL) was added and the mixture was extracted with EtOAc (50 mL×3). The combined organic layers were washed with brine, dried over Na$_2$SO$_4$, and concentrated in vacuo to give the crude, which was purified with silica gel chromatography (DCM/MeOH=20/1) to give ethyl 1-((8-cyano-6-cyclopropylimidazo[1,2-a]pyridin-2-yl)methyl)-1H-pyrazole-4-carboxylate (433 mg, yield: 60%) as a white solid. ESI-MS [M+H]+: 336.2.

Synthesis of 1-((8-cyano-6-cyclopropylimidazo[1,2-a]pyridin-2-yl)methyl)-1H-pyrazole-4-carboxylic acid. To a solution of 1-((8-cyano-6-cyclopropylimidazo[1,2-a]pyridin-2-yl)methyl)-1H-pyrazole-4-carboxylate (400 mg, 1.19 mmol) in THF (15 mL) and H$_2$O (5 mL) was added LiOH (464 mg, 146 mmol). The mixture was stirred at RT for 16 h. Most of the THF was removed in vacuo and the mixture was adjusted to pH 4-5 by addition of HCl (1 M). The resulting precipitate was collected and dried to give 1-((8-cyano-6-cyclopropylimidazo[1,2-a]pyridin-2-yl)methyl)-1H-pyrazole-4-carboxylic acid as a white solid (300 mg, 82%). ESI-MS [M+H]$^+$: 308.2.

Synthesis of N-(6-cyano-2-fluoro-3-methoxybenzyl)-1-((8-cyano-6-cyclopropylimidazo[1,2-a]pyridin-2-yl)methyl)-1H-pyrazole-4-carboxamide. A solution of 1-((8-cyano-6-cyclopropylimidazo[1,2-a]pyridin-2-yl)methyl)-1H-pyrazole-4-carboxylic acid (100 mg, 0.326 mmol) in SOCl$_2$ (0.5 mL) was stirred at RT for 1 h. After concentrating in vacuo, a solution of 2-(aminomethyl)-3-fluoro-4-methoxybenzonitrile (70 mg, 0.39 mmol) in THF (2 mL) was added, followed by LiHMDS (1 M in THF, 1.3 mL). The reaction mixture was stirred at RT for 2 h. The reaction was quenched with saturated aq. ammonium chloride (10 mL) and extracted with ethyl acetate (3×30 mL). The combined organic layers were washed with brine, dried over sodium sulfate and concentrated to give the residue, which was purified by Prep-TLC (MeOH/DCM=1/10) to give N-(6-cyano-2-fluoro-3-methoxybenzyl)-1-((8-cyano-6-cyclopropylimidazo[1,2-a]pyridin-2-yl)methyl)-1H-pyrazole-4-carboxamide (8 mg, yield: 5%) as a white solid. ESI-MS [M+H]+: 470.1. $^1$H NMR (400 MHz, DMSO) δ 8.68 (d, J=1.4 Hz, 1H), 8.59 (t, J=5.0 Hz, 1H), 8.24 (s, 1H), 7.87 (s, 2H), 7.78 (d, J=1.6 Hz, 1H), 7.67 (dd, J=8.6, 1.3 Hz, 1H), 7.28 (t, J=8.4 Hz, 1H), 5.48 (s, 2H), 4.51 (d, J=4.7 Hz, 2H), 3.92 (s, 3H), 1.97 (ddd, J=13.5, 8.5, 5.1 Hz, 1H), 0.99-0.90 (m, 2H), 0.79-0.71 (m, 2H).

Example 25

General Procedure B-1 for Amide Synthesis:

Scheme 25

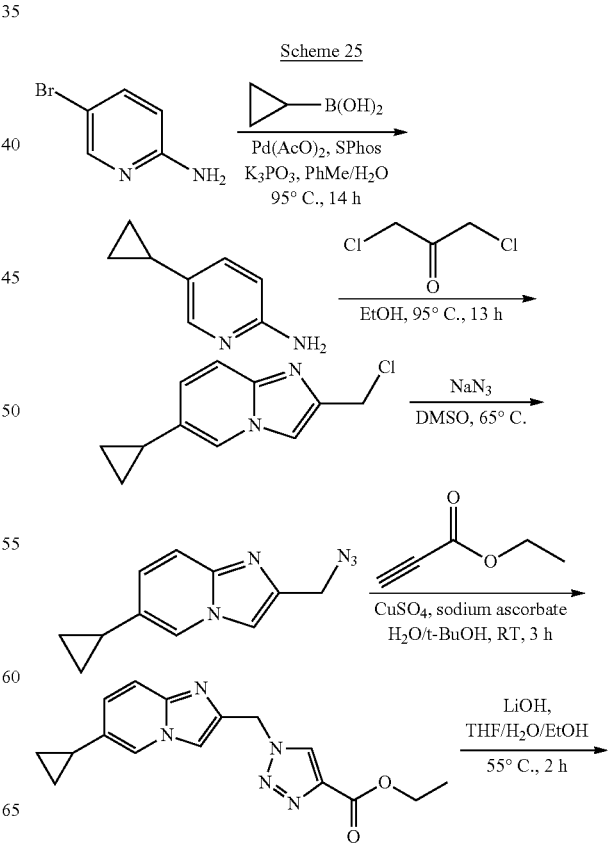

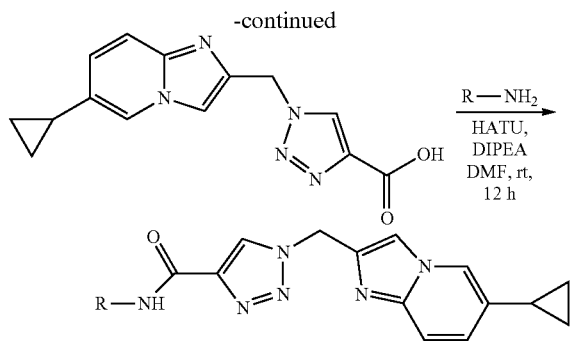

Synthesis of 5-cyclopropylpyridin-2-amine. A mixture of 5-bromopyridin-2-amine (100 g, 585 mmol), cyclopropylboronic acid (60 g, 701 mmol), Pd(AcO)$_2$ (6.5 g, 29 mmol), SPhos (24 g, 58.5 mmol) and K$_3$PO$_4$ (372 g, 1.755 mol) in toluene/H$_2$O (1.2 L/0.12 L) was stirred at 90° C. for 14 h under N$_2$. The reaction was concentrated in vacuo to give the crude, which was purified with silica gel chromatography (PE/EA=1/2) to give the 5-cyclopropylpyridin-2-amine (61 g, yield: 78%) as a yellow solid. ESI-MS [M+H]$^+$: 135.1.

Synthesis of 2-(chloromethyl)-6-cyclopropylimidazo[1,2-a]pyridine. A mixture of 5-cyclopropylpyridin-2-amine (61 g, 455 mmol) and 1,3-dichloropropan-2-one (172 g, 1365 mmol) in EtOH (1 L) was stirred at 95° C. for 13 h. The reaction was concentrated to remove the EtOH. The pH of the residue was adjusted to 9 by addition of aqueous NaHCO$_3$ and extracted with EtOAc (1 L x 3). The combined organic layers were washed with brine, dried over Na$_2$SO$_4$ and concentrated in vacuo to give the crude, which was purified with silica gel chromatography (EA) to give the 2-(chloromethyl)-6-cyclopropylimidazo[1,2-a]pyridine (40 g, yield: 42%) as a yellow solid. ESI-MS [M+H]$^+$: 207.1.

Synthesis of 2-(azidomethyl)-6-cyclopropylimidazo[1,2-a]pyridine. To a solution of 2-(chloromethyl)-6-cyclopropylimidazo[1,2-a]pyridine (40 g, 193 mmol) in DMF (600 mL) was added NaN$_3$ (18.8 g, 290 mmol). The resulting reaction was stirred at RT for 2 h.

The reaction was diluted with H$_2$O (500 mL) and extracted with EtOAc (500 mL×3). The combined organic layers were washed with brine, dried over Na$_2$SO$_4$ and concentrated in vacuo to give the crude, which was purified with silica gel chromatography (PE/EA=2/1) to give the 2-(azidomethyl)-6-cyclopropylimidazo[1,2-a]pyridine (35 g, yield: 85%) as a yellow solid. ESI-MS [M+H]$^+$: 214.1.

Synthesis of ethyl 1-((6-cyclopropylimidazo[1,2-a]pyridin-2-yl)methyl)-1H-1,2,3-triazole-4-carboxylate. A mixture of 2-(azidomethyl)-6-cyclopropylimidazo[1,2-a]pyridine (35 g, 163.5 mmol), ethyl propiolate (17.6 g, 180 mmol), CuSO$_4$ (2.6 g, 16.35 mmol) and sodium ascorbate (3.3 g, 16.35 mmol) in H$_2$O/t-BuOH (150 mL/150 mL) was stirred at RT for 3 h. Yellow solid was precipitated after 3 h and the mixture was filtered. The cake was dried to give the ethyl 1-((6-cyclopropylimidazo[1,2-a]pyridin-2-yl)methyl)-1H-1,2,3-triazole-4-carboxylate (29 g, yield: 57%) as a yellow solid, which was used in the next step without further purification. ESI-MS [M+H]$^+$: 312.1.

Synthesis of 1-((6-cyclopropylimidazo[1,2-a]pyridin-2-yl)methyl)-1H-1,2,3-triazole-4-carboxylic acid. A mixture of ethyl 1-((6-cyclopropylimidazo[1,2-a]pyridin-2-yl)methyl)-1H-1,2,3-triazole-4-carboxylate (29 g, 93.2 mmol) and LiOH (6.7 g, 279.6 mmol, solution in 50 mL H$_2$O) in THF/EtOH (150 mL/150 mL) was stirred at 50° C. for 2 h. The reaction was concentrated to remove most of the solvent. The pH of the residue was adjusted to 4 by 2 N HCl and a pink solid was precipitated out. The mixture was filtered and the filter cake was dried to give 1-((6-cyclopropylimidazo[1,2-a]pyridin-2-yl)methyl)-1H-1,2,3-triazole-4-carboxylic acid (20 g, 77%) as a pink solid. ESI-MS [M+H]$^+$: 284.1.

General synthesis of amide compounds (Procedure B-1). To a solution of 1-((6-cyclopropylimidazo[1,2-a]pyridin-2-yl)methyl)-1H-1,2,3-triazole-4-carboxylic acid (60 mg, 0.21 mmol), amine (0.32 mmol) and HATU (120 mg, 0.31 mmol) in DMF (8 mL) was added DIPEA (81 mg, 0.63 mmol). The reaction mixture was stirred at room temperature for 12 h.

Water (25 mL) was added and the mixture was extracted with EtOAc (30 mL×3). The combined organic layers were washed with brine, dried over Na$_2$SO$_4$, filtered, and concentrated in vacuo to give the crude product, which was purified by Prep-TLC, Prep-HPLC, or silica gel chromatography to give the desired product.

The following compounds were synthesized according to General Procedure B-1 starting from 1-((6-cyclopropylimidazo[1,2-a]pyridin-2-yl)methyl)-1H-1,2,3-triazole-4-carboxylic acid and the indicated amine: N-(3-chloro-2-fluoro-6-(1H-tetrazol-1-yl)benzyl)-1-((6-cyclopropylimidazo[1,2-a]pyridin-2-yl)methyl)-1H-1,2,3-triazole-4-carboxamide (I-106), 1-((6-cyclopropylimidazo[1,2-a]pyridin-2-yl)methyl)-N-(2-fluoro-3-methoxy-6-(1H-tetrazol-1-yl)benzyl)-1H-1,2,3-triazole-4-carboxamide (I-105), 1-((6-cyclopropylimidazo[1,2-a]pyridin-2-yl)methyl)-N-(2-fluoro-3-methoxybenzyl)-1H-1,2,3-triazole-4-carboxamide (I-100), N-(6-chloro-8,9-dihydro-7H-imidazo[4,5,1-ij]quinolin-9-yl)-1-((6-cyclopropylimidazo[1,2-a]pyridin-2-yl)methyl)-1H-1,2,3-triazole-4-carboxamide (I-135), 1-((6-cyclopropylimidazo[1,2-a]pyridin-2-yl)methyl)-N-(2-fluoro-6-(1H-tetrazol-1-yl)-3-(trifluoromethoxy)benzyl)-1H-1,2,3-triazole-4-carboxamide (I-98), 1-((6-cyclopropylimidazo[1,2-a]pyridin-2-yl)methyl)-N-(2-fluoro-3-methoxy-6-(4H-1,2,4-triazol-4-yl)benzyl)-1H-1,2,3-triazole-4-carboxamide (I-96), 1-((6-cyclopropylimidazo[1,2-a]pyridin-2-yl)methyl)-N-(2-fluoro-3-methoxy-6-(1H-pyrazol-1-yl)benzyl)-1H-1,2,3-triazole-4-carboxamide (I-95), N-(3-bromo-2-fluoro-6-(1H-tetrazol-1-yl)benzyl)-1-((6-cyclopropylimidazo[1,2-a]pyridin-2-yl)methyl)-1H-1,2,3-triazole-4-carboxamide (I-X), methyl 2'-((1-((6-cyclopropylimidazo[1,2-a]pyridin-2-yl)methyl)-1H-1,2,3-triazole-4-carboxamido)methyl)-3'-fluoro-4'-methoxy-[1,1'-biphenyl]-4-carboxylate (I-87), 1-((6-cyclopropylimidazo[1,2-a]pyridin-2-yl)methyl)-N-(2-fluoro-3-methoxy-6-(pyridazin-4-yl)benzyl)-1H-1,2,3-triazole-4-carboxamide (I-86), 1-((6-cyclopropylimidazo[1,2-a]pyridin-2-yl)methyl)-N-(3-ethyl-2-fluoro-6-(1H-tetrazol-1-yl)benzyl)-1H-1,2,3-triazole-4-carboxamide (I-83), N-(3-chloro-6-(difluoromethyl)-2-fluorobenzyl)-1-((6-cyclopropylimidazo[1,2-a]pyridin-2-yl)methyl)-1H-1,2,3-triazole-4-carboxamide (I-79), N-(3-cyclopropyl-2-fluoro-6-(1H-tetrazol-1-yl)benzyl)-1-((6-cyclopropylimidazo[1,2-a]pyridin-2-yl)methyl)-1H-1,2,3-triazole-4-carboxamide (I-78), 1-((6-cyclopropylimidazo[1,2-a]pyridin-2-yl)methyl)-N-(imidazo[1,2-a]pyridin-6-ylmethyl)-1H-1,2,3-triazole-4-carboxamide (I-136), 1-((6-cyclopropylimidazo[1,2-a]pyridin-2-yl)methyl)-N-(2-fluoro-3-methoxy-6-(1H-1,2,3-triazol-1-yl)benzyl)-1H-1,2,3-triazole-4-carboxamide (I-76), methyl 5-(2-((1-((6-cyclopropylimidazo[1,2-a]pyridin-2-yl)methyl)-1H-1,2,3-triazole-4-carboxamido)methyl)-3-fluoro-4-methoxyphenyl)pyrimidine-2-carboxylate (I-75), 1-((6-cyclopropylimidazo[1,2-a]pyridin-2-yl)methyl)-N-(6-(3,4-dimethyl-1H-pyrazol-1-yl)-2-fluoro-3-methoxybenzyl)-1H-1,2,3-triazole-4-carboxamide (I-73), 1-((6-cyclopropylimidazo[1,2-a]pyridin-2-yl)methyl)-N-(2-fluoro-6-(imidazo[1,2-a]pyridin-2-yl)-3-methoxybenzyl)-1H-1,2,3-triazole-4-carboxamide (I-70), 1-((6-cyclopropylimidazo[1,2-a]pyridin-2-yl)methyl)-N-(2-fluoro-3-methoxy-6-(1H-pyrazol-4-yl)benzyl)-1H-1,2,3-triazole-4-carboxamide (I-67), 1-((6-cyclopropylimidazo[1,2-a]pyridin-2-yl)methyl)-N-(2-fluoro-3-methoxy-6-(1H-tetrazol-1-yl)benzyl)-N-methyl-1H-1,2,3-triazole-4-carboxamide (I-66), N-((3-chloro-1H-indol-5-yl)methyl)-1-((6-cyclopropylimidazo[1,2-a]pyridin-2-yl)methyl)-1H-1,2,3-triazole-4-carboxamide (I-65), 1-((6-cyclopropylimidazo[1,2-a]pyridin-2-yl)methyl)-N-(2-fluoro-3-methoxy-6-(pyrazolo[1,5-a]pyridin-2-yl)benzyl)-1H-1,2,3-triazole-4-carboxamide (I 63), 1-((6-cyclopropylimidazo[1,2-a]pyridin-2-yl)methyl)-N-(2-fluoro-3-methoxy-6-(3-(trifluoromethyl)-1H-1,2,4-triazol-1-yl)benzyl)-1H-1,2,3-triazole-4-carboxamide (I-52), 1-((6-cyclopropylimidazo[1,2-a]pyridin-2-yl)methyl)-N-(2-fluoro-3-methoxy-6-(1H-1,2,3-triazol-4-yl)benzyl)-1H-1,2,3-triazole-4-carboxamide (I-49), 1-((6-cyclopropylimidazo[1,2-a]pyridin-2-yl)methyl)-N-(1-(2-fluoro-3-methoxy-6-(1H-tetrazol-1-yl)phenyl)ethyl)-1H-1,2,3-triazole-4-carboxamide (I-31), N-((6-amino-2,4-dimethylpyridin-3-yl)methyl)-1-((6-cyclopropylimidazo[1,2-a]pyridin-2-yl)methyl)-1H-1,2,3-triazole-4-carboxamide (I-26), N-((5-amino-1,3,4-thiadiazol-2-yl)methyl)-1-((6-cyclopropylimidazo[1,2-a]pyridin-2-yl)methyl)-1H-1,2,3-triazole-4-carboxamide (I-20), N-((5-amino-1,3,4-oxadiazol-2-yl)methyl)-1-((6-cyclopropylimidazo[1,2-a]pyridin-2-yl)methyl)-1H-1,2,3-triazole-4-carboxamide (I-19), N-((2-aminothiazol-5-yl)methyl)-1-((6-cyclopropylimidazo[1,2-a]pyridin-2-yl)methyl)-1H-1,2,3-triazole-4-carboxamide (I-18), and N-(6-(4-chloro-1H-1,2,3-triazol-1-yl)-2-fluoro-3-methoxybenzyl)-1-((6-cyclopropylimidazo[1,2-a]pyridin-2-yl)methyl)-1H-1,2,3-triazole-4-carboxamide (I-1).

Example 26

General Procedure B-2 for Amide Synthesis:

Scheme 26

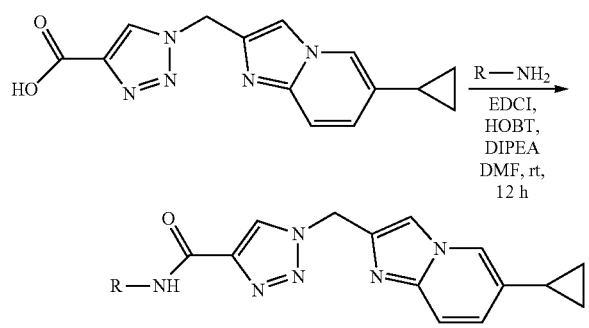

General synthesis of amide compounds (Procedure B-2). To a solution of 1-((6-cyclopropylimidazo[1,2-a]pyridin-2-yl)methyl)-1H-1,2,3-triazole-4-carboxylic acid (150 mg, 0.53 mmol), amine (1.01 mmol), HOBT (130 mg, 0.96 mmol) and EDCI (184 mg, 0.96 mmol) in DMF (10 mL) was added DIPEA (413 mg, 3.2 mmol). The reaction mixture was stirred at room temperature for 12 h. Water (20 mL) was added and the mixture was extracted with EtOAc (30 mL×3). The combined organic layers were washed with brine, dried over Na$_2$SO$_4$, filtered, and concentrated in vacuo to give the crude product, which was purified by Prep-TLC, Prep-HPLC, or silica gel chromatography to give the desired product.

The following compounds were synthesized according to General Procedure B-2 starting from 1-((6-cyclopropylimidazo[1,2-a]pyridin-2-yl)methyl)-1H-1,2,3-triazole-4-carboxylic acid and the indicated amine: 4-((4-carbamimidoyl-2,6-dimethylbenzyl)amino)-6-((6-cyclopropylimidazo[1,2-a]pyridin-2-yl)methoxy)pyrimidine-2-carboxylic acid (I-115), N-(6-bromo-2-fluoro-3-methoxybenzyl)-1-((6-cyclopropylimidazo[1,2-a]pyridin-2-yl)methyl)-1H-1,2,3-triazole-4-carboxamide (I-102), 1-((6-cyclopropylimidazo[1,2-a]pyridin-2-yl)methyl)-N-(2-fluoro-3-methoxy-6-(pyridin-4-yl)benzyl)-1H-1,2,3-triazole-4-carboxamide (I-101), N-(benzo[b]thiophen-5-ylmethyl)-1-((6-cyclopropylimidazo[1,2-a]pyridin-2-yl)methyl)-1H-1,2,3-triazole-4-carboxamide (I-84), 7-(6-cyclopropylimidazo[1,2-a]pyridin-2-yl)-N-(2-fluoro-3-methoxy-6-(1H-tetrazol-1-yl)benzyl)-6,7-dihydro-5H-pyrrolo[1,2-b][1,2,4]triazole-2-carboxamide (I-82), N-(3-chloro-2-methyl-6-(1H-tetrazol-1-yl)benzyl)-1-((6-cyclopropylimidazo[1,2-a]pyridin-2-yl)methyl)-1H-1,2,3-triazole-4-carboxamide (I-80), N-((6-chlorobenzo[b]thiophen-2-yl)methyl)-1-((6-cyclopropylimidazo[1,2-a]pyridin-2-yl)methyl)-1H-1,2,3-triazole-4-carboxamide (I-77), N-((5-cyano-3-fluoro-2-methoxypyridin-4-yl)methyl)-1-((6-cyclopropylimidazo[1,2-a]pyridin-2-yl)methyl)-1H-1,2,3-triazole-4-carboxamide (I-72), 1-((6-cyclopropylimidazo[1,2-a]pyridin-2-yl)methyl)-N-(2,6-difluoro-3-methoxybenzyl)-1H-1,2,3-triazole-4-carboxamide (I-64), 1-((6-cyclopropylimidazo[1,2-a]pyridin-2-yl)methyl)-N-(2-fluoro-3-methoxy-6-(3-(trifluoromethyl)-1H-pyrazol-1-yl)benzyl)-1H-1,2,3-triazole-4-carboxamide (I-62), N-benzyl-1-((6-cyclopropylimidazo[1,2-a]pyridin-2-yl)methyl)-1H-1,2,3-triazole-4-carboxamide (I-60), 1-((6-cyclopropylimidazo[1,2-a]pyridin-2-yl)methyl)-N-(2-fluoro-3-methoxy-6-(methylsulfinyl)benzyl)-1H-1,2,3-triazole-4-carboxamide (I-58), 1-((6-cyclopropylimidazo[1,2-a]pyridin-2-yl)methyl)-N-(6-(N,N-dimethylsulfamoyl)-2-fluoro-3-methoxybenzyl)-1H-1,2,3-triazole-4-carboxamide (I-57), 1-((6-cyclopropylimidazo[1,2-a]pyridin-2-yl)methyl)-N-(2-(methylsulfonyl)benzyl)-1H-1,2,3-triazole-4-carboxamide (I-51), 1-((6-cyclopropylimidazo[1,2-a]pyridin-2-yl)methyl)-N-(2-fluoro-3-methoxy-6-(morpholinosulfonyl)benzyl)-1H-1,2,3-triazole-4-carboxamide (I-48), N-(1-amino-6,7-dihydro-5H-cyclopenta[c]pyridin-5-yl)-1-((6-cyclopropylimidazo[1,2-a]pyridin-2-yl)methyl)-1H-1,2,3-triazole-4-carboxamide (I-23), N-((5-amino-4H-1,2,4-triazol-3-yl)methyl)-1-((6-cyclopropylimidazo[1,2-a]pyridin-2-yl)methyl)-1H-1,2,3-triazole-4-carboxamide (I-21), N-(1-amino-3-methyl-6,7-dihydro-5H-cyclopenta[c]pyridin-5-yl)-1-((6-cyclopropylimidazo[1,2-a]pyridin-2-yl)methyl)-1H-1,2,3-triazole-4-carboxamide (I-16), N-((4-chlorothieno[3,2-c]pyridin-2-yl)methyl)-1-((6-cyclopropylimidazo[1,2-a]pyridin-2-yl)methyl)-1H-1,2,3-triazole-4-carboxamide (I-11), 1-((6-cyclopropylimidazo[1,2-a]pyridin-2-yl)methyl)-N-((3-fluoro-4-methoxypyridin-2-yl)methyl)-1H-1,2,3-triazole-4-carboxamide (I-7), and N-(5-chloro-2-(4-chloro-1H-1,2,3-triazol-1-yl)benzyl)-1-((6-cyclopropylimidazo[1,2-a]pyridin-2-yl)methyl)-1H-1,2,3-triazole-4-carboxamide (I-3).

Example 27

4-((4-carbamimidoyl-2,6-dimethylbenzyl)amino)-6-((6-cyclopropylimidazo[1,2-a]pyridin-2-yl)methoxy)pyrimidine-2-carboxylic acid (I-115)

Scheme 27

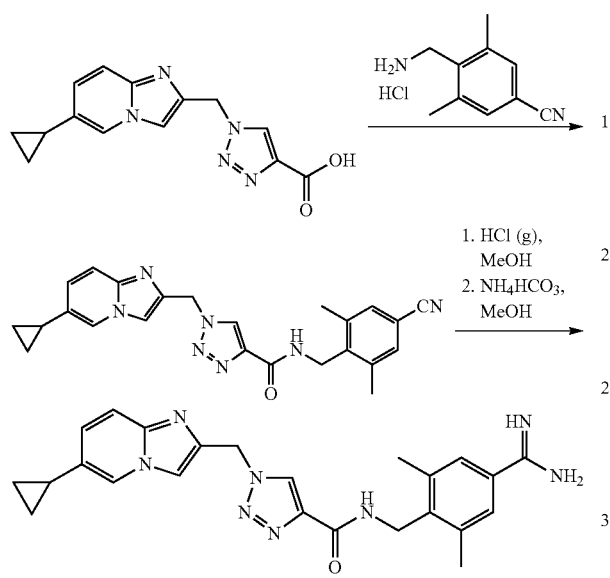

Synthesis of N-(4-cyano-2,6-dimethylbenzyl)-1-((6-cyclopropylimidazo[1,2-a]pyridin-2-yl)methyl)-1H-1,2,3-triazole-4-carboxamide. N-(4-cyano-2,6-dimethylbenzyl)-1-((6-cyclopropylimidazo[1,2-a]pyridin-2-yl)methyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and 4-(aminomethyl)-3,5-dimethylbenzonitrile hydrochloride. The crude product was purified by prep-TLC (DCM/MeOH=15/1) to yield the product (100 mg, yield: 44.3%) as a yellow solid. ESI-MS [M+H]$^+$: 426.1

Synthesis of N-(4-carbamimidoyl-2,6-dimethylbenzyl)-1-((6-cyclopropylimidazo[1,2-a]pyridin-2-yl)methyl)-1H-1,2,3-triazole-4-carboxamide. To a solution of N-(4-cyano-2,6-dimethylbenzyl)-1-((6-cyclopropylimidazo[1,2-a]pyridin-2-yl)methyl)-1H-1,2,3-triazole-4-carboxamide (100 mg, 0.24 mmol) in MeOH (10 mL) was bubbled HCl (g) for 4 h. The reaction mixture was concentrated in vacuo, and MeOH (15 mL) and NH$_4$HCO$_3$ (182 mg, 2.3 mmol) were added. The resulting mixture was stirred at room temperature for 13 h. The reaction was concentrated in vacuo to give the crude, which was purified by Prep-HPLC to give N-(4-carbamimidoyl-2,6-dimethylbenzyl)-1-((6-cyclopropylimidazo[1,2-a]pyridin-2-yl)methyl)-1H-1,2,3-triazole-4-carboxamide as a white solid. ESI-MS [M+H]$^+$: 443.0 $^1$H NMR (400 MHz, DMSO) δ 11.07 (s, 1H), 8.88 (s, 1H), 8.71 (t, J=5.3 Hz, 1H), 8.55 (s, 1H), 8.43 (s, 1H), 8.35 (s, 1H), 7.84 (s, 1H), 7.46 (s, 2H), 7.40 (d, J=9.3 Hz, 1H), 7.01 (dd, J=9.4, 1.7 Hz, 1H), 5.72 (s, 2H), 4.51 (d, J=5.3 Hz, 2H), 2.44 (s, 6H), 1.98-1.89 (m, 1H), 0.94-0.90 (m, 2H), 0.69-0.65 (m, 2H).

Example 28

N-(3-chloro-2-fluoro-6-(1H-tetrazol-1-yl)benzyl)-1-((6-cyclopropylimidazo[1,2-a]pyridin-2-yl)methyl)-1H-1,2,3-triazole-4-carboxamide (I-106)

Scheme 28

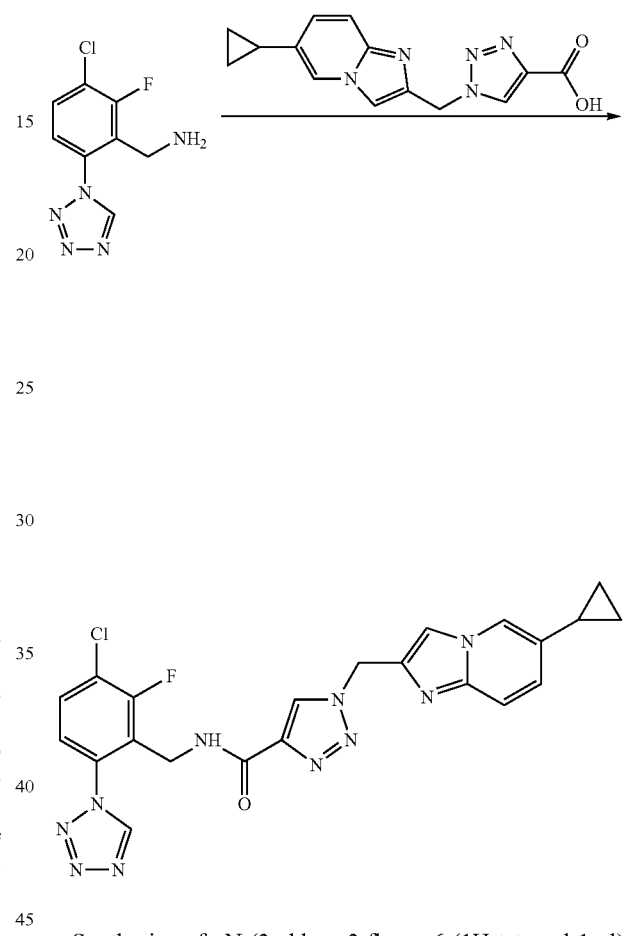

Synthesis of N-(3-chloro-2-fluoro-6-(1H-tetrazol-1-yl)benzyl)-1-((6-cyclopropylimidazo[1,2-a]pyridin-2-yl)methyl)-1H-1,2,3-triazole-4-carboxamide. N-(4-cyano-2,6-dimethylbenzyl)-1-((6-cyclopropylimidazo[1,2-a]pyridin-2-yl)methyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (3-chloro-2-fluoro-6-(1H-tetrazol-1-yl)phenyl)methanamine. The crude product was purified by flash chromatography (DCM/MeOH=10/1) to yield the product (40 mg 45%) as a white solid. ESI-MS [M+H]+: 493.1. Purity: 99.32 (214 nm), 100.00 (254 nm). $^1$H NMR (400 MHz, DMSO) δ 9.85 (s, 1H), 8.90 (t, J=5.4 Hz, 1H), 8.49 (s, 1H), 8.34 (s, 1H), 7.86-7.82 (m, 2H), 7.50 (dd, J=8.7 Hz, 1.3 Hz, 1H), 7.40 (d, J=9.3 Hz, 1H), 7.00 (dd, J=9.4 Hz, 1.7 Hz, 1H), 5.70 (s, 2H), 4.37 (d, J=5.1 Hz, 2H), 1.94-1.90 (m, 1H), 0.93-0.90 (m, 2H), 0.69-0.65 (m, 2H).

Example 29

1-((6-cyclopropylimidazo[1,2-a]pyridin-2-yl)methyl)-N-(2-fluoro-3-methoxy-6-(1H-tetrazol-1-yl)benzyl)-1H-1,2,3-triazole-4-carboxamide (I-105)

Scheme 29

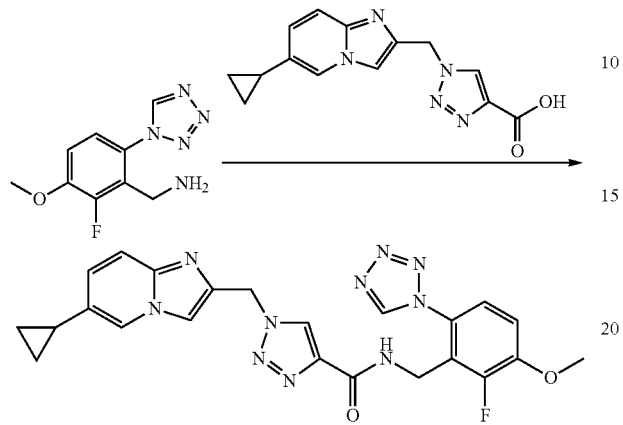

Synthesis of 1-((6-cyclopropylimidazo[1,2-a]pyridin-2-yl)methyl)-N-(2-fluoro-3-methoxy-6-(1H-tetrazol-1-yl)benzyl)-1H-1,2,3-triazole-4-carboxamide. 1-((6-cyclopropylimidazo[1,2-a]pyridin-2-yl)methyl)-N-(2-fluoro-3-methoxy-6-(1H-tetrazol-1-yl)benzyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (2-fluoro-3-methoxy-6-(1H-tetrazol-1-yl)phenyl)methanamine. The crude product was purified by prep-TLC (DCM/MeOH=13/1) to yield the product (14.3 mg, yield: 21%) as a white solid. ESI-MS [M+H]+: 489.2. $^1$H NMR (400 MHz, DMSO) δ 9.74 (s, 1H), 8.76 (t, J=5.4 Hz, 1H), 8.49 (s, 1H), 8.36 (s, 1H), 7.84 (s, 1H), 7.44-7.32 (m, 3H), 7.06-7.03 (m, 1H), 5.72 (s, 2H), 4.29 (d, J=5.2 Hz, 2H), 3.92 (s, 3H), 1.93-1.90 (m, 1H), 0.93-0.90 (m, 2H), 0.70-0.67 (m, 2H).

Example 30

N-(6-bromo-2-fluoro-3-methoxybenzyl)-1-((6-cyclopropylimidazo[1,2-a]pyridin-2-yl)methyl)-1H-1,2,3-triazole-4-carboxamide (I-102)

Scheme 30

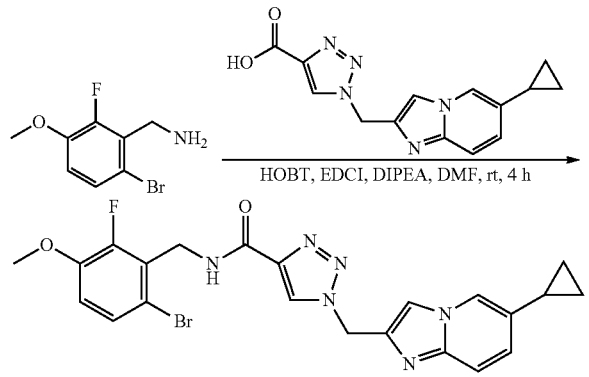

Synthesis of N-(6-bromo-2-fluoro-3-methoxybenzyl)-1-((6-cyclopropylimidazo[1,2-a]pyridin-2-yl)methyl)-1H-1,2,3-triazole-4-carboxamide. 1-((6-cyclopropylimidazo[1,2-a]pyridin-2-yl)methyl)-N-(2-fluoro-3-methoxy-6-(1H-tetrazol-1-yl)benzyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and (6-bromo-2-fluoro-3-methoxyphenyl)methanamine. The crude product was purified by prep-TLC (DCM/MeOH=20/1) to yield the product (390 mg, yield: 84%) as a white solid. ESI-MS [M+H]+: 499.1. $^1$H NMR (400 MHz, DMSO) δ 8.68-8.61 (m, 1H), 8.55 (s, 1H), 8.35 (s, 1H), 7.83 (s, 1H), 7.42-7.39 (m, 2H), 7.09 (t, J=8.7 Hz, 1H), 7.01 (d, J=9.3 Hz, 1H), 5.72 (s, 2H), 4.55 (d, J=2.8 Hz, 2H), 3.83 (s, 3H), 1.95-1.89 (m, 1H), 0.93-0.91 (m, 2H), 0.68-0.67 (m, 2H).

Example 31

1-((6-cyclopropylimidazo[1,2-a]pyridin-2-yl)methyl)-N-(2-fluoro-6-(1H-imidazol-1-yl)-3-methoxybenzyl)-1H-1,2,3-triazole-4-carboxamide (I-104)

Scheme 31

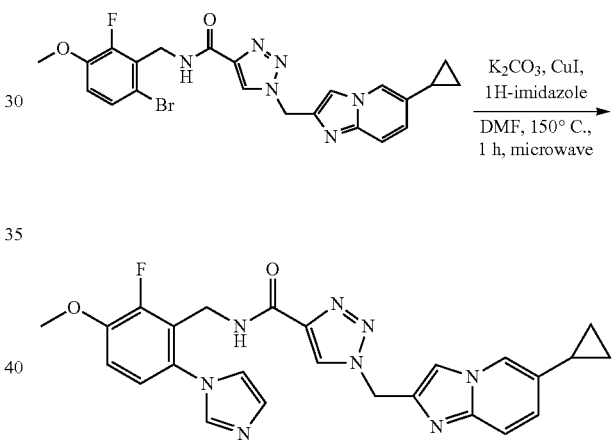

Synthesis of 1-((6-cyclopropylimidazo[1,2-a]pyridin-2-yl)methyl)-N-(2-fluoro-6-(1H-imidazol-1-yl)-3-methoxybenzyl)-1H-1,2,3-triazole-4-carboxamide. A mixture of N-(6-bromo-2-fluoro-3-methoxybenzyl)-1-((6-cyclopropylimidazo[1,2-a]pyridin-2-yl)methyl)-1H-1,2,3-triazole-4-carboxamide (75 mg, 0.15 mmol), 1H-imidazole (81 mg, 1.19 mmol), K$_2$CO$_3$ (245 mg, 1.78 mmol) and CuI (33 mg, 0.17 mmol) in DMF (2 mL) was stirred at 150° C. in the microwave for 1 h. The reaction mixture was diluted with H$_2$O (20 mL) and extracted with EtOAc (30 mL×3). The organic layers were concentrated to give the crude, which was purified by Prep-TLC (DCM:MeOH=20:1) to give 1-((6-cyclopropylimidazo[1,2-a]pyridin-2-yl)methyl)-N-(2-fluoro-6-(1H-imidazol-1-yl)-3-methoxybenzyl)-1H-1,2,3-triazole-4-carboxamide (26.1 mg, yield: 36%) as a white solid. ESI-MS [M+H]+: 487.1. Purity: 99.51% (214 nm), 100.00% (254 nm). $^1$H NMR (400 MHz, DMSO) δ 8.72 (t, J=4.9 Hz, 1H), 8.52 (s, 1H), 8.35 (s, 1H), 7.82 (d, J=5.0 Hz, 2H), 7.42-7.39 (m, 2H), 7.24 (t, J=8.8 Hz, 1H), 7.16 (d, J=9.0 Hz, 1H), 7.04-7.00 (m, 2H), 5.72 (s, 2H), 4.23 (d, J=4.7 Hz, 2H), 3.88 (s, 3H), 1.96-1.89 (m, 1H), 0.92-0.89 (m, 2H), 0.69-0.65 (m, 2H).

Example 32

1-((6-cyclopropylimidazo[1,2-a]pyridin-2-yl)methyl)-N-(2-fluoro-3-methoxy-6-(1,3,4-oxadiazol-2-yl)benzyl)-1H-1,2,3-triazole-4-carboxamide (I-97)

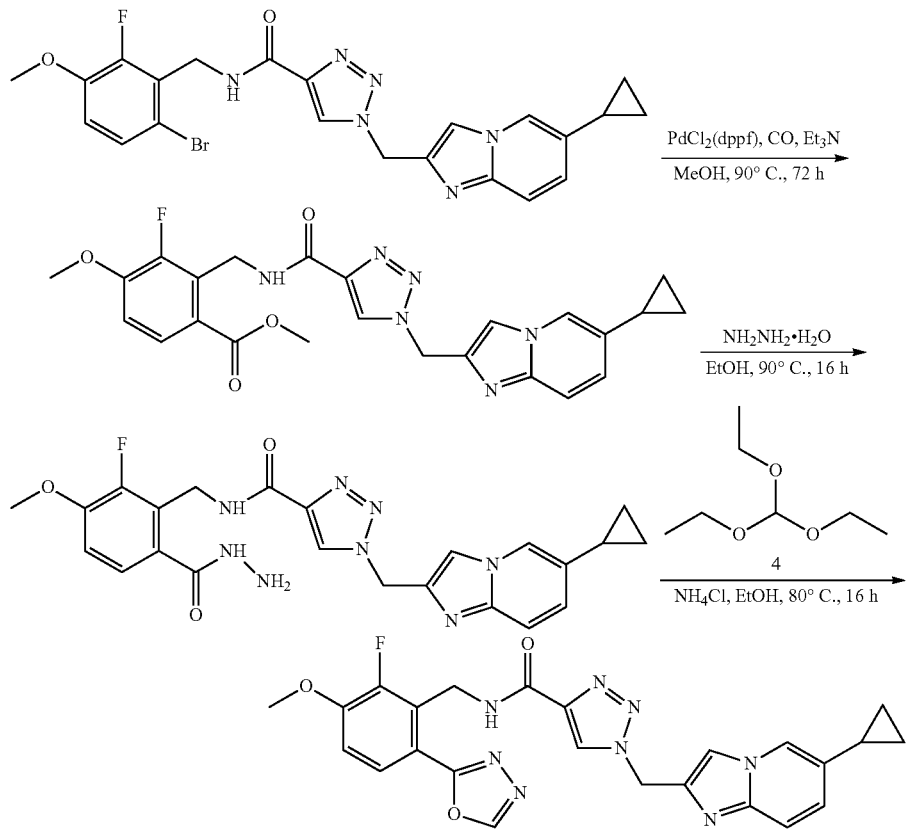

Scheme 32

Synthesis of methyl 2-((1-((6-cyclopropylimidazo[1,2-a]pyridin-2-yl)methyl)-1H-1,2,3-triazole-4-carboxamido)methyl)-3-fluoro-4-methoxybenzoate. A solution of N-(6-bromo-2-fluoro-3-methoxybenzyl)-1-((6-cyclopropylimidazo[1,2-a]pyridin-2-yl)methyl)-1H-1,2,3-triazole-4-carboxamide (100 mg, 0.20 mmol), Pd(dppf)Cl$_2$ (33 mg, 0.045 mmol) and Et$_3$N (76 mg, 0.75 mmol) in MeOH (10 mL) was stirred at 90° C. under CO for 72 h. The solution was filtered and the filtrate extracted with EtOAc (50 mL×2). The combined organic layers were concentrated and purified by Prep-TLC (DCM/MeOH=15:1) to give methyl 2-((1-((6-cyclopropylimidazo[1,2-a]pyridin-2-yl)methyl)-1H-1,2,3-triazole-4-carboxamido)methyl)-3-fluoro-4-methoxybenzoate as a white solid (35 mg, yield: 36.6%). ESI-MS [M+H]$^+$: 479.1.

Synthesis of 1-((6-cyclopropylimidazo[1,2-a]pyridin-2-yl)methyl)-N-(2-fluoro-6-(hydrazinecarbonyl)-3-methoxybenzyl)-1H-1,2,3-triazole-4-carboxamide. A solution of methyl 2-((1-((6-cyclopropylimidazo[1,2-a]pyridin-2-yl)methyl)-1H-1,2,3-triazole-4-carboxamido)methyl)-3-fluoro-4-methoxybenzoate (35 mg, 0.073 mmol) and hydrazine hydrate (purity: 80%) (0.25 mL) in EtOH (1 mL) was stirred at 90° C. for 16 h. The mixture was concentrated in vacuo and purified by Prep-TLC (DCM/MeOH=12:1) to give 1-((6-cyclopropylimidazo[1,2-a]pyridin-2-yl)methyl)-N-(2-fluoro-6-(hydrazinecarbonyl)-3-methoxybenzyl)-1H-1,2,3-triazole-4-carboxamide (15 mg, yield: 43%) as a white solid. ESI-MS [M+H]$^+$: 479.2.

Synthesis of 1-((6-cyclopropylimidazo[1,2-a]pyridin-2-yl)methyl)-N-(2-fluoro-3-methoxy-6-(1,3,4-oxadiazol-2-yl)benzyl)-1H-1,2,3-triazole-4-carboxamide. A solution of 1-((6-cyclopropylimidazo[1,2-a]pyridin-2-yl)methyl)-N-(2-fluoro-6-(hydrazinecarbonyl)-3-methoxybenzyl)-1H-1,2,3-triazole-4-carboxamide (15 mg, 0.03 mmol), triethoxymethane (0.25 mL) and NH$_4$Cl (10 mg, 0.15 mmol) in EtOH (1 mL) was stirred at 80° C. for 16 h. The reaction mixture was concentrated in vacuo and purified by Prep-TLC (DCM/MeOH=10:1) to give 1-((6-cyclopropylimidazo[1,2-a]pyridin-2-yl)methyl)-N-(2-fluoro-3-methoxy-6-(1,3,4-oxadiazol-2-yl)benzyl)-1H-1,2,3-triazole-4-carboxamide as a white solid (2.9 mg, yield: 20%). ESI-MS [M+H]+: 489.2. $^1$H NMR (400 MHz, DMSO) δ 9.37 (s, 1H), 8.75 (t, J=5.7 Hz, 1H), 53 (s, 1H), 8.33 (s, 1H), 7.79 (s, 1H), 7.74 (d, J=8.8 Hz, 1H), 7.38-7.31 (m, 2H), 7.00 (d, J=9.2 Hz, 1H), 5.70 (s, 2H), 4.88 (d, J=5.1 Hz, 2H), 3.92 (s, 3H), 1.94-1.88 (m, 1H), 0.94-0.90 (m, 2H), 0.68-0.66 (m, 2H).

Example 33

1-((6-cyclopropylimidazo[1,2-a]pyridin-2-yl)methyl)-N-(2-fluoro-3-methoxy-6-(pyridin-4-yl)benzyl)-1H-1,2,3-triazole-4-carboxamide (I-101)

Scheme 33

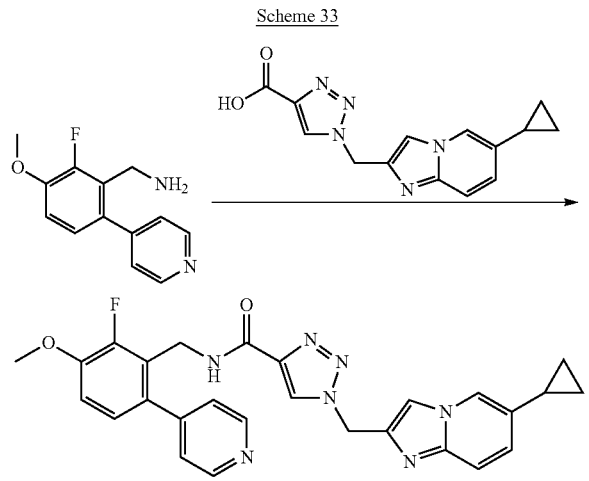

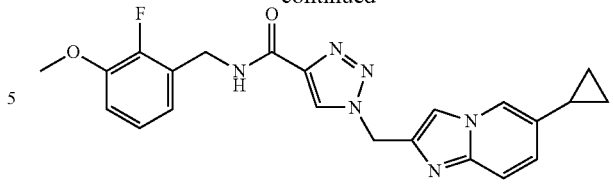

Synthesis of 1-((6-cyclopropylimidazo[1,2-a]pyridin-2-yl)methyl)-N-(2-fluoro-3-methoxy-6-(pyridin-4-yl)benzyl)-1H-1,2,3-triazole-4-carboxamide. 1-((6-cyclopropylimidazo[1,2-a]pyridin-2-yl)methyl)-N-(2-fluoro-3-methoxy-6-(pyridin-4-yl)benzyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and (2-fluoro-3-methoxy-6-(pyridin-4-yl)phenyl)methanamine. The crude product was purified by prep-TLC (DCM/MeOH=10/1) to yield the product (7 mg, yield: 18%) as a white solid. ESI-MS [M+H]+: 498.2. $^1$H NMR (400 MHz, DMSO) δ 8.65 (t, J=4.9 Hz, 1H), 8.58-8.57 (m, 2H), 8.51 (s, 1H), 8.35 (s, 1H), 7.83 (s, 1H), 7.43-7.40 (m, 3H), 7.23 (t, J=8.6 Hz, 1H), 7.08 (d, J=8.6 Hz, 1H), 7.01 (dd, J=9.4, 1.7 Hz, 1H), 5.71 (s, 2H), 4.40 (d, J=4.5 Hz, 2H), 3.87 (s, 3H), 1.96-1.89 (m, 1H), 0.93-0.90 (m, 2H), 0.65-0.69 (m, 2H).

Example 34

1-((6-cyclopropylimidazo[1,2-a]pyridin-2-yl)methyl)-N-(2-fluoro-3-methoxybenzyl)-1H-1,2,3-triazole-4-carboxamide (I-100)

Scheme 34

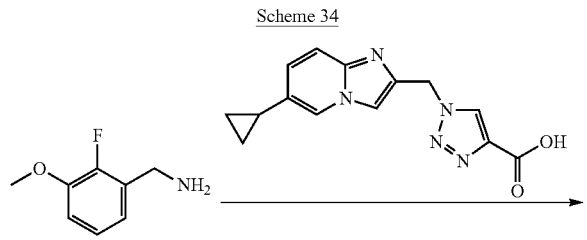

Synthesis of 1-((6-cyclopropylimidazo[1,2-a]pyridin-2-yl)methyl)-N-(2-fluoro-3-methoxybenzyl)-1H-1,2,3-triazole-4-carboxamide. 1-((6-cyclopropylimidazo[1,2-a]pyridin-2-yl)methyl)-N-(2-fluoro-3-methoxybenzyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (2-fluoro-3-methoxyphenyl)methanamine. The crude product was purified by prep-HPLC to yield the product (2 mg, yield: 7%) as a white solid. ESI-MS [M+H]+: 421.2. $^1$H NMR (400 MHz, DMSO) δ 8.98 (t, J=6.1 Hz, 1H), 8.52 (s, 1H), 8.32-8.30 (m, 1H), 7.79 (s, 1H), 7.35 (d, J=9.3 Hz, 1H), 7.00-6.94 (m, 3H), 6.82-6.79 (m, 1H), 5.68 (s, 2H), 4.41 (d, J=6.1 Hz, 2H), 3.76 (s, 3H), 1.89-1.84 (m, 1H), 0.89-0.84 (m, 2H), 0.64-0.60 (m, 2H).

Example 35

N-(6-chloro-8,9-dihydro-7H-imidazo[4,5,1-ij]quinolin-9-yl)-1-((6-cyclopropylimidazo[1,2-a]pyridin-2-yl)methyl)-1H-1,2,3-triazole-4-carboxamide (I-135)

Scheme 35

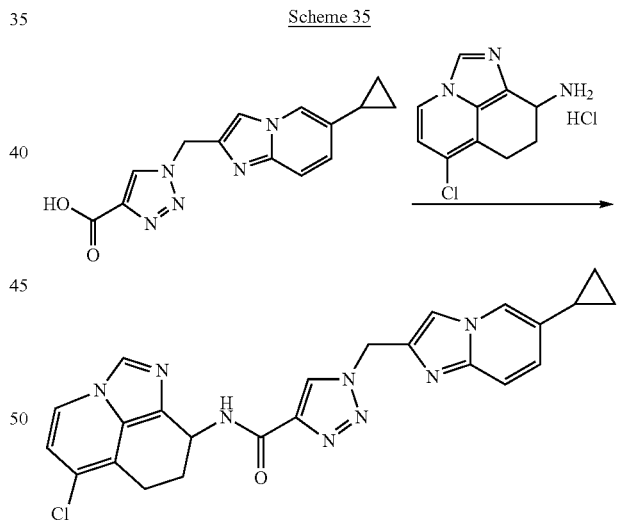

Synthesis of N-(6-chloro-8,9-dihydro-7H-imidazo[4,5,1-ij]quinolin-9-yl)-1-((6-cyclopropylimidazo[1,2-a]pyridin-2-yl)methyl)-1H-1,2,3-triazole-4-carboxamide. N-(6-chloro-8,9-dihydro-7H-imidazo[4,5,1-ij]quinolin-9-yl)-1-((6-cyclopropylimidazo[1,2-a]pyridin-2-yl)methyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and 6-chloro-8,9-dihydro-7H-imidazo[4,5,1-ij]quinolin-9-amine hydrochloride. The crude product was purified by prep-HPLC to yield the product (18.3 mg, yield: 19.4%) as a white solid. ESI-MS [M+H]+: 473.1. $^1$H NMR (400 MHz, DMSO) δ 8.59 (s, 1H), 8.56 (d, J=8.4 Hz, 1H), 8.35 (s, 1H), 8.27 (s, 1H), 8.17 (d, J=7.4 Hz, 1H), 7.83 (s, 1H), 7.41 (d, J=9.3 Hz, 1H), 7.01 (dd, J=9.3, 1.6 Hz, 1H), 6.65 (d, J=7.4 Hz, 1H), 5.73 (s, 2H), 5.50-5.35 (m, 1H), 2.93-2.89 (m, 2H), 2.18-2.08 (m, 2H), 1.96-1.89 (m, 1H), 1.00-0.85 (m, 2H), 0.76-0.61 (m, 2H).

Example 36

1-((6-cyclopropylimidazo[1,2-a]pyridin-2-yl)methyl)-N-(2-fluoro-6-(1H-tetrazol-1-yl)-3-(trifluoromethoxy)benzyl)-1H-1,2,3-triazole-4-carboxamide (I-98)

Scheme 36

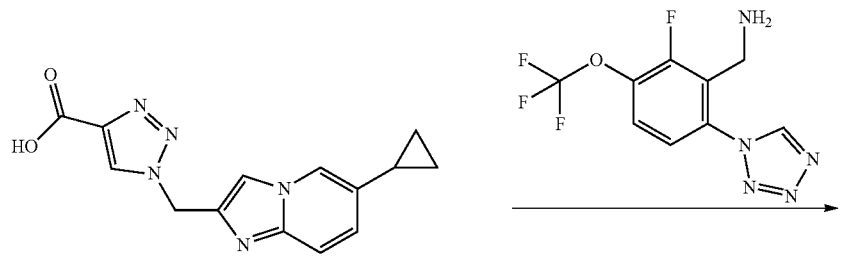

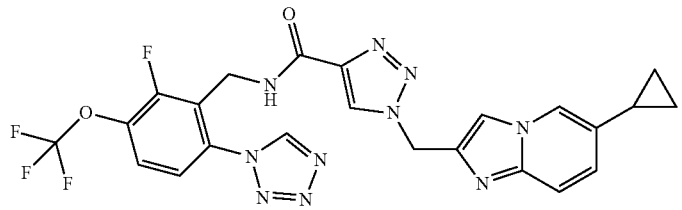

Synthesis of 1-((6-cyclopropylimidazo[1,2-a]pyridin-2-yl)methyl)-N-(2-fluoro-6-(1H-tetrazol-1-yl)-3-(trifluoromethoxy)benzyl)-1H-1,2,3-triazole-4-carboxamide. 1-((6-cyclopropylimidazo[1,2-a]pyridin-2-yl)methyl)-N-(2-fluoro-6-(1H-tetrazol-1-yl)-3-(trifluoromethoxy)benzyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (2-fluoro-6-(1H-tetrazol-1-yl)-3-(trifluoromethoxy)phenyl)methanamine. The crude product was purified by prep-TLC (DCM/MeOH=10:1) to yield the product (70 mg, yield: 33%) as a white solid. ESI-MS [M+H]+: 543.20. ¹H NMR (400 MHz, DMSO-d6) δ 9.86 (s, 1H), 8.91 (t, J=5.3 Hz, 1H), 8.49 (s, 1H), 8.34 (s, 1H), 7.88-7.80 (m, 2H), 7.60 (m, 1H), 7.40 (d, J=9.3 Hz, 1H), 7.01 (m, 1H), 5.71 (s, 2H), 4.40 (d, J=5.2 Hz, 2H), 1.97-1.87 (m, 1H), 0.96-0.87 (m, 2H), 0.70-0.63 (m, 2H).

Example 37

1-((6-cyclopropylimidazo[1,2-a]pyridin-2-yl)methyl)-N-(2-fluoro-3-methoxy-6-(4H-1,2,4-triazol-4-yl)benzyl)-1H-1,2,3-triazole-4-carboxamide (I-96)

Scheme 37

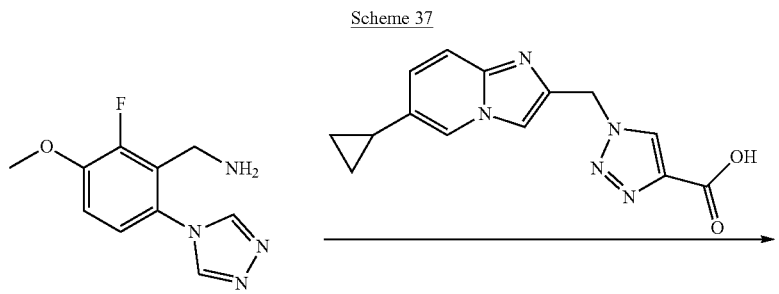

-continued

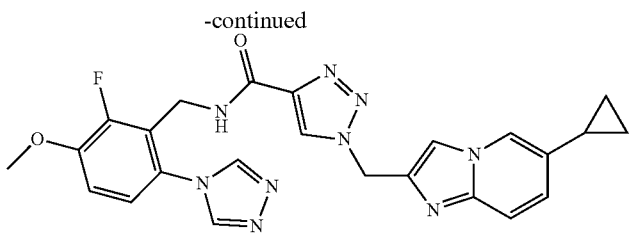

Synthesis of 1-((6-cyclopropylimidazo[1,2-a]pyridin-2-yl)methyl)-N-(2-fluoro-3-methoxy-6-(4H-1,2,4-triazol-4-yl)benzyl)-1H-1,2,3-triazole-4-carboxamide. 1-((6-cyclopropylimidazo[1,2-a]pyridin-2-yl)methyl)-N-(2-fluoro-3-methoxy-6-(4H-1,2,4-triazol-4-yl)benzyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (2-fluoro-3-methoxy-6-(4H-1,2,4-triazol-4-yl)phenyl)methanamine. The crude product was purified by prep-TLC (DCM/MeOH=10:1) to yield the product (46 mg, yield: 28.6%) as a yellow solid. ESI-MS [M+H]+: 488.1. $^1$H NMR (400 MHz, DMSO) δ 8.83 (t, J=5.2 Hz, 1H), 8.74 (s, 1H), 8.52 (s, 1H), 8.35 (d, J=0.7 Hz, 1H), 7.82 (s, 1H), 7.41 (d, J=9.3 Hz, 1H), 7.26 (dt, J=18.9, 9.3 Hz, 2H), 7.01 (dd, J=9.4, 1.8 Hz, 1H), 5.72 (s, 2H), 4.21 (d, J=5.0 Hz, 2H), 3.89 (s, 3H), 1.99-1.83 (m, 1H), 0.98-0.83 (m, 2H), 0.75-0.55 (m, 2H).

Example 38

1-((6-cyclopropylimidazo[1,2-a]pyridin-2-yl)methyl)-N-(2-fluoro-3-methoxy-6-(1H-pyrazol-1-yl)benzyl)-1H-1,2,3-triazole-4-carboxamide (I-95)

Scheme 38

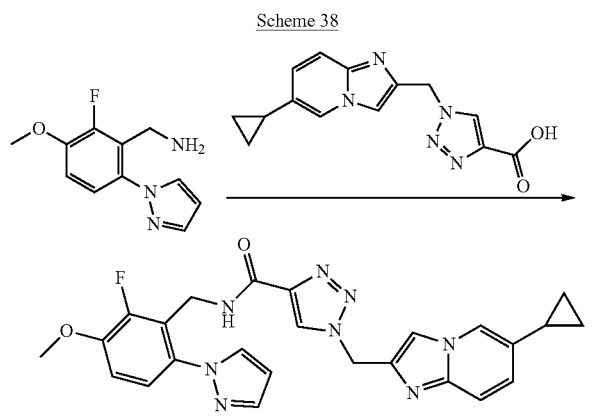

Synthesis of 1-((6-cyclopropylimidazo[1,2-a]pyridin-2-yl)methyl)-N-(2-fluoro-3-methoxy-6-(1H-pyrazol-1-yl)benzyl)-1H-1,2,3-triazole-4-carboxamide. 1-((6-cyclopropylimidazo[1,2-a]pyridin-2-yl)methyl)-N-(2-fluoro-3-methoxy-6-(1H-pyrazol-1-yl)benzyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (2-fluoro-3-methoxy-6-(1H-pyrazol-1-yl)phenyl)methanamine. The crude product was purified by prep-TLC (DCM/MeOH=10:1) to yield the product (33 mg, yield: 39.8%) as a white solid. ESI-MS [M+H]$^+$: 487.2. $^1$H NMR (400 MHz, DMSO) δ 8.55 (s, 1H), 8.47 (t, J=5.6 Hz, 1H), 8.34 (s, 1H), 8.09 (d, J=2.2 Hz, 1H), 7.81 (s, 1H), 7.77 (d, J=1.6 Hz, 1H), 7.41 (d, J=9.2 Hz, 1H), 7.28-7.22 (m, 2H), 7.02-6.99 (m, 1H), 6.51 (t, J=2.1 Hz, 1H), 5.71 (s, 2H), 4.38 (d, J=4.7 Hz, 2H), 3.88 (s, 3H), 1.96-1.89 (m, 1H), 0.93-0.89 (m, 2H), 0.69-0.65 (m, 2H).

Example 39

N-(3-bromo-2-fluoro-6-(1H-tetrazol-1-yl)benzyl)-1-((6-cyclopropylimidazo[1,2-a]pyridin-2-yl)methyl)-1H-1,2,3-triazole-4-carboxamide (I-90)

Scheme 39

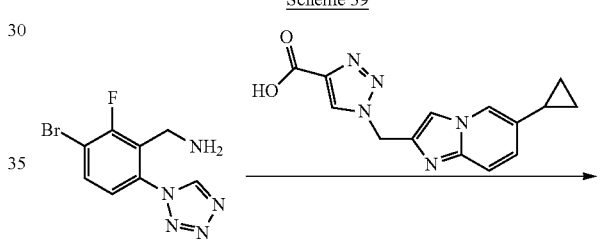

Synthesis of N-(3-bromo-2-fluoro-6-(1H-tetrazol-1-yl)benzyl)-1-((6-cyclopropylimidazo[1,2-a]pyridin-2-yl)methyl)-1H-1,2,3-triazole-4-carboxamide. N-(3-bromo-2-fluoro-6-(1H-tetrazol-1-yl)benzyl)-1-((6-cyclopropylimidazo[1,2-a]pyridin-2-yl)methyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (3-bromo-2-fluoro-6-(1H-tetrazol-1-yl)phenyl)methanamine. The crude product was purified by prep-TLC (DCM/MeOH=10:1) to yield the product as a white solid (72 mg, yield: 24.4%). ESI-MS [M+H]+: 538.2. $^1$H NMR (400 MHz, DMSO) δ 9.85 (s, 1H), 8.89 (t, J=5.4 Hz, 1H), 8.49 (s, 1H), 8.36 (s, 1H), 7.95 (dd, J=8.5, 7.3 Hz, 1H), 7.83 (s, 1H), 7.44-7.40 (m, 2H), 7.03 (dd, J=9.4, 1.7 Hz, 1H), 5.71 (s, 2H), 4.37 (d, J=5.1 Hz, 2H), 1.96-1.90 (m, 1H), 0.95-0.90 (m, 2H), 0.69-0.65 (m, 2H).

Example 40 methyl 2'-((1-((6-cyclopropylimidazo[1,2-a]pyridin-2-yl)methyl)-1H-1,2,3-triazole-4-carboxamido)methyl)-3'-fluoro-4'-methoxy-[1,1'-biphenyl]-4-carboxylate (I-87)

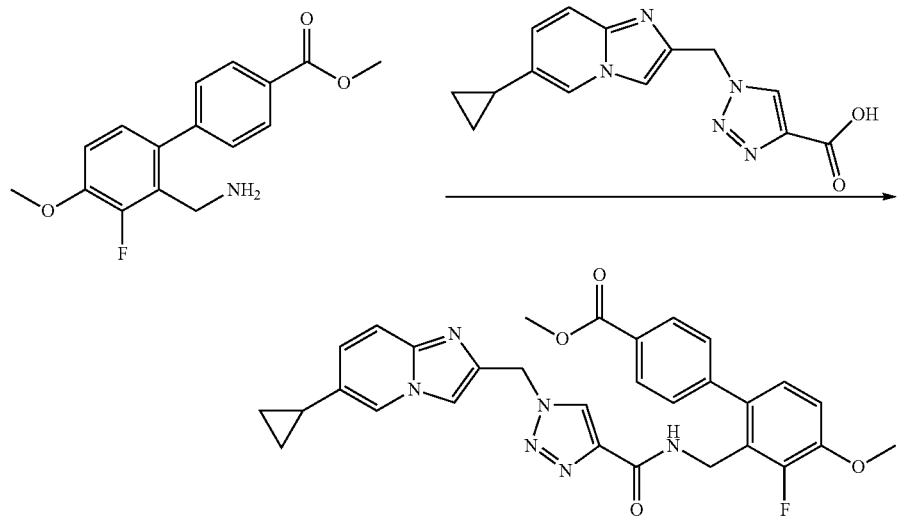

Scheme 40

Synthesis of methyl 2'-((1-((6-cyclopropylimidazo[1,2-a]pyridin-2-yl)methyl)-1H-1,2,3-triazole-4-carboxamido)methyl)-3'-fluoro-4'-methoxy-[1,1'-biphenyl]-4-carboxylate. Methyl 2'-((1-((6-cyclopropylimidazo[1,2-a]pyridin-2-yl)methyl)-1H-1,2,3-triazole-4-carboxamido)methyl)-3'-fluoro-4'-methoxy-[1,1'-biphenyl]-4-carboxylate was synthesized according to General Procedure B-1 starting from 1-((6-cyclopropylimidazo[1,2-a]pyridin-2-yl)methyl)-1H-1,2,3-triazole-4-carboxylic acid and methyl 2'-(aminomethyl)-3'-fluoro-4'-methoxy-[1,1'-biphenyl]-4-carboxylate. The crude product was purified by prep-HPLC to yield the product (27.7 mg, yield: 35.7%) as a white solid. ESI-MS [M+H]$^+$: 555.2. $^1$H NMR (400 MHz, DMSO) δ 8.58 (t, J=4.8 Hz, 1H), 8.51 (s, 1H), 8.35 (s, 1H), 7.97 (d, J=8.1 Hz, 2H), 7.82 (s, 1H), 7.53 (d, J=8.1 Hz, 2H), 7.41 (d, J=9.4 Hz, 1H), 7.21 (t, J=8.5 Hz, 1H), 7.07 (d, J=8.5 Hz, 1H), 7.01 (d, J=9.0 Hz, 1H), 5.71 (s, 2H), 4.38 (d, J=4.4 Hz, 2H), 3.87 (d, J=4.2 Hz, 6H), 1.92-1.91 (m, 1H), 0.96-0.88 (m, 2H), 0.67 (m, 2H).

Example 41

2'-((1-((6-cyclopropylimidazo[1,2-a]pyridin-2-yl)methyl)-1H-1,2,3-triazole-4-carboxamido)methyl)-3'-fluoro-4'-methoxy-[1,1'-biphenyl]-4-carboxylic acid (I-88)

Scheme 41

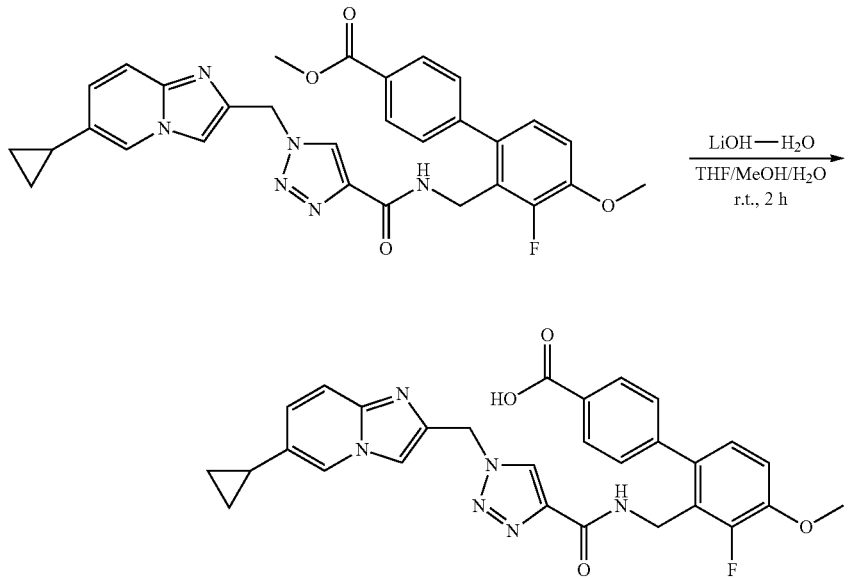

Synthesis of 2'-((1-((6-cyclopropylimidazo[1,2-a]pyridin-2-yl)methyl)-1H-1,2,3-triazole-4-carboxamido)methyl)-3'-fluoro-4'-methoxy-[1,1'-biphenyl]-4-carboxylic acid. A solution of methyl 2'-((1-((6-cyclopropylimidazo[1,2-a]pyridin-2-yl)methyl)-1H-1,2,3-triazole-4-carboxamido)methyl)-3'-fluoro-4'-methoxy-[1,1'-biphenyl]-4-carboxylate (20 mg, 0.036 mmol) and LiOH—H$_2$O (7.6 mg, 0.18 mmol) in THF/MeOH/water (1 mL/1 mL/1 mL) was stirred at room temperature for 2 h. The reaction mixture was concentrated in vacuo and purified by prep-HPLC to give 2'-((1-((6-cyclopropylimidazo[1,2-a]pyridin-2-yl)methyl)-1H-1,2,3-triazole-4-carboxamido)methyl)-3'-fluoro-4'-methoxy-[1,1'-biphenyl]-4-carboxylic acid (7.6 mg, yield: 40%) as a white solid. ESI-MS [M+H]$^+$: 541.2. $^1$H NMR (400 MHz, DMSO) δ 8.55 (t, J=4.7 Hz, 1H), 8.52 (s, 1H), 8.35 (s, 1H), 8.31 (s, 1H), 7.94 (d, J=7.8 Hz, 2H), 7.82 (s, 1H), 7.46-7.40 (m, 3H), 7.20 (t, J=8.6 Hz, 1H), 7.06 (d, J=8.4 Hz, 1H), 7.01 (d, J=8.0 Hz, 1H), 5.71 (s, 2H), 4.39 (d, J=4.1 Hz, 2H), 3.87 (s, 3H), 1.94-1.89 (m, 1H), 0.94-0.89 (m, 2H), 0.71-0.65 (m, 2H).

Example 42

1-((6-cyclopropylimidazo[1,2-a]pyridin-2-yl)methyl)-N-(2-fluoro-3-methoxy-6-(pyridazin-4-yl)benzyl)-1H-1,2,3-triazole-4-carboxamide (I-86)

Scheme 42

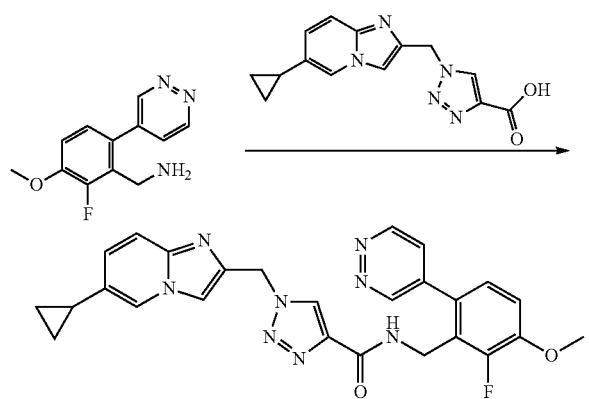

Synthesis of 1-((6-cyclopropylimidazo[1,2-a]pyridin-2-yl)methyl)-N-(2-fluoro-3-methoxy-6-(pyridazin-4-yl)benzyl)-1H-1,2,3-triazole-4-carboxamide. 1-((6-cyclopropylimidazo[1,2-a]pyridin-2-yl) methyl)-N-(2-fluoro-3-methoxy-6-(pyridazin-4-yl)benzyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (2-fluoro-3-methoxy-6-(pyridazin-4-yl)phenyl)methanamine. The crude product was purified by prep-HPLC to yield the product (21 mg, yield: 32.4%) as a white solid. ESI-MS [M+H]$^+$: 499.2. $^1$H NMR (400 MHz, DMSO) δ 9.31-9.23 (m, 1H), 9.20 (dd, J=5.3, 0.9 Hz, 1H), 8.73 (t, J=5.1 Hz, 1H), 8.45 (s, 1H), 8.32 (s, 1H), 7.79 (s, 1H), 7.72 (dd, J=5.3, 2.4 Hz, 1H), 7.38 (d, J=9.4 Hz, 1H), 7.24 (t, J=8.5 Hz, 1H), 7.13 (d, J=8.6 Hz, 1H), 6.98 (dd, J=9.4, 1.7 Hz, 1H), 5.68 (s, 2H), 4.38 (d, J=4.9 Hz, 2H), 3.86 (s, 3H), 1.94-1.84 (m, 1H), 0.96-0.87 (m, 2H), 0.70-0.62 (m, 2H).

Example 43

N-(benzo[b]thiophen-5-ylmethyl)-1-((6-cyclopropylimidazo[1,2-a]pyridin-2-yl)methyl)-1H-1,2,3-triazole-4-carboxamide (I-84)

Scheme 43

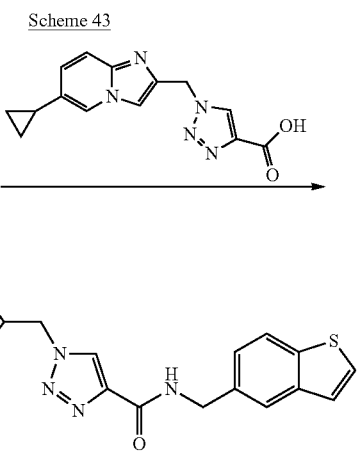

Synthesis of N-(benzo[b]thiophen-5-ylmethyl)-1-((6-cyclopropylimidazo[1,2-a]pyridin-2-yl)methyl)-1H-1,2,3-triazole-4-carboxamide. N-(benzo[b]thiophen-5-ylmethyl)-1-((6-cyclopropylimidazo[1,2-a]pyridin-2-yl)methyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and benzo[b]thiophen-5-ylmethanamine hydrochloride. The crude product was purified by prep-TLC (MeOH/DCM=1/10) to yield the product (40 mg, 52% yield) as a white solid. ESI-MS [M+H]+: 429.1. $^1$H NMR (400 MHz, DMSO) δ 9.16 (t, J=6.2 Hz, 1H), 8.58 (s, 1H), 8.36 (s, 1H), 7.93 (d, J=8.3 Hz, 2H), 7.85 (s, 1H), 7.78 (s, 1H), 7.73 (d, J=5.4 Hz, 1H), 7.46-7.38 (m, 2H), 7.33 (dd, J=8.3, 1.2 Hz, 1H), 7.02 (dd, J=9.4, 1.6 Hz, 1H), 5.74 (s, 2H), 4.55 (d, J=6.3 Hz, 2H), 1.95-1.91 (m, 1H), 0.98-0.87 (m, 2H), 0.75-0.65 (m, 2H).

Example 44

1-((6-cyclopropylimidazo[1,2-a]pyridin-2-yl)methyl)-N-(3-ethyl-2-fluoro-6-(1H-tetrazol-1-yl)benzyl)-1H-1,2,3-triazole-4-carboxamide (I-83)

Scheme 44

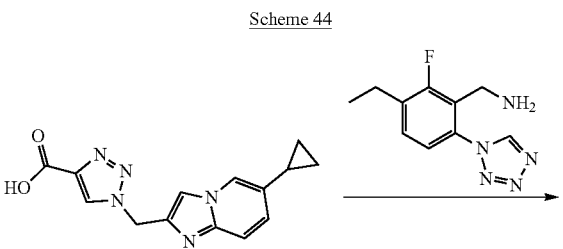

-continued

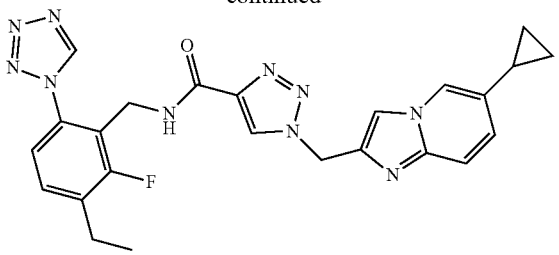

Synthesis of 1-((6-cyclopropylimidazo[1,2-a]pyridin-2-yl)methyl)-N-(3-ethyl-2-fluoro-6-(1H-tetrazol-1-yl)benzyl)-1H-1,2,3-triazole-4-carboxamide. 1-((6-cyclopropylimidazo[1,2-a]pyridin-2-yl)methyl)-N-(3-ethyl-2-fluoro-6-(1H-tetrazol-1-yl)benzyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (3-ethyl-2-fluoro-6-(1H-tetrazol-1-yl)phenyl)methanamine. The crude product was purified by prep-TLC (MeOH/DCM=1/10) to yield the product (114 mg, yield: 65.1%) as a white solid. ESI-MS [M+H]+: 487.1. $^1$H NMR (400 MHz, DMSO) δ 9.80 (s, 1H), 8.76 (t, J=5.5 Hz, 1H), 8.49 (s, 1H), 8.34 (s, 1H), 7.82 (s, 1H), 7.51 (t, J=8.0 Hz, 1H), 7.37 (dd, J=20.4, 8.8 Hz, 2H), 7.01 (dd, J=9.4, 1.8 Hz, 1H), 5.70 (s, 2H), 4.32 (d, J=5.3 Hz, 2H), 2.72 (q, J=7.5 Hz, 2H), 1.92-1.89 (m, 1H), 1.21 (t, J=7.6 Hz, 3H), 0.94-0.89 (m, 2H), 0.69-0.65 (m, 2H).

Example 45

7-(6-cyclopropylimidazo[1,2-a]pyridin-2-yl)-N-(2-fluoro-3-methoxy-6-(1H-tetrazol-1-yl)benzyl)-6,7-dihydro-5H-pyrrolo[1,2-b][1,2,4]triazole-2-carboxamide (I-82)

Scheme 45

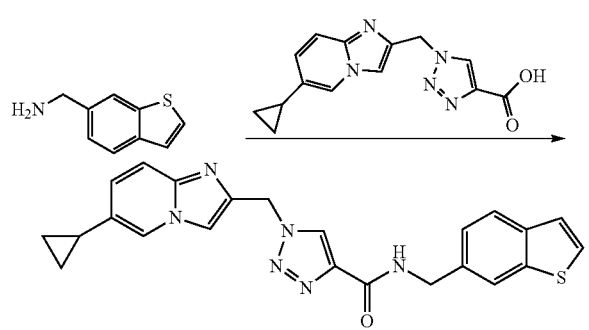

Synthesis of 7-(6-cyclopropylimidazo[1,2-a]pyridin-2-yl)-N-(2-fluoro-3-methoxy-6-(1H-tetrazol-1-yl)benzyl)-6,7-dihydro-5H-pyrrolo[1,2-b][1,2,4]triazole-2-carboxamide. N-(benzo[b]thiophen-6-ylmethyl)-1-((6-cyclopropylimidazo[1,2-a]pyridin-2-yl)methyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and benzo[b]thiophen-6-ylmethanamine. The crude product was purified by prep-TLC (7% MeOH/DCM) to yield the product (20 mg, 26% yield) as a white solid. ESI-MS [M+H]+: 429.1. $^1$H NMR (400 MHz, DMSO) δ 9.20 (t, J=6.3 Hz, 1H), 8.63 (s, 1H), 8.54 (s, 1H), 8.05 (s, 1H), 7.88 (s, 1H), 7.81 (d, J=8.2 Hz, 1H), 7.71 (d, J=5.4 Hz, 1H), 7.61 (d, J=9.4 Hz, 1H), 7.41 (d, J=5.4 Hz, 1H), 7.37-7.34 (m, 2H), 5.88 (s, 2H), 4.56 (d, J=6.2 Hz, 2H), 2.05-1.95 (m, 1H), 1.03-0.93 (m, 2H), 0.75-0.69 (m, 2H).

Example 46

N-(3-chloro-2-methyl-6-(1H-tetrazol-1-yl)benzyl)-1-((6-cyclopropylimidazo[1,2-a]pyridin-2-yl)methyl)-1H-1,2,3-triazole-4-carboxamide (I-80)

Scheme 46

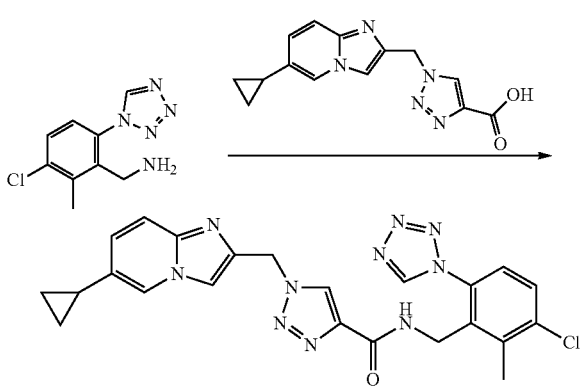

Synthesis of N-(3-chloro-2-methyl-6-(1H-tetrazol-1-yl)benzyl)-1-((6-cyclopropylimidazo[1,2-a]pyridin-2-yl)methyl)-1H-1,2,3-triazole-4-carboxamide. N-(3-chloro-2-methyl-6-(1H-tetrazol-1-yl)benzyl)-1-((6-cyclopropylimidazo[1,2-a]pyridin-2-yl)methyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and (3-chloro-2-methyl-6-(1H-tetrazol-1-yl)phenyl)methanamine. The crude product was purified by prep-TLC (MeOH/DCM=1/10) to yield the product (35 mg, yield: 20%). ESI-MS [M+H]+: 489.2. $^1$H NMR (400 MHz, DMSO) δ 9.76 (s, 1H), 8.78 (t, J=6.0 Hz, 1H), 8.52 (s, 1H), 8.34 (s, 1H), 7.82 (s, 1H), 7.68 (d, J=8.0 Hz, 1H), 7.44-7.39 (m, 2H), 7.02-6.99 (m, 1H), 5.71 (s, 2H), 4.22 (d, J=8.0 Hz, 2H), 2.47 (s, 3H), 1.96-1.89 (m, 1H), 0.94-0.89 (m, 2H), 0.69-0.65 (m, 2H).

Example 47

N-(3-chloro-6-(difluoromethyl)-2-fluorobenzyl)-1-((6-cyclopropylimidazo[1,2-a]pyridin-2-yl)methyl)-1H-1,2,3-triazole-4-carboxamide (I-79)

Scheme 47

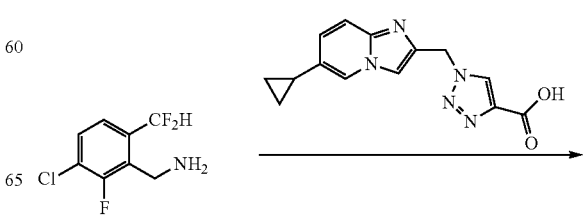

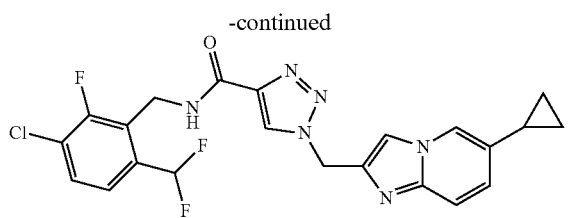

Synthesis of N-(3-chloro-6-(difluoromethyl)-2-fluorobenzyl)-1-((6-cyclopropylimidazo[1,2-a]pyridin-2-yl)methyl)-1H-1,2,3-triazole-4-carboxamide. N-(3-chloro-6-(difluoromethyl)-2-fluorobenzyl)-1-((6-cyclopropylimidazo[1,2-a]pyridin-2-yl)methyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (3-chloro-6-(difluoromethyl)-2-fluorophenyl)methanamine. The crude product was purified by prep-TLC (MeOH/DCM=1/10) to yield the product (80 mg, 42%) as a white solid. ESI-MS [M+H]+: 475.1. $^1$H NMR (400 MHz, DMSO) δ 9.10 (t, J=5.5 Hz, 1H), 8.56 (s, 1H), 8.35 (s, 1H), 7.83 (s, 1H), 7.71-7.68 (m, 1H), 7.60-7.32 (m, 3H), 7.01 (dd, J=9.4, 1.7 Hz, 1H), 5.72 (s, 2H), 4.58 (d, J=5.2 Hz, 2H), 1.96-1.89 (m, 1H), 0.93-0.89 (m, 2H), 0.69-0.65 (m, 2H).

Example 48

N-(3-cyclopropyl-2-fluoro-6-(1H-tetrazol-1-yl)benzyl)-1-((6-cyclopropylimidazo[1,2-a]pyridin-2-yl)methyl)-1H-1,2,3-triazole-4-carboxamide (I-78)

Scheme 48

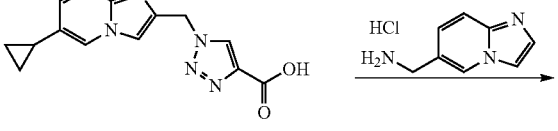

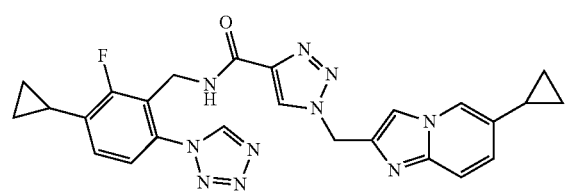

Synthesis of N-(3-cyclopropyl-2-fluoro-6-(1H-tetrazol-1-yl)benzyl)-1-((6-cyclopropylimidazo[1,2-a]pyridin-2-yl)methyl)-1H-1,2,3-triazole-4-carboxamide. N-(3-cyclopropyl-2-fluoro-6-(1H-tetrazol-1-yl)benzyl)-1-((6-cyclopropylimidazo[1,2-a]pyridin-2-yl)methyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (3-cyclopropyl-2-fluoro-6-(1H-tetrazol-1-yl)phenyl)methanamine. The crude product was purified by prep-TLC (MeOH/DCM=1/10) to yield the product (23.4 mg, yield: 13.69%) as a white solid. ESI-MS [M+H]+: 499.2. $^1$H NMR (400 MHz, DMSO) δ 9.78 (s, 1H), 8.77 (t, J=5.5 Hz, 1H), 8.49 (s, 1H), 8.34 (s, 1H), 7.82 (s, 1H), 7.40 (d, J=9.3 Hz, 1H), 7.30 (d, J=8.4 Hz, 1H), 7.16 (t, J=8.1 Hz, 1H), 7.01 (dd, J=9.4, 1.7 Hz, 1H), 5.70 (s, 2H), 4.32 (d, J=5.1 Hz, 2H), 2.18-2.10 (m, 1H), 1.96-1.88 (m, 1H), 1.09-1.01 (m, 2H), 0.95-0.88 (m, 2H), 0.85-0.78 (m, 2H), 0.70-0.64 (m, 2H).

Example 49

1-((6-cyclopropylimidazo[1,2-a]pyridin-2-yl)methyl)-N-(imidazo[1,2-a]pyridin-6-ylmethyl)-1H-1,2,3-triazole-4-carboxamide (I-136)

Scheme 49

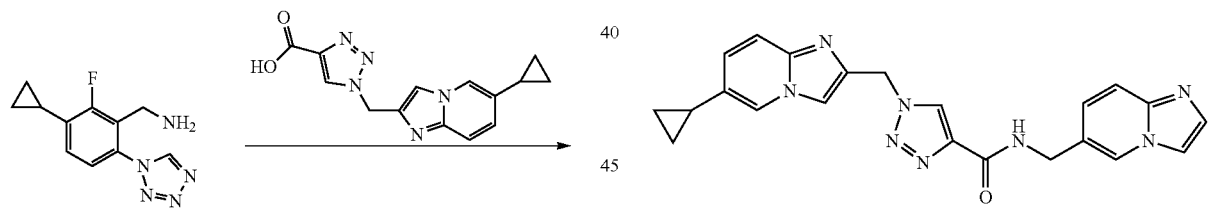

Synthesis of 1-((6-cyclopropylimidazo[1,2-a]pyridin-2-yl)methyl)-N-(imidazo[1,2-a]pyridin-6-ylmethyl)-1H-1,2,3-triazole-4-carboxamide. 1-((6-cyclopropylimidazo[1,2-a]pyridin-2-yl)methyl)-N-(imidazo[1,2-a]pyridin-6-ylmethyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and imidazo[1,2-a]pyridin-6-ylmethanamine hydrochloride. The crude product was purified by prep-TLC (MeOH/DCM=1/15) to yield the product (6 mg, yield:8%) as a white solid. ESI-MS [M+H]+: 413.2. $^1$H NMR (400 MHz, DMSO) δ 9.16 (t, J=6.0 Hz, 1H), 8.58 (s, 1H), 8.45 (s, 1H), 8.36 (s, 1H), 7.97 (s, 1H), 7.85 (s, 1H), 7.51 (s, 2H), 7.41 (d, J=9.3 Hz, 1H), 7.23 (s, 1H), 7.01 (d, J=9.1 Hz, 1H), 5.74 (s, 2H), 4.42 (d, J=6.0 Hz, 2H), 1.98-1.87 (m Hz, 1H), 0.96-0.88 (m, 2H), 0.71-0.63 (m, 2H).

Example 50

N-((6-chlorobenzo[b]thiophen-2-yl)methyl)-1-((6-cyclopropylimidazo[1,2-a]pyridin-2-yl)methyl)-1H-1,2,3-triazole-4-carboxamide (I-77)

Scheme 50

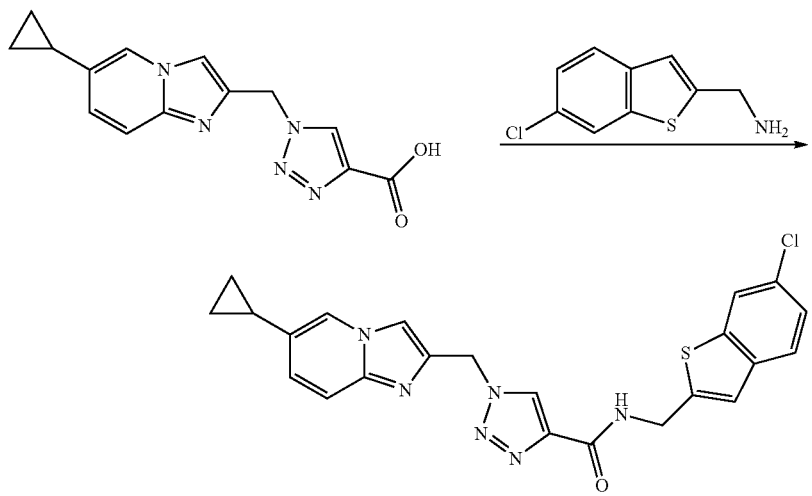

Synthesis of N-((6-chlorobenzo[b]thiophen-2-yl)methyl)-1-((6-cyclopropylimidazo[1,2-a]pyridin-2-yl)methyl)-1H-1,2,3-triazole-4-carboxamide. N-((6-chlorobenzo[b]thiophen-2-yl)methyl)-1-((6-cyclopropylimidazo[1,2-a]pyridin-2-yl)methyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and (6-chlorobenzo[b]thiophen-2-yl)methanamine. The crude product was purified by prep-HPLC (MeOH/DCM=1/15) to yield the product (15 mg, yield: 12%) as a white solid. ESI-MS [M+H]+: 462.7. $^1$H NMR (400 MHz, DMSO) δ 9.31 (t, J=5.6 Hz, 1H), 8.61 (s, 1H), 8.36 (s, 1H), 8.03 (s, 1H), 7.85 (s, 1H), 7.78 (d, J=8.6 Hz, 1H), 7.41 (d, J=9.4 Hz, 1H), 7.36 (d, J=8.5 Hz, 1H), 7.29 (s, 1H), 7.01 (d, J=9.5 Hz, 1H), 5.75 (s, 2H), 4.67 (d, J=5.6 Hz, 2H), 1.96-1.90 (m, 1H), 0.93-0.91 (m, 2H), 0.68-0.67 (m, 2H).

Example 51

1-((6-cyclopropylimidazo[1,2-a]pyridin-2-yl)methyl)-N-(2-fluoro-3-methoxy-6-(1H-1,2,3-triazol-1-yl)benzyl)-1H-1,2,3-triazole-4-carboxamide (I-76)

Scheme 51

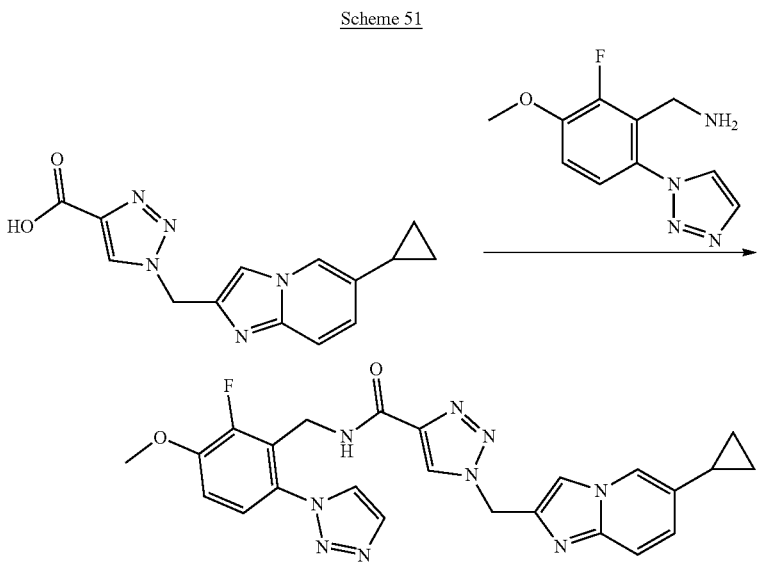

Synthesis of 1-((6-cyclopropylimidazo[1,2-a]pyridin-2-yl)methyl)-N-(2-fluoro-3-methoxy-6-(1H-1,2,3-triazol-1-yl)benzyl)-1H-1,2,3-triazole-4-carboxamide. 1-((6-cyclopropylimidazo[1,2-a]pyridin-2-yl)methyl)-N-(2-fluoro-3-methoxy-6-(1H-1,2,3-triazol-1-yl)benzyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (2-fluoro-3-methoxy-6-(1H-1,2,3-triazol-1-yl)phenyl)methanamine. The crude product was purified by prep-HPLC (MeOH/DCM=1/15) to yield the product (25 mg, 14%) as a pink solid. ESI-MS [M+H]+: 488.2. $^1$H NMR (400 MHz, DMSO) δ 8.63-8.60 (m, 3H), 8.50 (d, J=0.9 Hz, 1H), 8.14 (s, 1H), 7.93 (d, J=0.9 Hz, 1H), 7.71 (d, J=9.3 Hz, 1H), 7.55 (d, J=9.5 Hz, 1H), 7.35-7.29 (m, 2H), 5.92 (s, 2H), 4.31 (d, J=5.1 Hz, 2H), 3.91 (s, 3H), 2.09-2.03 (m, 1H), 1.05-1.01 (m, 2H), 0.78-0.74 (m, 2H).

Example 52 methyl 5-(2-((1-((6-cyclopropylimidazo[1,2-a]pyridin-2-yl)methyl)-1H-1,2,3-triazole-4-carboxamido)methyl)-3-fluoro-4-methoxyphenyl)pyrimidine-2-carboxylate (I-75)

Scheme 52

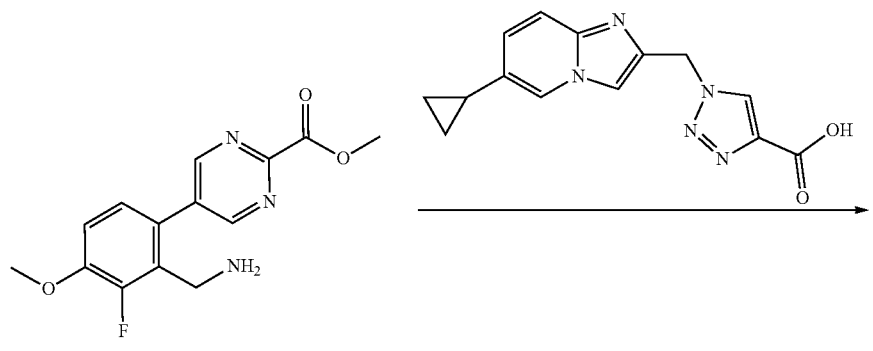

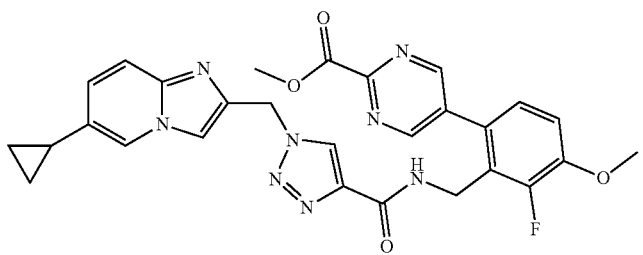

Synthesis of methyl 5-(2-((1-((6-cyclopropylimidazo[1,2-a]pyridin-2-yl)methyl)-1H-1,2,3-triazole-4-carboxamido)methyl)-3-fluoro-4-methoxyphenyl)pyrimidine-2-carboxylate. Methyl 5-(2-((1-((6-cyclopropylimidazo[1,2-a]pyridin-2-yl)methyl)-1H-1,2,3-triazole-4-carboxamido)methyl)-3-fluoro-4-methoxyphenyl)pyrimidine-2-carboxylate was synthesized according to General Procedure B-1 starting from 1-((6-cyclopropylimidazo[1,2-a]pyridin-2-yl)methyl)-1H-1,2,3-triazole-4-carboxylic acid and methyl 5-(2-(aminomethyl)-3-fluoro-4-methoxyphenyl)pyrimidine-2-carboxylate. The crude product was purified by prep-HPLC (MeOH/DCM=1/10) to yield the product (80 mg, yield: 48%) as a yellow solid. ESI-MS [M+H]$^+$: 557.2. $^1$H NMR (400 MHz, DMSO) δ 9.00 (s, 2H), 8.79 (t, J=5.2 Hz, 1H), 8.48 (s, 1H), 8.34 (s, 1H), 7.81 (s, 1H), 7.40 (d, J=9.3 Hz, 1H), 7.28 (t, J=8.5 Hz, 1H), 7.18 (d, J=8.5 Hz, 1H), 7.01 (dd, J=9.4, 1.7 Hz, 1H), 5.70 (s, 2H), 4.39 (d, J=4.8 Hz, 2H), 3.92 (s, 3H), 3.89 (s, 3H), 1.92-1.88 (m, 1H), 1.01-0.85 (m, 2H), 0.73-0.65 (m, 2H).

Example 53

5-(2-((1-((6-cyclopropylimidazo[1,2-a]pyridin-2-yl)methyl)-1H-1,2,3-triazole-4-carboxamido)methyl)-3-fluoro-4-methoxyphenyl)pyrimidine-2-carboxylic acid (I-74)

Scheme 53

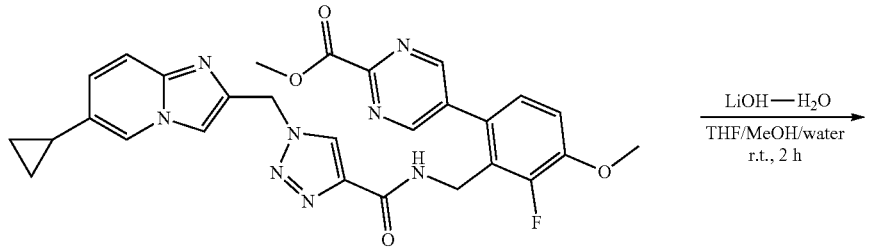

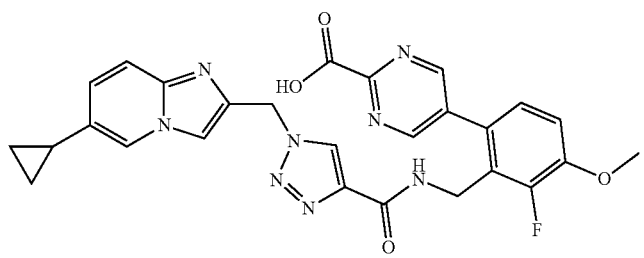

Synthesis 5-(2-((1-((6-cyclopropylimidazo[1,2-a]pyridin-2-yl)methyl)-1H-1,2,3-triazole-4-carboxamido)methyl)-3-fluoro-4-methoxyphenyl)pyrimidine-2-carboxylic acid. A solution of methyl 5-(2-((1-((6-cyclopropylimidazo[1,2-a]pyridin-2-yl)methyl)-1H-1,2,3-triazole-4-carboxamido)methyl)-3-fluoro-4-methoxyphenyl)pyrimidine-2-carboxylate (56 mg, 0.1 mmol) and LiOH—H$_2$O (21 mg, 0.5 mmol) in THF/MeOH/water (1 mL/1 mL/1 mL) was stirred at room temperature for 2 h. The reaction mixture was concentrated in vacuo and purified by prep-HPLC to give 5-(2-((1-((6-cyclopropylimidazo[1,2-a]pyridin-2-yl)methyl)-1H-1,2,3-triazole-4-carboxamido)methyl)-3-fluoro-4-methoxyphenyl)pyrimidine-2-carboxylic acid (12 mg, yield: 22%) as a light yellow solid. ESI-MS [M+H]$^+$: 543.2. $^1$H NMR (400 MHz, DMSO) δ 13.57 (s, 1H), 8.96 (s, 2H), 8.80 (t, J=5.1 Hz, 1H), 8.49 (s, 1H), 8.34 (s, 1H), 7.80 (s, 1H), 7.40 (d, J=9.3 Hz, 1H), 7.27 (t, J=8.5 Hz, 1H), 7.17 (d, J=8.6 Hz, 1H), 7.01 (dd, J=9.3, 1.6 Hz, 1H), 5.70 (s, 2H), 4.39 (d, J=4.7 Hz, 2H), 3.89 (s, 3H), 1.95-1.91 (m, 1H), 0.95-0.81 (m, 2H), 0.75-0.65 (m, 2H).

Example 54

1-((6-cyclopropylimidazo[1,2-a]pyridin-2-yl)methyl)-N-(6-(3,4-dimethyl-1H-pyrazol-1-yl)-2-fluoro-3-methoxybenzyl)-1H-1,2,3-triazole-4-carboxamide (I-73)

Scheme 54

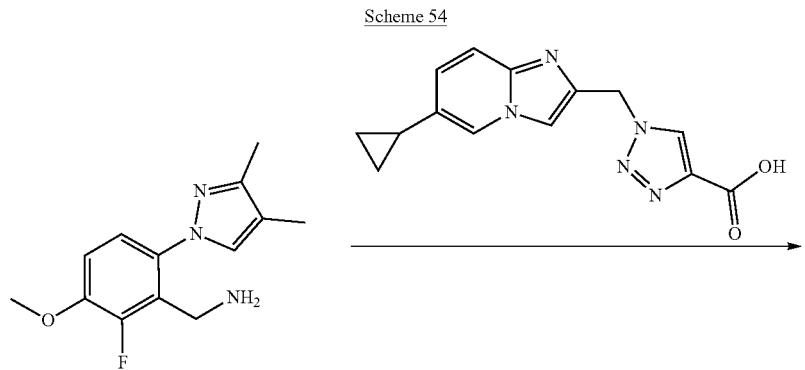

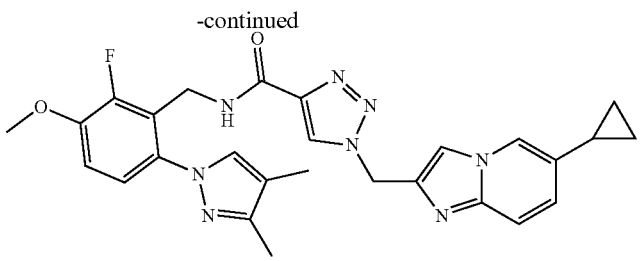

Synthesis of 1-((6-cyclopropylimidazo[1,2-a]pyridin-2-yl)methyl)-N-(6-(3,4-dimethyl-1H-pyrazol-1-yl)-2-fluoro-3-methoxybenzyl)-1H-1,2,3-triazole-4-carboxamide. 1-((6-cyclopropylimidazo[1,2-a]pyridin-2-yl)methyl)-N-(6-(3,4-dimethyl-1H-pyrazol-1-yl)-2-fluoro-3-methoxybenzyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (6-(3,4-dimethyl-1H-pyrazol-1-yl)-2-fluoro-3-methoxyphenyl) methanamine. The crude product was purified by prep-HPLC (MeOH/DCM=1/10) to yield the product (37.6 mg, yield: 37%, two steps) as a yellow solid. ESI-MS [M+H]$^+$: 515.2. $^1$H NMR (400 MHz, DMSO) δ 8.80 (t, J=5.8 Hz, 1H), 8.58 (s, 1H), 8.43 (s, 1H), 7.92 (s, 1H), 7.78 (s, 1H), 7.50 (d, J=9.4 Hz, 1H), 7.21-7.16 (m, 3H), 5.79 (s, 2H), 4.42 (d, J=4.9 Hz, 2H), 3.86 (s, 3H), 2.19 (s, 3H), 2.00 (s, 3H), 1.95-1.91 (m, 1H), 1.02-0.88 (m, 2H), 0.78-0.64 (m, 2H).

Example 55

N-((5-cyano-3-fluoro-2-methoxypyridin-4-yl)methyl)-1-((6-cyclopropylimidazo[1,2-a]pyridin-2-yl)methyl)-1H-1,2,3-triazole-4-carboxamide (I-72)

Scheme 55

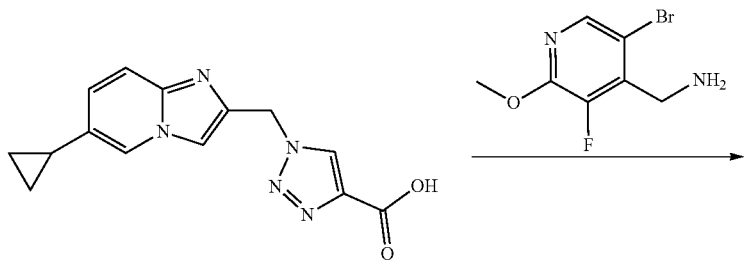

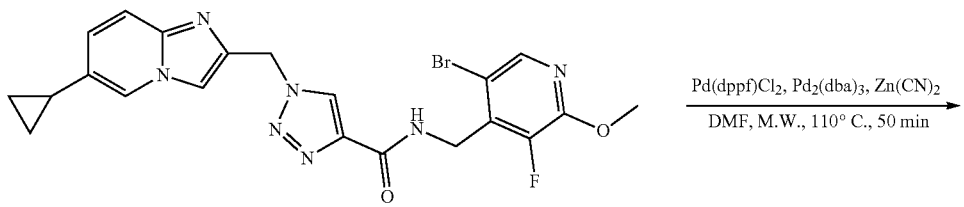

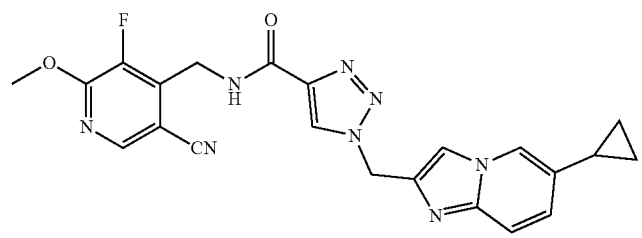

Synthesis of N-((5-bromo-3-fluoro-2-methoxypyridin-4-yl)methyl)-1-((6-cyclopropylimidazo[1,2-a]pyridin-2-yl)methyl)-1H-1,2,3-triazole-4-carboxamide. N-((5-bromo-3-fluoro-2-methoxypyridin-4-yl)methyl)-1-((6-cyclopropylimidazo[1,2-a]pyridin-2-yl)methyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and (5-bromo-3-fluoro-2-methoxypyridin-4-yl)methanamine. The crude product was purified by recrystallization from MeOH to yield the product (160 mg, yield: 76%) as a white solid. ESI-MS [M+H]+: 500.1.

Synthesis of N-((5-cyano-3-fluoro-2-methoxypyridin-4-yl)methyl)-1-((6-cyclopropylimidazo[1,2-a]pyridin-2-yl)methyl)-1H-1,2,3-triazole-4-carboxamide. A solution of N-((5-bromo-3-fluoro-2-methoxypyridin-4-yl)methyl)-1-((6-cyclopropylimidazo[1,2-a]pyridin-2-yl)methyl)-1H-1,2,3-triazole-4-carboxamide (110 mg, 0.22 mmol), Zn(CN)$_2$ (52 mg, 0.44 mmol), Pd(dppf)Cl$_2$ (19.7 mg, 0.027 mmol) and Pd$_2$(dba)$_3$ (25 mg, 0.027 mmol) in DMF (4 mL) was stirred at 110° C. for 50 min with microwave. The reaction mixture was washed with water (30 mL) and extracted with EtOAc (50 mL×2). The combined organic layers were washed with brine (30 mL), dried over Na$_2$SO$_4$, concentrated and purified by Prep-TLC (DCM/MeOH=15:1) to give N-((5-cyano-3-fluoro-2-methoxypyridin-4-yl)methyl)-1-((6-cyclopropylimidazo[1,2-a]pyridin-2-yl)methyl)-1H-1,2,3-triazole-4-carboxamide (55.4 mg, yield: 56%) as a white solid. ESI-MS [M+H]+: 447.1. $^1$H NMR (400 MHz, DMSO) δ 9.18 (t, J=5.3 Hz, 1H), 8.56 (s, 1H), 8.48 (s, 1H), 8.34 (s, 1H), 7.83 (s, 1H), 7.40 (d, J=9.3 Hz, 1H), 7.00 (dd, J=9.4, 1.4 Hz, 1H), 5.73 (s, 2H), 4.56 (d, J=5.2 Hz, 2H), 4.00 (s, 3H), 1.95-1.88 (m, 1H), 0.91-0.88 (m, 2H), 0.68-0.64 (m, 2H).

Example 56

1-((6-cyclopropylimidazo[1,2-a]pyridin-2-yl)methyl)-N-(2-fluoro-6-(imidazo[1,2-a]pyridin-2-yl)-3-methoxybenzyl)-1H-1,2,3-triazole-4-carboxamide (I-70)

Scheme 56

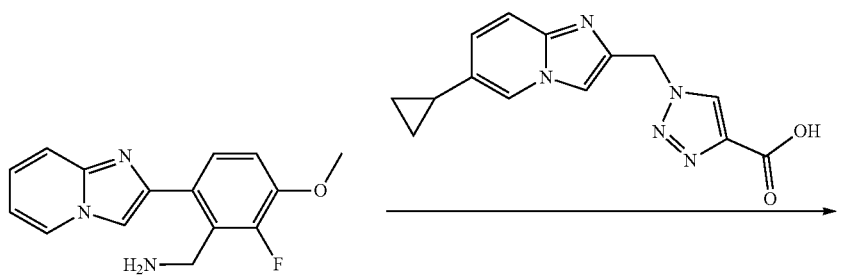

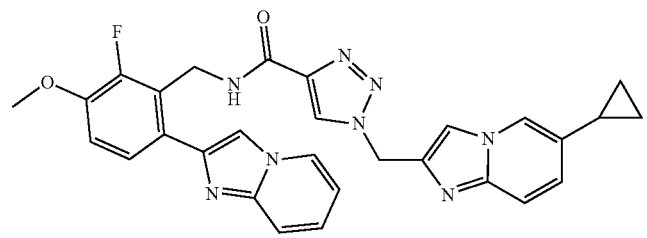

Synthesis of 1-((6-cyclopropylimidazo[1,2-a]pyridin-2-yl)methyl)-N-(2-fluoro-3-methoxy-6-(pyrazolo[1,5-a]pyridin-2-yl)benzyl)-1H-1,2,3-triazole-4-carboxamide. 1-((6-cyclopropylimidazo[1,2-a]pyridin-2-yl)methyl)-N-(2-fluoro-6-(imidazo[1,2-a]pyridin-2-yl)-3-methoxybenzyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (2-fluoro-6-(imidazo[1,2-a]pyridin-2-yl)-3-methoxyphenyl)methanamine. The crude product was purified by prep-HPLC to yield the product (80 mg, 42% over two steps) as a white solid. ESI-MS [M+H]+: 537.2. $^1$H NMR (400 MHz, DMSO) δ 9.37 (s, 1H), 8.67 (d, J=6.7 Hz, 1H), 8.52 (s, 1H), 8.41 (s, 1H), 8.32 (s, 1H), 7.89 (s, 1H), 7.67 (d, J=8.9 Hz, 1H), 7.52-7.42 (m, 3H), 7.22 (t, J=8.6 Hz, 1H), 7.16-7.11 (m, 2H), 5.75 (s, 2H), 4.67 (d, J=5.5 Hz, 2H), 3.86 (s, 3H), 1.97-1.91 (m, 1H), 0.94-0.90 (m, 2H), 0.69-0.66 (m, 2H).

Example 57

1-((6-cyclopropylimidazo[1,2-a]pyridin-2-yl)methyl)-N-(2-fluoro-3-methoxy-6-(1H-pyrazol-4-yl)benzyl)-1H-1,2,3-triazole-4-carboxamide (I-67)

Scheme 57

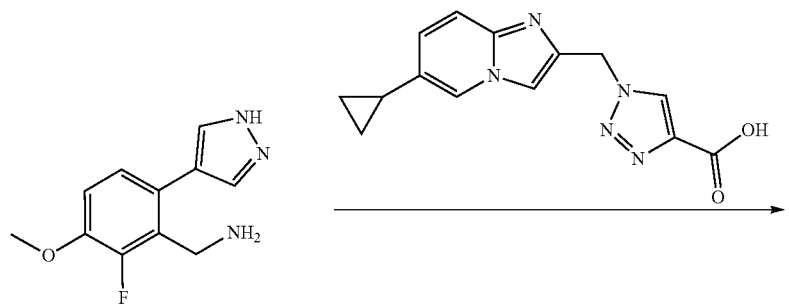

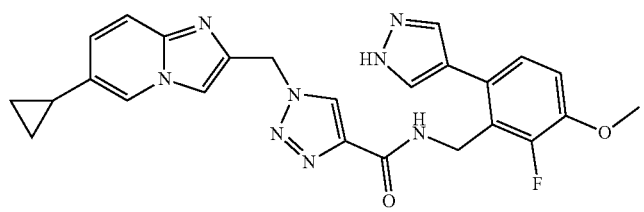

Synthesis of 1-((6-cyclopropylimidazo[1,2-a]pyridin-2-yl)methyl)-N-(2-fluoro-3-methoxy-6-(1H-pyrazol-4-yl)benzyl)-1H-1,2,3-triazole-4-carboxamide. 1-((6-cyclopropylimidazo[1,2-a]pyridin-2-yl)methyl)-N-(2-fluoro-3-methoxy-6-(1H-pyrazol-4-yl)benzyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (2-fluoro-3-methoxy-6-(1H-pyrazol-4-yl)phenyl)methanamine. The crude product was purified by prep-HPLC to yield the product (2.5 mg, yield: 2%) as a yellow solid. ESI-MS [M+H]$^+$: 487.2. $^1$H NMR (400 MHz, DMSO) δ 8.72-8.63 (m, 2H), 8.60-8.57 (m, 1H), 8.19-8.14 (m, 1H), 7.77-7.73 (m, 3H), 7.64-7.58 (m, 1H), 7.17-7.12 (m, 2H), 5.96 (s, 2H), 4.51-4.50 (m, 2H), 3.84 (s, 3H), 2.11-2.03 (m, 1H), 1.09-0.95 (m, 2H), 0.82-0.69 (m, 2H).

Example 58

1-((6-cyclopropylimidazo[1,2-a]pyridin-2-yl)methyl)-N-(2-fluoro-3-methoxy-6-(1H-tetrazol-1-yl)benzyl)-N-methyl-1H-1,2,3-triazole-4-carboxamide (I-66)

Scheme 58

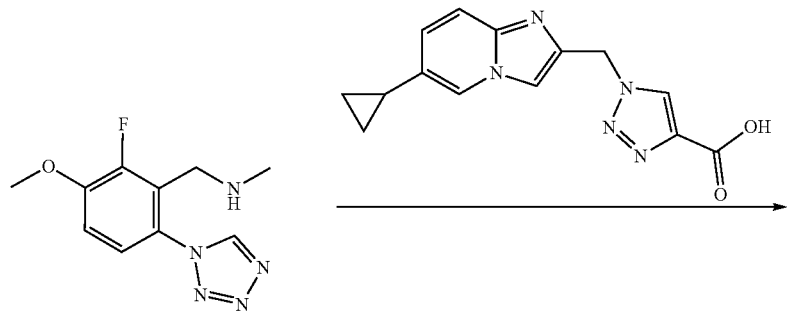

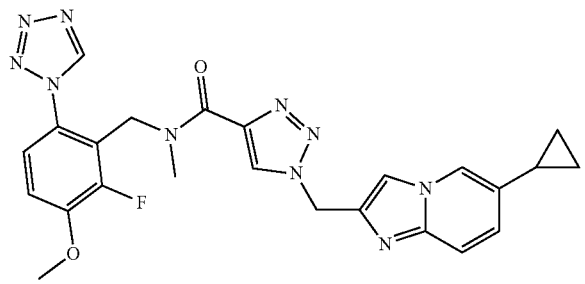

Synthesis of 1-((6-cyclopropylimidazo[1,2-a]pyridin-2-yl) methyl)-N-(2-fluoro-3-methoxy-6-(1H-tetrazol-1-yl)benzyl)-N-methyl-1H-1,2,3-triazole-4-carboxamide. 1-((6-cyclopropylimidazo[1,2-a]pyridin-2-yl) methyl)-N-(2-fluoro-3-methoxy-6-(1H-tetrazol-1-yl)benzyl)-N-methyl-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and 1-(2-fluoro-3-methoxy-6-(1H-tetrazol-1-yl)phenyl)-N-methylmethanamine. The crude product was purified by prep-TLC (DCM/MeOH=10:1) to yield the product (30 mg, 15%) as a white solid. ESI-MS [M+H]+: 503.2. $^1$H NMR (400 MHz, DMSO) δ 9.72 (s, 1H), 8.45-8.35 (m, 2H), 7.84 (d, J=11.1 Hz, 1H), 7.42-7.35 (m, 3H), 7.02 (d, J=9.4 Hz, 1H), 5.71 (d, J=10.4 Hz, 2H), 5.20 (s, 1H), 4.54 (s, 1H), 3.94 (s, 3H), 3.17 (s, 2H), 2.68 (s, 1H), 1.96-1.89 (m, 1H), 0.94-0.86 (m, 2H), 0.69-0.66 (m, 2H).

Example 59

N-((3-chloro-1H-indol-5-yl)methyl)-1-((6-cyclopropylimidazo[1,2-a]pyridin-2-yl)methyl)-1H-1,2,3-triazole-4-carboxamide (I-65)

Scheme 59

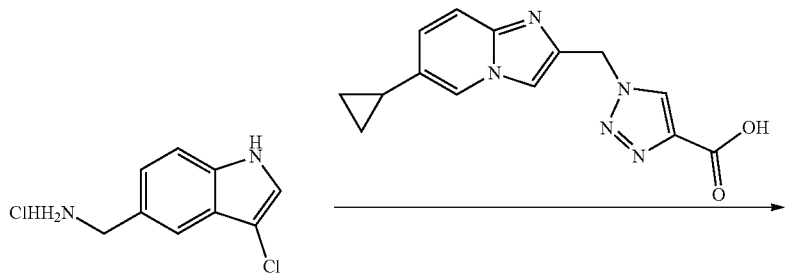

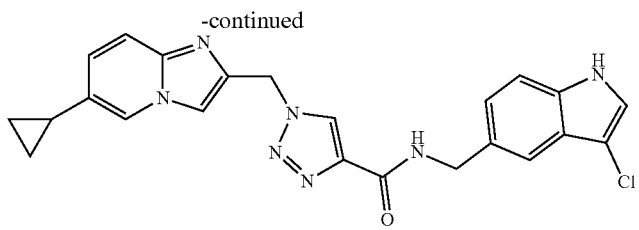

Synthesis of N-((3-chloro-1H-indol-5-yl)methyl)-1-((6-cyclopropylimidazo[1,2-a]pyridin-2-yl)methyl)-1H-1,2,3-triazole-4-carboxamide. N-((3-chloro-1H-indol-5-yl)methyl)-1-((6-cyclopropylimidazo[1,2-a]pyridin-2-yl)methyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (3-chloro-1H-indol-5-yl)methanamine hydrochloride. The crude product was purified by prep-HPLC to yield the product (20 mg, yield: 25%) as a light yellow solid. ESI-MS [M+H]+: 445.8. 1H NMR (400 MHz, MeOD) δ 8.51 (d, J=4.0 Hz, 2H), 8.14 (s, 1H), 7.69 (d, J=3.0 Hz, 2H), 7.51 (s, 1H), 7.33 (d, J=5.0 Hz, 1H), 7.24 (s, 1H), 7.21 (d, J=4.0 Hz, 1H) 5.97 (s, 2H), 4.68 (s, 2H), 2.14-2.05 (m, 1H), 1.15-1.06 (m, 2H), 0.86-0.79 (m, 2H).

Example 60

1-((6-cyclopropylimidazo[1,2-a]pyridin-2-yl)methyl)-N-(2,6-difluoro-3-methoxybenzyl)-1H-1,2,3-triazole-4-carboxamide (I-64)

Scheme 60

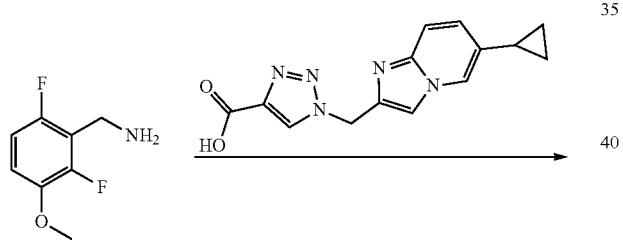

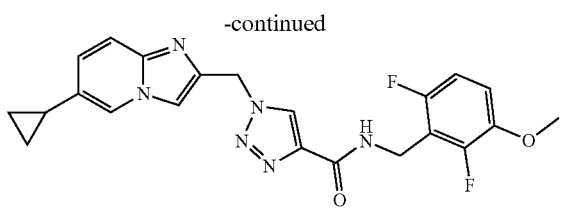

Synthesis of 1-((6-cyclopropylimidazo[1,2-a]pyridin-2-yl)methyl)-N-(2,6-difluoro-3-methoxybenzyl)-1H-1,2,3-triazole-4-carboxamide. 1-((6-cyclopropylimidazo[1,2-a]pyridin-2-yl)methyl)-N-(2,6-difluoro-3-methoxybenzyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and (2,6-difluoro-3-methoxyphenyl)methanamine. The crude product was purified by flash column chromatography (0-4% MeOH in DCM) to yield the product (90 mg, 62%) as a white solid. ESI-MS [M+H]+: 439.1. 1H NMR (400 MHz, DMSO) δ 8.82 (t, J=5.4 Hz, 1H), 8.54 (s, 1H), 8.34 (s, 1H), 7.82 (s, 1H), 7.40 (d, J=9.3 Hz, 1H), 7.15-7.05 (m, 1H), 7.04-6.94 (m, 2H), 5.72 (s, 2H), 4.49 (d, J=5.3 Hz, 2H), 3.80 (s, 3H), 1.97-1.86 (m, 1H), 0.97-0.86 (m, 2H), 0.71-0.61 (m, 2H).

Example 61

1-((6-cyclopropylimidazo[1,2-a]pyridin-2-yl)methyl)-N-(2-fluoro-3-methoxy-6-(pyrazolo[1,5-a]pyridin-2-yl)benzyl)-1H-1,2,3-triazole-4-carboxamide (I-63)

Scheme 61

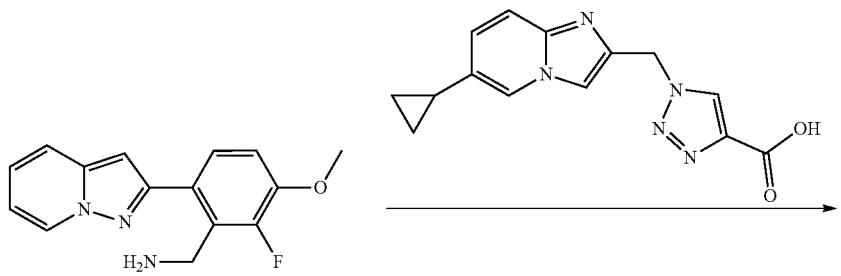

-continued

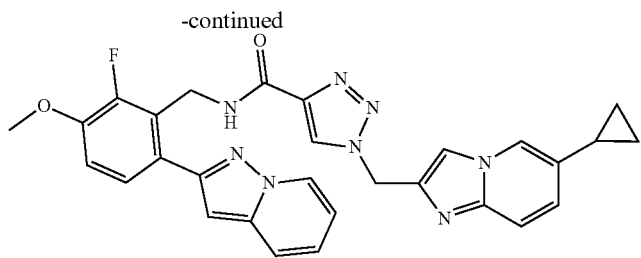

Synthesis of 1-((6-cyclopropylimidazo[1,2-a]pyridin-2-yl)methyl)-N-(2-fluoro-3-methoxy-6-(pyrazolo[1,5-a]pyridin-2-yl)benzyl)-1H-1,2,3-triazole-4-carboxamide. 1-((6-cyclopropylimidazo[1,2-a]pyridin-2-yl)methyl)-N-(2-fluoro-3-methoxy-6-(pyrazolo[1,5-a]pyridin-2-yl)benzyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (2-fluoro-3-methoxy-6-(pyrazolo[1,5-a]pyridin-2-yl)phenyl)methanamine. The crude product was purified by prep-HPLC to yield the product (2.0 mg 12.9%) as a white solid. ESI-MS [M+H]+: 537.2. $^1$H NMR (400 MHz, DMSO) δ 8.97 (t, J=5.9 Hz, 1H), 8.64 (d, J=6.9 Hz, 1H), 8.56 (s, 1H), 8.33 (s, 1H), 7.80 (s, 1H), 7.71 (d, J=8.9 Hz, 1H), 7.53 (d, J=8.7 Hz, 1H), 7.39 (d, J=9.3 Hz, 1H), 7.24 (d, J=8.8 Hz, 2H), 7.01-6.98 (m, 1H), 6.94 (d, J=6.9 Hz, 1H), 6.91 (s, 1H), 5.71 (s, 2H), 4.73 (d, J=4.9 Hz, 2H), 3.87 (s, 3H), 2.00-1.96 (m, 1H), 0.91-0.89 (m, 2H), 0.67-0.64 (m, 2H).

Example 62

1-((6-cyclopropylimidazo[1,2-a]pyridin-2-yl)methyl)-N-(2-fluoro-3-methoxy-6-(3-(trifluoromethyl)-1H-pyrazol-1-yl)benzyl)-1H-1,2,3-triazole-4-carboxamide (I-62)

Scheme 62

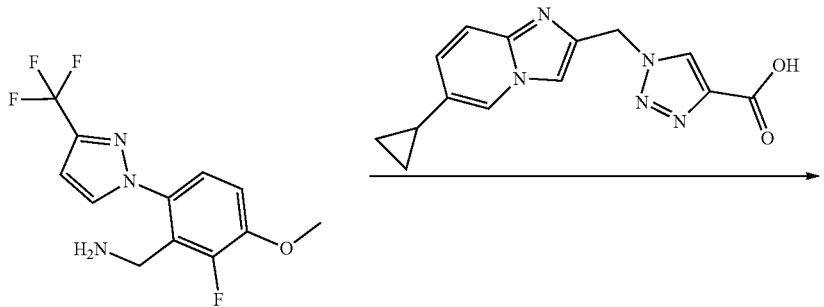

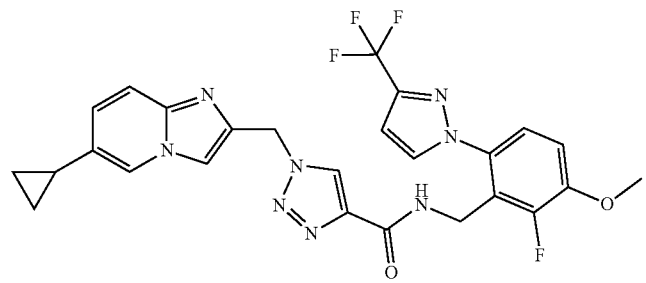

Synthesis of 1-((6-cyclopropylimidazo[1,2-a]pyridin-2-yl)methyl)-N-(2-fluoro-3-methoxy-6-(3-(trifluoromethyl)-1H-pyrazol-1-yl)benzyl)-1H-1,2,3-triazole-4-carboxamide. 1-((6-cyclopropylimidazo[1,2-a]pyridin-2-yl)methyl)-N-(2-fluoro-3-methoxy-6-(3-(trifluoromethyl)-1H-pyrazol-1-yl)benzyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and (2-fluoro-3-methoxy-6-(3-(trifluoromethyl)-1H-pyrazol-1-yl)phenyl)methanamine. The crude product was purified by prep-TLC (DCM/MeOH=10/1) to yield the product (29.1 mg, yield: 66%) as a white solid. ESI-MS [M+H]+: 555.1. $^1$H NMR (400 MHz, DMSO) δ 8.55 (t, J=5.5 Hz, 1H), 8.51 (s, 1H), 8.34 (s, 1H), 8.31 (dd, J=2.3 Hz, J=0.9 Hz, 1H), 7.81 (s, 1H), 7.40 (d, J=9.3 Hz, 1H), 7.33-7.25 (m, 2H), 7.01 (dd, J=9.4 Hz, J=1.8 Hz, 1H), 6.96 (d, J=2.3 Hz, 1H), 5.70 (s, 2H), 4.34 (d, J=5.2 Hz, 2H), 3.90 (s, 3H), 1.96-1.89 (m, 1H), 0.92-0.89 (m, 2H), 0.69-0.65 (m, 2H).

Example 63

1-((6-cyclopropylimidazo[1,2-a]pyridin-2-yl)methyl)-N-(2-fluoro-3-methoxy-6-(1H-1,2,4-triazol-1-yl)benzyl)-1H-1,2,3-triazole-4-carboxamide (I-61)

Scheme 63

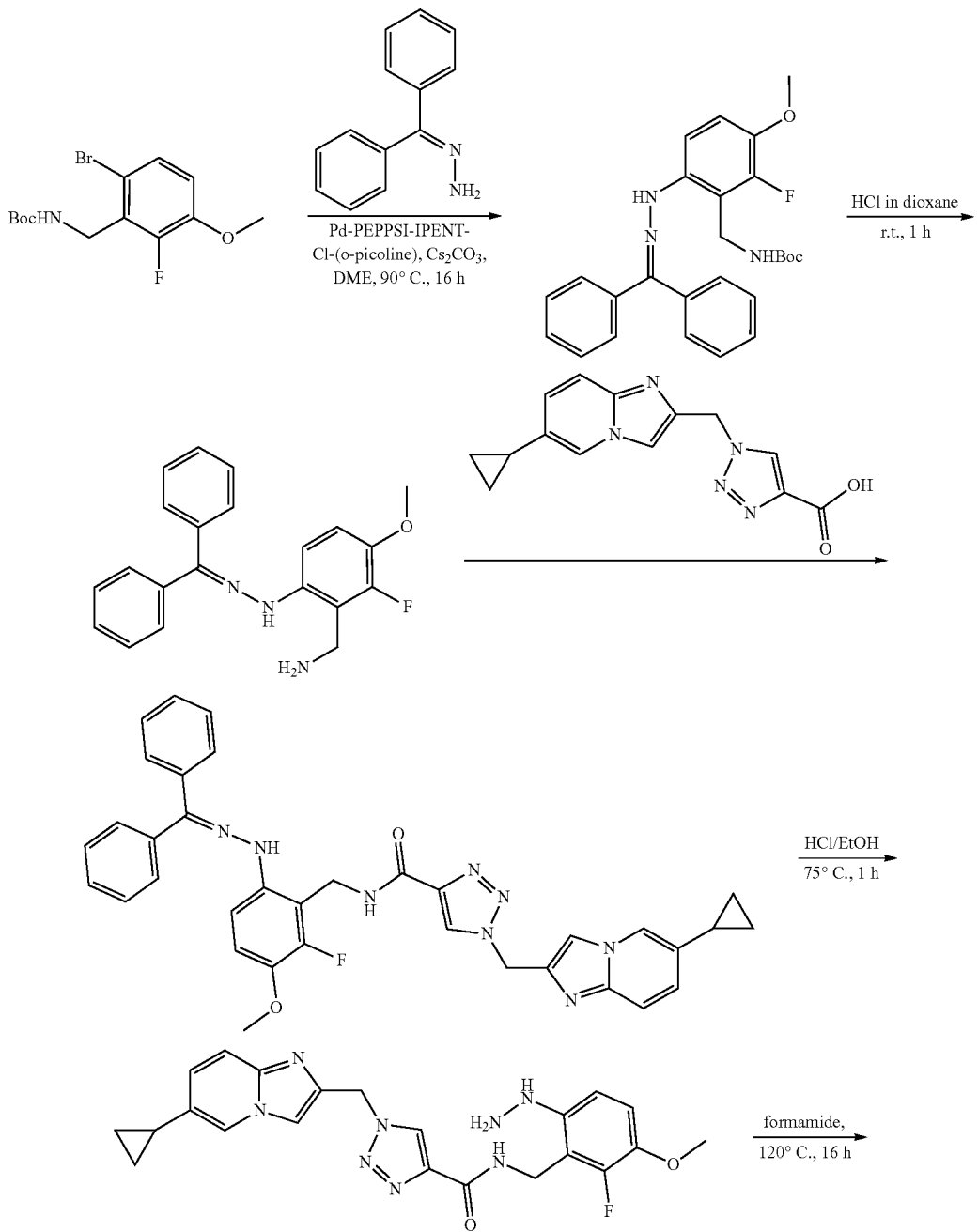

-continued

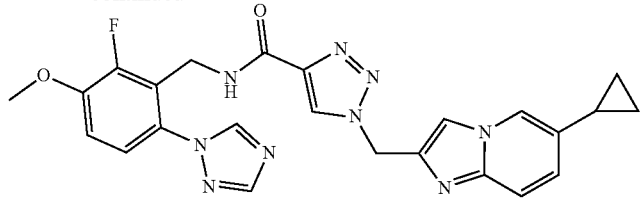

Synthesis of tert-butyl (6-(2-(diphenylmethylene)hydrazinyl)-2-fluoro-3-methoxybenzyl)carbamate. A mixture of tert-butyl (6-bromo-2-fluoro-3-methoxybenzyl)carbamate (333 mg, 1.0 mmol), (diphenylmethylene)hydrazine (245 mg, 1.25 mmol), Pd-PEPPSI-IPENT-Cl-(o-picoline), (42 mg, 0.05 mmol) and $Cs_2CO_3$ (652 mg, 2.0 mmol) in DME (15 mL) was stirred at 90° C. under $N_2$ for 16 h. The reaction mixture was concentrated in vacuo and purified by silica gel chromatography with DCM/MeOH=10/1 to give tert-butyl (6-(2-(diphenylmethylene)hydrazinyl)-2-fluoro-3-methoxybenzyl)carbamate (210 mg, 47%) as a yellow oil. ESI-MS [M+H]$^+$: 450.1.

Synthesis of (6-(2-(diphenylmethylene)hydrazinyl)-2-fluoro-3-methoxyphenyl)methanamine hydrochloride. A mixture of tert-butyl (6-(2-(diphenylmethylene)hydrazinyl)-2-fluoro-3-methoxybenzyl) carbamate (200 mg, 0.445 mmol) in HCl (4M in dioxane, 5.0 mL) was stirred at RT for 1 h. The reaction mixture was concentrated in vacuo to give (6-(2-(diphenylmethylene) hydrazinyl)-2-fluoro-3-methoxyphenyl)methanamine hydrochloride (160 mg, crude) as a yellow solid which was used in the next step directly without further purification. ESI-MS [M+H]$^+$: 350.1.

Synthesis of 1-((6-cyclopropylimidazo[1,2-a]pyridin-2-yl)methyl)-N-(6-(2-(diphenylmethylene)hydrazinyl)-2-fluoro-3-methoxybenzyl)-1H-1,2,3-triazole-4-carboxamide. 1-((6-cyclopropylimidazo[1,2-a]pyridin-2-yl)methyl)-N-(6-(2-(diphenylmethylene)hydrazinyl)-2-fluoro-3-methoxybenzyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (6-(2-(diphenylmethylene) hydrazinyl)-2-fluoro-3-methoxyphenyl)methanamine hydrochloride. The crude product was purified by prep-TLC (DCM/MeOH=20/1) to yield the product (120 mg, yield: 44%, two steps) as a yellow solid. ESI-MS [M+H]$^+$: 615.2.

Synthesis of 1-((6-cyclopropylimidazo[1,2-a]pyridin-2-yl)methyl)-N-(2-fluoro-6-hydrazinyl-3-methoxybenzyl)-1H-1,2,3-triazole-4-carboxamide. A mixture of 1-((6-cyclopropylimidazo[1,2-a]pyridin-2-yl)methyl)-N-(6-(2-(diphenylmethylene)hydrazinyl)-2-fluoro-3-methoxybenzyl)-1H-1,2,3-triazole-4-carboxamide (122.8 mg, 0.2 mmol) in conc. HCl/EtOH (2.0 mL/4.0 mL) was stirred at 75° C. for 1 h. The reaction mixture was concentrated in vacuo to give the desired product (90 mg, crude) as a yellow solid which was used in the next step directly without further purification. ESI-MS [M+H]$^+$: 451.1.

Synthesis of 1-((6-cyclopropylimidazo[1,2-a]pyridin-2-yl)methyl)-N-(2-fluoro-3-methoxy-6-(1H-1,2,4-triazol-1-yl)benzyl)-1H-1,2,3-triazole-4-carboxamide. A mixture of 1-((6-cyclopropylimidazo[1,2-a]pyridin-2-yl)methyl)-N-(2-fluoro-6-hydrazinyl-3-methoxybenzyl)-1H-1,2,3-triazole-4-carboxamide (90 mg, crude) in formamide (3 mL) was stirred at 120° C. for 16 h. The reaction mixture was diluted with EtOAc (50 mL) and washed with water (50 mL). The organic layer was separated, dried over $Na_2SO_4$, and concentrated in vacuo to give the crude product, which was purified by prep-HPLC to give 1-((6-cyclopropylimidazo[1,2-a]pyridin-2-yl)methyl)-N-(2-fluoro-3-methoxy-6-(1H-1,2,4-triazol-1-yl)benzyl)-1H-1,2,3-triazole-4-carboxamide (7.3 mg, yield: 7.5% over two steps) as a white solid. ESI-MS [M+H]$^+$: 488.1. Purity: 95.8% (214 nm), 95.5% (254 nm). $^1$H NMR (400 MHz, DMSO) δ 8.84 (s, 1H), 8.56 (t, J=5.4 Hz, 1H), 8.51 (s, 1H), 8.34 (s, 1H), 8.22 (s, 1H), 7.81 (s, 1H), 7.40 (d, J=9.3 Hz, 1H), 7.34-7.24 (m, 2H), 7.01 (dd, J=9.4, 1.7 Hz, 1H), 5.71 (s, 2H), 4.36 (d, J=4.9 Hz, 2H), 3.90 (s, 3H), 1.93-1.86 (m, 1H), 0.98-0.89 (m, 2H), 0.73-0.65 (m, 2H).

Example 64

N-benzyl-1-((6-cyclopropylimidazo[1,2-a]pyridin-2-yl)methyl)-1H-1,2,3-triazole-4-carboxamide (I-60)

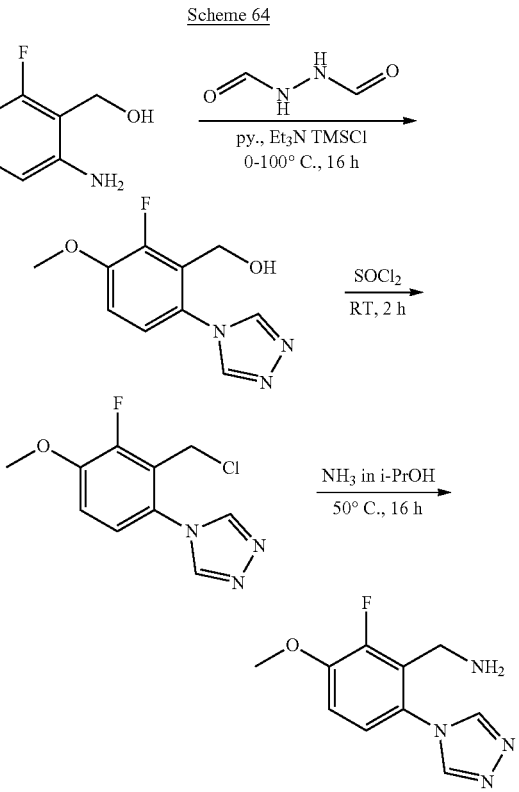

Synthesis of N-benzyl-1-((6-cyclopropylimidazo[1,2-a]pyridin-2-yl)methyl)-1H-1,2,3-triazole-4-carboxamide. N-benzyl-1-((6-cyclopropylimidazo[1,2-a]pyridin-2-yl)methyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and benzylamine. The crude product was purified by prep-TLC (DCM/MeOH=10/1) to yield the product (120 mg, yield: 45%) as a white solid. ESI-MS [M+H]+: 373.2. $^1$H NMR (400 MHz, DMSO) δ 9.08 (t, J=6.3 Hz, 1H), 8.57 (s, 1H), 8.36 (s, 1H), 7.85 (s, 1H), 7.41 (d, J=9.3 Hz, 1H), 7.34-7.27 (m, 4H), 7.25-7.17 (m, 1H), 7.04-7.00 (m, 1H), 5.75 (d, J=7.0 Hz, 2H), 4.43 (d, J=6.3 Hz, 2H), 1.97-1.87 (m, 1H), 0.96-0.87 (m, 2H), 0.72-0.63 (m, 2H).

Example 65

1-((6-cyclopropylimidazo[1,2-a]pyridin-2-yl)methyl)-N-(2-fluoro-3-methoxy-6-(methylsulfinyl)benzyl)-1H-1,2,3-triazole-4-carboxamide (I-58)

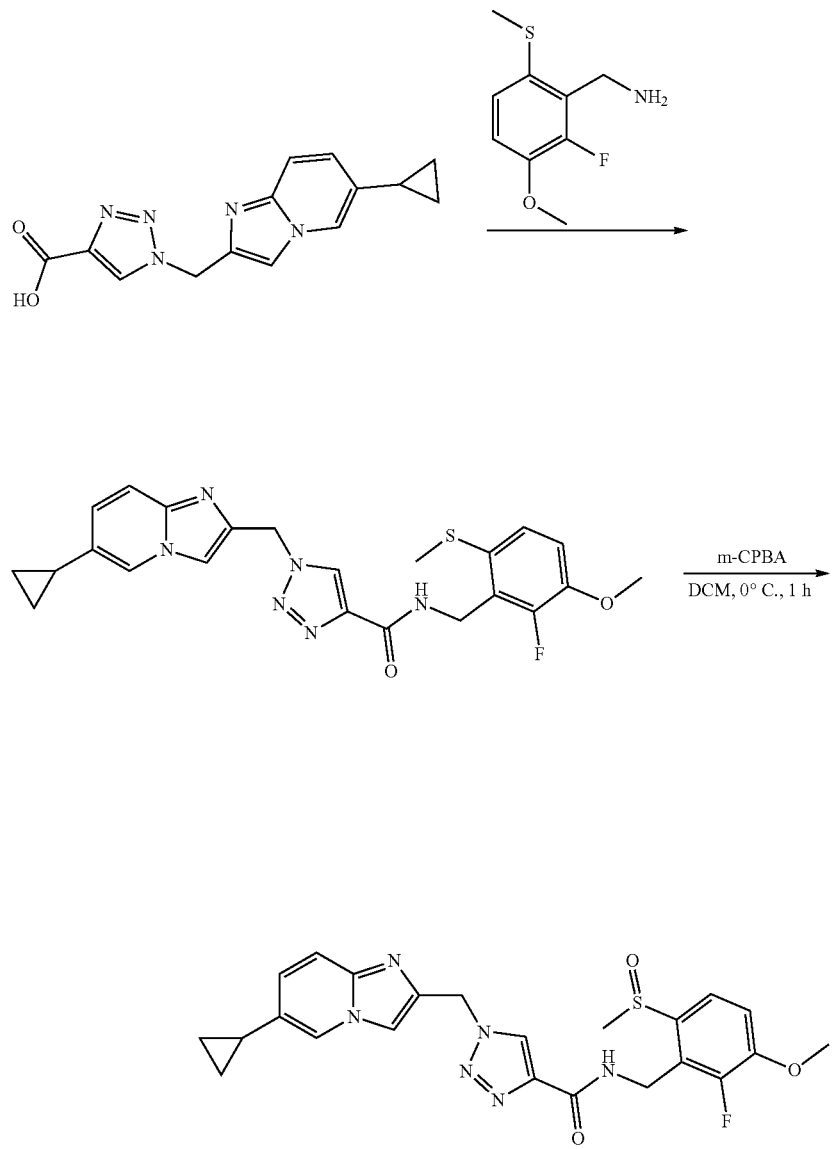

Scheme 65

Synthesis of 1-((6-cyclopropylimidazo[1,2-a]pyridin-2-yl)methyl)-N-(2-fluoro-3-methoxy-6-(methylthio)benzyl)-1H-1,2,3-triazole-4-carboxamide. 1-((6-cyclopropylimidazo[1,2-a]pyridin-2-yl)methyl)-N-(2-fluoro-3-methoxy-6-(methylthio)benzyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and (2-fluoro-3-methoxy-6-(methylthio)phenyl)methanamine. The crude product was purified by prep-TLC (DCM/MeOH=10/1) to yield the product (300 mg, 49.5%) as a yellow solid. ESI-MS [M+H]$^+$: 467.1.

Synthesis of 1-((6-cyclopropylimidazo[1,2-a]pyridin-2-yl)methyl)-N-(2-fluoro-3-methoxy-6-(methylsulfinyl)benzyl)-1H-1,2,3-triazole-4-carboxamide. To a solution of 1-((6-cyclopropylimidazo[1,2-a]pyridin-2-yl)methyl)-N-(2-fluoro-3-methoxy-6-(methylthio)benzyl)-1H-1,2,3-triazole-4-carboxamide (100 mg, 0.21 mmol) in DCM (5 mL) was added 3-chlorobenzoperoxoic acid (36 mg, 0.21 mmol) at 0° C. The reaction mixture was stirred at 0° C. for 1 h. The mixture was diluted with DCM (15 mL), washed with brine (30 mL), dried over Na$_2$SO$_4$ and concentrated in vacuo to give the crude product, which was purified by Prep-TLC (DCM/MeOH=10/1) to give 1-((6-cyclopropylimidazo[1,2-a]pyridin-2-yl)methyl)-N-(2-fluoro-3-methoxy-6-(methylsulfinyl)benzyl)-1H-1,2,3-triazole-4-carboxamide (20 mg, yield: 19.4%) as a white solid. ESI-MS [M+H]$^+$: 483.1. Purity: 91.77 (214 nm), 91.39 (254 nm). $^1$H NMR (400 MHz, CDCl3) δ=8.27 (t, J=6.4 Hz, 1H), 8.23 (s, 1H), 7.85 (s, 1H), 7.53 (d, J=8.0 Hz, 1H), 7.46 (s, 1H), 7.14 (t, J=8.8 Hz, 1H), 7.01 (dd, J=9.2, 1.6 Hz, 1H), 6.82 (dd, J=9.2, 4.0 Hz, 1H), 5.75 (s, 2H), 5.12 (dd, J=14.4, 6.4 Hz 1H), 4.91 (dd, J=14.4, 6.4 Hz, 1H), 3.85 (s, 3H), 3.03 (s, 3H), 1.92-1.85 (m, 1H), 0.98 (dd, J=14.0, 5.6 Hz, 2H), 0.67 (q, J=5.6 Hz, 2H).

Example 66

1-((6-cyclopropylimidazo[1,2-a]pyridin-2-yl)methyl)-N-(2-fluoro-3-methoxy-6-(methylsulfonyl)benzyl)-1H-1,2,3-triazole-4-carboxamide (I-53)

Scheme 66

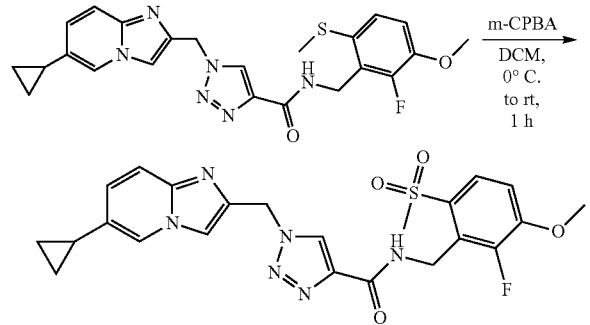

Synthesis of 1-((6-cyclopropylimidazo[1,2-a]pyridin-2-yl)methyl)-N-(2-fluoro-3-methoxy-6-(methylsulfonyl)benzyl)-1H-1,2,3-triazole-4-carboxamide. To a solution of 1-((6-cyclopropylimidazo[1,2-a]pyridin-2-yl)methyl)-N-(2-fluoro-3-methoxy-6-(methylthio)benzyl)-1H-1,2,3-triazole-4-carboxamide (100 mg, 0.21 mmol) in DCM (5 mL) was added 3-chlorobenzoperoxoic acid (72 mg, 0.42 mmol) at 0° C. The reaction mixture was stirred at room temperature for 1 h. The mixture was diluted with DCM (15 mL), washed with brine (30 mL), dried over Na$_2$SO$_4$ and concentrated to give the crude product, which was purified by Prep-HPLC to give 1-((6-cyclopropylimidazo[1,2-a]pyridin-2-yl)methyl)-N-(2-fluoro-3-methoxy-6-(methylsulfonyl)benzyl)-1H-1,2,3-triazole-4-carboxamide (20 mg, yield: 19%) as a white solid. ESI-MS [M+H]$^+$: 498.8. Purity: 99.79 (214 nm), 99.16 (254 nm). $^1$H NMR (400 MHz, CDCl$_3$) δ=8.37 (s, 1H), 8.12 (s, 1H), 8.04 (t, J=6.4 Hz, 1H), 7.92 (d, J=9.2 Hz, 1H), 7.77 (s, 1H), 7.44 (d, J=9.2 Hz, 1H), 7.32 (t, J=9.2 Hz, 1H), 7.02 (dd, J=9.2, 4.0 Hz, 1H), 5.96 (s, 2H), 5.04 (d, J=6.0 Hz, 2H), 3.96 (s, 3H), 3.34 (s, 3H), 2.02-1.95 (m, 1H), 1.1 (q, J=6.4 Hz, 2H), 0.77 (q, J=5.6 Hz, 2H).

Example 67

1-((6-cyclopropylimidazo[1,2-a]pyridin-2-yl)methyl)-N-(6-(N,N-dimethylsulfamoyl)-2-fluoro-3-methoxybenzyl)-1H-1,2,3-triazole-4-carboxamide (I-57)

Scheme 67

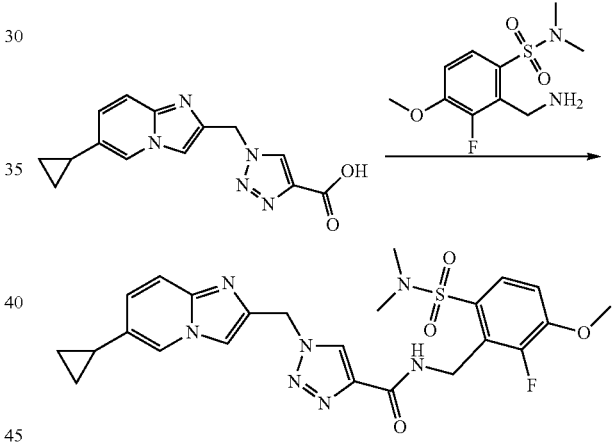

Synthesis of 1-((6-cyclopropylimidazo[1,2-a]pyridin-2-yl)methyl)-N-(6-(N,N-dimethylsulfamoyl)-2-fluoro-3-methoxybenzyl)-1H-1,2,3-triazole-4-carboxamide. 1-((6-cyclopropylimidazo[1,2-a]pyridin-2-yl)methyl)-N-(6-(N,N-dimethylsulfamoyl)-2-fluoro-3-methoxybenzyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and 2-(aminomethyl)-3-fluoro-4-methoxy-N,N-dimethylbenzenesulfonamide. The crude product was purified by prep-TLC (DCM/MeOH=10/1) to yield the product (30 mg, yield: 20%) as a white solid. ESI-MS [M+H]+: 528.2. $^1$H NMR (400 MHz, DMSO) δ 8.58 (s, 1H), 8.34 (s, 1H), 8.30 (t, J=5.3 Hz, 1H), 7.82 (s, 1H), 7.67 (d, J=8.9 Hz, 1H), 7.40 (d, J=9.3 Hz, 1H), 7.33 (t, J=8.5 Hz, 1H), 7.02-6.99 (m, 1H), 5.72 (s, 2H), 4.81 (d, J=4.3 Hz, 2H), 3.93 (s, 3H), 2.71 (s, 6H), 1.96-1.90 (m, 1H), 0.96-0.85 (m, 2H), 0.73-0.64 (m, 2H).

Example 68

1-((6-cyclopropylimidazo[1,2-a]pyridin-2-yl)methyl)-N-(2-fluoro-3-methoxy-6-(3-(trifluoromethyl)-1H-1,2,4-triazol-1-yl)benzyl)-1H-1,2,3-triazole-4-carboxamide (I-52)

Scheme 68

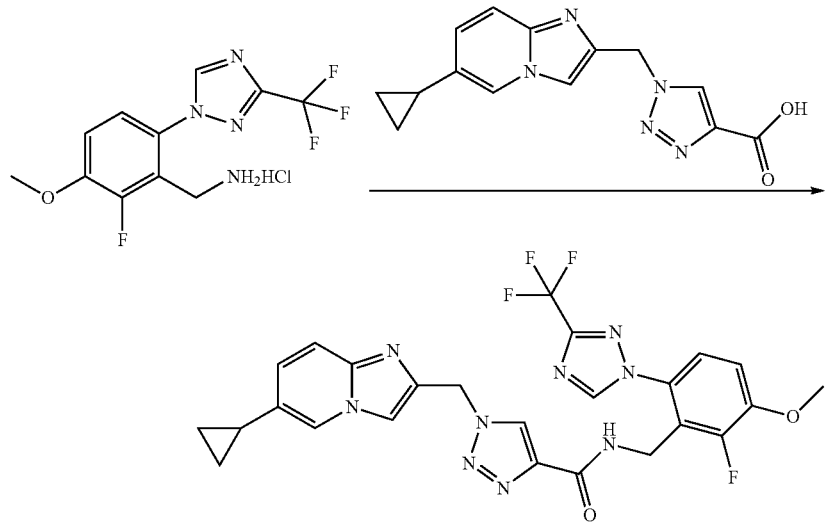

Synthesis of 1-((6-cyclopropylimidazo[1,2-a]pyridin-2-yl)methyl)-N-(2-fluoro-3-methoxy-6-(3-(trifluoromethyl)-1H-1,2,4-triazol-1-yl)benzyl)-1H-1,2,3-triazole-4-carboxamide. 1-((6-cyclopropylimidazo[1,2-a]pyridin-2-yl)methyl)-N-(2-fluoro-3-methoxy-6-(3-(trifluoromethyl)-1H-1,2,4-triazol-1-yl)benzyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (2-fluoro-3-methoxy-6-(3-(trifluoromethyl)-1H-1,2,4-triazol-1-yl)phenyl)methanamine hydrochloride. The crude product was purified by prep-HPLC to yield the product (27.8 mg, yield: 33%) as a yellow solid. ESI-MS [M+H]+: 556.2. $^1$H NMR (400 MHz, DMSO) δ 9.13 (s, 1H), 8.71 (s, 1H), 8.48 (s, 1H), 8.34 (s, 1H), 7.81 (s, 1H), 7.40 (d, J=9.2 Hz, 2H), 7.31 (t, J=8.7 Hz, 1H), 7.01 (d, J=9.2 Hz, 1H), 5.70 (s, 2H), 4.37 (d, J=5.1 Hz, 2H), 3.91 (s, 3H), 2.00-1.82 (m, 1H), 1.02-0.83 (m, 2H), 0.76-0.58 (m, 2H).

Example 69

1-((6-cyclopropylimidazo[1,2-a]pyridin-2-yl)methyl)-N-(2-(methylsulfonyl)benzyl)-1H-1,2,3-triazole-4-carboxamide (I-51)

Scheme 69

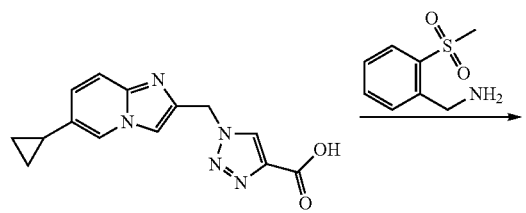

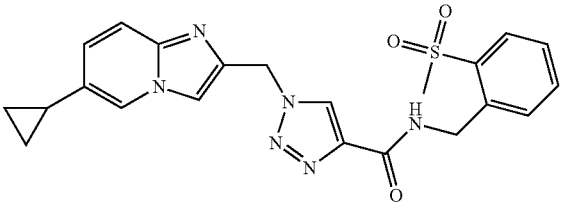

Synthesis of 1-((6-cyclopropylimidazo[1,2-a]pyridin-2-yl)methyl)-N-(2-(methylsulfonyl)benzyl)-1H-1,2,3-triazole-4-carboxamide. 1-((6-cyclopropylimidazo[1,2-a]pyridin-2-yl)methyl)-N-(2-(methylsulfonyl)benzyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and (2-(methylsulfonyl)phenyl)methanamine. The crude product was purified by prep-TLC (DCM/MeOH=10/1) to yield the product (30 mg, yield: 8%) as a white solid. ESI-MS [M+H]+: 451.2. $^1$H NMR (400 MHz, DMSO) δ 9.22 (t, J=6.1 Hz, 1H), 8.61 (s, 1H), 8.36 (s, 1H), 8.27 (s, 1H), 7.92 (d, J=7.8 Hz, 1H), 7.86 (s, 1H), 7.68 (t, J=7.5 Hz, 1H), 7.61-7.47 (m, 2H), 7.41 (d, J=9.3 Hz, 1H), 7.01 (d, J=9.4 Hz, 1H), 5.75 (s, 2H), 4.83 (d, J=6.1 Hz, 2H), 3.37 (s, 3H), 1.96-1.91 (m, 1H), 0.98-0.92 (m, 2H), 0.74-0.66 (m, 2H).

Example 70

1-((6-cyclopropylimidazo[1,2-a]pyridin-2-yl)methyl)-N-(2-fluoro-3-methoxy-6-(1H-1,2,3-triazol-4-yl)benzyl)-1H-1,2,3-triazole-4-carboxamide (I-49)

Scheme 70

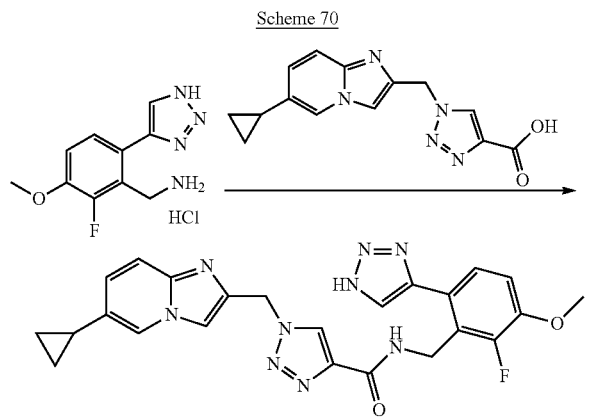

Synthesis of 1-((6-cyclopropylimidazo[1,2-a]pyridin-2-yl)methyl)-N-(2-fluoro-3-methoxy-6-(1H-1,2,3-triazol-4-yl)benzyl)-1H-1,2,3-triazole-4-carboxamide. 1-((6-cyclopropylimidazo[1,2-a]pyridin-2-yl)methyl)-N-(2-fluoro-3-methoxy-6-(1H-1,2,3-triazol-4-yl)benzyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (2-fluoro-3-methoxy-6-(1H-1,2,3-triazol-4-yl)phenyl)methanamine hydrochloride. The crude product was purified by prep-HPLC to yield the product (3.1 mg, yield: 3.2%, for two steps) as a yellow solid. ESI-MS [M+H]+: 488.2. $^1$H NMR (400 MHz, DMSO) δ 8.81 (s, 1H), 8.55 (s, 1H), 8.43 (s, 2H), 8.33 (s, 1H), 8.16 (s, 1H), 7.79 (s, 1H), 7.52-7.31 (m, 2H), 7.20-7.18 (m, 1H), 7.00 (d, J=9.2 Hz, 1H), 5.72 (s, 2H), 4.65 (s, 2H), 3.86 (s, 3H), 1.98-1.84 (m, 1H), 1.00-0.82 (m, 2H), 0.68-0.66 (m, 2H).

Example 71

1-((6-cyclopropylimidazo[1,2-a]pyridin-2-yl)methyl)-N-(2-fluoro-3-methoxy-6-(morpholinosulfonyl)benzyl)-1H-1,2,3-triazole-4-carboxamide (I-48)

Scheme 71

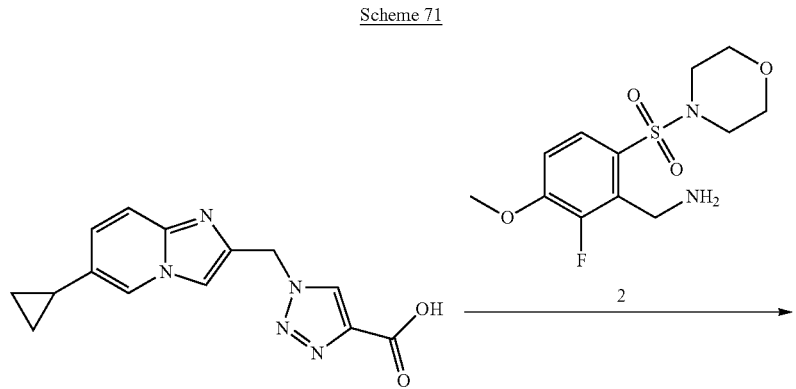

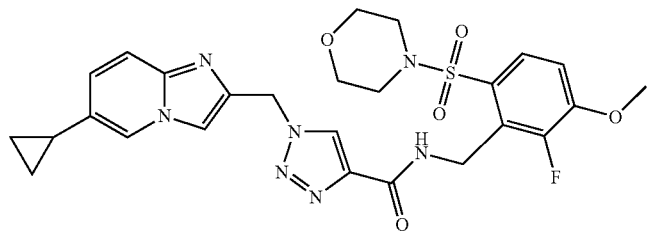

Synthesis of 1-((6-cyclopropylimidazo[1,2-a]pyridin-2-yl)methyl)-N-(2-fluoro-3-methoxy-6-(morpholinosulfonyl)benzyl)-1H-1,2,3-triazole-4-carboxamide. 1-((6-cyclopropylimidazo[1,2-a]pyridin-2-yl)methyl)-N-(2-fluoro-3-methoxy-6-(morpholinosulfonyl)benzyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and (2-fluoro-3-methoxy-6-(morpholinosulfonyl)phenyl)methanamine. The crude product was purified by Prep-TLC (DCM/MeOH=10/1) to yield the product (30 mg, yield: 14%) as a white solid. ESI-MS [M+H]+: 570.2. $^1$H NMR (400 MHz, DMSO) δ 8.59 (s, 1H), 8.38-8.33 (m, 2H), 7.82 (s, 1H), 7.70 (d, J=8.9 Hz, 1H), 7.42-7.31 (m, 2H), 7.04-6.95 (m, 1H), 5.73 (s, 2H), 4.83-4.79 (m, 2H), 3.95 (s, 3H), 3.62-3.55 (m, 4H), 3.04-2.95 (m, 4H), 1.93-1.88 (m, 1H), 0.95-0.85 (m, 2H), 0.71-0.60 (m, 2H).

Example 72

1-((6-cyclopropylimidazo[1,2-a]pyridin-2-yl)methyl)-N-(1-(2-fluoro-3-methoxy-6-(1H-tetrazol-1-yl)phenyl)ethyl)-1H-1,2,3-triazole-4-carboxamide (I-31)

Scheme 72

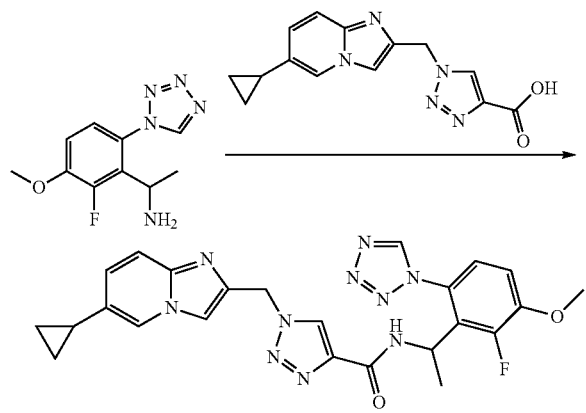

Synthesis of 1-((6-cyclopropylimidazo[1,2-a]pyridin-2-yl)methyl)-N-(1-(2-fluoro-3-methoxy-6-(1H-tetrazol-1-yl)phenyl)ethyl)-1H-1,2,3-triazole-4-carboxamide. 1-((6-cyclopropylimidazo[1,2-a]pyridin-2-yl)methyl)-N-(1-(2-fluoro-3-methoxy-6-(1H-tetrazol-1-yl)phenyl)ethyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and 1-(2-fluoro-3-methoxy-6-(1H-tetrazol-1-yl)phenyl)ethan-1-amine. The crude product was purified by Prep-TLC (DCM/MeOH=18/1) to yield the product (17.4 mg, 41%) as an off-white solid. ESI-MS [M+H]$^+$: 503.2. $^1$H NMR (400 MHz, DMSO) δ 9.78 (s, 1H), 8.77 (d, J=6.4 Hz, 1H), 8.51 (s, 1H), 8.34 (s, 1H), 7.81 (s, 1H), 7.41-7.30 (m, 3H), 7.01 (d, J=9.3 Hz, 1H), 5.71 (s, 2H), 4.47-4.43 (m, 1H), 3.90 (s, 3H), 1.95-1.89 (m, 1H), 1.56 (d, J=7.0 Hz, 3H), 0.92-0.91 (m, 2H), 0.67-0.66 (m, 2H).

Example 73

N-((6-amino-2,4-dimethylpyridin-3-yl)methyl)-1-((6-cyclopropylimidazo[1,2-a]pyridin-2-yl)methyl)-1H-1,2,3-triazole-4-carboxamide (I-26)

Scheme 73

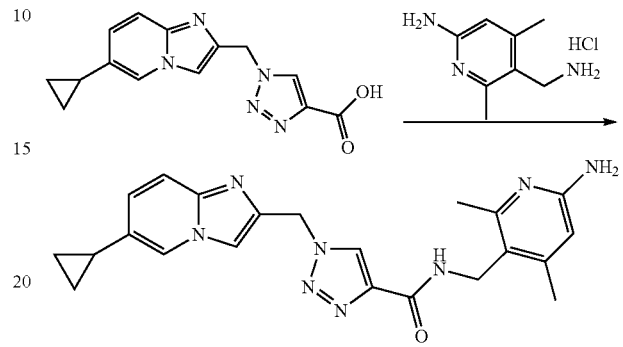

Synthesis of N-((6-amino-2,4-dimethylpyridin-3-yl)methyl)-1-((6-cyclopropylimidazo[1,2-a]pyridin-2-yl)methyl)-1H-1,2,3-triazole-4-carboxamide. N-((6-amino-2,4-dimethylpyridin-3-yl)methyl)-1-((6-cyclopropylimidazo[1,2-a]pyridin-2-yl)methyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and 5-(aminomethyl)-4,6-dimethylpyridin-2-amine hydrochloride. The crude product was purified by Prep-TLC (DCM/MeOH=10/1) to yield the product (50 mg, yield: 35%) as an off-white solid. ESI-MS [M+H]+: 417.2. $^1$H NMR (400 MHz, DMSO) δ 8.55 (s, 1H), 8.35 (s, 1H), 8.31 (t, J=5.1 Hz, 1H), 7.83 (s, 1H), 7.40 (d, J=9.3 Hz, 1H), 7.02-7.00 (m, 1H), 6.09 (s, 1H), 5.71 (s, 2H), 5.65 (s, 2H), 4.32 (d, J=5.2 Hz, 2H), 2.30 (s, 3H), 2.17 (s, 3H), 1.97-1.88 (m, 1H), 0.96-0.88 (m, 2H), 0.70-0.65 (m, 2H).

Example 74

N-(1-amino-6,7-dihydro-5H-cyclopenta[c]pyridin-5-yl)-1-((6-cyclopropylimidazo[1,2-a]pyridin-2-yl)methyl)-1H-1,2,3-triazole-4-carboxamide (I-23)

Scheme 74

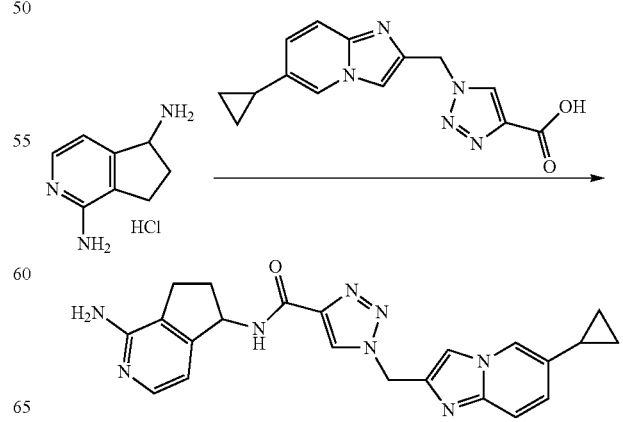

Synthesis of N-(1-amino-6,7-dihydro-5H-cyclopenta[c]pyridin-5-yl)-1-((6-cyclopropylimidazo[1,2-a]pyridin-2-yl)methyl)-1H-1,2,3-triazole-4-carboxamide. N-(1-amino-6,7-dihydro-5H-cyclopenta[c]pyridin-5-yl)-1-((6-cyclopropylimidazo[1,2-a]pyridin-2-yl)methyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and 6,7-dihydro-5H-cyclopenta[c]pyridine-1,5-diamine hydrochloride. The crude product was purified by Prep-TLC (DCM/MeOH=10/1) to yield the product (30 mg, 42%) as a white solid. ESI-MS [M+H]+: 415.2. ¹H NMR (400 MHz, DMSO) δ 8.74 (d, J=8.6 Hz, 1H), 8.59 (d, J=6.2 Hz, 1H), 8.36 (s, 1H), 7.85 (s, 1H), 7.72 (d, J=5.1 Hz, 1H), 7.41 (d, J=9.3 Hz, 1H), 7.02 (dd, J=9.4, 1.3 Hz, 1H), 6.39 (d, J=5.1 Hz, 1H), 5.77 (s, 2H), 5.74 (s, 2H), 5.42 (q, J=8.2 Hz, 1H), 2.79-2.73 (m, 1H), 2.58-2.50 (m, 1H), 2.41-2.34 (m, 1H), 2.05-1.90 (m, 2H), 0.95-0.90 (m, 2H), 0.69-0.66 (m, 2H).

Example 75

N-((5-amino-4H-1,2,4-triazol-3-yl)methyl)-1-((6-cyclopropylimidazo[1,2-a]pyridin-2-yl)methyl)-1H-1,2,3-triazole-4-carboxamide (I-21)

Scheme 75

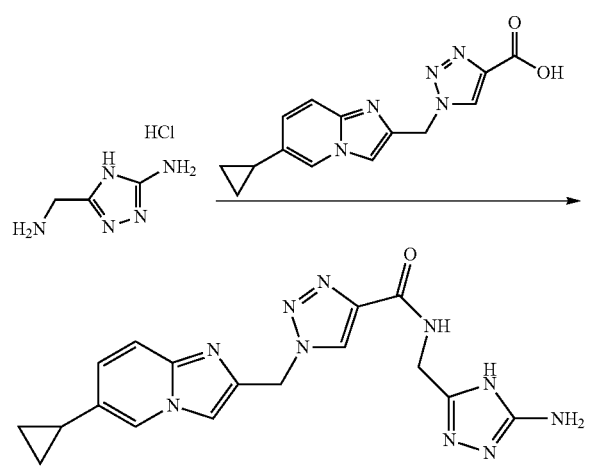

Synthesis of N-((5-amino-4H-1,2,4-triazol-3-yl)methyl)-1-((6-cyclopropylimidazo[1,2-a]pyridin-2-yl)methyl)-1H-1,2,3-triazole-4-carboxamide. N-((5-amino-4H-1,2,4-triazol-3-yl)methyl)-1-((6-cyclopropylimidazo[1,2-a]pyridin-2-yl)methyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and 5-(aminomethyl)-4H-1,2,4-triazol-3-amine hydrochloride. The crude product was purified by trituration with DCM/MeOH (200/100 mL) to yield the product (100 mg, 31%). ESI-MS [M+H]+: 379.2. ¹H NMR (400 MHz, DMSO) δ 11.71 (s, 1H), 8.56 (s, 1H), 8.45 (s, 1H), 8.34 (s, 1H), 7.83 (s, 1H), 7.40 (d, J=9.4 Hz, 1H), 7.00 (dd, J=9.4 Hz, 1.6 Hz, 1H), 5.86 (s, 2H), 5.72 (s, 2H), 4.25 (d, J=4.9 Hz, 2H), 1.94-1.90 (m, 1H), 0.92-0.90 (m, 2H), 0.68-0.64 (m, 2H).

Example 76

N-((5-amino-1,3,4-thiadiazol-2-yl)methyl)-1-((6-cyclopropylimidazo[1,2-a]pyridin-2-yl)methyl)-1H-1,2,3-triazole-4-carboxamide (I-20)

Scheme 76

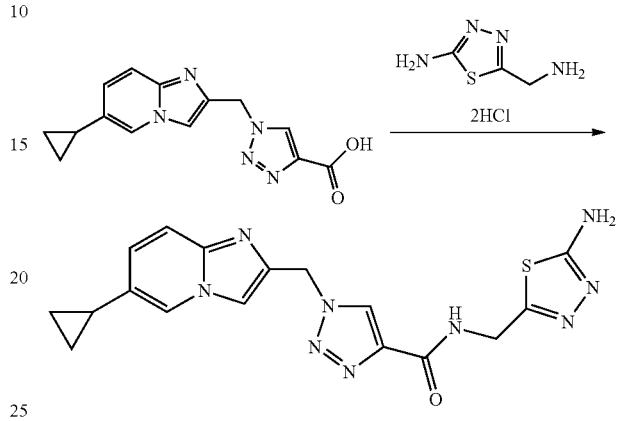

Synthesis of N-((5-amino-1,3,4-thiadiazol-2-yl)methyl)-1-((6-cyclopropylimidazo[1,2-a]pyridin-2-yl)methyl)-1H-1,2,3-triazole-4-carboxamide. N-((5-amino-1,3,4-thiadiazol-2-yl)methyl)-1-((6-cyclopropylimidazo[1,2-a]pyridin-2-yl)methyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and 5-(aminomethyl)-1,3,4-thiadiazol-2-amine hydrochloride. The crude product was purified by Prep-TLC (MeOH/DCM=1/10) to yield the product (40 mg, yield: 21%) as a white solid. ESI-MS [M+H]+: 396.1. ¹H NMR (400 MHz, DMSO) δ 9.26 (t, J=5.9 Hz, 1H), 8.61 (s, 1H), 8.35 (s, 1H), 7.84 (s, 1H), 7.42 (d, J=9.3 Hz, 1H), 7.10-6.97 (m, 3H), 5.74 (s, 2H), 4.53 (d, J=5.9 Hz, 2H), 1.93-1.90 (m, 1H), 0.93-0.90 (m, 2H), 0.68-0.65 (m, 2H).

Example 77

N-((5-amino-1,3,4-oxadiazol-2-yl)methyl)-1-((6-cyclopropylimidazo[1,2-a]pyridin-2-yl)methyl)-1H-1,2,3-triazole-4-carboxamide (I-19)

Scheme 77

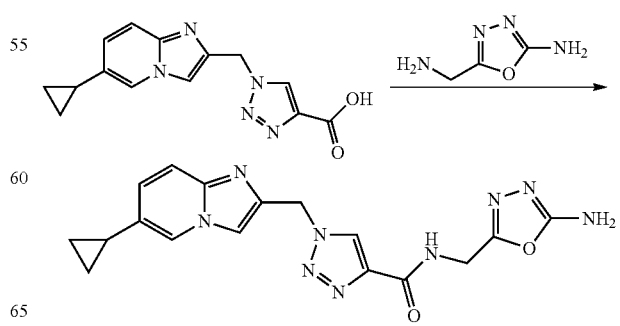

Synthesis of N-((5-amino-1,3,4-oxadiazol-2-yl)methyl)-1-((6-cyclopropylimidazo[1,2-a]pyridin-2-yl)methyl)-1H-1,2,3-triazole-4-carboxamide. N-((5-amino-1,3,4-oxadiazol-2-yl)methyl)-1-((6-cyclopropylimidazo[1,2-a]pyridin-2-yl)methyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and 5-(aminomethyl)-1,3,4-oxadiazol-2-amine. The crude product was purified by Prep-HPLC to yield the product (29 mg, yield:36.2%) as a white solid. ESI-MS [M+H]+: 380.2. ¹H NMR (400 MHz, DMSO) δ=9.11 (s, 1H), 8.61 (s, 1H), 8.37 (s, 1H), 7.85 (s, 1H), 7.42-7.40 (m, 1H), 7.03-6.95 (m, 3H), 5.75 (s, 2H), 4.46 (s, 2H), 1.95-1.90 (m, 1H), 0.95-0.91 (m, 2H), 0.69-0.65 (m, 2H).

Example 78

N-((2-aminothiazol-5-yl)methyl)-1-((6-cyclopropylimidazo[1,2-a]pyridin-2-yl)methyl)-1H-1,2,3-triazole-4-carboxamide (I-18)

Scheme 78

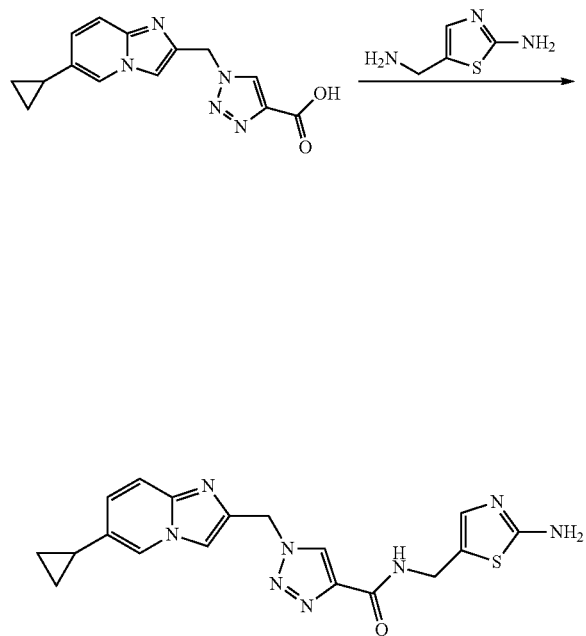

Synthesis of N-((2-aminothiazol-5-yl)methyl)-1-((6-cyclopropylimidazo[1,2-a]pyridin-2-yl)methyl)-1H-1,2,3-triazole-4-carboxamide. N-((2-aminothiazol-5-yl)methyl)-1-((6-cyclopropylimidazo[1,2-a]pyridin-2-yl)methyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and 5-(aminomethyl)thiazol-2-amine. The crude product was purified by Prep-HPLC to yield the product (6.0 mg, yield: 7.5%) as a white solid. ESI-MS [M+H]+: 395.1. ¹H NMR (400 MHz, DMSO) δ 8.94 (t, J=6.0, 1H), 8.56 (s, 1H), 8.35 (s, 1H), 8.18 (s, 1H), 7.83 (s, 1H), 7.41 (d, J=9.4, 1H), 7.01-6.96 (m, 1H), 6.75 (d, J=4.9, 2H), 5.73 (s, 2H), 4.34 (d, J=6.0, 2H), 1.93-1.90 (m, 1H), 0.97-0.87 (m, 2H), 0.73-0.62 (m, 2H).

Example 79

N-(1-amino-3-methyl-6,7-dihydro-5H-cyclopenta[c]pyridin-5-yl)-1-((6-cyclopropylimidazo[1,2-a]pyridin-2-yl)methyl)-1H-1,2,3-triazole-4-carboxamide (I-16)

Scheme 79

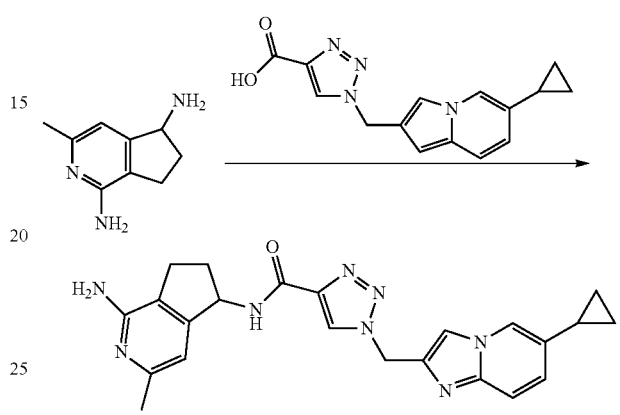

Synthesis of N-(1-amino-3-methyl-6,7-dihydro-5H-cyclopenta[c]pyridin-5-yl)-1-((6-cyclopropylimidazo[1,2-a]pyridin-2-yl)methyl)-1H-1,2,3-triazole-4-carboxamide. N-(1-amino-3-methyl-6,7-dihydro-5H-cyclopenta[c]pyridin-5-yl)-1-((6-cyclopropylimidazo[1,2-a]pyridin-2-yl)methyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and 3-methyl-6,7-dihydro-5H-cyclopenta[c]pyridine-1,5-diamine. The crude product was purified by Prep-HPLC to yield the product (8 mg, yield: 21%) as a white solid. ESI-MS [M+H]+: 429.2. ¹H NMR (400 MHz, DMSO) δ 8.70 (d, J=8.7 Hz, 1H), 8.58 (s, 1H), 8.36 (s, 1H), 7.85 (s, 1H), 7.42 (d, J=9.3 Hz, 1H), 7.02 (d, J=9.4 Hz, 1H), 6.25 (s, 1H), 5.74 (s, 2H), 5.77 (s, 2H), 5.38 (m, 1H), 2.65-2.75 (m, 1H), 2.46-2.50 (m, 1H), 2.42-2.30 (m, 1H), 2.18 (s, 3H), 1.90-2.03 (m, 2H), 0.96-0.88 (m, 2H), 0.71-0.68 (m, 2H).

Example 80

N-((4-chlorothieno[3,2-c]pyridin-2-yl)methyl)-1-((6-cyclopropylimidazo[1,2-a]pyridin-2-yl)methyl)-1H-1,2,3-triazole-4-carboxamide (I-11)

Scheme 80

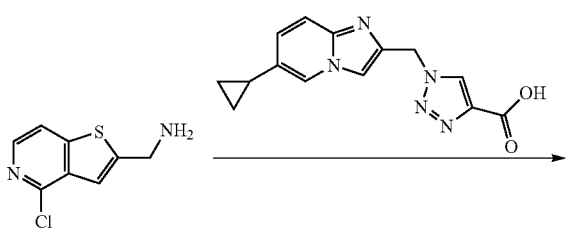

-continued

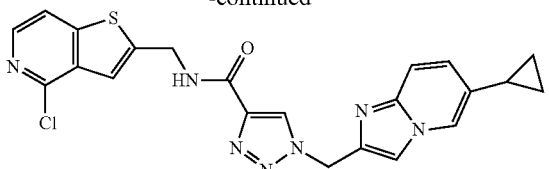

Synthesis of N-((4-chlorothieno[3,2-c]pyridin-2-yl)methyl)-1-((6-cyclopropylimidazo[1,2-a]pyridin-2-yl)methyl)-1H-1,2,3-triazole-4-carboxamide. N-((4-chlorothieno[3,2-c]pyridin-2-yl)methyl)-1-((6-cyclopropylimidazo[1,2-a]pyridin-2-yl)methyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and (4-chlorothieno[3,2-c]pyridin-2-yl)methanamine. The crude product was purified by Prep-TLC (10% MeOH/DCM) to yield the product (9.2 mg, 2.6% yield) as an off-white solid. ESI-MS [M+H]+: 464.1. $^1$H NMR (400 MHz, DMSO) δ 9.40 (t, J=6.1 Hz, 1H)., 8.62 (s, 1H), 8.35 (s, 1H), 8.19 (d, J=5.5 Hz, 1H), 8.01 (d, J=5.5 Hz, 1H), 7.85 (s, 1H), 7.44-7.38 (m, 2H), 7.05-6.98 (m, 1H), 5.75 (s, 2H), 4.75 (d, J=6.0 Hz, 2H), 1.98-1.87 (m, 1H), 0.97-0.87 (m, 2H), 0.72-0.62 (m, 2H).

Example 81

1-((6-cyclopropylimidazo[1,2-a]pyridin-2-yl)methyl)-N-((3-fluoro-4-methoxypyridin-2-yl)methyl)-1H-1,2,3-triazole-4-carboxamide (I-7)

Scheme 81

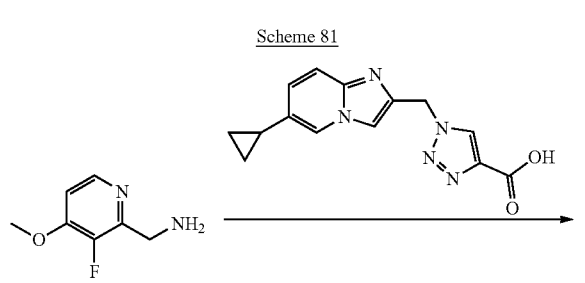

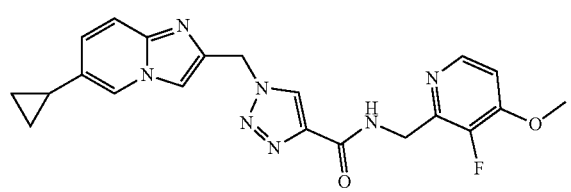

Synthesis of 1-((6-cyclopropylimidazo[1,2-a]pyridin-2-yl)methyl)-N-((3-fluoro-4-methoxypyridin-2-yl)methyl)-1H-1,2,3-triazole-4-carboxamide. 1-((6-cyclopropylimidazo[1,2-a]pyridin-2-yl)methyl)-N-((3-fluoro-4-methoxypyridin-2-yl)methyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and (3-fluoro-4-methoxypyridin-2-yl)methanamine. The crude product was purified by Prep-TLC (MeOH/DCM=1/10) to yield the product (55 mg, 58.5%) as a white solid. ESI-MS: [M+H]+, 422.2. $^1$H NMR (400 MHz, DMSO) δ 8.80-8.76 (m, 1H), 8.58 (s, 1H), 8.38-8.33 (m, 1H), 8.22 (d, J=5.5 Hz, 1H), 7.84 (s, 1H), 7.41 (d, J=9.3 Hz, 1H), 7.21-7.14 (m, 1H), 7.05-6.98 (m, 1H), 5.74 (s, 2H), 4.61-4.55 (m, 2H), 3.92 (s, 3H), 1.98-1.87 (m, 1H), 0.95-0.88 (m, 2H), 0.70-0.63 (m, 2H).

Example 82

N-(5-chloro-2-(4-chloro-1H-1,2,3-triazol-1-yl)benzyl)-1-((6-cyclopropylimidazo[1,2-a]pyridin-2-yl)methyl)-1H-1,2,3-triazole-4-carboxamide (I-3)

Scheme 82

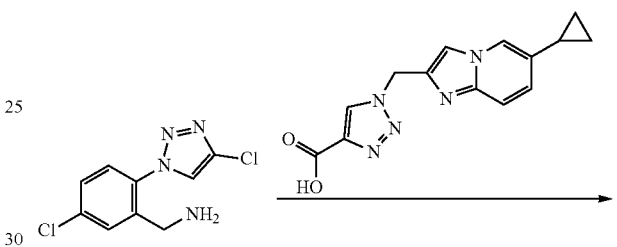

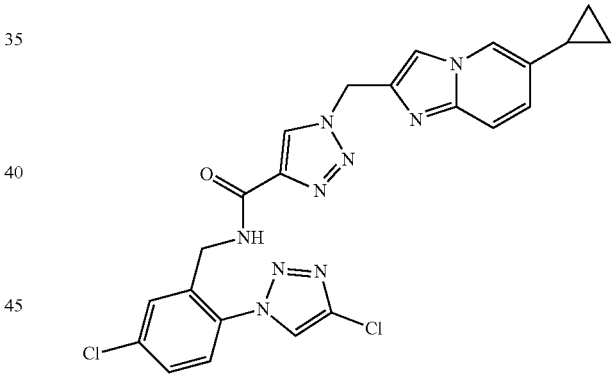

Synthesis of N-(5-chloro-2-(4-chloro-1H-1,2,3-triazol-1-yl)benzyl)-1-((6-cyclopropylimidazo[1,2-a]pyridin-2-yl)methyl)-1H-1,2,3-triazole-4-carboxamide. N-(5-chloro-2-(4-chloro-1H-1,2,3-triazol-1-yl)benzyl)-1-((6-cyclopropylimidazo[1,2-a]pyridin-2-yl)methyl)-1H-1,2,3-triazole-4-carboxamide was synthesized according to General Procedure B-2 starting from 1-((6-cyclopropylimidazo[1,2-a]pyridin-2-yl)methyl)-1H-1,2,3-triazole-4-carboxylic acid and (5-chloro-2-(4-chloro-1H-1,2,3-triazol-1-yl)phenyl)methanamine. The crude product was purified by Prep-TLC (DCM/MeOH=15/1) to yield the product (50 mg, yield: 46%) as a white solid. ESI-MS [M+H]+: 508.1. $^1$H NMR (400 MHz, MeOD) S 8.45 (s, 1H), 8.37 (s, 1H), 8.21-8.19 (m, 1H), 7.80 (s, 1H), 7.62 (d, J=2.2 Hz, 1H), 7.50 (dd, J=8.5, 2.3 Hz, 1H), 7.46 (d, J=8.5 Hz, 1H), 7.39 (d, J=9.4 Hz, 1H), 7.11 (dd, J=9.4, 1.7 Hz, 1H), 5.75 (s, 2H), 4.45 (s, 2H), 1.98-1.90 (m, 1H), 1.00-0.95 (m, 2H), 0.74-0.69 (m, 2H).

Example 83

N-(6-(4-chloro-1H-1,2,3-triazol-1-yl)-2-fluoro-3-methoxybenzyl)-1-((6-cyclopropylimidazo[1,2-a]pyridin-2-yl)methyl)-1H-1,2,3-triazole-4-carboxamide (I-1)

Scheme 83

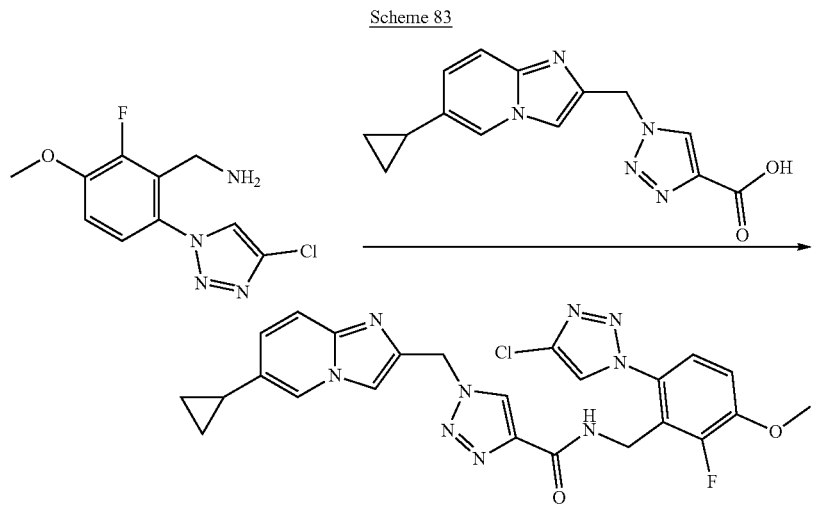

Synthesis of N-(6-(4-chloro-1H-1,2,3-triazol-1-yl)-2-fluoro-3-methoxybenzyl)-1-((6-cyclopropylimidazo[1,2-a]pyridin-2-yl)methyl)-1H-1,2,3-triazole-4-carboxamide. N-(5-chloro-2-(4-chloro-1H-1,2,3-triazol-1-yl)benzyl)-1-((6-cyclopropylimidazo[1,2-a]pyridin-2-yl)methyl)-1H-1,2,3-triazole-4-carboxamide was synthesized according to General Procedure B-1 starting from 1-((6-cyclopropylimidazo[1,2-a]pyridin-2-yl)methyl)-1H-1,2,3-triazole-4-carboxylic acid and (6-(4-chloro-1H-1,2,3-triazol-1-yl)-2-fluoro-3-methoxyphenyl)methanamine. The crude product was purified by flash chromatography (PE/EtOAc=1/1) to yield the product (30 mg, yield: 29.7%) as a white solid. ESI-MS [M+H]+: 522.2. $^1$H NMR (400 MHz, DMSO) δ 8.76 (s, 1H), 8.69-8.61 (m, 1H), 8.50 (s, 1H), 8.34 (s, 1H), 7.82 (s, 1H), 7.40 (d, J=9.3 Hz, 1H), 7.45-7.28 (m, 2H), 7.05-6.97 (m, 1H), 5.71 (s, 2H), 4.35 (d, J=5.2 Hz, 2H), 3.91 (s, 3H), 1.98-1.85 (m, 1H), 0.95-0.85 (m, 2H), 0.71-0.60 (m, 2H).

Example 84 ethyl 3-(2-((4-((3-chloro-2-fluoro-6-(1H-tetrazol-1-yl)benzyl)carbamoyl)-1H-1,2,3-triazol-1-yl)methyl)-6-cyclopropylimidazo[1,2-a]pyridin-8-yl)propanoate (I-113)

Scheme 84

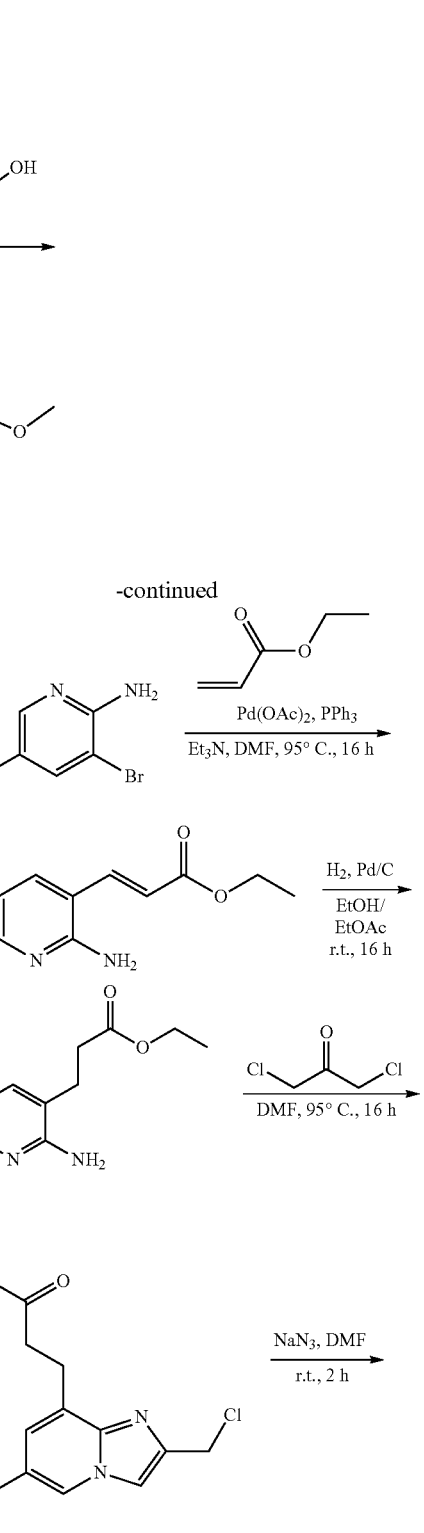

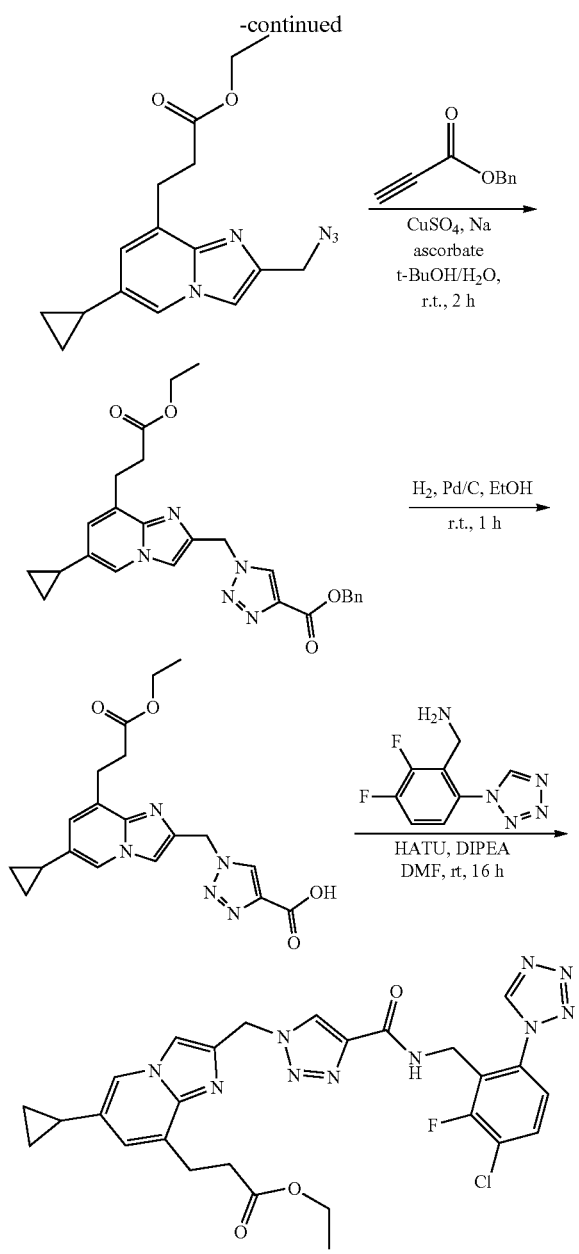

Synthesis of ethyl 3-(2-amino-5-cyclopropylpyridin-3-yl) propanoate. To a solution of ethyl 3-(2-amino-5-cyclopropylpyridin-3-yl)acrylate (5 g, 21.53 mmol) in EtOH (50 mL)/EtOAc (10 mL) was added Pd/C (500 mg). The mixture was stirred at RT under hydrogen atmosphere for 16 h. The mixture was filtered and concentrated in vacuo to give ethyl 3-(2-amino-5-cyclopropylpyridin-3-yl)propanoate (5.4 g, crude) as a yellow oil which was used in the next step without further purification. ESI-MS [M+H]+: 235.1.

Synthesis of ethyl 3-(2-(chloromethyl)-6-cyclopropylimidazo[1,2-a]pyridin-8-yl)propanoate. To a solution of ethyl 3-(2-amino-5-cyclopropylpyridin-3-yl)propanoate (5.4 g, crude) in DMF (60 mL) was added 1,3-dichloropropan-2-one (11.7 g, 92.16 mmol) at RT. The reaction mixture was heated to 95° C. and stirred for 16 h. The mixture was concentrated in vacuo and purified by flash chromatography (0-60% EtOAc in PE) to give ethyl 3-(2-(chloromethyl)-6-cyclopropylimidazo[1,2-a]pyridin-8-yl)propanoate (2.2 g, yield: 31.1%) as a red oil. ESI-MS [M+H]+: 307.1.

Synthesis of ethyl 3-(2-(azidomethyl)-6-cyclopropylimidazo[1,2-a]pyridin-8-yl)propanoate. To a solution of ethyl 3-(2-(chloromethyl)-6-cyclopropylimidazo[1,2-a]pyridin-8-yl)propanoate (2.2 g, 7.17 mmol) in DMF (30 mL) was added NaN₃ (416 mg, 6.40 mmol). The reaction mixture was stirred at room temperature for 2 h. The reaction was diluted with H₂O (30 mL) and extracted with EtOAc (50 mL×3). The combined organic phases were washed with brine (50 mL) and concentrated in vacuo to give ethyl 3-(2-(azidomethyl)-6-cyclopropylimidazo[1,2-a]pyridin-8-yl)propanoate (1.6 g, crude) as a red oil, which was used in the next step without further purification. ESI-MS [M+H]+: 314.1.

Synthesis of benzyl 1-((6-cyclopropyl-8-(3-ethoxy-3-oxopropyl)imidazo[1,2-a]pyridin-2-yl)methyl)-1H-1,2,3-triazole-4-carboxylate. To a solution of ethyl 3-(2-(azidomethyl)-6-cyclopropylimidazo[1,2-a]pyridin-8-yl)propanoate (1.6 g, 5.11 mmol) in t-BuOH/H₂O (20 mL/20 mL) was added benzyl propiolate (0.98 g, 6.13 mmol), sodium ascorbate (0.202 g, 1.02 mmol) and CuSO₄ (0.163 g, 1.02 mmol) at RT. The mixture was stirred for 2 h. The reaction was diluted with water (30 mL) and extracted with EtOAc (50 mL×3). The combined organic phases were washed with brine (50 mL) and concentrated in vacuo to give give benzyl 1-((6-cyclopropyl-8-(3-ethoxy-3-oxopropyl)imidazo[1,2-a]pyridin-2-yl)methyl)-1H-1,2,3-triazole-4-carboxylate (1.4 g, crude) as a red oil which was used in the next step without further purification. ESI-MS [M+H]+: 474.2.

Synthesis of 1-((6-cyclopropyl-8-(3-ethoxy-3-oxopropyl)imidazo[1,2-a]pyridin-2-yl)methyl)-1H-1,2,3-triazole-4-carboxylic acid. A mixture of benzyl 1-((6-cyclopropyl-8-(3-ethoxy-3-oxopropyl)imidazo[1,2-a]pyridin-2-yl)methyl)-1H-1,2,3-triazole-4-carboxylate (1.4 g, 2.97 mmol) and Pd/C (2 g) in EtOH/EtOAc (20 mL/20 mL) was stirred at room temperature for 1 h under hydrogen atmosphere. The mixture was filtered and washed with MeOH (100 mL). The filtrate was concentrated in vacuo to give 1-((6-cyclopropyl-8-(3-ethoxy-3-oxopropyl)imidazo[1,2-a]pyridin-2-yl)methyl)-1H-1,2,3-triazole-4-carboxylic acid (600 mg, crude) as a white solid. ESI-MS [M+H]+: 384.1.

Synthesis of ethyl 3-(2-((4-((3-chloro-2-fluoro-6-(1H-tetrazol-1-yl)benzyl)carbamoyl)-1H-1,2,3-triazol-1-yl)methyl)-6-cyclopropylimidazo[1,2-a]pyridin-8-yl)propanoate. To a solution of 1-((6-cyclopropyl-8-(3-ethoxy-3-oxopropyl)imidazo[1,2-a]pyridin-2-yl)methyl)-1H-1,2,3-triazole-4-carboxylic acid (100 mg, 0.261 mmol) in DMF (3 mL) was added HATU (119.01 mg, 0.313 mmol), DIPEA (134.84 mg, 1.04 mmol) and (3-chloro-2-fluoro-6-(1H-tetrazol-1-yl)phenyl)methanamine (59.9 mg, 0.261 mmol) at Synthesis of 3-bromo-5-cyclopropylpyridin-2-amine. To a solution of 5-cyclopropylpyridin-2-amine (10.00 g, 74.5 mmol) in MeCN (130 mL) was added 1-bromo-2,5-pyrrolidinedione (16 g, 89.4 mmol) at RT. The reaction mixture was stirred for 3 h and then concentrated in vacuo to give 3-bromo-5-cyclopropylpyridin-2-amine (15.0 g, crude) as a yellow solid which was used in the next reaction without further purification. ESI-MS [M+H]+: 213.0

Synthesis of ethyl 3-(2-amino-5-cyclopropylpyridin-3-yl) acrylate. To a solution of 3-bromo-5-cyclopropylpyridin-2-amine (7.00 g, 32.85 mmol) in DMF (60 mL) was added Et₃N (15 mL), PPh₃ (1.74 g, 16.43 mmol), Pd(OAc)₂ (0.75 g 3.3 mmol) and ethyl acrylate (6 mL, 65.7 mmol) at RT. The reaction mixture was heated to 95° C. and stirred for 16 h. The mixture was concentrated in vacuo and washed with EtOAc to give ethyl 3-(2-amino-5-cyclopropylpyridin-3-yl) acrylate (4 g, yield: 52.42%) as a yellow solid. ESI-MS [M+H]+: 233.1.

room temperature. After stirring for 16 h, the reaction mixture was quenched with water (20 mL) and extracted with EtOAc (50 mL×3). The combined organic layers were washed with brine, dried over Na$_2$SO$_4$, concentrated and purified by prep-HPLC to give ethyl 3-(2-((4-((3-chloro-2-fluoro-6-(1H-tetrazol-1-yl)benzyl)carbamoyl)-1H-1,2,3-triazol-1-yl)methyl)-6-cyclopropylimidazo[1,2-a]pyridin-8-yl)propanoate (95.4 mg, yield: 61.68%) as a white solid. ESI-MS [M+H]+: 593.2. $^1$H NMR (400 MHz, DMSO) (9.84 (s, 1H), 8.93 (t, J=5.3 Hz, 1H), 8.53 (s, 1H), 8.36 (s, 1H), 7.95 (s, 1H), 7.88-7.82 (m, 1H), 7.53-7.48 (m, 1H), 5.81 (s, 2H), 4.38 (d, J=5.1 Hz, 2H), 4.04 (q, J=7.1 Hz, 2H), 3.08 (t, J=7.6 Hz, 2H), 2.77 (t, J=7.7 Hz, 2H), 2.00-1.90 (m, 1H), 1.14 (t, J=7.1 Hz, 3H), 1.00-0.90 (m, 2H), 0.75-0.65 (m, 2H).

Example 85

3-(2-((4-((3-chloro-6-cyanamido-2-fluorobenzyl) carbamoyl)-1H-1,2,3-triazol-1-yl)methyl)-6-cyclopropylimidazo[1,2-a]pyridin-8-yl)propanoic acid (I-110) and 3-(2-((4-((3-chloro-2-fluoro-6-(1H-tetrazol-1-yl)benzyl)carbamoyl)-1H-1,2,3-triazol-1-yl) methyl)-6-cyclopropylimidazo[1,2-a]pyridin-8-yl) propanoic acid (I-109)

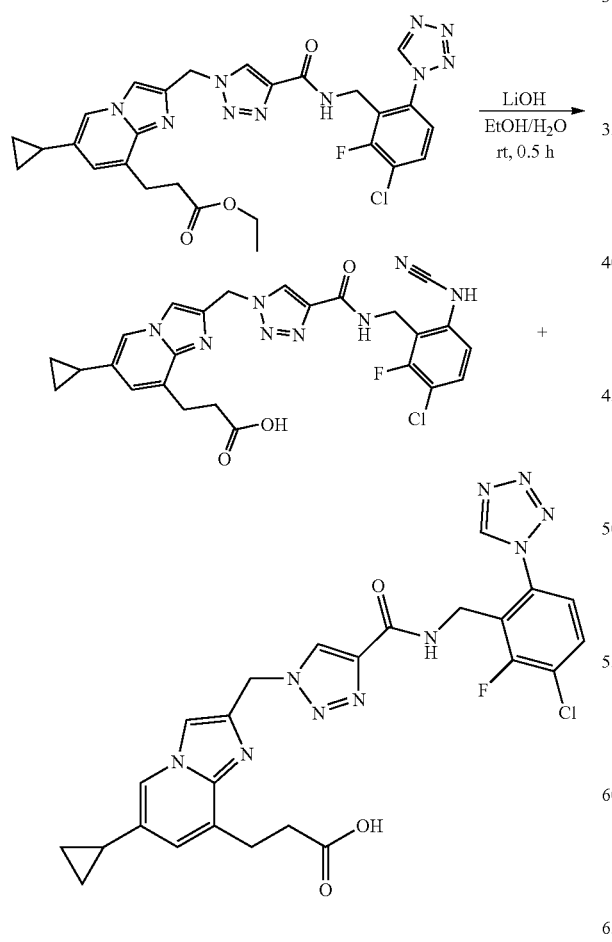

Scheme 85

Synthesis of 3-(2-((4-((3-chloro-6-cyanamido-2-fluorobenzyl)carbamoyl)-1H-1,2,3-triazol-1-yl)methyl)-6-cyclopropylimidazo[1,2-a]pyridin-8-yl)propanoic acid and 3-(2-((4-((3-chloro-2-fluoro-6-(1H-tetrazol-1-yl)benzyl) carbamoyl)-1H-1,2,3-triazol-1-yl)methyl)-6-cyclopropylimidazo[1,2-a]pyridin-8-yl)propanoic acid. To a solution of ethyl 3-(2-((4-((3-chloro-2-fluoro-6-(1H-tetrazol-1-yl)benzyl)carbamoyl)-1H-1,2,3-triazol-1-yl)methyl)-6-cyclopropylimidazo[1,2-a]pyridin-8-yl)propanoate (80 mg, 0.135 mmol) in EtOH/H$_2$O (10 mL/10 mL) was added LiOH·H2O (10.8 mg, 0.27 mmol) at RT. The reaction mixture was stirred at RT for 0.5 h. The mixture was adjusted to pH 3 by adding HCl (1M, aq.) and the mixture was extracted with EtOAc (20 mL×3). The combined organic layers were concentrated in vacuo and purified by prep-HPLC to give 3-(2-((4-((3-chloro-6-cyanamido-2-fluorobenzyl)carbamoyl)-1H-1,2,3-triazol-1-yl)methyl)-6-cyclopropylimidazo [1,2-a]pyridin-8-yl)propanoic acid (I-110, 32.4 mg, yield: 44.7%) as a white solid and 3-(2-((4-((3-chloro-2-fluoro-6-(1H-tetrazol-1-yl)benzyl)carbamoyl)-1H-1,2,3-triazol-1-yl) methyl)-6-cyclopropylimidazo[1,2-a]pyridin-8-yl)propanoic acid (I-109, 5.4 mg, yield: 7.1%) as a white solid. I-110: ESI-MS [M+H]+: 537.1. 1H NMR (400 MHz, DMSO) δ 12.16 (s, 1H), 10.20 (s, 1H), 9.22 (s, 1H), 8.62 (s, 1H), 8.20 (s, 1H), 7.78 (s, 1H), 7.53 (t, J=8.4 Hz, 1H), 6.96 (d, J=8.8 Hz, 1H), 6.85 (s, 1H), 5.75 (s, 2H), 4.44 (d, J=4.7 Hz, 2H), 3.03 (t, J=7.6 Hz, 2H), 2.69 (t, J=7.6 Hz, 2H), 1.93-1.84 (m, 1H), 0.96-0.86 (m, 2H), 0.70-0.62 (m, 2H). I-109: ESI-MS [M+H]+: 565.1. $^1$H NMR (400 MHz, DMSO) d 12.18 (s, 1H), 9.85 (s, 1H), 8.91 (d, J=5.4 Hz, 1H), 8.49 (s, 1H), 8.20 (d, J=1.2 Hz, 1H), 7.87-7.82 (m, 1H), 7.76 (s, 1H), 7.50 (dd, J=8.7, 1.4 Hz, 1H), 6.84 (s, 1H), 5.71 (s, 2H), 4.37 (d, J=4.9 Hz, 2H), 3.03 (t, J=7.6 Hz, 2H), 2.70-2.66 (m, 2H), 1.91-1.85 (m, 1H), 0.94-0.86 (m, 2H), 0.68-0.60 (m, 2H).

Example 86 ethyl 3-(2-((4-((6-cyano-2-fluoro-3-methoxybenzyl) carbamoyl)-1H-1,2,3-triazol-1-yl)methyl)-6-cyclopropylimidazo[1,2-a]pyridin-8-yl)propanoate (I-108)

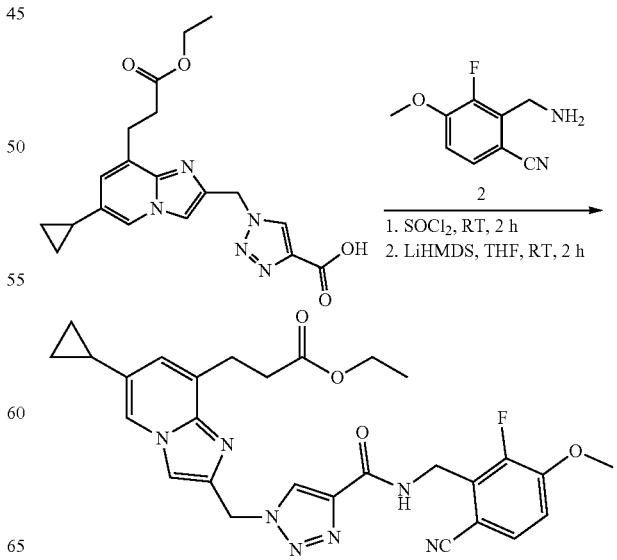

Scheme 86

Synthesis of ethyl 3-(2-((4-((6-cyano-2-fluoro-3-methoxybenzyl)carbamoyl)-1H-1,2,3-triazol-1-yl)methyl)-6-cyclopropylimidazo[1,2-a]pyridin-8-yl)propanoate. A mixture of 1-((6-cyclopropyl-8-(3-ethoxy-3-oxopropyl)imidazo[1,2-a]pyridin-2-yl)methyl)-1H-1,2,3-triazole-4-carboxylic acid (192 mg, 0.5 mmol) in SOCl$_2$ (2 mL) was stirred at room temperature for 2 h and then concentrated in vacuo. The residue was re-dissolved in THF (3 mL) and added to the solution of 2-(aminomethyl)-3-fluoro-4-methoxybenzonitrile (90 mg, 0.5 mmol) and LiHMDS (1M in THF, 2 mL) in THF (5 mL) at 0° C. The resulting mixture was stirred at room temperature for 2 h. The reaction was quenched with saturated aqueous NH$_4$Cl (10 mL) and extracted with EtOAc (20×3 mL). The combined organic layers were washed with brine (30 mL) and dried over Na$_2$SO$_4$, filtered and concentrated in vacuo to give the crude, which was purified by Prep-HPLC to give ethyl 3-(2-((4-((6-cyano-2-fluoro-3-methoxybenzyl)carbamoyl)-1H-1,2,3-triazol-1-yl)methyl)-6-cyclopropylimidazo[1,2-a]pyridin-8-yl)propanoate (20 mg, yield: 7%) as an off-white solid. ESI-MS [M+H]+: 546.2. $^1$H NMR (400 MHz, DMSO) δ 9.04 (t, J=5.3 Hz, 1H), 8.55 (s, 1H), 8.22 (s, 1H), 7.78 (s, 1H), 7.65 (dd, J=8.6, 1.3 Hz, 1H), 7.27 (t, J=8.4 Hz, 1H), 6.84 (s, 1H), 5.74 (s, 2H), 4.58 (d, J=5.1 Hz, 2H), 4.03 (q, J=7.1 Hz, 2H), 3.91 (s, 3H), 3.07 (t, J=7.6 Hz, 2H), 2.76 (t, J=7.6 Hz, 2H), 1.91-1.85 (m, 1H), 1.14 (t, J=7.1 Hz, 3H), 0.97-0.82 (m, 2H), 0.74-0.56 (m, 2H).

Example 87

3-(2-((4-((6-cyano-2-fluoro-3-methoxybenzyl)carbamoyl)-1H-1,2,3-triazol-1-yl)methyl)-6-cyclopropylimidazo[1,2-a]pyridin-8-yl)propanoic acid (I-107)

Scheme 87

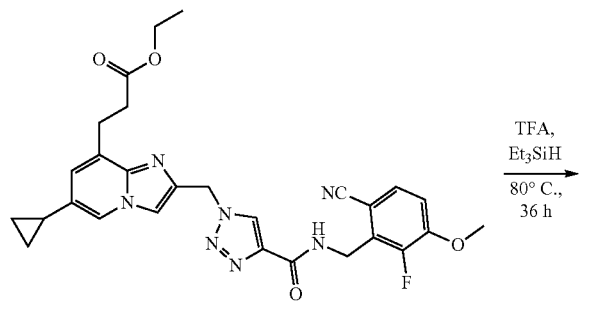

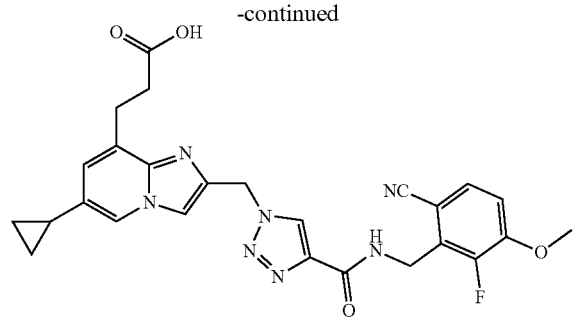

Synthesis of 3-(2-((4-((6-cyano-2-fluoro-3-methoxybenzyl)carbamoyl)-1H-1,2,3-triazol-1-yl)methyl)-6-cyclopropylimidazo[1,2-a]pyridin-8-yl)propanoic acid. A mixture of ethyl 3-(2-((4-((6-cyano-2-fluoro-3-methoxybenzyl)carbamoyl)-1H-1,2,3-triazol-1-yl)methyl)-6-cyclopropylimidazo[1,2-a]pyridin-8-yl)propanoate (55 mg, 0.1 mol) in TFA (2 mL) and Et$_3$SiH (1 mL) was stirred at 80° C. for 36 h. The reaction mixture was concentrated in vacuo to give the crude, which was purified by Prep-HPLC to give 3-(2-((4-((6-cyano-2-fluoro-3-methoxybenzyl)carbamoyl)-1H-1,2,3-triazol-1-yl)methyl)-6-cyclopropylimidazo[1,2-a]pyridin-8-yl)propanoic acid (5 mg, yield: 10%) as a white solid. ESI-MS [M+H]+: 518.2. $^1$H NMR (400 MHz, DMSO) δ 12.17 (s, 1H), 9.04 (t, J=5.4 Hz, 1H), 8.56 (s, 1H), 8.21 (s, 1H), 7.77 (s, 1H), 7.65 (dd, J=8.6, 1.3 Hz, 1H), 7.27 (t, J=8.4 Hz, 1H), 6.84 (s, 1H), 5.74 (s, 2H), 4.58 (d, J=5.2 Hz, 2H), 3.91 (s, 3H), 3.04 (t, J=7.6 Hz, 2H), 2.68 (t, J=7.6 Hz, 2H), 1.92-1.85 (m, 1H), 0.94-0.85 (m, 2H), 0.70-0.59 (m, 2H).

Example 88 ethyl 3-(6-cyclopropyl-2-((4-((2-fluoro-3-methoxy-6-(1H-tetrazol-1-yl)benzyl)carbamoyl)-1H-1,2,3-triazol-1-yl)methyl)imidazo[1,2-a]pyridin-8-yl)propanoate (I-89) and 3-(6-cyclopropyl-2-((4-((2-fluoro-3-methoxy-6-(1H-tetrazol-1-yl)benzyl)carbamoyl)-1H-1,2,3-triazol-1-yl)methyl)imidazo[1,2-a]pyridin-8-yl)propanoic acid (I-92)

Scheme 88

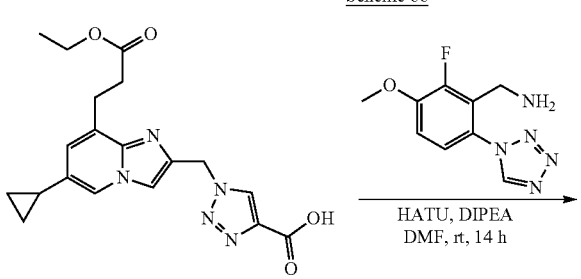

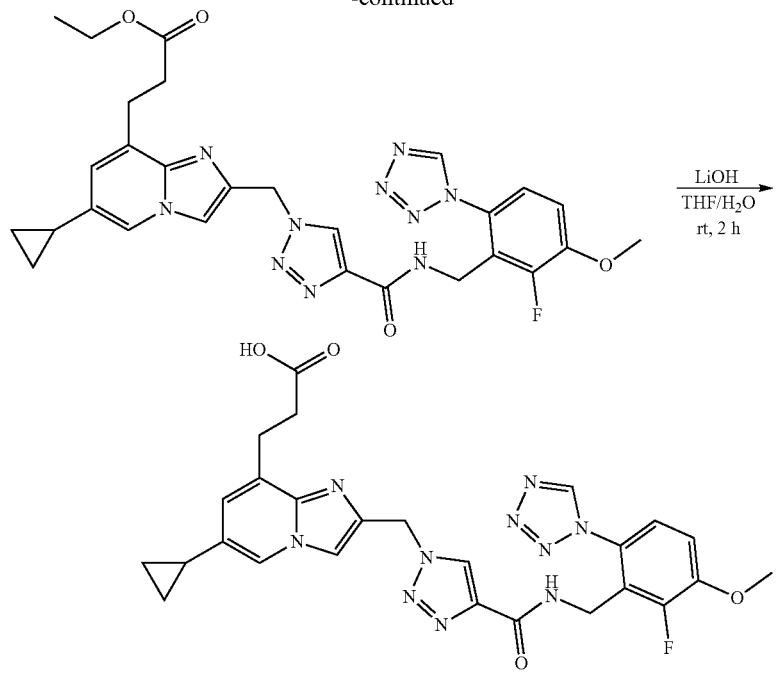

Synthesis of ethyl 3-(6-cyclopropyl-2-((4-((2-fluoro-3-methoxy-6-(1H-tetrazol-1-yl)benzyl)carbamoyl)-1H-1,2,3-triazol-1-yl)methyl)imidazo[1,2-a]pyridin-8-yl)propanoate. To a solution of 1-((6-cyclopropyl-8-(3-ethoxy-3-oxopropyl)imidazo[1,2-a]pyridin-2-yl)methyl)-1H-1,2,3-triazole-4-carboxylic acid (200 mg, 0.52 mmol), (2-fluoro-3-methoxy-6-(1H-tetrazol-1-yl)phenyl)methanamine (116 mg, 0.52 mmol) and HATU (257 mg, 0.678 mmol) in DMF (5 mL) was added DIPEA (335 mg, 2.6 mmol). The reaction mixture was stirred at room temperature for 14 h. Water (20 mL) was added and the mixture was extracted with EtOAc (20 mL×3). The combined organic layers were concentrated in vacuo and purified by Prep-TLC (DCM/MeOH=10/1) to give ethyl 3-(6-cyclopropyl-2-((4-((2-fluoro-3-methoxy-6-(1H-tetrazol-1-yl)benzyl)carbamoyl)-1H-1,2,3-triazol-1-yl)methyl)imidazo[1,2-a]pyridin-8-yl)propanoate as a white solid (150 mg, yield: 49%). ESI-MS [M+H]+: 589.3. $^1$H NMR (400 MHz, DMSO) 9.74 (s, 1H), 8.77 (t, J=5.4 Hz, 1H), 8.50 (s, 1H), 8.27 (s, 1H), 7.84 (s, 1H), 7.39-7.32 (m, 2H), 6.95 (s, 1H), 5.75 (s, 2H), 4.29 (d, J=5.2 Hz, 2H), 4.03 (q, J=7.1 Hz, 2H), 3.92 (s, 3H), 3.07 (t, J=7.6 Hz, 2H), 2.76 (t, J=7.6 Hz, 2H), 1.90 (d, J=4.6 Hz, 1H), 1.14 (t, J=7.1 Hz, 3H), 0.93 (d, J=6.7 Hz, 2H), 0.67 (d, J=5.3 Hz, 2H).

Synthesis of 3-(6-cyclopropyl-2-((4-((2-fluoro-3-methoxy-6-(1H-tetrazol-1-yl)benzyl)carbamoyl)-1H-1,2,3-triazol-1-yl)methyl)imidazo[1,2-a]pyridin-8-yl)propanoic acid. To a solution of ethyl 3-(6-cyclopropyl-2-((4-((2-fluoro-3-methoxy-6-(1H-tetrazol-1-yl)benzyl)carbamoyl)-1H-1,2,3-triazol-1-yl)methyl)imidazo[1,2-a]pyridin-8-yl)propanoate (80 mg, 0.136 mmol) in THF/H$_2$O (5 mL/1 mL) was added LiOH H$_2$O (17 mg, 0.408 mmol). The reaction mixture was stirred at room temperature for 2 h. The mixture was adjusted to pH 5 by adding HCl (1M, aq.) and the mixture was extracted with EtOAc (20 mL×3). The combined organic layers were concentrated in vacuo and purified by Prep-TLC (DCM/MeOH=10/1) to give 3-(6-cyclopropyl-2-((4-((2-fluoro-3-methoxy-6-(1H-tetrazol-1-yl)benzyl)carbamoyl)-1H-1,2,3-triazol-1-yl)methyl)imidazo[1,2-a]pyridin-8-yl)propanoic acid as a white solid (28 mg, yield: 36.8%). ESI-MS [M+H]+: 561.2. $^1$H NMR (400 MHz, DMSO) δ 12.17 (s, 1H), 9.74 (s, 1H), 8.77 (t, J=5.4 Hz, 1H), 8.50 (s, 1H), 8.23 (s, 1H), 7.79 (s, 1H), 7.47-7.21 (m, 2H), 6.89 (s, 1H), 5.73 (s, 2H), 4.29 (d, J=5.2 Hz, 2H), 3.92 (s, 3H), 3.03 (t, J=7.6 Hz, 2H), 2.68 (t, J=7.6 Hz, 2H), 1.97-1.83 (m, 1H), 0.94-0.89 (m, 2H), 0.68-0.65 (m, 2H).

Example 89 ethyl 2-((4-((4-carbamimidoyl-2,6-dimethylbenzyl)carbamoyl)-1H-1,2,3-triazol-1-yl)methyl)-6-cyclopropylimidazo[1,2-a]pyridine-8-carboxylate (I-112) and 2-((4-((4-carbamimidoyl-2,6-dimethylbenzyl)carbamoyl)-1H-1,2,3-triazol-1-yl)methyl)-6-cyclopropylimidazo[1,2-a]pyridine-8-carboxylic acid (I-111)

Scheme 89

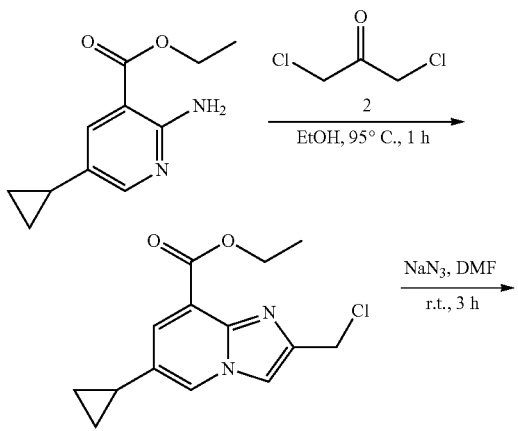

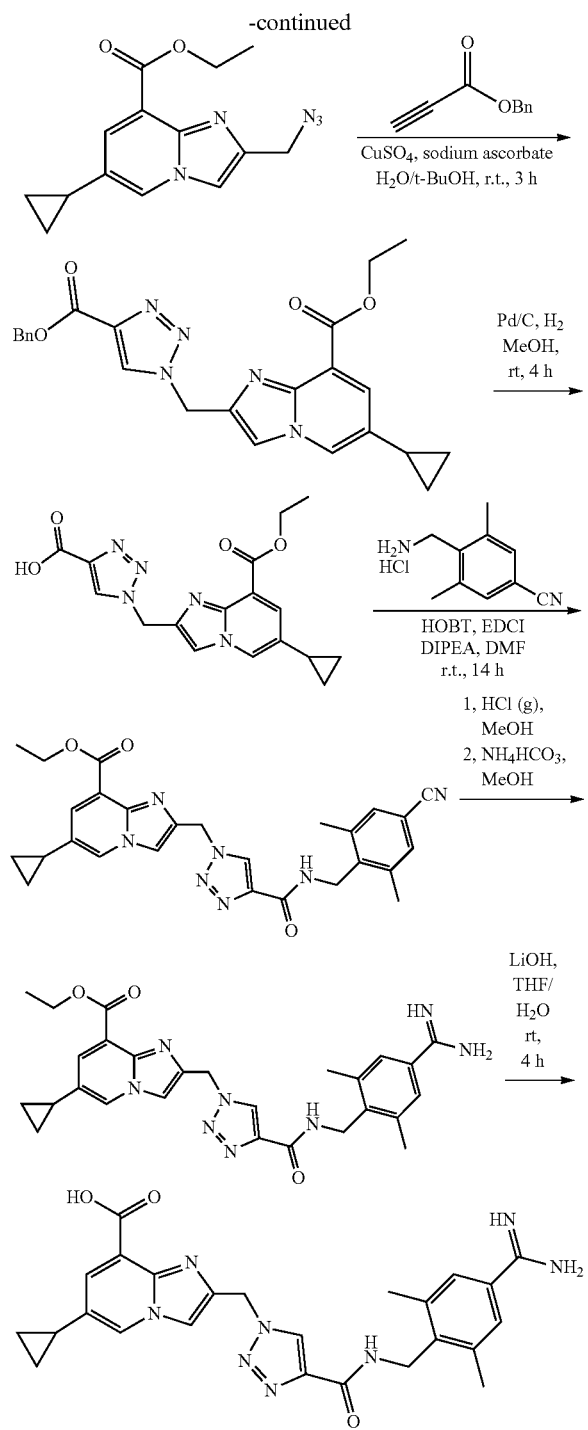

2-(chloromethyl)-6-cyclopropylimidazo[1,2-a]pyridine-8-carboxylate (2.5 g, yield: 61.7%). ESI-MS [M+H]$^+$: 279.2.

Synthesis of ethyl 2-(azidomethyl)-6-cyclopropylimidazo[1,2-a]pyridine-8-carboxylate. To a solution of ethyl 2-(chloromethyl)-6-cyclopropylimidazo[1,2-a]pyridine-8-carboxylate (2.5 g, 9 mmol) in DMF (50 mL) was added NaN$_3$ (0.88 g, 13.5 mmol). The reaction mixture was stirred at room temperature for 3 h. H$_2$O (100 mL) was added and the mixture was extracted with EtOAc (150 mL×2). The combined organic layers were washed with brine, dried over Na$_2$SO$_4$, and concentrated in vacuo to give crude ethyl 2-(azidomethyl)-6-cyclopropylimidazo[1,2-a]pyridine-8-carboxylate as a brown solid, which was used into next step without further purification (2.6 g crude). ESI-MS [M+H]$^+$: 286.2.

Synthesis of ethyl 2-((4-((benzyloxy)carbonyl)-1H-1,2,3-triazol-1-yl)methyl)-6-cyclopropylimidazo[1,2-a]pyridine-8-carboxylate. To a solution of ethyl 2-(azidomethyl)-6-cyclopropylimidazo[1,2-a]pyridine-8-carboxylate (2.6 g crude from previous step) and benzyl propiolate (1.58 g, 9.9 mmol) in t-BuOH/H$_2$O (20 mL/20 mL) was added CuSO$_4$ (288 mg, 1.8 mmol) and sodium ascorbate (356 mg, 1.8 mmol). The reaction mixture was stirred at room temperature for 3 h. H$_2$O (50 mL) was added and the mixture was extracted with DCM (100 mL×3). The combined organic layers were washed with brine, dried over Na$_2$SO$_4$, and concentrated in vacuo to give the crude, which was purified by column chromatography (DCM/MeOH=20/1) to give ethyl 2-((4-((benzyloxy)carbonyl)-1H-1,2,3-triazol-1-yl)methyl)-6-cyclopropylimidazo[1,2-a]pyridine-8-carboxylate (1.5 g, 38% over 2 steps). ESI-MS [M+H]$^+$: 446.2.

Synthesis of ethyl 2-((4-((benzyloxy)carbonyl)-1H-1,2,3-triazol-1-yl)methyl)-6-cyclopropylimidazo[1,2-a]pyridine-8-carboxylate. A mixture of ethyl 2-((4-((benzyloxy)carbonyl)-1H-1,2,3-triazol-1-yl)methyl)-6-cyclopropylimidazo[1,2-a]pyridine-8-carboxylate (700 mg, 1.57 mmol) and Pd/C (300 mg) in MeOH (20 mL) was stirred under H2 atmosphere at RT for 4 h. The reaction mixture was filtered to give 1-((6-cyclopropyl-8-(ethoxycarbonyl)imidazo[1,2-a]pyridin-2-yl)methyl)-1H-1,2,3-triazole-4-carboxylic acid (300 mg, yield: 53.8%), which was used into next step without further purification. ESI-MS [M+H]$^+$: 356.2.

Synthesis of ethyl 2-((4-((4-cyano-2,6-dimethylbenzyl)carbamoyl)-1H-1,2,3-triazol-1-yl)methyl)-6-cyclopropylimidazo[1,2-a]pyridine-8-carboxylate. To a solution of 1-((6-cyclopropyl-8-(ethoxycarbonyl)imidazo[1,2-a]pyridin-2-yl)methyl)-1H-1,2,3-triazole-4-carboxylic acid (300 mg, 0.84 mmol), 4-(aminomethyl)-3,5-dimethylbenzonitrile hydrochloride (215 mg, 1.34 mmol), HOBT (176 mg, 1.3 mmol) and EDCI (250 mg, 1.3 mmol) in DMF (20 mL) was added DIPEA (549 mg, 4.25 mmol). The reaction mixture was stirred at room temperature for 14 h. H$_2$O (50 mL) was added and the mixture was extracted with EtOAc (50 mL×3). The combined organic layers were washed brine, dried over Na$_2$SO$_4$, and concentrated in vacuo to give the crude, which was purified by column chromatography (DCM/MeOH=20/1) to give ethyl 2-((4-((4-cyano-2,6-dimethylbenzyl)carbamoyl)-1H-1,2,3-triazol-1-yl)methyl)-6-cyclopropylimidazo[1,2-a]pyridine-8-carboxylate (250 mg, 59.8%) as a brown solid. ESI-MS [M+H]$^+$: 498.2

Synthesis of ethyl 2-((4-((4-carbamimidoyl-2,6-dimethylbenzyl)carbamoyl)-1H-1,2,3-triazol-1-yl)methyl)-6-cyclopropylimidazo[1,2-a]pyridine-8-carboxylate. To a solution of ethyl 2-((4-((4-cyano-2,6-dimethylbenzyl)carbamoyl)-1H-1,2,3-triazol-1-yl)methyl)-6-cyclopropylimidazo[1,2-a]pyridine-8-carboxylate (280 mg, 0.56 mmol) in MeOH (20 mL) was bubbled HCl(g) for 3 h. The reaction mixture was Synthesis of ethyl 2-(chloromethyl)-6-cyclopropylimidazo[1,2-a]pyridine-8-carboxylate. A mixture of ethyl 2-amino-5-cyclopropylnicotinate (3 g, 14.55 mmol) and 1,3-dichloropropan-2-one (5.5 g, 43.32 mmol) in EtOH (100 mL) was stirred at 95° C. for 1 h. The reaction mixture was concentrated in vacuo to remove EtOH. The residue was adjusted to pH 9 using saturated aq. NaHCO$_3$, then extracted with EtOAc (100 mL×3). The combined organic layers were washed with brine (150 mL), dried over Na$_2$SO$_4$, and concentrated in vacuo to give the crude, which was purified by flash chromatography (PE/EtOAc=1/1) to give ethyl concentrated in vacuo. MeOH (20 mL) and NH₄HCO₃ (442 mg, 5.6 mmol) were added. The reaction mixture was stirred at room temperature for 14 h. The mixture was concentrated in vacuo to give the crude, which was purified by Prep-HPLC to give ethyl 2-((4-((4-carbamimidoyl-2,6-dimethylbenzyl)carbamoyl)-1H-1,2,3-triazol-1-yl)methyl)-6-cyclopropylimidazo[1,2-a]pyridine-8-carboxylate (140 mg, 48.6%) as a white solid. ESI-MS [M+H]⁺: 515.2. ¹H NMR (400 MHz, DMSO) δ 10.20 (s, 2H), 9.02 (s, 1H), 8.74 (t, J=5.4 Hz, 1H), 8.59-8.57 (m, 2H), 8.38 (s, 1H), 7.91 (s, 1H), 7.62 (d, J=1.8 Hz, 1H), 7.46 (s, 2H), 5.78 (s, 2H), 4.52 (d, J=5.3 Hz, 2H), 4.33 (q, J=7.1 Hz, 2H), 2.45 (s, 6H), 2.01-1.98 (m, 1H), 1.31 (t, J=7.1 Hz, 2H), 1.02-0.89 (m, 2H), 0.79-0.65 (m, 2H).

Synthesis of 2-((4-((4-carbamimidoyl-2,6-dimethylbenzyl)carbamoyl)-1H-1,2,3-triazol-1-yl)methyl)-6-cyclopropylimidazo[1,2-a]pyridine-8-carboxylic acid. To a solution of ethyl 2-((4-((4-carbamimidoyl-2,6-dimethylbenzyl)carbamoyl)-1H-1,2,3-triazol-1-yl)methyl)-6-cyclopropylimidazo[1,2-a]pyridine-8-carboxylate (90 mg, 0.17 mmol) in THF/H₂O (15 mL/15 mL) was added LiOH (22 mg, 0.52 mmol). The reaction mixture was stirred at room temperature for 3 h. The mixture was concentrated in vacuo to give the crude, which was purified by Prep-HPLC to give 2-((4-((4-carbamimidoyl-2,6-dimethylbenzyl)carbamoyl)-1H-1,2,3-triazol-1-yl)methyl)-6-cyclopropylimidazo[1,2-a]pyridine-8-carboxylic acid (20 mg, 24%) as a white solid. ESI-MS [M+H]⁺: 487.2. ¹H NMR (400 MHz, DMSO) δ 9.20 (s, 2H), 8.92 (s, 2H), 8.80 (t, J=5.4 Hz, 1H), 8.74 (s, 1H), 8.61 (s, 1H), 8.12 (s, 1H), 7.92 (s, 1H), 7.47 (s, 2H), 5.88 (s, 2H), 4.52 (d, J=5.4 Hz, 2H), 2.45 (s, 6H), 2.19-2.04 (m, 1H), 1.05-1.00 (m, 2H), 0.79-0.75 (m, 2H).

Example 90

1-((6-cyclopropyl-8-fluoroimidazo[1,2-a]pyridin-2-yl)methyl)-N-(2-fluoro-3-methoxy-6-(1H-tetrazol-1-yl)benzyl)-1H-1,2,3-triazole-4-carboxamide (I-99)

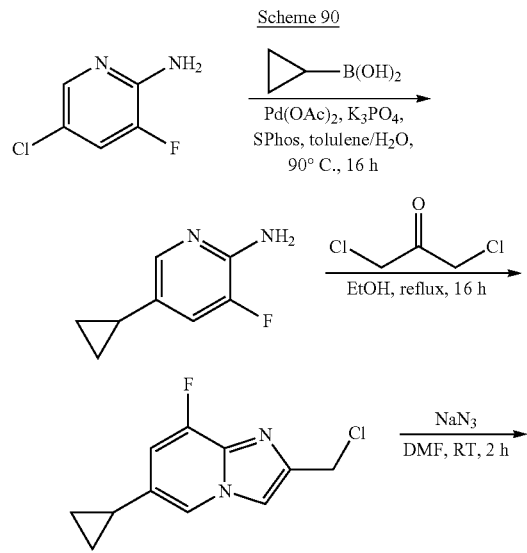

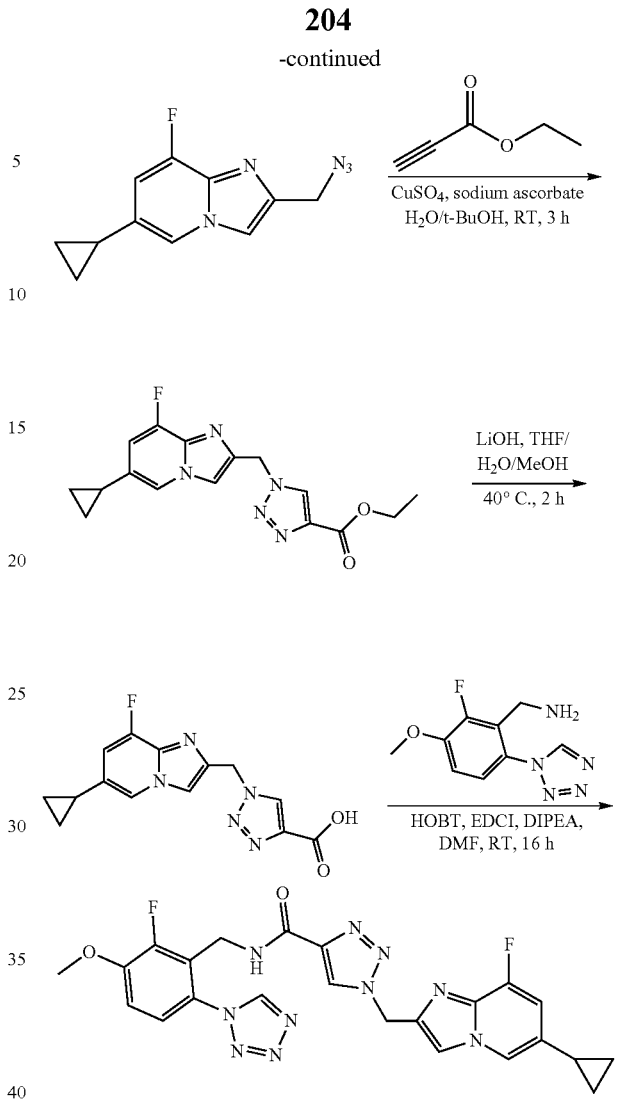

Synthesis of 5-cyclopropyl-3-fluoropyridin-2-amine. A mixture of 5-chloro-3-fluoropyridin-2-amine (2 g, 13.65 mmol), cyclopropylboronic acid (1.76 g, 20.47 mmol), Pd(OAc)₂ (306 mg, 1.365 mmol), SPhos (1.12 g, 2.73 mmol) and K₃PO₄ (10.14 g, 47.78 mmol) in toluene (40 mL) and H₂O (10 mL) was stirred at 90° C. for 16 h under N₂. The reaction mixture was filtered and washed with EtOAc. The combined filtrate was washed with H₂O (100 mL) and brine (100 mL), dried over Na₂SO₄, concentrated and purified by silica gel chromatography (EA/PE=1/2) to give 5-cyclopropyl-3-fluoropyridin-2-amine (2.2 g, yield: 100%) as a yellow syrup. ESI-MS [M+H]⁺: 153.2.

Synthesis of 2-(chloromethyl)-6-cyclopropyl-8-fluoroimidazo[1,2-a]pyridine. A mixture of 5-cyclopropyl-3-fluoropyridin-2-amine (2.2 g, 13.65 mmol) and 1,3-dichloropropan-2-one (5.5 g, 43.38 mmol) in EtOH (40 mL) was stirred at 85° C. for 16 h. The reaction mixture was concentrated. The residue was washed with NaHCO₃ aqueous solution and extracted with EtOAc (100 mL×3). The organic layers were washed with brine (100 mL), dried over Na₂SO₄, concentrated and purified by silica gel chromatography (EA/PE=1/2) to give 2-(chloromethyl)-6-cyclopropyl-8-fluoroimidazo[1,2-a]pyridine (1.8 g, 58%) as a yellow solid. ESI-MS [M+H]⁺: 225.1.

Synthesis of 2-(azidomethyl)-6-cyclopropyl-8-fluoroimidazo[1,2-a]pyridine. A mixture of 2-(chloromethyl)-6-cyclopropyl-8-fluoroimidazo[1,2-a]pyridine (1.8 g, 8.01 mmol) and NaN₃ (625 mg, 9.61 mmol) in DMF (20 mL) was stirred at RT for 3 h. The reaction mixture was poured into H₂O (100 mL) and extracted with EtOAc (80 mL×2). The combined organics was washed with brine (160 mL), concentrated and dried in vacuo to give 2-(azidomethyl)-6-cyclopropyl-8-fluoroimidazo[1,2-a]pyridine (1.75 g, yield: 95%) as a white solid. ESI-MS [M+H]⁺: 232.1.

Synthesis of ethyl 1-((6-cyclopropyl-8-fluoroimidazo[1,2-a]pyridin-2-yl)methyl)-1H-1,2,3-triazole-4-carboxylate. A mixture of 2-(azidomethyl)-6-cyclopropyl-8-fluoroimidazo[1,2-a]pyridine (1.75 g, 7.57 mmol), ethyl propiolate (891 mg, 9.08 mmol), CuSO₄ (362 mg, 2.27 mmol) and sodium ascorbate (750 mg, 3.79 mmol) in t-BuOH (20 mL) and H₂O (20 mL) was stirred at RT for 3 h. H₂O (50 mL) was added to the reaction, extracted with EtOAc (100 mL×3). The combined organics were washed with brine (100 mL), dried over Na₂SO₄, concentrated to give the crude product, which was purified by silica gel chromatography (EA/PE=1/2) to give ethyl 1-((6-cyclopropyl-8-fluoroimidazo[1,2-a]pyridin-2-yl)methyl)-1H-1,2,3-triazole-4-carboxylate (1.0 g, yield: 40%) as a white solid. ESI-MS [M+H]⁺: 330.1.

Synthesis of 1-((6-cyclopropyl-8-fluoroimidazo[1,2-a]pyridin-2-yl)methyl)-1H-1,2,3-triazole-4-carboxylic acid. To a solution of ethyl 1-((6-cyclopropyl-8-fluoroimidazo[1,2-a]pyridin-2-yl)methyl)-1H-1,2,3-triazole-4-carboxylate (270 mg, 0.82 mmol) in methanol (4 mL), THF (4 mL) and H₂O (2 mL) was added lithium hydroxide monohydrate (138 mg, 3.28 mmol). The mixture was stirred at 40° C. for 2 h. MeOH and THF was removed. The residue was diluted in H₂O (20 mL), the pH was acidified to 5-6 by HCl (1N) and yellow solid was precipitated. The mixture was filtered and dried in vacuo to give 1-((6-cyclopropyl-8-fluoroimidazo[1,2-a]pyridin-2-yl)methyl)-1H-1,2,3-triazole-4-carboxylic acid (220 mg, 89%) as a yellow solid. ESI-MS [M+H]⁺: 302.1.

Synthesis of 1-((6-cyclopropyl-8-fluoroimidazo[1,2-a]pyridin-2-yl)methyl)-N-(2-fluoro-3-methoxy-6-(1H-tetrazol-1-yl)benzyl)-1H-1,2,3-triazole-4-carboxamide. A mixture of 1-((6-cyclopropyl-8-fluoroimidazo[1,2-a]pyridin-2-yl)methyl)-1H-1,2,3-triazole-4-carboxylic acid (60 mg, 0.2 mmol), (2-fluoro-3-methoxy-6-(1H-tetrazol-1-yl)phenyl)methanamine (45 mg, 0.2 mmol), HATU (114 mg, 0.3 mmol) and DIPEA (155 mg, 1.2 mmol) in DMF (3 mL) was stirred at room temperature for 16 h. The reaction mixture was poured into water (40 mL) and white solid was precipitated. The mixture was filtered, washed with water (30 mL), dried in vacuo and purified by silica gel chromatography (DCM/MeOH=20/1) to give 1-((6-cyclopropyl-8-fluoroimidazo[1,2-a]pyridin-2-yl)methyl)-N-(2-fluoro-3-methoxy-6-(1H-tetrazol-1-yl)benzyl)-1H-1,2,3-triazole-4-carboxamide (40 mg, yield: 40%) as a white solid. ESI-MS [M+H]⁺: 507.2. ¹H NMR (400 MHz, DMSO) δ 9.75 (s, 1H), 8.77 (t, J=5.5 Hz, 1H), 8.51 (s, 1H), 8.26 (d, J=0.8 Hz, 1H), 7.94 (d, J=3.0 Hz, 1H), 7.40-7.31 (m, 2H), 6.95 (dd, J=12.4, 1.2 Hz, 1H), 5.73 (s, 2H), 4.29 (d, J=5.1 Hz, 2H), 3.92 (s, 3H), 1.97-1.91 (m, 1H), 0.96-0.89 (m, 2H), 0.72-0.67 (m, 2H).

Example 91

1-((6-cyclopropyl-8-(trifluoromethyl)imidazo[1,2-a]pyridin-2-yl)methyl)-N-(2-fluoro-3-methoxy-6-(1H-tetrazol-1-yl)benzyl)-1H-1,2,3-triazole-4-carboxamide (I-93)

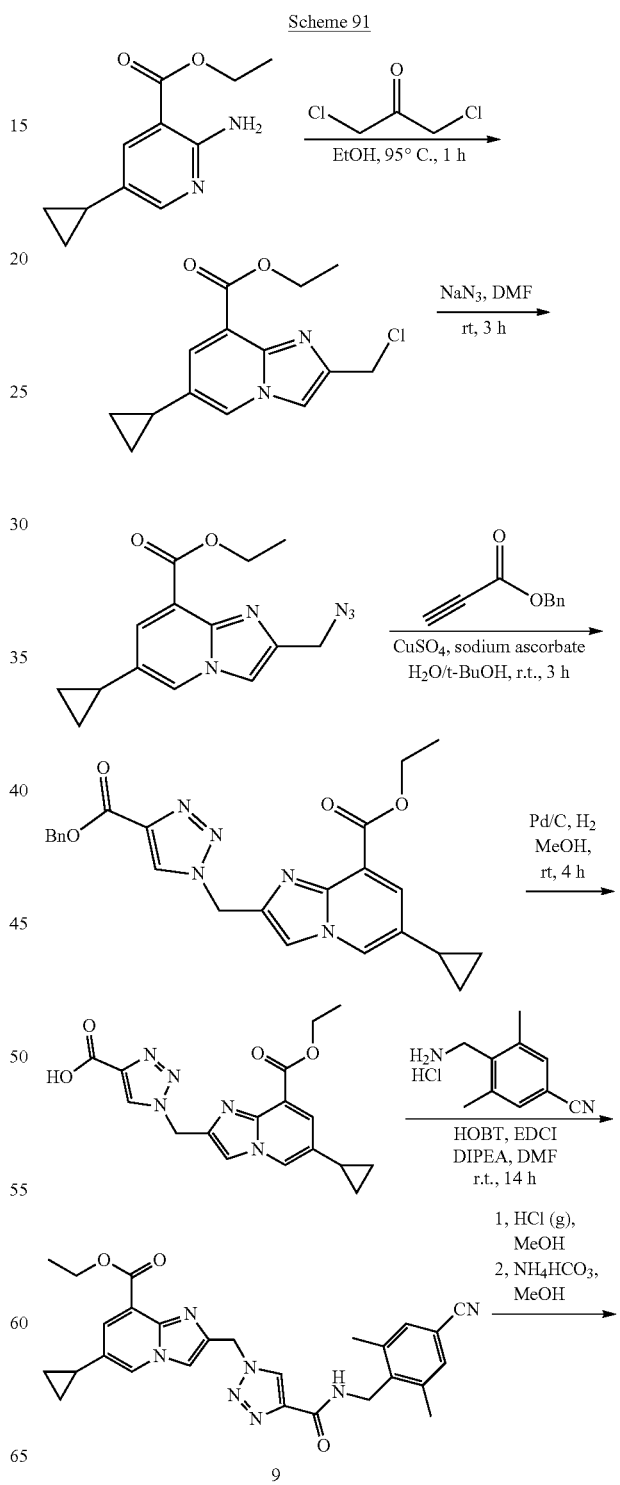

Scheme 91

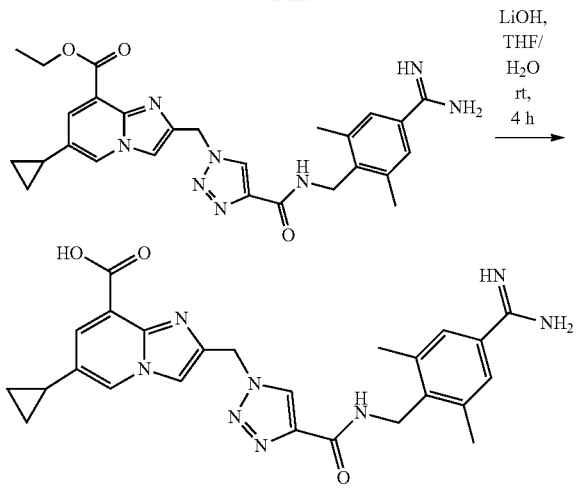

Synthesis of 2-(chloromethyl)-6-cyclopropyl-8-(trifluoromethyl)imidazo[1,2-a]pyridine. A mixture of 5-cyclopropyl-3-(trifluoromethyl)pyridin-2-amine (600 mg, 2.97 mmol) and 1,3-dichloropropan-2-one (1.14 g, 8.98 mmol) in EtOH (5 mL) was stirred at 85° C. overnight. The reaction mixture was concentrated in vacuo, diluted with saturated aqueous NaHCO₃(50 mL), and extracted with EtOAc (50 mL×3). The combined organic layers were washed with brine (50 mL), dried over Na₂SO₄, concentrated and purified by silica gel chromatography (PE/EtOAc=2/1) to give 2-(chloromethyl)-6-cyclopropyl-8-(trifluoromethyl)imidazo[1,2-a]pyridine (350 mg, yield: 43%) as a brown solid. ESI-MS [M+H]⁺: 275.1.

Synthesis of 2-(azidomethyl)-6-cyclopropyl-8-(trifluoromethyl)imidazo[1,2-a]pyridine. A mixture of 2-(chloromethyl)-6-cyclopropyl-8-(trifluoromethyl)imidazo[1,2-a]pyridine (350 mg, 1.27 mmol) and NaN₃ (413 mg, 6.4 mmol) in DMF (10 mL) was stirred at room temperature for 3 h. Water (20 mL) was added and the mixture was extracted with EtOAc (20 mL×3). The combined organic layers were washed by brine (20 mL), dried over Na₂SO₄, and concentrated to give 2-(azidomethyl)-6-cyclopropyl-8-(trifluoromethyl)imidazo[1,2-a]pyridine (400 mg crude) as a yellow solid. ESI-MS [M+H]⁺: 282.1.

Synthesis of ethyl 1-((6-cyclopropyl-8-(trifluoromethyl)imidazo[1,2-a]pyridin-2-yl)methyl)-1H-1,2,3-triazole-4-carboxylate. A mixture of 2-(azidomethyl)-6-cyclopropyl-8-(trifluoromethyl)imidazo[1,2-a]pyridine (400 mg, 1.4 mmol), ethyl propiolate (420 mg, 4.25 mmol), CuSO₄ (115 mg, 0.7 mmol) and sodium ascorbate (125 mg, 0.7 mmol) in H₂O/t-BuOH (10 mL/10 mL) was stirred at room temperature for 3 h. The reaction mixture was concentrated, diluted with water (45 mL), and extracted with EtOAc (30 mL×5). The combined organic layers were washed by brine (40 mL), dried over Na₂SO₄, and concentrated in vacuo to give the crude, which was purified by silica gel chromatography (DCM/MeOH=15/1) to give ethyl 1-((6-cyclopropyl-8-(trifluoromethyl)imidazo[1,2-a]pyridin-2-yl)methyl)-1H-1,2,3-triazole-4-carboxylate (350 mg, yield: 66%) as a yellow solid. ESI-MS [M+H]+: 380.1.

Synthesis of 1-((6-cyclopropyl-8-(trifluoromethyl)imidazo[1,2-a]pyridin-2-yl)methyl)-1H-1,2,3-triazole-4-carboxylic acid. A mixture of ethyl 1-((6-cyclopropyl-8-(trifluoromethyl)imidazo[1,2-a]pyridin-2-yl)methyl)-1H-1,2,3-triazole-4-carboxylate (350 mg, 0.9 mmol) and LiOH·H2O (76 mg, 1.8 mmol) in THF/EtOH/H₂O (4 mL/4 mL/2 mL) was stirred at 50° C. for 3 h. The reaction mixture was concentrated in vacuo to give the residue, which was diluted with water (10 mL) and acidified to pH 2-3 with HCl (3 M). The resulting precipitate was collected by filtration and dried to give 1-((6-cyclopropyl-8-(trifluoromethyl)imidazo[1,2-a]pyridin-2-yl)methyl)-1H-1,2,3-triazole-4-carboxylic acid (300 mg, yield: 95%) as a white solid. ESI-MS [M+H]+: 352.1.

Synthesis of 1-((6-cyclopropyl-8-(trifluoromethyl)imidazo[1,2-a]pyridin-2-yl)methyl)-N-(2-fluoro-3-methoxy-6-(1H-tetrazol-1-yl)benzyl)-1H-1,2,3-triazole-4-carboxamide. A mixture of 1-((6-cyclopropyl-8-(trifluoromethyl)imidazo[1,2-a]pyridin-2-yl)methyl)-1H-1,2,3-triazole-4-carboxylic acid (35 mg, 0.1 mmol), (2-fluoro-3-methoxy-6-(1H-tetrazol-1-yl)phenyl)methanamine (25 mg, 0.11 mmol), HOBT (27 mg, 0.2 mmol), EDCI (38 mg, 0.2 mmol) and DIPEA (65 mg, 0.5 mmol) in DMF (2 mL) was stirred at RT for 16 h. Water (20 mL) was added and the mixture was extracted with EtOAc (20 mL×3). The combined organic layers were washed with brine (30 mL), dried over Na₂SO₄, concentrated and purified by silica gel chromatography (DCM/MeOH=10/1) to give 1-((6-cyclopropyl-8-(trifluoromethyl)imidazo[1,2-a]pyridin-2-yl)methyl)-N-(2-fluoro-3-methoxy-6-(1H-tetrazol-1-yl)benzyl)-1H-1,2,3-triazole-4-carboxamide (24.8 mg, yield:45%) as a white solid. ESI-MS [M+H]+: 557.2. ¹H NMR (400 MHz, DMSO) δ 9.74 (s, 1H), 8.78 (t, J=5.4 Hz, 1H), 8.60 (s, 1H), 8.51 (s, 1H), 7.92 (s, 1H), 7.50 (s, 1H), 7.50-7.32 (m, 2H), 5.78 (s, 2H), 4.29 (d, J=5.2 Hz, 2H), 3.92 (s, 3H), 2.07-1.99 (m, 1H), 0.98-0.93 (m, 2H), 0.77-0.0.73 (m, 2H).

Example 92

1-((6-cyclopropyl-8-(3-fluorooxetan-3-yl)imidazo[1,2-a]pyridin-2-yl)methyl)-N-(2-fluoro-3-methoxy-6-(1H-tetrazol-1-yl)benzyl)-1H-1,2,3-triazole-4-carboxamide (I-91)

Scheme 92

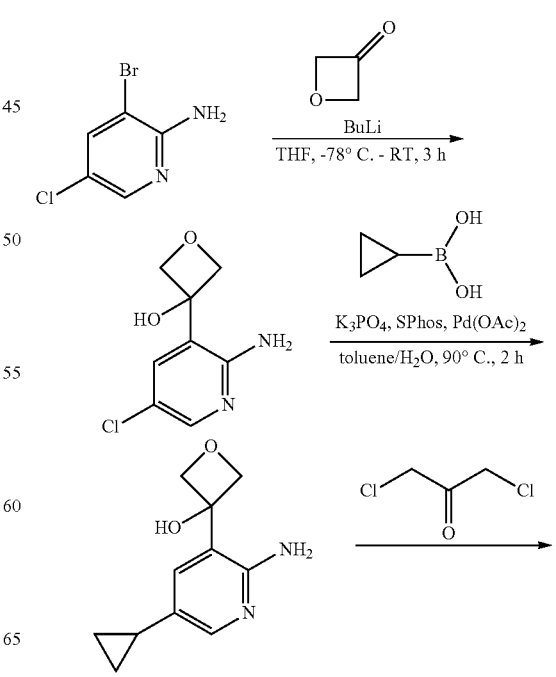

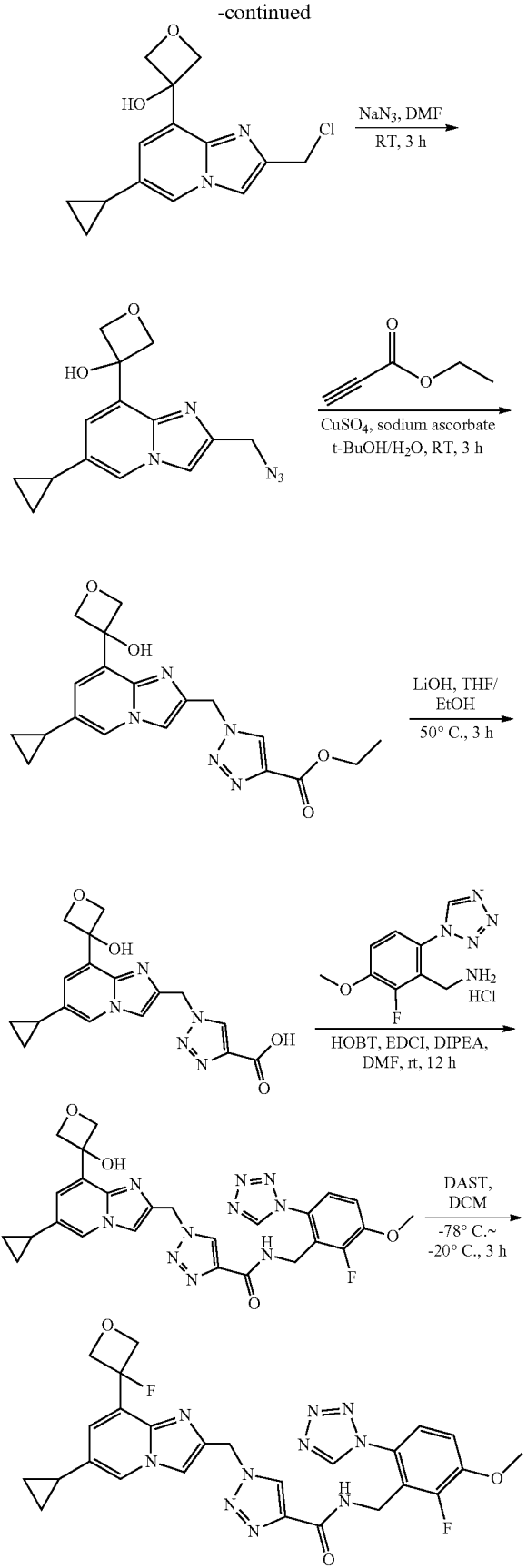

Synthesis of 3-(2-amino-5-chloropyridin-3-yl)oxetan-3-ol. To the solution of 3-bromo-5-chloropyridin-2-amine (5 g, 24 mmol) in THF (100 mL) was added n-BuLi (35 mL, 2.4 M solution in hexanes, 84 mmol) dropwise at −78° C. After 5 minutes, oxetan-3-one (17 g, 240 mmol) in THF (50 mL) was added thereto and stirred at −78° C. for 2 h. The reaction was quenched with saturated aqueous NH$_4$Cl (100 mL), extracted with ethyl acetate (100 mL×3). The combined organic layers were washed by brine (50 mL) and dried over Na$_2$SO$_4$, concentrated to give the crude, which was purified by silica gel column chromatography (DCM/MeOH=15/1) to give 3-(2-amino-5-chloropyridin-3-yl)oxetan-3-ol (2.8 g, 58% yield) as a yellow solid. ESI-MS [M+H]$^+$: 201.1. $^1$H NMR (400 MHz, DMSO-d6) δ 7.93 (d, J=2.5 Hz, 1H), 7.61 (d, J=2.5 Hz, 1H), 6.49 (s, 1H), 5.81 (s, 2H), 4.84 (d, J=7.4 Hz, 2H), 4.72 (d, J=7.4 Hz, 2H).

Synthesis of 3-(2-amino-5-cyclopropylpyridin-3-yl)oxetan-3-ol. A mixture of 3-(2-amino-5-chloropyridin-3-yl)oxetan-3-ol (2.8 g, 14 mmol), cyclopropylboronic acid (2.4 g, 28 mmol), K$_3$PO$_4$ (8.9 g, 42 mmol), SPhos (1.1 g, 2.7 mmol) and Pd(OAc)$_2$ (0.3 g, 1.3 mmol) in toluene/H$_2$O (50 mL/5 mL) was stirred at 90° C. for 16 h. The reaction mixture was filtered through celite, washed with EtOAc (100 mL). The filtrate was concentrated to give the crude, which was purified by silica gel column chromatography (DCM/MeOH=8/1) to give 3-(2-amino-5-cyclopropylpyridin-3-yl)oxetan-3-ol (2.1 g, 73% yield) as a yellow solid. ESI-MS [M+H]$^+$: 207.2. $^1$H NMR (400 MHz, DMSO-d$_6$) δ 7.75 (d, J=1.8 Hz, 1H), 7.17 (d, J=2.1 Hz, 1H), 6.34 (s, 1H), 5.34 (s, 2H), 4.85 (d, J=7.1 Hz, 2H), 4.70 (d, J=7.2 Hz, 2H), 3.61 (s, 1H), 1.85-1.78 (m, 1H), 0.86-0.80 (m, 2H), 0.64-0.59 (m, 2H).

Synthesis of 3-(2-(chloromethyl)-6-cyclopropylimidazo[1,2-a]pyridin-8-yl)oxetan-3-ol. A mixture of 3-(2-amino-5-cyclopropylpyridin-3-yl)oxetan-3-ol (2 g, 9.7 mmol), 1,3-dichloropropan-2-one (3.85 g, 31 mmol) in EtOH (50 mL) was stirred at 80° C. for 16 h. The reaction was concentrated and the residue was diluted with ethyl acetate (50 mL), washed by saturated aqueous NaHCO$_3$ (30 mL), H$_2$O (30 mL) and brine (30 mL), dried over Na$_2$SO$_4$, and concentrated to give the crude, which was purified by silica gel column chromatography (DCM/MeOH=8/1) to give 3-(2-(chloromethyl)-6-cyclopropylimidazo[1,2-a]pyridin-8-yl)oxetan-3-ol (1.2 g, 44% yield) as a yellow solid. ESI-MS [M+H]$^+$: 279.1. $^1$H NMR (400 MHz, DMSO-d$_6$) δ 8.54 (s, 1H), 8.15 (s, 1H), 7.54 (s, 1H), 5.10 (d, J=6.5 Hz, 2H), 4.96 (s, 2H), 4.80 (d, J=6.4 Hz, 2H), 2.07 (d, J=4.7 Hz, 1H), 1.06-0.98 (m, 2H), 0.80 (d, J=5.1 Hz, 2H).

Synthesis of ethyl 1-((6-cyclopropyl-8-(3-hydroxyoxetan-3-yl)imidazo[1,2-a]pyridin-2-yl)methyl)-1H-pyrazole-4-carboxylate. A mixture of 3-(2-(chloromethyl)-6-cyclopropylimidazo[1,2-a]pyridin-8-yl)oxetan-3-ol (500 mg, 1.8 mmol) and NaN$_3$ (176 mg, 2.7 mmol) in DMF (15 mL) was stirred at RT for 3 h. H$_2$O (30 mL) was added to the reaction, extracted with EtOAc (50 mL×3). The combined organic layers were washed brine, dried over Na$_2$SO$_4$, concentrate in vauo to give the crude product, which was purified with silica gel chromatography (EA/PE=1/1) to give the 3-(2-(azidomethyl)-6-cyclopropylimidazo[1,2-a]pyridin-8-yl)oxetan-3-ol (420 mg, yield: 82%) as a yellow solid. ESI-MS [M+H]$^+$: 286.1

Synthesis of ethyl 1-((8-(3-hydroxyoxetan-3-yl)imidazo[1,2-a]pyridin-2-yl)methyl)-1H-1,2,3-triazole-4-carboxylate. To a solution of 3-(2-(azidomethyl)-6-cyclopropylimidazo[1,2-a]pyridin-8-yl)oxetan-3-ol (420 mg, 1.47 mmol) in t-BuOH/H$_2$O (10 mL/10 mL) was added ethyl propiolate (158 mg, 1.6 mmol), CuSO$_4$ (70 mg, 0.44 mmol) and sodium ascorbate (87 mg, 0.44 mmol). The resulting reaction was stirred at RT for 3 h. The reaction was concentrated in vauco to give the residue, which was purified with silica gel chromatography (EA/PE=1/1) to give the ethyl 1-((8-(3-hydroxyoxetan-3-yl)imidazo[1,2-a]pyridin-2-yl)methyl)-1H-1,2,3-triazole-4-carboxylate (400 mg, yield: 71%) as a yellow solid. ESI-MS [M+H]$^+$: 383.2

Synthesis of 1-((8-(3-hydroxyoxetan-3-yl)imidazo[1,2-a]pyridin-2-yl)methyl)-1H-1,2,3-triazole-4-carboxylic acid. A mixture of ethyl 1-((8-(3-hydroxyoxetan-3-yl)imidazo[1,2-a]pyridin-2-yl)methyl)-1H-1,2,3-triazole-4-carboxylate (400 mg, 1.05 mmol) and LiOH (140 mg, 5.8 mmol) in THF/H$_2$O (15 mL/5 mL) was stirred at 50° C. for 3 h. The reaction was concentrate in vacuo to give crude product, which was purified with Prep-HPLC to give 1 ((8-(3-hydroxyoxetan-3-yl)imidazo[1,2-a]pyridin-2-yl)methyl)-1H-1,2,3-triazole-4-carboxylic acid (220 mg, yield: 58%) as a yellow solid. ESI-MS [M+H]$^+$: 356.2

Synthesis of 1-((6-cyclopropyl-8-(3-hydroxyoxetan-3-yl)imidazo[1,2-a]pyridin-2-yl)methyl)-N-(2-fluoro-3-methoxy-6-(1H-tetrazol-1-yl)benzyl)-1H-1,2,3-triazole-4-carboxamide. To a solution of 1-((6-cyclopropyl-8-(3-hydroxyoxetan-3-yl)imidazo[1,2-a]pyridin-2-yl)methyl)-1H-1,2,3-triazole-4-carboxylic acid (125 mg, 0.35 mmol), (2-fluoro-3-methoxy-6-(1H-tetrazol-1-yl)phenyl)methanamine hydrochloride (178 mg, 0.70 mmol), EDCI (102 mg, 0.53 mmol) and HOBT (72 mg, 0.53 mmol) in DMF (10 mL) was added DIPEA (135 mg, 1.05 mmol). The reaction mixture was stirred at room temperature for 12 h. H$_2$O (30 mL) was added and the mixture was extracted with EtOAc (30 mL×3). The combined organic layers were washed with brine (30 mL), dried over Na$_2$SO$_4$, and concentrated in vacuo to give the crude, which was purified with Prep-TLC (DCM/MeOH=10/1) to give 1-((6-cyclopropyl-8-(3-hydroxyoxetan-3-yl)imidazo[1,2-a]pyridin-2-yl)methyl)-N-(2-fluoro-3-methoxy-6-(1H-tetrazol-1-yl)benzyl)-1H-1,2,3-triazole-4-carboxamide (20 mg, yield: 10%) as a white solid. ESI-MS [M+H]+: 561.2.

Synthesis of 1-((6-cyclopropyl-8-(3-fluorooxetan-3-yl)imidazo[1,2-a]pyridin-2-yl)methyl)-N-(2-fluoro-3-methoxy-6-(1H-tetrazol-1-yl)benzyl)-1H-1,2,3-triazole-4-carboxamide. To a solution of 1-((6-cyclopropyl-8-(3-hydroxyoxetan-3-yl)imidazo[1,2-a]pyridin-2-yl)methyl)-N-(2-fluoro-3-methoxy-6-(1H-tetrazol-1-yl)benzyl)-1H-1,2,3-triazole-4-carboxamide (20 mg, 0.036 mmol) in DCM (5 ml) was added DAST (11 mg, 0.072 mmol) at-78° C. under nitrogen. The mixture was stirred at −20° C. for 3 h. The reaction was quenched with saturated aqueous NaHCO$_3$(15 mL) and extracted with EtOAc (20 mL×3). The combined organic layers were washed with brine (20 mL), dried over Na$_2$SO$_4$, and concentrated in vacuo to give the crude, which was purified by silica gel chromatography (DCM/MeOH=10/1) to give 1-((6-cyclopropyl-8-(3-fluorooxetan-3-yl)imidazo[1,2-a]pyridin-2-yl)methyl)-N-(2-fluoro-3-methoxy-6-(1H-tetrazol-1-yl)benzyl)-1H-1,2,3-triazole-4-carboxamide (10 mg, yield: 49%) as a white solid. ESI-MS [M+H]$^+$: 563.2. $^1$H NMR (400 MHz, DMSO) δ 9.74 (d, J=2.6 Hz, 1H), 8.778-8.74 (m, 1H), 8.48 (d, J=2.6 Hz, 1H), 8.42 (s, 1H), 7.81 (s, 1H), 7.39-7.35 (m, 2H), 7.17 (s, 1H), 5.75 (s, 2H), 5.33-5.25 (m, 2H), 4.99-4.91 (m, 2H), 4.29 (s, 2H), 3.93 (s, 3H), 1.98-1.95 (m, 1H), 0.95-0.92 (m, 2H), 0.74-071 (m, 2H).

Example 93 ethyl 3-(6-cyclopropyl-2-((4-((2-fluoro-3-methoxy-6-(1H-tetrazol-1-yl)benzyl)carbamoyl)-1H-1,2,3-triazol-1-yl)methyl)imidazo[1,2-a]pyridin-8-yl)-2,2-dimethylpropanoate (I-85)

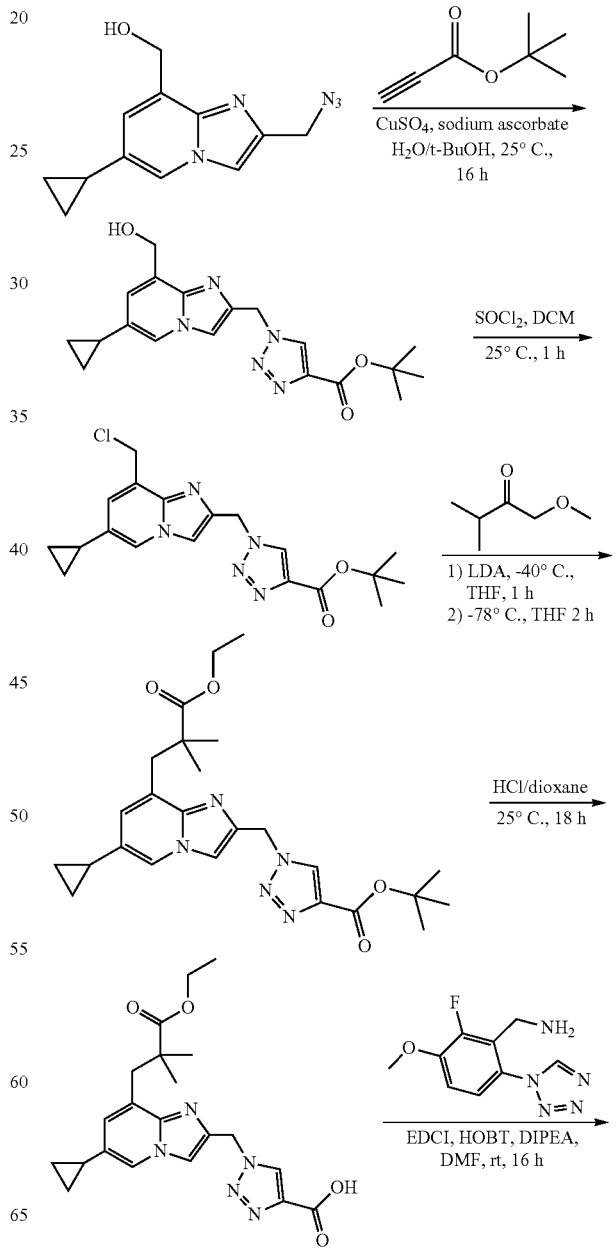

Scheme 93

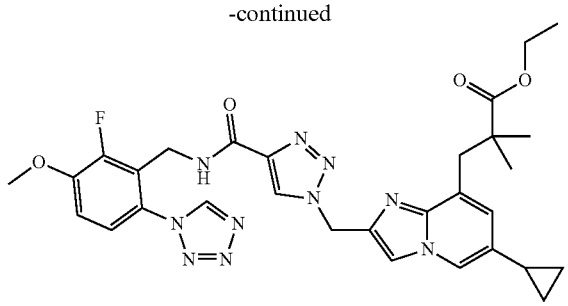

Synthesis of tert-butyl 1-((6-cyclopropyl-8-(hydroxymethyl)imidazo[1,2-a]pyridin-2-yl)methyl)-1H-1,2,3-triazole-4-carboxylate. The mixture of (2-(azidomethyl)-6-cyclopropylimidazo[1,2-a]pyridin-8-yl)methanol (20 g, 82.38 mmol), tert-butyl propiolate (10.4 g, 82.38 mmol), CuSO$_4$ (657 mg, 4.12 mmol) and sodium ascorbate (1.63 g, 8.24 mmol) in t-BuOH (100 mL) and H$_2$O (100 mL) was stirred at 25° C. for 16 h. t-BuOH was removed to give the residue, which was diluted in H$_2$O (100 mL), extracted with DCM (150 mL×3). The combined organics were washed with brine (300 mL), dried over Na$_2$SO$_4$, concentrated to give the crude, which was triturated with EtOAc and dried to afford tert-butyl 1-((6-cyclopropyl-8-(hydroxymethyl)imidazo[1,2-a]pyridin-2-yl)methyl)-1H-1,2,3-triazole-4-carboxylate (18 g, yield: 59%) as a light brown solid. ESI-MS [M+H]$^+$: 370.1.

Synthesis of tert-butyl 1-((8-(chloromethyl)-6-cyclopropylimidazo[1,2-a]pyridin-2-yl)methyl)-1H-1,2,3-triazole-4-carboxylate. To a stirred solution of tert-butyl 1-((6-cyclopropyl-8-(hydroxymethyl)imidazo[1,2-a]pyridin-2-yl)methyl)-1H-1,2,3-triazole-4-carboxylate (2 g, 5.41 mmol) in DCM (30 mL) was added dropwise SOCl$_2$ (1.29 g, 10.82 mmol) at 0° C. The mixture was stirred at 25° C. for 1 h. The reaction mixture was concentrated and the residue was dissolved in DCM (80 mL), washed with saturated aqueous NaHCO$_3$ (80 mL) and brine, dried over Na$_2$SO$_4$, concentrated to give the crude, which was purified by silica gel chromatography (EtOAc/PE=1/1) to give tert-butyl 1-((8-(chloromethyl)-6-cyclopropylimidazo[1,2-a]pyridin-2-yl)methyl)-1H-1,2,3-triazole-4-carboxylate (1.8 g, yield: 86%) as a light brown solid. ESI-MS [M+H]$^+$: 388.1.

Synthesis of tert-butyl 1-((6-cyclopropyl-8-(3-ethoxy-2,2-dimethyl-3-oxopropyl)imidazo[1,2-a]pyridin-2-yl)methyl)-1H-1,2,3-triazole-4-carboxylate. To a stirred solution of ethyl isobutyrate (808 mg, 6.96 mmol) in THF (20 mL) was added LDA (3.7 mL, 2 M, 7.4 mmol) dropwise at −40° C. under N$_2$. After 1 h, the solution of tert-butyl 1-((8-(chloromethyl)-6-cyclopropylimidazo[1,2-a]pyridin-2-yl)methyl)-1H-1,2,3-triazole-4-carboxylate (1.8 g, 4.64 mmol) in THF (15 mL) was added to the reaction above at −78° C. over 30 min. The resulting mixture was stirred at −78° C. for another 1.5 h. The reaction mixture was quenched with NH$_4$Cl aqueous (100 mL), extracted with EtOAc (100 mL×3). The combined organics were washed with brine (140 mL), dried over Na$_2$SO$_4$, concentrated to give the crude, which was purified by silica gel chromatography (EtOAc/PE=1/2) to give tert-butyl 1-((6-cyclopropyl-8-(3-ethoxy-2,2-dimethyl-3-oxopropyl)imidazo[1,2-a]pyridin-2-yl)methyl)-1H-1,2,3-triazole-4-carboxylate (1.24 g, yield: 57%) as a colorless syrup. ESI-MS [M+H]$^+$: 468.2.

Synthesis of 1-((6-cyclopropyl-8-(3-ethoxy-2,2-dimethyl-3-oxopropyl)imidazo[1,2-a]pyridin-2-yl)methyl)-1H-1,2,3-triazole-4-carboxylic acid. A mixture of tert-butyl 1-((6-cyclopropyl-8-(3-ethoxy-2,2-dimethyl-3-oxopropyl)imidazo[1,2-a]pyridin-2-yl)methyl)-1H-1,2,3-triazole-4-carboxylate (1.24 g, 2.65 mmol) and HCl in dioxane (10 mL, 4N) was stirred at 25° C. for 18 h. The reaction mixture was concentrated and dried in vacuo to afford give 1-((6-cyclopropyl-8-(3-ethoxy-2,2-dimethyl-3-oxopropyl)imidazo[1,2-a]pyridin-2-yl)methyl)-1H-1,2,3-triazole-4-carboxylic acid (1.3 g, yield: 100%) as a colorless syrup. ESI-MS [M+H]$^+$: 412.2.

Synthesis of ethyl 3-(6-cyclopropyl-2-((4-((2-fluoro-3-methoxy-6-(1H-tetrazol-1-yl)benzyl)carbamoyl)-1H-1,2,3-triazol-1-yl)methyl)imidazo[1,2-a]pyridin-8-yl)-2,2-dimethylpropanoate. A mixture of 1-((6-cyclopropyl-8-(3-ethoxy-2,2-dimethyl-3-oxopropyl)imidazo[1,2-a]pyridin-2-yl)methyl)-1H-1,2,3-triazole-4-carboxylic acid (167 mg, 0.406 mmol), (2-fluoro-3-methoxy-6-(1H-tetrazol-1-yl)phenyl)methanamine (91 mg, 0.406 mmol), EDCI (156 mg, 0.812 mmol), HOBT (110 mg, 0.812 mmol) and DIPEA (525 mg, 4.06 mmol) in DMF (5 mL) was stirred at room temperature for 16 h. The reaction mixture was poured into water (50 mL) and extracted with EtOAc/THF (50 mL x 2, 5/1). The combined organic layers were washed sequentially with water (100 mL×3) and brine (100 mL×1), dried over Na$_2$SO$_4$, concentrated in vacuo and purified by Prep-TLC (DCM/MeOH=10/1) to give ethyl 3-(6-cyclopropyl-2-((4-((2-fluoro-3-methoxy-6-(1H-tetrazol-1-yl)benzyl)carbamoyl)-1H-1,2,3-triazol-1-yl)methyl)imidazo[1,2-a]pyridin-8-yl)-2,2-dimethylpropanoate as a pale white solid (100 mg, yield: 40%). ESI-MS [M+H]$^+$: 617.2. $^1$H NMR (400 MHz, DMSO) δ 9.71 (s, 1H), 8.72 (t, J=5.4 Hz, 1H), 8.41 (s, 1H), 8.19 (s, 1H), 7.73 (s, 1H), 7.36-7.29 (m, 2H), 6.63 (s, 1H), 5.65 (s, 2H), 4.26 (d, J=5.4 Hz, 2H), 3.94-3.88 (m, 5H), 3.05 (s, 2H), 1.87-1.82 (m, 1H), 1.08-1.03 (m, 9H), 0.90-0.85 (m, 2H), 0.60-0.55 (m, 2H).

Example 94

3-(6-cyclopropyl-2-((4-((2-fluoro-3-methoxy-6-(1H-tetrazol-1-yl)benzyl)carbamoyl)-1H-1,2,3-triazol-1-yl)methyl)imidazo[1,2-a]pyridin-8-yl)-2,2-dimethylpropanoic acid (I-81)

Scheme 94

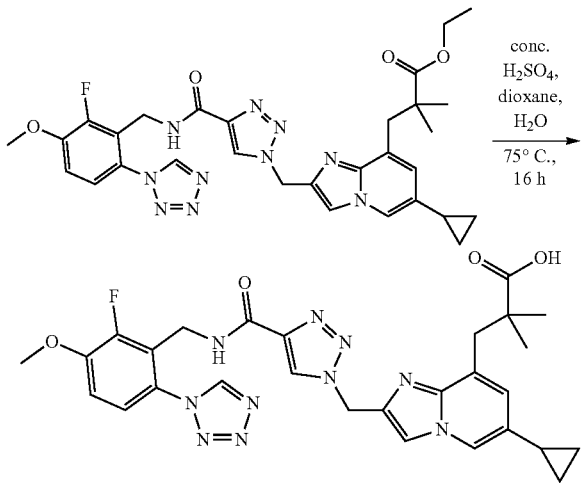

Synthesis of 3-(6-cyclopropyl-2-((4-((2-fluoro-3-methoxy-6-(1H-tetrazol-1-yl)benzyl)carbamoyl)-1H-1,2,3- triazol-1-yl)methyl)imidazo[1,2-a]pyridin-8-yl)-2,2-dimethylpropanoic acid. To a solution of ethyl 3-(6-cyclopropyl-2-((4-((2-fluoro-3-methoxy-6-(1H-tetrazol-1-yl)benzyl)carbamoyl)-1H-1,2,3-triazol-1-yl)methyl)imidazo[1,2-a]pyridin-8-yl)-2,2-dimethylpropanoate (75 mg, 0.122 mmol) in dioxane (3 mL) and H₂O (1 mL) was added conc. H₂SO₄ (1 mL). The reaction mixture was stirred at 75° C. for 16 h and then poured onto water (30 mL). The mixture was adjusted to pH 4-5 using sat. aq. NaHCO₃ and then extracted with EtOAc/THF (40 mL x 2, 5/1). The combined organic layers were washed with brine (80 mL), dried over Na₂SO₄, concentrated and purified by Prep-HPLC to give 3-(6-cyclopropyl-2-((4-((2-fluoro-3-methoxy-6-(1H-tetrazol-1-yl)benzyl)carbamoyl)-1H-1,2,3-triazol-1-yl)methyl)imidazo[1,2-a]pyridin-8-yl)-2,2-dimethylpropanoic acid as a white solid (30 mg, yield: 42%). ESI-MS [M+H]⁺: 589.2. ¹H NMR (400 MHz, DMSO) δ 12.34 (s, 1H), 9.74 (s, 1H), 8.76 (s, 1H), 8.45 (s, 1H), 8.21 (d, J=1.4 Hz, 1H), 7.74 (s, 1H), 7.39-7.32 (m, 2H), 6.72 (d, J=1.3 Hz, 1H), 5.70 (s, 2H), 4.29 (d, J=5.2 Hz, 2H), 3.92 (s, 3H), 3.09 (s, 2H), 1.90-1.83 (m, 1H), 1.06 (s, 6H), 0.93-0.87 (m, 2H), 0.65-0.59 (m, 2H).

Example 95

1-((8-(2-cyano-2-methylpropyl)-6-cyclopropylimidazo[1,2-a]pyridin-2-yl)methyl)-N-(2,6-difluoro-3-methoxybenzyl)-1H-1,2,3-triazole-4-carboxamide (I-12)

Scheme 95

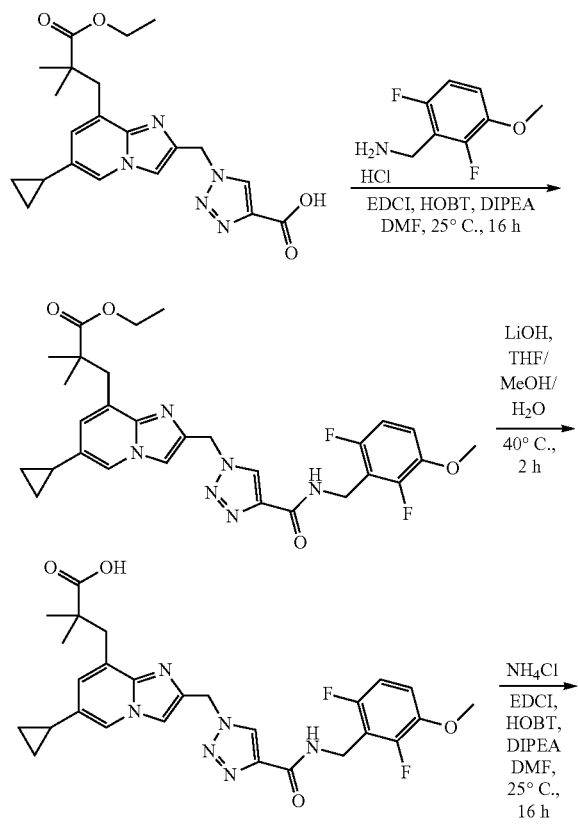

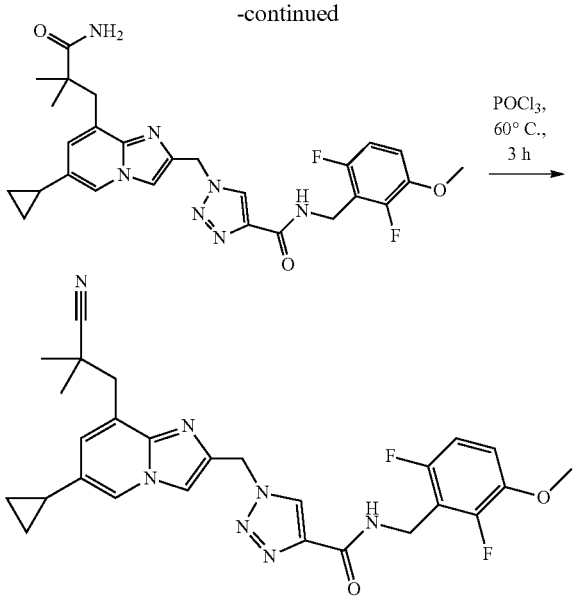

Synthesis of ethyl 3-(6-cyclopropyl-2-((4-((2,6-difluoro-3-methoxybenzyl)carbamoyl)-1H-1,2,3-triazol-1-yl)methyl)imidazo[1,2-a]pyridin-8-yl)-2,2-dimethylpropanoate. A mixture of 1-((6-cyclopropyl-8-(3-ethoxy-2,2-dimethyl-3-oxopropyl)imidazo[1,2-a]pyridin-2-yl)methyl)-1H-1,2,3-triazole-4-carboxylic acid (352 mg, crude), (2,6-difluoro-3-methoxyphenyl)methanamine hydrochloride (179 mg, 0.855 mmol), EDCI (328 mg, 1.71 mmol), HOBT (231 mg, 1.71 mmol) and DIPEA (662 mg, 5.13 mmol) in DMF (15 mL) was stirred at room temperature for 16 h. The reaction mixture was poured into water (80 mL) and extracted with EtOAc/THF (60 mL x 2, 5/1). The combined organics were washed with water (120 mL×3) and brine (120 mL), dried over Na₂SO₄, concentrated and purified by silica gel chromatography (EtOAc/PE=1/1) to give ethyl 3-(6-cyclopropyl-2-((4-((2,6-difluoro-3-methoxybenzyl)carbamoyl)-1H-1,2,3-triazol-1-yl)methyl)imidazo[1,2-a]pyridin-8-yl)-2,2-dimethylpropanoate (320 mg, yield: 66%, two steps) as a pale white solid. ESI-MS [M+H]⁺: 567.2.

Synthesis of 3-(6-cyclopropyl-2-((4-((2,6-difluoro-3-methoxybenzyl)carbamoyl)-1H-1,2,3-triazol-1-yl)methyl)imidazo[1,2-a]pyridin-8-yl)-2,2-dimethylpropanoic acid. To a solution of ethyl 3-(6-cyclopropyl-2-((4-((2,6-difluoro-3-methoxybenzyl)carbamoyl)-1H-1,2,3-triazol-1-yl)methyl)imidazo[1,2-a]pyridin-8-yl)-2,2-dimethylpropanoate (320 mg, 0.565 mmol) in methanol (6 mL), THF (6 mL) and water (4 mL) was added lithium hydroxide monohydrate (95 mg, 2.26 mmol). The reaction mixture was stirred at 40° C. for 2 h. MeOH and THF was removed in vacuo and the mixture was diluted in water (40 mL) and extracted with EtOAc (40 mL). The organic layer was discarded. The aqueous layer was acidified to pH=5-6 using HCl (2 M, aq.) and extracted with EtOAc (40 mL×2). The combined organics were washed with brine (80 mL), dried over Na₂SO₄, concentrated and dried in vacuo to give 3-(6-cyclopropyl-2-((4-((2,6-difluoro-3-methoxybenzyl)carbamoyl)-1H-1,2,3-triazol-1-yl)methyl)imidazo[1,2-a]pyridin-8-yl)-2,2-dimethylpropanoic acid (270 mg, 88%) as a white solid. ESI-MS [M+H]⁺: 539.2.

Synthesis of 1-((8-(3-amino-2,2-dimethyl-3-oxopropyl)-6-cyclopropylimidazo[1,2-a]pyridin-2-yl)methyl)-N-(2,6-difluoro-3-methoxybenzyl)-1H-1,2,3-triazole-4-carboxamide. A mixture of 3-(6-cyclopropyl-2-((4-((2,6-difluoro-3-methoxybenzyl)carbamoyl)-1H-1,2,3-triazol-1-yl)methyl)imidazo[1,2-a]pyridin-8-yl)-2,2-dimethylpropanoic acid (270 mg, 0.501 mmol), NH₄Cl (266 mg, 5.01 mmol), EDCI (192 mg, 1.0 mmol), HOBT (135 mg, 1.0 mmol) and DIPEA (324 mg, 2.51 mmol) in DMF (8 mL) was stirred at room temperature for 16 h. The reaction mixture was poured into water (60 mL) and extracted with EtOAc (60 mL×2). The combined organics were washed with water (120 mL×3) and brine (120 mL×1), dried over Na₂SO₄, concentrated and purified by silica gel chromatography (EtOAc/MeOH=10/1) to give 1-((8-(3-amino-2,2-dimethyl-3-oxopropyl)-6-cyclopropylimidazo[1,2-a]pyridin-2-yl)methyl)-N-(2,6-difluoro-3-methoxybenzyl)-1H-1,2,3-triazole-4-carboxamide (240 mg, yield: 89%) as a pale white solid. ESI-MS [M+H]⁺: 538.2.

Synthesis of 1-((8-(2-cyano-2-methylpropyl)-6-cyclopropylimidazo[1,2-a]pyridin-2-yl)methyl)-N-(2,6-difluoro-3-methoxybenzyl)-1H-1,2,3-triazole-4-carboxamide. A mixture of 1-((8-(3-amino-2,2-dimethyl-3-oxopropyl)-6-cyclopropylimidazo[1,2-a]pyridin-2-yl)methyl)-N-(2,6-difluoro-3-methoxybenzyl)-1H-1,2,3-triazole-4-carboxamide (120 mg, 0.223 mmol) in POCl₃ (4 mL) was stirred at 60° C. for 3 h. The reaction mixture was poured into water (30 mL). The mixture was adjusted to pH 9-10 with sat. aq. NaHCO₃solution and extracted with EtOAc (30 mL×2). The combined organics were washed with brine (60 mL), dried over Na₂SO₄, concentrated and purified by silica gel chromatography (EtOAc/PE=1/2) to give 1-((8-(2-cyano-2-methylpropyl)-6-cyclopropylimidazo[1,2-a]pyridin-2-yl)methyl)-N-(2,6-difluoro-3-methoxybenzyl)-1H-1,2,3-triazole-4-carboxamide (50 mg, 43%) as a white solid. ESI-MS [M+H]+: 520.2. ¹H NMR (400 MHz, DMSO) δ 8.79 (t, J=5.5 Hz, 1H), 8.49 (s, 1H), 8.31 (s, 1H), 7.81 (s, 1H), 7.15-7.06 (m, 1H), 7.02-6.94 (m, 2H), 5.72 (s, 2H), 4.48 (d, J=5.4 Hz, 2H), 3.80 (s, 3H), 3.12 (s, 2H), 1.92-1.89 (m, 1H), 1.29 (s, 6H), 0.97-0.90 (m, 2H), 0.69-0.64 (m, 2H).

Example 96

1-((6-cyclopropyl-8-(4H-1,2,4-triazol-4-yl)imidazo[1,2-a]pyridin-2-yl)methyl)-N-(2-fluoro-3-methoxy-6-(1H-tetrazol-1-yl)benzyl)-1H-1,2,3-triazole-4-carboxamide (I-71)

Scheme 96

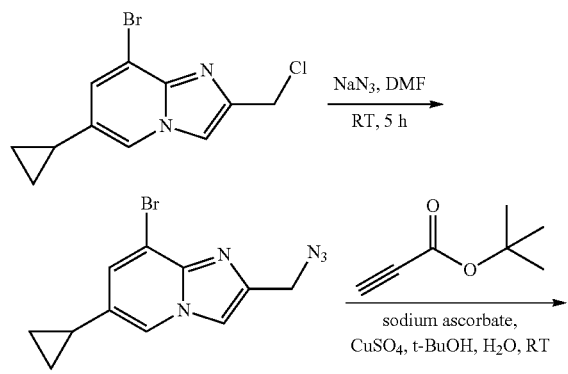

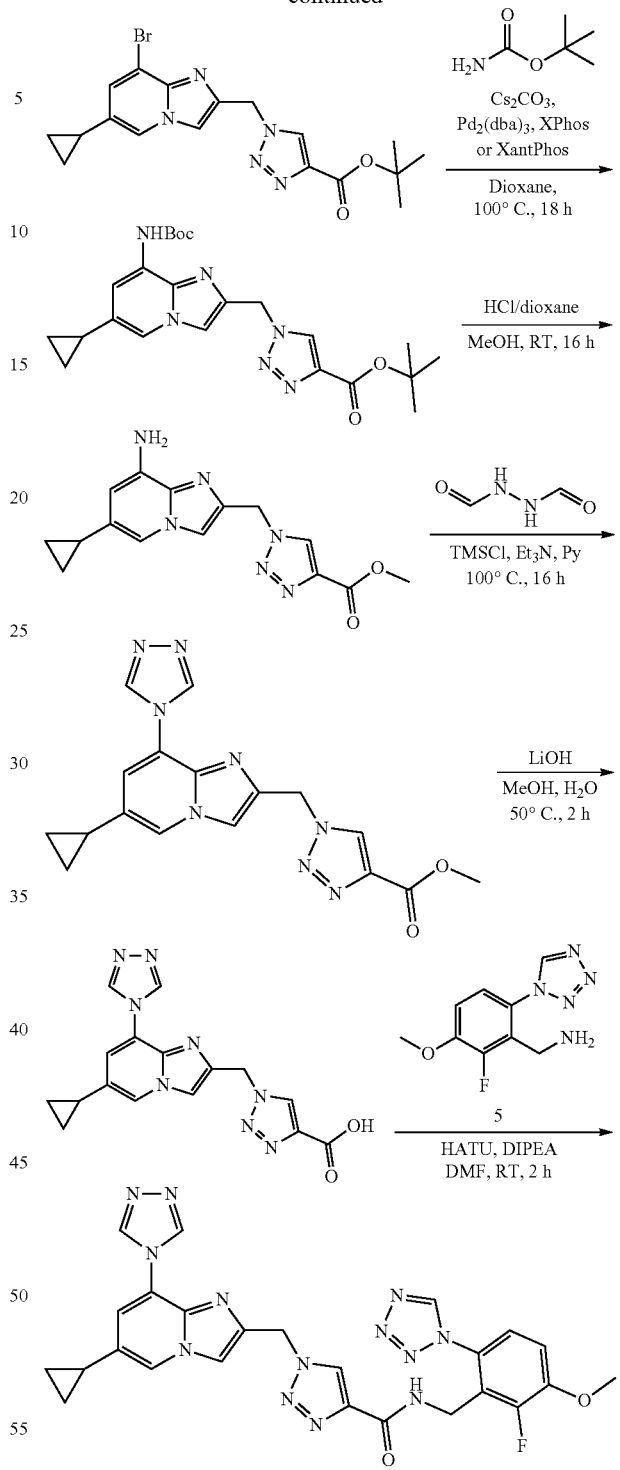

Synthesis of 2-(azidomethyl)-8-bromo-6-cyclopropylimidazo[1,2-a]pyridine. To a solution of 8-bromo-2-(chloromethyl)-6-cyclopropylimidazo[1,2-a]pyridine (1 g, 3.5 mmol) in DMF (15 mL) was added NaN₃ (230 mg, 3.5 mmol). The resulting mixture was stirred at 50° C. for 24 h under nitrogen. H₂O (50 mL) was added to the reaction, extracted with EtOAc (50 mL×3). The combined organic layers were washed brine, dried over Na₂SO₄, concentrated in vacuo to give 2-(azidomethyl)-8-bromo-6-cyclopropylimidazo[1,2-a]

pyridine (1.1 g, crude), which was used into next step without further purification. ESI-MS [M+H]$^+$: 292.0.

Synthesis of tert-butyl 1-((8-bromo-6-cyclopropylimidazo[1,2-a]pyridin-2-yl)methyl)-1H-1,2,3-triazole-4-carboxylate. To a solution 2-(azidomethyl)-8-bromo-6-cyclopropylimidazo[1,2-a]pyridine (1.1 g, crude from previous step) and tert-butyl propiolate (860 mg, 6.8 mmol) in t-BuOH/H$_2$O (15 mL/15 mL) was added CuSO$_4$ (170 mg, 0.68 mmol), sodium ascorbate (180 mg, 1.02 mmol). The reaction mixture was stirred at RT for 12 h. The mixture was concentrated in vacuo to give the crude product, which was purified by silica gel chromatography (PE/EtOAc=1/2) to give tert-butyl 1-((8-bromo-6-cyclopropylimidazo[1,2-a]pyridin-2-yl)methyl)-1H-1,2,3-triazole-4-carboxylate (500 mg, 34% over 2 steps) as brown oil. ESI-MS [M+H]$^+$: 417.7.

Synthesis of tert-butyl 1-((8-((tert-butoxycarbonyl)amino)-6-cyclopropylimidazo[1,2-a]pyridin-2-yl)methyl)-1H-1,2,3-triazole-4-carboxylate. To a solution of tert-butyl 1-((8-bromo-6-cyclopropylimidazo[1,2-a]174yridine-2-yl)methyl)-1H-1,2,3-triazole-4-carboxylate (1 g, 2 mmol) and tert-butyl carbamate (0.56 g, 4 mmol) in dioxane (10 mL) was added Pd$_2$(dba)$_3$ (0.18 g, 0.2 mmol), XantPhos (0.23 g, 0.4 mmol), Cs$_2$CO$_3$ (1.95 g, 6 mmol). The reaction mixture was stirred at 100° C. for 16 h under N$_2$. The reaction mixture was cooled to RT and H$_2$O (50 mL) was added. The aqueous phase was extracted with ethyl acetate (100 mL×3), the combined organic layers were dried over sodium sulfate, evaporated and the residue was purified by silica gel chromatography (DCM:MeOH=15:1) to give the tert-butyl 1-((8-((tert-butoxycarbonyl)amino)-6-cyclopropylimidazo[1,2-a]174yridine-2-yl)methyl)-1H-1,2,3-triazole-4-carboxylate (900 mg, 99%) as a yellow solids. ESI-MS [M+H]$^+$: 455.2.

Synthesis of methyl 1-((8-amino-6-cyclopropylimidazo[1,2-a]pyridine-2-yl)methyl)-1H-1,2,3-triazole-4-carboxylate. A solution of tert-butyl 1-((8-((tert-butoxycarbonyl)amino)-6-cyclopropylimidazo[1,2-a]pyridin-2-yl)methyl)-1H-1,2,3-triazole-4-carboxylate (300 mg, 0.66 mmol) in MeOH (5 mL) and HCl in dioxane (4 M, 5 mL) was stirred at RT for 16 h. LCMS showed the reaction was complete. The solvent of the reaction mixture was evaporated to give the crude product which was used in next step without further purification. (230 mg, yield 100%) as a yellow solid. ESI-MS [M+H]$^+$: 313.3.

Synthesis of 1-((6-cyclopropyl-8-(4H-1,2,4-triazol-4-yl)imidazo[1,2-a]pyridin-2-yl)methyl)-N-(2-fluoro-3-methoxy-6-(1H-tetrazol-1-yl)benzyl)-1H-1,2,3-triazole-4-carboxamide. To a solution of 1-((6-cyclopropyl-8-(4H-1,2,4-triazol-4-yl)imidazo[1,2-a]pyridin-2-yl)methyl)-1H-1,2,3-triazole-4-carboxylic acid (120 mg, 0.34 mmol) in dry DMF (3 mL) was added (2-fluoro-3-methoxy-6-(1H-tetrazol-1-yl)phenyl)methanamine (152 mg, 0.68 mmol), HATU (155.8 mg, 0.41 mmol) and DIPEA (175 mg, 1.36 mmol). The reaction mixture was stirred at room temperature for 2 hours, then diluted with water (20 mL) and extracted with ethyl acetate (30 mL×3). The combined organic layer was washed with brine (20 mL×2), dried over sodium sulfate and concentrated in vacuo. The residue was purified by Prep-TLC (DCM/MeOH=10:1) to afford 1-((6-cyclopropyl-8-(4H-1,2,4-triazol-4-yl)imidazo[1,2-a]pyridin-2-yl)methyl)-N-(2-fluoro-3-methoxy-6-(1H-tetrazol-1-yl)benzyl)-1H-1,2,3-triazole-4-carboxamide (80 mg, yield: 43%) as a white solid. ESI-MS [M+H]$^+$: 556.2. $^1$H NMR (400 MHz, HDMSO-d6) δ 9.74 (s, 1H), 9.39 (s, 2H), 8.77 (t, J=5.4 Hz, 1H), 8.57 (s, 1H), 8.47 (s, 1H), 8.00 (s, 1H), 7.45 (d, J=1.1 Hz, 1H), 7.42-7.32 (m, 2H), 5.77 (d, J=6.9 Hz, 2H), 4.29 (d, J=5.1 Hz, 2H), 3.90 (s, 3H), 2.01-1.93 (m, 1H), 1.03-0.93 (m, 2H), 0.86-0.77 (m, 2H).

Example 97

1-((6-cyclopropyl-8-(oxetan-3-ylmethyl) imidazo[1,2-a]pyridin-2-yl) methyl)-N-(2-fluoro-3-methoxy-6-(1H-tetrazol-1-yl)benzyl)-1H-1,2,3-triazole-4-carboxamide (I-68)

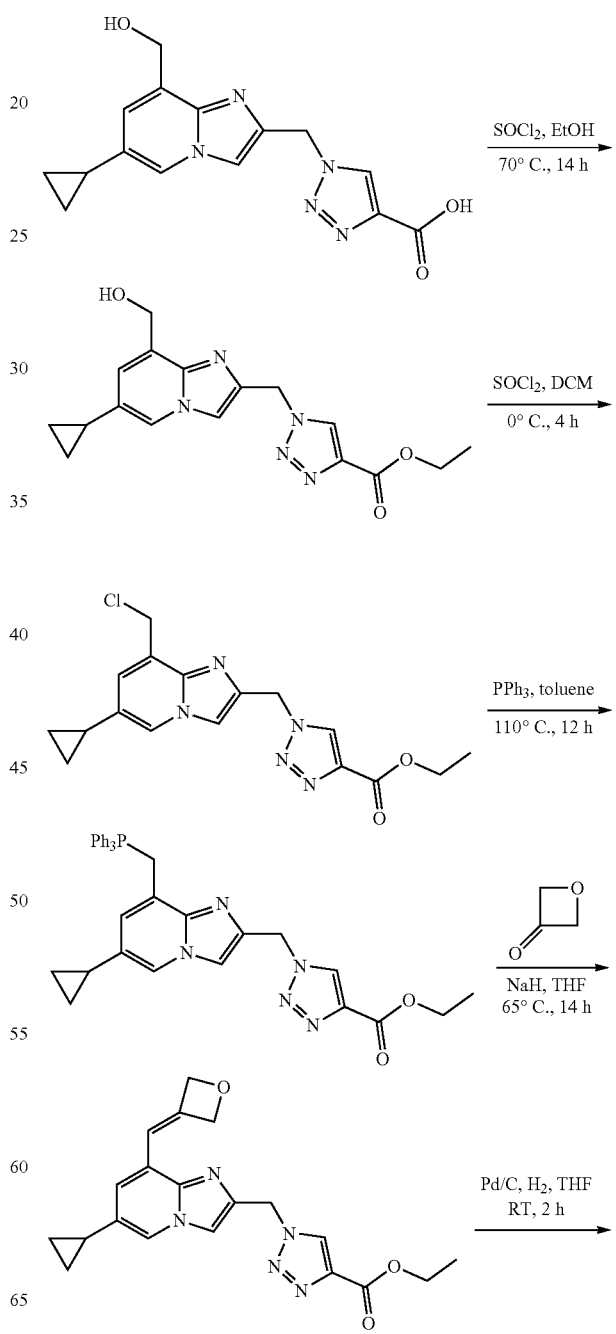

Scheme 97

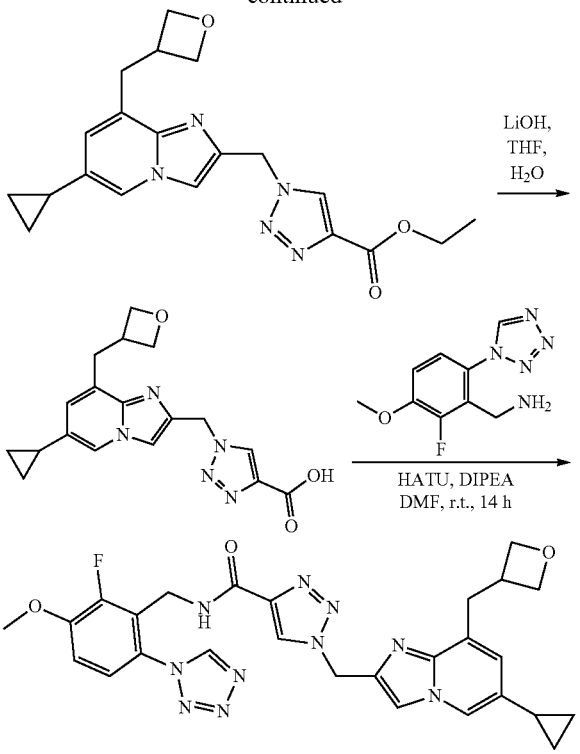

Synthesis of ethyl 1-((6-cyclopropyl-8-(hydroxymethyl)imidazo[1,2-a]pyridin-2-yl)methyl)-1H-1,2,3-triazole-4-carboxylate. To a solution of 1-((6-cyclopropyl-8-(hydroxymethyl)imidazo[1,2-a]pyridin-2-yl)methyl)-1H-1,2,3-triazole-4-carboxylic acid (800 mg, 2.56 mmol) in EtOH (50 mL) was added SOCl$_2$ (10 mL). The resulting reaction was stirred at 70° C. for 14 h. The reaction was concentrated in vacuo to give the ethyl 1-((6-cyclopropyl-8-(hydroxymethyl)imidazo[1,2-a]pyridin-2-yl)methyl)-1H-1,2,3-triazole-4-carboxylate as a yellow solid. (850 mg, 97.5%). ESI-MS [M+H]$^+$: 342.2

Synthesis of ethyl 1-((8-(chloromethyl)-6-cyclopropylimidazo[1,2-a]pyridin-2-yl)methyl)-1H-1,2,3-triazole-4-carboxylate. To a solution of ethyl 1-((6-cyclopropyl-8-(hydroxymethyl)imidazo[1,2-a]pyridin-2-yl)methyl)-1H-1,2,3-triazole-4-carboxylate (850 mg, 2.49 mmol) in DCM (25 mL) was added SOCl$_2$ (3 mL) at 0° C. The resulting reaction was stirred at RT for 4 h. The reaction was concentrated in vacuo to give the ethyl 1-((8-(chloromethyl)-6-cyclopropylimidazo[1,2-a]pyridin-2-yl)methyl)-1H-1,2,3-triazole-4-carboxylate as a yellow solid (900 mg crude). ESI-MS [M+H]$^+$: 360.3.

Synthesis of ethyl 1-((6-cyclopropyl-8-((triphenyl-14-phosphanyl)methyl)imidazo[1,2-a]pyridin-2-yl)methyl)-1H-1,2,3-triazole-4-carboxylate. A mixture of ethyl 1-((8-(chloromethyl)-6-cyclopropylimidazo[1,2-a]pyridin-2-yl)methyl)-1H-1,2,3-triazole-4-carboxylate (900 mg crude form previous step) and PPh$_3$ (720 mg, 2.74 mmol) in toluene (40 mL) was stirred at 110° C. for 12 h. The reaction was concentrated in vacuo to give the ethyl 1-((6-cyclopropyl-8-((triphenyl-14-phosphanyl)methyl)imidazo[1,2-a]pyridin-2-yl)methyl)-1H-1,2,3-triazole-4-carboxylate as a yellow solid, which was used into next step without further purification (1.62 g crude). ESI-MS [M+H]$^+$: 586.1.

Synthesis of ethyl 1-((6-cyclopropyl-8-(oxetan-3-ylidenemethyl)imidazo[1,2-a]pyridin-2-yl)methyl)-1H-1,2,3-triazole-4-carboxylate. A mixture of ethyl 1-((6-cyclopropyl-8-((triphenyl-14-phosphanyl)methyl)imidazo[1,2-a]pyridin-2-yl)methyl)-1H-1,2,3-triazole-4-carboxylate (1 g crude from previous step), oxetan-3-one (369 mg, 5.1 mmol) and NaH (340 mg, 8.5 mmol, 60 wt % in oil) in THF (30 mL) was stirred at 65° C. for 14 h under N$_2$. The reaction was quenched with aqueous NH$_4$Cl (50 mL), extracted with EtOAc (50 mL×3). The combined organic layers were washed with brine, dried over Na$_2$SO$_4$, concentrated in vacuo to give the crude product, which was purified with silica gel (eluent: DCM/MeOH=30/1) to give the ethyl 1-((6-cyclopropyl-8-(oxetan-3-ylidenemethyl)imidazo[1,2-a]pyridin-2-yl)methyl)-1H-1,2,3-triazole-4-carboxylate as a yellow solid. (450 mg, 47.7% over 3 steps). ESI-MS [M+H]$^+$: 380.2.

Synthesis of ethyl 1-((6-cyclopropyl-8-(oxetan-3-ylmethyl)imidazo[1,2-a]pyridin-2-yl)methyl)-1H-1,2,3-triazole-4-carboxylate. A mixture of ethyl 1-((6-cyclopropyl-8-(oxetan-3-ylidenemethyl)imidazo[1,2-a]pyridin-2-yl)methyl)-1H-1,2,3-triazole-4-carboxylate (450 mg, 1.19 mmol) and Pd/C (100 mg) in THF (25 mL) was stirred under H$_2$ atmosphere for 2 h. The reaction was filtered and concentrated in vacuo to give the ethyl 1-((6-cyclopropyl-8-(oxetan-3-ylmethyl)imidazo[1,2-a]pyridin-2-yl)methyl)-1H-1,2,3-triazole-4-carboxylate as a yellow solid (180 mg, 40%). ESI-MS [M+H]$^+$: 382.2

Synthesis of 1-((6-cyclopropyl-8-(oxetan-3-ylmethyl)imidazo[1,2-a]pyridin-2-yl)methyl)-1H-1,2,3-triazole-4-carboxylic acid. To a solution of ethyl 1-((6-cyclopropyl-8-(oxetan-3-ylmethyl)imidazo[1,2-a]pyridin-2-yl)methyl)-1H-1,2,3-triazole-4-carboxylate (180 mg, 0.47 mmol) in THF/H$_2$O (8 mL/8 mL) was added LiOH H$_2$O (79 mg, 1.88 mmol). The resulting mixture was stirred at RT for 4 h. The reaction was concentrated in vacuo to give the crude product, which was purified with Prep-HPLC to give 1-((6-cyclopropyl-8-(oxetan-3-ylmethyl)imidazo[1,2-a]pyridin-2-yl)methyl)-1H-1,2,3-triazole-4-carboxylic acid as a white solid (90 mg, 54%). ESI-MS [M+H]$^+$: 354.2.

Synthesis of 1-((6-cyclopropyl-8-(oxetan-3-ylmethyl)imidazo[1,2-a]pyridin-2-yl)methyl)-N-(2-fluoro-3-methoxy-6-(1H-tetrazol-1-yl)benzyl)-1H-1,2,3-triazole-4-carboxamide. To a mixture of 1-((6-cyclopropyl-8-(oxetan-3-ylmethyl)imidazo[1,2-a]pyridin-2-yl)methyl)-1H-1,2,3-triazole-4-carboxylic acid (50 mg, 0.14 mmol), HATU (80 mg, 0.21 mmol) and DIPEA (90 mg, 0.70 mmol) in DMF (10 mL) was added (2-fluoro-3-methoxy-6-(1H-tetrazol-1-yl)phenyl)methanamine (47 mg, 0.21 mmol). The reaction mixture was stirred at room temperature for 14 h and then quenched with H$_2$O (20 mL). The aqueous phase was extracted with EtOAc (20 mL×3). The combined organic layers were washed with brine (30 mL×2), dried over Na$_2$SO$_4$, and concentrated in vacuo to give the crude, which was purified by prep-HPLC to give 1-((6-cyclopropyl-8-(oxetan-3-ylmethyl)imidazo[1,2-a]pyridin-2-yl)methyl)-N-(2-fluoro-3-methoxy-6-(1H-tetrazol-1-yl)benzyl)-1H-1,2,3-triazole-4-carboxamide (10 mg, 12.8%) as a white solid. ESI-MS [M+H]+: 559.2. $^1$H NMR (400 MHz, DMSO) δ 9.74 (s, 1H), 8.76 (t, J=5.4 Hz, 1H), 8.47 (s, 1H), 8.19 (d, J=1.3 Hz, 1H), 7.76 (s, 1H), 7.39-7.32 (m, 2H), 6.80 (s, 1H), 5.70 (s, 2H), 4.61 (dd, J=7.7, 5.9 Hz, 2H), 4.36 (t, J=6.0 Hz, 2H), 4.29 (d, J=5.1 Hz, 2H), 3.92 (s, 3H), 3.42-3.37 (m, 1H), 3.15 (d, J=7.7 Hz, 2H), 1.91-1.84 (m, 1H), 0.92-0.88 (m, 2H), 0.68-0.64 (m, 2H).

Example 98

1-((6-cyclopropyl-8-(hydroxy(oxetan-3-yl)methyl)
imidazo[1,2-a]pyridin-2-yl)methyl)-N-(2-fluoro-3-
methoxy-6-(1H-tetrazol-1-yl)benzyl)-1H-1,2,3-triaz-
ole-4-carboxamide (I-27)

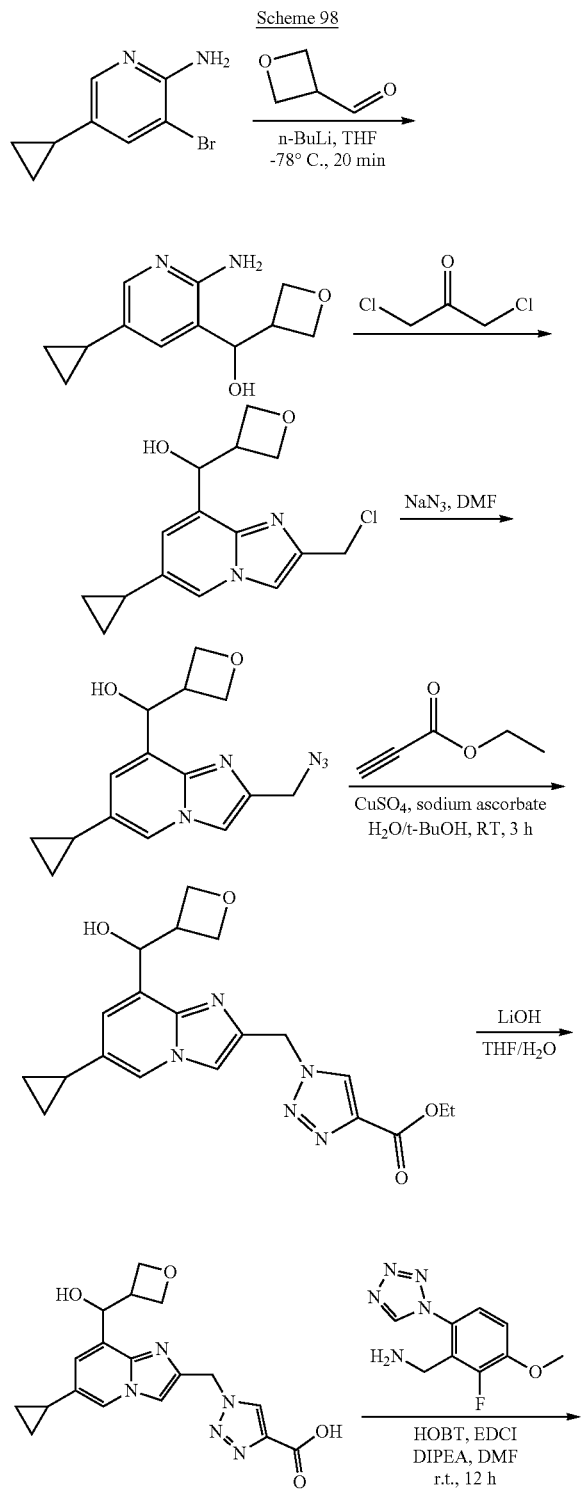

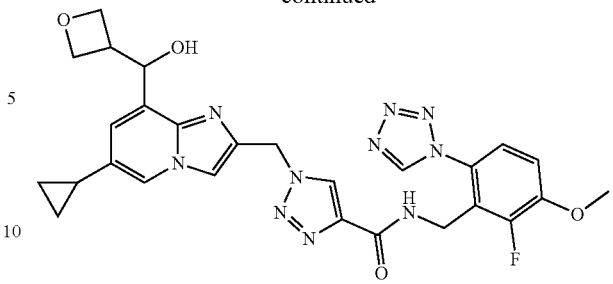

Synthesis of (2-amino-5-cyclopropylpyridin-3-yl) (oxetan-3-yl)methanol. To a solution of 3-bromo-5-cyclopropylpyridin-2-amine (500 mg, 2.35 mmol) in dry THF (25 mL) was added n-BuLi (3.5 mL, 2.4 M solution in hexanes, 8.4 mmol) at −60° C. The resulting mixture was stirred at −60° C. for 30 min. Then a solution of oxetane-3-carbaldehyde (714 mg, 8.3 mmol) in 3 mL THF was added slowly at −60° C. and stirred for another 30 min. The reaction was quenched with water (10 mL) and concentrated in vacuo to give the crude residue, which was purified by Prep-TLC (DCM/MeOH=6/1) to give (2-amino-5-cyclopropylpyridin-3-yl)(oxetan-3-yl)methanol as a yellow oil (310 mg, 60%). ESI-MS [M+H]$^+$: 221.2.

Synthesis of (2-(chloromethyl)-6-cyclopropylimidazo[1,2-a]pyridin-8-yl)(oxetan-3-yl)methanol. A mixture of (2-amino-5-cyclopropylpyridin-3-yl)(oxetan-3-yl)methanol (310 mg, 1.41 mmol) and 1,3-dichloropropan-2-one (533 mg, 4.23 mmol) in EtOH (25 mL) was stirred at 80° C. for 14 h. The reaction mixture was adjusted to pH 8 using saturated aqueous NaHCO$_3$ and concentrated in vacuo to give the crude residue, which was purified by Prep-TLC (DCM/MeOH=10/1) to give (2-(chloromethyl)-6-cyclopropylimidazo[1,2-a]pyridin-8-yl)(oxetan-3-yl)methanol as a yellow oil (210 mg, 51%). ESI-MS [M+H]$^+$: 293.2.

Synthesis of (2-(chloromethyl)-6-cyclopropylimidazo[1,2-a]pyridin-8-yl)(oxetan-3-yl)methanol. To a solution of (2-(chloromethyl)-6-cyclopropylimidazo[1,2-a]pyridin-8-yl)(oxetan-3-yl)methanol (210 mg, 0.72 mmol) in DMF (5 mL) was added NaN$_3$ (70 mg, 1.08 mmol). The resulting mixture was stirred at RT for 3 h. The reaction was concentrated in vacuo to give the crude residue (280 mg, crude), which was used in next step without further purification. ESI-MS [M+H]$^+$: 300.2.

Synthesis of ethyl 1-((6-cyclopropyl-8-(hydroxy(oxetan-3-yl)methyl)imidazo[1,2-a]pyridin-2-yl)methyl)-1H-1,2,3-triazole-4-carboxylate. To a solution of (2-(azidomethyl)-6-cyclopropylimidazo[1,2-a]pyridin-8-yl)(oxetan-3-yl)methanol (210 mg, 0.7 mmol) in t-BuOH/H$_2$O (15 mL/15 mL) was added ethyl propiolate (89 mg, 0.91 mmol), CuSO$_4$ (45 mg, 0.28 mmol) and sodium ascorbate (54 mg, 0.28 mmol). The reaction was stirred at RT for 3 h. Water (15 mL) was added to the reaction, and the mixture was extracted with DCM/MeOH (15/1, 30 mL x 3). The combined organic layers were dried over Na$_2$SO$_4$ and concentrated in vacuo to give the crude residue, which was purified by Prep-TLC (DCM/MeOH=10/1) to give ethyl 1-((6-cyclopropyl-8-(hydroxy(oxetan-3-yl)methyl)imidazo[1,2-a]pyridin-2-yl)methyl)-1H-1,2,3-triazole-4-carboxylate as yellow solid. (210 mg, 75%). ESI-MS [M+H]$^+$: 398.2.

Synthesis of 1-((6-cyclopropyl-8-(hydroxy(oxetan-3-yl)methyl)imidazo[1,2-a]pyridin-2-yl)methyl)-1H-1,2,3-triazole-4-carboxylic acid. To a solution of ethyl 1-((6-cyclopropyl-8-(hydroxy(oxetan-3-yl)methyl)imidazo[1,2-a]pyridin-2-yl)methyl)-1H-1,2,3-triazole-4-carboxylate (210 mg, 0.53 mmol) in THF/H$_2$O (8 mL/8 mL) was added LiOH·H$_2$O (65 mg, 1.58 mmol). The reaction was stirred at RT for 2 h. The reaction mixture was then adjusted to pH 5 using 1 N HCl, and freeze-dried to give 1-((6-cyclopropyl-8-(hydroxy (oxetan-3-yl)methyl)imidazo[1,2-a]pyridin-2-yl)methyl)-1H-1,2,3-triazole-4-carboxylic acid (300 mg crude) which was used into next step without further purification. ESI-MS [M+H]$^+$: 370.1.

Synthesis of 1-((6-cyclopropyl-8-(hydroxy(oxetan-3-yl) methyl)imidazo[1,2-a]pyridin-2-yl)methyl)-N-(2-fluoro-3-methoxy-6-(1H-tetrazol-1-yl)benzyl)-1H-1,2,3-triazole-4-carboxamide. To a solution of 1-((6-cyclopropyl-8-(hydroxy (oxetan-3-yl)methyl)imidazo[1,2-a]pyridin-2-yl)methyl)-1H-1,2,3-triazole-4-carboxylic acid (100 mg) in DMF (10 mL) was added (2-fluoro-3-methoxy-6-(1H-tetrazol-1-yl) phenyl)methanamine (52 mg, 0.23 mmol), HOBT (36.5 mg, 0.27 mmol), EDCI (52 mg, 0.27 mmol) and DIPEA (110 mg, 0.85 mmol). The reaction mixture was stirred at room temperature for 12 h. The reaction was concentrated in vacuo to give the crude product, which was purified with Prep-HPLC to give 1-((6-cyclopropyl-8-(hydroxy(oxetan-3-yl)methyl)imidazo[1,2-a]pyridin-2-yl)methyl)-N-(2-fluoro-3-methoxy-6-(1H-tetrazol-1-yl)benzyl)-1H-1,2,3-triazole-4-carboxamide (8 mg, 6%) as a white solid.

ESI-MS [M+H]$^+$: 575.2. Purity: 98.39% (214 nm), 100% (254 nm). $^1$H NMR (400 MHz, DMSO) δ 9.75 (s, 1H), 8.90 (t, J=4.6 Hz, 1H), 8.66-8.60 (m, 2H), 8.49 (s, 2H), 8.31 (d, J=5.6 Hz, 1H), 7.65 (d, J=9.4 Hz, 1H), 6.14 (d, J=12.3 Hz, 2H), 5.32 (t, J=4.7 Hz, 1H), 5.02 (d, J=2.0 Hz, 0.5H), 4.88 (d, J=9.1 Hz, 0.5H), 4.56-4.48 (m, 1H), 4.30 (d, J=5.1 Hz, 2H), 4.10-4.05 (m, 0.5H), 3.92 (s, 3H), 3.87 (d, J=11.8 Hz, 0.5H), 3.80-3.63 (m, 3H), 2.02-1.95 (m, 1H), 1.09-1.05 (m, 2H), 0.85-0.74 (m, 2H).

Example 99

1-((8-(aminomethyl)-6-cyclopropylimidazo[1,2-a] pyridin-2-yl)methyl)-N-(2-fluoro-3-methoxy-6-(1H-tetrazol-1-yl)benzyl)-1H-1,2,3-triazole-4-carboxamide (I-25)

Scheme 99

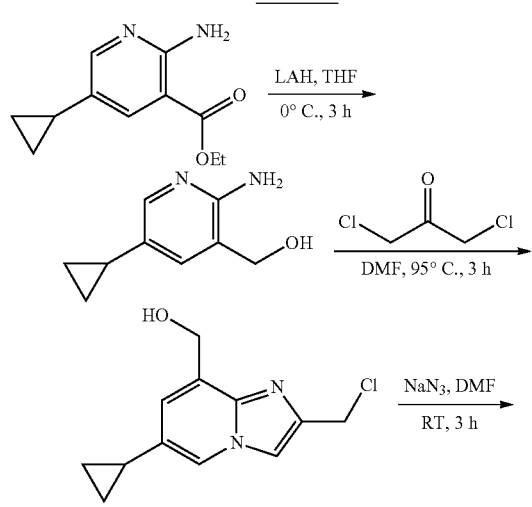

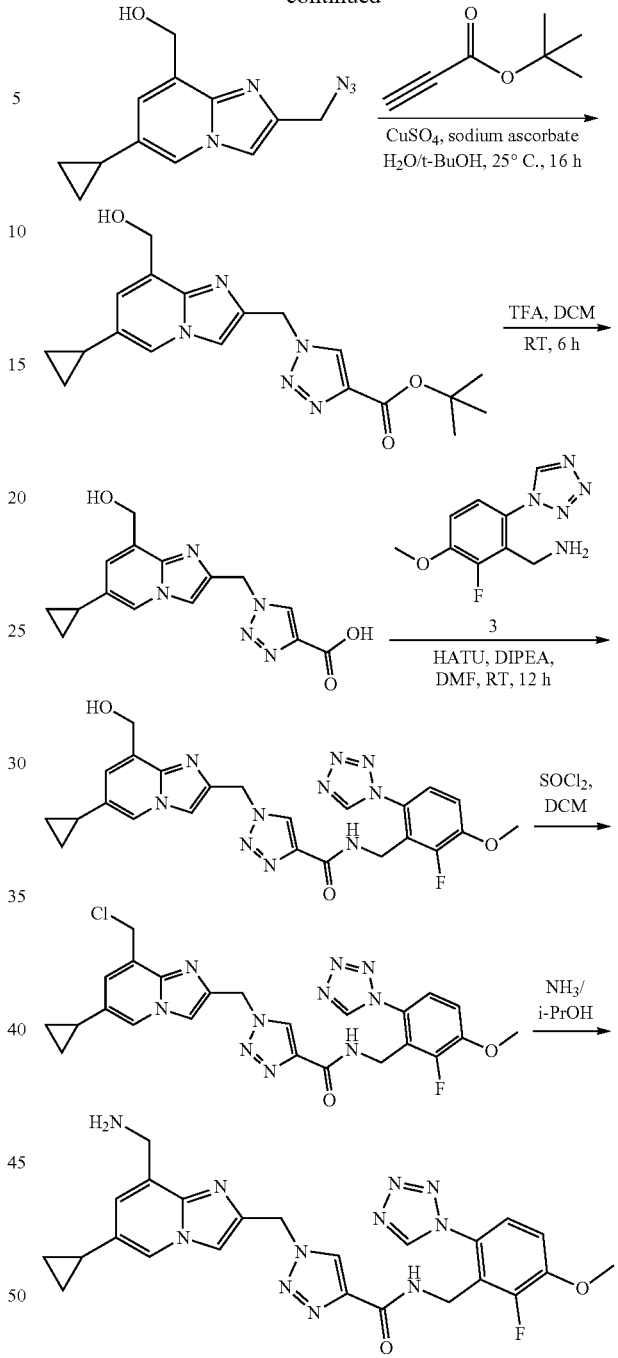

Synthesis of (2-amino-5-cyclopropylpyridin-3-yl)methanol. To a mixture of ethyl 2-amino-5-cyclopropylnicotinate (7.4 g, 36 mmol) in THF (70 mL) was added LAH (2.3 g, 61 mmol) was stirred at 0° C. The mixture was stirred at 0° C. for 3 h under N$_2$ atmosphere. The reaction was monitored by LCMS until the starting material consumed. The reaction was quenched with H$_2$O (5 mL), NaOH (15% aq., 5 mL), H$_2$O (15 mL), after the mixture was stirred for 10 min, the mixture was filtered through celite and concentrated to give a residue. Which was diluted with H$_2$O (100 mL) and extracted with EtOAc (100 mL×5). The combined organic layers were washed with brine, dried over Na$_2$SO$_4$, concentrated in vacuo to give the crude product, which was purified with silica gel (eluent: EtOAc/PE: 1/2 to I/O) to give the (2-amino-5-cyclopropylpyridin-3-yl)methanol (5 g, yield: 84%) as a white solid. ESI-MS [M+H]+: 165.2.

Synthesis of (2-(chloromethyl)-6-cyclopropylimidazo[1,2-a]pyridin-8-yl)methanol. To a solution of (2-amino-5-cyclopropylpyridin-3-yl)methanol (5 g, 30 mmol) in DMF (30 mL) was added 1,3-dichloropropan-2-one (14.8 g, 117 mmol). The mixture was stirred at 95° C. for 3 h. The reaction was monitored by LCMS until the starting material consumed. The reaction was quenched with saturated aqueous NaHCO3 until pH=8 and extracted with EtOAc (100 mL×3). The combined organic layers were washed with brine, dried over Na2SO4, concentrated in vacuo to give the crude product, which was purified with silica gel (eluent: DCM/MeOH: 50/1 to 10/1) to give (2-(chloromethyl)-6-cyclopropylimidazo[1,2-a]pyridin-8-yl)methanol (4.7 g, yield: 66%) as a yellow solid. ESI-MS [M+H]+: 237.1.

Synthesis of (2-(azidomethyl)-6-cyclopropylimidazo[1,2-a]pyridin-8-yl)methanol. To a solution of (2-(chloromethyl)-6-cyclopropylimidazo[1,2-a]pyridin-8-yl)methanol (4.7 g, 20 mmol) in DMF (30 mL) was added sodium azide (1.82 g, 28 mmol). The mixture was stirred at RT for 3 h. The reaction was monitored by LCMS until the starting material consumed. The reaction was quenched with H2O (100 mL) and extracted with EtOAc (100 mL×3). The combined organic layers were washed with brine, dried over Na2SO4, concentrated in vacuo to give the crude product, which was purified with silica gel (eluent: DCM/MeOH: 50/1 to 10/1) to give (2-(azidomethyl)-6-cyclopropylimidazo[1,2-a]pyridin-8-yl)methanol (2.1 g, yield: 43%) as a white solid. ESI-MS [M+H]+: 244.2.

Synthesis of tert-butyl 1-((6-cyclopropyl-8-(hydroxymethyl)imidazo[1,2-a]pyridin-2-yl)methyl)-1H-1,2,3-triazole-4-carboxylate. The mixture of (2-(azidomethyl)-6-cyclopropylimidazo[1,2-a]pyridin-8-yl)methanol (20 g, 82.38 mmol), tert-butyl propiolate (10.4 g, 82.38 mmol), CuSO4 (657 mg, 4.12 mmol) and sodium ascorbate (1.63 g, 8.24 mmol) in t-BuOH (100 mL) and H2O (100 mL) was stirred at 25° C. for 16 h. t-BuOH was removed to give the residue, which was diluted in H2O (100 mL), extracted with DCM (150 mL×3). The combined organics were washed with brine (300 mL), dried over Na2SO4, concentrated to give the crude, which was triturated with EtOAc and dried to afford tert-butyl 1-((6-cyclopropyl-8-(hydroxymethyl)imidazo[1,2-a]pyridin-2-yl)methyl)-1H-1,2,3-triazole-4-carboxylate (18 g, yield: 59%) as a light brown solid. ESI-MS [M+H]+: 370.1.

Synthesis of 1-((6-cyclopropyl-8-(hydroxymethyl)imidazo[1,2-a]pyridin-2-yl)methyl)-1H-1,2,3-triazole-4-carboxylic acid. To a solution of tert-butyl 1-((6-cyclopropyl-8-(hydroxymethyl)imidazo[1,2-a]pyridin-2-yl)methyl)-1H-1,2,3-triazole-4-carboxylate (400 mg, 1.08 mmol) in DCM (5 mL) was added TFA (1 mL, 14 mmol) under N2 atmosphere. After stirring at room temperature for 6 h, the reaction mixture was concentrated in vacuo to give the crude product (300 mg, crude) which was used in the next step without further purification. ESI-MS [M+H]+: 314.1.

Synthesis of 1-((6-cyclopropyl-8-(hydroxymethyl)imidazo[1,2-a]pyridin-2-yl)methyl)-N-(2-fluoro-3-methoxy-6-(1H-tetrazol-1-yl)benzyl)-1H-1,2,3-triazole-4-carboxamide. A mixture of 1-((6-cyclopropyl-8-(hydroxymethyl)imidazo[1,2-a]pyridin-2-yl)methyl)-1H-1,2,3-triazole-4-carboxylic acid (340 mg, 1.08 mmol), HATU (620 mg, 1.63 mmol) and DIPEA (420 mg, 3.26 mmol) in DMF (8 mL) was added (2-fluoro-3-methoxy-6-(1H-tetrazol-1-yl)phenyl)methanamine (290 mg, 1.30 mmol). The resulting mixture was stirred at room temperature for 12 h. Water (50 mL) was added and the mixture was extracted with EtOAc (80 mL×3). The combined organic layers were washed with brine (50 mL), dried over Na2SO4, and concentrated in vacuo to give the crude, which was purified by column chromatography (MeOH/DCM: 1/10) to give 1-((6-cyclopropyl-8-(hydroxymethyl)imidazo[1,2-a]pyridin-2-yl)methyl)-N-(2-fluoro-3-methoxy-6-(1H-tetrazol-1-yl)benzyl)-1H-1,2,3-triazole-4-carboxamide as a white solid (350 mg, yield: 62.6%). ESI-MS [M+H]+: 519.2.

Synthesis of 1-((8-(chloromethyl)-6-cyclopropylimidazo[1,2-a]pyridin-2-yl)methyl)-N-(2-fluoro-3-methoxy-6-(1H-tetrazol-1-yl)benzyl)-1H-1,2,3-triazole-4-carboxamide. To a solution of 1-((6-cyclopropyl-8-(hydroxymethyl)imidazo[1,2-a]pyridin-2-yl)methyl)-N-(2-fluoro-3-methoxy-6-(1H-tetrazol-1-yl)benzyl)-1H-1,2,3-triazole-4-carboxamide (350 mg, 0.67 mmol) in DCM (5 mL) at 0° C. was added SOCl2 (1 mL, 13 mmol). After stirring at room temperature for 1 h, the reaction mixture was concentrated in vacuo to give the crude product, which was purified by column chromatography (MeOH/DCM: 1/10) to give 1-((8-(chloromethyl)-6-cyclopropylimidazo[1,2-a]pyridin-2-yl)methyl)-N-(2-fluoro-3-methoxy-6-(1H-tetrazol-1-yl)benzyl)-1H-1,2,3-triazole-4-carboxamide as white solid (90 mg, yield: 25%). ESI-MS [M+H]+: 537.1.

Synthesis of 1-((8-(aminomethyl)-6-cyclopropylimidazo[1,2-a]pyridin-2-yl)methyl)-N-(2-fluoro-3-methoxy-6-(1H-tetrazol-1-yl)benzyl)-1H-1,2,3-triazole-4-carboxamide. A solution of 1-((8-(chloromethyl)-6-cyclopropylimidazo[1,2-a]pyridin-2-yl)methyl)-N-(2-fluoro-3-methoxy-6-(1H-tetrazol-1-yl)benzyl)-1H-1,2,3-triazole-4-carboxamide (90 mg, 0.168 mmol) in ammonia (2M solution in i-PrOH, 20 mL) was stirred in a sealed tube at 70° C. for 8 h. The reaction mixture was concentrated to give the crude product, which was purified by prep-TLC (MeOH/DCM: 1/10) to give 1-((8-(aminomethyl)-6-cyclopropylimidazo[1,2-a]pyridin-2-yl)methyl)-N-(2-fluoro-3-methoxy-6-(1H-tetrazol-1-yl)benzyl)-1H-1,2,3-triazole-4-carboxamide as white solid (40 mg, yield: 46%). ESI-MS [M+H]+: 518.2. Purity: 99.88 (214 nm), 100 (254 nm). 1H NMR (400 MHz, DMSO) δ 9.75 (s, 1H), 8.76 (t, J=5.4 Hz, 1H), 8.49 (s, 1H), 8.23 (s, 1H), 7.80 (s, 1H), 7.39-7.32 (m, 2H), 7.01 (s, 1H), 5.71 (s, 2H), 4.29 (d, J=5.2 Hz, 2H), 3.94-3.92 (m, 5H), 1.93-1.89 (m, 1H), 0.92-0.88 (m, 2H), 0.70-0.66 (m, 2H).

Example 100

1-((8-((2-aminoethoxy)methyl)-6-cyclopropylimidazo[1,2-a]pyridin-2-yl)methyl)-N-(2-fluoro-3-methoxy-6-(1H-tetrazol-1-yl)benzyl)-1H-1,2,3-triazole-4-carboxamide (I-17)

Scheme 100

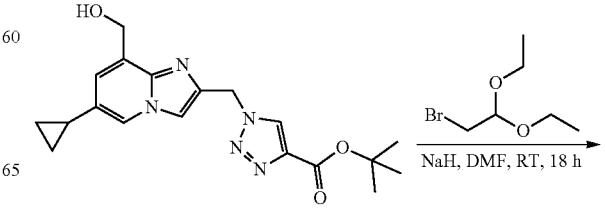

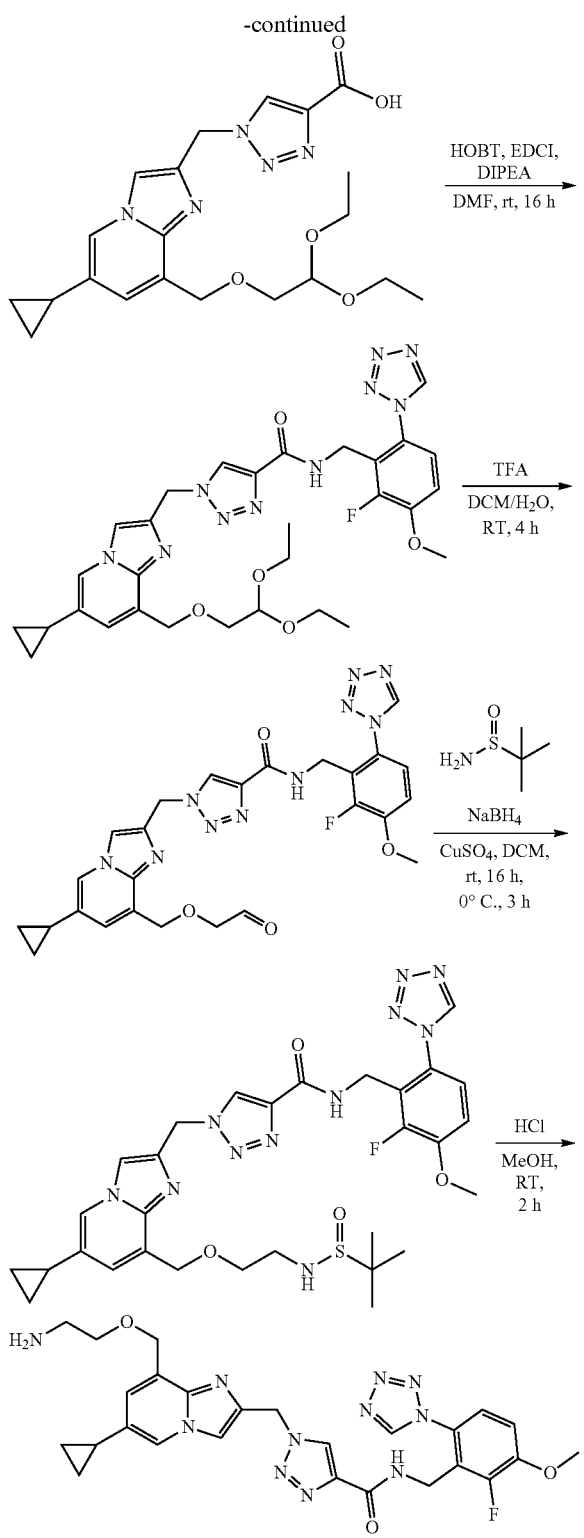

Synthesis of 1-((6-cyclopropyl-8-((2,2-diethoxyethoxy)methyl)imidazo[1,2-a]pyridin-2-yl)methyl)-1H-1,2,3-triazole-4-carboxylic acid. To a mixture of tert-butyl 1-((6-cyclopropyl-8-(hydroxymethyl)imidazo[1,2-a]pyridin-2-yl)methyl)-1H-1,2,3-triazole-4-carboxylate (500 mg, 1.35 mmol) in dry DMF (2 mL) at 0° C. was added NaH (260 mg, 6.77 mmol). The reaction mixture was stirred at room temperature for 30 min. 2-bromo-1,1-diethoxyethane (798 mg, 4.05 mmol) was added and the reaction was stirred at room temperature for 16 h. The reaction was quenched with ice water (3 mL) and extracted with EtOAc (50 mL×3). The combined organic layers were concentrated in vacuo and purified by silica gel chromatography (DCM/MeOH=50/1) to give 1-((6-cyclopropyl-8-((2,2-diethoxyethoxy)methyl)imidazo[1,2-a]pyridin-2-yl)methyl)-1H-1,2,3-triazole-4-carboxylic acid (300 mg, yield: 51.5%) as a white solid. ESI-MS [M+H]⁺: 430.1.

Synthesis of 1-((6-cyclopropyl-8-((2,2-diethoxyethoxy)methyl)imidazo[1,2-a]pyridin-2-yl)methyl)-N-(2-fluoro-3-methoxy-6-(1H-tetrazol-1-yl)benzyl)-1H-1,2,3-triazole-4-carboxamide. A solution of 1-((6-cyclopropyl-8-((2,2-diethoxyethoxy)methyl)imidazo[1,2-a]pyridin-2-yl)methyl)-1H-1,2,3-triazole-4-carboxylic acid (300 mg, 0.699 mmol), (2-fluoro-3-methoxy-6-(1H-tetrazol-1-yl)phenyl)methanamine (232 mg, 1.04 mmol), HOBT (113.2 mg, 0.838 mmol), EDCI (161 mg, 0.838 mmol) and DIPEA (541 mg, 4.19 mmol) in DMF (10 mL) was stirred at room temperature for 16 h. Water (100 mL) was added and the mixture was extracted with EtOAc (100 mL×3). The combined organic layers were concentrated in vacuo and purified by silica gel chromatography (MeOH/DCM=1/50) to give 1-((6-cyclopropyl-8-((2,2-diethoxyethoxy)methyl)imidazo[1,2-a]pyridin-2-yl)methyl)-N-(2-fluoro-3-methoxy-6-(1H-tetrazol-1-yl)benzyl)-1H-1,2,3-triazole-4-carboxamide (200 mg, yield: 45%) as a white solid. ESI-MS [M+H]⁺: 635.2.

Synthesis of 1-((6-cyclopropyl-8-((2-oxoethoxy)methyl)imidazo[1,2-a]pyridin-2-yl)methyl)-N-(2-fluoro-3-methoxy-6-(1H-tetrazol-1-yl)benzyl)-1H-1,2,3-triazole-4-carboxamide. A solution of 1-((6-cyclopropyl-8-((2,2-diethoxyethoxy)methyl)imidazo[1,2-a]pyridin-2-yl)methyl)-N-(2-fluoro-3-methoxy-6-(1H-tetrazol-1-yl)benzyl)-1H-1,2,3-triazole-4-carboxamide (200 mg, 0.315 mmol) in DCM (10 mL), TFA (2 mL), and H₂O (2 mL) was stirred at room temperature for 4 h. The mixture was extracted with DCM (50 mL×3). The combined organic layers were washed with brine (30 mL), dried over Na₂SO₄, filtered and concentrated in vacuo to give the crude, which was purified by silica gel chromatography (MeOH/DCM=1/50) to give 1-((6-cyclopropyl-8-((2-oxoethoxy)methyl)imidazo[1,2-a]pyridin-2-yl)methyl)-N-(2-fluoro-3-methoxy-6-(1H-tetrazol-1-yl)benzyl)-1H-1,2,3-triazole-4-carboxamide (130 mg, yield: 73%) as a yellow solid. ESI-MS [M+H]+: 561.2.

Synthesis of 1-((8-((2-((tert-butylsulfinyl)amino)ethoxy)methyl)-6-cyclopropylimidazo[1,2-a]pyridin-2-yl)methyl)-N-(2-fluoro-3-methoxy-6-(1H-tetrazol-1-yl)benzyl)-1H-1,2,3-triazole-4-carboxamide. A solution of 1-((6-cyclopropyl-8-((2-oxoethoxy)methyl)imidazo[1,2-a]pyridin-2-yl)methyl)-N-(2-fluoro-3-methoxy-6-(1H-tetrazol-1-yl)benzyl)-1H-1,2,3-triazole-4-carboxamide (130 mg, 0.232 mmol), 2-methylpropane-2-sulfinamide (28 mg, 0.232 mmol) and CuSO₄ (36.9 mg, 0.232 mmol) in DCM (5 mL) was stirred at room temperature for 16 h. NaBH₄ (26 mg, 0.696 mmol) was added slowly at 0° C. and the reaction was stirred at room temperature for 1 h. The mixture was quenched with water (4 mL) and extracted with EtOAc (50 mL×3). The combined organic layers were concentrated in vacuo and purified by silica gel chromatography (DCM/MeOH=20/1) to give 1-((8-((2-((tert-butylsulfinyl)amino)ethoxy)methyl)-6-cyclopropylimidazo[1,2-a]pyridin-2-yl)methyl)-N-(2-fluoro-3-methoxy-6-(1H-tetrazol-1-yl)benzyl)-1H-1,2,3-triazole-4-carboxamide (100 mg, yield: 64.9%) as a white solid. ESI-MS [M+H]+: 666.2.

Synthesis of 1-((8-((2-aminoethoxy)methyl)-6-cyclopropylimidazo[1,2-a]pyridin-2-yl)methyl)-N-(2-fluoro-3- methoxy-6-(1H-tetrazol-1-yl)benzyl)-1H-1,2,3-triazole-4-carboxamide. A solution of 1-((8-((2-(((tert-butylsulfinyl)amino)ethoxy)methyl)-6-cyclopropylimidazo[1,2-a]pyridin-2-yl)methyl)-N-(2-fluoro-3-methoxy-6-(1H-tetrazol-1-yl)benzyl)-1H-1,2,3-triazole-4-carboxamide (100 mg, 0.150 mmol) in MeOH (4 ml) and 4M HCl in dioxane (0.4 mL) was stirred at room temperature for 4 h and then concentrated in vacuo. The residue was purified by Prep-HPLC to give 1-((8-((2-aminoethoxy)methyl)-6-cyclopropylimidazo[1,2-a]pyridin-2-yl)methyl)-N-(2-fluoro-3-methoxy-6-(1H-tetrazol-1-yl)benzyl)-1H-1,2,3-triazole-4-carboxamide (5.8 mg, yield: 6.9%) as a white solid. ESI-MS [M+H]+: 562.2. $^1$H NMR (400 MHz, DMSO) δ 9.74 (s, 1H), 8.77 (s, 1H), 8.47 (s, 1H), 8.27 (s, 1H), 7.82 (s, 1H), 7.37 (s, 2H), 7.04 (s, 1H), 5.71 (s, 2H), 4.72 (s, 2H), 4.29 (d, J=4.8, 2H), 3.92 (s, 3H), 3.57-3.46 (m, 2H), 2.74-2.70 (m, 2H), 2.00-1.90 (m, 1H), 1.23 (s, 2H), 0.96-0.88 (m, 2H), 0.71-0.63 (m, 2H).

Example 101

N-(1-amino-6,7-dihydro-5H-cyclopenta[c]pyridin-5-yl)-1-((8-cyano-6-cyclopropylimidazo[1,2-a]pyridin-2-yl)methyl)-1H-1,2,3-triazole-4-carboxamide (I-14)

Scheme 101

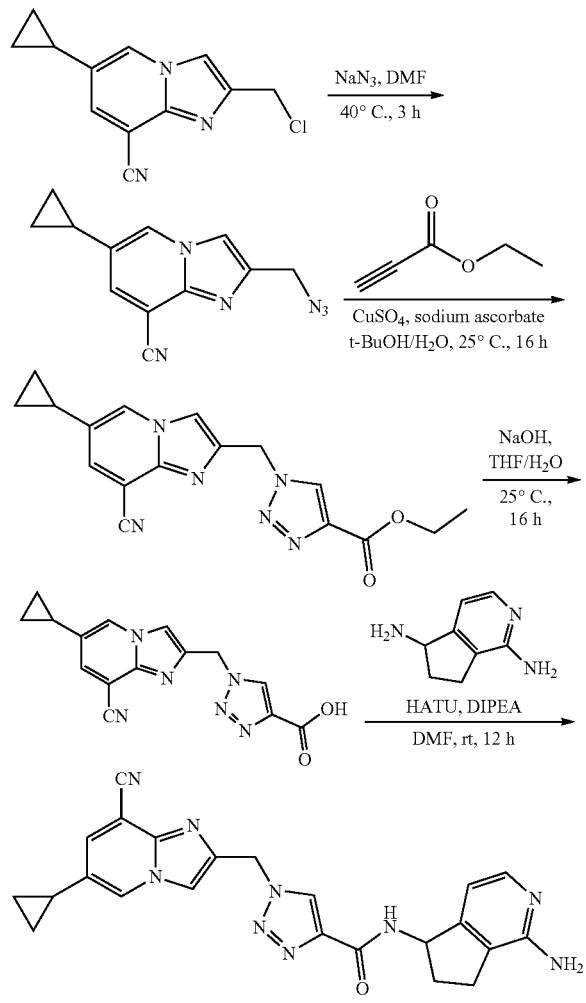

Synthesis of 2-(azidomethyl)-6-cyclopropylimidazo[1,2-a]pyridine-8-carbonitrile. To a mixture of 2-(chloromethyl)-6-cyclopropylimidazo[1,2-a]pyridine-8-carbonitrile (100 mg, 0.43 mmol) in dry DMF (2 mL) was added NaN$_3$ (39 mg, 0.65 mmol). The mixture was stirred at 25° C. for 3 h. Then H$_2$O (20 mL) was added and extracted with EtOAc (20 mL×3). The combined organic layers were washed with brine, dried over Na$_2$SO$_4$ and concentrated to give the crude, which was purified by prep-TLC (EA/PE=3/2) to give 2-(azidomethyl)-6-cyclopropylimidazo[1,2-a]pyridine-8-carbonitrile (70 mg, yield: 68%) as a yellow solid. ESI-MS [M+H]$^+$: 239.2.

Synthesis of ethyl 1-((8-cyano-6-cyclopropylimidazo[1,2-a]pyridin-2-yl)methyl)-1H-1,2,3-triazole-4-carboxylate. To a mixture of 2-(azidomethyl)-6-cyclopropylimidazo[1,2-a]pyridine-8-carbonitrile (70 mg, 0.29 mmol), CuSO$_4$ (24 mg, 0.15 mmol), sodium ascorbate (30 mg, 0.15 mmol) in t-BuOH/H$_2$O (3/3 mL) was added ethyl propiolate (43 mg, 0.44 mmol). The mixture was stirred at 25° C. for 16 h and then concentrated to give the crude product. PE/EA (10 mL/1 mL) was added, stirred at 25° C. for 5 min, and a solid was filtered and washed with PE to give ethyl 1-((8-cyano-6-cyclopropylimidazo[1,2-a]pyridin-2-yl)methyl)-1H-1,2,3-triazole-4-carboxylate (95 mg, yield: 96%) as a yellow solid, which was used into next step without purification. ESI-MS [M+H]$^+$: 337.2.

Synthesis of 1-((8-cyano-6-cyclopropylimidazo[1,2-a]pyridin-2-yl)methyl)-1H-1,2,3-triazole-4-carboxylic acid. To a mixture of ethyl 1-((8-cyano-6-cyclopropylimidazo[1,2-a]pyridin-2-yl)methyl)-1H-1,2,3-triazole-4-carboxylate (95 mg, 0.28 mmol) in THF/H$_2$O (4 mL/2 mL) was added NaOH (34 mg, 0.85 mmol). The mixture was stirred at 25° C. for 16 h. The pH of the mixture was adjusted to 5 with 1 M HCl, then extracted with EtOAc (50 mL×3). The combined organic layers were washed with brine, dried over Na$_2$SO$_4$ and concentrated to give 1-((8-cyano-6-cyclopropylimidazo[1,2-a]pyridin-2-yl)methyl)-1H-1,2,3-triazole-4-carboxylic acid (70 mg, yield: 80%) as a grey solid. ESI-MS [M+H]$^+$: 309.2.

Synthesis N-(1-amino-6,7-dihydro-5H-cyclopenta[c]pyridin-5-yl)-1-((8-cyano-6-cyclopropylimidazo[1,2-a]pyridin-2-yl)methyl)-1H-1,2,3-triazole-4-carboxamide. A mixture of 1-((8-cyano-6-cyclopropylimidazo[1,2-a]pyridin-2-yl)methyl)-1H-1,2,3-triazole-4-carboxylic acid (20 mg, 0.065 mmol), 6,7-dihydro-5H-cyclopenta[c]pyridine-1,5-diamine (12 mg, 0.078 mmol), HATU (30 mg, 0.078 mmol), DIPEA (34 mg, 0.26 mmol) and DMF (3 mL) was stirred at rt for 12 h. Water (30 mL) was added and the mixture was extracted with EtOAc (10 mL×3). The combined organic layers were washed with brine (20 mL), dried over Na$_2$SO$_4$, filtered and concentrated to give the crude, which was purified by Prep-HPLC to give N-(1-amino-6,7-dihydro-5H-cyclopenta[c]pyridin-5-yl)-1-((8-cyano-6-cyclopropylimidazo[1,2-a]pyridin-2-yl)methyl)-1H-1,2,3-triazole-4-carboxamide (6 mg, yield: 21%) as a white solid. ESI-MS [M+H]+: 440.2. $^1$H NMR (400 MHz, DMSO) δ 8.76 (d, J=8.5 Hz, 1H), 8.71 (s, 1H), 8.62 (s, 1H), 8.29 (s, 2H), 8.02 (s, 1H), 7.81 (s, 1H), 7.73 (d, J=4.9 Hz, 1H), 6.40 (d, J=5.1 Hz, 1H), 5.82 (s, 2H), 5.78 (s, 1H), 5.42-5.39 (m, 1H), 2.80-2.74 (m, 1H), 2.56-2.50 (m, 1H), 2.38-2.28 (m, 2H), 2.06-1.96 (m, 2H), 0.99-0.94 (m, 2H), 0.78-0.75 (m, 2H).

Example 102

1-((8-(aminomethyl)-6-cyclopropylimidazo[1,2-a]pyridin-2-yl)methyl)-N-(2,6-difluoro-3-methoxybenzyl)-1H-1,2,3-triazole-4-carboxamide (I-13)

Scheme 102

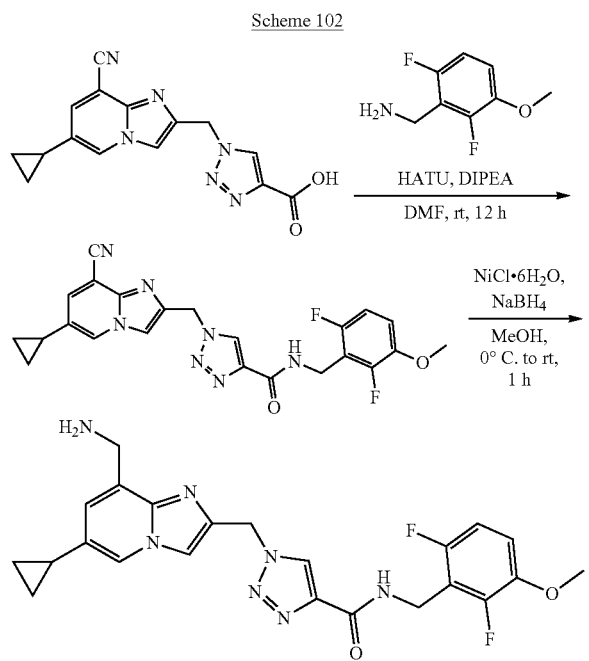

Synthesis of 1-((8-cyano-6-cyclopropylimidazo[1,2-a]pyridin-2-yl)methyl)-N-(2,6-difluoro-3-methoxybenzyl)-1H-1,2,3-triazole-4-carboxamide. A mixture of 1-((8-cyano-6-cyclopropylimidazo[1,2-a]pyridin-2-yl)methyl)-1H-1,2,3-triazole-4-carboxylic acid (60 mg, 0.19 mmol), HATU (87.4 mg, 0.23 mmol), DIPEA (100.6 mg, 0.78 mmol) and DMF(3 mL) was stirred at RT for 12 h. Water (30 mL) was added and the mixture was extracted with EtOAc (40 mL×3). The combined organic layers were washed with brine (20 mL), dried over Na$_2$SO$_4$, filtered and concentrated in vacuo to give the crude, which was purified by silica gel chromatography (DCM/MeOH=50/1) to give 1-((8-cyano-6-cyclopropylimidazo[1,2-a]pyridin-2-yl)methyl)-N-(2,6-difluoro-3-methoxybenzyl)-1H-1,2,3-triazole-4-carboxamide (60 mg, yield: 67%) as a white solid. ESI-MS [M+H]+: 464.1.

Synthesis of 1-((8-(aminomethyl)-6-cyclopropylimidazo[1,2-a]pyridin-2-yl)methyl)-N-(2,6-difluoro-3-methoxybenzyl)-1H-1,2,3-triazole-4-carboxamide. To a solution of 1-((8-cyano-6-cyclopropylimidazo[1,2-a]pyridin-2-yl)methyl)-N-(2,6-difluoro-3-methoxybenzyl)-1H-1,2,3-triazole-4-carboxamide (60 mg, 0.13 mmol) in MeOH (5 mL) was added NiCl$_2$·6H$_2$O (42.8 mg, 0.18 mmol) and NaBH$_4$ (19.6 mg, 0.56 mmol) at 0° C. slowly. The mixture was stirred at room temperature for 1 h and then concentrated to give the crude, which was purified by Prep-HPLC to give 1-((8-(aminomethyl)-6-cyclopropylimidazo[1,2-a]pyridin-2-yl)methyl)-N-(2,6-difluoro-3-methoxybenzyl)-1H-1,2,3-triazole-4-carboxamide (40 mg, yield: 65%) as a white solid. ESI-MS [M+H]+: 468.2. $^1$H NMR (400 MHz, DMSO) δ 8.85 (s, 1H), 8.56 (s, 1H), 8.29 (s, 1H), 7.85 (s, 1H), 7.17-6.90 (m, 3H), 5.73 (s, 2H), 4.48 (s, 2H), 4.05 (s, 2H), 3.80 (s, 3H), 2.00-1.98 (m, 1H), 0.94-0.69 (m, 2H), 0.69-0.65 (m, 2H).

Example 103

N-(1-amino-6,7-dihydro-5H-cyclopenta[c]pyridin-5-yl)-1-((8-(aminomethyl)-6-cyclopropylimidazo[1,2-a]pyridin-2-yl)methyl)-1H-1,2,3-triazole-4-carboxamide (I-10)

Scheme 103

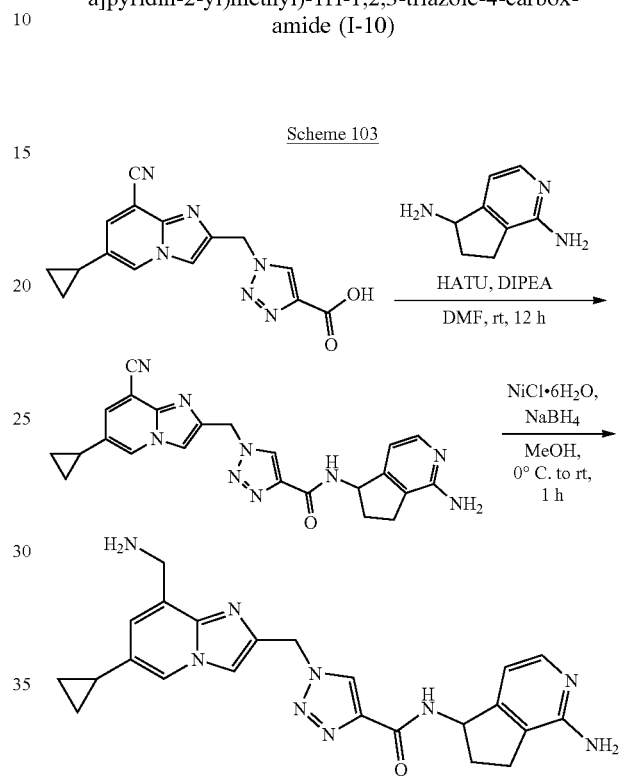

Synthesis of N-(1-amino-6,7-dihydro-5H-cyclopenta[c]pyridin-5-yl)-1-((8-cyano-6-cyclopropylimidazo[1,2-a]pyridin-2-yl)methyl)-1H-1,2,3-triazole-4-carboxamide. A mixture of 1-((8-cyano-6-cyclopropylimidazo[1,2-a]pyridin-2-yl)methyl)-1H-1,2,3-triazole-4-carboxylic acid (60 mg, 0.195 mmol), 6,7-dihydro-5H-cyclopenta[c]pyridine-1,5-diamine (33.9 mg, 0.227 mmol), HATU (174.9 mg, 0.46 mmol) and DIPEA (201.3 mg, 1.56 mmol) in DMF (5 mL) was stirred at RT for 12 h. Water (30 mL) was added and the mixture was extracted with EtOAc (20 mL×3). The combined organic layers were washed with brine (30 mL×2), dried over Na$_2$SO$_4$, filtered and concentrated in vacuo to give the crude, which was purified by silica gel chromatography (DCM/MeOH=60/1) to give N-(1-amino-6,7-dihydro-5H-cyclopenta[c]pyridin-5-yl)-1-((8-cyano-6-cyclopropylimidazo[1,2-a]pyridin-2-yl)methyl)-1H-1,2,3-triazole-4-carboxamide (20 mg, yield: 23%) as a white solid. ESI-MS [M+H]+: 440.1.

Synthesis of N-(1-amino-6,7-dihydro-5H-cyclopenta[c]pyridin-5-yl)-1-((8-(aminomethyl)-6-cyclopropylimidazo[1,2-a]pyridin-2-yl)methyl)-1H-1,2,3-triazole-4-carboxamide. To a solution of N-(2-(3-chlorophenyl)cyclopropyl)-1-((8-cyano-6-cyclopropylimidazo[1,2-a]pyridin-2-yl)methyl)-1H-1,2,3-triazole-4-carboxamide (20 mg, 0.046 mmol) in MeOH (3 mL) was added NiCl$_2$·6H$_2$O (14.0 mg, 0.059 mmol) and NaBH$_4$ (6.9 mg, 0.182 mmol) slowly at 0° C. The reaction mixture was stirred at rt for 1 h and then concentrated to give the crude, which was purified by prep-HPLC to give N-(1-amino-6,7-dihydro-5H-cyclopenta[c]pyridin-5-yl)-1-((8-(aminomethyl)-6-cyclopropylimidazo[1,2-a]pyridin-2-yl)methyl)-1H-1,2,3-triazole-4-carboxamide (3 mg, yield: 15%) as a white solid. ESI-MS [M+H]+: 444.2. $^1$H NMR (400 MHz, DMSO) δ 8.75 (d, J=8.6 Hz, 1H), 8.59 (s, 1H), 8.39 (s, 2H), 8.28 (s, 1H), 7.86 (s, 1H), 7.73 (d, J=4.9 Hz, 1H), 7.04 (s, 1H), 6.39 (d, J=4.8 Hz, 1H), 5.78 (s, 3H), 5.75 (s, 1H), 5.46-5.38 (m, 1H), 4.01 (s, 2H), 2.84-2.71 (m, 1H), 2.42-2.32 (m, 2H), 2.10-1.88 (m, 2H), 0.93 (d, J=8.2 Hz, 2H), 0.69 (d, J=4.1 Hz, 2H).

Example 104

1-((6-cyclopropyl-8-((2-(dimethylamino)ethoxy)methyl)imidazo[1,2-a]pyridin-2-yl)methyl)-N-(2,6-difluoro-3-methoxybenzyl)-1H-1,2,3-triazole-4-carboxamide (I-8)

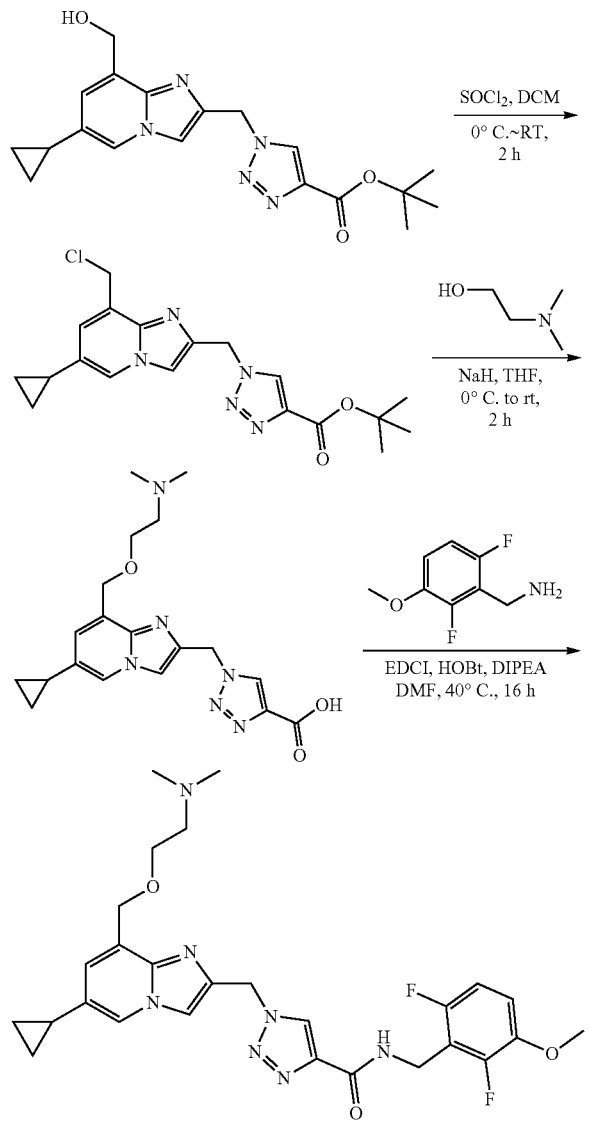

Synthesis of tert-butyl 1-((8-(chloromethyl)-6-cyclopropylimidazo[1,2-a]pyridin-2-yl)methyl)-1H-1,2,3-triazole-4-carboxylate. To a solution of tert-butyl 1-((6-cyclopropyl-8-(hydroxymethyl)imidazo[1,2-a]pyridin-2-yl)methyl)-1H-1,2,3-triazole-4-carboxylate (500 mg, 1.355 mmol) in dry DCM (10 mL) was added SOCl$_2$ (320 mg, 2.7 mmol) at 0° C. The mixture was stirred at 25° C. for 3 h. The mixture was concentrated to give the crude product which was purified by silica gel chromatography (MeOH/DCM=1/50) to give tert-butyl 1-((8-(chloromethyl)-6-cyclopropylimidazo[1,2-a]pyridin-2-yl)methyl)-1H-1,2,3-triazole-4-carboxylate (420 mg, yield: 81%) as a yellow solid. ESI-MS [M+H]+: 388.1.

Synthesis of 1-((6-cyclopropyl-8-((2-(dimethylamino)ethoxy)methyl)imidazo[1,2-a]pyridin-2-yl)methyl)-1H-1,2,3-triazole-4-carboxylic acid. To a mixture of 2-(dimethylamino)ethan-1-ol (82.7 mg, 0.928 mmol) in THF (10 mL) was added NaH (160 mg, 4.16 mmol). The reaction mixture was stirred at RT for 0.5 h. Then tert-butyl 1-((8-(chloromethyl)-6-cyclopropylimidazo[1,2-a]pyridin-2-yl)methyl)-1H-1,2,3-triazole-4-carboxylate (120 mg, 0.309 mmol) was added and the mixture was stirred at RT for 2 h. The reaction was quenched with MeOH (10 mL), then the mixture was concentrated to give the crude product. The residue was purified by flash chromatography (MeOH in DCM=0 to 50%) to give 1-((6-cyclopropyl-8-((2-(dimethylamino)ethoxy)methyl)imidazo[1,2-a]pyridin-2-yl)methyl)-1H-1,2,3-triazole-4-carboxylic acid as a light yellow solid (99 mg, 84% yield). ESI-MS [M+H]+: 385.2

Synthesis of 1-((6-cyclopropyl-8-((2-(dimethylamino)ethoxy)methyl)imidazo[1,2-a]pyridin-2-yl)methyl)-N-(2,6-difluoro-3-methoxybenzyl)-1H-1,2,3-triazole-4-carboxamide. A mixture of 1-((6-cyclopropyl-8-((2-(dimethylamino)ethoxy)methyl)imidazo[1,2-a]pyridin-2-yl)methyl)-1H-1,2,3-triazole-4-carboxylic acid (70 mg, 0.182 mmol), (2,6-difluoro-3-methoxyphenyl)methanamine (37.8 mg, 0.218 mmol), EDCI (52.3 mg, 0.273 mmol), HOBT (36.9 mg, 0.273) and DIPEA (47.06 mg, 0.365 mmol) in DMF (10 mL) was stirred at 40° C. for 16 h. The mixture was diluted with H$_2$O (100 mL), then extracted with EtOAc (20 mL×3), washed with brine (30 mL×2), dried over Na$_2$SO$_4$ and concentrated to give the crude product. The crude product was purified by Prep-TLC (10% MeOH in DCM) to give 1-((6-cyclopropyl-8-((2-(dimethylamino)ethoxy)methyl)imidazo[1,2-a]pyridin-2-yl)methyl)-N-(2,6-difluoro-3-methoxybenzyl)-1H-1,2,3-triazole-4-carboxamide (14 mg, 14.3% yield) as an off-white solid. ESI-MS [M+H]+: 540.3. $^1$H NMR (400 MHz, DMSO) δ 8.83 (t, J=5.4 Hz, 1H), 8.52 (s, 1H), 8.28 (s, 1H), 7.83 (s, 1H), 7.14-7.07 (m, 1H), 7.04-6.87 (m, 2H), 5.72 (s, 2H), 4.72 (s, 2H), 4.48 (d, J=5.3 Hz, 2H), 3.80 (s, 3H), 3.62 (t, J=5.7 Hz, 2H), 3.32 (s, 2H), 2.19 (s, 6H), 1.94 (s, 1H), 0.92 (d, J=6.7 Hz, 2H), 0.65 (d, J=5.0 Hz, 2H).

Example 105

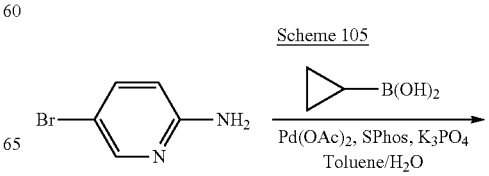

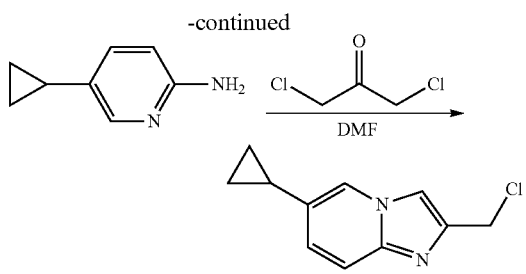

Synthesis of 5-cyclopropylpyridin-2-amine. A solution of 5-bromopyridin-2-amine (5 g, 29.1 mmol), cyclopropylboronic acid (3.75 g, 43.6 mmol), Pd(OAc)$_2$ (651 mg, 2.91 mmol), SPhos (1.19 g, 2.91 mmol) and K$_3$PO$_4$ (18.5 g, 87.3 mmol) in toluene/H$_2$O (100 mL/10 mL) was stirred at 95° C. for 12 h under nitrogen. Then the reaction mixture was quenched with H$_2$O (50 mL) and extracted with DCM (200 mL). The combined organic layers were dried over Na$_2$SO$_4$ and concentrated in vacuo to give the crude residue which was purified by silica gel chromatography (PE/EtOAc=1/1) to give the 5-cyclopropylpyridin-2-amine as yellow solid (3.8 g, 97.4% yield). ESI-MS [M+H]$^+$: 135.2.

Synthesis of 2-(chloromethyl)-6-cyclopropylimidazo[1,2-a]pyridine. To a solution 5-cyclopropyl-4-methylpyridin-2-amine (500 mg, 3.70 mmol) in DMF (10 mL) was added 1,3-dichloropropan-2-one (1409 mg, 11.1 mmol) at RT. The resulting reaction was stirred at 85° C. for 2 h. The solution was quenched with H$_2$O (60 mL), adjusted to pH 8 by adding saturated NaHCO$_3$ solution, and extracted with EtOAc (50 mL×3). The combined organic layers were washed with brine, dried over Na$_2$SO$_4$, and concentrated in vacuo to give the crude, which was purified with prep-TLC (PE/EtOAc=1/1) to give the 2-(chloromethyl)-6-cyclopropyl-7-methylimidazo[1,2-a]pyridine (300 mg, yield:39%) as a light yellow oil. ESI-MS [M+H]$^+$: 207.2.

Scheme 106

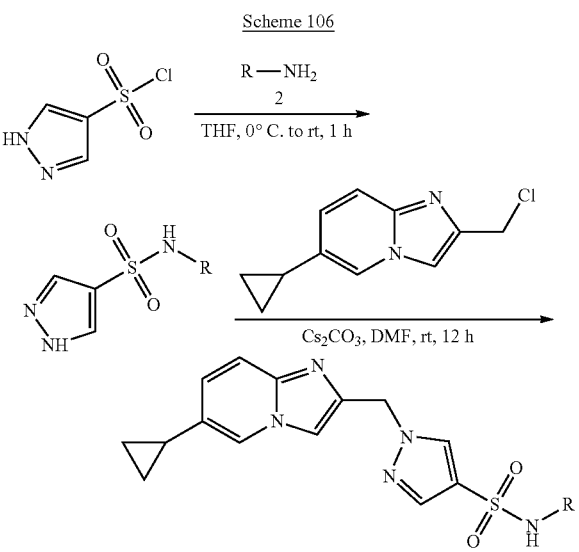

General Procedure F-1 for Sulfonamide Synthesis. To a solution of amine 2 (4.2 mmol) in THF (20 mL) was added a solution of 1H-pyrazole-4-sulfonyl chloride (1, 232.4 mg, 1.4 mmol) in THF (25 mL) at 0° C. The resulting mixture was stirred at room temperature for 1 h. The reaction was concentrated in vacuo to give the crude, which was purified by Prep-TLC, Prep-HPLC, or silica gel chromatography to give the corresponding sulfonamide.

To a solution of sulfonamide (0.44 mmol) and Cs$_2$CO$_3$ (287 mg, 0.88 mmol) in DMF (20 mL) was added 2-(chloromethyl)-6-cyclopropylimidazo[1,2-a]pyridine (109 mg, 0.53 mmol) in DMF (2 mL). The reaction mixture was stirred at room temperature for 12 h under N$_2$. Water (30 mL) was added and the mixture was extracted with EtOAc (40 mL×3). The combined organic layers were washed with brine, dried over Na$_2$SO$_4$ and concentrated in vacuo to give the crude, which was purified by prep-TLC, prep-HPLC, or silica gel chromatography to give the desired product.

The following compounds were synthesized according to General Procedure F-1 from 1H-pyrazole-4-sulfonyl chloride, the indicated amine, and 2-(chloromethyl)-6-cyclopropylimidazo[1,2-a]pyridine: N-(3-chlorobenzyl)-1-((6-cyclopropylimidazo[1,2-a]pyridin-2-yl)methyl)-1H-pyrazole-4-sulfonamide (I-47), N-(3-chlorophenethyl)-1-((6-cyclopropylimidazo[1,2-a]pyridin-2-yl)methyl)-1H-pyrazole-4-sulfonamide (I-44), N-(4-chlorobenzyl)-1-((6-cyclopropylimidazo[1,2-a]pyridin-2-yl)methyl)-1H-pyrazole-4-sulfonamide (I-42), 1-((6-cyclopropylimidazo[1,2-a]pyridin-2-yl)methyl)-N-(2-phenoxyethyl)-1H-pyrazole-4-sulfonamide (I-36), and N-(4-chlorophenethyl)-1-((6-cyclopropylimidazo[1,2-a]pyridin-2-yl)methyl)-1H-pyrazole-4-sulfonamide (I-35).

Scheme 107

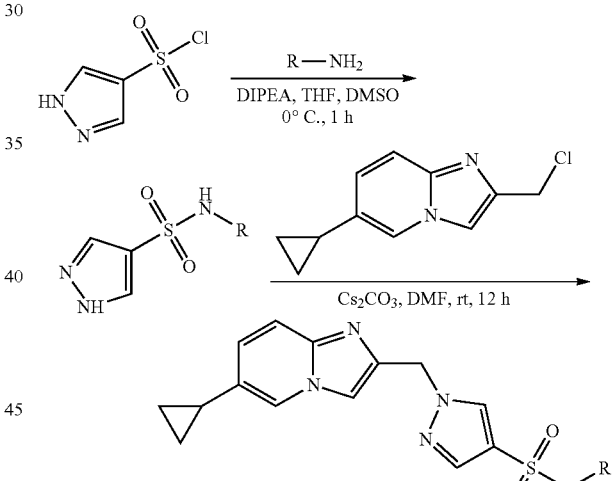

General Synthetic Procedure F-1 for Sulfonamide Synthesis. To a solution of amine (4.5 mmol) and DIPEA (1.33 mL, 7.5 mmol) in THF (15 mL) was added a solution of 1H-pyrazole-4-sulfonyl chloride (250 mg, 1.5 mmol) in DMSO (5 mL) at 0° C. The resulting reaction was stirred at 0° C. for 1 h. Water (30 mL) was added and the mixture was extracted with EtOAc (50 mL×3). The combined organic layers were washed with brine, dried over Na$_2$SO$_4$, and concentrated in vacuo to give the crude, which was purified by Prep-TLC, Prep-HPLC, or silica gel chromatography to give the corresponding sulfonamide.

To a solution of sulfonamide (0.44 mmol) and Cs$_2$CO$_3$ (287 mg, 0.88 mmol) in DMF (20 mL) was added 2-(chloromethyl)-6-cyclopropylimidazo[1,2-a]pyridine (109 mg, 0.53 mmol) in DMF (2 mL). The reaction mixture was stirred at room temperature for 12 h under N$_2$. Water (30 mL) was added and the mixture was extracted with EtOAc (40 mL×3). The combined organic layers were washed with brine, dried over Na$_2$SO$_4$ and concentrated in vacuo to give the crude, which was purified by prep-TLC, prep-HPLC, or silica gel chromatography to give the desired product.

The following compounds were synthesized according to General Procedure F-2 from 1H-pyrazole-4-sulfonyl chloride, the indicated amine, and 2-(chloromethyl)-6-cyclopropylimidazo[1,2-a]pyridine: N-((6-amino-2,4-dimethylpyridin-3-yl)methyl)-1-((6-cyclopropylimidazo[1,2-a]pyridin-2-yl)methyl)-1H-pyrazole-4-sulfonamide (I-46), 1-((6-cyclopropylimidazo[1,2-a]pyridin-2-yl)methyl)-N-(2-fluoro-3-methoxy-6-(1H-tetrazol-1-yl)benzyl)-1H-pyrazole-4-sulfonamide (I-45), N-(4-cyano-2,6-dimethylbenzyl)-1-((6-cyclopropylimidazo[1,2-a]pyridin-2-yl)methyl)-1H-pyrazole-4-sulfonamide (I-43), N-(1-(3-chlorophenyl)ethyl)-1-((6-cyclopropylimidazo[1,2-a]pyridin-2-yl)meth yl)-1H-pyrazole-4-sulfonamide (I-38), and N-(4-cyanobenzyl)-1-((6-cyclopropylimidazo[1,2-a]pyridin-2-yl)methyl)-1H-pyrazole-4-sulfonamide (I-34).

Example 106

N-(3-chlorobenzyl)-1-((6-cyclopropylimidazo[1,2-a]pyridin-2-yl)methyl)-1H-pyrazole-4-sulfonamide (I-47)

Scheme 108

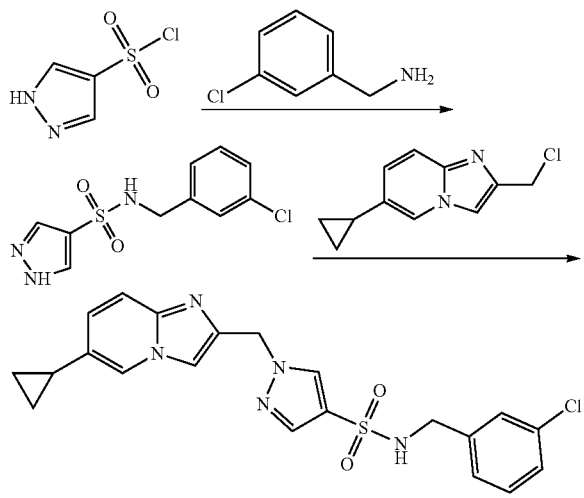

Synthesis of N-(3-chlorobenzyl)-1-((6-cyclopropylimidazo[1,2-a]pyridin-2-yl)methyl)-1H-pyrazole-4-sulfonamide. N-(3-chlorobenzyl)-1-((6-cyclopropylimidazo[1,2-a]pyridin-2-yl)methyl)-1H-pyrazole-4-sulfonamide was synthesized according to General Procedure F-1 using (3-chlorophenyl)methanamine. The crude product was purified by prep-HPLC to yield the product (30 mg, yield: 15%) as white solid. Intermediate sulfonamide: ESI-MS [M+H]+: 272.7 Product: ESI-MS [M+H]+: 442.1. $^1$H NMR (400 MHz, DMSO) δ 8.35 (s, 1H), 8.28 (s, 1H), 8.00 (t, J=6.3 Hz, 1H), 7.76 (d, J=10.7 Hz, 2H), 7.42 (d, J=9.3 Hz, 1H), 7.33-7.26 (m, 3H), 7.23-7.21 (m, 1H), 7.01 (dd, J=9.4, 1.7 Hz, 1H), 5.44 (s, 2H), 4.02 (d, J=6.3 Hz, 2H), 1.97-1.90 (m, 1H), 0.95-0.90 (m, 2H), 0.70-0.66 (m, 2H).

Example 107

N-((6-amino-2,4-dimethylpyridin-3-yl)methyl)-1-((6-cyclopropylimidazo[1,2-a]pyridin-2-yl)methyl)-1H-pyrazole-4-sulfonamide (I-46)

Scheme 109

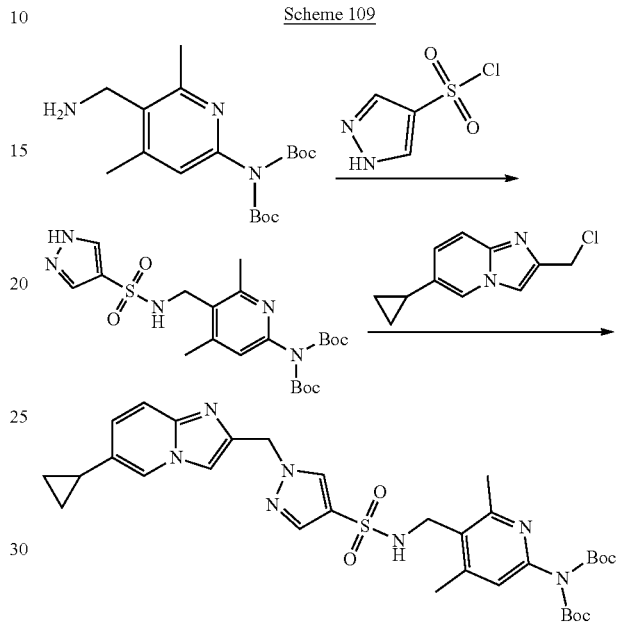

Synthesis of (N-Boc)$_2$-N-((6-amino-2,4-dimethylpyridin-3-yl)methyl)-1-((6-cyclopropylimidazo[1,2-a]pyridin-2-yl)methyl)-1H-pyrazole-4-sulfonamide. (N-Boc)$_2$-N-((6-amino-2,4-dimethylpyridin-3-yl)methyl)-1-((6-cyclopropylimidazo[1,2-a]pyridin-2-yl)methyl)-1H-pyrazole-4-sulfonamide was synthesized according to General Procedure F-2 using 2-[5-(aminomethyl)-4,6-dimethyl-2-pyridinyl]-di-tert-butyl-iminodicarboxylate. The crude product was purified by Prep-TLC (eluent: DCM/MeOH=10/1) to yield the product (80 mg, 20%). Intermediate sulfonamide: ESI-MS [M+H]+: 482.2. Product: ESI-MS [M+H]+: 652.2.

Synthesis of N-((6-amino-2,4-dimethylpyridin-3-yl)methyl)-1-((6-cyclopropylimidazo[1,2-a]pyridin-2-yl)methyl)-1H-pyrazole-4-sulfonamide. To a solution of N(Boc)$_2$-((6-amino-2,4-dimethylpyridin-3-yl)methyl)-1-((6cyclopropylimidazo[1,2-a]pyridin-2-yl)methyl)-1H-pyrazole-4-sulfonamide (80 mg 0.122 mmol) in DCM (5 mL) was added TFA (2 mL). The resulting reaction was stirred at room temperature for 12 h. The reaction was concentrated in vacuo to give the crude, which was purified with Prep-HPLC to give N-((6-amino-2,4-dimethylpyridin-3-yl)methyl)-1-((6-cyclopropylimidazo[1,2-a]pyridin-2-yl)methyl)-1H-pyrazole-4-sulfonamide as a white solid. (15 mg, 27.3%). ESI-MS [M+H]+: 452.1. Purity: 100% (214 nm), 100% (254 nm). $^1$H NMR (400 MHz, DMSO) δ 8.36 (s, 1H), 8.30 (s, 1H), 8.15 (s, 1H), 7.77 (s, 2H), 7.40 (d, J=9.3 Hz, 1H), 7.27 (t, J=5.4 Hz, 1H), 7.01 (dd, J=9.4, 1.8 Hz, 1H), 6.05 (s, 1H), 5.70 (s, 2H), 5.48 (s, 2H), 3.77 (d, J=5.4 Hz, 2H), 2.11 (s, 3H), 2.00 (s, 3H), 1.97-1.90 (m, 1H), 0.95-0.90 (m, 2H), 0.70-0.66 (m, 2H).

Example 108

1-((6-cyclopropylimidazo[1,2-a]pyridin-2-yl)methyl)-N-(2-fluoro-3-methoxy-6-(1H-tetrazol-1-yl)benzyl)-1H-pyrazole-4-sulfonamide (I-45)

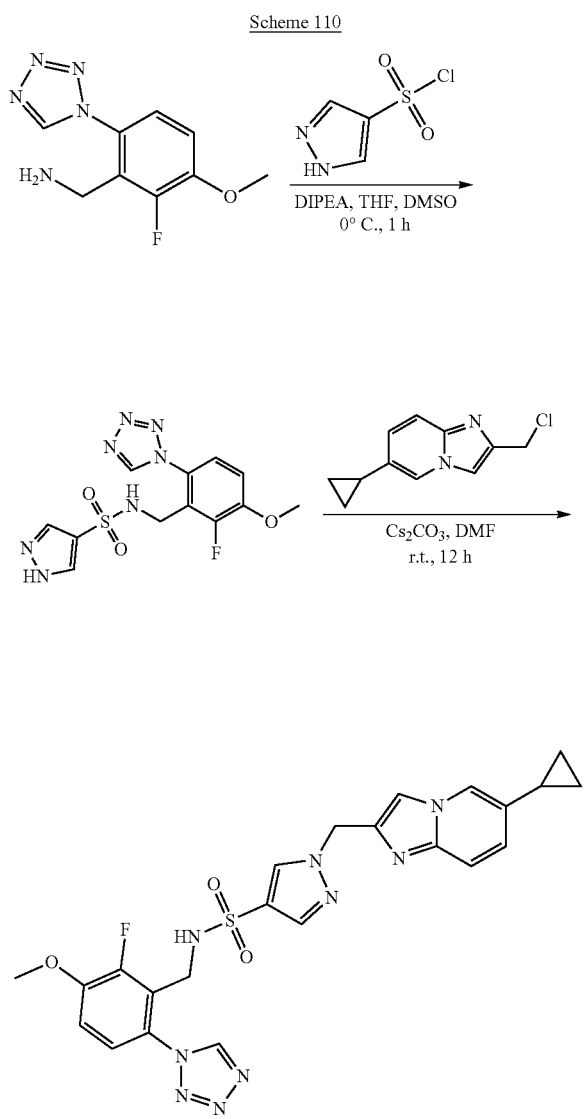

Scheme 110

Synthesis of 1-((6-cyclopropylimidazo[1,2-a]pyridin-2-yl)methyl)-N-(2-fluoro-3-methoxy-6-(1H-tetrazol-1-yl)benzyl)-1H-pyrazole-4-sulfonamide. 1-((6-cyclopropylimidazo[1,2-a]pyridin-2-yl)methyl)-N-(2-fluoro-3-methoxy-6-(1H-tetrazol-1-yl)benzyl)-1H-pyrazole-4-sulfonamide was synthesized according to General Procedure F-2 using (2-fluoro-3-methoxy-6-(1H-tetrazol-1-yl)phenyl)methanamine. The crude product was purified by prep-HPLC to yield the product as a white solid (16 mg, 8.2%). Intermediate sulfonamide: ESI-MS [M+H]+: 354.2. I-45: ESI-MS [M+H]+: 524.2, Purity: 98.95%(214 nm), 99.03% (254 nm). $^1$H NMR (400 MHz, DMSO) δ 9.70 (s, 1H), 8.36 (s, 1H), 8.11 (s, 1H), 7.75 (s, 2H), 7.55 (s, 1H), 7.43-7.30 (m, 3H), 7.02 (d, J=9.2 Hz, 1H), 5.44 (s, 2H), 3.92-3.90 (m, 5H), 1.97-1.90 (m, 1H), 0.95-0.91 (m, 2H), 0.69-0.66 (m, 2H).

Example 109

N-(3-chlorophenethyl)-1-((6-cyclopropylimidazo[1,2-a]pyridin-2-yl)methyl)-1H-pyrazole-4-sulfonamide (I-44)

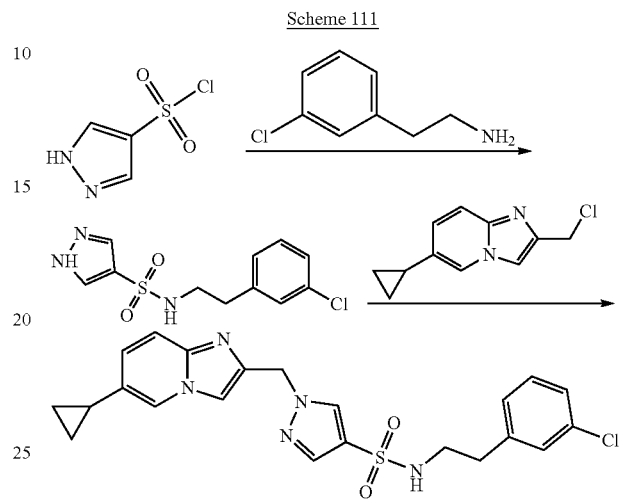

Scheme 111

Synthesis of N-(3-chlorophenethyl)-1-((6-cyclopropylimidazo[1,2-a]pyridin-2-yl)methyl)-1H-pyrazole-4-sulfonamide. N-(3-chlorophenethyl)-1-((6-cyclopropylimidazo[1,2-a]pyridin-2-yl)methyl)-1H-pyrazole-4-sulfonamide was synthesized according to General Procedure F-1 using 2-(3-chlorophenyl)ethan-1-amine. The crude product 5 was purified by prep-HPLC to yield the product as a white solid (50 mg, 8.3%). Intermediate sulfonamide: ESI-MS [M+H]+: 286.1. I-44: ESI-MS [M+H]+: 456.1. $^1$H NMR (400 MHz, DMSO) δ 8.34 (s, 1H), 8.28 (s, 1H), 7.77 (s, 1H), 7.72 (s, 1H), 7.47 (t, J=5.8 Hz, 1H), 7.38 (d, J=9.3 Hz, 1H), 7.31-7.24 (m, 3H), 7.15-7.13 (m, 1H), 7.00 (dd, J=9.4, 1.7 Hz, 1H), 5.45 (s, 2H), 3.03-2.98 (m, 2H), 2.71 (t, J=7.2 Hz, 2H), 1.96-1.89 (m, 1H), 0.94-0.88 (m, 2H), 0.71-0.65 (m, 2H).

Example 110

N-(4-cyano-2,6-dimethylbenzyl)-1-((6-cyclopropylimidazo[1,2-a]pyridin-2-yl)methyl)-1H-pyrazole-4-sulfonamide (I-43)

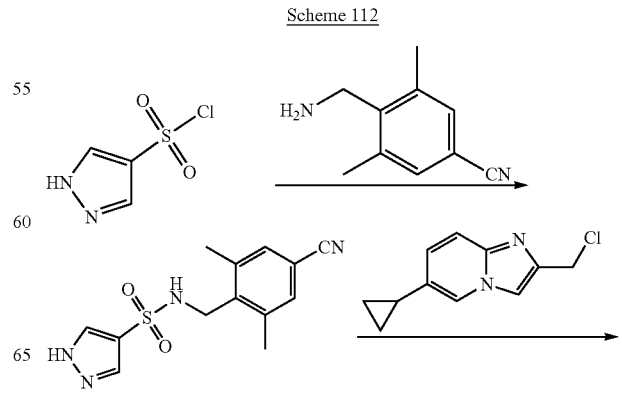

Scheme 112

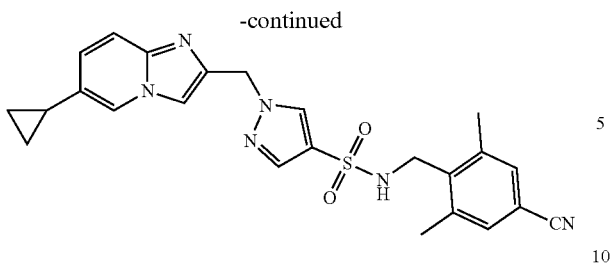

Synthesis of N-(4-cyano-2,6-dimethylbenzyl)-1-((6-cyclopropylimidazo[1,2-a]pyridin-2-yl)methyl)-1H-pyrazole-4-sulfonamide. N-(4-cyano-2,6-dimethylbenzyl)-1-((6-cyclopropylimidazo[1,2-a]pyridin-2-yl)methyl)-1H-pyrazole-4-sulfonamide was synthesized according to General Procedure F-2 using 4-(aminomethyl)-3,5-dimethylbenzonitrile. The crude product 5 was purified by prep-TLC (eluent: DCM/MeOH=10/1) to yield the product as a white solid (350 mg, 58%). Intermediate sulfonamide: ESI-MS [M+H]+: 291.1. I-43: ESI-MS [M+H]+: 461.2. $^1$H NMR (400 MHz, DMSO) δ 8.36 (s, 1H), 8.33 (s, 1H), 7.78 (s, 2H), 7.58 (t, J=5.7 Hz, 1H), 7.46 (s, 2H), 7.41 (d, J=9.3 Hz, 1H), 7.01 (dd, J=9.3, 1.6 Hz, 1H), 5.48 (s, 2H), 3.95 (d, J=5.6 Hz, 2H), 2.25 (s, 6H), 1.97-1.90 (m, 1H), 0.95-0.90 (m, 2H), 0.70-0.66 (m, 2H).

Example 111

N-(4-(aminomethyl)-2,6-dimethylbenzyl)-1-((6-cyclopropylimidazo[1,2-a]pyridin-2-yl)methyl)-1H-pyrazole-4-sulfonamide (I-41)

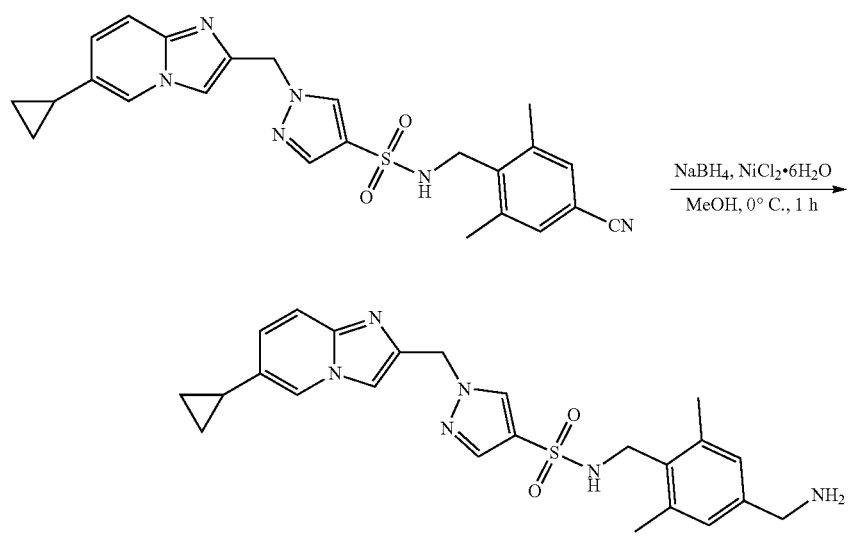

Synthesis of N-(4-(aminomethyl)-2,6-dimethylbenzyl)-1-((6-cyclopropylimidazo[1,2-a]pyridin-2-yl)methyl)-1H-pyrazole-4-sulfonamide. To a solution of N-(4-cyano-2,6-dimethylbenzyl)-1-((6-cyclopropylimidazo[1,2-a]pyridin-2-yl)methyl)-1H-pyrazole-4-sulfonamide (120 mg, 0.261 mmol) and NiCl$_2$·6H$_2$O (62 mg, 0.261 mmol) in MeOH (10 mL) was added NaBH$_4$ (60 mg, 1.59 mmol) at 0° C. The resulting mixture was stirred at 0° C. for 1 h under N$_2$. The reaction was quenched with H$_2$O (15 mL) and the aqueous phase was extracted with EtOAc (20 mL×3). The combined organic layers were washed with brine (20 mL×1), dried over Na$_2$SO$_4$ and concentrated in vacuo to give the crude, which was purified by Prep-TLC (eluent: DCM/MeOH=7/1) to give N-(4-(aminomethyl)-2,6-dimethylbenzyl)-1-((6-cyclopropylimidazo[1,2-a]pyridin-2-yl)methyl)-1H-pyrazole-4-sulfonamide as a white solid (10 mg, 8%). ESI-MS [M+H]+: 465.2. $^1$H NMR (400 MHz, DMSO) δ 8.36 (s, 1H), 8.31 (s, 1H), 7.78 (d, J=2.1 Hz, 2H), 7.42-7.15 (m, 3H), 7.02 (dd, J=9.4, 1.7 Hz, 1H), 6.92 (s, 2H), 5.48 (s, 2H), 3.88 (s, 2H), 3.62 (s, 2H), 2.16 (s, 6H), 1.96-1.90 (m, 1H), 0.95-0.90 (m, 2H), 0.73-0.66 (m, 2H).

Example 112

4-(((1-((6-cyclopropylimidazo[1,2-a]pyridin-2-yl)methyl)-1H-pyrazole)-4-sulfonamido)methyl)-3,5-dimethylbenzimidamide (I-39)

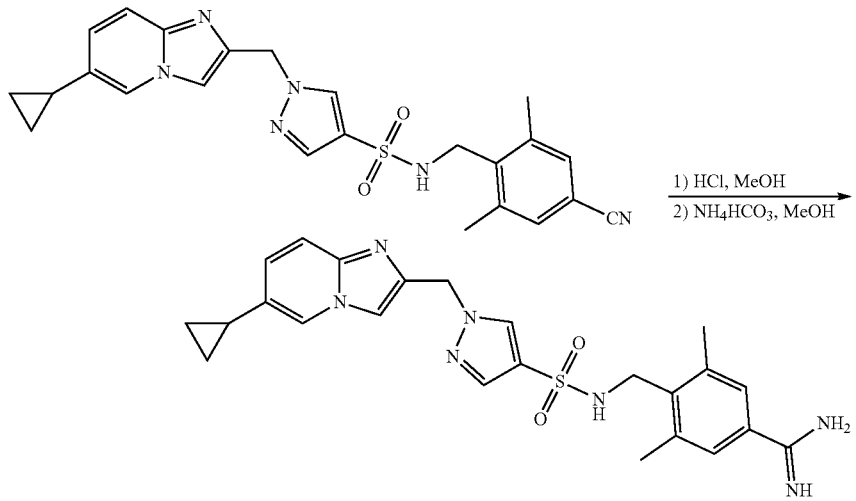

Synthesis of 4-(((1-((6-cyclopropylimidazo[1,2-a]pyridin-2-yl)methyl)-1H-pyrazole)-4-sulfonamido)methyl)-3,5-dimethylbenzimidamide. To a solution of N-(4-cyano-2,6-dimethylbenzyl)-1-((6-cyclopropylimidazo[1,2-a]pyridin-2-yl)methyl)-1H-pyrazole-4-sulfonamide (120 mg, 0.26 mmol) in MeOH (20 mL) was bubbled HCl(g) for 3 h. The reaction mixture was concentrated in vacuo and MeOH (20 mL) and NH$_4$HCO$_3$ (205.4 mg, 2.6 mmol) were added. The reaction was stirred at room temperature for 14 h, then concentrated in vacuo to give the crude (100 mg), which was purified by Prep-HPLC to give 4-(((1-((6-cyclopropylimidazo[1,2-a]pyridin-2-yl)methyl)-1H-pyrazole)-4-sulfonamido)methyl)-3,5-dimethylbenzimidamide (12 mg, yield: 10%) as a white solid. ESI-MS [M+H]$^+$: 478.2. $^1$H NMR (400 MHz, DMSO) δ 10.88 (s, 2H), 9.09 (s, 2H), 8.47 (s, 1H), 8.37 (s, 1H), 8.32 (s, 1H), 7.80 (d, J=1.6 Hz, 2H), 7.69-7.35 (m, 4H), 7.02 (dd, J=9.4, 1.7 Hz, 1H), 5.49 (s, 2H), 3.98 (s, 2H), 2.29 (s, 6H), 1.97-1.90 (m, 1H), 0.93 (ddd, J=8.3, 6.3, 4.3 Hz, 2H), 0.70-0.66 (m, 2H).

Example 113

N-(4-chlorobenzyl)-1-((6-cyclopropylimidazo[1,2-a]pyridin-2-yl)methyl)-1H-pyrazole-4-sulfonamide (I-42)

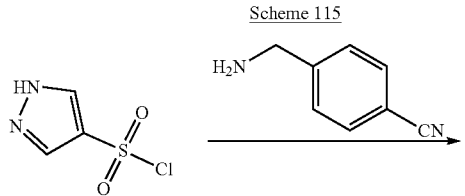

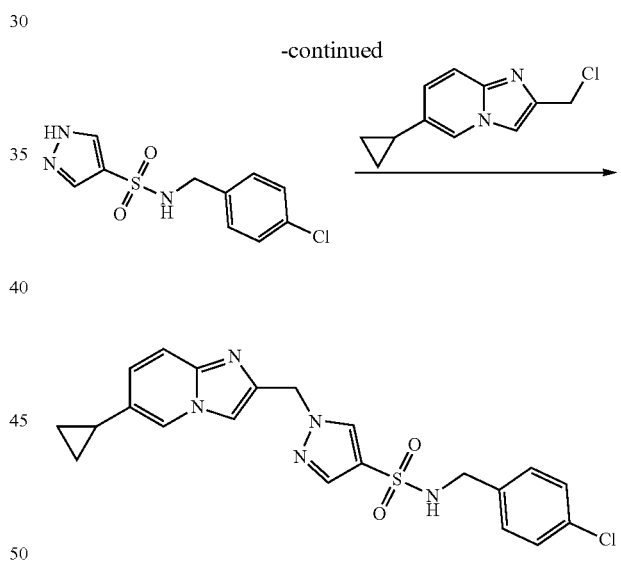

Synthesis of N-(4-chlorobenzyl)-1-((6-cyclopropylimidazo[1,2-a]pyridin-2-yl)methyl)-1H-pyrazole-4-sulfonamide. N-(4-chlorobenzyl)-1-((6-cyclopropylimidazo[1,2-a]pyridin-2-yl)methyl)-1H-pyrazole-4-sulfonamide was synthesized according to General Procedure F-1 using (4-chlorophenyl)methanamine. The crude product was purified by prep-HPLC to yield the product (30 mg, yield: 26.1%) as a white solid. Intermediate sulfonamide: ESI-MS [M+H]$^+$: 272.0. I-42: ESI-MS [M+H]+: 442.1. Purity: 99.47 (214 nm), 99.61(254 nm). $^1$H NMR (400 MHz, DMSO) δ 8.36 (s, 1H), 8.29 (s, 1H), 7.97 (t, J=6.3 Hz, 1H), 7.83-7.69 (m, 2H), 7.42 (d, J=9.3 Hz, 1H), 7.37-7.30 (m, 2H), 7.27 (d, J=8.6 Hz, 2H), 6.97-7.05 (m, 1H), 5.40 (d, J=32.3 Hz, 2H), 4.00 (d, J=6.3 Hz, 2H), 1.99-1.87 (m, 1H), 0.98-0.85 (m, 2H), 0.75-0.60 (m, 2H)

Example 114

1-((6-cyclopropylimidazo[1,2-a]pyridin-2-yl)
methyl)-N-(2-fluoro-3-methoxy-6-(1H-tetrazol-1-yl)
benzyl)-1H-1,2,3-triazole-4-sulfonamide (I-40)

Scheme 116

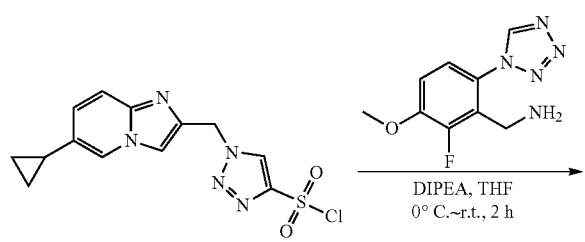

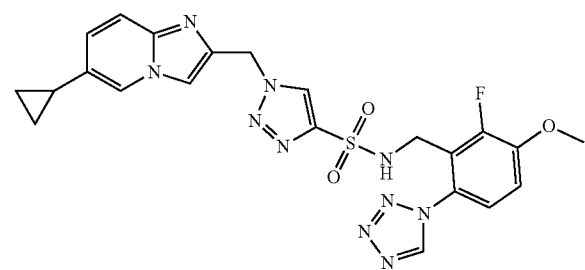

Synthesis of 1-((6-cyclopropylimidazo[1,2-a]pyridin-2-yl)methyl)-N-(2-fluoro-3-methoxy-6-(1H-tetrazol-1-yl)benzyl)-1H-1,2,3-triazole-4-sulfonamide. To a solution of (2-fluoro-3-methoxy-6-(1H-tetrazol-1-yl)phenyl)methanamine (72 mg, 0.32 mmol) and DIPEA (410 mg. 3.2 mmol) in THF (20 mL) was added a solution of 1-((6-cyclopropylimidazo[1,2-a]pyridin-2-yl)methyl)-1H-1,2,3-triazole-4-sulfonyl chloride (540 mg crude) in THF (5 mL) at 0° C. The reaction mixture was stirred at room temperature for 2 h. The reaction was quenched with $H_2O$ (30 mL) and extracted with EtOAc (50 mL×3). The combined organic layers were washed with brine (50 mL), dried over $Na_2SO_4$ and concentrated in vacuo to give the crude, which was purified with Prep-HPLC to give 1-((6-cyclopropylimidazo[1,2-a]pyridin-2-yl)methyl)-N-(2-fluoro-3-methoxy-6-(1H-tetrazol-1-yl)benzyl)-1H-1,2,3-triazole-4-sulfonamide as a white solid. (23 mg, 13.7%). ESI-MS [M+H]+: 525.1. $^1$H NMR (400 MHz, DMSO) δ 9.69 (s, 1H), 8.55 (s, 1H), 8.38 (s, 2H), 7.87 (s, 1H), 7.47-7.25 (m, 3H), 7.03 (d, J=9.3 Hz, 1H), 5.73 (s, 2H), 4.06 (s, 2H), 3.92 (s, 3H), 2.00-1.90 (m, 1H), 0.95-0.92 (m, 2H), 0.69-0.66 (m, 2H).

Example 115

N-(1-(3-chlorophenyl)ethyl)-1-((6-cyclopropylimidazo[1,2-a]pyridin-2-yl)methyl)-1H-pyrazole-4-sulfonamide (I-38)

Scheme 117

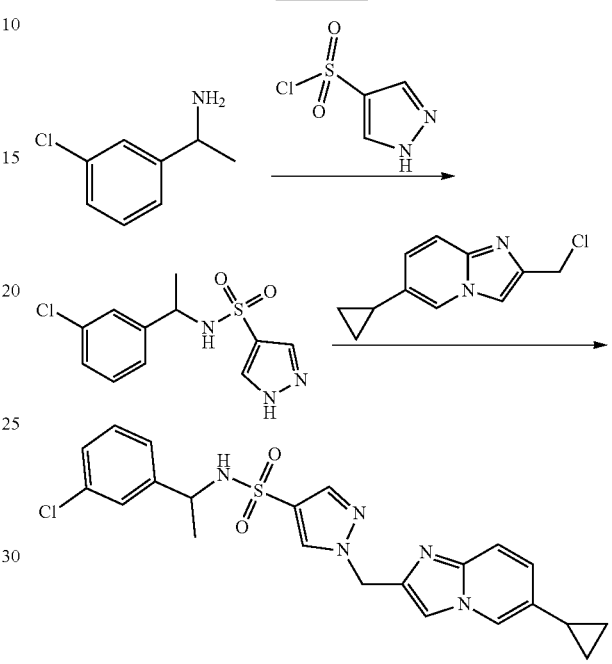

Synthesis of N-(1-(3-chlorophenyl)ethyl)-1-((6-cyclopropylimidazo[1,2-a]pyridin-2-yl)methyl)-1H-pyrazole-4-sulfonamide. N-(1-(3-chlorophenyl)ethyl)-1-((6-cyclopropylimidazo[1,2-a]pyridin-2-yl)methyl)-1H-pyrazole-4-sulfonamide was synthesized according to General Procedure F-2 using 1-(3-chlorophenyl)ethan-1-amine. The crude product was purified by prep-HPLC to yield the product as white solid (22.6 mg, yield: 14%). Intermediate sulfonamide: ESI-MS [M+H]+: 286.1. I-38: ESI-MS [M+H]+: 456.2. $^1$H NMR (400 MHz, $CD_3OD$) δ 8.34 (s, 1H), 8.06-8.04 (m, 2H), 7.71 (s, 1H), 7.54 (s, 1H), 7.40 (d, J=7.4 Hz, 1H), 7.26 (s, 1H), 7.22-7.15 (m, 3H), 7.00 (d, J=7.0 Hz, 1H), 5.35 (s, 2H), 4.36-4.32 (m, 1H), 1.95-1.88 (m, 1H), 1.21 (d, J=1.2 Hz, 3H), 0.93-0.88 (m, 2H), 0.68-0.64 (m, 2H).

Example 116

1-((6-cyclopropylimidazo[1,2-a]pyridin-2-yl)
methyl)-N-(2-phenoxyethyl)-1H-pyrazole-4-sulfonamide (I-36)

Scheme 118

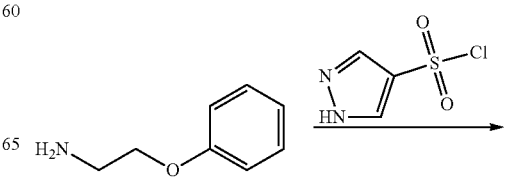

-continued

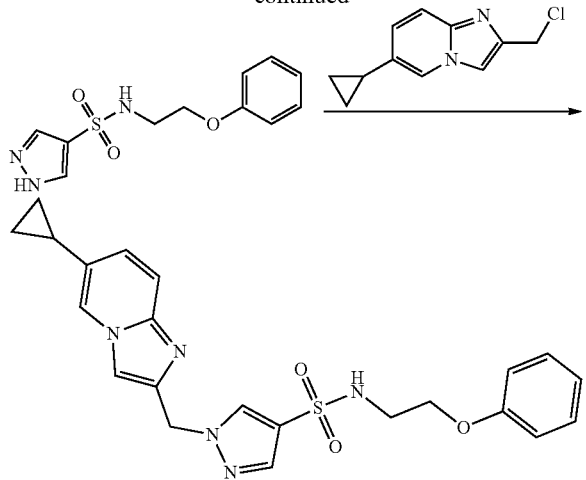

Synthesis of 1-((6-cyclopropylimidazo[1,2-a]pyridin-2-yl)methyl)-N-(2-phenoxyethyl)-1H-pyrazole-4-sulfonamide. 1-((6-cyclopropylimidazo[1,2-a]pyridin-2-yl)methyl)-N-(2-phenoxyethyl)-1H-pyrazole-4-sulfonamide was synthesized according to General Procedure F-1 using 2-phenoxyethan-1-amine. The crude product was purified by prep-HPLC to yield the product as a white solid. (85 mg, 16.7%). Intermediate sulfonamide: ESI-MS [M+H]+: 268.1. I-36: ESI-MS [M+H]+: 438.1. $^1$H NMR (400 MHz, DMSO) δ 8.35-8.33 (m, 1H), 8.32 (d, J=0.5 Hz, 1H), 7.77-7.74 (m, 2H), 7.69 (s, 1H), 7.40 (d, J=9.3 Hz, 1H), 7.28-7.23 (m, 2H), 7.00 (dd, J=9.4, 1.8 Hz, 1H), 6.94-6.90 (m, 1H), 6.88-6.85 (m, 2H), 5.44 (s, 2H), 3.97 (t, J=5.7 Hz, 2H), 3.15 (t, J=5.7 Hz, 2H), 1.96-1.89 (m, 1H), 0.95-0.90 (m, 2H), 0.69-0.65 (m, 2H).

Example 117

N-(4-chlorophenethyl)-1-((6-cyclopropylimidazo[1,2-a]pyridin-2-yl)methyl)-1H-pyrazole-4-sulfonamide
(I-35)

Scheme 119

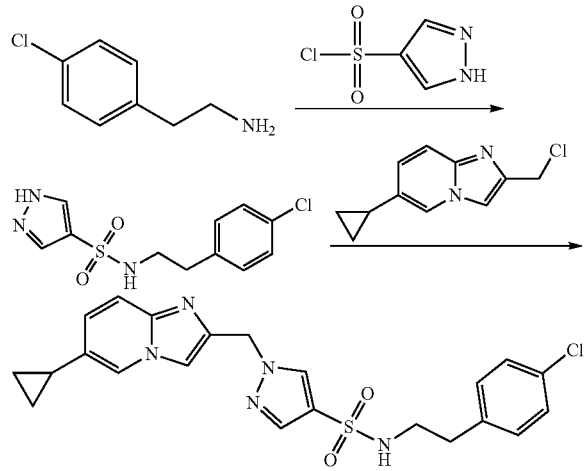

Synthesis of N-(4-chlorophenethyl)-1-((6-cyclopropylimidazo[1,2-a]pyridin-2-yl)methyl)-1H-pyrazole-4-sulfonamide. N-(4-chlorophenethyl)-1-((6-cyclopropylimidazo[1,2-a]pyridin-2-yl)methyl)-1H-pyrazole-4-sulfonamide was synthesized according to General Procedure F-1 using 2-(4-chlorophenyl)ethan-1-amine. The crude product was purified by prep-HPLC to yield the product (59.4 mg, yield: 12.9%) as a white solid. Intermediate sulfonamide: ESI-MS [M+H]+, 286.1. I-35: ESI-MS: [M+H]+ 456.1. $^1$H NMR (400 MHz, DMSO) δ 8.34 (s, 1H), 8.27 (s, 1H), 7.77 (s, 1H), 7.71 (s, 1H), 7.48-7.43 (m, 1H), 7.38 (d, J=9.3 Hz, 1H), 7.31-7.27 (m, 2H), 7.19-7.15 (m, 2H), 7.02-6.97 (m, 1H), 5.45 (s, 2H), 3.01-2.94 (m, 2H), 2.70-2.65 (m, 2H), 1.96-1.88 (m, 1H), 1.12-0.83 (m, 2H), 0.79-0.59 (m, 2H).

Example 118

N-(4-cyanobenzyl)-1-((6-cyclopropylimidazo[1,2-a]pyridin-2-yl)methyl)-1H-pyrazole-4-sulfonamide
(I-34)

Scheme 120

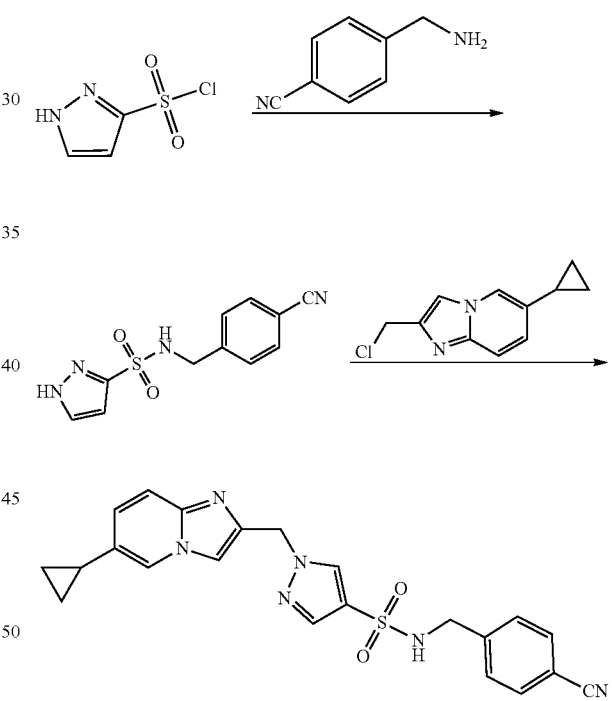

Synthesis of N-(4-cyanobenzyl)-1-((6-cyclopropylimidazo[1,2-a]pyridin-2-yl)methyl)-1H-pyrazole-4-sulfonamide. N-(4-cyanobenzyl)-1-((6-cyclopropylimidazo[1,2-a]pyridin-2-yl)methyl)-1H-pyrazole-4-sulfonamide was synthesized according to General Procedure F-2 using 4-(aminomethyl)benzonitrile. The crude product was purified by prep-HPLC to yield the product (150 mg, yield: 37.3%) as a white solid. Intermediate sulfonamide: ESI-MS [M+H]+: 263.1. I-34: ESI-MS [M+H]+: 433.1. $^1$H NMR (400 MHz, DMSO) δ 8.36 (s, 1H), 8.30 (s, 1H), 8.10-8.05 (m, 1H), 7.80-7.72 (m, 4H), 7.50-7.40 (m, 3H), 7.02 (dd, J=9.4, 1.7 Hz, 1H), 5.44 (s, 2H), 4.10 (d, J=4.8 Hz, 2H), 1.93-1.90 (m, 1H), 0.92-0.89 (m, 2H), 0.71-0.64 (m, 2H).

Example 119

N-(4-(aminomethyl)benzyl)-1-((6-cyclopropylimidazo[1,2-a]pyridin-2-yl)methyl)-1H-pyrazole-4-sulfonamide (I-33)

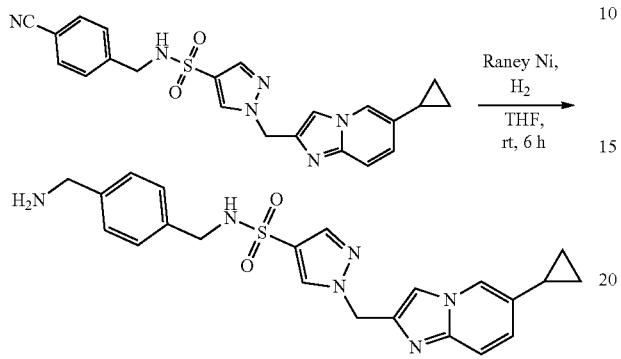

Scheme 121

Synthesis of N-(4-(aminomethyl)benzyl)-1-((6-cyclopropylimidazo[1,2-a]pyridin-2-yl)methyl)-1H-pyrazole-4-sulfonamide. A solution of N-(4-cyanobenzyl)-1-((6-cyclopropylimidazo[1,2-a]pyridin-2-yl)methyl)-1H-pyrazole-4-sulfonamide (40 mg, 0.092 mmol) and Raney Ni (20 mg,) in THF (5 mL) was stirred at room temperature for 6 h under H₂ atmosphere. Then the mixture was filtered, concentrated in vacuo, and purified by Prep-HPLC to give N-(4-(aminomethyl)benzyl)-1-((6-cyclopropylimidazo[1,2-a]pyridin-2-yl)methyl)-1H-pyrazole-4-sulfonamide (1.1 mg, yield: 2.75%) as a white solid. ESI-MS [M+H]+: 437.1. ¹H NMR (400 MHz, DMSO) δ=8.33 (s, 1H), 8.24 (s, 1H), 7.75 (s, 1H), 7.71 (s, 1H), 7.39 (d, J=8 Hz, 1H), 7.21-7.13 (m, 5H), 7.00-6.98 (m, 1H), 5.42 (s, 1H), 3.93 (s, 1H), 3.65 (s, 1H), 1.93-1.89 (m, 1H), 0.92-0.88 (m, 2H), 0.67-0.63 (m, 2H).

Example 120

4-(((1-((6-cyclopropylimidazo[1,2-a]pyridin-2-yl)methyl)-1H-pyrazole)-4-sulfonamido)methyl)benzimidamide (I-32)

Scheme 122

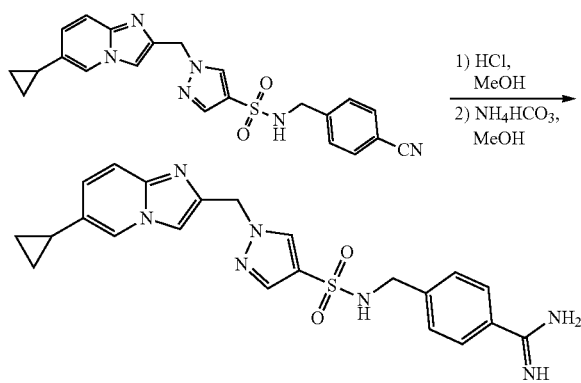

Synthesis of 4-(((1-((6-cyclopropylimidazo[1,2-a]pyridin-2-yl)methyl)-1H-pyrazole)-4-sulfonamido)methyl)benzimidamide. To a solution of N-(4-cyanobenzyl)-1-((6-cyclopropylimidazo[1,2-a]pyridin-2-yl)methyl)-1H-pyrazole-4-sulfonamide (100 mg, 0.231 mmol) in MeOH (5 mL) was bubbled HCl (gas) for 3 h. The reaction was concentrated in vacuo, then MeOH (10 mL) and NH₄HCO₃ (182 mg, 2.31 mmol) were added. The mixture reaction was stirred at room temperature for another 16 h. The reaction mixture was concentrated in vacuo to give the crude, which was purified by Prep-HPLC to give 4-(((1-((6-cyclopropylimidazo[1,2-a]pyridin-2-yl)methyl)-1H-pyrazole)-4-sulfonamido)methyl)benzimidamide (39 mg, yield: 37.8%) as a white solid. ESI-MS [M+H]+: 450.1. ¹H NMR (400 MHz, DMSO) δ=8.47 (s, 1H), 8.36 (s, 1H), 8.29 (s, 1H), 7.79-7.72 (m, 4H), 7.47-7.41 (m, 3H), 7.01 (dd, J=9.4, 1.7, 1H), 5.45 (s, 2H), 4.11 (s, 2H), 1.94-1.90 (m, 1H), 0.95-0.90 (m, 2H), 0.70-0.65 (m, 2H).

Example 121

N-(3-chloro-2-fluoro-6-(1H-tetrazol-1-yl)benzyl)-1-((6-cyclopropylimidazo[1,2-a]pyridin-2-yl)methyl)-1H-1,2,3-triazole-4-sulfonamide (I-30)

Scheme 123

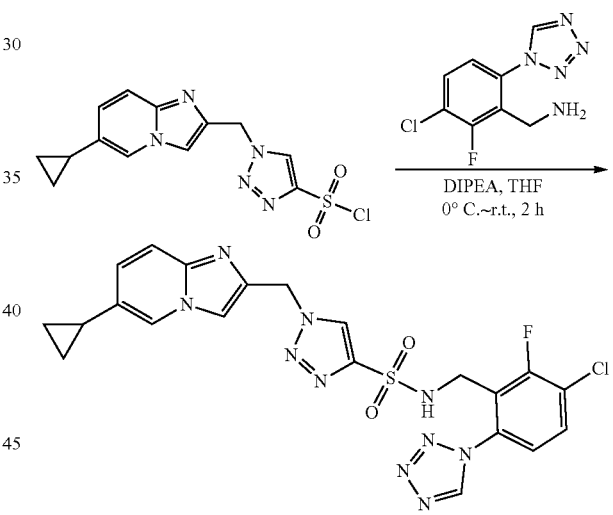

Synthesis of N-(3-chloro-2-fluoro-6-(1H-tetrazol-1-yl)benzyl)-1-((6-cyclopropylimidazo[1,2-a]pyridin-2-yl)methyl)-1H-1,2,3-triazole-4-sulfonamide. To a solution of (3-chloro-2-fluoro-6-(1H-tetrazol-1-yl)phenyl)methanamine (100 mg, 0.44 mmol) and DIPEA (568 mg, 4.4 mmol) in THF (15 mL) was added 1-((6-cyclopropylimidazo[1,2-a]pyridin-2-yl)methyl)-1H-1,2,3-triazole-4-sulfonyl chloride (370 mg, 40 w/w %, 0.44 mmol) in THF (5 mL) at 0° C. The reaction mixture was stirred at room temperature for 2 h, then quenched with H₂O (20 mL) and extracted with EtOAc (30 mL×3). The combined organic layers were washed with brine, dried over Na₂SO₄, and concentrated in vacuo to give the crude, which was purified with Prep-HPLC to give N-(3-chloro-2-fluoro-6-(1H-tetrazol-1-yl)benzyl)-1-((6-cyclopropylimidazo[1,2-a]pyridin-2-yl)methyl)-1H-1,2,3-triazole-4-sulfonamide (18 mg, 7.7%) as a white solid. ESI-MS [M+H]+: 529.1. ¹H NMR (400 MHz, DMSO) δ 9.81 (s, 1H), 8.56-8.26 (m, 3H), 7.88 (s, 1H), 7.81 (t, J=8.2

Hz, 1H), 7.52-7.42 (m, 2H), 7.04 (d, J=9.4 Hz, 1H), 5.74 (s, 2H), 4.15 (s, 2H), 1.98-1.91 (m, 1H), 0.96-0.91 (m, 2H), 0.71-0.67 (m, 2H).

Example 122

5-((6-cyclopropylimidazo[1,2-a]pyridin-2-yl)methyl)-N-(2-fluoro-3-methoxy-6-(1H-tetrazol-1-yl)benzyl)-1,3,4-oxadiazole-2-carboxamide (I-94)

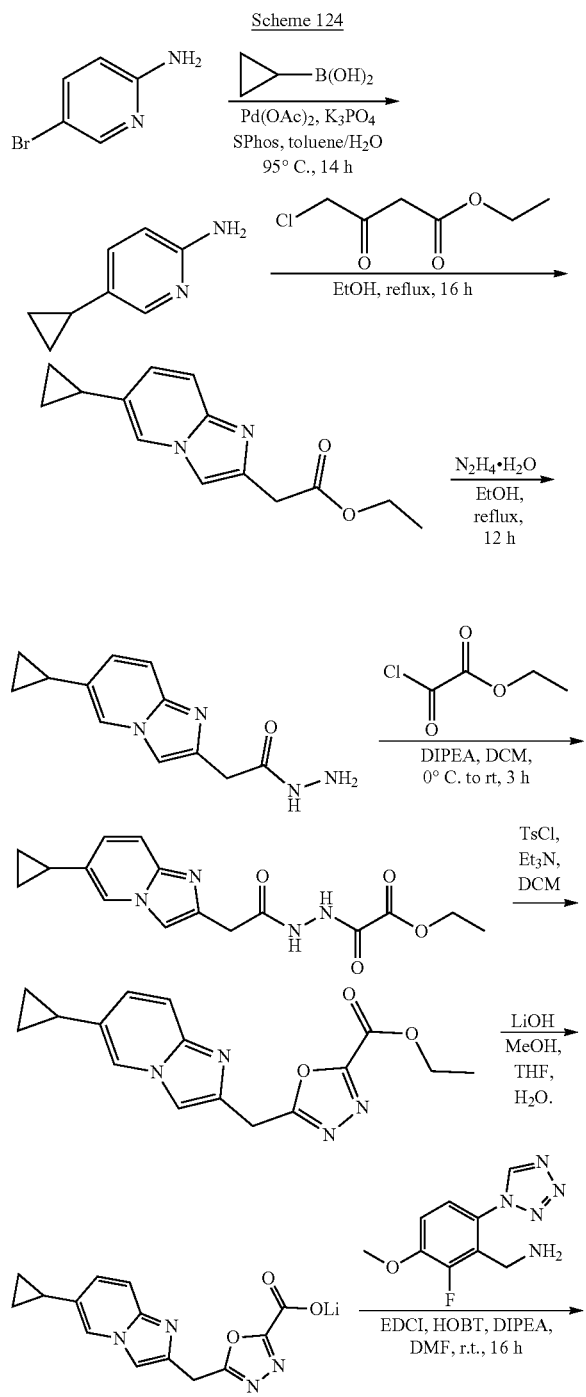

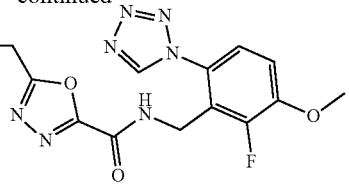

Synthesis of 5-cyclopropylpyridin-2-amine. To a solution of 5-bromopyridin-2-amine (50 g, 290 mmol) in toluene/H₂O (700 mL/70 mL) was added cyclopropylboronic acid (37.4 g, 435 mmol), Pd(OAc)₂ (6.49 g, 29.0 mmol), SPhos (12.8 g, 29.0 mmol) and K₃PO₄ (184.4 g, 870 mmol). The reaction mixture was stirred at 95° C. for 14 h under nitrogen. Then the mixture was concentrated in vacuo. Water (400 mL) was added and the mixture was extracted with DCM (500 mL×2). The combined organic layers were concentrated to give the crude product, which was purified by silica gel chromatography (PE/EtOAc=1/1) to give the 5-cyclopropylpyridin-2-amine as a yellow solid (38 g, yield: 97%). ESI-MS [M+H]⁺: 135.2.

Synthesis of ethyl 2-(6-cyclopropylimidazo[1,2-a]pyridin-2-yl)acetate. To a solution 5-cyclopropyl-4-methylpyridin-2-amine (30 g, 223.9 mmol) in EtOH (400 mL) was added ethyl 4-chloro-3-oxobutanoate (110 g, 671.7 mmol) at RT. The resulting mixture was stirred at 90° C. for 16 h and then concentrated in vacuo. H₂O (500 mL) was added, the pH value of the mixture was adjusted to 8 by adding saturated NaHCO₃ solution, and then the mixture was extracted with EtOAc (400 mL×3). The combined organic layers were washed with brine, dried over Na₂SO₄, and concentrated to give the crude product, which was purified by silica gel chromatography (DCM/MeOH=10/1) to give ethyl 2-(6-cyclopropylimidazo[1,2-a]pyridin-2-yl)acetate (40 g, impure) as a black solid. ESI-MS [M+H]⁺: 245.2.

Synthesis of 2-(6-cyclopropylimidazo[1,2-a]pyridin-2-yl)acetohydrazide. A mixture of ethyl 2-(6-cyclopropylimidazo[1,2-a]pyridin-2-yl)acetate (40 g, impure) and N₂H₄·H₂O (50 mL) in EtOH (300 mL) was stirred at 85° C. for 12 h. The mixture was then concentrated and purified by silica gel chromatography (DCM/MeOH=10/1) to give 2-(6-cyclopropylimidazo[1,2-a]pyridin-2-yl)acetohydrazide (17.1 g, yield: 31.5% in 2 steps) as a yellow solid. ESI-MS [M+H]⁺: 231.1.

Synthesis of ethyl 2-(2-(2-(6-cyclopropylimidazo[1,2-a]pyridin-2-yl)acetyl)hydrazinyl)-2-oxoacetate. To a solution of 2-(6-cyclopropylimidazo[1,2-a]pyridin-2-yl)acetohydrazide (17 g, 73.9 mmol) and DIPEA (38 mL, 222 mmol) in DCM (300 mL) was added ethyl 2-chloro-2-oxoacetate (15 g, 111 mmol) slowly at 0° C. The reaction mixture was stirred at RT for 2 h. Water (200 mL) was added and the mixture was extracted with DCM (200 mL×2). The combined organic layers were concentrated to give the crude product, which was purified by silica gel chromatography (DCM/MeOH=10/1) to give (ethyl 2-(2-(2-(6-cyclopropylimidazo[1,2-a]pyridin-2-yl)acetyl)hydrazinyl)-2-oxoacetate (17 g, yield: 70%) as a yellow solid. ESI-MS [M+H]⁺: 331.1.

Synthesis of ethyl 5-((6-cyclopropylimidazo[1,2-a]pyridin-2-yl)methyl)-1,3,4-oxadiazole-2-carboxylate. To a solution of ethyl 2-(2-(2-(6-cyclopropylimidazo[1,2-a]pyridin-2-yl)acetyl) hydrazinyl)-2-oxoacetate (17 g, 51.5 mmol) and Et₃N (14 mL, 2 mmol) in DCM (300 mL) was added a solution of TsCl (11.8 g, 61.8 mmol) in DCM (50 mL) at RT. The reaction mixture was stirred at this temperature for 16 h. Water (200 mL) was added and the mixture was extracted with DCM (200 mL×2). The combined organic layers were concentrated and purified by silica gel chromatography (DCM/MeOH=10/1) to give 2-(chloromethyl)-5-methylimidazo[1,2-a]pyridine (8.2 g, yield: 51%) as a yellow oil. ESI-MS [M+H]$^+$: 313.2.

Synthesis of lithium 5-((6-cyclopropylimidazo[1,2-a]pyridin-2-yl)methyl)-1,3,4-oxadiazole-2-carboxylate. A solution of ethyl 5-((6-cyclopropylimidazo[1,2-a]pyridin-2-yl)methyl)-1,3,4-oxadiazole-2-carboxylate (8.0 g, 25.6 mmol) and LiOH·H$_2$O (2.1 g, 51.2 mmol) in a mixed solvent of THF/MeOH/H$_2$O (50 mL/50 mL/50 mL) was stirred at RT for 2 h. THF and methanol were removed in vacuo at 20° C. and the remaining H$_2$O phase was lyophilized to give lithium 5-((6-cyclopropylimidazo[1,2-a]pyridin-2-yl)methyl)-1,3,4-oxadiazole-2-carboxylate (7.4 g, yield: 100%) as a yellow solid. This material was used directly in the next step without further purification. ESI-MS [M+H]$^+$: 285.1.

Synthesis of 5-((6-cyclopropylimidazo[1,2-a]pyridin-2-yl)methyl)-N-(2-fluoro-3-methoxy-6-(1H-tetrazol-1-yl)benzyl)-1,3,4-oxadiazole-2-carboxamide. A mixture of lithium 5-((6-cyclopropylimidazo[1,2-a]pyridin-2-yl)methyl)-1,3,4-oxadiazole-2-carboxylate (57 mg, 0.2 mmol), (2-fluoro-3-methoxy-6-(1H-tetrazol-1-yl)phenyl)methanamine (44.6 mg, 0.2 mmol), EDCI (115.2 g, 0.6 mmol), HOBt (81 mg, 0.6 mmol) and DIPEA (77.4 mg, 0.6 mmol) in DMF (2 mL) was stirred at rt for 16 h. The reaction mixture was concentrated in vacuo to remove DMF, diluted with DCM/MeOH (60 mL, 10/1 v/v) and washed with water (40 mL×2), and brine (40 mL). The organic layer was separated, dried over Na$_2$SO$_4$, and concentrated in vacuo to give the crude product, which was purified by prep-HPLC to give 5-((6-cyclopropylimidazo[1,2-a]pyridin-2-yl)methyl)-N-(2-fluoro-3-methoxy-6-(1H-tetrazol-1-yl)benzyl)-1,3,4-oxadiazole-2-carboxamide (13.3 mg, yield: 13.6%) as a white solid. ESI-MS [M+H]$^+$: 490.2. $^1$H NMR (400 MHz, DMSO) δ 9.73 (s, 1H), 9.63-9.62 (m, 1H), 8.33 (s, 1H), 7.78 (s, 1H), 7.53-7.28 (m, 3H), 6.99 (d, J=9.5 Hz, 1H), 4.41 (s, 2H), 4.31 (d, J=4.9 Hz, 2H), 3.93 (s, 3H), 1.93-1.90 (m, 1H), 0.94-0.89 (m, 2H), 0.69-0.67 (m, 2H).

Example 123

2-((6-cyclopropyl-8-fluoroimidazo[1,2-a]pyridin-2-yl)methyl)-N-(2-fluoro-3-methoxy-6-(1H-tetrazol-1-yl)benzyl)-2H-tetrazole-5-carboxamide (I-69)

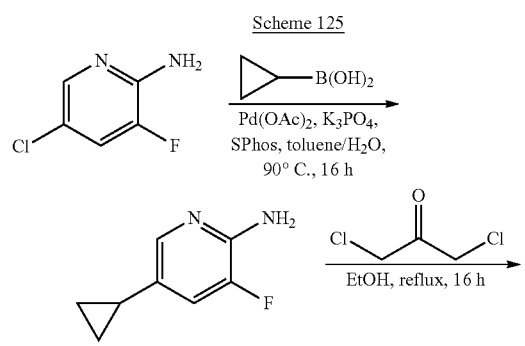

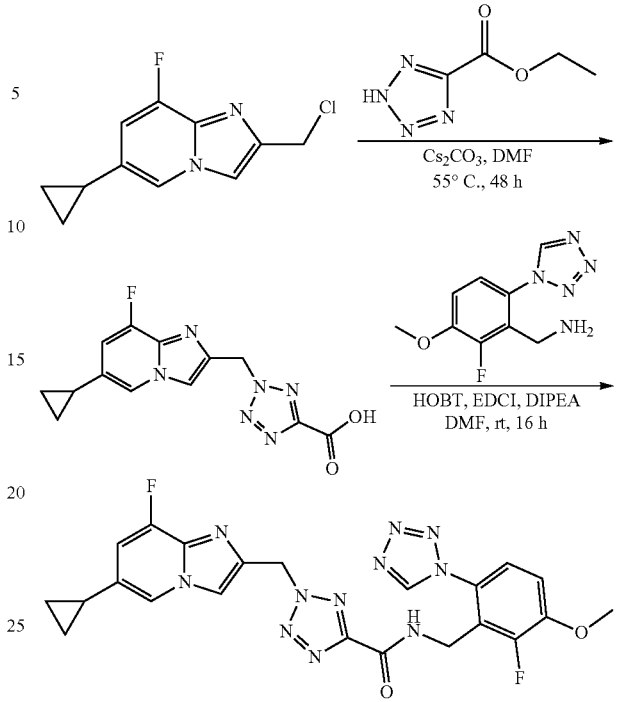

Synthesis of 5-cyclopropyl-3-fluoropyridin-2-amine. A mixture of 5-chloro-3-fluoropyridin-2-amine (2 g, 13.65 mmol), cyclopropylboronic acid (1.76 g, 20.47 mmol), Pd(OAc)$_2$ (306 mg, 1.365 mmol), SPhos (1.12 g, 2.73 mmol) and K$_3$PO$_4$ (10.14 g, 47.78 mmol) in toluene (40 mL) and H$_2$O (10 mL) was stirred at 90° C. for 16 h under N$_2$. The reaction mixture was filtered and washed with EtOAc. The combined filtrate was washed with H$_2$O (100 mL) and brine (100 mL), dried over Na$_2$SO$_4$, concentrated and purified by silica gel chromatography (EA/PE=1/2) to give 5-cyclopropyl-3-fluoropyridin-2-amine (2.2 g, yield: 100%) as a yellow syrup. ESI-MS [M+H]$^+$: 153.2.

Synthesis of 2-(chloromethyl)-6-cyclopropyl-8-fluoroimidazo[1,2-a]pyridine. A mixture of 5-cyclopropyl-3-fluoropyridin-2-amine (2.2 g, 13.65 mmol) and 1,3-dichloropropan-2-one (5.5 g, 43.38 mmol) in EtOH (40 mL) was stirred at 85° C. for 16 h. The reaction mixture was concentrated. The residue was washed with NaHCO$_3$ aqueous solution and extracted with EtOAc (100 mL×3). The organic layers were washed with brine (100 mL), dried over Na$_2$SO$_4$, concentrated and purified by silica gel chromatography (EA/PE=1/2) to give 2-(chloromethyl)-6-cyclopropyl-8-fluoroimidazo[1,2-a]pyridine (1.8 g, 58%) as a yellow solid. ESI-MS [M+H]$^+$: 225.1.

Synthesis of 2-((6-cyclopropyl-8-fluoroimidazo[1,2-a]pyridin-2-yl)methyl)-2H-tetrazole-5-carboxylic acid. A mixture of 2-(chloromethyl)-6-cyclopropyl-8-fluoroimidazo[1,2-a]pyridine (440 mg, 1.96 mmol), ethyl 1H-tetrazole-5-carboxylate (557 mg, 3.92 mmol) and Cs$_2$CO$_3$ (3.82 g, 11.72 mmol) in DMF (10 mL) was stirred at 55° C. for 48 h. The reaction mixture was washed with H$_2$O (30 mL) and extracted with EtOAc (50 mL). The aqueous layer was acidified with HCl (3 M) and extracted with EtOAc (50 mL×5). The combined organic layers were concentrated and purified by silica gel chromatography (DCM/MeOH=10:1) to give 2-((6-cyclopropyl-8-fluoroimidazo[1,2-a]pyridin-2-yl)methyl)-2H-tetrazole-5-carboxylic acid (60 mg, yield: 10%) as a yellow oil. ESI-MS [M+H]$^+$: 303.1.

Synthesis of 2-((6-cyclopropyl-8-fluoroimidazo[1,2-a]pyridin-2-yl)methyl)-N-(2-fluoro-3-methoxy-6-(1H-tetrazol-1-yl)benzyl)-2H-tetrazole-5-carboxamide. A mixture of 2-((6-cyclopropyl-8-fluoroimidazo[1,2-a]pyridin-2-yl)methyl)-2H-tetrazole-5-carboxylic acid (50 mg, 0.16 mmol), (2-fluoro-3-methoxy-6-(1H-tetrazol-1-yl)phenyl)methanamine (55 mg, 0.25 mmol), HOBT (43 mg, 0.32 mmol), EDCI (61 mg, 0.32 mmol) and DIPEA (103 mg, 0.8 mmol) in DMF (3.5 mL) was stirred at rt for 16 h. Water (20 mL) was added and the mixture was extracted with EtOAc (20 mL×2). The combined organic layer was washed by brine (20 mL) and then concentrated in vacuo. The crude was purified by prep-TLC (DCM/MeOH=10:1), then repurified by prep-TLC (DCM/MeOH=20/1) to give 2-((6-cyclopropyl-8-fluoroimidazo[1,2-a]pyridin-2-yl)methyl)-N-(2-fluoro-3-methoxy-6-(1H-tetrazol-1-yl)benzyl)-2H-tetrazole-5-carboxamide (9 mg, yield: 11%) as a white solid. ESI-MS [M+H]+: 508.1. Purity: 100% (214 nm), 95.65% (254 nm). $^1$H NMR (400 MHz, DMSO) δ 9.74 (s, 1H), 9.33 (t, J=5.2 Hz, 1H), 8.28 (d, J=0.9 Hz, 1H), 8.06 (d, J=3.0 Hz, 1H), 7.40-7.33 (m, 2H), 6.96 (dd, J=12.4 Hz, J=1.2 Hz, 1H), 6.08 (s, 2H), 4.33 (d, J=4.8 Hz, 2H), 3.93 (s, 3H), 1.98-1.91 (m, 1H), 0.95-0.91 (m, 2H), 0.73-0.69 (m, 2H).

Example 124

1-((6-cyclopropylimidazo[1,2-a]pyridin-2-yl)methyl)-N-(2-fluoro-3-methoxy-6-(1H-tetrazol-1-yl)benzyl)-1H-imidazole-5-carboxamide (I-59)

Scheme 126

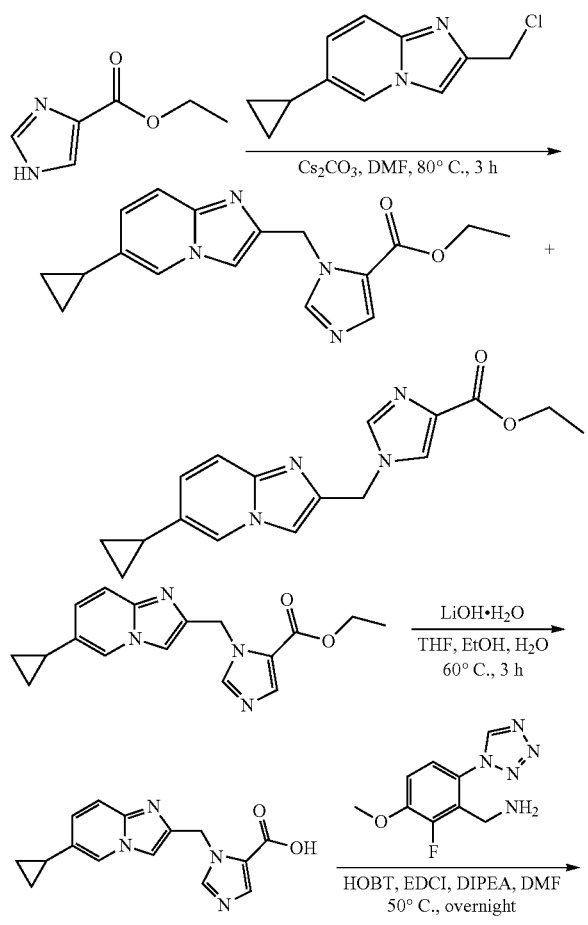

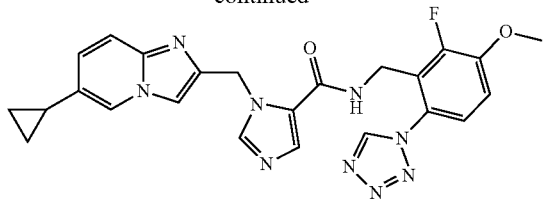

Synthesis of ethyl 1-((6-cyclopropylimidazo[1,2-a]pyridin-2-yl)methyl)-1H-imidazole-5-carboxylate. A mixture of 2-(chloromethyl)-6-cyclopropylimidazo[1,2-a]pyridine (207 mg, 1.0 mmol), ethyl 1H-imidazole-4-carboxylate (140 mg, 1.0 mmol) and Cs$_2$CO$_3$ (652 mg, 2 mmol) in DMF (6 mL) was stirred at 80° C. for 3 h. The reaction mixture was quenched with H$_2$O (30 mL) and extracted with EtOAc (50 mL×3). The combined organic layers were washed with brine (50 mL), dried over Na$_2$SO$_4$, filtered and concentrated in vacuo to give the crude, which was purified by Prep-TLC (DCM:MeOH=20:1) to afford ethyl 1-((6-cyclopropylimidazo[1,2-a]pyridin-2-yl)methyl)-1H-imidazole-5-carboxylate (45 mg, yield: 14.5%) as a white solid and ethyl 1-((6-cyclopropylimidazo[1,2-a]pyridin-2-yl)methyl)-1H-imidazole-4-carboxylate (40 mg, yield: 13%) as a white solid. 3: ESI-MS [M+H]$^+$: 311.2. 4: ESI-MS [M+H]$^+$: 311.2.

Synthesis of 1-((6-cyclopropylimidazo[1,2-a]pyridin-2-yl)methyl)-1H-imidazole-5-carboxylic acid To a solution of ethyl 1-((6-cyclopropylimidazo[1,2-a]pyridin-2-yl)methyl)-1H-imidazole-5-carboxylate (45 mg, 0.145 mmol) in ethanol (2 mL), THF (2 mL) and H$_2$O (1 mL) was added LiOH·H$_2$O (12 mg, 0.29 mmol). The reaction mixture was stirred at 60° C. for 3 h, then adjusted to pH 3 and concentrated in vacuo to give crude 1-((6-cyclopropylimidazo[1,2-a]pyridin-2-yl)methyl)-1H-imidazole-5-carboxylic acid as a white solid (41 mg, crude, yield: 100%), which was used in the next step without further purification. ESI-MS [M+H]$^+$: 283.1.

Synthesis of 1-((6-cyclopropylimidazo[1,2-a]pyridin-2-yl)methyl)-N-(2-fluoro-3-methoxy-6-(1H-tetrazol-1-yl)benzyl)-1H-imidazole-5-carboxamide. A mixture of crude 1-((6-cyclopropylimidazo[1,2-a]pyridin-2-yl)methyl)-1H-imidazole-5-carboxylic acid (41 mg, 0.145 mmol), (2-fluoro-3-methoxy-6-(1H-tetrazol-1-yl)phenyl)methanamine (41 mg, 0.16 mmol), HOBT (39 mg, 0.29 mmol), EDCI (56 mg, 0.29 mmol) and DIPEA (94 mg, 0.73 mmol) in DMF (3 mL) was stirred at 50° C. overnight. H$_2$O (30 mL) was added and the mixture was extracted with EtOAc (50 mL×3). The combined organic layers were washed with brine (30 mL), dried over Na$_2$SO$_4$, and concentrated in vacuo to give the crude, which was purified by Prep-TLC (DCM:MeOH=10:1) to give 1-((6-cyclopropylimidazo[1,2-a]pyridin-2-yl)methyl)—N-(2-fluoro-3-methoxy-6-(1H-tetrazol-1-yl)benzyl)-1H-imidazole-5-carboxamide (30.7 mg, yield: 43% over 2 steps) as a white solid. ESI-MS [M+H]$^+$: 488.2. $^1$H NMR (400 MHz, DMSO) δ 9.75 (s, 1H), 8.59 (t, J=4.9 Hz, 1H), 8.27 (s, 1H), 7.81 (s, 1H), 7.49 (s, 1H), 7.40-7.32 (m, 4H), 6.97 (dd, J=9.3, 1.4 Hz, 1H), 5.48 (s, 2H), 4.26 (d, J=4.6 Hz, 2H), 3.93 (s, 3H), 1.95-1.88 (m, 1H), 0.93-0.89 (m, 2H), 0.68-0.64 (m, 2H).

Example 125

1-((6-cyclopropylimidazo[1,2-a]pyridin-2-yl)methyl)-N-(2-fluoro-3-methoxy-6-(1H-tetrazol-1-yl)benzyl)-1H-imidazole-4-carboxamide (I-55)

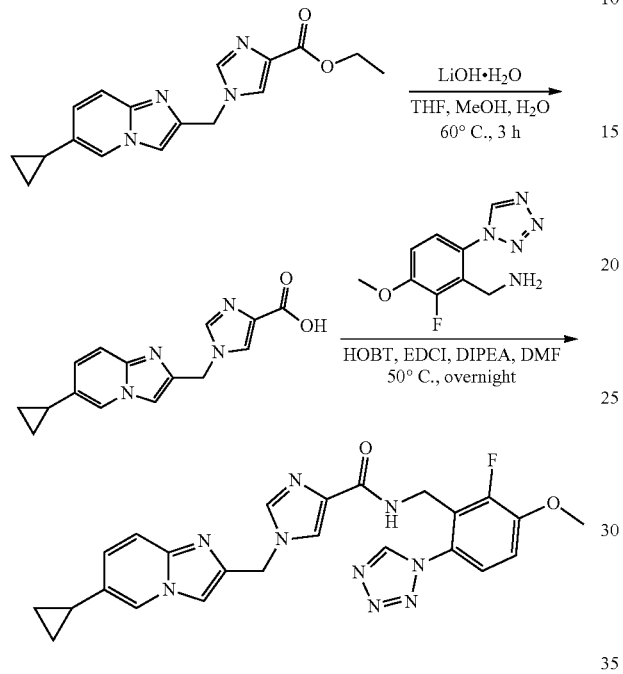

Scheme 127

Synthesis of 1-((6-cyclopropylimidazo[1,2-a]pyridin-2-yl)methyl)-1H-imidazole-4-carboxylic acid. To a solution of ethyl 1-((6-cyclopropylimidazo[1,2-a]pyridin-2-yl)methyl)-1H-imidazole-4-carboxylate (40 mg, 0.13 mmol) in THF/MeOH/H$_2$O (2 mL/2 mL/1 mL) was added LiOH H$_2$O (11 mg, 0.26 mmol). The reaction mixture was stirred at 60° C. for 3 h, then adjusted to pH 3 and concentrated in vacuo to give crude 1-((6-cyclopropylimidazo[1,2-a]pyridin-2-yl)methyl)-1H-imidazole-4-carboxylic acid as a white solid (52 mg, crude), which was used in the next step without further purification. ESI-MS [M+H]$^+$: 283.1.

Synthesis of 1-((6-cyclopropylimidazo[1,2-a]pyridin-2-yl)methyl)-N-(2-fluoro-3-methoxy-6-(1H-tetrazol-1-yl)benzyl)-1H-imidazole-4-carboxamide. A mixture of 1-((6-cyclopropylimidazo[1,2-a]pyridin-2-yl)methyl)-1H-imidazole-4-carboxylic acid (52 mg, 0.13 mmol, crude), (2-fluoro-3-methoxy-6-(1H-tetrazol-1-yl)phenyl)methanamine (37 mg, 0.14 mmol), HOBT (35 mg, 0.26 mmol), EDCI (49 mg, 0.26 mmol) and DIPEA (83 mg, 0.65 mmol) in DMF (3 mL) was stirred at 50° C. overnight. H$_2$O (40 mL) was added and the mixture was extracted with EtOAc (20 mL×5). The combined organic layers were washed with brine (30 mL), dried over Na$_2$SO$_4$, and concentrated in vacuo to give the crude, which was purified by Prep-TLC (DCM:MeOH=10:1) to give 1-((6-cyclopropylimidazo[1,2-a]pyridin-2-yl)methyl)—N-(2-fluoro-3-methoxy-6-(1H-tetrazol-1-yl)benzyl)-1H-imidazole-4-carboxamide (8.9 mg, yield: 14% over two steps) as a white solid. ESI-MS [M+H]$^+$: 488.1. $^1$H NMR (400 MHz, DMSO) δ 9.76 (s, 1H), 8.32 (s, 1H), 8.07 (t, J=5.7 Hz, 1H), 7.77 (s, 1H), 7.71 (s, 1H), 7.64 (s, 1H), 7.42-7.30 (m, 3H), 7.00 (d, J=9.4 Hz, 1H), 5.28 (s, 2H), 4.24 (d, J=5.6 Hz, 2H), 3.92 (s, 3H), 1.93-1.88 (m, 1H), 0.93-0.89 (m, 2H), 0.68-0.64 (m, 2H).

Example 126

7-chloro-N-((1-((6-cyclopropylimidazo[1,2-a]pyridin-2-yl)methyl)-1H-1,2,3-triazol-4-yl)methyl)-8-fluoroimidazo[1,5-a]pyridine-3-carboxamide (I-56)

Scheme 128

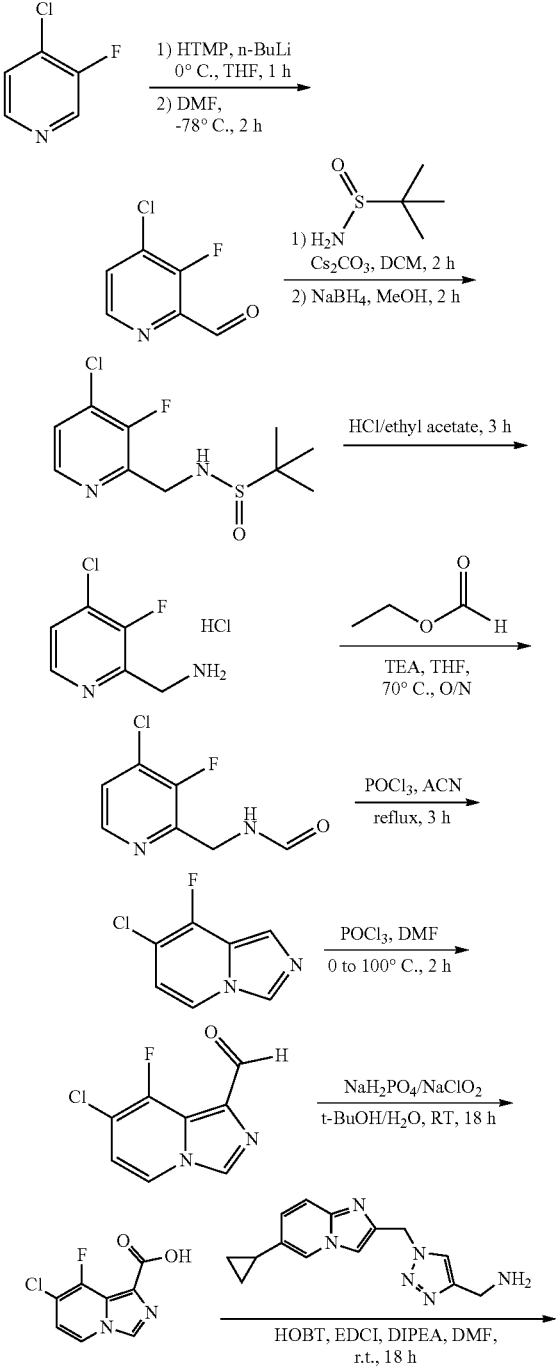

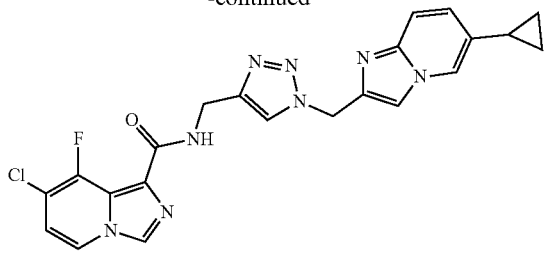

Synthesis of 4-chloro-3-fluoropicolinaldehyde. To a solution of 2,2,6,6-tetramethylpiperidine (35.4 g, 250.88 mmol) in 200 mL THF was added n-Butyllithium (2.4 M in hexane, 100 mL, 240 mmol) dropwise at 0° C. The reaction mixture was cooled to −78° C. after stirring at 0° C. for 1 h and a solution of 4-chloro-3-fluoropyridine (30.0 g, 228.08 mmol) in THF (100 mL) was added dropwise. The resulting reaction mixture was stirred at −78° C. for 2 h, a solution of DMF (17.5 g, 239.48 mmol) in THF (50 mL) was added dropwise, and the resulting reaction mixture was stirred at −78° C. for another 1 h. The reaction was quenched with H$_2$O (50 mL), and extracted with ethyl acetate (200 mL×3). The combined organic layers were washed with brine, dried over with anhydrous magnesium sulphate, filtered, and concentrated. The residue was purified by silica gel column chromatography (petroleum ether/ethyl acetate=3/1) to afford 4-chloro-3-fluoropicolinaldehyde (26.0 g, yield: 71%). ESI-MS [M+H]$^+$: 160.1.

Synthesis of N-((4-chloro-3-fluoropyridin-2-yl)methyl)-2-methylpropane-2-sulfinamide. To a solution of 4-chloro-3-fluoropicolinaldehyde (26.0 g, mixutre, 163.0 mmol) in DCM (100 mL) was added cesium carbonate (96.0 g, 293.3 mmol) and 2-methylpropane-2-sulfinamide (19.8 g, 163.0 mmol) at RT. The reaction mixture was stirred for 3 h at RT. After the reaction was complete, the reaction mixture was filtrated and washed with DCM three times. To the combined mixture was added MeOH (40 mL), and then the resulting mixture was cooled to 0° C. by ice-water bath. Sodium borohydride (15.5 g, 409.0 mmol) was added slowly in portions.

The reaction mixture was warmed up to RT and stirred at this temperature for 2 h. The reaction was quenched with H$_2$O carefully. The resulting mixture was extracted with DCM (100 mL×3), the combined organic solvent was dried by sodium sulfate, filtered, and concentrated to get crude N-((4-chloro-3-fluoropyridin-2-yl)methyl)-2-methylpropane-2-sulfinamide (43.3 g, crude) as yellow solid. ESI-MS [M+H]$^+$: 265.1.

Synthesis of (4-chloro-3-fluoropyridin-2-yl)methanamine hydrochloride. To a solution of N-((4-chloro-3-fluoropyridin-2-yl)methyl)-2-methylpropane-2-sulfinamide (about 162.4 mmol) in ethyl acetate (100 mL) was added a solution of hydrochloride acid in ethyl acetate (3 M, 200 mL). The resulting reaction mixture was stirred at RT for 3 h. After the reaction was completed, the reaction mixture was filtered to give the crude product, which was washed with ethyl acetate and dried in vacuum to afford (4-chloro-3-fluoropyridin-2-yl)methanamine hydrochloride (25.0 g, 78%, mixture) as a pink solid. $^1$H NMR (400 MHz, DMSO) δ 8.75 (br, 3H), 8.47 (d, J=5.2 Hz, 1H), 7.80 (t, J=5.6 Hz, 1H), 4.28-4.26 (m, 2H).

Synthesis of N-((4-chloro-3-fluoropyridin-2-yl)methyl)formamide. To a solution of (4-chloro-3-fluoropyridin-2-yl)methanamine hydrochloride (25.0 g, mixture, 127.0 mmol) in THF (200 mL) was added triethylamine (38.5 g, 380.6 mmol) and ethyl formate (100 mL) at RT. The resulting reaction mixture was stirred at 70° C. overnight. After the reaction was complete, the reaction mixture was filtered, the solid was washed with DCM three times. The combined organic solvent was washed with brine, dried by sodium sulfate, filtrated, and concentrated to afford N-((4-chloro-3-fluoropyridin-2-yl)methyl)formamide (crude), which was used in the next step directly without purification. ESI-MS [M+H]$^+$: 189.1.

Synthesis of 7-chloro-8-fluoroimidazo[1,5-a]pyridine. To a solution of N-((4-chloro-3-fluoropyridin-2-yl)methyl)formamide (crude, about 126.89 mmol) in dry acetonitrile (200 mL) was added phosphoryl trichloride (18 mL, 1.5 eq), and the resulting reaction mixture was stirred at reflux for 3 h. After the reaction was completed, the reaction mixture was cooled down to RT, and then poured into H$_2$O (200 mL) carefully. The pH was adjusted to 8 with saturated sodium bicarbonate, and then the resulting mixture was extracted with ethyl acetate (200 mL×3). The combined organic phase was washed with brine, dried over sodium sulphate, filtrated, and concentrated in vacuo. The residue was purified by silica gel chromatography (ethyl acetate) to afford 7-chloroimidazo[1,5-a]pyridine (12.0 g, yield: 56%) as a white solid. ESI-MS [M+H]$^+$: 171.1.

Synthesis of 7-chloro-8-fluoroimidazo[1,5-a]pyridine-1-carbaldehyde. A solution of 7-chloro-8-fluoroimidazo[1,5-a]pyridine (9.0 g, 52.6 mmol) in dry DMF (12 mL) was cooled with an ice-water bath to 0-5° C. Phosphorus oxychloride (7.4 g, 78.9 mmol, 1.5 eq) was added dropwise, and then the reaction mixture was stirred at 100° C. for 2 h. After the reaction was completed, the reaction mixture was cooled down to RT and poured into saturated sodium bicarbonate aqueous (200 mL) carefully. The resulting mixture was stirred at RT for 2 h and extracted with ethyl acetate (3×200 mL). The combined organic phase was washed with brine, dried over sodium sulphate, filtered, and concentrated in vacuo. The residue was purified by recrystallization (petroleum ether/ethyl acetate=1/1) to afford 7-chloroimidazo[1,5-a]pyridine-1-carbaldehyde (5.2 g, yield: 47%) as a brown solid. ESI-MS [M+H]$^+$: 181.1.

Synthesis of 7-chloro-8-fluoroimidazo[1,5-a]pyridine-1-carboxylic acid. To a 7-chloro-8-fluoroimidazo[1,5-a]pyridine-1-carbaldehyde (300 mg, 1.5 mmol) in t-BuOH/H$_2$O (10 mL/5 mL) was added NaH$_2$PO$_4$ (364 mg, 3.0 mmol) and NaClO$_2$ (270 mg, 3.0 mmol). The reaction mixture was stirred at RT for 18 h, then quenched with water (30 mL) and extracted with EtOAc (30 mL×5). The combined organic layers were washed with brine (30 mL), dried over Na$_2$SO$_4$ and concentrated in vacuo to afford crude 7-chloro-8-fluoroimidazo[1,5-a]pyridine-1-carboxylic acid (160 mg, crude) as a white solid which was used in next step directly without further purification. ESI-MS [M+H]+: 215.0.

Synthesis of 7-chloro-N-((1-((6-cyclopropylimidazo[1,2-a]pyridin-2-yl)methyl)-1H-1,2,3-triazol-4-yl)methyl)-8-fluoroimidazo[1,5-a]pyridine-1-carboxamide. A mixture of 7-chloro-8-fluoroimidazo[1,5-a]pyridine-1-carboxylic acid (160 mg, 0.93 mmol), (1-((6-cyclopropylimidazo[1,2-a]pyridin-2-yl)methyl)-1H-1,2,3-triazol-4-yl)methanamine (200 mg, 0.75 mmol), HOBT (122 mg, 0.90 mmol), EDCI (172 mg, 0.90 mmol) and DIPEA (194 mg, 1.50 mmol) in DMF (5 mL) was stirred at room temperature for 18 h. The reaction mixture was diluted with water (60 mL) and extracted with EtOAc (30 mL×5). The combined organic layers were washed with brine (50 mL), dried over Na$_2$SO$_4$ and concentrated in vacuo. The residue was purified by prep-HPLC to afford 7-chloro-N-((1-((6-cyclopropylimidazo[1,2-a]pyridin-2-yl)methyl)-1H-1,2,3-triazol-4-yl)

methyl)-8-fluoroimidazo[1,5-a]pyridine-1-carboxamide (46 mg, 13% yield) as a white solid. ESI-MS [M+H]+: 465.2. 1H NMR (400 MHz, DMSO) δ 9.24 (t, J=5.8 Hz, 1H), 9.18 (d, J=7.5 Hz, 1H), 8.34 (s, 1H), 7.97 (s, 1H), 7.80 (d, J=10.2 Hz, 2H), 7.39 (d, J=9.3 Hz, 1H), 7.11 (t, J=7.2 Hz, 1H), 7.00 (d, J=9.4 Hz, 1H), 5.63 (s, 2H), 4.53 (d, J=5.9 Hz, 2H), 1.86-1.96 (m, 1H), 0.87-0.97 (m, 2H), 0.56-0.76 (m, 2H).

Example 127

1-((6-cyclopropylimidazo[1,2-a]pyridin-2-yl)methyl)-N-(2-fluoro-3-methoxy-6-(1H-tetrazol-1-yl)benzyl)-1H-pyrrole-3-carboxamide (I-54)

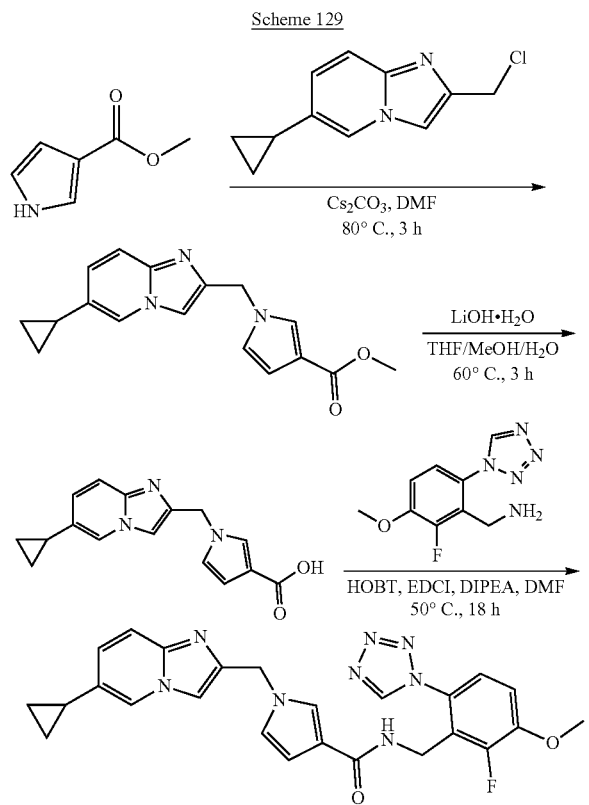

Synthesis of methyl 1-((6-cyclopropylimidazo[1,2-a]pyridin-2-yl)methyl)-1H-pyrrole-3-carboxylate. A mixture of 2-(chloromethyl)-6-cyclopropylimidazo[1,2-a]pyridine (207 mg, 1.0 mmol), methyl 1H-pyrrole-3-carboxylate (140 mg, 1.12 mmol), and Cs2CO3 (652 mg, 2 mmol) in DMF (5 mL) was stirred at 80° C. for 3 h. The reaction mixture was diluted with water (60 mL) and extracted with EtOAc (40 mL×3). The combined organic layers were washed with brine (40 mL), dried over Na2SO4 and concentrated in vacuo. The residue was purified by Prep-TLC (DCM: MeOH=20:1) to afford methyl 1-((6-cyclopropylimidazo[1,2-a]pyridin-2-yl)methyl)-1H-pyrrole-3-carboxylate (72 mg, yield: 24%) as a white solid. ESI-MS [M+H]+: 296.1.

Synthesis of 1-((6-cyclopropylimidazo[1,2-a]pyridin-2-yl)methyl)-1H-pyrrole-3-carboxylic acid. To a solution of methyl 1-((6-cyclopropylimidazo[1,2-a]pyridin-2-yl)methyl)-1H-pyrrole-3-carboxylate (72 mg, 0.24 mmol) in THF/MeOH/H2O (2 mL/2 mL/1 mL) was added LiOH H2O (20 mg, 0.47 mmol). The reaction mixture was stirred at 60° C. for 3 h. The mixture was adjusted to pH 3 and concentrated to give crude 1-((6-cyclopropylimidazo[1,2-a]pyridin-2-yl)methyl)-1H-pyrrole-3-carboxylic acid (90 mg, crude) as a white solid which was used in the next step without further purification. ESI-MS [M+H]+: 282.1.

Synthesis of 1-((6-cyclopropylimidazo[1,2-a]pyridin-2-yl)methyl)-N-(2-fluoro-3-methoxy-6-(1H-tetrazol-1-yl)benzyl)-1H-pyrrole-3-carboxamide. A mixture of 1-((6-cyclopropylimidazo[1,2-a]pyridin-2-yl)methyl)-1H-pyrrole-3-carboxylic acid (52 mg, 0.13 mmol, crude), (2-fluoro-3-methoxy-6-(1H-tetrazol-1-yl)phenyl)methanamine (33 mg, 0.13 mmol), HOBT (64 mg, 0.47 mmol), EDCI (96 mg, 0.47 mmol) and DIPEA (150 mg, 1.2 mmol) in DMF (3 mL) was stirred at 50° C. for 18 h. The reaction mixture was diluted with water (40 mL) and extracted with EtOAc (20 mL×5). The combined organic layers were washed with brine (30 mL), dried over Na2SO4 and concentrated in vacuo. The residue was purified by Prep-TLC (DCM:MeOH=10:1) to give 1-((6-cyclopropylimidazo[1,2-a]pyridin-2-yl)methyl)-N-(2-fluoro-3-methoxy-6-(1H-tetrazol-1-yl)benzyl)-1H-pyrrole-3-carboxamide (9.7 mg, yield: 17% over 2 steps) as a white solid. ESI-MS [M+H]+: 487.2. 1H NMR (400 MHz, DMSO) δ 9.74 (s, 1H), 8.31 (s, 1H), 8.07 (t, J=5.1 Hz, 1H), 7.63 (s, 1H), 7.37-7.27 (m, 4H), 6.97 (d, J=9.3 Hz, 1H), 6.79-6.75 (m, 1H), 6.34-6.31 (m, 1H), 5.11 (s, 2H), 4.13 (d, J=4.7 Hz, 2H), 3.91 (s, 3H), 1.91-1.85 (m, 1H), 0.94-0.85 (m, 2H), 0.69-0.61 (m, 2H).

Example 128

1-(1-((6-cyclopropylimidazo[1,2-a]pyridin-2-yl)methyl)-1H-1,2,3-triazol-4-yl)-N-(2-fluoro-3-methoxy-6-(1H-tetrazol-1-yl)benzyl)methanamine (I-29)

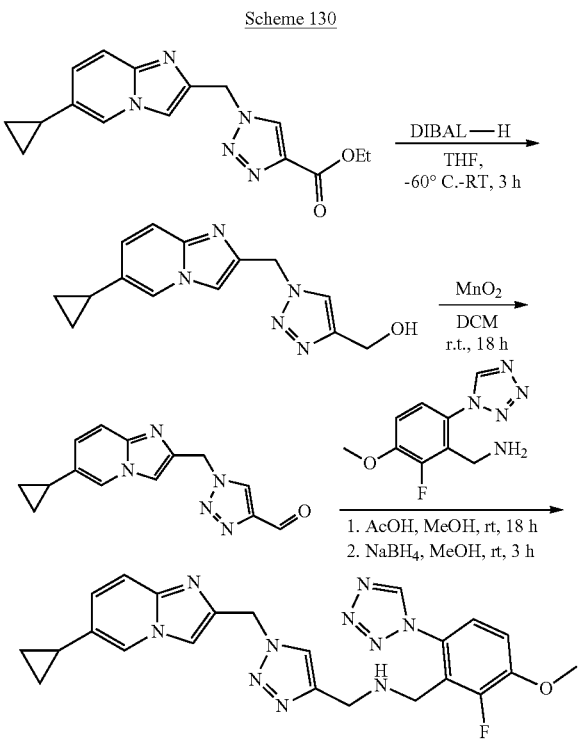

Synthesis of (1-((6-cyclopropylimidazo[1,2-a]pyridin-2-yl)methyl)-1H-1,2,3-triazol-4-yl)methanol. To a solution of ethyl 1-((6-cyclopropylimidazo[1,2-a]pyridin-2-yl)methyl)-1H-1,2,3-triazole-4-carboxylate (10.0 g, 33.7 mmol) in THF (100 mL) was added DIBAL-H (67.3 mL, 67.3 mmol) at −60° C. The mixture was stirred at room temperature for 3 h and then quenched with saturated aq. NaHCO$_3$ solution (300 mL) and extracted with EtOAc (150 mL×3). The combined organic layers were washed with brine (200 mL), dried over Na$_2$SO$_4$ and concentrated in vacuo. The residue was purified by flash column chromatography (PE/EtOAc from 0 to 20%) to give (1-((6-cyclopropylimidazo[1,2-a]pyridin-2-yl)methyl)-1H-1,2,3-triazol-4-yl)methanol (7.5 g, yield: 82%) as an off-white solid. ESI-MS [M+H]$^+$: 270.1.

Synthesis of 1-((6-cyclopropylimidazo[1,2-a]pyridin-2-yl)methyl)-1H-1,2,3-triazole-4-carbaldehyde. A mixture of (1-((6-cyclopropylimidazo[1,2-a]pyridin-2-yl)methyl)-1H-1,2,3-triazol-4-yl)methanol (300 mg, 1.12 mmol) and MnO$_2$ (963 mg, 11.2 mmol) in DCM (10 mL) was stirred at room temperature for 18 h. The reaction mixture was then filtered and concentrated in vacuo to give 1-((6-cyclopropylimidazo[1,2-a]pyridin-2-yl)methyl)-1H-1,2,3-triazole-4-carbaldehyde (220 mg, yield: 74%) as a yellow solid which was used in the next step without purification. ESI-MS [M+H]$^+$: 268.1

Synthesis of 1-(1-((6-cyclopropylimidazo[1,2-a]pyridin-2-yl)methyl)-1H-1,2,3-triazol-4-yl)-N-(2-fluoro-3-methoxy-6-(1H-tetrazol-1-yl)benzyl)methanamine. A mixture of (2-fluoro-3-methoxy-6-(1H-tetrazol-1-yl)phenyl)methanamine (50 mg, 0.22 mmol) and 1-((6-cyclopropylimidazo[1,2-a]pyridin-2-yl)methyl)-1H-1,2,3-triazole-4-carbaldehyde (60 mg, 0.22 mmol) in MeOH (5 mL) was added AcOH (0.1 mL) at rt. The reaction mixture was stirred at rt for 18 h. Then NaBH$_4$ (12.5 mg, 0.33 mmol) was added and the mixture was stirred for 3 h. The reaction was quenched with H$_2$O (20 mL) and extracted with EtOAc (20 mL×3). The combined organic layers were washed with brine (20 mL), dried over Na$_2$SO$_4$, concentrated in vacuo and purified by Prep-HPLC to give 1-(1-((6-cyclopropylimidazo[1,2-a]pyridin-2-yl)methyl)-1H-1,2,3-triazol-4-yl)-N-(2-fluoro-3-methoxy-6-(1H-tetrazol-1-yl)penzyl)methanamine (32.8 mg, 30.7%) as a white solid. ESI-MS [M+H]+: 475.1. $^1$H NMR (400 MHz, DMSO) δ 9.77 (s, 1H), 8.34 (s, 1H), 7.81 (s, 1H), 7.77 (s, 1H), 7.42-7.39 (m, 2H), 7.34-7.29 (m, 1H), 7.01 (dd, J=9.3, 1.5 Hz, 1H), 5.61 (s, 2H), 3.93 (s, 3H), 3.56 (d, J=6.5 Hz, 2H), 3.51 (d, J=5.5 Hz, 2H), 2.44-2.30 (m, 1H), 2.01-1.80 (m, 1H), 1.00-0.91 (m, 2H), 0.70-0.65 (m, 2H).

Example 129

2-((6-cyclopropylimidazo[1,2-a]pyridin-2-yl)methyl)-N-(2-fluoro-3-methoxy-6-(1H-tetrazol-1-yl)benzyl)-2H-tetrazole-5-carboxamide (I-28)

Scheme 131

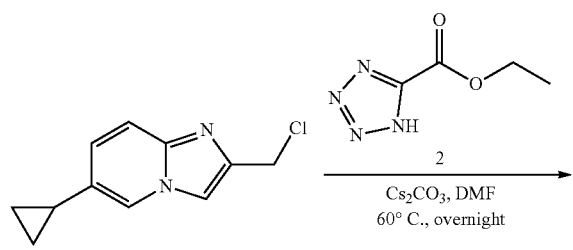

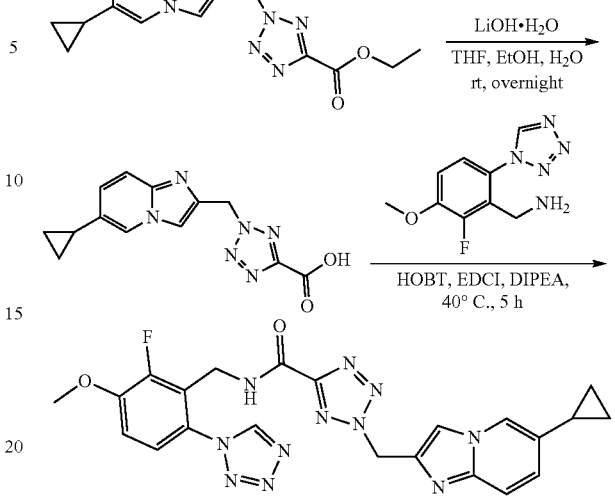

Synthesis of ethyl 2-((6-cyclopropylimidazo[1,2-a]pyridin-2-yl)methyl)-2H-tetrazole-5-carboxylate. A solution of 2-(chloromethyl)-6-cyclopropylimidazo[1,2-a]pyridine (206 mg, 1.0 mmol), ethyl 1H-tetrazole-5-carboxylate (284 mg, 2.0 mmol) and Cs$_2$CO$_3$ (652 mg, 2.0 mmol) in DMF (5 mL) was stirred at 60° C. overnight. Water (20 mL) was added and the mixture was extracted with EtOAc (50 mL×5). The combined organic layers were washed with brine (25 mL), dried over Na$_2$SO$_4$, concentrated and purified by Prep-TLC (DCM/MeOH=40/1) to afford ethyl 2-((6-cyclopropylimidazo[1,2-a]pyridin-2-yl)methyl)-2H-tetrazole-5-carboxylate as a white solid (70 mg, 22%). ESI-MS [M+H]$^+$: 313.2.

Synthesis of 2-((6-cyclopropylimidazo[1,2-a]pyridin-2-yl)methyl)-2H-tetrazole-5-carboxylic acid. A mixture of ethyl 2-((6-cyclopropylimidazo[1,2-a]pyridin-2-yl)methyl)-2H-tetrazole-5-carboxylate (35 mg, 0.112 mmol) and LiOH H$_2$O (9.5 mg, 0.224 mmol) in THF (2 mL), ethanol (2 mL) and H$_2$O (0.5 mL) was stirred at room temperature overnight. The reaction mixture was adjusted to pH=1 by adding HCl (3 M, aq.), and concentrated in vacuo to give crude 2-((6-cyclopropylimidazo[1,2-a]pyridin-2-yl)methyl)-2H-tetrazole-5-carboxylic acid, which was used in the next step without further purification. ESI-MS [M+H]$^+$: 285.1.

Synthesis of 2-((6-cyclopropylimidazo[1,2-a]pyridin-2-yl)methyl)-N-(2-fluoro-3-methoxy-6-(1H-tetrazol-1-yl)benzyl)-2H-tetrazole-5-carboxamide. A solution of crude 2-((6-cyclopropylimidazo[1,2-a]pyridin-2-yl)methyl)-2H-tetrazole-5-carboxylic acid (50 mg crude from previous step), (2-fluoro-3-methoxy-6-(1H-tetrazol-1-yl)phenyl)methanamine (30 mg, 0.134 mmol), HOBT (30 mg, 0.224 mmol), EDCI (43 mg, 0.224 mmol) and DIPEA (72 mg, 0.56 mmol) in DMF (2 mL) was stirred at 40° C. for 5 h. Water (30 mL) was added and the mixture was extracted with EtOAc (50 mL×3). The combined organic layers were washed with brine, dried over Na$_2$SO$_4$, and concentrated in vacuo to give the crude, which was purified by Prep-TLC (DCM/MeOH=40/1) to afford 2-((6-cyclopropylimidazo[1,2-a]pyridin-2-yl)methyl)—N-(2-fluoro-3-methoxy-6-(1H-tetrazol-1-yl)benzyl)-2H-tetrazole-5-carboxamide as a white solid (31.2 mg, 57%, 2 steps). ESI-MS [M+H]$^+$: 490.1. $^1$H NMR (400 MHz, DMSO) δ 9.74 (s, 1H), 9.32 (t, J=5.3 Hz, 1H), 8.35 (s, 1H), 7.93 (s, 1H), 7.39-7.35 (m, 3H), 7.01 (dd, J=9.4, 1.5 Hz, 1H), 6.04 (s, 2H), 4.33 (d, J=5.0 Hz, 2H), 3.92 (s, 3H), 1.96-1.89 (m, 1H), 0.94-0.89 (m, 2H), 0.69-0.65 (m, 2H).

Example 130

1-((6-cyclopropylimidazo[1,2-a]pyridin-2-yl)methyl)-N-(2-fluoro-3-methoxy-6-(1H-tetrazol-1-yl)benzyl)-3,5-dimethyl-1H-pyrazole-4-carboxamide (I-15)

Scheme 132

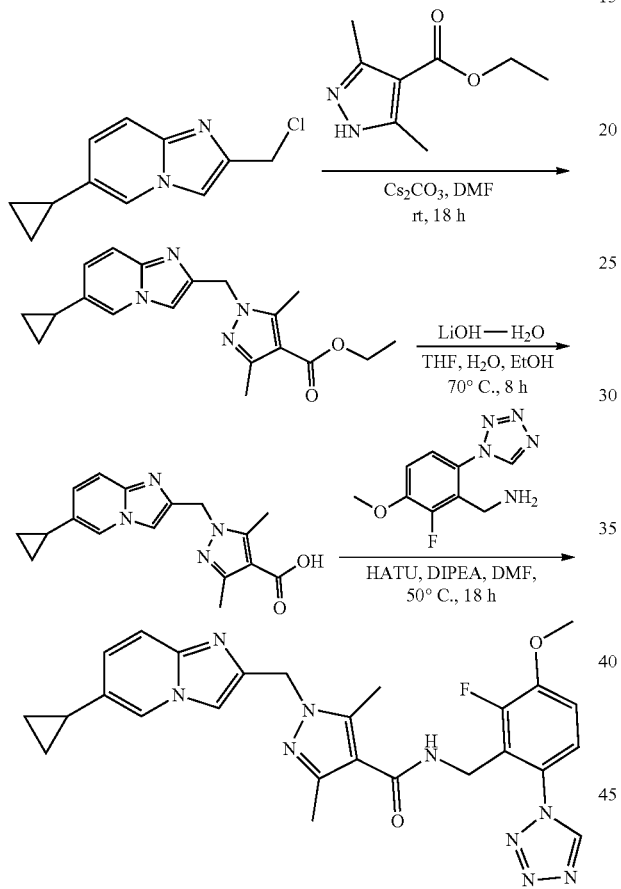

Synthesis of ethyl 1-((6-cyclopropylimidazo[1,2-a]pyridin-2-yl)methyl)-3,5-dimethyl-1H-pyrazole-4-carboxylate. A mixture of 2-(chloromethyl)-6-cyclopropylimidazo[1,2-a]pyridine (100 mg, 0.485 mmol), ethyl 3,5-dimethyl-1H-pyrazole-4-carboxylate (98 mg, 0.582 mmol) and $Cs_2CO_3$ (474 mg, 1.455 mmol) in DMF (1 ml) was stirred at room temperature for 18 h. Water (20 mL) was added and the mixture was extracted with EtOAc (10 mL×3). The combined organic layers were washed with brine (20 mL), dried over $Na_2SO_4$ and concentrated to give the crude which was purified by Prep-TLC (DCM/MeOH=20/1) to give 1-((6-cyclopropylimidazo[1,2-a]pyridin-2-yl)methyl)-3,5-dimethyl-1H-pyrazole-4-carboxylate (150 mg, yield: 91%) as a yellow solid. ESI-MS: [M+H]$^+$, 339.2.

Synthesis of 1-((6-cyclopropylimidazo[1,2-a]pyridin-2-yl)methyl)-3,5-dimethyl-1H-pyrazole-4-carboxylic acid. A solution of ethyl 1-((6-cyclopropylimidazo[1,2-a]pyridin-2-yl)methyl)-3,5-dimethyl-1H-pyrazole-4-carboxylate (150 mg, 0.443 mmol) and LiOH—$H_2O$ (56 mg, 1.331 mmol) in EtOH (0.5 ml), THF (0.75 ml) and (1.0 ml) was stirred at 70° C. for 8 h. The mixture was adjusted to pH 3 using 1M HCl and then concentrated in vacuo to give crude 1-((6-cyclopropylimidazo[1,2-a]pyridin-2-yl)methyl)-3,5-dimethyl-1H-pyrazole-4-carboxylic acid (200 mg, crude) as a yellow solid which was used in the next step without further purification. ESI-MS: [M+H]$^+$, 311.3.

Synthesis of 1-((6-cyclopropylimidazo[1,2-a]pyridin-2-yl)methyl)-N-(2-fluoro-3-methoxy-6-(1H-tetrazol-1-yl)benzyl)-3,5-dimethyl-1H-pyrazole-4-carboxamide. A solution of 1-((6-cyclopropylimidazo[1,2-a]pyridin-2-yl)methyl)-3,5-dimethyl-1H-pyrazole-4-carboxylic acid (50 mg, 0.161 mmol), (2-fluoro-3-methoxy-6-(1H-tetrazol-1-yl)phenyl)methanamine (36 mg, 0.161 mmol), DIPEA (62 mg, 0.483 mmol) and HATU (92 mg, 0.242 mmol) in DMF (1 mL) was stirred at 50° C. for 18 h. Water (20 mL) was added and the mixture was extracted with EtOAc (10 mL×3). The combined organic layers were washed with brine (30 mL), dried over $Na_2SO_4$ and concentrated to give the crude which was purified by Prep-TLC (DCM/MeOH=10/1) to afford 1-((6-cyclopropylimidazo[1,2-a]pyridin-2-yl)methyl)—N-(2-fluoro-3-methoxy-6-(1H-tetrazol-1-yl)benzyl)-3,5-dimethyl-1H-pyrazole-4-carboxamide (12 mg, 14.5%) as a white solid. ESI-MS: [M+H]$^+$, 516.3. $^1$H NMR (400 MHz, DMSO) δ 9.79 (s, 1H), 8.28 (s, 1H), 7.79-7.75 (m, 1H), 7.56 (s, 1H), 7.41-7.30 (m, 3H), 6.99-6.94 (m, 1H), 5.22 (s, 2H), 4.25 (d, J=4.7 Hz, 2H), 3.94 (s, 3H), 2.31 (s, 3H), 2.07 (s, 3H), 1.94-1.86 (m, 1H), 0.94-0.84 (m, 2H), 0.68-0.62 (m, 2H).

Example 131

5-(6-cyclopropylimidazo[1,2-a]pyridin-2-yl)-N-(2-fluoro-3-methoxy-6-(1H-tetrazol-1-yl)benzyl)-6,7-dihydro-5H-pyrrolo[1,2-a]imidazole-3-carboxamide (I-24)

Scheme 133

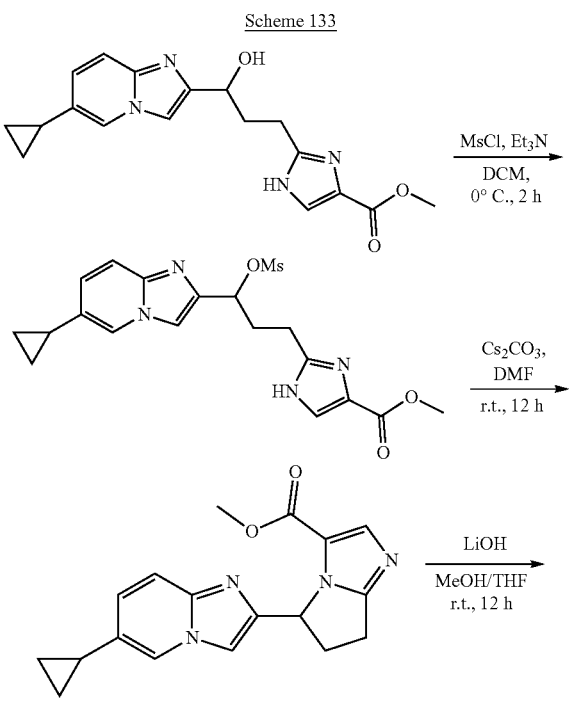

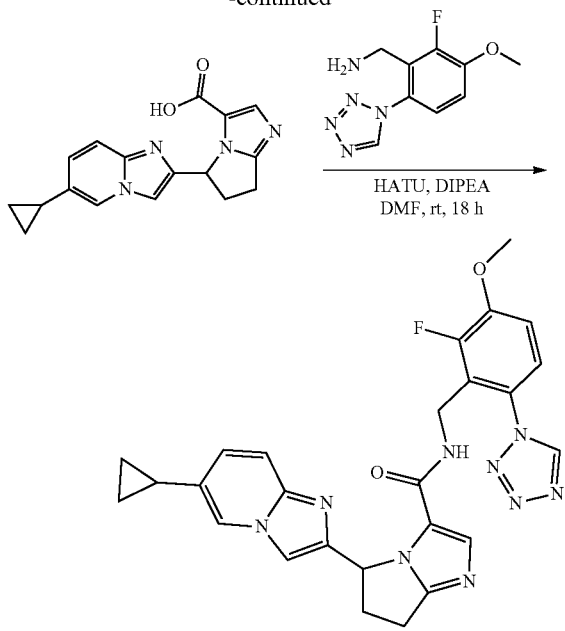

Synthesis of methyl 2-(3-(6-cyclopropylimidazo[1,2-a]pyridin-2-yl)-3-((methylsulfonyl)oxy)propyl)-1H-imidazole-4-carboxylate. To a solution of methyl 2-(3-(6-cyclopropylimidazo[1,2-a]pyridin-2-yl)-3-hydroxypropyl)-1H-imidazole-4-carboxylate (200 mg, 0.59 mmol) in DCM (4 mL) at 0° C. was added triethylamine (119.3 mg, 1.18 mmol) and MsCl (101.2 g, 0.88 mmol). After stirring at 0° C. for 2 h, the reaction was concentrated in vacuo to give methyl 2-(3-(6-cyclopropylimidazo[1,2-a]pyridin-2-yl)-3-((methylsulfonyl)oxy)propyl)-1H-imidazole-4-carboxylate (240 mg, yield: 98%) as a black solid which was used in the subsequent step without further purification. ESI-MS [M+H]$^+$: 419.1.

Synthesis of methyl 5-(6-cyclopropylimidazo[1,2-a]pyridin-2-yl)-6,7-dihydro-5H-pyrrolo[1,2-a]imidazole-3-carboxylate. A mixture of methyl 2-(3-(6-cyclopropylimidazo[1,2-a]pyridin-2-yl)-3-((methylsulfonyl)oxy)propyl)-1H-imidazole-4-carboxylate (240 mg, 0.57 mmol) and Cs$_2$CO$_3$ (557 mg, 1.71 mmol) in DMF (15 mL) was stirred at room temperature for 12 h. Water (30 mL) was added and the mixture was extracted with EtOAc (50 mL×3). The combined organic layers were washed with brine, dried over Na$_2$SO$_4$, and concentrated in vacuo to give the crude, which was purified by silica gel chromatography (EtOAc/PE=1/1) to give methyl 5-(6-cyclopropylimidazo[1,2-a]pyridin-2-yl)-6,7-dihydro-5H-pyrrolo[1,2-a]imidazole-3-carboxylate (102 mg, yield: 55.7%) as a yellow solid. ESI-MS [M+H]$^+$: 323.1.

Synthesis of 5-(6-cyclopropylimidazo[1,2-a]pyridin-2-yl)-6,7-dihydro-5H-pyrrolo[1,2-a]imidazole-3-carboxylic acid. To a solution of methyl 5-(6-cyclopropylimidazo[1,2-a]pyridin-2-yl)-6,7-dihydro-5H-pyrrolo[1,2-a]imidazole-3-carboxylate (102 mg, 0.32 mmol) in MeOH (1 mL) and THF (1 mL) was added LiOH (31.6 mg, 1.32 mmol) and H$_2$O (0.5 mL). The reaction mixture was stirred at room temperature for 12 h. The mixture was adjusted pH 5 with 1 N HCl and then extracted with EtOAc (30 mL×3). The combined organic layers were concentrated to give 5-(6-cyclopropylimidazo[1,2-a]pyridin-2-yl)-6,7-dihydro-5H-pyrrolo[1,2-a]imidazole-3-carboxylic acid (65 mg, yield:67%) as a white solid which was used in the subsequent reaction without further purification. ESI-MS [M+H]+: 309.1.

Synthesis of 5-(6-cyclopropylimidazo[1,2-a]pyridin-2-yl)-N-(2-fluoro-3-methoxy-6-(1H-tetrazol-1-yl)benzyl)-6,7-dihydro-5H-pyrrolo[1,2-a]imidazole-3-carboxamide. To a solution of 5-(6-cyclopropylimidazo[1,2-a]pyridin-2-yl)-6,7-dihydro-5H-pyrrolo[1,2-a]imidazole-3-carboxylic acid (65 mg, 0.21 mmol) in DMF (2 mL) was added (2-fluoro-3-methoxy-6-(1H-tetrazol-1-yl)phenyl)methanamine (60.2 mg, 0.27 mmol), HATU (102.6 mg, 0.27 mmol) and DIPEA (387 mg, 3.0 mmol). The reaction mixture was stirred at room temperature for 18 h. Water (20 mL) was added and the mixture was extracted with EtOAc (20 mL×3). The combined organic layers were washed with brine (30 mL), dried over Na$_2$SO$_4$, filtered and concentrated to give the crude, which was purified by Prep-HPLC to give 5-(6-cyclopropylimidazo[1,2-a]pyridin-2-yl)-N-(2-fluoro-3-methoxy-6-(1H-tetrazol-1-yl)benzyl)-6,7-dihydro-5H-pyrrolo[1,2-a]imidazole-3-carboxamide as a white solid (32 mg, yield: 30%). ESI-MS [M+H]+: 514.2. Purity: 99.04% (214 nm), 99.44% (254 nm). $^1$H NMR (400 MHz, DMSO) δ 9.67 (s, 1H), 8.41-8.38 (m, 1H), 8.26 (s, 1H), 7.42 (s, 1H), 7.41-7.38 (m, 4H), 6.98 (d, J=9.3 Hz, 1H), 5.73 (d, J=7.6 Hz, 1H), 4.26-4.21 (m, 1H), 4.16-4.10 (m, 1H), 3.92 (s, 3H), 2.96-2.90 (m, 2H), 2.80-2.72 (m, 1H), 2.69-2.60 (m, 1H), 1.93-1.86 (m, 1H), 0.93-0.83 (m, 2H), 0.71-0.65 (m, 2H).

Example 132

5-(6-cyclopropylimidazo[1,2-a]pyridin-2-yl)-N-(2-fluoro-3-methoxy-6-(1H-tetrazol-1-yl)benzyl)-6,7-dihydro-5H-pyrrolo[1,2-a]imidazole-2-carboxamide (I-22)

Scheme 134

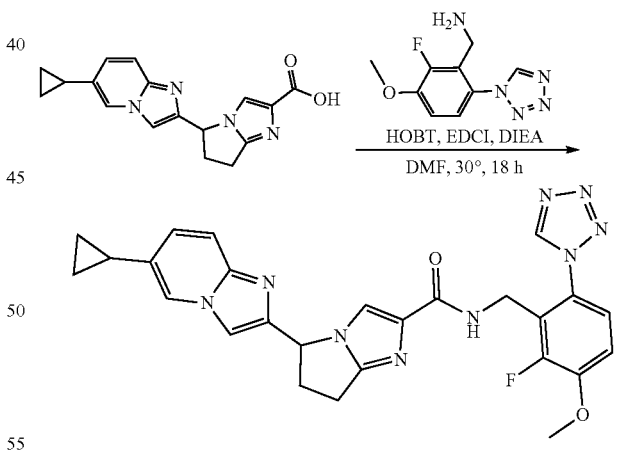

Synthesis of 5-(6-cyclopropylimidazo[1,2-a]pyridin-2-yl)-N-(2-fluoro-3-methoxy-6-(1H-tetrazol-1-yl)benzyl)-6,7-dihydro-5H-pyrrolo[1,2-a]imidazole-2-carboxamide. A mixture of 5-(6-cyclopropylimidazo[1,2-a]pyridin-2-yl)-6,7-dihydro-5H-pyrrolo[1,2-a]imidazole-2-carboxylic acid (80 mg, 0.26 mmol crude), (2-fluoro-3-methoxy-6-(1H-tetrazol-1-yl)phenyl)methanamine (66 mg, 0.29 mmol), HOBT (39 mg, 0.29 mmol), EDCI (55 mg, 0.29 mmol) and DIPEA (75 mg, 0.58 mmol) in DMF (3 mL) was stirred at 30° C. for 18 h. The reaction mixture was diluted with water (50 mL) and extracted with EtOAc (15 mL×3). The combined organic layer was washed with brine and concentrated in vacuo. The residue was purified by prep-HPLC to afford 5-(6-cyclopropylimidazo[1,2-a]pyridin-2-yl)-N-(2-fluoro-3-methoxy-6-(1H-tetrazol-1-yl)benzyl)-6,7-dihydro-5H-pyrrolo[1,2-a]imidazole-2-carboxamide as white solid (28 mg, yield: 21%). ESI-MS [M+H]+: 514.2. ¹H NMR (400 MHz, DMSO) δ 9.76 (s, 1H), 8.41 (s, 1H), 8.21 (s, 1H), 7.85 (s, 1H), 7.51-7.49 (m, 2H), 7.42-7.33 (m, 2H), 7.17 (d, J=7.2 Hz, 1H), 5.66-5.63 (m, 1H), 4.25 (d, J=5.0 Hz, 2H), 3.93 (s, 3H), 3.03-2.89 (m, 3H), 2.79-2.71 (m, 1H), 2.03-1.91 (m, 1H), 1.01-0.90 (m, 2H), 0.74-0.67 (m, 2H).

Example 133

3-(6-cyclopropylimidazo[1,2-a]pyridin-2-yl)-N-(2-fluoro-3-methoxy-6-(1H-tetrazol-1-yl)benzyl)-2,3-dihydroimidazo[2,1-b]oxazole-6-carboxamide (I-9)

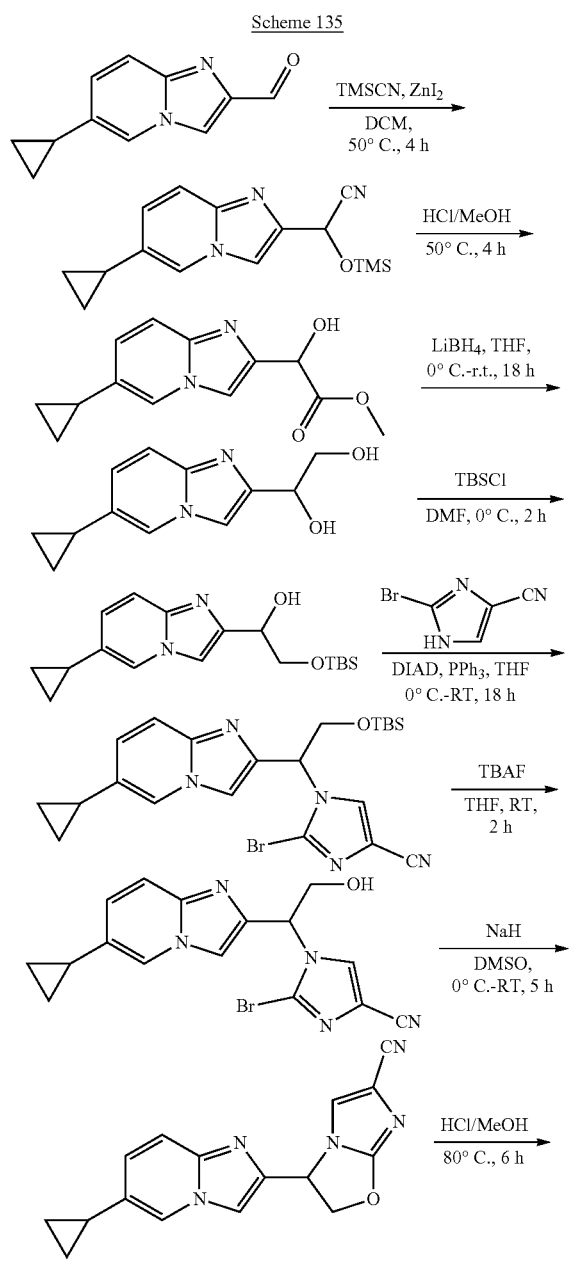

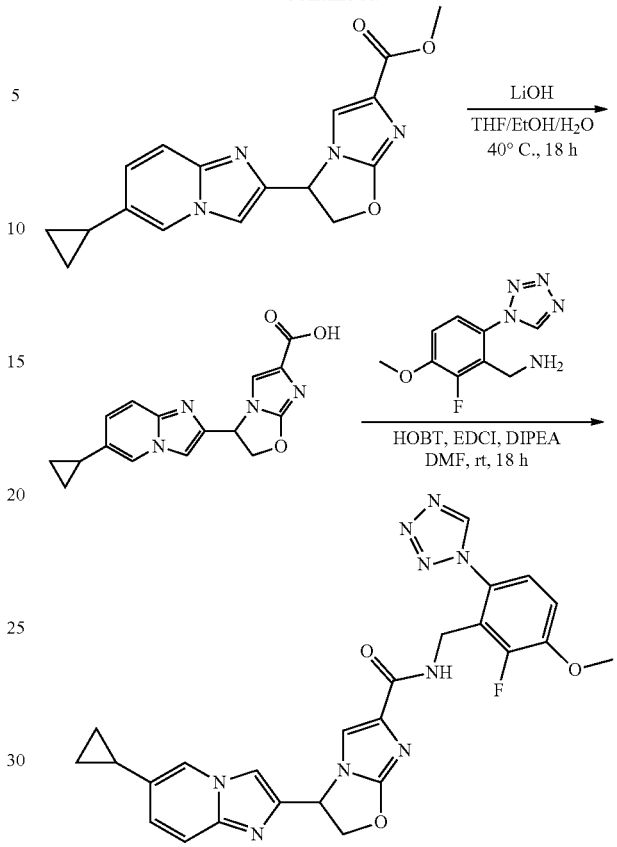

Synthesis of 2-(6-cyclopropylimidazo[1,2-a]pyridin-2-yl)-2-((trimethylsilyl)oxy)acetonitrile. To a solution of 6-cyclopropylimidazo[1,2-a]pyridine-2-carbaldehyde (3.0 g, 16.1 mmol) and ZnI₂ (510 mg, 1.6 mmol) in DCM (80 mL) was added TMSCN (2.4 g, 24.2 mmol) at room temperature. The reaction mixture was stirred at 50° C. for 4 h. Water (30 mL) was added and the mixture was extracted with DCM (50 mL×3). The combined organic layers were washed with brine (50 mL), dried over Na₂SO₄, and concentrated in vacuo to give 2-(6-cyclopropylimidazo[1,2-a]pyridin-2-yl)-2-((trimethylsilyl)oxy)acetonitrile (4.0 g, crude) as a brown oil, which was used into next step directly without further purification. ESI-MS [M+H]+: 286.1.

Synthesis of methyl 2-(6-cyclopropylimidazo[1,2-a]pyridin-2-yl)-2-hydroxyacetate. A solution of 2-(6-cyclopropylimidazo[1,2-a]pyridin-2-yl)-2-((trimethylsilyl)oxy)acetonitrile (3.4 g, 11.9 mmol) in HCl/MeOH (80 mL, 4M) was stirred at 50° C. for 4 h. The reaction mixture was concentrated in vacuo. The residue was purified by flash chromatography (MeOH/DCM from 0 to 5%) to give methyl 2-(6-cyclopropylimidazo[1,2-a]pyridin-2-yl)-2-hydroxyacetate (2.2 g, yield: 75%) as a yellow solid. ESI-MS [M+H]+: 247.1.

Synthesis of 1-(6-cyclopropylimidazo[1,2-a]pyridin-2-yl)ethane-1,2-diol. To a mixture of methyl 2-(6-cyclopropylimidazo[1,2-a]pyridin-2-yl)-2-hydroxyacetate (1.0 g, 4.1 mmol) in THF (15 mL) was added LiBH₄ (179 mg, 8.2 mmol) at 0° C. The reaction mixture was stirred at room temperature for 18 h. The reaction was quenched with saturated aqueous NaHCO₃ (50 mL) and extracted with EtOAc (30 mL×5). The organic layers were washed with brine (50 mL), dried over Na₂SO₄ and concentrated in vacuo to give the crude, which was purified by flash chromatography (MeOH/DCM from 0 to 10%) to give 1-(6-cyclopropylimidazo[1,2-a]pyridin-2-yl)ethane-1,2-diol (750 mg, yield: 83.8%) as a yellow oil. ESI-MS [M+H]+: 219.1.

Synthesis of 2-((tert-butyldimethylsilyl)oxy)-1-(6-cyclopropylimidazo[1,2-a]pyridin-2-yl)ethan-1-ol. To a mixture of 1-(6-cyclopropylimidazo[1,2-a]pyridin-2-yl)ethane-1,2-diol (750 mg, 3.44 mmol) and imidazole (468 mg, 6.88 mmol) in DMF (10 mL) was added TBSCl (628 mg, 3.78 mmol) in DMF (2 mL) at 0° C. The reaction mixture was stirred at 0° C. for 2 h. The reaction was quenched with saturated aq. NaHCO$_3$(150 mL) and extracted with EtOAc (30 mL×5). The organic layers were washed with brine (50 mL), dried over Na$_2$SO$_4$ and concentrated in vacuo. The residue was purified by flash column chromatography (MeOH/DCM from 0 to 5%) to give 2-((tert-butyldimethylsilyl)oxy)-1-(6-cyclopropylimidazo[1,2-a]pyridin-2-yl)ethan-1-ol (700 mg, yield: 61%) as an off-white solid. ESI-MS [M+H]$^+$: 333.2.

Synthesis of 2-bromo-1-(2-((tert-butyldimethylsilyl)oxy)-1-(6-cyclopropylimidazo[1,2-a]pyridin-2-yl)ethyl)-1H-imidazole-4-carbonitrile. To a solution of 2-((tert-butyldimethylsilyl)oxy)-1-(6-cyclopropylimidazo[1,2-a]pyridin-2-yl)ethan-1-ol (600 mg, 1.8 mmol), 2-bromo-1H-imidazole-4-carbonitrile (464 mg, 2.7 mmol) and PPh$_3$ (943 mg, 3.6 mmol) in THF (100 mL) was added DIAD (727 mg, 3.6 mmol) at 0° C. The reaction mixture was stirred at RT for 18 h. The reaction was quenched with saturated aqueous NaHCO$_3$ solution (50 mL) and extracted with DCM (30 mL×3). The organic layers were washed with brine (30 mL), dried over Na$_2$SO$_4$ and concentrated in vacuo. The residue was purified by flash chromatography (MeOH/DCM from 0 to 3%) to give 2-bromo-1-(2-((tert-butyldimethylsilyl)oxy)-1-(6-cyclopropylimidazo[1,2-a]pyridin-2-yl)ethyl)-1H-imidazole-4-carbonitrile (900 mg). ESI-MS [M+H]$^+$: 486.1

Synthesis of 2-bromo-1-(1-(6-cyclopropylimidazo[1,2-a]pyridin-2-yl)-2-hydroxyethyl)-1H-imidazole-4-carbonitrile. A mixture of 2-bromo-1-(2-((tert-butyldimethylsilyl)oxy)-1-(6-cyclopropylimidazo[1,2-a]pyridin-2-yl)ethyl)-1H-imidazole-4-carbonitrile (850 mg, 1.75 mmol) and TBAF (1.75 mL, 1.75 mmol) in THF (10 mL) was stirred at room temperature for 2 h. The reaction was quenched with saturated aqueous NaHCO$_3$(50 mL) and extracted with DCM (30 mL×3). The organic layers were washed with brine (30 mL), dried over Na$_2$SO$_4$ and concentrated in vacuo. The residue was purified by flash column chromatography (MeOH/DCM from 0 to 5%) to give 2-bromo-1-(1-(6-cyclopropylimidazo[1,2-a]pyridin-2-yl)-2-hydroxyethyl)-1H-imidazole-4-carbonitrile (80 mg, 12% yield for two steps) as a yellow oil. ESI-MS [M+H]$^+$: 372.0.

Synthesis of 3-(6-cyclopropylimidazo[1,2-a]pyridin-2-yl)-2,3-dihydroimidazo[2,1-b]oxazole-6-carbonitrile. To a mixture of 2-bromo-1-(1-(6-cyclopropylimidazo[1,2-a]pyridin-2-yl)-2-hydroxyethyl)-1H-imidazole-4-carbonitrile (80 mg, 0.22 mmol) in DMSO (2 mL) was added NaH (17 mg, 0.43 mmol) at 0° C. The reaction mixture was stirred at RT for 5 h. The reaction was quenched with saturated aqueous NH$_4$Cl solution (30 mL) and extracted with DCM (30 mL×3). The organic layers were washed with brine (30 mL), dried over Na$_2$SO$_4$ and concentrated in vacuo. The residue was purified by Prep-TLC (MeOH/DCM=1/15) to give 3-(6-cyclopropylimidazo[1,2-a]pyridin-2-yl)-2,3-dihydroimidazo[2,1-b]oxazole-6-carbonitrile (30 mg, yield: 48%) as an off-white solid. ESI-MS [M+H]$^+$: 292.1.

Synthesis of methyl 3-(6-cyclopropylimidazo[1,2-a]pyridin-2-yl)-2,3-dihydroimidazo[2,1-b]oxazole-6-carboxylate. A mixture of 3-(6-cyclopropylimidazo[1,2-a]pyridin-2-yl)-2,3-dihydroimidazo[2,1-b]oxazole-6-carbonitrile (30 mg, 0.1 mmol) in HCl/MeOH (5 mL, 4M) was stirred at 80° C. for 6 h. The reaction mixture was concentrated in vacuo to give methyl 3-(6-cyclopropylimidazo[1,2-a]pyridin-2-yl)-2,3-dihydroimidazo[2,1-b]oxazole-6-carboxylate (40 mg, crude) as a yellow oil which was used in next step directly without further purification. ESI-MS [M+H]$^+$: 325.1.

Synthesis of 3-(6-cyclopropylimidazo[1,2-a]pyridin-2-yl)-2,3-dihydroimidazo[2,1-b]oxazole-6-carboxylic acid. A mixture of methyl 3-(6-cyclopropylimidazo[1,2-a]pyridin-2-yl)-2,3-dihydroimidazo[2,1-b]oxazole-6-carboxylate (40 mg, ~0.1 mmol, crude) and LiOH—H$_2$O (8 mg, 0.2 mmol) in THF/EtOH/H$_2$O (2 mL/2 mL/0.5 mL) was stirred at 40° C. for 18 h. The mixture was adjusted to pH 4 with HCl (1N), and concentrated in vacuo to give crude 3-(6-cyclopropylimidazo[1,2-a]pyridin-2-yl)-2,3-dihydroimidazo[2,1-b]oxazole-6-carboxylic acid (50 mg, crude) as a yellow oil, which was used in next step directly without further purification. ESI-MS [M+H]$^+$: 311.1.

Synthesis of 3-(6-cyclopropylimidazo[1,2-a]pyridin-2-yl)-N-(2-fluoro-3-methoxy-6-(1H-tetrazol-1-yl)benzyl)-2,3-dihydroimidazo[2,1-b]oxazole-6-carboxamide. A mixture of 3-(6-cyclopropylimidazo[1,2-a]pyridin-2-yl)-2,3-dihydroimidazo[2,1-b]oxazole-6-carboxylic acid (50 mg, ~0.1 mmol, crude), (2-fluoro-3-methoxy-6-(1H-tetrazol-1-yl)phenyl)methanamine (33 mg, 0.2 mmol), HOBT (20 mg, 0.15 mmol), EDCI (29 mg, 0.15 mmol) and DIPEA (39 mg, 0.30 mmol) in dry DMF (2 mL) was stirred at room temperature for 18 h. Water (30 mL) was added and the mixture was extracted with EtOAc (30 mL×3). The organic layers were washed with brine (30 mL), dried over Na$_2$SO$_4$ and concentrated in vacuo. The residue was purified by Prep-TLC (MeOH/DCM=1/10) to give 3-(6-cyclopropylimidazo[1,2-a]pyridin-2-yl)-N-(2-fluoro-3-methoxy-6-(1H-tetrazol-1-yl)benzyl)-2,3-dihydroimidazo[2,1-b]oxazole-6-carboxamide (5 mg, yield: 10% over three steps) as a yellow solid. ESI-MS [M+H]$^+$: 516.3. $^1$H NMR (400 MHz, DMSO) δ 10.63 (s, 1H), 9.74 (s, 1H), 8.31 (s, 1H), 8.26 (s, 1H), 7.75 (s, 1H), 7.49-7.31 (m, 3H), 7.24 (s, 1H), 7.04 (d, J=10.0 Hz, 1H), 5.88 (s, 1H), 5.44 (s, 1H), 4.23 (d, J=3.6 Hz, 2H), 3.94 (s, 3H), 2.02-1.91 (m, 1H), 0.97-0.89 (m, 2H), 0.71-0.64 (m, 2H).

Example 134

5-(6-cyclopropylimidazo[1,2-a]pyridin-2-yl)-N-((3-fluoro-4-methoxypyridin-2-yl)methyl)-6,7-dihydro-5H-pyrrolo[1,2-a]imidazole-3-carboxamide (I-6)

Scheme 136

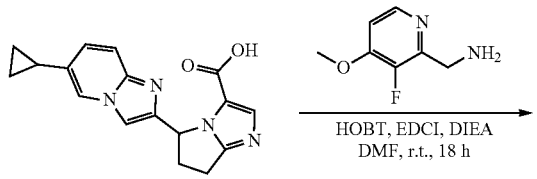

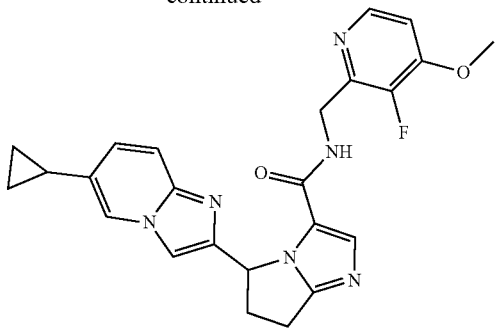

Synthesis of 5-(6-cyclopropylimidazo[1,2-a]pyridin-2-yl)-N-((3-fluoro-4-methoxypyridin-2-yl)methyl)-6,7-dihydro-5H-pyrrolo[1,2-a]imidazole-3-carboxamide. The mixture of 5-(6-cyclopropylimidazo[1,2-a]pyridin-2-yl)-6,7-dihydro-5H-pyrrolo[1,2-a]imidazole-3-carboxylic acid (45 mg, 0.1 mmol, crude), (3-fluoro-4-methoxypyridin-2-yl)methanamine (23 mg, 0.15 mmol), HOBT (20 mg, 0.15 mmol), EDCI (29 mg, 0.15 mmol) and DIEA (39 mg, 0.30 mmol) in DMF (2 mL) was stirred at room temperature in $N_2$ for 18 h. The reaction mixture was diluted with water (30 mL) and extracted with EtOAc (20 mL×5). The combined organic layers were washed with brine (20 mL), dried over $Na_2SO_4$ and concentrated in vacuo. The residue was purified by prep-TLC (MeOH/DCM=1/15) to afford 5-(6-cyclopropylimidazo[1,2-a]pyridin-2-yl)-N-((3-fluoro-4-methoxypyridin-2-yl)methyl)-6,7-dihydro-5H-pyrrolo[1,2-a]imidazole-3-carboxamide (12 mg, 27% yield) as a white solid. ESI-MS [M+H]+: 447.2. $^1$H NMR (400 MHz, DMSO) δ=8.60 (t, J=5.8, 1H), 8.25 (s, 1H), 8.16 (d, J=5.5, 1H), 7.63 (s, 1H), 7.38 (s, 1H), 7.34 (d, J=9.3, 1H), 7.17-7.11 (m, 1H), 7.01-6.95 (m 1H), 5.82 (d, J=8.0, 1H), 4.58-4.51 (m, 1H), 4.37-4.28 (m, 1H), 3.90 (s, 3H), 3.01-2.92 (m, 2H), 2.69-2.59 (m, 2H), 1.93-1.86 (m, 1H), 0.93-0.87 (m, 2H), 0.67-0.63 (m, 2H).

Example 135

5-(6-cyclopropylimidazo[1,2-a]pyridin-2-yl)-N-((3-fluoro-4-methoxypyridin-2-yl)methyl)-6,7-dihydro-5H-pyrrolo[1,2-a]imidazole-2-carboxamide (I-5)

Synthesis of 5-(6-cyclopropylimidazo[1,2-a]pyridin-2-yl)-N-((3-fluoro-4-methoxypyridin-2-yl)methyl)-6,7-dihydro-5H-pyrrolo[1,2-a]imidazole-2-carboxamide. To a solution of 5-(6-cyclopropylimidazo[1,2-a]pyridin-2-yl)-6,7-dihydro-5H-pyrrolo[1,2-a]imidazole-2-carboxylic acid (55 mg crude from previous step), (3-fluoro-4-methoxypyridin-2-yl)methanamine (25 mg, 0.16 mmol), HOBT (32 mg, 0.24 mmol), EDCI (46 mg, 0.24 mmol) in DMF (5 mL) was added DIPEA (80 mg, 0.62 mmol). The reaction mixture was stirred at room temperature for 18 h. Water (50 mL) was added and the mixture was extracted with EtOAc (25 mL×3). The combined organic layers were washed with brine (25 mL), dried over $Na_2SO_4$, and concentrated in vacuo to give the crude product. The residue was purified by Prep-TLC (DCM/MeOH=10/1) to give 5-(6-cyclopropylimidazo[1,2-a]pyridin-2-yl)-N-((3-fluoro-4-methoxypyridin-2-yl)methyl)-6,7-dihydro-5H-pyrrolo[1,2-a]imidazole-2-carboxamide (7 mg, over 2 step yield: 12.7%) as a white solid. ESI-MS [M+H]+: 447.2. $^1$H NMR (400 MHz, DMSO) δ 8.33 (s, 1H), 8.29-8.20 (m, 2H), 7.76 (s, 1H), 7.47 (s, 1H), 7.42 (d, J=9.3 Hz, 1H), 7.20 (t, J=4.0 Hz, 1H), 7.02 (d, J=9.0 Hz, 1H), 5.60-5.54 (m, 1H), 4.55 (s, 2H), 3.93 (s, 3H), 3.01-2.86 (m, 3H), 2.78-2.72 (m, 1H), 2.02-1.95 (m, J=16.3, 6.8 Hz, 1H), 0.93-0.90 (m, 2H), 0.73-0.62 (m, 2H).

Example 136

7-(6-cyclopropylimidazo[1,2-a]pyridin-2-yl)-N-(2-fluoro-3-methoxy-6-(1H-tetrazol-1-yl)benzyl)-6,7-dihydro-5H-pyrrolo[1,2-b][1,2,4]triazole-2-carboxamide (I-4)

Scheme 137

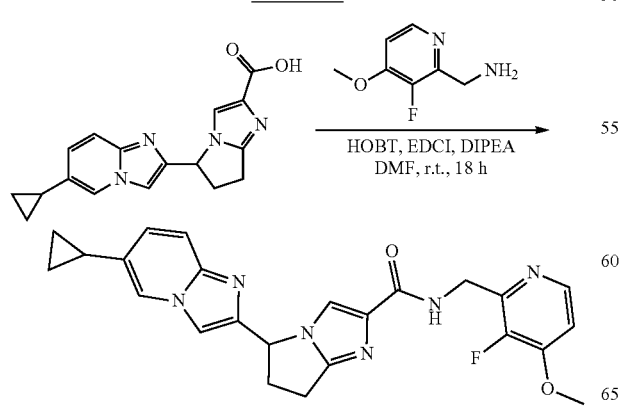

HOBT, EDCI, DIPEA
DMF, r.t., 18 h

Scheme 138

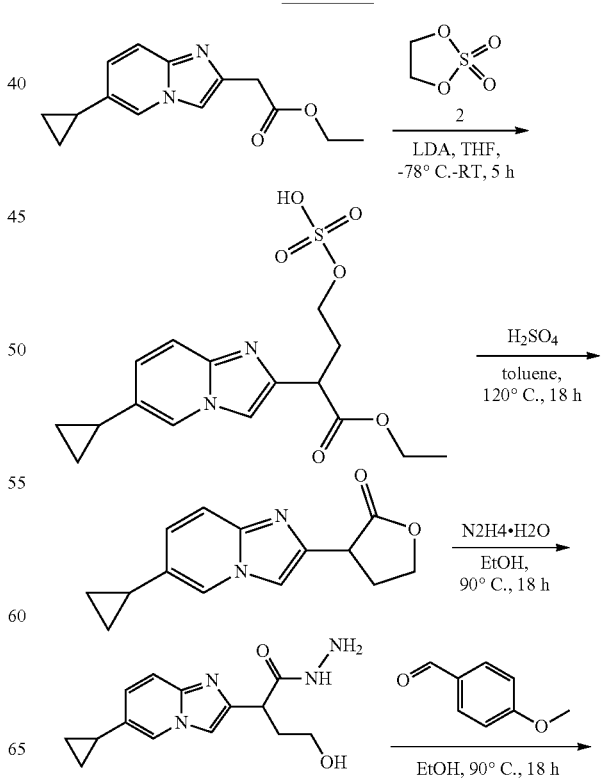

2
LDA, THF,
-78° C.-RT, 5 h $H_2SO_4$
toluene,
120° C., 18 h

N2H4•H2O
EtOH,
90° C., 18 h

EtOH, 90° C., 18 h

-continued

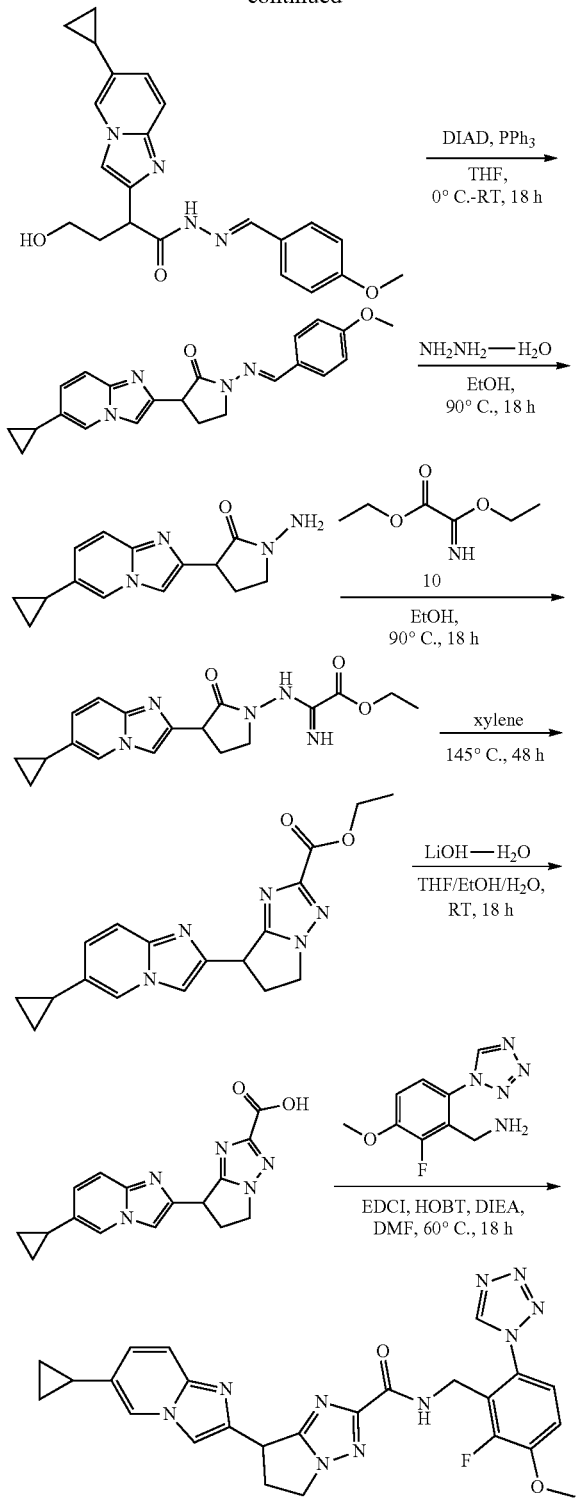

Synthesis of ethyl 2-(6-cyclopropylimidazo[1,2-a]pyridin-2-yl)-4-(sulfooxy)butanoate. To a mixture of ethyl 2-(6-cyclopropylimidazo[1,2-a]pyridin-2-yl)acetate (3.5 g, 14.3 mmol) in THF (50 mL) was added LDA (8.6 mL, 17.2 mmol) at −78° C. and the mixture stirred at −78° C. for 0.5 h. 1,3,2-dioxathiolane 2,2-dioxide (2.1 g, 17.2 mmol) was added at −78° C. and the mixture was warmed to RT and stirred for 5 h. The reaction mixture was quenched with saturated NH₄Cl solution (200 mL) and extracted with EtOAc (100 mL×5). The combined organic layers were washed with brine (100 mL), dried over Na₂SO₄ and concentrated in vacuo to give crude ethyl 2-(6-cyclopropylimidazo[1,2-a]pyridin-2-yl)-4-(sulfooxy)butanoate (3.5 g, crude) as a brown oil, which was used in next step directly without further purification. ESI-MS [M+H]+: 369.1.

Synthesis of 3-(6-cyclopropylimidazo[1,2-a]pyridin-2-yl)dihydrofuran-2(3H)-one. A mixture of ethyl 2-(6-cyclopropylimidazo[1,2-a]pyridin-2-yl)-4-(sulfooxy)butanoate (3.5 g, crude) in H₂SO₄ (150 mL, 20% solution) and toluene was stirred at 120° C. for 18 h under N₂.

The reaction mixture was cooled to room temperature, adjusted to pH-7 and extracted with EtOAc (50 mL×3). The combined organic layers were washed with brine (50 mL), dried over Na₂SO₄ and concentrated in vacuo. The residue was purified by flash column chromatography (MeOH/DCM from 0 to 3%) to give 3-(6-cyclopropylimidazo[1,2-a]pyridin-2-yl)dihydrofuran-2(3H)-one (1.25 g, 36% yield for two steps) as a yellow oil. ESI-MS [M+H]+: 243.1.

Synthesis of 2-(6-cyclopropylimidazo[1,2-a]pyridin-2-yl)-4-hydroxybutanehydrazide. A mixture of 3-(6-cyclopropylimidazo[1,2-a]pyridin-2-yl)dihydrofuran-2(3H)-one (1.25 g, 5.2 mmol) in EtOH (15 mL) was stirred at 90° C. for 18 h under N₂. The reaction mixture was cooled to room temperature and concentrated in vacuo to give crude 2-(6-cyclopropylimidazo[1,2-a]pyridin-2-yl)-4-hydroxybutanehydrazide (1.4 g, crude) as a yellow oil, which was used in next step directly without further purification. ESI-MS [M+H]+: 275.2.

Synthesis of 2-(6-cyclopropylimidazo[1,2-a]pyridin-2-yl)-4-hydroxy-N'-(4-methoxybenzylidene)butanehydrazide. A mixture of 2-(6-cyclopropylimidazo[1,2-a]pyridin-2-yl)-4-hydroxybutanehydrazide (1.4 g, 5.2 mmol) and 4-methoxybenzaldehyde (0.7 g, 5.2 mmol) in EtOH (20 mL) was stirred at 90° C. for 18 h under N₂. The reaction mixture was cooled to room temperature and concentrated in vacuo to give crude 2-(6-cyclopropylimidazo[1,2-a]pyridin-2-yl)-4-hydroxy-N'-(4-methoxybenzylidene)butanehydrazide (2.0 g, crude) as a yellow oil which was used in next step directly without further purification. ESI-MS [M+H]+: 393.2

Synthesis of (E)-3-(6-cyclopropylimidazo[1,2-a]pyridin-2-yl)-1-((4-methoxybenzylidene)amino)pyrrolidin-2-one. To the mixture of 2-(6-cyclopropylimidazo[1,2-a]pyridin-2-yl)-4-hydroxy-N'-(4-methoxybenzylidene)butanehydrazide (0.9 g, 2.3 mmol) and PPh₃ (1.2 g, 4.6 mmol) in THF (10 mL) was added DIAD (0.93 g, 4.6 mmol) at 0° C. and the mixture stirred at RT for 18 h. The reaction mixture was diluted with water (100 mL) and extracted with EtOAc (50 mL×3). The combined organic layers were washed with brine (50 mL), dried over Na₂SO₄ and concentrated in vacuo. The residue was purified by flash column chromatography (MeOH/DCM from 0 to 3%) to give 3-(6-cyclopropylimidazo[1,2-a]pyridin-2-yl)-1-((4-methoxybenzylidene)amino)pyrrolidin-2-one (0.32 g, 37% yield) as an off-white solid. ESI-MS [M+H]+: 375.2

Synthesis of 1-amino-3-(6-cyclopropylimidazo[1,2-a]pyridin-2-yl)pyrrolidin-2-one. A mixture of hydrazine hydrate (2.0 mL) and 3-(6-cyclopropylimidazo[1,2-a]pyridin-2-yl)-1-((4-methoxybenzylidene)amino)pyrrolidin-2-one (300 mg, 0.8 mmol) in EtOH (10.0 mL) was stirred at 90° C. for 18 h under N₂. The reaction mixture was cooled to room temperature and concentrated to give the crude product, which was purified by flash column chromatography (MeOH/DCM from 0 to 10%) to give 1-amino-3-(6- cyclopropylimidazo[1,2-a]pyridin-2-yl)pyrrolidin-2-one (200 mg, 97.6% yield) as a colorless oil. ESI-MS [M+H]+: 257.1.

Synthesis of ethyl 2-((3-(6-cyclopropylimidazo[1,2-a]pyridin-2-yl)-2-oxopyrrolidin-1-yl)amino)-2-iminoacetate. A mixture of 1-amino-3-(6-cyclopropylimidazo[1,2-a]pyridin-2-yl)pyrrolidin-2-one (190 mg, 0.74 mmol) and ethyl 2-ethoxy-2-iminoacetate (118 mg, 0.81 mmol) in EtOH (2.0 mL) was stirred at 90° C. for 18 h under N$_2$. The reaction mixture was cooled to room temperature and concentrated in vacuo to give ethyl 2-((3-(6-cyclopropylimidazo[1,2-a]pyridin-2-yl)-2-oxopyrrolidin-1-yl)amino)-2-iminoacetate (250 mg, crude) as a colorless oil which was used in next step directly without further purification. ESI-MS [M+H]+: 356.2

Synthesis of 2-((tert-butyldimethylsilyl)oxy)-1-(6-cyclopropylimidazo[1,2-a]pyridin-2-yl)ethan-1-ol. A mixture of ethyl 2-((3-(6-cyclopropylimidazo[1,2-a]pyridin-2-yl)-2-oxopyrrolidin-1-yl)amino)-2-iminoacetate (200 mg, 0.56 mmol) in xylene (5 mL) was stirred at 160° C. for 48 h under N$_2$. The reaction mixture was concentrated in vacuo and the crude product was purified by flash chromatography (MeOH/DCM from 0 to 5%) to give ethyl 7-(6-cyclopropylimidazo[1,2-a]pyridin-2-yl)-6,7-dihydro-5H-pyrrolo[1,2-b][1,2,4]triazole-2-carboxylate(90 mg, 47.6% yield) as a black oil. ESI-MS [M+H]$^+$: 338.2

Synthesis of 7-(6-cyclopropylimidazo[1,2-a]pyridin-2-yl)-6,7-dihydro-5H-pyrrolo[1,2-b][1,2,4]triazole-2-carboxylic acid A mixture of ethyl 7-(6-cyclopropylimidazo[1,2-a]pyridin-2-yl)-6,7-dihydro-5H-pyrrolo[1,2-b][1,2,4]triazole-2-carboxylate (45.0 mg, 0.13 mmol) and LiOH H$_2$O (16.8 mg, 0.40 mmol) in EtOH/THF/H$_2$O (3 mL/3 mL/3 mL) was stirred at room temperature for 18 h. The pH value of the reaction mixture was adjusted to 5 with 1 M HCl solution. The mixture was concentrated in vacuo to afford crude 7-(6-cyclopropylimidazo[1,2-a]pyridin-2-yl)-6,7-dihydro-5H-pyrrolo[1,2-b][1,2,4]triazole-2-carboxylic acid (60 mg, crude) as a yellow oil which was used in next step directly without further purification. ESI-MS [M+H]$^+$: 310.1.

Synthesis of 7-(6-cyclopropylimidazo[1,2-a]pyridin-2-yl)-N-(2-fluoro-3-methoxy-6-(1H-tetrazol-1-yl)benzyl)-6,7-dihydro-5H-pyrrolo[1,2-b][1,2,4]triazole-2-carboxamide. A mixture of 7-(6-cyclopropylimidazo[1,2-a]pyridin-2-yl)-6,7-dihydro-5H-pyrrolo[1,2-b][1,2,4]triazole-2-carboxylic acid (60.0 mg, 0.19 mmol), (2-fluoro-3-methoxy-6-(1H-tetrazol-1-yl)phenyl)methanamine (44.6 mg, 0.20 mmol), HOBT (27.0 mg, 0.20 mmol), EDCI (38.3 mg, 0.20 mmol) and DIPEA (38.8 mg, 0.30 mmol) in DMF (2 mL) was stirred at 60° C. under N$_2$ for 18 h. The reaction mixture was diluted with water (40 mL) and extracted with EtOAc (20 mL×5). The combined organic layers were washed with brine (10 mL), dried over Na$_2$SO$_4$ and concentrated in vacuo. The residue was purified by prep-TLC (MeOH/DCM=7%) to afford 7-(6-cyclopropylimidazo[1,2-a]pyridin-2-yl)-N-(2-fluoro-3-methoxy-6-(1H-tetrazol-1-yl)benzyl)-6,7-dihydro-5H-pyrrolo[1,2-b][1,2,4]triazole-2-carboxamide (14 mg, 21% yield) as an off-white solid. ESI-MS [M+H]$^+$: 515.2. Purity:97.50% (214 nm), 97.68% (254 nm). $^1$H NMR (400 MHz, DMSO) δ 9.74 (s, 1H), 8.63 (t, J=5.6 Hz, 1H), 8.31 (s, 1H), 7.74 (s, 1H), 7.40-7.30 (m, 3H), 7.00-6.95 (m, 1H), 4.65-4.59 (m, 1H), 4.35-4.29 (m, 1H), 4.25 (d, J=5.7 Hz, 2H), 4.23-4.17 (m, 1H), 3.18-3.06 (m, 1H), 2.89-2.79 (m, 1H), 1.95-1.89 (m, 1H), 0.96-0.87 (m, 2H), 0.71-0.63 (m, 2H).

Example 137

4-(6-cyclopropylimidazo[1,2-a]pyridin-2-yl)-N-(2-fluoro-3-methoxy-6-(1H-tetrazol-1-yl)benzyl)-5,6-dihydro-4H-pyrrolo[1,2-b]pyrazole-2-carboxamide (I-2)

Scheme 139

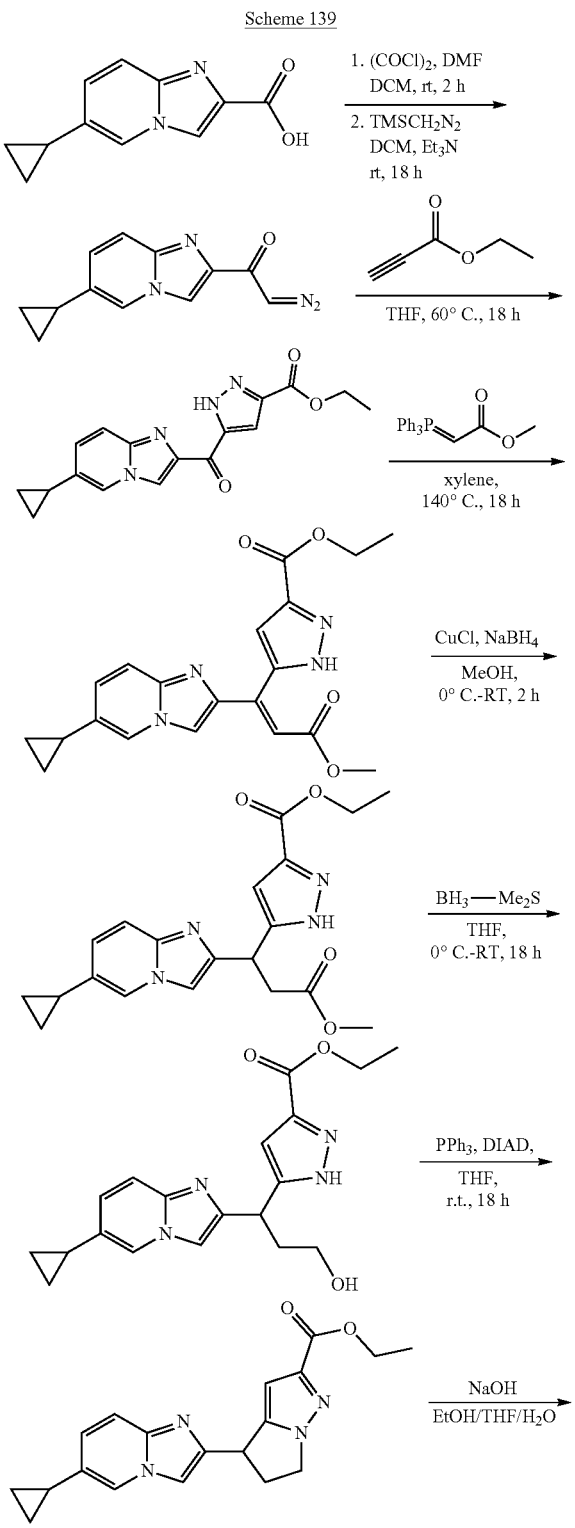

-continued

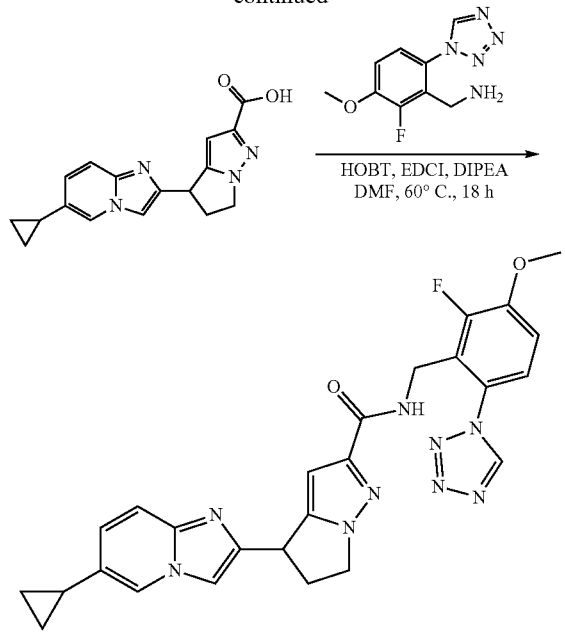

HOBT, EDCI, DIPEA
DMF, 60° C., 18 h

Synthesis of 1-(6-cyclopropylimidazo[1,2-a]pyridin-2-yl)-2-diazoethan-1-one. To a mixture of 6-cyclopropylimidazo[1,2-a]pyridine-2-carboxylic acid (1.2 g, 5.94 mmol) in DCM (20 mL) was added oxalyl chloride (2.5 mL, 29.7 mmol) and a drop of DMF. The reaction mixture was stirred at room temperature for 2 h and then concentrated in vacuo. DCM (20 mL) was added, followed by Et$_3$N (1.65 mL, 11.9 mmol) and TMSCH$_2$N$_2$ (5.94 mL, 11.9 mmol). The reaction mixture was stirred at room temperature for 18 h. Then the reaction was concentrated in vacuo to afford crude 1-(6-cyclopropylimidazo[1,2-a]pyridin-2-yl)-2-diazoethan-1-one (3.0 g, 13.26 mol) as a black solid which was used in next step directly without further purification. ESI-MS [M+H]+: 227.1.

Synthesis of ethyl 5-(6-cyclopropylimidazo[1,2-a]pyridine-2-carbonyl)-1H-pyrazole-3-carboxylate. A mixture of 1-(6-cyclopropylimidazo[1,2-a]pyridin-2-yl)-2-diazoethan-1-one (3.0 g, 13.26 mol) and ethyl propiolate (1.46 g, 14.9 mol) in THF (50 mL) was stirred at 60° C. for 18 h. The reaction was quenched with water (150 mL) and extracted with EtOAc (50 mL×5). The combined organic layers were washed with brine (30 mL), dried over Na$_2$SO$_4$ and concentrated in vacuo. The residue was purified by flash chromatography (MeOH/DCM from 0 to 5%) to afford ethyl 5-(6-cyclopropylimidazo[1,2-a]pyridine-2-carbonyl)-1H-pyrazole-3-carboxylate (400 mg, 9.3% yield) as a yellow solid. ESI-MS [M+H]+: 325.1.

Synthesis of ethyl 5-(1-(6-cyclopropylimidazo[1,2-a]pyridin-2-yl)-3-methoxy-3-oxoprop-1-en-1-yl)-1H-pyrazole-3-carboxylate. A mixture of ethyl 5-(6-cyclopropylimidazo[1,2-a]pyridine-2-carbonyl)-1H-pyrazole-3-carboxylate (560 mg, 1.73 mol) and methyl 2-(triphenyl-15-phosphanylidene)acetate (1.15 g, 3.44 mol) in xylene (20 mL) was stirred at 140° C. for 18 h. The reaction mixture was concentrated in vacuo. The residue was purified by flash chromatography (MeOH/DCM from 0 to 5%) to afford ethyl 5-(1-(6-cyclopropylimidazo[1,2-a]pyridin-2-yl)-3-methoxy-3-oxoprop-1-en-1-yl)-1H-pyrazole-3-carboxylate (280 mg, 43% yield) as a yellow solid. ESI-MS [M+H]+: 381.2.

Synthesis of ethyl 5-(1-(6-cyclopropylimidazo[1,2-a]pyridin-2-yl)-3-methoxy-3-oxopropyl)-1H-pyrazole-3-carboxylate. To a mixture of ethyl 5-(1-(6-cyclopropylimidazo[1,2-a]pyridin-2-yl)-3-methoxy-3-oxoprop-1-en-1-yl)-1H-pyrazole-3-carboxylate (300 mg, 0.79 mmol) and CuCl (117 mg, 1.18 mmol) in MeOH (10 mL) was added NaBH$_4$ (240 mg, 6.34 mmol) at 0° C. portionwise. The reaction mixture was stirred at 0° C. for 2 h. Then the reaction was quenched with water (50 mL) and extracted with EtOAc (30 mL×5). The combined organic layers were washed with brine (30 mL), dried over Na$_2$SO$_4$ and concentrated in vacuo. The residue was purified by flash chromatography (MeOH/DCM from 0 to 5%) to afford ethyl 5-(1-(6-cyclopropylimidazo[1,2-a]pyridin-2-yl)-3-methoxy-3-oxopropyl)-1H-pyrazole-3-carboxylate (180 mg, 59.6% yield) as a yellow oil. ESI-MS [M+H]+: 383.2

Synthesis of ethyl 5-(1-(6-cyclopropylimidazo[1,2-a]pyridin-2-yl)-3-hydroxypropyl)-1H-pyrazole-3-carboxylate. To a mixture of ethyl 5-(1-(6-cyclopropylimidazo[1,2-a]pyridin-2-yl)-3-methoxy-3-oxopropyl)-1H-pyrazole-3-carboxylate (180 mg, 0.47 mol) in THF (10 mL) was added BH$_3$-Me$_2$S (0.47 mL, 0.94 mol) at 0° C. The reaction mixture was stirred at room temperature for 18 h. Then the reaction was quenched with water (50 mL) and extracted with EtOAc (30 mL×5). The combined organic layers were washed with brine (30 mL×2), dried over Na$_2$SO$_4$ and concentrated in vacuo. The residue was purified by flash chromatography (MeOH/DCM from 0 to 5%) to afford ethyl 5-(1-(6-cyclopropylimidazo[1,2-a]pyridin-2-yl)-3-hydroxypropyl)-1H-pyrazole-3-carboxylate (100 mg, 60% yield, about 40% purity) as a yellow oil. ESI-MS [M+H]+: 355.2.

Synthesis of ethyl 4-(6-cyclopropylimidazo[1,2-a]pyridin-2-yl)-5,6-dihydro-4H-pyrrolo[1,2-b]pyrazole-2-carboxylate. To a mixture of ethyl 5-(1-(6-cyclopropylimidazo[1,2-a]pyridin-2-yl)-3-hydroxypropyl)-1H-pyrazole-3-carboxylate (100 mg, 0.28 mol) and PPh$_3$ (148 mg, 0.56 mol) in THF (10 mL) was added DIAD (113 mg, 0.56 mol) at 0° C. The reaction mixture was stirred at room temperature for 18 h. Then the reaction was quenched with water (50 mL) and extracted with EtOAc (30 mL×5). The combined organic layers were washed with brine (30 mL), dried over Na$_2$SO$_4$ and concentrated in vacuo. The residue was purified by flash column chromatography (MeOH/DCM from 0 to 5%) to afford ethyl 4-(6-cyclopropylimidazo[1,2-a]pyridin-2-yl)-5,6-dihydro-4H-pyrrolo[1,2-b]pyrazole-2-carboxylate (25 mg, 27% yield) as a yellow oil. ESI-MS [M+H]+: 337.2.

Synthesis of 4-(6-cyclopropylimidazo[1,2-a]pyridin-2-yl)-5,6-dihydro-4H-pyrrolo[1,2-b]pyrazole-2-carboxylic acid. A mixture of ethyl 4-(6-cyclopropylimidazo[1,2-a]pyridin-2-yl)-5,6-dihydro-4H-pyrrolo[1,2-b]pyrazole-2-carboxylate (25.0 mg, 0.074 mmol) and NaOH (6 mg, 0.149 mmol) in EtOH/THF/H$_2$O (3 mL/3 mL/3 mL) was stirred at room temperature for 2 h. The mixture was adjusted pH 5 using 1M HCl solution and then concentrated in vacuo to afford crude 4-(6-cyclopropylimidazo[1,2-a]pyridin-2-yl)-5,6-dihydro-4H-pyrrolo[1,2-b]pyrazole-2-carboxylic acid (30 mg, crude) as a yellow oil which was used in next step directly without further purification. ESI-MS [M+H]+: 309.1.

Synthesis of 4-(6-cyclopropylimidazo[1,2-a]pyridin-2-yl)-N-(2-fluoro-3-methoxy-6-(1H-tetrazol-1-yl)benzyl)-5,6-dihydro-4H-pyrrolo[1,2-b]pyrazole-2-carboxamide. A mixture of 4-(6-cyclopropylimidazo[1,2-a]pyridin-2-yl)-5,6-dihydro-4H-pyrrolo[1,2-b]pyrazole-2-carboxylic acid (30 mg, 0.097 mmol), (2-fluoro-3-methoxy-6-(1H-tetrazol-1-yl)phenyl)methanamine (25 mg, 0.112 mmol), HOBT (15 mg, 0.111 mmol), EDCI (21 mg, 0.111 mmol) and DIPEA (29 mg, 0.222 mmol) in DMF (2 mL) was stirred at 60° C. under $N_2$ for 18 h. The mixture was diluted with water (40 mL) and extracted with EtOAc (20 mL×5).

The combined organic layers were washed with brine (10 mL), dried over $Na_2SO_4$ and concentrated in vacuo. The residue was purified by prep-TLC (MeOH/DCM=7%) to afford 4-(6-cyclopropylimidazo[1,2-a]pyridin-2-yl)-N-(2-fluoro-3-methoxy-6-(1H-tetrazol-1-yl)benzyl)-5,6-dihydro-4H-pyrrolo[1,2-b]pyrazole-2-carboxamide (13 mg, 26% yield) as an off-white solid. ESI-MS $[M+H]^+$: 514.3. $^1$H NMR (400 MHz, MeOD) δ 9.49 (s, 1H), 8.14 (s, 1H), 7.55 (s, 1H), 7.35 (d, J=9.4 Hz, 1H), 7.31-7.26 (m, 2H), 7.10-7.05 (m, 1H), 6.43 (s, 1H), 4.65-4.59 (m, 1H), 4.41 (s, 2H), 4.35-4.29 (m, 1H), 4.24-4.18 (m, 1H), 3.97 (s, 3H), 3.17-3.07 (m, 1H), 2.80-2.70 (m, 1H), 1.97-1.88 (m, 1H), 1.00-0.93 (m, 2H), 0.73-0.67 (m, 2H).

Example 138

Synthesis of (5-chlorobenzo[d]isothiazol-3-yl)methanamine

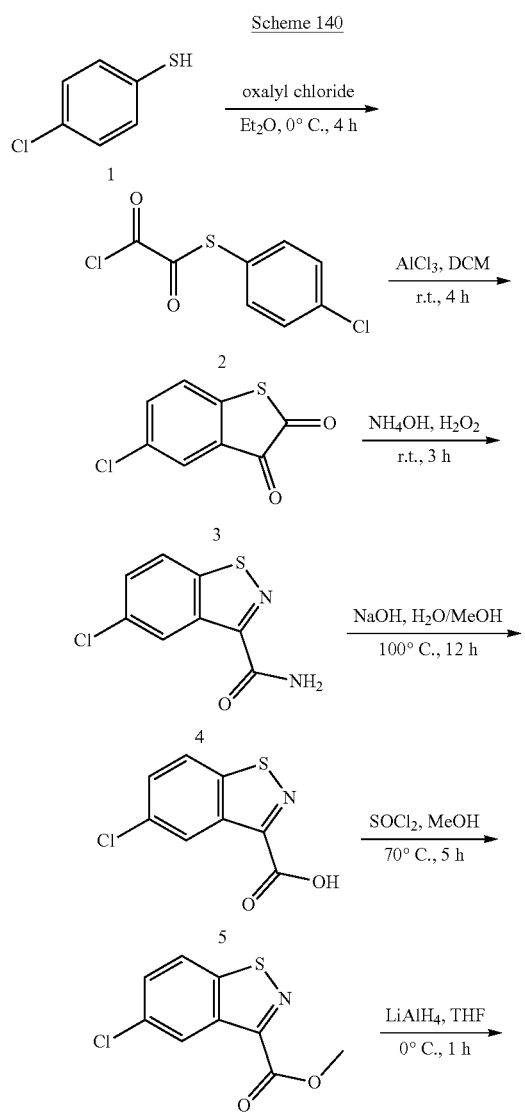

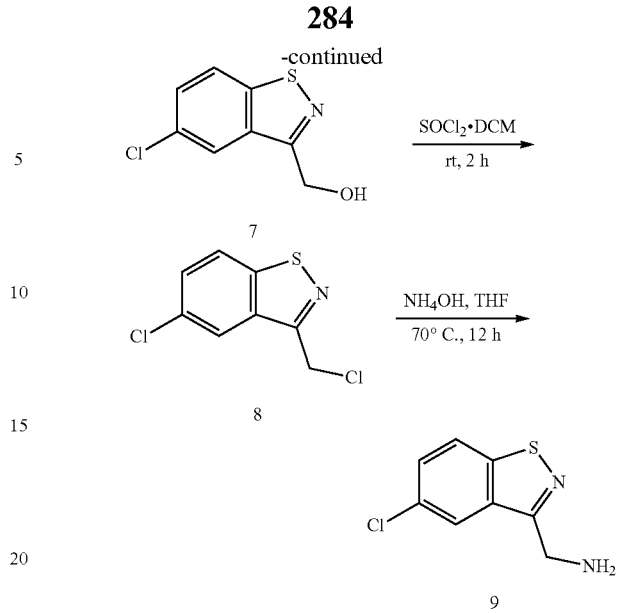

Synthesis of S-4-chlorophenyl 2-chloro-2-oxoethanethioate. To a solution of 4-chlorobenzenethiol (5 g, 34.7 mmol) in $Et_2O$ (50 mL) was added oxalyl chloride (7.06 g, 55.6 mmol) under nitrogen at 0° C. The reaction was stirred at 0° C. for 4 h. Then the mixture was concentrated in vacuo to give S-4-chlorophenyl 2-chloro-2-oxoethanethioate (5 g, crude), which was used in the next step directly without further purification. ESI-MS $[M+H]^+$: 235.2.

Synthesis of 5-chlorobenzo[b]thiophene-2,3-dione. To a solution of S-4-chlorophenyl 2-chloro-2-oxoethanethioate (5 g, 21.4 mmol) in DCM (100 mL) was added $AlCl_3$ (18.5 g, 138.8 mmol). The reaction was stirred at room temperature for 4 h. $H_2O$ (150 mL) was added and the mixture was extracted with DCM (100 mL×3). The combined organic layers were washed with brine, dried over $Na_2SO_4$, and concentrated in vacuo to give S-4-chlorophenyl 2-chloro-2-oxoethanethioate (3 g, crude), which was used in the next step directly without further purification. ESI-MS $[M+H]^+$: 199.2.

Synthesis of 5-chlorobenzo[d]isothiazole-3-carboxamide. To a solution of 5-chlorobenzo[b]thiophene-2,3-dione (1 g, 5.05 mmol) in $NH_4OH$ (20 mL) at room temperature was added $H_2O_2$ (687 mg, 20.2 mmol). The resulting reaction was stirred at room temperature for 3 h. $H_2O$ (50 mL) was added and the mixture was extracted with EtOAc (50 mL×3). The combined organic layers were washed with brine, dried over $Na_2SO_4$, filtered, and concentrated in vacuo to give the crude, which was purified by silica gel chromatography (PE/EtOAc=1/1) to give 5-chlorobenzo[d]isothiazole-3-carboxamide (150 mg, yield: 14%) as yellow oil. ESI-MS $[M+H]^+$: 213.3.

Synthesis of 5-chlorobenzo[d]isothiazole-3-carboxylic acid. To a solution of 5-chlorobenzo[d]isothiazole-3-carboxamide (150 mg, 0.71 mmol) in MeOH (5 mL) was added NaOH (5M, 0.7 mL) at room temperature. The resulting reaction was stirred at 100° C. for 12 h. $H_2O$ (15 mL) was added, the mixture was adjusted to pH 3 by adding 1M HCl solution, and then extracted with EtOAc (50 mL×3). The combined organic layers were dried over $Na_2SO_4$, filtered, and concentrated in vacuo to give 5-chlorobenzo[d]isothiazole-3-carboxylic acid (100 mg, crude) which was used in the next step directly without further purification. ESI-MS $[M+H]^+$: 214.2.

Synthesis of methyl 5-chlorobenzo[d]isothiazole-3-carboxylate. To a solution of 5-chlorobenzo[d]isothiazole-3-carboxylic acid (100 mg, 0.47 mmol) in MeOH (10 mL) was added SOCl$_2$ (554 mg, 4.7 mmol) at room temperature. The reaction mixture was stirred at 70° C. for 5 h. The mixture was concentrated in vacuo to give 5-chlorobenzo[d]isothiazole-3-carboxylic acid (100 mg, crude), which was used in the next step directly without further purification. ESI-MS [M+H]$^+$: 213.2.

Synthesis of (5-chlorobenzo[d]isothiazol-3-yl)methanol. To a solution of methyl 5-chlorobenzo[d]isothiazole-3-carboxylate (100 mg, 0.45 mmol) in THF (5 mL) was added LiAlH4 (0.45 mL, 0.45 mmol) at 0° C. The reaction mixture was stirred at 0° C. for 1 h. H$_2$O (15 mL) was added and the mixture was extracted with EtOAc (30 mL×3). The combined organic layers were washed with brine, dried over Na$_2$SO$_4$, and concentrated in vacuo to give the crude, which was purified by Prep-TLC (DCM/MeOH=10/1) to give (5-chlorobenzo[d]isothiazol-3-yl)methanol (30 mg, yield: 33%). ESI-MS [M+H]$^+$: 199.2.

Synthesis of 5-chloro-3-(chloromethyl)benzo[d]isothiazole. To a solution of (5-chlorobenzo[d]isothiazol-3-yl)methanol (30 mg, 0.15 mmol) in DCM (10 mL) was added SOCl$_2$ (177 mg, 1.5 mmol) at room temperature. The reaction mixture was stirred at room temperature for 2 h. The mixture was concentrated in vacuo to give 5-chloro-3-(chloromethyl)benzo[d]isothiazole (30 mg, crude), which was used in the next step without further purification. ESI-MS [M+H]$^+$: 218.1.

Synthesis of (5-chlorobenzo[d]isothiazol-3-yl)methanamine. To a solution of 5-chloro-3-(chloromethyl)benzo[d]isothiazole (30 mg, crude) in THF (10 mL) was added NH$_4$OH (10 mL) at room temperature. The resulting reaction was stirred at 70° C. for 12 h. The mixture was concentrated in vacuo to give (5-chlorobenzo[d]isothiazol-3-yl)methanamine (30 mg, crude) as a yellow oil, which was used in the next step without further purification. ESI-MS [M+H]$^+$: 199.2.

Example 139

Synthesis of 4-(aminomethyl)quinolin-2(1H)-one

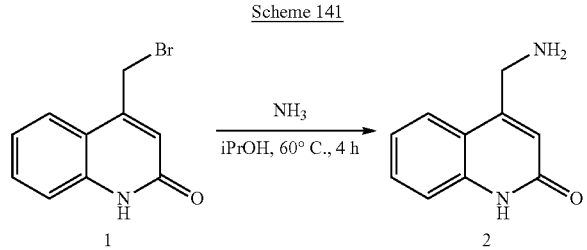

Scheme 141

Synthesis of 4-(aminomethyl)quinolin-2(1H)-one. A solution of 4-(bromomethyl)quinolin-2(1H)-one (100 mg, 0.42 mmol) and NH$_3$ (10 mL, 2 M solution in iPrOH) was stirred at 60° C. for 4 h. The reaction mixture was diluted with water (50 mL) and extracted with EtOAc (15 mL×3). The combined organic layers were dried over Na$_2$SO$_4$ and concentrated to give 4-(aminomethyl)quinolin-2(1H)-one (yellow solid, 70 mg, yield: 95%), which was used into next step without further purification. ESI-MS [M+H]+: 175.0.

Example 140

Synthesis of 2-(aminomethyl)-3-fluoro-4-methoxybenzonitrile

Scheme 142

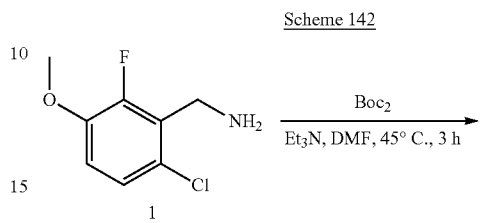

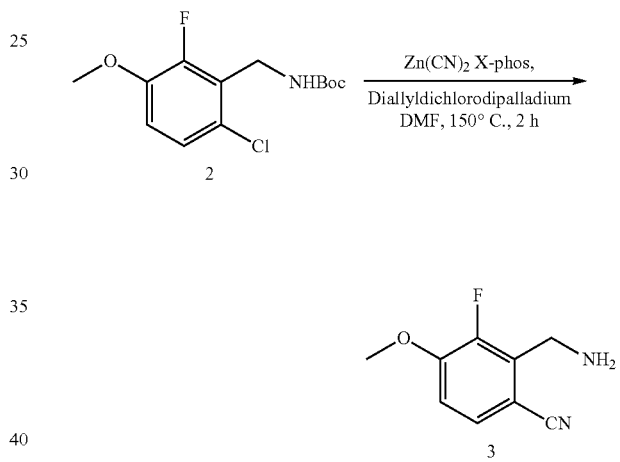

Synthesis of tert-butyl (6-chloro-2-fluoro-3-methoxybenzyl)carbamate. To a solution of (6-chloro-2-fluoro-3-methoxyphenyl)methanamine (2.00 g, 10.6 mmol) and Et$_3$N (4.4 mL, 31.8 mmol) in dry DMF (25 mL) was added Boc$_2$O (3.44 g, 15.9 mmol). The reaction mixture was heated at 45° C. for 3 h, then poured into water (60 mL) and extracted with EtOAc (50 mL×3). The combined organic layers were washed with brine, dried over sodium sulfate and concentrated in vacuo to give the crude, which was purified by silica gel chromatography (PE:EtOAc=5:1) to give tert-butyl (6-chloro-2-fluoro-3-methoxybenzyl)carbamate (1.6 g, yield: 52.3%) as a white solid. ESI-MS [M-55]+: 234.1; [M+23]$^+$: 312.1.

Synthesis of 2-(aminomethyl)-3-fluoro-4-methoxybenzonitrile. A mixture of tert-butyl (6-chloro-2-fluoro-3-methoxybenzyl)carbamate (1.6 g, 5.5 mmol), Zn(CN)$_2$ (650 mg, 5.5 mmol), X-phos (1.3 g, 2.75 mmol) and diallyldichlorodipalladium (1.0 g, 2.75 mmol) in dry DMF (30 mL) in a sealed tube was stirred at 150° C. for 2 h. The reaction mixture was concentrated in vacuo to give the crude, which was purified by silica gel column (DCM/MeOH=10/1) to give 2-(aminomethyl)-3-fluoro-4-methoxybenzonitrile (582 mg, yield: 58.5%) as a brown black solid. ESI-MS [M+H]$^+$: 181.1

Example 141

Synthesis of (5-chloro-2-(1H-tetrazol-5-yl)phenyl)methanamine

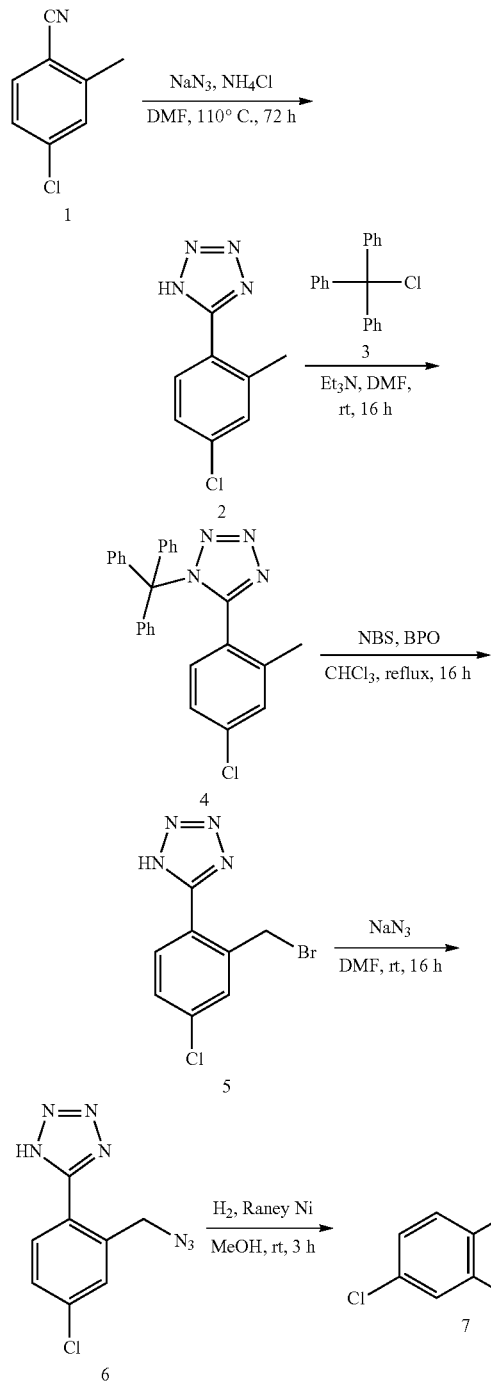

Scheme 143

Synthesis of 5-(4-chloro-2-methylphenyl)-1H-tetrazole. A mixture of 4-chloro-2-methylbenzonitrile (11.66 g, 76.92 mmol), NaN$_3$ (5 g, 76.92 mmol) and NH$_4$Cl (6.17 g, 115.38 mmol) in DMF (100 mL) was stirred at 110° C. for 72 h. The reaction mixture was poured onto water (500 mL) and extracted with EtOAc/THF (3×200 mL, 5/1 v/v). The combined organics were washed with brine (500 mL×3), dried over Na$_2$SO$_4$, concentrated and purified by silica gel chromatography (DCM/MeOH=10/1) to give 5-(4-chloro-2-methylphenyl)-1H-tetrazole (9.5 g, yield: 63%) as a yellow solid. ESI-MS [M+H]$^+$: 195.1.

Synthesis of 5-(4-chloro-2-methylphenyl)-1-trityl-1H-tetrazole. The mixture of 5-(4-chloro-2-methylphenyl)-1H-tetrazole (4.0 g, 20.55 mmol), TrCl (6.3 g, 22.61 mmol) and Et$_3$N (4.16 g, 41.1 mmol) in DMF (60 mL) was stirred at room temperature for 16 h. The reaction mixture was poured onto water (500 mL) and extracted with EtOAc/THF (3×200 mL, 5/1 v/v). The combined organics were washed with brine (400 mL×3), dried over Na$_2$SO$_4$, concentrated and purified by silica gel chromatography (EtOAc/PE=1/30) to give 5-(4-chloro-2-methylphenyl)-1-trityl-1H-tetrazole (6.5 g, yield: 72.4%) as a yellow solid. ESI-MS [M+H]$^+$: no mass.

Synthesis of 5-(2-(bromomethyl)-4-chlorophenyl)-1H-tetrazole. A mixture of 5-(4-chloro-2-methylphenyl)-1-trityl-1H-tetrazole (3.5 g, 8.0 mmol), NBS (1.71 g, 9.6 mmol) and BPO (97 mg, 0.4 mmol) in CHCl$_3$ (60 mL) was stirred at reflux for 16 h. The reaction mixture was concentrated and purified by silica gel chromatography (EtOAc/MeOH=20/1) to give 5-(2-(bromomethyl)-4-chlorophenyl)-1H-tetrazole (790 mg, yield: 36%) as a yellow solid. ESI-MS [M+H]$^+$: 273.0.

Synthesis of 5-(2-(azidomethyl)-4-chlorophenyl)-1H-tetrazole. A mixture of 5-(2-(bromomethyl)-4-chlorophenyl)-1H-tetrazole (790 mg, 2.89 mmol) and NaN$_3$ (225 mg, 3.47 mmol) in DMF (10 mL) was stirred at room temperature for 16 h. The reaction mixture was concentrated. The residue was dissolved in DCM/MeOH (100 mL), filtered and the filtrate was concentrated in vacuo. The crude was purified by silica gel chromatography (DCM/MeOH=10/1) to give 5-(2-(azidomethyl)-4-chlorophenyl)-1H-tetrazole (500 mg, yield: 73.5%) as a yellow solid. ESI-MS [M+H]$^+$: 236.1.

Synthesis of (5-chloro-2-(1H-tetrazol-5-yl)phenyl)methanamine. The mixture of 5-(2-(azidomethyl)-4-chlorophenyl)-1H-tetrazole (250 mg, 1.06 mmol) and Raney Ni (30 mg) in MeOH (5 mL) was stirred at room temperature for 3 h under H$_2$ atmosphere. The reaction mixture was filtered and rinsed with EtOAc (50 mL). The filtrate was concentrated and dried in vacuo to give (5-chloro-2-(1H-tetrazol-5-yl)phenyl)methanamine (222 mg, yield: 100%) as a yellow solid. ESI-MS [M+H]$^+$: 210.1.

Example 142

Synthesis of (5-chloro-2-(1H-tetrazol-1-yl)phenyl)methanamine

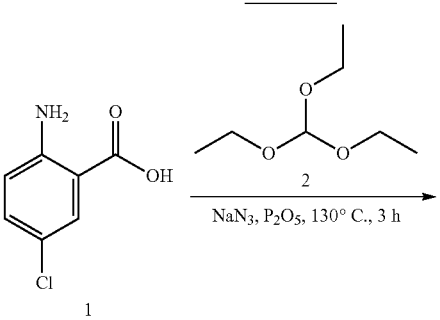

Scheme 144

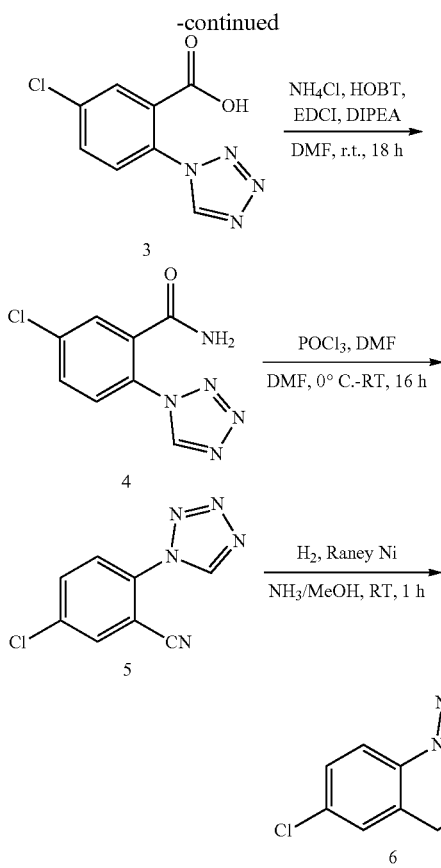

Synthesis of 5-chloro-2-(1H-tetrazol-1-yl)benzoic acid. To a mixture of 2-amino-5-chlorobenzoic acid (100 mg, 0.58 mmol) and NaN$_3$ (38 mg, 0.58 mmol) in triethoxymethane (3 mL) was added P$_2$O$_5$ (16 mg, 0.12 mmol). The reaction mixture was stirred at 130° C. for 3 h and then cooled to RT. Water (20 mL) was added and the mixture was extracted with i-PrOH/CHCl$_3$ (1/3, 20 mL x 3). The combined organic layers were washed with brine (20 mL), dried over Na$_2$SO$_4$ and concentrated in vacuo. The residue was purified by recrystallization from DCM to give 5-chloro-2-(1H-tetrazol-1-yl)benzoic acid (55 mg, yield: 42%) as a yellow solid. ESI-MS [M+H]+: 225.1.

Synthesis of 5-chloro-2-(1H-tetrazol-1-yl)benzamide. To a solution of 5-chloro-2-(1H-tetrazol-1-yl)benzoic acid (55 mg, 0.24 mmol), NH$_4$Cl (26 mg, 0.49 mmol), HOBT (66 mg, 0.49 mmol), EDCI (94 mg, 0.49 mmol) in DMF (5 mL) was added DIPEA (127 mg, 0.98 mmol). The reaction mixture was stirred at RT for 18 h. Water (50 mL) was added and the mixture was extracted with i-PrOH/CHCl$_3$ (1/3, 30 mL x 3). The combined organic layers were washed with brine (30 mL), dried over Na$_2$SO$_4$ and concentrated in vacuo. The residue was purified by prep-TLC (7% MeOH/DCM) to afford 5-chloro-2-(1H-tetrazol-1-yl)benzamide (40 mg, yield: 74.5%) as a yellow oil. ESI-MS [M+H]+: 224.0.

Synthesis of 5-chloro-2-(1H-tetrazol-1-yl)benzonitrile. To a mixture of 5-chloro-2-(1H-tetrazol-1-yl)benzamide (40 mg, 0.18 mmol) in DMF (2 mL) was added POCl$_3$ (165 mg, 1.08 mmol) at 0° C. The reaction mixture was stirred at RT for 16 h. Ice-water (20 mL) was added and the mixture was extracted with DCM (10 mLx3). The combined organic layers were washed with brine (10 mL), dried over Na$_2$SO$_4$ and concentrated in vacuo to give 5-chloro-2-(1H-tetrazol-1-yl)benzonitrile (30 mg, yield: 81.1%) as an oil which was used in the next step without further purification. ESI-MS [M+H]+: 206.1.

Synthesis of (5-chloro-2-(1H-tetrazol-1-yl)phenyl)methanamine. To a solution of 5-chloro-2-(1H-tetrazol-1-yl)benzonitrile (30 mg, 0.15 mmol) in NH$_3$/MeOH (2 mL, 7M) was added Raney-Ni (30 mg). The mixture was stirred at RT for 1 h under H$_2$, then filtered and concentrated in vacuo to give (5-chloro-2-(1H-tetrazol-1-yl)phenyl)methanamine (21 mg, yield: 66.8%) as a yellow oil which was used in next step directly without further purification. ESI-MS [M+H]+: 210.1.

Example 143

Synthesis of (3-chloro-2-fluoro-6-(1H-tetrazol-1-yl)phenyl)methanamine

Scheme 145

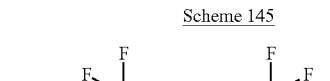
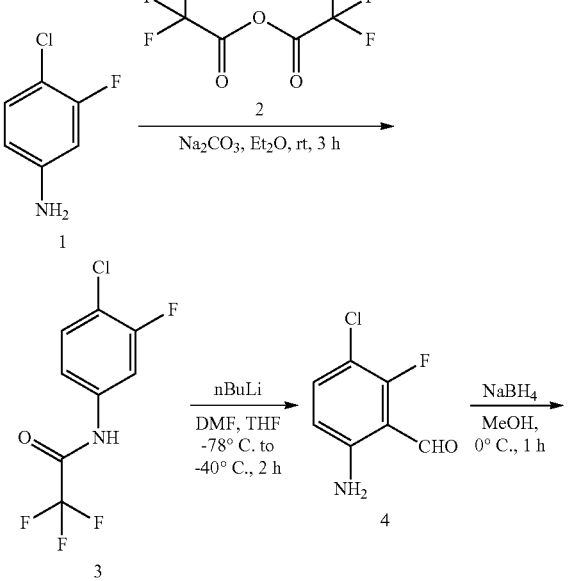
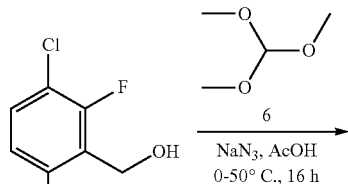
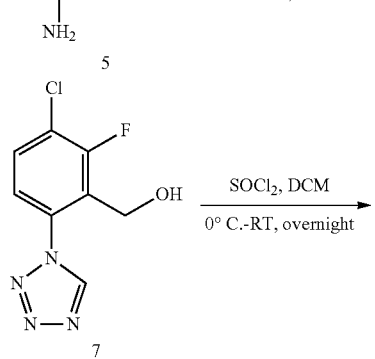

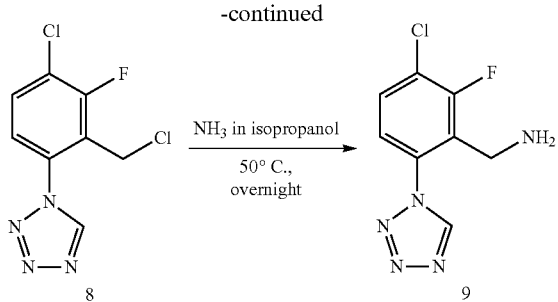

Synthesis of N-(4-chloro-3-fluorophenyl)-2,2,2-trifluoroacetamide. A mixture of 4-chloro-3-fluoroaniline (3.0 g, 20.6 mmol), 2,2,2-trifluoroacetic anhydride (5.6 g, 26.7 mmol) and $Na_2CO_3$ (6.5 g, 61.8 mmol) in dry diethyl ether (100 mL) was stirred at RT for 3 h. PE (50 mL) was added, the mixture was filtered, and the filter cake was washed with PE (100 mL×2). The combined organics were washed with 10% $NaHCO_3$ (50 mL) and brine (50 mL), dried over with $Na_2SO_4$, and concentrated in vacuo to give N-(4-chloro-3-fluorophenyl)-2,2,2-trifluoroacetamide (4.8 g, yield: 98.0%) as a white solid. ESI-MS $[M+H]^+$: 241.1.

Synthesis of 6-amino-3-chloro-2-fluorobenzaldehyde. To a solution of N-(4-chloro-3-fluorophenyl)-2,2,2-trifluoroacetamide (1.0 g, 4.1 mmol) in dry THF (10 mL) at −78° C. was added n-butyllithium (3.6 mL, 8.7 mmol) dropwise. The mixture was stirred at −78° C. for 10 min, then warmed up to −50° C. and DMF (0.96 mL 12.42 mmol) was added. The reaction was stirred at −40° C. for 2 h and quenched with water (50 mL). The reaction mixture was extracted with EtOAc (200 mL×2). The combined organic layers were concentrated and purified by silica gel chromatography (EtOAc/PE=1/2) to give 6-amino-3-chloro-2-fluorobenzaldehyde (700.0 mg, yield: 97%) as a yellow solid. ESI-MS $[M+H]^+$: 174.1.

Synthesis of (6-amino-3-chloro-2-fluorophenyl)methanol. To a solution of 6-amino-3-chloro-2-fluorobenzaldehyde (700 mg, 4.0 mmol) in MeOH (50 mL) at 0° C. was added $NaBH_4$ (465.3 mg, 12.3 mmol). The mixture was stirred at 0° C. for 1 h. Water (20 mL) was added and the mixture was extracted with DCM (100 mL×3). The combined organic layers were washed with brine and dried over $Na_2SO_4$. The combined organic layers were concentrated and purified by silica gel chromatography (EtOAc/PE=1/2) to give (6-amino-3-chloro-2-fluorophenyl)methanol (550.0 mg, yield: 78.3%) as a yellow solid. ESI-MS $[M+H]^+$: 176.0.

Synthesis of (3-chloro-2-fluoro-6-(1H-tetrazol-1-yl)phenyl)methanol. To a solution of (6-amino-3-chloro-2-fluorophenyl)methanol (550.0 g, 3.1 mmol) and $NaN_3$ (806.1 mg, 12.4 mmol) in trimethoxymethane (1.3 mL, 12.4 mmol) was added AcOH (60 mL) slowly at 0° C. The mixture was heated to 50° C. and stirred overnight, then quenched with $NaHCO_3$. Water (100 mL) was added and the mixture was extracted with EtOAc (200 mL×2). The combined organic layers were concentrated and purified by silica gel chromatography (EtOAc/PE=1/1) to give (3-chloro-2-fluoro-6-(1H-tetrazol-1-yl)phenyl)methanol (450 mg, yield: 63.5%) as a white solid. ESI-MS $[M+H]^+$: 229.0.

Synthesis of 1-(4-chloro-2-(chloromethyl)-3-fluorophenyl)-1H-tetrazole. To a solution of (3-chloro-2-fluoro-6-(1H-tetrazol-1-yl)phenyl)methanol (400.0 mg, 1.75 mmol) in DCM (25 mL) was added thionyl chloride (5.0 mL) at 0° C. over 10 min. The reaction mixture was warmed to RT and stirred overnight, then concentrated in vacuo to give 1-(4-chloro-2-(chloromethyl)-3-fluorophenyl)-1H-tetrazole (300.0 mg, yield: 69.4%) as a white solid, which was used in the subsequent step without further purification. ESI-MS $[M+H]^+$: 246.9.

Synthesis of (3-chloro-2-fluoro-6-(1H-tetrazol-1-yl)phenyl)methanamine. A solution of 1-(4-chloro-2-(chloromethyl)-3-fluorophenyl)-1H-tetrazole (300.0 mg, 1.2 mmol) in $NH_3$ in isopropanol (25.0 mL) was stirred at 50° C. overnight. The mixture was concentrated and purified by silica gel chromatography (DCM/MeOH=10/1) to give (3-chloro-2-fluoro-6-(1H-tetrazol-1-yl)phenyl)methanamine (120.0 mg, yield: 43.5%) as a white solid. ESI-MS $[M+H]^+$: 228.1.

Example 144

Synthesis of 6-(aminomethyl)-5,7-dimethylbenzo[d]isoxazol-3-amine hydrochloride

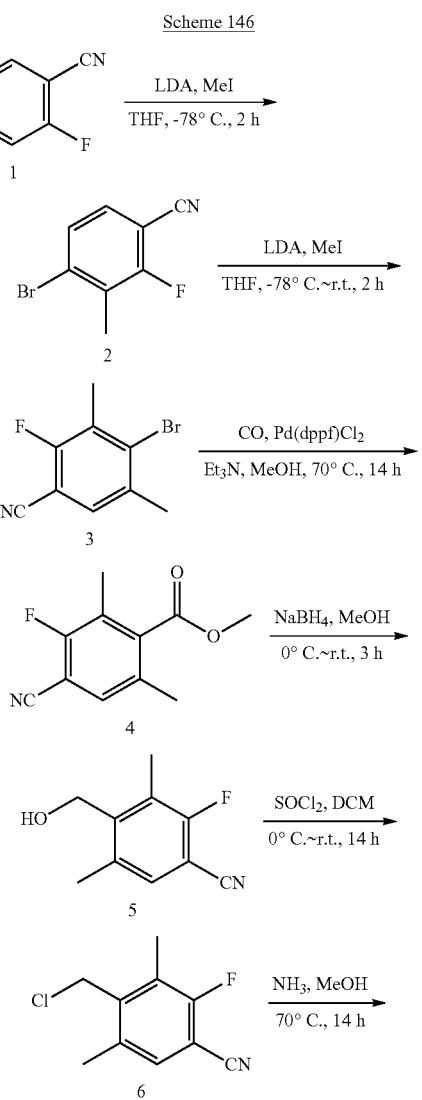

Scheme 146

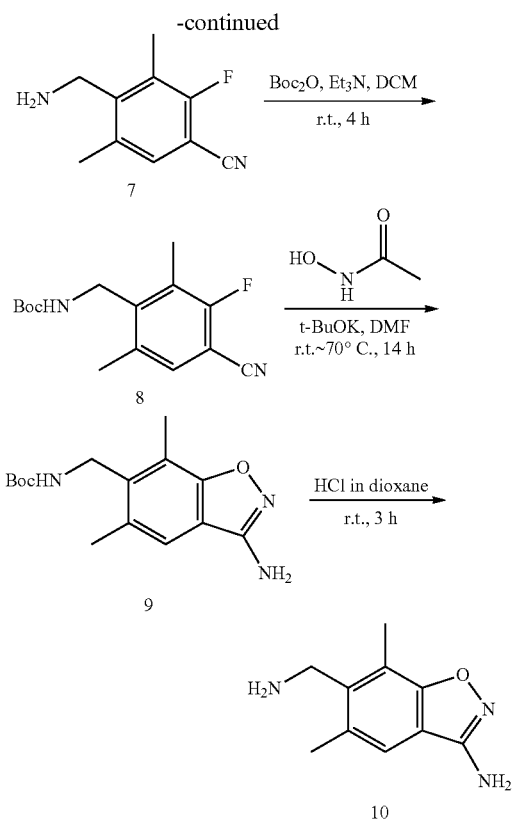

Synthesis of 4-bromo-2-fluoro-3-methylbenzonitrile. To a solution of 4-bromo-2-fluorobenzonitrile (4 g, 20 mmol) in THF (100 mL) was added LDA (15 mL, 2 M solution in THF, 30 mmol) dropwise at −78° C. The resulting solution was stirred at −78° C. for 30 min. Then a solution of MeI (3.4 g, 24 mmol) in THF (15 mL) was added. After stirring at −78° C. for 2 h, the reaction was quenched with saturated aqueous NH$_4$Cl (100 mL) and extracted with EtOAc (100 mL×3). The combined organic layers were washed with brine (50 mL), dried over Na$_2$SO$_4$ and concentrated in vacuo to give the crude, which was purified with silica gel chromatography (eluent: PE/EtOAc=25/1) to give 4-bromo-2-fluoro-3-methylbenzonitrile (3 g, yield: 70%) as a white solid. ESI-MS [M+H]$^+$: 214.1.

Synthesis of 4-bromo-2-fluoro-3,5-dimethylbenzonitrile. To a solution of 4-bromo-2-fluoro-3-methylbenzonitrile (3 g, 14 mmol) in THF (75 mL) was added LDA (10.5 mL, 2 M solution in THF, 21 mmol) dropwise at −78° C. The resulting reaction was stirred at −78° C. for 30 min, then a solution of MeI (3.2 g, 22.4 mmol) in THF (15 mL) was added. The reaction mixture was allowed to warm to room temperature and stirred for another 2 h. The reaction was quenched with saturated aqueous NH$_4$Cl (70 mL) and extracted with EtOAc (75 mL×3). The combined organic layers were washed with brine (50 mL), dried over Na$_2$SO$_4$ and concentrated in vacuo to give the crude, which was purified with silica gel chromatography (eluent: PE/EtOAc=20/1) to give 4-bromo-2-fluoro-3,5-dimethylbenzonitrile (2 g, yield: 62.9%) as a white solid. ESI-MS [M+H]$^+$: 228.1.

Synthesis of methyl 4-cyano-3-fluoro-2,6-dimethylbenzoate. A mixture of 4-bromo-2-fluoro-3,5-dimethylbenzonitrile (2 g, 8.8 mmol), Pd(dppf)Cl$_2$ (643 mg, 0.88 mmol) and Et$_3$N (2 mL) in MeOH (20 mL) was stirred at 70° C. for 14 h under CO atmosphere. The reaction mixture was concentrated in vacuo to give the crude, which was purified with silica gel chromatography (eluent: PE/EtOAc=10/1) to give methyl 4-cyano-3-fluoro-2,6-dimethylbenzoate (1.6 g, yield: 89%) as a white solid. ESI-MS [M+H]$^+$: 208.2.

Synthesis of 2-fluoro-4-(hydroxymethyl)-3,5-dimethylbenzonitrile. To a solution of methyl 4-cyano-3-fluoro-2,6-dimethylbenzoate (1.6 g, 7.73 mmol) in MeOH (40 mL) was added NaBH$_4$ (1.47 g, 38.6 mmol) slowly at 0° C. The resulting mixture was stirred at room temperature for 3 h. The reaction was quenched with saturated aqueous NH$_4$Cl (50 mL) and extracted with EtOAc (100 mL×4). The combined organic layers were washed with brine (50 mL), dried over Na$_2$SO$_4$, and concentrated in vacuo to give the crude, which was purified with chromatography (eluent: PE/EtOAc=1/1) to give 2-fluoro-4-(hydroxymethyl)-3,5-dimethylbenzonitrile (1.2 g, yield: 87%) as a white solid. ESI-MS [M+H]$^+$: 180.2.

Synthesis of 4-(chloromethyl)-2-fluoro-3,5-dimethylbenzonitrile. To a solution of 2-fluoro-4-(hydroxymethyl)-3,5-dimethylbenzonitrile (1.2 g, 6.7 mmol) in DCM (10 mL) was added SOCl$_2$ (3 mL) at 0° C. The resulting solution was stirred at room temperature for 14 h. The reaction was concentrated in vacuo to give 4-(chloromethyl)-2-fluoro-3,5-dimethylbenzonitrile (1.3 g crude) as yellow oil, which was used into next step without further purification. ESI-MS [M+H]$^+$: 198.2.

Synthesis of 4-(aminomethyl)-2-fluoro-3,5-dimethylbenzonitrile. A mixture of 4-(chloromethyl)-2-fluoro-3,5-dimethylbenzonitrile (1.3 g crude from previous step) in NH$_3$ (50 mL, 7 M solution in MeOH) was stirred at 70° C. in a sealed tube for 14 h. The reaction mixture was concentrated in vacuo to give 4-(aminomethyl)-2-fluoro-3,5-dimethylbenzonitrile (1.2 g crude) as a yellow solid, which was used into next step without further purification. ESI-MS [M+H]$^+$: 179.2.

Synthesis of tert-butyl (4-cyano-3-fluoro-2,6-dimethylbenzyl)carbamate. A mixture of 4-(aminomethyl)-2-fluoro-3,5-dimethylbenzonitrile (1.2 g crude from previous step), Boc$_2$O (2.9 g, 13.4 mmol) and Et$_3$N (2.7 g, 26.8 mmol) in DCM (40 mL) was stirred at room temperature for 4 h. The reaction was quenched with H$_2$O (50 mL) and extracted with DCM (50 mL×3). The combined organic layers were washed with brine (40 mL), dried over Na$_2$SO$_4$ and concentrated in vacuo to give the crude, which was purified with silica gel chromatography (eluent: PE/EA=10/1) to give tert-butyl (4-cyano-3-fluoro-2,6-dimethylbenzyl)carbamate (800 mg, over 3 steps yield: 43%) as a white solid. ESI-MS [M+H]$^+$: 279.1.

Synthesis of tert-butyl ((3-amino-5,7-dimethylbenzo[d]isoxazol-6-yl)methyl)carbamate. To a solution of N-hydroxyacetamide (430 mg, 5.73 mmol) in dry DMF (25 mL) was added t-BuOK (642 mg, 5.73 mmol). The resulting mixture was stirred at room temperature for 30 min. Then a solution of tert-butyl (4-cyano-3-fluoro-2,6-dimethylbenzyl)carbamate (800 mg, 2.87 mmol) in DMF (5 mL) was added. After stirring at 70° C. for 14 h, the reaction was quenched with H$_2$O (50 mL) and extracted with EtOAc (50 mL×3). The combined organic layers were washed with brine (50 mL), dried over Na$_2$SO$_4$ and concentrated in vacuo to give the crude, which was purified with silica gel chromatography (eluent: PE/EtOAc=1/1) to get tert-butyl ((3-amino-5,7-dimethylbenzo[d]isoxazol-6-yl)methyl)carbamate (500 mg, yield: 60%) as a white solid. ESI-MS [M+H]$^+$: 292.2.

Synthesis of 6-(aminomethyl)-5,7-dimethylbenzo[d]isoxazol-3-amine hydrochloride. A solution of tert-butyl ((3-amino-5,7-dimethylbenzo[d]isoxazol-6-yl)methyl)carbamate (500 mg, 1.7 mmol) in HCl (30 mL, 4 M solution in dioxane) was stirred at room temperature for 3 h. The reaction was concentrated in vacuo to give 6-(aminomethyl)-5,7-dimethylbenzo[d]isoxazol-3-amine hydrochloride (350 mg, yield: 91%), which was used in the subsequent step without further purification. ESI-MS [M+H]$^+$: 192.2.

Example 145

Synthesis of (7-bromonaphthalen-1-yl)methanamine

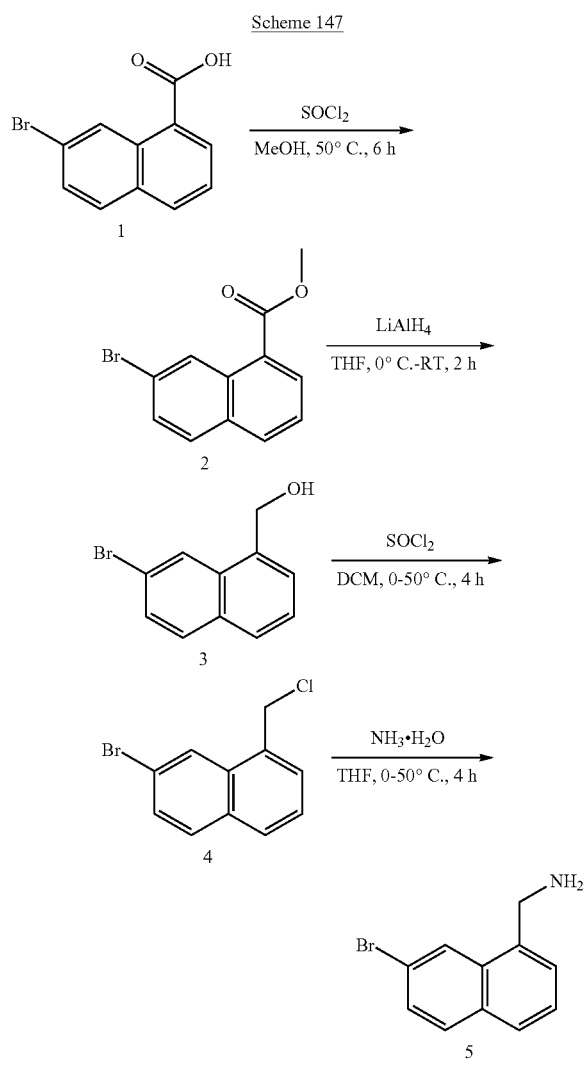

Synthesis of methyl 7-bromo-1-naphthoate. To a solution of 7-bromo-1-naphthoic acid (200 mg, 0.797 mmol) in dry MeOH (10 mL) was added SOCl$_2$ (600 mg, 5.042 mmol) dropwise at 0° C. The mixture was stirred at 50° C. for 6 h, then concentrated in vacuo to afford methyl 7-bromo-1-naphthoate (230 mg, crude) as a colorless oil which was used in next step directly without further purification. ESI-MS [M+H]+: 265.0.

Synthesis of (7-bromonaphthalen-1-yl)methanol. To a solution of 7-bromo-1-naphthoate (21 mg, 0.0792 mmol) in THF (2 mL) was added LiAlH$_4$ (4 mg, 0.1021 mmol) at 0° C. The reaction mixture was warmed to room temperature and stirred for 2 h, then quenched with water (20 mL) and extracted with EtOAc (15 mL×3). The combined organic layer was washed with brine (20 mL), dried over Na$_2$SO$_4$ and concentrated in vacuo. The residue was purified by Prep-TLC (60% EtOAc/PE) to give (7-bromonaphthalen-1-yl)methanol (18 mg, yield: 95.9%) as a light yellow solid. ESI-MS [M+H]+: 237.0.

Synthesis of 7-bromo-1-(chloromethyl)naphthalene. To a solution of 7-bromo-1-(chloromethyl)naphthalene (18 mg, 0.076 mmol) in anhydrous DCM (5 mL) was added SOCl2 (0.5 ml) by dropwise at 0° C. The mixture was stirred at 50° C. for 4 h and then concentrated in vacuo to give 7-bromo-1-(chloromethyl)naphthalene (20 mg, crude) as a yellow oil which was used in next step directly without further purification. ESI-MS [M+H]+: 255.0.

Synthesis of (7-bromonaphthalen-1-yl)methanamine. To a solution of 7-bromo-1-(chloromethyl)naphthalene (20 mg, 0.078 mmol) in anhydrous THF (2 mL) was added NH3·H2O (2 mL) at 0° C. The reaction mixture was stirred at 50° C. for 4 h and then cooled to room temperature. Water (20 mL) was added and the mixture was extracted with EtOAc (15 mL×3). The combined organic layer was washed with brine (20 mL), dried over Na$_2$SO$_4$ and concentrated in vacuo. The residue was purified by Prep-TLC (MeOH/DCM=1/20) to give (7-bromonaphthalen-1-yl)methanamine (17 mg, yield: 94%) as a light yellow oil. ESI-MS [M+H]+: 236.0.

Example 146

Synthesis of (7-chloroisoquinolin-1-yl)methanamine

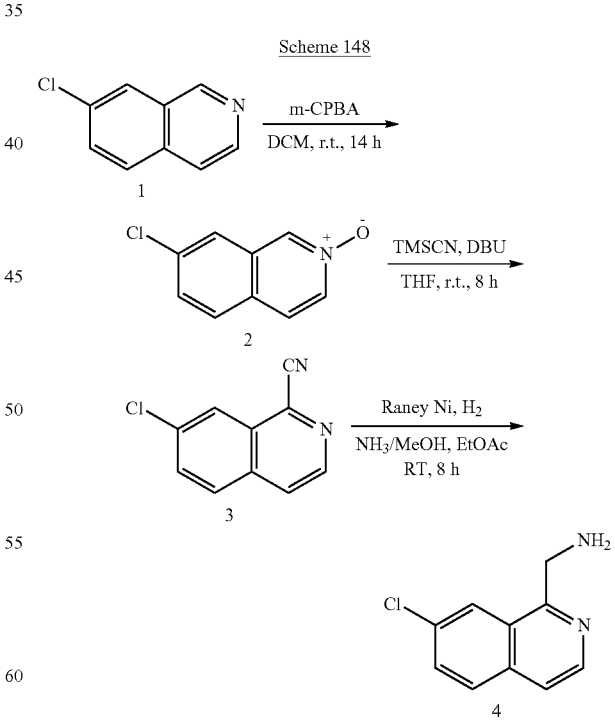

Synthesis of 7-chloroisoquinoline 2-oxide. To a solution of 7-chloroisoquinoline (1 g, 6.11 mmol) in DCM (25 mL) was added m-CPBA (2.12 g, 12.27 mmol). The reaction mixture was stirred at room temperature for 14 h. The reaction was quenched with saturated aqueous NaHCO$_3$ (50 mL) and extracted with DCM (50 mL×3). The combined organic layers were washed with brine (50 mL), dried over Na$_2$SO$_4$ and concentrated in vacuo to give 7-chloroisoquinoline 2-oxide (1.1 g crude) as a white solid which was used in the next step without further purification. ESI-MS [M+H]$^+$: 180.0.

Synthesis of 7-chloroisoquinoline-1-carbonitrile. To a solution of 7-chloroisoquinoline 2-oxide (1.1 g crude from the previous step) and DBU (2.33 g, 15.30 mmol) in THF (25 mL) was added TMSCN (911 mg, 9.19 mmol) slowly. The reaction mixture was stirred at room temperature for 8 h. The reaction was quenched with saturated aqueous NH$_4$Cl (50 mL) and extracted with EtOAc (50 mL×4). The combined organic layers were washed with brine (50 mL), dried over Na$_2$SO$_4$, and concentrated in vacuo to give the crude product which was purified with silica gel chromatography (eluent: EtOAc/PE=1/1) to give 7-chloroisoquinoline-1-carbonitrile (400 mg, yield: 34.7% over 2 steps) as a yellow solid. ESI-MS [M+H]$^+$: 189.0.

Synthesis of (7-chloroisoquinolin-1-yl)methanamine. A mixture of 7-chloroisoquinoline-1-carbonitrile (150 mg, 0.8 mmol) and Raney Ni (30 mg) in NH$_3$/MeOH (7M, 4 mL) and EtOAc (4 mL) was stirred at room temperature under hydrogen atmosphere for 8 h. The reaction mixture was filtered and washed with MeOH (30 mL). The filtrate was concentrated in vacuo to give (7-chloroisoquinolin-1-yl)methanamine (80 mg, 52.6%, crude) as a yellow solid which was used in the next step without further purification. ESI-MS [M+H]$^+$: 193.1

Example 147

Synthesis of (7-chloronaphthalen-1-yl)methanamine

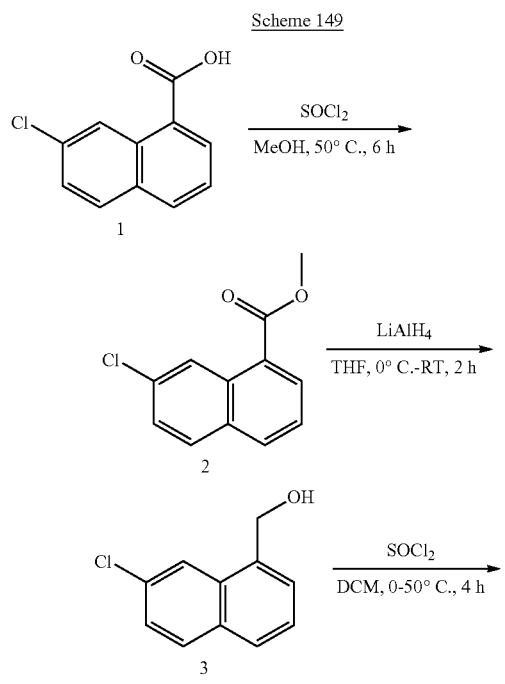

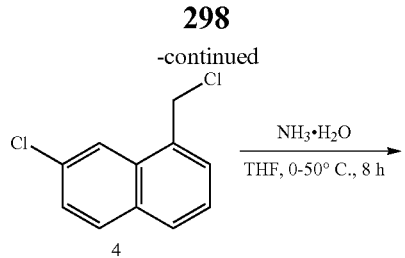

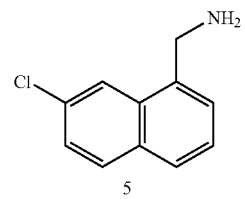

Synthesis of methyl 7-chloro-1-naphthoate. To a solution of 7-chloro-1-naphthoic acid (200 mg, 0.968 mmol) in anhydrous MeOH (10 mL) was added SOCl$_2$ (2 mL) dropwise at 0° C. The mixture was stirred at 50° C. for 6 h and then concentrated in vacuo to afford methyl 7-chloro-1-naphthoate (230 mg, crude) as a yellow oil which was used in next step directly without further purification. ESI-MS [M+H]+: 221.1.

Synthesis of (7-chloronaphthalen-1-yl)methanol. To a solution of methyl 7-chloro-1-naphthoate (200 mg, 0.906 mmol) in THF (5 mL) at 0° C. was added LiAlH$_4$ (42 mg, 1.021 mmol). The reaction mixture was warmed to room temperature and stirred for 2 h, then quenched with water (20 mL) and extracted with EtOAc (15 mL×3). The combined organic layer was washed with brine (20 mL), dried over Na$_2$SO$_4$ and concentrated in vacuo. The residue was purified by flash chromatography (EtOAc/PE from 0 to 100%) to give (7-chloronaphthalen-1-yl)methanol (166 mg, yield: 95%) as a light yellow solid. ESI-MS [M+H]+: 193.0.

Synthesis of 7-chloro-1-(chloromethyl)naphthalene. To a solution of (7-chloronaphthalen-1-yl)methanol (166 mg, 0.861 mmol) in anhydrous DCM (5 mL) was added SOCl$_2$ (0.5 mL) dropwise at 0° C. The reaction mixture was stirred at 50° C. for 4 h and then concentrated in vacuo to give 7-chloro-1-(chloromethyl)naphthalene (200 mg, crude) as a yellow oil which was used in next step directly without further purification. ESI-MS [M+H]+: 211.0.

Synthesis of (7-chloronaphthalen-1-yl)methanamine. To a solution of 7-chloro-1-(chloromethyl)naphthalene (200 mg, crude) in anhydrous THF (5 mL) was added NH3·H2O (5 mL) at 0° C. The reaction mixture was stirred at 50° C. for 8 h and then cooled to room temperature. Water (30 mL) was added and the mixture was extracted with EtOAc (20 mL×3). The combined organic layer was washed with brine (20 mL), dried over Na$_2$SO$_4$ and concentrated in vacuo. The residue was purified by flash chromatography (MeOH/DCM from 0 to 5%) to give (7-chloronaphthalen-1-yl)methanamine (100 mg, yield: 62%, for two steps) as a light yellow oil. ESI-MS [M+H]+: 192.1.

Example 148

Synthesis of (6-chloroimidazo[1,5-a]pyridin-3-yl)methanamine

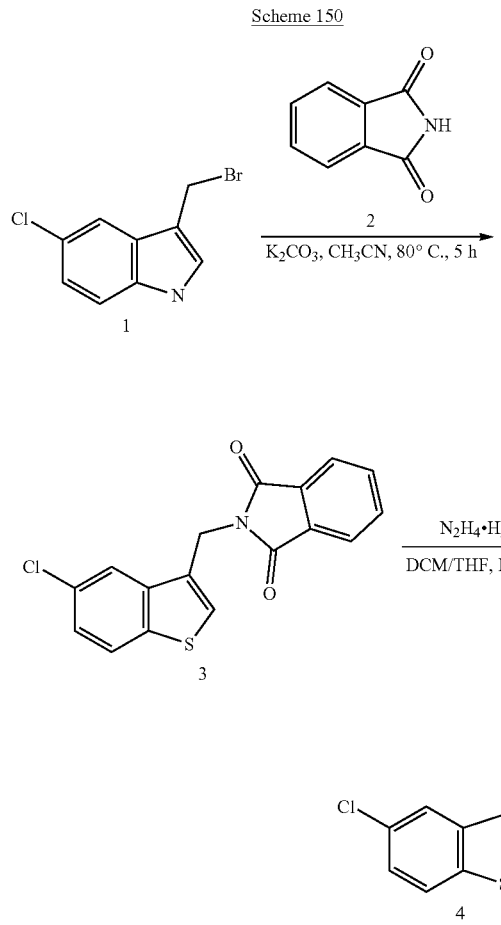

Synthesis of 2-((5-chlorobenzo[b]thiophen-3-yl)methyl)isoindoline-1,3-dione. A solution of 3-(bromomethyl)-5-chlorobenzo[b]thiophene (563 mg, 2.0 mmol), isoindoline-1,3-dione (324 mg, 2.2 mmol) and $K_2CO_3$ (829 mg, 6.0 mmol) in $CH_3CN$ (20 mL) was stirred at 80° C. for 5 h. The mixture was cooled to room temperature and filtered. The filtrate was concentrated in vacuo, diluted with water (50 mL), and extracted with EtOAc (30 mL×3). The combined organic layers were washed with brine, dried over $Na_2SO_4$ and concentrated to give crude 2-((5-chlorobenzo[b]thiophen-3-yl)methyl)isoindoline-1,3-dione (115 mg, 18%) as a white solid which was used in next step directly without further purification. ESI-MS [M+Na]+: 350.0.

Synthesis of (6-chloroimidazo[1,5-a]pyridin-3-yl)methanamine. A mixture of 2-((5-chlorobenzo[b]thiophen-3-yl)methyl)isoindoline-1,3-dione (115 mg, 0.35 mmol), and $N_2H_4H_2O$ (126 mg, 2.0 mmol) in DCM (2 mL) and THF (2 mL) was stirred at room temperature for 5 h. The mixture was concentrated in vacuo and purified by Prep-TLC (DCM/MeOH=8/1) to give (5-chlorobenzo[b]thiophen-3-yl)methanamine (30 mg, yield: 44%) as a white solid. ESI-MS [M−$NH_3$]+: 181.1.

Example 149

Synthesis of (4,6-dimethyl-1H-indol-5-yl)methanamine

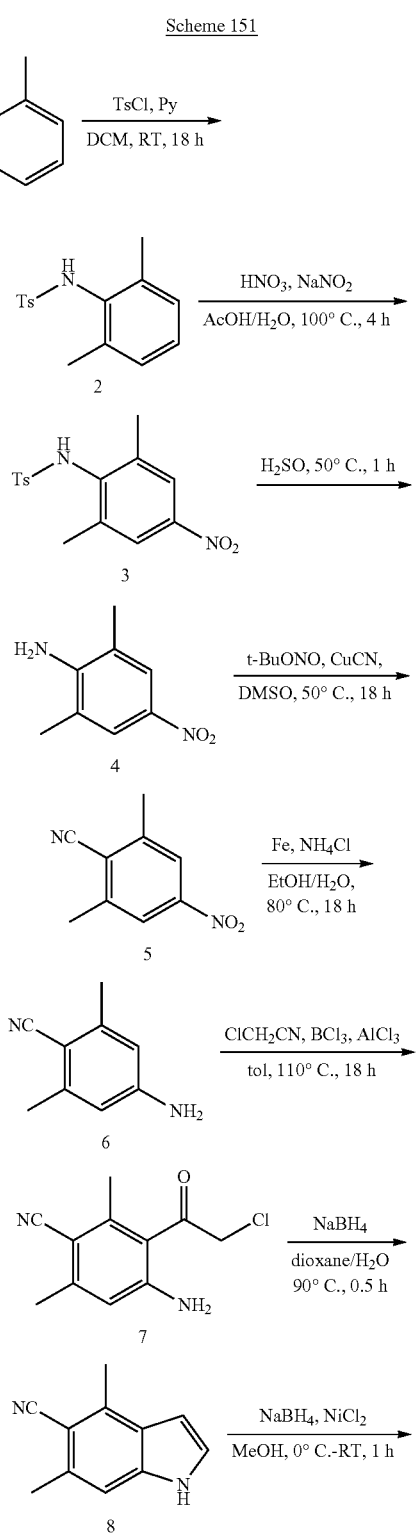

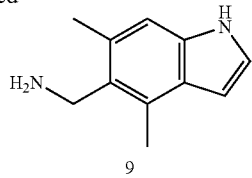

9

Synthesis of N-(2,6-dimethylphenyl)-4-methylbenzenesulfonamide. A solution of 2,6-dimethylaniline (40 g, 0.33 mol), TsCl (69 g, 0.36 mol) and pyridine (39 g, 0.50 mol) in DCM (500 mL) was stirred at room temperature for 18 h. Saturated NaHCO$_3$ solution (500 mL) was added and the mixture was extracted with DCM (300 mL×3). The combined organic layers were washed with brine (300 mL), dried over Na$_2$SO$_4$ and concentrated in vacuo. The residue was purified by flash column chromatography (EtOAc/PE from 0 to 10%) to give N-(2,6-dimethylphenyl)-4-methylbenzenesulfonamide (80 g, yield: 88%) as a yellow solid. ESI-MS [M+H]+: 276.1.

Synthesis of N-(2,6-dimethyl-4-nitrophenyl)-4-methylbenzenesulfonamide. To a mixture of N-(2,6-dimethylphenyl)-4-methylbenzenesulfonamide (40 g, 0.145 mol) in AcOH/H$_2$O/HNO$_3$ (250 mL/250 mL/50 mL) was added NaNO$_2$ (20 g, 0.290 mol) portionwise at 0° C. The reaction mixture was stirred at 100° C. for 4 h, then cooled and concentrated in vacuo. The residue was adjusted to pH ~8 with saturated aq. NaHCO$_3$, and the resulting mixture was extracted with DCM (400 mL×3). The combined organic layers were washed with brine (300 mL), dried over Na$_2$SO$_4$ and concentrated in vacuo. The residue was purified by flash column chromatography (EtOAc/PE from 0 to 10%) to give N-(2,6-dimethyl-4-nitrophenyl)-4-methylbenzenesulfonamide (28 g, yield: 60%) as a red solid. ESI-MS [M+H]+: 321.1.

Synthesis of 2,6-dimethyl-4-nitroaniline. A mixture of N-(2,6-dimethyl-4-nitrophenyl)-4-methylbenzenesulfonamide (55 g, 0.17 mol) in conc. H$_2$SO$_4$ (200 mL) was stirred at 50° C. for 1 h. The reaction mixture was cooled to room temperature and adjusted to pH ~8 with saturated aq. NaHCO$_3$. The resulting mixture was extracted with DCM (400 mL×3). The combined organic layers were washed with brine (400 mL), dried over Na$_2$SO$_4$ and concentrated in vacuo. The residue was purified by flash chromatography (EtOAc/PE from 0 to 15%) to give 2,6-dimethyl-4-nitroaniline (20 g, yield: 70%) as a yellow solid. ESI-MS [M+H]+: 167.1.

Synthesis of 2,6-dimethyl-4-nitrobenzonitrile. To a solution of 2,6-dimethyl-4-nitroaniline (9.0 g, 54.2 mmol) and CuCN (6.3 g, 70.5 mmol) in DMSO (100 mL) was added t-BuNO (16.8 g, 162.7 mmol). The reaction mixture was stirred at 50° C. for 18 h, then quenched with saturated aq. NaHCO$_3$ solution (500 mL) and extracted with DCM (200 mL×3). The organic layers were washed with brine (50 mL×3), dried over Na$_2$SO$_4$ and concentrated in vacuo. The residue was purified by flash chromatography (EtOAc/PE from 0 to 10%) to give 2,6-dimethyl-4-nitrobenzonitrile (3.2 g, 33.5% yield) as a brown solid. ESI-MS [M+H]+: 177.1

Synthesis of 4-amino-2,6-dimethylbenzonitrile. A mixture of 2,6-dimethyl-4-nitrobenzonitrile (5.2 g, 29.52 mmol), Fe (8.8 g, 156.3 mmol) and NH$_4$Cl (16.7 g, 312.5 mmol) in EtOH/H$_2$O (50 mL/5 mL) was stirred at 80° C. for 18 h. The reaction mixture was filtered and concentrated in vacuo. The residue was purified by flash chromatography (EtOAc/PE from 0 to 15%) to give 4-amino-2,6-dimethylbenzonitrile (2.3 g, 53.5% yield) as a brown solid. ESI-MS [M+H]+: 147.1.

Synthesis of 4-amino-3-(2-chloroacetyl)-2,6-dimethylbenzonitrile. To a mixture of 4-amino-2,6-dimethylbenzonitrile (4.5 g, 30.8 mmol) and C$_l$CH$_2$CN (3.47 g, 46.2 mmol) in toluene (50 mL) was added BCl$_3$ (40.4 mL, 40.4 mmol) and AlCl$_3$ (5.37 g, 40.4 mmol) at 0° C. The mixture was stirred at 110° C. for 18 hours, then cooled to room temperature and quenched with saturated aq. NaHCO$_3$(200 mL) and extracted with DCM (100 mL×3). The organic layers were washed with brine (100 mL), dried over Na$_2$SO$_4$ and concentrated in vacuo. The residue was purified by flash chromatography (EtOAc/PE from 0 to 15%) to give 4-amino-3-(2-chloroacetyl)-2,6-dimethylbenzonitrile (3.0 g, yield: 44%) as a yellow solid. ESI-MS [M+H]+: 223.1.

Synthesis of 4,6-dimethyl-1H-indole-5-carbonitrile. A mixture of 4-amino-3-(2-chloroacetyl)-2,6-dimethylbenzonitrile (2.1 g, 9.43 mmol) and NaBH$_4$ (259 mg, 6.85 mmol) in dioxane/H$_2$O (20 mL/2 mL) was stirred at 90° C. for 0.5 h. The reaction mixture was quenched with saturated aq. NH$_4$Cl (100 mL) and extracted with DCM (50 mL×3). The organic layers were washed with brine (50 mL), dried over Na$_2$SO$_4$ and concentrated in vacuo. The residue was purified by flash chromatography (EtOAc/PE from 0 to 10%) to give 4,6-dimethyl-1H-indole-5-carbonitrile (420 mg, yield: 26.2%) as a yellow oil. ESI-MS [M+H]+: 171.1.

Synthesis of (4,6-dimethyl-1H-indol-5-yl)methanamine. To the mixture of 4,6-dimethyl-1H-indole-5-carbonitrile (240 mg, 1.41 mmol) and NiCl$_2$-6H$_2$O (672 mg, 2.82 mmol) in MeOH (5 mL) was added NaBH$_4$ (1.07 g, 28.2 mmol) portionwise at 0° C. The reaction mixture was stirred at RT for 1 h, then quenched with saturated aq. NH$_4$Cl (30 mL) and extracted with CH$_3$C$_1$/i-PrOH (3/1, 30 mL x 3). The combined organic layers were washed with brine (30 mL), dried over Na$_2$SO$_4$ and concentrated in vacuo. The residue was purified by flash chromatography (MeOH/DCM from 0 to 10%) to give (4,6-dimethyl-1H-indol-5-yl)methanamine (110 mg, yield: 44.8%) as a pale yellow solid. ESI-MS [M+H]+: 175.1.

Example 150

Synthesis of (3-chloro-4,6-dimethyl-1H-indol-5-yl)methanamine

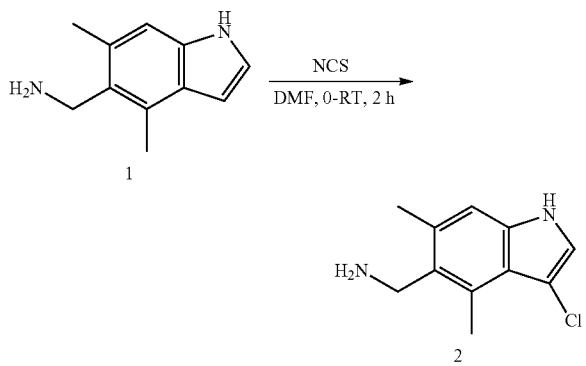

To the mixture of (4,6-dimethyl-1H-indol-5-yl)methanamine (65 mg, 0.37 mmol) in DMF (2 mL) was added NCS (51 mg, 0.39 mmol) at 0° C. The mixture was stirred at RT for 2 h, then quenched with water (40 mL) and extracted with EtOAc (30 mL×3). The organic layers were washed with brine (30 mL), dried over Na$_2$SO$_4$ and concentrated in vacuo to give crude (3-chloro-4,6-dimethyl-1H-indol-5-yl)methanamine (77 mg, crude) as a yellow oil which was used in next step directly without further purification. ESI-MS [M+H]$^+$: 209.1.

Example 151

Synthesis of 4-(aminomethyl)-6-bromoquinolin-2(1H)-one

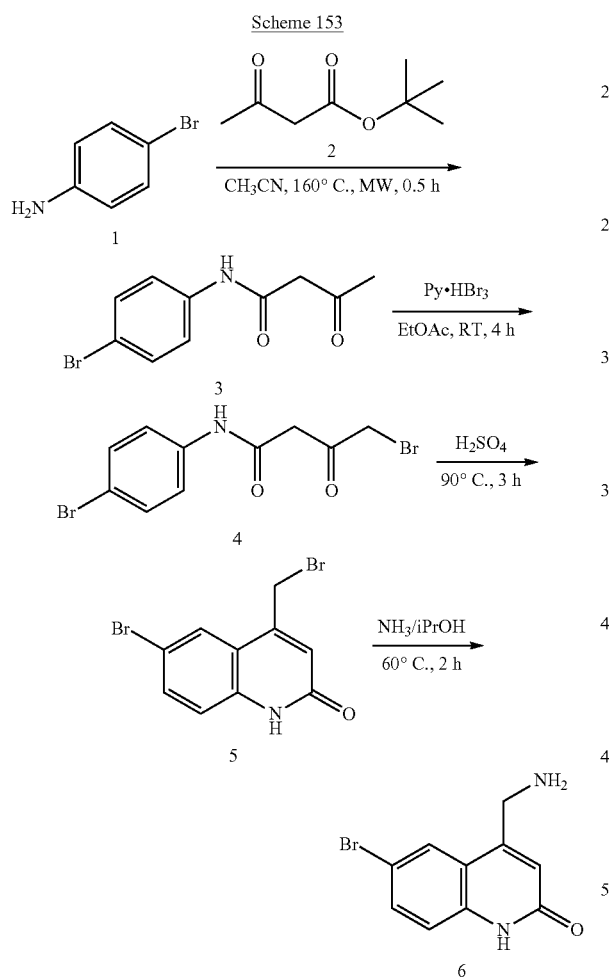

Synthesis of N-(4-bromophenyl)-3-oxobutanamide. A solution of 4-bromoaniline (1.72 g, 10 mmol) and tert-butyl 3-oxobutanoate (1.74 g, 11 mmol) in CH$_3$CN (5 mL) was stirred at 160° C. for 0.5 h under microwave. The reaction mixture was cooled to room temperature and concentrated in vacuo. The residue was dispersed in boiling cyclohexane (25 mL) and filtered to give N-(4-bromophenyl)-3-oxobutanamide (1.02 g, yield: 40%) as a white solid. ESI-MS [M+H]+: 256.1.

Synthesis of 4-bromo-N-(4-bromophenyl)-3-oxobutanamide. A mixture of N-(4-bromophenyl)-3-oxobutanamide (256 mg, 1.0 mmol) and pyridinium tribromide (333 mg, 1.05 mmol) in EtOAc (6 mL) was stirred at room temperate for 4 h. The reaction mixture was diluted with water (40 mL) and extracted with EtOAc (30 mL×3). The combined organic layers were washed with brine (30 mL), dried over Na$_2$SO$_4$ and concentrated in vacuo. The residue was purified by Prep-TLC (EtOAc/PE=1/2) to give 4-bromo-N-(4-bromophenyl)-3-oxobutanamide (164 mg, yield: 49%) as a white solid. ESI-MS [M−NH$_3$]$^+$: 334.0.

Synthesis of 6-bromo-4-(bromomethyl)quinolin-2(1H)-one. A mixture of 4-bromo-N-(4-bromophenyl)-3-oxobutanamide (140 mg, 0.42 mmol) in conc. H$_2$SO$_4$ (4 mL) was stirred at 90° C. for 3 h. Ice (10 g) was added and the mixture was stirred for another 0.5 h. The mixture was filtered to give 6-bromo-4-(bromomethyl)quinolin-2(1H)-one (134 mg, yield: 100%) as a white solid. ESI-MS [M+H]+: 315.9.

Synthesis of 4-(aminomethyl)-6-bromoquinolin-2(1H)-one. A mixture of 6-bromo-4-(bromomethyl)quinolin-2(1H)-one (134 mg, 0.42 mmol) in NH$_3$/$^1$PrOH (3 mL, 6 mmol, 2M) was stirred at 60° C. for 2 h. The reaction mixture was concentrated to give 4-(aminomethyl)-6-bromoquinolin-2(1H)-one (106 mg, crude) as a white solid which was used in next step directly without further purification. ESI-MS [M+H]+: 253.1.

Example 152

Synthesis of (6-chloro-[1,2,4]triazolo[4,3-a]pyridin-3 yl)methanamine hydrobromide

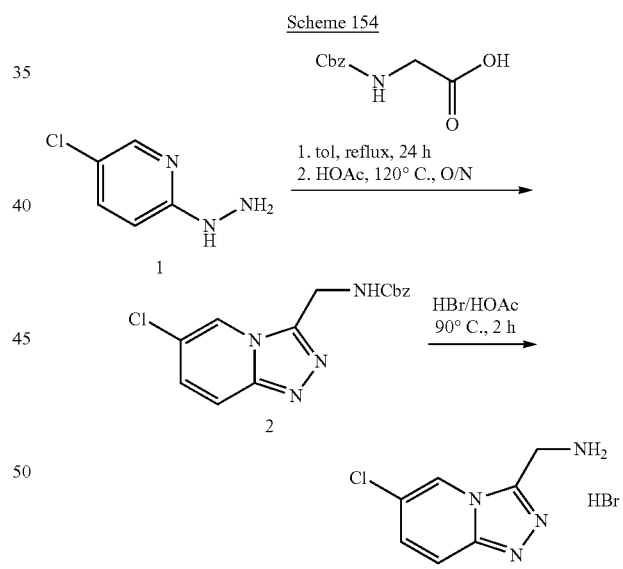

Synthesis of benzyl ((6-chloro-[1,2,4]triazolo[4,3-a]pyridin-3-yl)methyl)carbamate. A mixture of 5-chloro-2-hydrazinylpyridine (1) (720 mg, 5.0 mmol) and 2-(((benzyloxy)carbonyl)amino)acetic acid (1.16 g, 5.5 mmol) in toluene (15 mL) was heated to reflux for 24 hours. After removal of the solvent, acetic acid (20 mL) was added, and the mixture was stirred at 120° C. overnight. The mixture was concentrated and the residue was purified by column chromatography (Dichloromethane:Ethyl acetate=1:2 to 0:1) to give benzyl ((6-chloro-[1,2,4]triazolo[4,3-a]pyridin-3-yl)methyl)carbamate (2) (800 mg, yield: 51%) as a gray solid. ESI-MS [M+H]$^+$: 317.1.

Synthesis of (6-chloro-[1,2,4]triazolo[4,3-a]pyridin-3-yl)methanamine (SS-033-012). To a solution of benzyl ((6-chloro-[1,2,4]triazolo[4,3-a]pyridin-3-yl)methyl)carbamate (2) (800 mg, 2.53 mmol) in acetic acid (10 mL) was added hydrobromic acid in acetic acid (1M, 10 mL). The mixture was stirred at 90° C. for 2 h, then filtered to give the crude product which was washed with ethyl acetate and dried in vacuum to afford (6-chloro-[1,2,4]triazolo[4,3-a]pyridin-3-yl)methanamine hydrobromide (660 mg, quant.) as a white solid. ESI-MS [M-NH$_2$]+: 182.2, 99.1% purity. $^1$H NMR (400 MHz, DMSO) δ 9.15 (s, 1H), 8.68 (br, 3H), 7.97 (d, J=10.0 Hz, 1H), 7.66-7.63 (m, 1H), 4.72 (q, J=5.6 Hz, 2H).

Example 153

Synthesis of (6-chloro-8 fluoroimidazo[1,5-a]pyridin-3 yl)methanamine hydrochloride

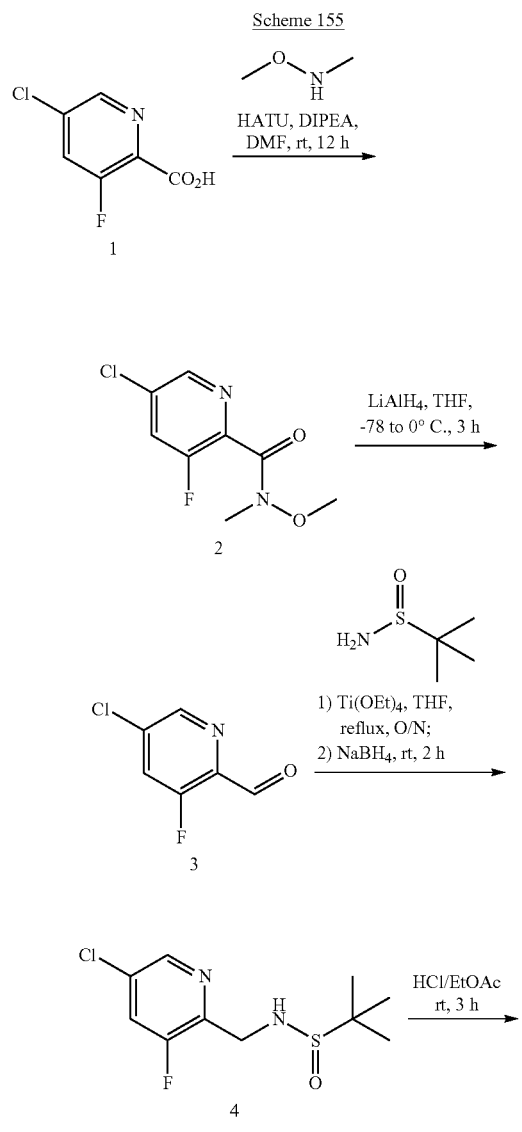

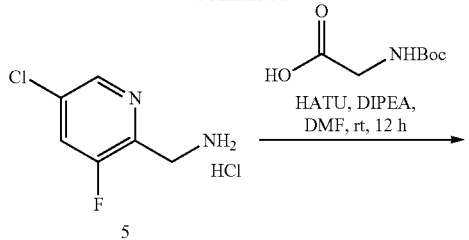

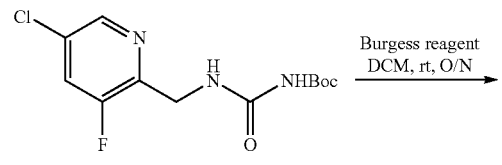

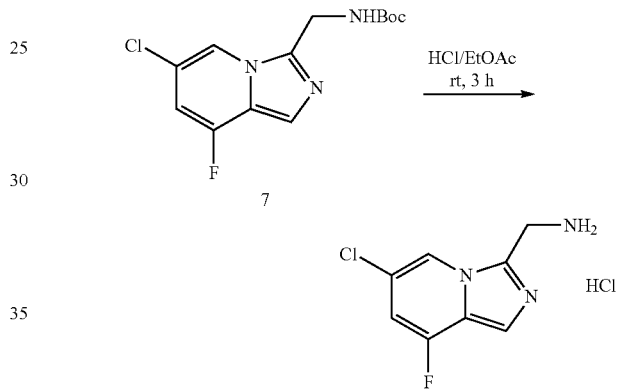

Synthesis of 5-chloro-3-fluoro-N-methoxy-N-methylpicolinamide. To a solution of 5-chloro-3-fluoropicolinic acid (1, 3 g, 18.4 mmol) in DMF (25 mL) at room temperature was added DIPEA (12 g, 62 mmol), HATU (7.69 g, 20 mmol), and N,O-dimethylhydroxylamine hydrochloride (4.46 g, 46 mmol). The reaction mixture was stirred at 25° C. for 12 h. The solvent was removed and the residue was diluted with 30 mL water, extracted with ethyl acetate (40 mL×3), and washed with 1 N lithium chloride (30 mL×3). The organic layer was dried over anhydrous sodium sulphate and concentrated. The residue was purified by silica column chromatography (petroleum ether:ethyl acetate=1:1) to afford 5-chloro-3-fluoro-N-methoxy-N-methylpicolinamide (2, 3.4 g, yield: 91%) as white solid. ESI-MS [M+H]$^+$: 219.1.

Synthesis of 5-chloro-3-fluoropicolinaldehyde. To a solution of 5-chloro-3-fluoro-N-methoxy-N-methylpicolinamide (2, 3.7 g, 16.9 mmol) in tetrahydrofuran (50 mL) was added Lithium aluminium hydride (8.4 mL, 1 mol/L) at −78° C. The mixture was stirred at 0° C. for 3 hours. After the reaction was completed, the mixture was poured into ice water and extracted with ethyl acetate three times. The combined organic layers were concentrated and the crude product was purified by silica gel column chromatography (petroleum ether:ethyl acetate=3:1) to afford 5-chloro-3-fluoropicolinaldehyde (3, 2.8 g, yield: 95%). ESI-MS [M+H]$^+$: 161.1.

Synthesis of N-((5-chloro-3-fluoropyridin-2-yl)methyl)-2-methylpropane-2-sulfinamide. To a solution of 5-chloro-3-fluoropicolinaldehyde (3, 2.5 g, 15.6 mmol) and 2-methylpropane-2-sulfinamide (1.89 g, 15.6 mmol) in tetrahydrofuran (30 mL) was added tetraethoxytitanium (17.8 g, 78.1 mol). The mixture was stirred at reflux overnight. After reaction was completed, sodium borohydride (1.78 g, 46.87 mmol) was added slowly and the mixture was stirred at room temperature for 2 h. The mixture was quenched with water and extracted with ethyl acetate (300 mL). The combined organic layers were concentrated and the crude product was purified by silica gel column chromatography (petroleum ether:ethyl acetate=1:1) to afford N-((5-chloro-3-fluoropyridin-2-yl)methyl)-2-methylpropane-2-sulfinamide (4, 2.0 g, yield: 49%). ESI-MS [M+H]$^+$: 254.1.

Synthesis of (5-chloro-3-fluoropyridin-2-yl)methanamine hydrochloride. To a solution of N-((5-chloro-3-fluoropyridin-2-yl)methyl)-2-methylpropane-2-sulfinamide (4, 2 g, 7.5 mmol) in ethyl acetate (15 mL) was added hydrochloride in Ethyl acetate (10 mL, 3 M). The mixture was stirred at room temperature for 3 h and then filtered to give the crude product, which was washed with ethyl acetate and dried in vacuo to afford (5-chloro-3-fluoropyridin-2-yl)methanamine hydrochloride (5, 1.7 g, quant.) as a white solid. ESI-MS [M+H]$^+$: 161.0.

Synthesis of tert-butyl (2-(((5-chloro-3-fluoropyridin-2-yl)methyl)amino)-2-oxoethyl)carbamate. To a solution of 2-((tert-butoxycarbonyl)amino)acetic acid (673 mg, 3.8 mmol) in N,N-dimethyl-formamide (5 mL) at room temperature was added DIPEA (777 mg, 7.7 mmol), HATU (1.46 g, 3.8 mmol), and (5-chloro-3-fluoropyridin-2-yl)methanamine hydrochloride (5,750 mg, 3.8 mmol). The resulting mixture was stirred at room temperature for 12 h. The solvent was removed and the residue was diluted with 30 mL water, extracted with ethyl acetate (40 mL×3), washed with 1 N lithium chloride (30 mL×3), the organic layer was dried over anhydrous sodium sulphate and concentrated. The residue was purified by silica column chromatography (petroleum ether:ethyl acetate=2:1) to give tert-butyl (2-(((5-chloro-3-fluoropyridin-2-yl)methyl)amino)-2-oxoethyl)carbamate (6, 600 g, yield: 49%) as yellow oil. ESI-MS [M+H]$^+$: 318.1.

Synthesis of tert-butyl ((6-chloro-8-fluoroimidazo[1,5-a]pyridin-3-yl)methyl)carbamate. To a solution of tert-butyl (2-(((5-chloro-3-fluoropyridin-2-yl)methyl)amino)-2-oxoethyl)carbamate (6, 600 mg, 1.88 mmol) in DCM (5 mL) at room temperature was added Burgess reagent (450 mg, 1.88 mmol). The resulting mixture was stirred at room temperature overnight. After removal of the solvent, the residue was purified by silica column chromatography (petroleum ether: ethyl acetate=2:1) to afford tert-butyl ((6-chloro-8-fluoroimidazo[1,5-a]pyridin-3-yl)methyl)carbamate (7, 210 mg, yield: 37%) as white solid. ESI-MS [M+H]$^+$: 244.1. $^1$H NMR (400 Hz, DMSO) S 8.43 (s, 1H), 7.56 (s, 2H), 6.94 (d, J=10.8 Hz, 1H), 4.56 (d, J=6.4 Hz, 1H), 1.39 (s, 9H).

Synthesis of (6-chloro-8-fluoroimidazo[1,5-a]pyridin-3-yl)methanamine hydrochloride (SS-033-014). To a solution of tert-butyl ((6-chloro-8-fluoroimidazo[1,5-a]pyridin-3-yl)methyl)carbamate (7, 430 mg, 1.43 mmol) in ethyl acetate (15 mL) was added hydrochloride in ethyl acetate (10 mL, 3 M). The mixture was stirred at room temperature for 3 h and then filtered to give the crude product, which was washed with ethyl acetate and dried in vacuo to afford (6-chloro-8-fluoroimidazo[1,5-a]pyridin-3-yl)methanamine hydrochloride (SS-033-014, 280 mg, yield: 91%) as a white solid. ESI-MS [M+H]$^+$: 200.1. $^1$H NMR (400 MHz, DMSO-d$^6$) δ 8.83 (br, 3H), 8.79 (s, 1H), 7.77 (s, 1H), 7.08 (dd, J=1.2, 6.8 Hz, 1H), 4.55 (dd, J=4.2, 11.2 Hz, 2H).

Example 154

Synthesis of I-((6-cyclopropylimidazo[1,2-a]pyridin-2 yl)methyl)-N-(2 fluoro-3-methoxy-6-(1H-tetrazol-1 yl)benzyl)-1H-1,2,3-triazole-4-carboxamide Scheme 156

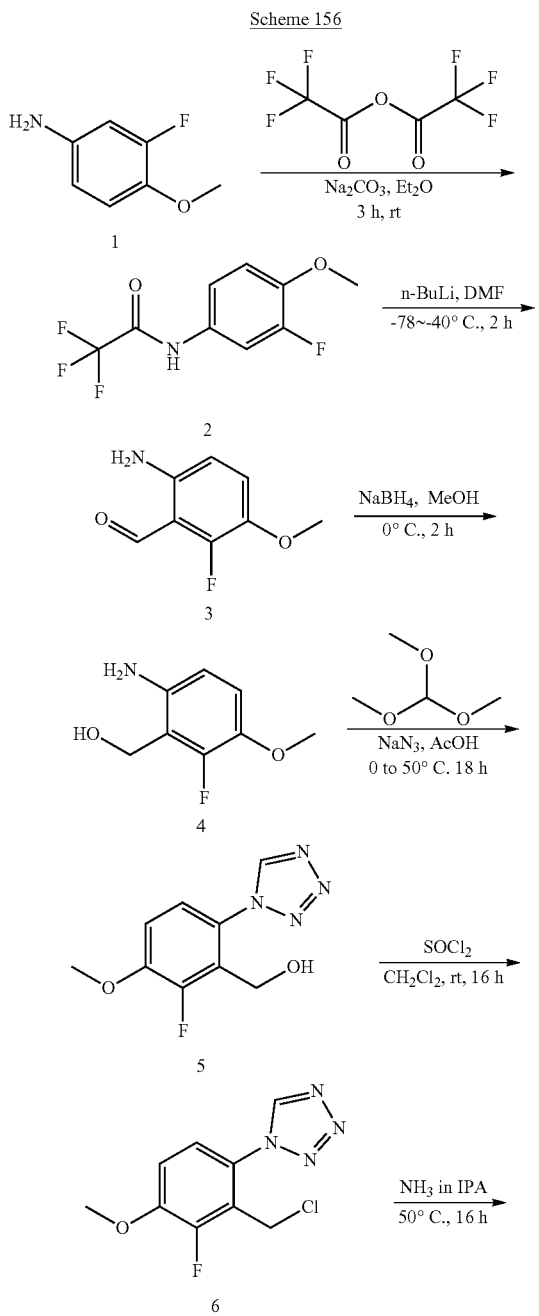

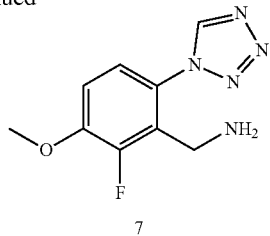

Synthesis of 2,2,2-trifluoro-N-(3-fluoro-4-methoxyphenyl)acetamide. To a mixture of 3-fluoro-4-methoxyaniline (10 g, 70.9 mmol) and Na$_2$CO$_3$ (22.5 g, 212.7 mmol) in dry diethyl ether (200 mL) was added 2,2,2-trifluoroacetic anhydride (19.4 g, 92.2 mmol) dropwise at 0° C. The mixture was stirred at room temperature for 3 h, then diluted with PE (200 mL) and filtered. The filtrate was washed sequentially with ice-water (100 mL), 10% NaHCO$_3$(aqueous, 100 mL), and brine (100 mL), dried over Na$_2$SO$_4$, and concentrated in vacuo to give 2,2,2-trifluoro-N-(3-fluoro-4-methoxyphenyl)acetamide (10 g, yield: 59.5%) as a yellow solid, which was used into next step without further purification. ESI-MS [M+H]+: 238.1.

Synthesis of 6-amino-2-fluoro-3-methoxybenzaldehyde. To a solution of 2,2,2-trifluoro-N-(3-fluoro-4-methoxyphenyl)acetamide (2 g, 8.43 mmol) in THF (20 mL) was added n-BuLi (7.4 mL, 2.4 M in THF, 17.7 mmol) at −78° C. The mixture was stirred at −78° C. for 0.5 h, and then DMF (1.85 g, 25.32 mmol) was added dropwise. After stirring at −78° C. for 30 min, the reaction was allowed to warm to −40° C. and stirred for another 1 h. The reaction was quenched with saturated aqueous NH$_4$Cl (20 mL) and extracted with EtOAc (50 mL×3). The combined organic layers were washed with brine (50 mL), dried over Na$_2$SO$_4$, filtered and concentrated to give the crude product, which was purified by flash chromatography (PE:EtOAc=10:1) to give 6-amino-2-fluoro-3-methoxybenzaldehyde (300 mg, yield: 21%) as a black oil. ESI-MS [M+H]+: 170.1.

Synthesis of (6-amino-2-fluoro-3-methoxyphenyl)methanol. To a mixture of 6-amino-2-fluoro-3-methoxybenzaldehyde (300 mg, 1.77 mmol) in MeOH (15 mL) at 0° C. was added NaBH$_4$ (202 mg, 5.34 mmol). After stirring at 0° C. for 2 h, the reaction was quenched with water (10 mL) and extracted with DCM (20 mL×3). The combined organic layers were washed with brine (30 mL), dried over Na$_2$SO$_4$, filtered and concentrated to give the crude product, which was purified by Prep-TLC (PE:EtOAc=2:1) to give (6-amino-2-fluoro-3-methoxyphenyl)methanol (240 mg, yield: 80%) as a yellow solid. ESI-MS [M+H]+: 172.1

Synthesis of (2 fluoro-3-methoxy-6-(1H-tetrazol-1 yl)phenyl)methanol. To a mixture of (6-amino-2-fluoro-3-methoxyphenyl)methanol (140 mg, 0.82 mmol) in trimethoxymethane (260 mg, 2.46 mmol) was added NaN$_3$ (160 mg, 2.46 mmol) at 0° C. The mixture was stirred at 0° C. for 0.5 h. Then AcOH (4 mL) was added and the reaction mixture was stirred at 50° C. for another 16 h. The mixture was diluted with saturated aqueous NaHCO$_3$(20 mL) and extracted with EtOAc (30 mL×3). The combined organic layers were washed with brine (30 mL), dried over Na$_2$SO$_4$, and concentrated in vacuo to give the crude product, which was purified by Prep-TLC (EtOAc:PE=3:1) to give (2-fluoro-3-methoxy-6-(1H-tetrazol-1-yl)phenyl)methanol (50 mg, yield: 27%) as a yellow solid. ESI-MS [M+H]+: 225.1.

Synthesis of I-(2-(chloromethyl)-3 fluoro-4-methoxyphenyl)-1H-tetrazole. To a mixture of (2-fluoro-3-methoxy-6-(1H-tetrazol-1-yl)phenyl)methanol (50 mg, 0.22 mmol) in DCM (1 mL) was added SOCl$_2$ (1 mL). The reaction mixture was stirred at room temperature for 16 h, and then concentrated in vacuo to give 1-(2-(chloromethyl)-3-fluoro-4-methoxyphenyl)-1H-tetrazole (50 mg, yield: 93%) as brown oil which was used in the next step without further purification. ESI-MS [M+H]+: 243.1.

Synthesis of (2 fluoro-3-methoxy-6-(1H-tetrazol-1 yl)phenyl)methanamine. A mixture of 1-(2-(chloromethyl)-3-fluoro-4-methoxyphenyl)-1H-tetrazole (50 mg, 0.2 mmol) and NH$_3$ in IPA (3 mL) was stirred at 50° C. in a sealed tube for 16 h. The reaction was concentrated to give (2-fluoro-3-methoxy-6-(1H-tetrazol-1-yl)phenyl)methanamine (40 mg, yield: 93%) as a yellow solid, which was used into next step without further purification. ESI-MS [M+H]+: 224.2.

Example 155

Synthesis of (6-bromo-2-fluoro-3-methoxyphenyl)methanamine

Scheme 157

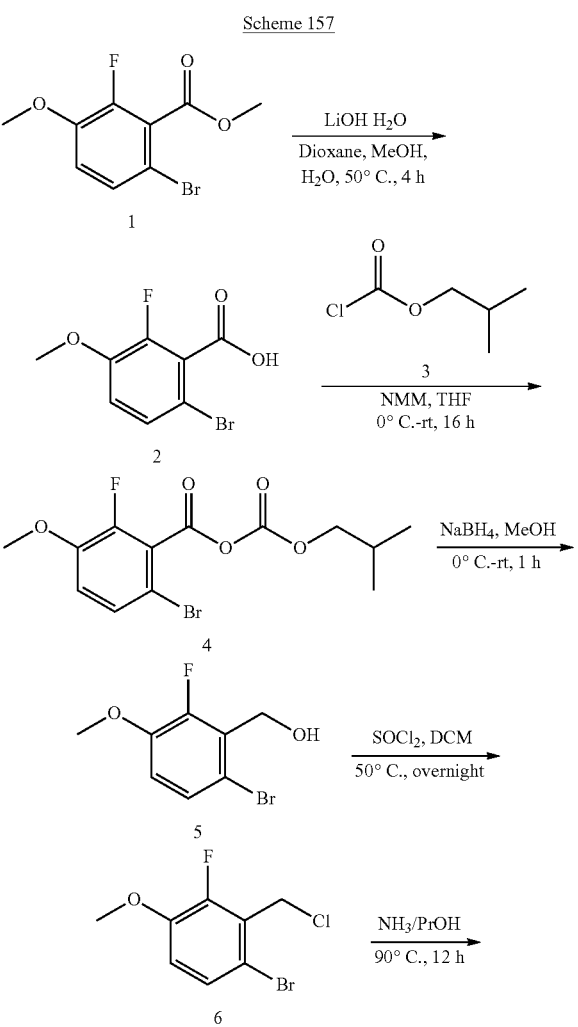

-continued

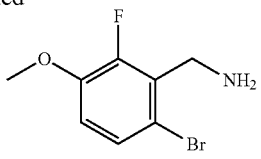

7

Synthesis of 6-bromo-2-fluoro-3-methoxybenzoic acid. A solution of methyl 6-bromo-2-fluoro-3-methoxybenzoate (2.63 g, 10.0 mmol) and LiOH H$_2$O (1.26 g, 30.0 mmol) in dioxane (10 mL), MeOH (5 mL) and H$_2$O (5 mL) was stirred at 50° C. for 4 h. The reaction mixture was concentrated in vacuo and the residue adjusted to pH 2 by adding HCl (1.0 M). The mixture was extracted with EtOAc (100 mL×3). The combined organics were washed with brine (20 mL), dried over Na$_2$SO$_4$, concentrated to give 6-bromo-2-fluoro-3-methoxybenzoic acid (2.3 g, yield: 92%) as a white solid which was used in the next step without further purification. ESI-MS [M+H]$^+$: 249.0.

Synthesis of 6-bromo-2-fluoro-3-methoxybenzoic (isobutyl carbonic) anhydride. To a solution of 6-bromo-2-fluoro-3-methoxybenzoic acid (1.8 g, 7.2 mmol) in THF (20 mL) was added isobutyl carbonochloridate (1.5 g, 10.98 mmol) and 4-methylmorpholine (1.6 mL, 13.0 mmol) at 0° C. The reaction mixture was stirred at room temperature overnight, and then filtered to remove any salts generated. The filtrate was concentrated in vacuo to give crude 6-bromo-2-fluoro-3-methoxybenzoic (isobutyl carbonic) anhydride which was used to the next step without further purification. ESI-MS [M+Na]$^+$: 371.0.

Synthesis of (6-bromo-2-fluoro-3-methoxyphenyl)methanol. To a solution of crude 6-bromo-2-fluoro-3-methoxybenzoic (isobutyl carbonic) anhydride (2.5 g, 7.2 mmol) in MeOH (10 mL) at 0° C. was added NaBH$_4$ (570 mg, 15 mmol). The reaction mixture was warmed to room temperature and stirred for 1 h. The mixture was concentrated in vacuo, diluted with H$_2$O (30 mL), and extracted with EtOAc (50 mL×3). The combined organic layers were washed with brine (50 mL), dried over Na$_2$SO$_4$, concentrated to give the crude, which was purified by silica gel chromatography (PE/EtOAc=1:5) to afford (6-bromo-2-fluoro-3-methoxyphenyl)methanol (1.6 g, yield: 94%) as colorless oil. ESI-MS [M−OH]$^+$: 217.0.

Synthesis of 1-bromo-2-(chloromethyl)-3-fluoro-4-methoxybenzene. A solution of (6-bromo-2-fluoro-3-methoxyphenyl)methanol (400 mg, 1.7 mmol) and SOCl$_2$ (0.5 mL) in DCM (10 mL) was stirred at 50° C. overnight. The mixture was concentrated in vacuo to give crude 1-bromo-2-(chloromethyl)-3-fluoro-4-methoxybenzene which was used to the next step without further purification.

Synthesis of (6-bromo-2-fluoro-3-methoxyphenyl)methanamine. A solution of 1-bromo-2-(chloromethyl)-3-fluoro-4-methoxybenzene (430 mg, 1.7 mmol) in NH$_3$ in i-PrOH (25 mL) was stirred at 90° C. overnight. The reaction mixture was concentrated in vacuo and purified by silica gel chromatography (DCM/MeOH=6:1) to afford (6-bromo-2-fluoro-3-methoxyphenyl)methanamine (218 mg, yield: 54.8%) as colorless oil. ESI-MS [M+H]$^+$: 234.0.

Example 156

Synthesis of (2-fluoro-3-methoxy-6-(pyridin-4-yl) phenyl)methanamine

Scheme 158

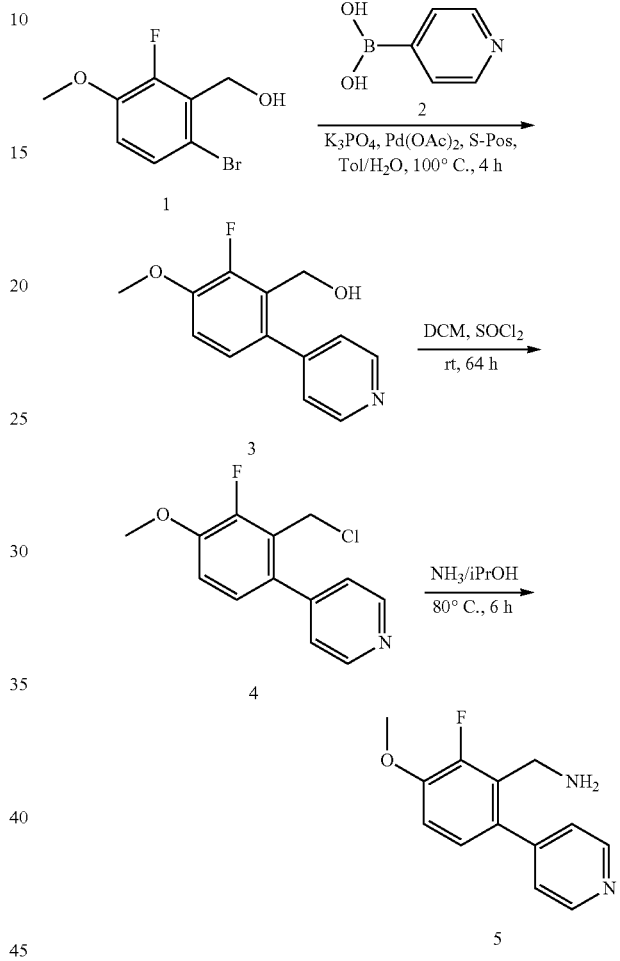

Synthesis of (2-fluoro-3-methoxy-6-(pyridin-4-yl)phenyl) methanol. A solution of (6-bromo-2-fluoro-3-methoxyphenyl)methanol (250 mg, 1.06 mmol), pyridin-4-ylboronic acid (2.61 g, 21.2 mmol), Pd(OAc)$_2$ (24 mg, 0.11 mmol), K$_3$PO$_4$ (450 mg, 2.12 mmol) and S-Phos (86.1 mg, 0.21 mmol) in toluene (4 mL) and H$_2$O (0.5 mL) was stirred at 100° C. for 4 h. The mixture was concentrated to give the residue, which was diluted with H$_2$O (15 mL) and extracted with EtOAc (25 mL×3). The combined organic layers were washed with brine (30 mL), dried over Na$_2$SO$_4$, and concentrated in vacuo to give the crude, which was purified by Prep-TLC (DCM/MeOH=15/1) to give (2-fluoro-3-methoxy-6-(pyridin-4-yl)phenyl)methanol (20 mg, yield: 8%) as colorless oil. ESI-MS [M+H]$^+$: 234.1.

Synthesis of 4-(2-(chloromethyl)-3-fluoro-4-methoxyphenyl)pyridine. A solution of (2-fluoro-3-methoxy-6-(pyridin-4-yl)phenyl)methanol (20 mg, 0.086 mmol) and SOCl$_2$ (0.5 mL) in DCM (1 mL) was stirred at room temperature for 64 h. The reaction mixture was concentrated in vacuo to give crude 4-(2-(chloromethyl)-3-fluoro-4-methoxyphenyl)pyridine which was submitted to the next reaction without further purification. ESI-MS [M+H]+: 252.1.

Synthesis of (2 fluoro-3-methoxy-6-(pyridin-4 yl)phenyl) methanamine. A solution of crude 4-(2-(chloromethyl)-3-fluoro-4-methoxyphenyl)pyridine (21.6 mg, 0.086 mmol) in NH$_3$ in i-PrOH (5 mL) was stirred at 80° C. in a sealed tube for 6 h. The reaction mixture was concentrated in vacuo to give crude (2-fluoro-3-methoxy-6-(pyridin-4-yl)phenyl) methanamine which was used in the next reaction without further purification. ESI-MS [M+H]+: 233.1.

Example 157

Synthesis of (2-fluoro-3-methoxyphenyl)methanamine

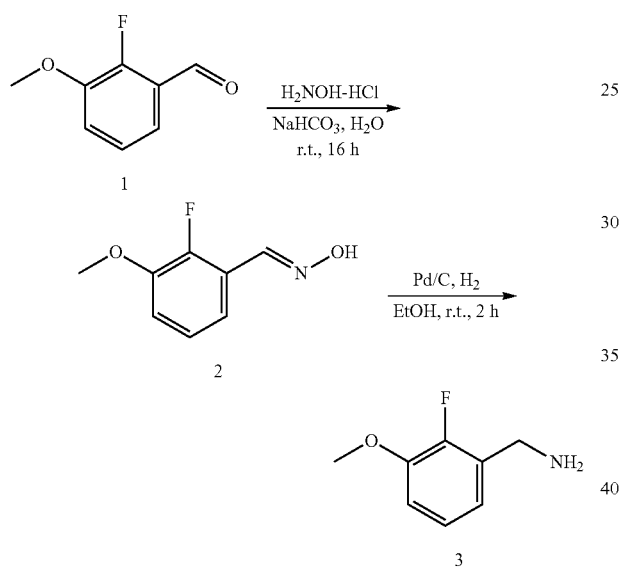

Synthesis of (E)-2-fluoro-3-methoxybenzaldehyde oxime. To a stirred solution of sodium bicarbonate (2.73 g, 32.5 mmol) in water (50 mL) was added hydroxylamine hydrochloride (2.30 g, 33.2 mmol) portionwise over 30 min. The resultant solution was added to a vigorously stirred suspension of 2-fluoro-3-methoxybenzaldehyde (5.0 g, 32.5 mmol) in ethanol (45 mL) and the reaction mixture was stirred at room temperature for 16 h. The resultant precipitate was removed by filtration and washed with water (3×100 mL) and then allowed to air dry to afford 2-fluoro-3-methoxybenzaldehyde oxime (4.69 g, 85%) as a white solid. ESI-MS [M+H]+: 170.2

Synthesis of (2-fluoro-3-methoxyphenyl)methanamine. A mixture of the 2-fluoro-3-methoxybenzaldehyde oxime (4.69 g, 27.8 mmol) and Pd/C (500 mg) in ethanol (150 mL) was stirred at room temperature for 2 h under hydrogen atmosphere. The reaction mixture was filtered through Celite and washed with MeOH (100 mL). The filtrate was concentrated in vacuo to give (2-fluoro-3-methoxyphenyl) methanamine (4 g crude) as a yellow solid, which was used into next step without further purification. ESI-MS [M+H]+: 156.2.

Example 158

Synthesis of (2 fluoro-6-(1H-tetrazol-1-yl)-3-(trifluoromethoxy)phenyl)methanamine

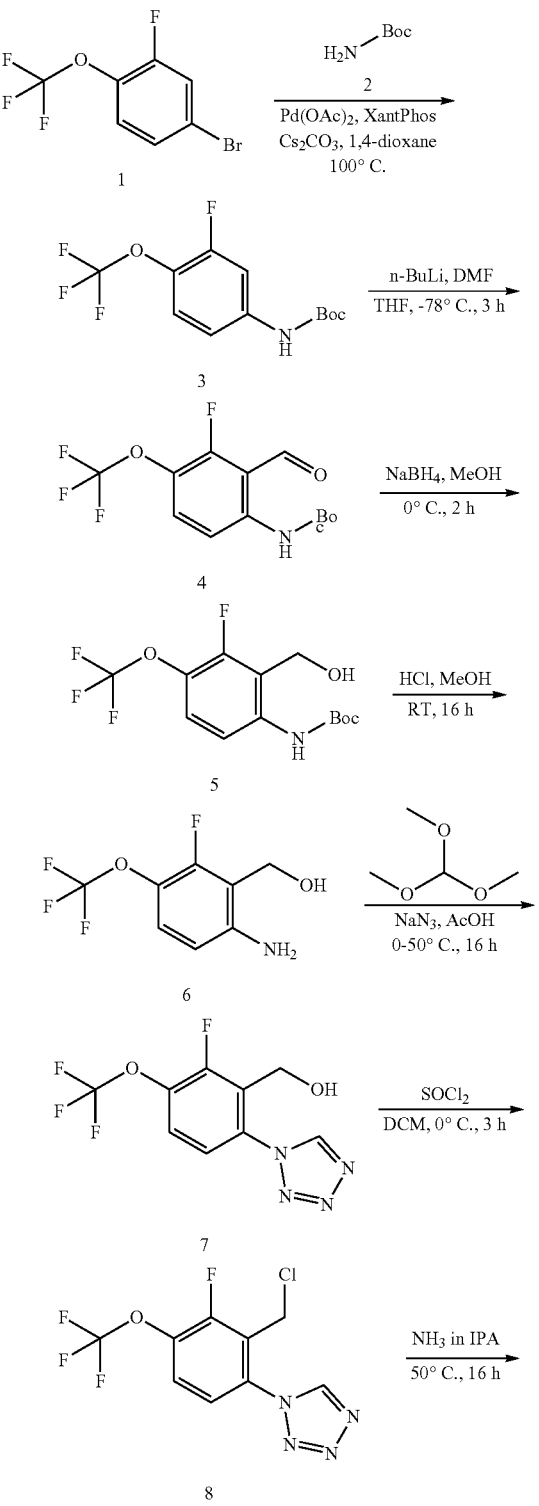

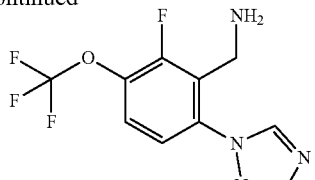

9

Synthesis of tert-butyl (3-fluoro-4-(trifluoromethoxy)phenyl)carbamate. To a solution of 4-bromo-2-fluoro-1-(trifluoromethoxy)benzene (5 g, 0.019 mol) and tert-butyl carbamate (3.38 g, 0.0 mol) in dioxane (30 mL) was added Pd(OAc)$_2$(0.425 g, 1.9 mmol), XantPhos (2.19 g, 3.8 mmol) and Cs$_2$CO$_3$ (18.52 g, 0.057 mmol). The reaction mixture was stirred at 100° C. for 16 hours under argon atmosphere, then cooled to room temperature and water (50 mL) was added. The aqueous phase was extracted with ethyl acetate (100 mL×4). The combined organic phases were dried over sodium sulfate, concentrated in vacuo, and the residue purified by silica gel chromatography (PE:EtOAc=2:1) to give tert-butyl (3-fluoro-4-(trifluoromethoxy)phenyl)carbamate (4.8 g, 86%) as a yellow solid. ESI-MS [M+H]$^+$: 296.2.

Synthesis of tert-butyl (3-fluoro-2-formyl-4-(trifluoromethoxy)phenyl)carbamate. To a solution of tert-butyl (3-fluoro-4-(trifluoromethoxy)phenyl)carbamate (4.8 g, 0.016 mol) in THF (50 mL) at −78° C. was added n-BuLi (15.5 mL, 0.037 mol) dropwise under argon atmosphere. The reaction mixture was stirred at −78° C. for 0.5 h, warmed up to −50° C. and stirred for 1 h. The reaction was cooled to −78° C. and then DMF (4.67 g, 0.064 mol) was added dropwise at −78° C. The reaction mixture was stirred at −78° C. for 30 min, then warmed up to −40° C. for 2 h. The reaction mixture was quenched with H$_2$O (20 mL). The mixture was extracted with EtOAc (100 mL×3). The combined organic layers were washed with brine (30 mL×3), dried over Na$_2$SO$_4$, filtered and concentrated in vacuo to give the crude product, which was purified by column chromatography (PE:EtOAc=10:1) to give tert-butyl (3-fluoro-2-formyl-4-(trifluoromethoxy)phenyl)carbamate (4.4 g, yield: 86%) as a white solid. ESI-MS [M+H]$^+$: 324.2.

Synthesis of tert-butyl (3-fluoro-2-(hydroxymethyl)-4-(trifluoromethoxy)phenyl)carbamate. To a mixture of tert-butyl (3-fluoro-2-(hydroxymethyl)-4-(trifluoromethoxy)phenyl)carbamate (1 g, 0.003 mol) in MeOH (5 mL) was added NaBH$_4$ (235 mg, 0.006 mmol) at 0° C. The reaction mixture was stirred at 0° C. for 2 h, then water (10 mL) was added and the mixture was extracted with DCM (50 mL×3). The combined organic layers were washed with brine, dried over Na$_2$SO$_4$, filtered and concentrated in vacuo to give the crude product, which was purified by column chromatography (PE:EtOAc=2:1) to give tert-butyl (3-fluoro-2-(hydroxymethyl)-4-(trifluoromethoxy)phenyl)carbamate (950 mg, yield: 80%) as a yellow solid. ESI-MS [M+H]$^+$: 326.2.

Synthesis of (6-amino-2-fluoro-3-(trifluoromethoxy)phenyl)methanol. To a solution of tert-butyl (3-fluoro-2-(hydroxymethyl)-4-(trifluoromethoxy)phenyl)carbamate (950 mg, 2.92 mmol) in MeOH (2 mL) was added HCl in MeOH (4M, 5 mL). The reaction mixture was stirred at RT for 16 hours. The reaction mixture was concentrated in vacuo to give crude (6-amino-2-fluoro-3-(trifluoromethoxy)phenyl)methanol, which was used in next step without further purification. (760 mg, yield 100%) as a yellow solid. ESI-MS [M+H]$^+$: 226.1.

Synthesis of (2-fluoro-6-(1H-tetrazol-1-yl)-3-(trifluoromethoxy)phenyl)methanol. To a mixture of (6-amino-2-fluoro-3-(trifluoromethoxy)phenyl)methanol (730 mg, 3.24 mmol) in trimethoxymethane (1.03 g, 9.72 mmol) was added NaN$_3$ (632 mg, 9.72 mmol) at 0° C. The mixture was stirred at 0° C. for 0.5 h. Then AcOH (5 mL) was added, and the reaction mixture was stirred at 50° C. for 16 h. The mixture was adjusted to pH 8 using sat. aq. NaHCO$_3$ and the mixture was extracted with EtOAc (100 mL×2), The combined organic layers were concentrated to give the crude product, which was purified by column chromatography (petroleum ether:ethyl acetate=1:1) to give (2-fluoro-6-(1H-tetrazol-1-yl)-3-(trifluoromethoxy)phenyl)methanol (240 mg, yield: 27%) as a yellow solid. ESI-MS [M+H]$^+$: 279.1.

Synthesis of 1-(2-(chloromethyl)-3-fluoro-4-(trifluoromethoxy)phenyl)-1H-tetrazole. To a mixture of (2-fluoro-6-(1H-tetrazol-1-yl)-3-(trifluoromethoxy)phenyl)methanol (240 mg, 0.86 mmol) in DCM (5 mL) was added SOCl$_2$ (0.2 mL, 2.58 mmol). The reaction mixture was stirred at 0° C. for 3 h and then concentrated in vacuo. The residue was diluted with water (5 mL) and the pH value was adjusted to 8 using sat. aq. NaHCO$_3$. The mixture was extracted with ethyl acetate (3×50 mL), the combined organic layers were washed with brine (30 mL), dried (MgSO$_4$) and concentrated in vacuo. The crude residue was purified by column chromatography (DCM:MeOH=15:1) to give 1-(2-(chloromethyl)-3-fluoro-4-(trifluoromethoxy)phenyl)-1H-tetrazole (230 mg, yield: 90%) as a white solid. ESI-MS [M+H]$^+$: 297.6.

Synthesis of (2-fluoro-6-(1H-tetrazol-1-yl)-3-(trifluoromethoxy)phenyl)methanamine. A mixture of 1-(2-(chloromethyl)-3-fluoro-4-(trifluoromethoxy)phenyl)-1H-tetrazole (170 mg, 0.57 mmol) and NH$_3$ in IPA (20 mL) was stirred at 50° C. for 16 h. The reaction mixture was concentrated in vacuo to give crude (2-fluoro-6-(1H-tetrazol-1-yl)-3-(trifluoromethoxy)phenyl)methanamine (150 mg, yield: 95%) as a white solid, which was used in the next step without further purification. ESI-MS [M+H]$^+$: 278.1.

Example 159

Synthesis of (2-fluoro-3-methoxy-6-(4H-1,2,4-triazol-4-yl)phenyl)methanamine

Scheme 161

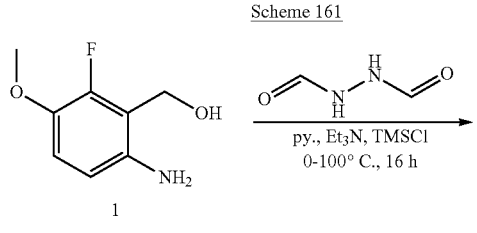

1

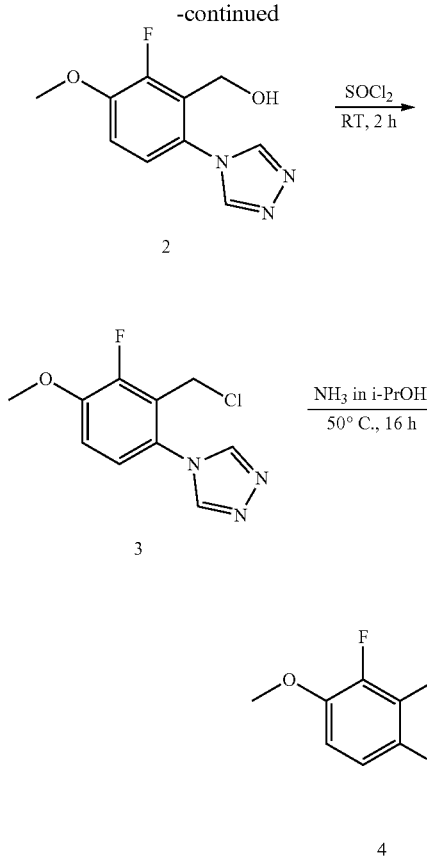

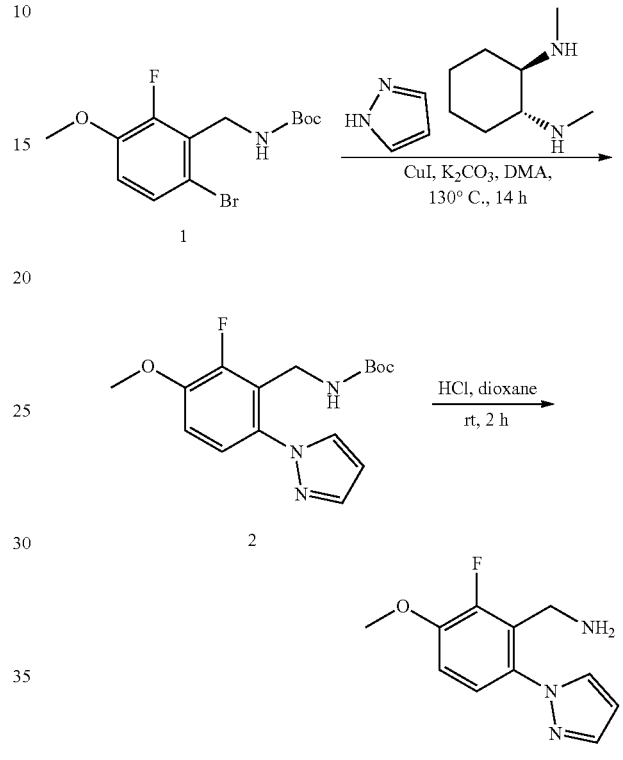

Example 160

Synthesis of (2 fluoro-3-methoxy-6-(1H pyrazol-1-yl)phenyl)methanamine

Scheme 162

Synthesis of (2-fluoro-3-methoxy-6-(4H-1,2,4-triazol-4-yl)phenyl)methanol. To a solution of (6-amino-2-fluoro-3-methoxyphenyl)methanol (500 mg, 2.92 mmol) in pyridine (20 mL) was added N'-formylformohydrazide (772 mg, 8.77 mmol) and Et$_3$N (1.47 g, 14.6 mmol). TMSCl (4.73 g, 43.8 mmol) was added dropwise at 0° C. The reaction mixture was heated to 100° C. and stirred for 16 h, then concentrated in vacuo. Water (50 mL) was added and the mixture was extracted with EtOAc (50 mL×3). The combined organic layers were washed with brine (50 mL), dried over Na$_2$SO$_4$, filtered and concentrated to give the crude, which was purified by washing with MeOH (10 mL) to give (2-fluoro-3-methoxy-6-(4H-1,2,4-triazol-4-yl)phenyl)methanol as a white solid (300 mg, yield: 46%). ESI-MS [M+H]$^+$: 224.1.

Synthesis of 4-(2-(chloromethyl)-3-fluoro-4-methoxyphenyl)-4H-1,2,4-triazole. To a solution of (2-fluoro-3-methoxy-6-(4H-1,2,4-triazol-4-yl)phenyl)methanol (80 mg, 0.36 mmol) in DCM (2 mL) at 0° C. was added SOCl$_2$ (0.2 mL). The reaction mixture was stirred at rt for 2 h. The mixture was concentrated in vacuo to give crude 4-(2-(chloromethyl)-3-fluoro-4-methoxyphenyl)-4H-1,2,4-triazole as a yellow oil, which was used in the next step without further purification (80 mg, crude). ESI-MS [M+H]$^+$: 242.1.

Synthesis of (2-fluoro-3-methoxy-6-(4H-1,2,4-triazol-4-yl)phenyl)methanamine. A mixture of 4-(2-(chloromethyl)-3-fluoro-4-methoxyphenyl)-4H-1,2,4-triazole (80 mg, 0.33 mmol) in NH$_3$/i-PrOH (20 mL) was stirred in a sealed tube at 50° C. for 16 h. The reaction mixture was concentrated in vacuo to give crude (2-fluoro-3-methoxy-6-(4H-1,2,4-triazol-4-yl)phenyl)methanamine as a yellow oil, which was used in the next step without further purification (75 mg, crude). ESI-MS [M+H]$^+$: 223.1.

Synthesis of tert-butyl (2-fluoro-3-methoxy-6-(1H-pyrazol-1-yl)benzyl)carbamate. A mixture of tert-butyl (6-bromo-2-fluoro-3-methoxybenzyl)carbamate (90 mg, 0.27 mmol), 1H-pyrazole (37 mg, 0.54 mmol), CuI (10 mg, 0.054 mmol), (1R,2R)—N$_1$,N$_2$-dimethylcyclohexane-1,2-diamine (15 mg, 0.108 mmol) and K$_2$CO$_3$ (112 mg, 0.81 mmol) in DMA (3 mL) was stirred at 130° C. under air atmosphere for 14 h. The reaction mixture was diluted with H$_2$O (20 mL) and extracted with EtOAc (30 mL×3). The combined organic layers were washed with brine (30 mL), dried over Na$_2$SO$_4$ and concentrated in vacuo to give the crude, which was purified by Prep-TLC (eluent: PE/EtOAc=1/1) to give tert-butyl (2-fluoro-3-methoxy-6-(1H-pyrazol-1-yl)benzyl)carbamate (60 mg, yield: 69%) as a yellow solid. ESI-MS [M+H]+: 322.2.

Synthesis of (2-fluoro-3-methoxy-6-(1H-pyrazol-1-yl)phenyl)methanamine. A mixture of tert-butyl (2-fluoro-3-methoxy-6-(1H-pyrazol-1-yl)benzyl)carbamate (60 mg, 0.19 mmol) and HCl (1 mL, 4 M solution in dioxane, 4 mmol) in dioxane (2 mL) was stirred at room temperature for 2 h. The reaction mixture was concentrated in vacuo to give (2-fluoro-3-methoxy-6-(1H-pyrazol-1-yl)phenyl)methanamine (40 mg crude) as a yellow solid, which was used in the next step without further purification. ESI-MS [M+H]+: 222.2.

Example 161

Synthesis of (3-bromo-2-fluoro-6-(1H-tetrazol-1-yl)phenyl)methanamine

Scheme 163

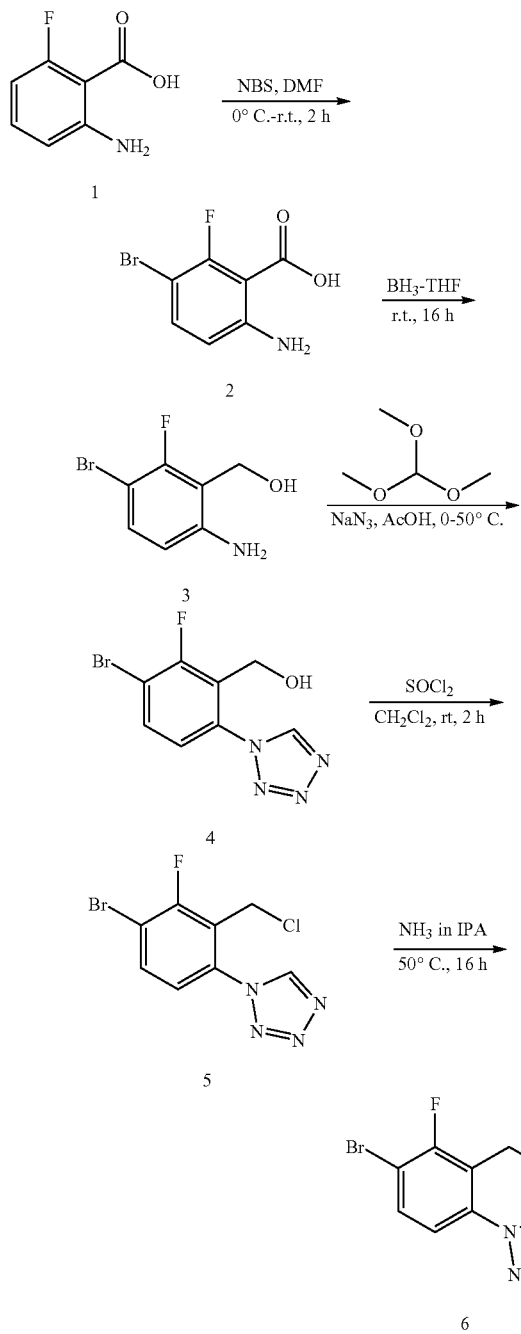

Synthesis of 6-amino-3-bromo-2-fluorobenzoic acid. To a mixture of 2-amino-6-fluorobenzoic acid (5 g, 32.23 mmol) in DMF (50 mL) was added NBS (5.7 g, 32.23 mmol) at 0° C. The reaction mixture was stirred at room temperature for 2 h. The mixture was diluted with H$_2$O (500 mL) and filtered. The filter cake was dried to give 6-amino-3-bromo-2-fluorobenzoic acid as a yellow solid (7 g, yield: 92.8%). ESI-MS [M+H]+: 235.1.

Synthesis of (6-amino-3-bromo-2-fluorophenyl)methanol. A solution of 6-amino-3-bromo-2-fluorobenzoic acid (7 g, 29.91 mmol) in BH$_3$-THF (1M, 100 mL) was stirred at r.t. for 16 h. The reaction mixture was quenched with MeOH (20 mL) and concentrated in vacuo. The residue was purified by flash chromatography (0~50% EtOAc in PE) to give (6-amino-3-bromo-2-fluorophenyl) methanol as a white solid (5.4 g, yield: 82%). ESI-MS [M+H]+: 220.1.

Synthesis of (3-bromo-2-fluoro-6-(1H-tetrazol-1-yl)phenyl)methanol. To a mixture of (6-amino-3-bromo-2-fluorophenyl)methanol (250 mg, 1.14 mmol) in trimethoxymethane (362.9 mg, 3.42 mmol) at 0° C. was added NaN$_3$ (222.3 mg, 3.42 mmol). The reaction mixture was stirred at 0° C. for 0.5 h. Then AcOH (9 mL) was added to the reaction and it was stirred at 50° C. for 16 h. The reaction was adjusted to pH 8 using sat. aq. NaHCO$_3$. The mixture was extracted with EtOAc (10 mL×2) and DCM (10 mL). The combined organic layers were concentrated and purified by flash chromatography (PE/EtOAc=1/1) to give (3-bromo-2-fluoro-6-(1H-tetrazol-1-yl)phenyl)methanol (200 mg, 64.5%) as a white solid. ESI-MS [M+H]+: 273.0.

Synthesis of 1-(4-bromo-2-(chloromethyl)-3-fluorophenyl)-1H-tetrazole. To a mixture of (3-bromo-2-fluoro-6-(1H-tetrazol-1-yl)phenyl)methanol (150 mg, 0.55 mmol) in DCM (3 mL) was added SOCl$_2$ (3 mL). The mixture was stirred at 25° C. for 2 h and concentrated to give 1-(4-bromo-2-(chloromethyl)-3-fluorophenyl)-1H-tetrazole as a brown oil, which was used in the next step without further purification (150 mg, crude). ESI-MS [M+H]+: 290.2.

Synthesis of (3-bromo-2-fluoro-6-(1H-tetrazol-1-yl)phenyl)methanamine. A mixture of 1-(4-bromo-2-(chloromethyl)-3-fluorophenyl)-1H-tetrazole (150 mg, crude) and NH$_3$ in IPA (6 mL) was stirred at 50° C. for 16 h. The reaction mixture was concentrated in vacuo to give (3-bromo-2-fluoro-6-(1H-tetrazol-1-yl)phenyl)methanamine as yellow oil (80 mg, crude), which was used in the next step without further purification. ESI-MS [M+H]+: 272.1.

Example 162

Synthesis of methyl 2'-(aminomethyl)-3' fluoro-4'-methoxy-[1,1'-biphenyl]-4-carboxylate Scheme 164

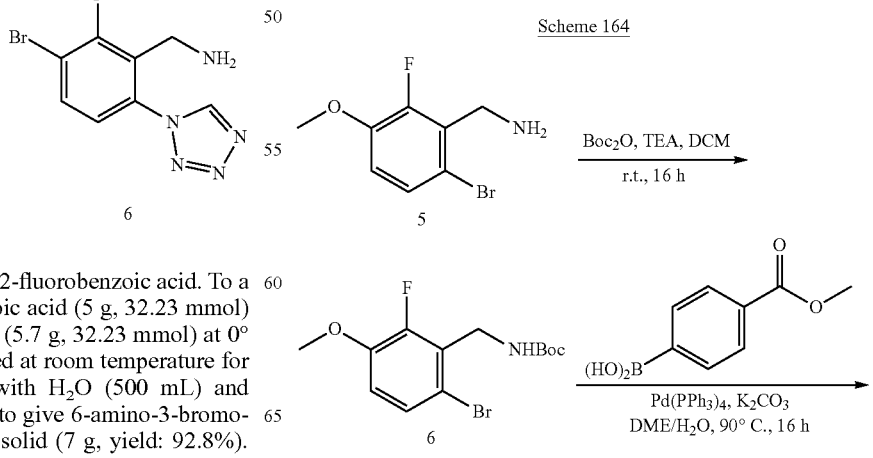

-continued

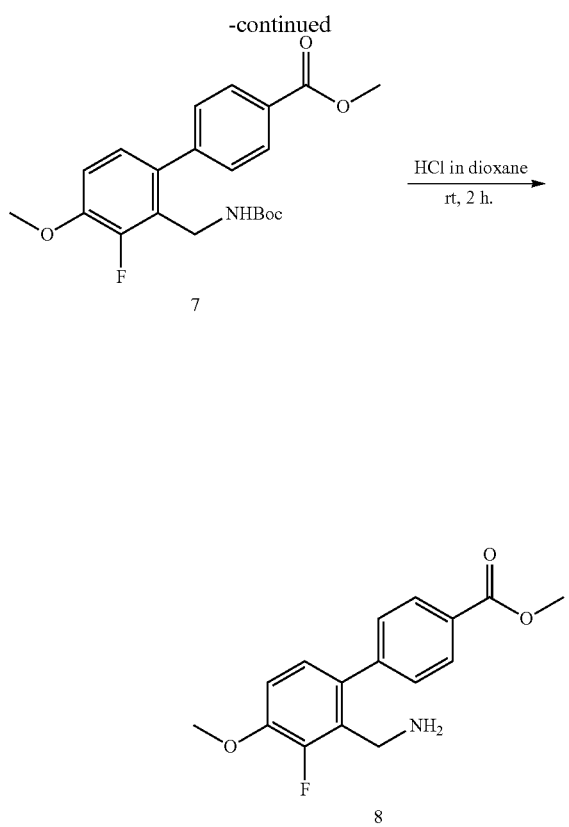

Example 163

Synthesis of (2-fluoro-3-methoxy-6-(pyridazin-4-yl)phenyl)methanamine

Scheme 165

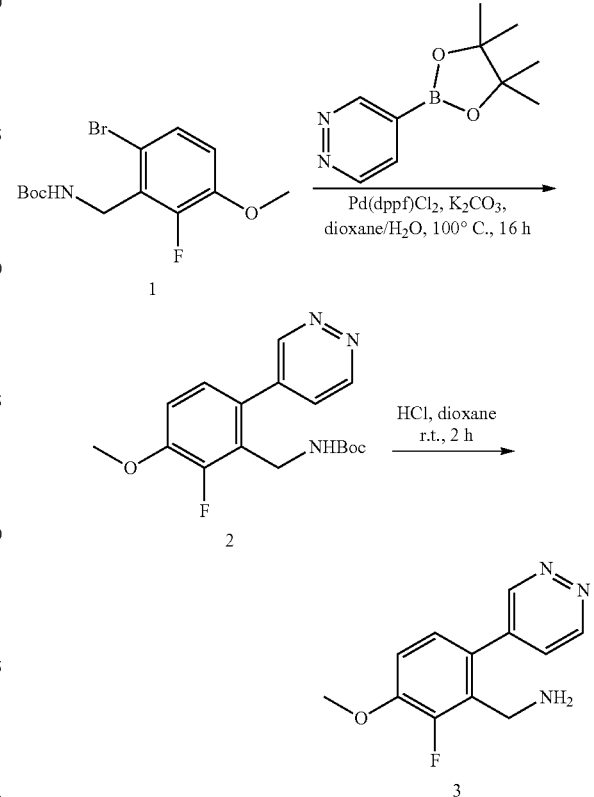

Synthesis of tert-butyl (6-bromo-2-fluoro-3-methoxybenzyl)carbamate. A mixture of (6-bromo-2-fluoro-3-methoxyphenyl)methanamine (385 mg, 1.65 mmol), (Boc)$_2$O (430 mg, 1.98 mmol) and Et$_3$N (0.46 mL, 3.3 mmol) in DCM (10.0 mL) was stirred at room temperature for 16 h. H$_2$O (20 mL) was added and the mixture was extracted with EtOAc (30 mL×3). The combined organic layers were washed with brine (30 mL), dried over Na$_2$SO$_4$ and concentrated in vacuo to give the crude, which was purified by column chromatography (eluent: PE/EtOAc=5/1) to give the desired product (500 mg, 91%) as colorless oil. ESI-MS [M+H]$^+$: 334.2.

Synthesis of methyl 2'-(((tert-butoxycarbonyl)amino)methyl)-3'-fluoro-4'-methoxy-[1,1'-biphenyl]-4-carboxylate. A mixture of tert-butyl (6-bromo-2-fluoro-3-methoxybenzyl)carbamate (200 mg, 0.60 mmol), (4-(methoxycarbonyl)phenyl)boronic acid (135 mg, 0.75 mmol), Pd(PPh$_3$)$_4$ (69 mg, 0.06 mmol) and K$_2$CO$_3$ (248 mg, 1.8 mmol) in DME/H$_2$O (10 mL/1 mL) was stirred at 90° C. under N$_2$ for 16 h. The reaction mixture was diluted with H$_2$O (15 mL) and extracted with EtOAc (30 mL×3). The combined organic layers were washed with brine (30 mL), dried over Na$_2$SO$_4$, and concentrated in vacuo to give the crude, which was purified by silica gel column chromatography with PE/EtOAc=3/1 to give the desired product (200 mg, 85.6%) as colorless oil. ESI-MS [M+H]$^+$: 390.1.

Synthesis of methyl 2'-(aminomethyl)-3'-fluoro-4'-methoxy-[1,1'-biphenyl]-4-carboxylate. A mixture of methyl 2'-(((tert-butoxycarbonyl)amino)methyl)-3'-fluoro-4'-methoxy-[1,1'-biphenyl]-4-carboxylate (50 mg, 0.13 mmol) in HCl (4M in dioxane, 2.0 mL) was stirred at room temperature for 2 h. The reaction mixture was concentrated in vacuo to give crude methyl 2'-(aminomethyl)-3'-fluoro-4'-methoxy-[1,1'-biphenyl]-4-carboxylate (40 mg, crude) as a yellow solid, which was used into the next step without further purification. ESI-MS [M+H]$^+$: 290.2.

Synthesis of tert-butyl (2-fluoro-3-methoxy-6-(pyridazin-4-yl)benzyl)carbamate. A mixture of tert-butyl (6-bromo-2-fluoro-3-methoxybenzyl)carbamate (130 mg, 0.39 mmol), 4-(4,4,5,5-tetramethyl-1,3,2-dioxaborolan-2-yl)pyridazine (80 mg, 0.39 mmol), Pd(dppf)Cl$_2$ (32 mg, 0.044 mmol) and K$_2$CO$_3$ (161 mg, 1.17 mmol) in dioxane/H$_2$O (10 mL/1 mL) was stirred at 100° C. under N$_2$ for 16 h. The reaction mixture was diluted with H$_2$O (10 mL) and extracted with EtOAc (30 mL×3). The combined organic layers were washed with brine (20 mL), dried over Na$_2$SO$_4$, and concentrated to give the crude, which was purified by silica gel column chromatography (eluent: DCM/MeOH=10/1) to give tert-butyl (2-fluoro-3-methoxy-6-(pyridazin-4-yl)benzyl)carbamate (40 mg, 31%) as yellow oil. ESI-MS [M+H]$^+$: 334.1.

Synthesis of (2-fluoro-3-methoxy-6-(pyridazin-4-yl)phenyl)methanamine. A mixture of tert-butyl (2-fluoro-3-methoxy-6-(pyridazin-4-yl)benzyl)carbamate (40 mg, 0.12 mmol) in HCl (4M in dioxane, 2.0 mL) was stirred at room temperature for 2 h. The reaction mixture was concentrated in vacuo to give crude (2-fluoro-3-methoxy-6-(pyridazin-4-yl)phenyl)methanamine (30 mg, crude) as a yellow solid, which was used into the next step without further purification. ESI-MS [M+H]$^+$: 290.1.

Example 164

Synthesis of (3-ethyl-2 fluoro-6-(1H-tetrazol-1-yl)phenyl)methanamine Scheme 1

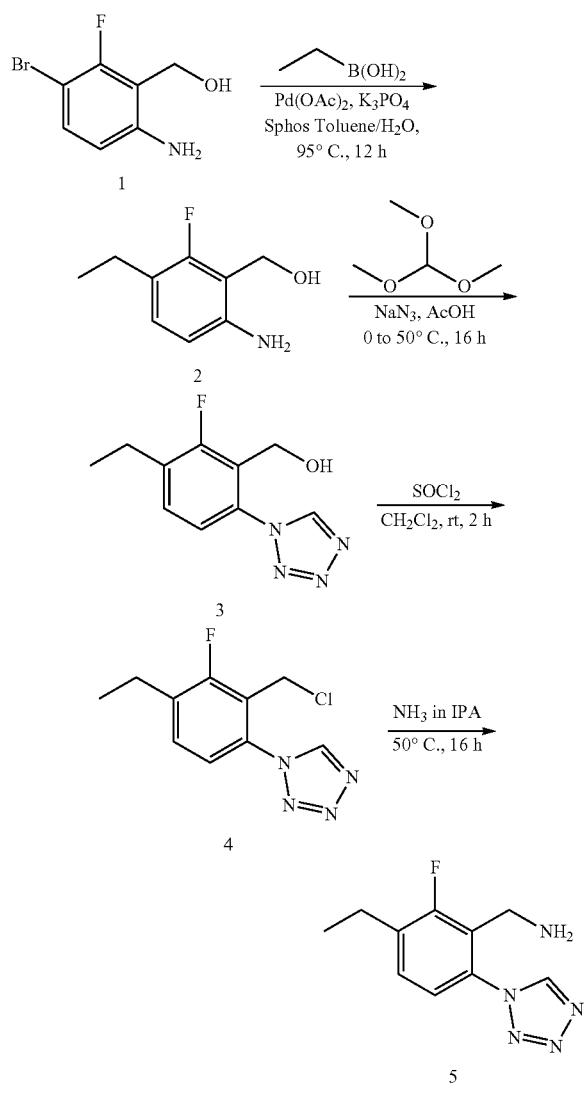

Scheme 166

Synthesis of (6-amino-3-ethyl-2-fluorophenyl)methanol. To a solution of (6-amino-3-bromo-2-fluorophenyl)methanol (1 g, 4.54 mmol) in toluene/H$_2$O (50 mL/5 mL) was added ethylboronic acid (504 mg, 6.81 mmol), Pd(OAc)$_2$ (509 mg, 2.27 mmol), S-phos (930 mg, 2.27 mmol) and K$_3$PO$_4$ (2.89 g, 13.6 mmol). The mixture was stirred at 95° C. for 12 h under N$_2$. The reaction mixture was concentrated in vacuo and water (30 mL) was added. The mixture was extracted with EtOAc (30 mL×3). The combined organic layers were concentrated and purified by flash silica gel chromatography (PE/EtOAc=20/1) to give (6-amino-3-ethyl-2-fluorophenyl)methanol (120 mg, yield: 15.6%) as a white solid. ESI-MS [M+H]+: 170.2

Synthesis of (3-ethyl-2-fluoro-6-(1H-tetrazol-1-yl)phenyl)methanol. To a mixture of (6-amino-3-ethyl-2-fluorophenyl)methanol (120 mg, 0.71 mmol) in trimethoxymethane (226 mg, 2.13 mmol) at 0° C. was added NaN$_3$ (138 mg, 2.13 mmol). The mixture was stirred at 0° C. for 0.5 h. Then AcOH (3 mL) was added and the reaction mixture was stirred at 50° C. for 16 h. The mixture was adjusted to pH 8 using sat. aq. NaHCO$_3$ and then extracted with EtOAc (20 mL×2). The combined organic layers were concentrated in vacuo and purified by flash silica gel chromatography (PE/EtOAc=1/1) to give (3-ethyl-2-fluoro-6-(1H-tetrazol-1-yl)phenyl)methanol as a white solid (80 mg, 50.7%). ESI-MS [M+H]+: 223.1.

Synthesis of 1-(2-(chloromethyl)-4-ethyl-3-fluorophenyl)-1H-tetrazole. To a mixture of (3-ethyl-2-fluoro-6-(1H-tetrazol-1-yl)phenyl)methanol (80 mg, 0.36 mmol) in DCM (3 mL) was added SOCl$_2$ (3 mL). The reaction mixture was stirred at room temperature for 2 h and then concentrated in vacuo to give 1-(2-(chloromethyl)-4-ethyl-3-fluorophenyl)-1H-tetrazole (80 mg, crude) as a yellow oil, which was used in the next step without further purification. ESI-MS [M+H]+: 241.2.

Synthesis of (3-ethyl-2-fluoro-6-(1H-tetrazol-1-yl)phenyl)methanamine. A mixture of 1-(2-(chloromethyl)-4-ethyl-3-fluorophenyl)-1H-tetrazole (80 mg, crude) and NH$_3$ in IPA (6 mL) was stirred at 50° C. for 16 h. The reaction mixture was concentrated in vacuo to give (3-ethyl-2-fluoro-6-(1H-tetrazol-1-yl)phenyl)methanamine as yellow oil (80 mg, crude), which was used in the next step without further purification. ESI-MS [M+H]+: 222.1.

Example 165

Synthesis of benzo[b]thiophen-6-ylmethanamine

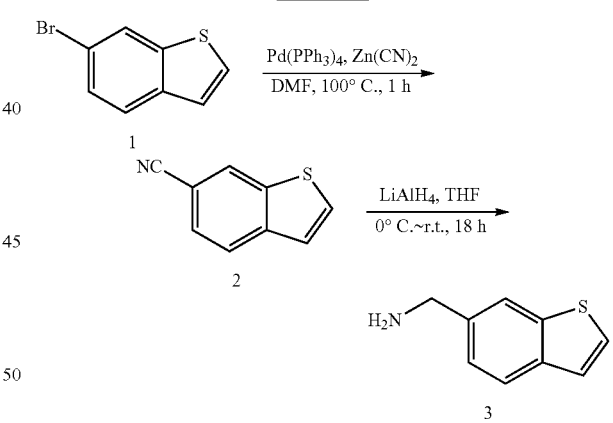

Scheme 167

Synthesis of benzo[b]thiophene-6-carbonitrile. To the mixture of 6-bromobenzo[b]thiophene (500 mg, 2.36 mmol) and Zn(CN)$_2$ (551 mg, 4.71 mmol) in DMF (5 mL) was added Pd(PPh$_3$)$_4$ (139 mg, 0.12 mmol). The reaction mixture was stirred at 100° C. for 1 h under N$_2$, then cooled to room temperature. Water (50 mL) was added and the mixture was extracted with EtOAc (30 mL×3). The combined organic layers were washed with brine (30 mL), dried over Na$_2$SO$_4$ and concentrated in vacuo. The residue was purified by flash column chromatography (EtOAc/PE from 0 to 10%) to afford benzo[b]thiophene-6-carbonitrile (300 mg, 80% yield) as a yellow oil. ESI-MS [M+H]+: 160.0.

Synthesis of benzo[b]thiophen-6-ylmethanamine. To the mixture of benzo[b]thiophene-6-carbonitrile (300 mg, 1.9 mmol) in THF (5 mL) at 0° C. was added LiAlH₄ (2.83 mL, 2.83 mmol, 1M solution in THF). The reaction mixture was stirred at room temperature for 18 h, then quenched with saturated aqueous NaHCO₃(50 mL) and extracted with EtOAc (30 mL×5). The combined organic layers were washed with brine (30 mL), dried over Na₂SO₄ and concentrated in vacuo. The residue was purified by flash chromatography (MeOH/DCM from 0 to 10%) to afford benzo[b]thiophen-6-ylmethanamine (200 mg, 65% yield) as a colorless oil. ESI-MS [M+H]+: 164.1

Example 166

Synthesis of (3-chloro-2-methyl-6-(1H-tetrazol-1-yl)phenyl)methanamine

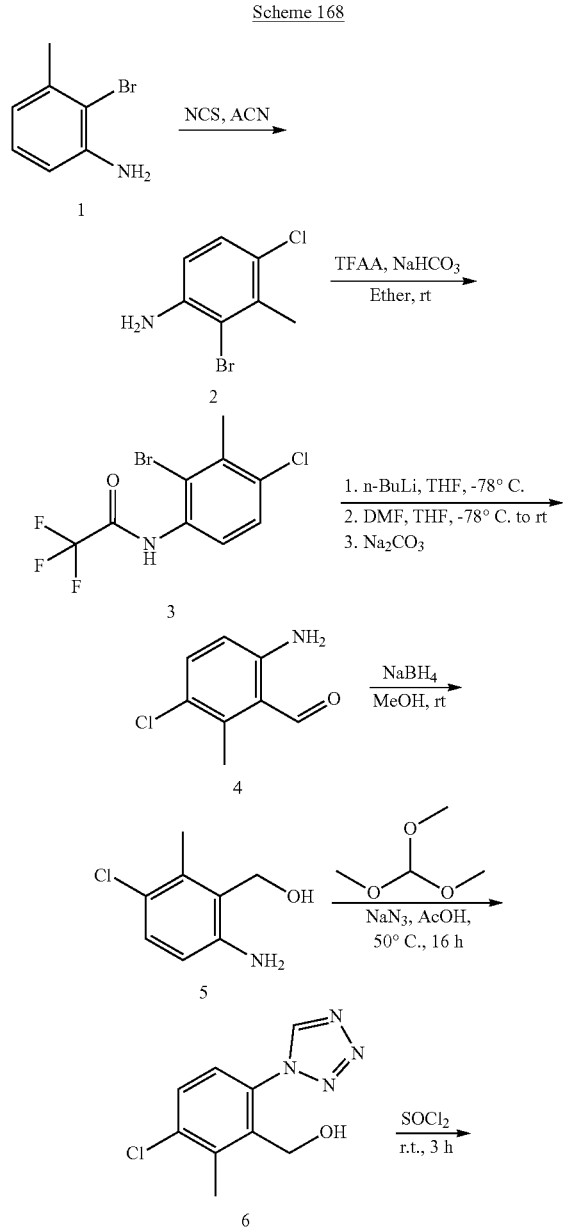

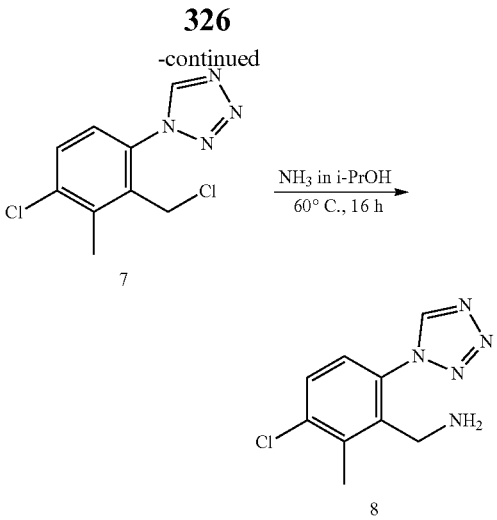

Synthesis of 2-bromo-4-chloro-3-methylaniline. A mixture of 2-bromo-3-methylaniline (5.0 g, 27 mmol) and NCS (3.78 g, 28.4 mmol) in CH₃CN (200 mL) was stirred at 60° C. for 16 h. The reaction was quenched with saturated aqueous NaHCO₃(100 mL) and extracted with EtOAc (100 mL×3). The combined organic layers were washed by brine (100 mL), dried over Na₂SO₄, filtered, concentrated in vacuo to give the crude, which was purified by silica gel chromatography (PE/EtOAc=15/1) to give 2-bromo-4-chloro-3-methylaniline (5.06 g, yield: 86%) as a yellow solid.

ESI-MS [M+H]⁺: 220.1.

Synthesis of N-(2-bromo-4-chloro-3-methylphenyl)-2,2,2-trifluoroacetamide. A solution of 2-bromo-4-chloro-3-methylaniline (3.0 g, 13.6 mmol), TFAA (3.16 g, 15.07 mmol) and NaHCO₃(2.9 g, 34 mmol) in diethyl ether (100 mL) was stirred at room temperature for 3 h. The reaction was quenched with saturated aqueous NaHCO₃(80 mL) and extracted with EtOAc (80 mL×3). The combined organic layers were washed with brine (80 mL), dried over Na₂SO₄, filtered, concentrated in vacuo to give N-(2-bromo-4-chloro-3-methylphenyl)-2,2,2-trifluoroacetamide (4.58 g, crude), which was used into the next step without further purification. ESI-MS [M+H]⁺: 316.1.

Synthesis of 6-amino-3-chloro-2-methylbenzaldehyde. To a mixture of N-(2-bromo-4-chloro-3-methylphenyl)-2,2,2-trifluoroacetamide (4.58 g, crude from previous step) in THF (100 mL) was added n-BuLi (12.5 mL, 30 mmol, 2.4 M) dropwise at −78° C. The reaction mixture was stirred at −78° C. for 30 min and then DMF (2.98 g, 40.8 mmol) was added dropwise at −78° C. The reaction mixture was allowed to warm to room temperature and stirred for another 16 h, then quenched with saturated aqueous NH₄Cl (80 mL) and extracted with EtOAc (80 mL×3). The combined organic layers were washed by brine (100 mL) followed by saturated aqueous Na₂CO₃ (80 mL), dried over Na₂SO₄, and concentrated in vacuo to give the 6-amino-3-chloro-2-methylbenzaldehyde (2.45 g, crude) as a yellow solid, which was used in the next step without further purification. ESI-MS [M+H]⁺: 170.1.

Synthesis of (6-amino-3-chloro-2-methylphenyl)methanol. To a solution of 6-amino-3-chloro-2-methylbenzaldehyde (2.45 g, crude) in MeOH (80 mL) was added NaBH₄ (1.55 g, 40.8 mmol) at 0° C. The reaction mixture was stirred at room temperature for 2 h, then quenched with saturated aqueous NH₄Cl (50 mL) and concentrated in vacuo to give the residue. Water (50 mL) was added and the mixture was extracted with EtOAc (50 mL×3). The combined organic layers were washed brine (50 mL), dried over Na₂SO₄, and concentrated in vacuo to give (6-amino-3-chloro-2-methylphenyl)methanol (765 mg, crude) as a yellow solid which was used in the next step without further purification. ESI-MS [M+H]⁺: 172.1.

Synthesis of (3-chloro-2-methyl-6-(1H-tetrazol-1-yl)phenyl)methanol. A mixture of (6-amino-3-chloro-2-methylphenyl)methanol (765 mg, crude from previous step), trimethoxymethane (2.8 g, 28.82 mmol) and NaN₃ (872 mg, 13.4 mmol) was stirred at 0° C. for 30 min. AcOH (4.6 mL) was added and the resulting reaction mixture was stirred at 50° C. for another 5 h. The reaction mixture was quenched with saturated aqueous NaHCO₃(50 mL) and extracted with EtOAc (80 mL×3). The combined organic layers were washed brine (50 mL), dried over Na₂SO₄, and concentrated in vacuo to give the crude, which was purified by silica gel chromatography (DCM:MeOH=10:1) to obtain (3-chloro-2-methyl-6-(1H-tetrazol-1-yl)phenyl)methanol (500 mg, over 4 steps yield: 16%) as a white solid.
ESI-MS [M+H]⁺: 225.1.

Synthesis of 1-(4-chloro-2-(chloromethyl)-3-methylphenyl)-1H-tetrazole. A mixture of (3-chloro-2-methyl-6-(1H-tetrazol-1-yl)phenyl)methanol (500 mg, 2.23 mmol) and SOCl₂ (10.5 g, 8.9 mmol) in DCM (5 mL) was stirred at room temperature for 5 h. The reaction mixture was concentrated in vacuo to obtain 1-(4-chloro-2-(chloromethyl)-3-methylphenyl)-1H-tetrazole (510 mg, crude) as yellow oil, which was used into next step without further purification. ESI-MS [M+H]⁺: 243.1.

Synthesis of (3-chloro-2-methyl-6-(1H-tetrazol-1-yl)phenyl)methanamine. A mixture of 1-(4-chloro-2-(chloromethyl)-3-methylphenyl)-1H-tetrazole (510 mg, crude) in NH₃ in IPA (100 mL) was stirred at 50° C. in a sealed tube for 16 h. The reaction mixture was concentrated in vacuo to obtain (3-chloro-2-methyl-6-(1H-tetrazol-1-yl)phenyl) methanamine (460 mg, crude) as a yellow solid, which was used into next step without further purification. ESI-MS [M+H]⁺: 224.1.

Example 167

Synthesis of (3-chloro-6-(difluoromethyl)-2-fluorophenyl)methanamine

Scheme 169

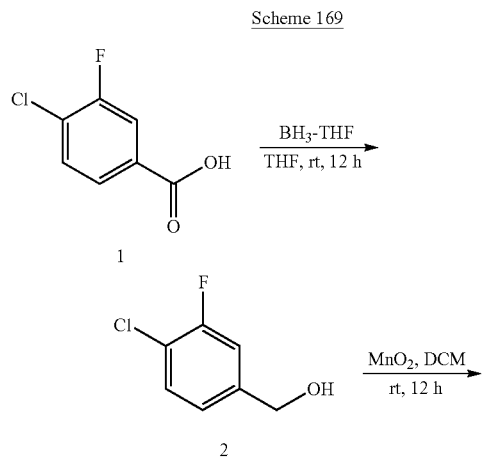

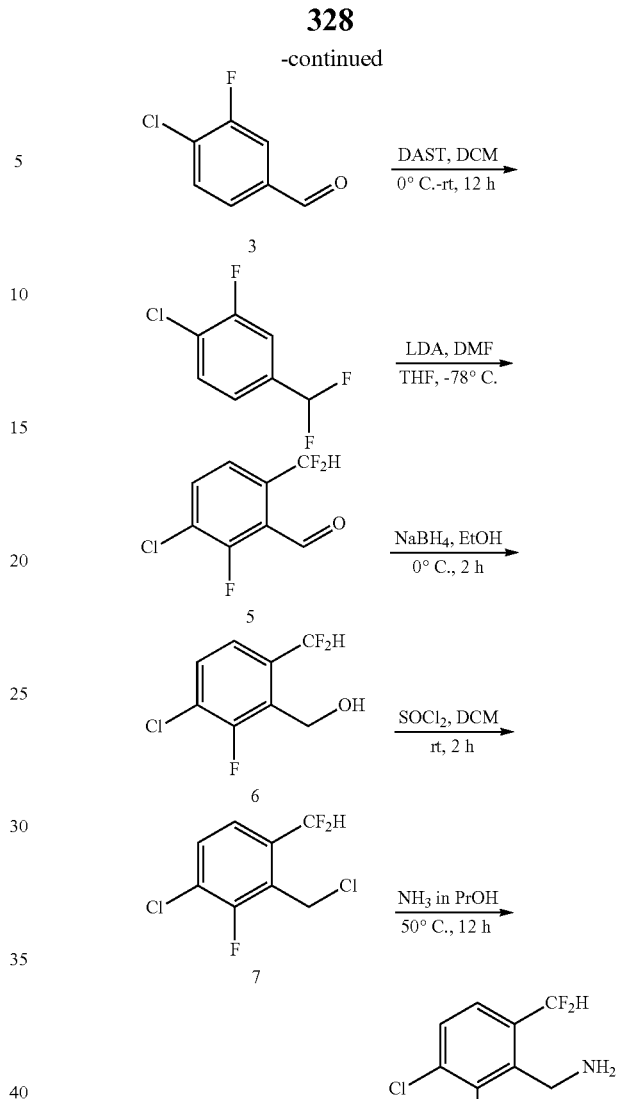

Synthesis of (4-chloro-3-fluorophenyl)methanol. To a solution of 4-chloro-3-fluorobenzoic acid (5 g, 28.7 mmol) in THF (50 mL) was added BH₃-THF (57 mL, 57.4 mmol) at 0° C. over 10 min. The reaction mixture was stirred at room temperature for 12 h. The reaction was quenched with methanol (20 mL) and concentrated in vacuo to give crude (4-chloro-3-fluorophenyl)methanol (4 g, crude), which was used to the next step without further purification. ESI-MS [M+H]+: 161.3

Synthesis of 4-chloro-3-fluorobenzaldehyde. A mixture of (4-chloro-3-fluorophenyl)methanol (4 g, 25.0 mmol) and MnO₂ (33 g, 375.0 mmol) in DCM (100 mL) was stirred at room temperature for 12 h. The reaction mixture was filtered and the filtrate was concentrated to give crude 4-chloro-3-fluorobenzaldehyde (3.7 g, crude) as a white solid, which was used to the next step without further purification. ESI-MS [M+H]+: 159.2

Synthesis of 1-chloro-4-(difluoromethyl)-2-fluorobenzene. To a solution of 4-chloro-3-fluorobenzaldehyde (3.7 g, 23.4 mmol) in DCM (150 mL) at 0° C. was added DAST (7.5 g, 46.8 mmol). The reaction mixture was stirred at room temperature for 12 h. The mixture was concentrated in vacuo, H₂O (50 mL) was added, and the mixture was extracted with EtOAc (70 mL×3). The combined organic layers were washed with brine, dried over Na₂SO₄, and concentrated in vacuo to give crude 1-chloro-4-(difluoromethyl)-2-fluorobenzene (3 g crude) as yellow oil, which was used to the next step without further purification. ESI-MS [M+H]+: 181.2.

Synthesis of 3-chloro-6-(difluoromethyl)-2-fluorobenzaldehyde. To a solution of 1-chloro-4-(difluoromethyl)-2-fluorobenzene (1.5 g, 8.3 mmol) in THF (50 mL) was added LDA (6.25 mL, 12.5 mmol) slowly at −78° C. The reaction mixture was stirred at −78° C. for 20 min. Then DMF (913 mg, 12.5 mmol) was added and the resulting mixture was stirred at −78° C. for another 20 min. The reaction was quenched with AcOH (2.2 g, 37.3 mmol). H₂O (50 mL) was added and the aqueous phase was extracted with EtOAc (70 mL×3). The combined organic layers were washed with brine, dried over Na₂SO₄, and concentrated in vacuo to give the crude, which was purified by Prep-TLC (PE/EtOAc=5/1) to give 3-chloro-6-(difluoromethyl)-2-fluorobenzaldehyde (500 mg, 16.7% over four steps) as a yellow oil. ESI-MS [M+H]+: 209.2.

Synthesis of (3-chloro-6-(difluoromethyl)-2-fluorophenyl)methanol. To a solution of 3-chloro-6-(difluoromethyl)-2-fluorobenzaldehyde (300 mg, 1.44 mmol) in EtOH (25 mL) at 0° C., was added NaBH₄ (109 mg, 2.88 mmol) slowly. The reaction mixture was stirred at 0° C. for 2 h, then quenched with H₂O (20 mL). The aqueous phase was extracted with EtOAc (30 mL×3). The combined organic layers were washed with brine, dried over Na₂SO₄, and concentrated in vacuo to give the crude, which was purified by Prep-TLC (PE/EtOAc=4/1) to give (3-chloro-6-(difluoromethyl)-2-fluorophenyl)methanol (280 mg, 93%) as a yellow solid. ESI-MS [M+H]+: 211.3.

Synthesis of 1-chloro-3-(chloromethyl)-4-(difluoromethyl)-2-fluorobenzene. To a solution of (3-chloro-6-(difluoromethyl)-2-fluorophenyl)methanol (280 mg, 1.33 mmol) in DCM (30 mL) was added SOCl₂ (6 mL). The reaction mixture was stirred at room temperature for 2 h. The mixture was concentrated in vacuo to give 1-chloro-3-(chloromethyl)-4-(difluoromethyl)-2-fluorobenzene (280 mg, crude) as yellow oil, which was used in the next step without further purification. ESI-MS [M+H]+: 230.1.

Synthesis of (3-chloro-6-(difluoromethyl)-2-fluorophenyl)methanamine. A mixture of 1-chloro-3-(chloromethyl)-4-(difluoromethyl)-2-fluorobenzene (280 mg, crude) in NH₃ in isopropyl alcohol (30 mL) was stirred at 50° C. in a sealed tube for 12 h. The reaction mixture was concentrated in vacuo to give (3-chloro-6-(difluoromethyl)-2-fluorophenyl)methanamine (250 mg crude) as a yellow solid, which was used in the next step without further purification. ESI-MS [M+H]+: 210.1.

Example 168

Synthesis of (3-cyclopropyl-2 fluoro-6-(1H-tetrazol-1-yl)phenyl)methanamine

Scheme 170

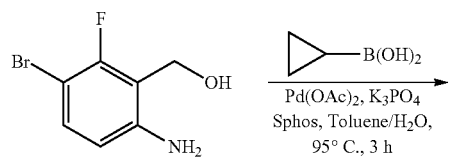

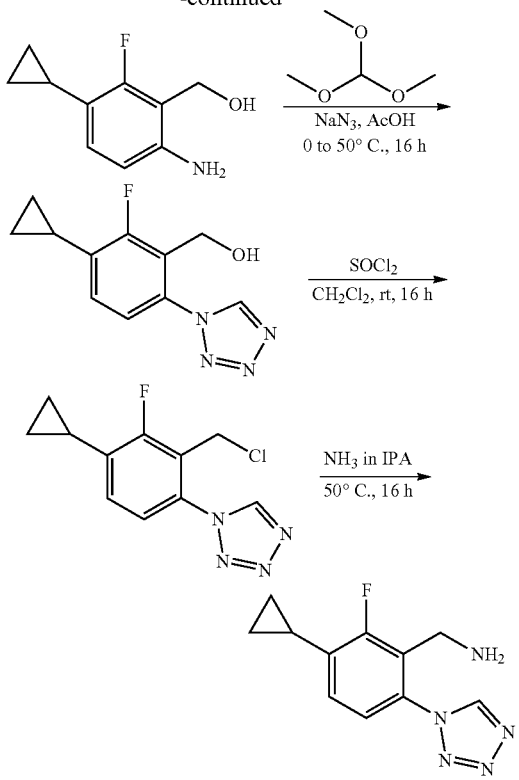

Synthesis of (6-amino-3-cyclopropyl-2-fluorophenyl)methanol. A mixture of (6-amino-3-bromo-2-fluorophenyl)methanol (1 g, 4.54 mmol) in toluene/H₂O (10 mL/1 mL) was added cyclopropylboronic acid (585 mg, 6.81 mmol), Pd(OAc)₂(102 mg, 0.454 mmol), K₃PO₄ (2.28 g, 10.74 mmol) and S-Phos (186 mg, 0.453 mmol) at rt. The reaction mixture was stirred at 95° C. for 3 h under N₂ atmosphere, then concentrated in vacuo. The residue was purified by flash chromatography (0-40% EtOAc in PE) to give (6-amino-3-cyclopropyl-2-fluorophenyl)methanol (170 mg, yield: 20.64%) as a yellow solid. ESI-MS [M+H]⁺: 182.0

Synthesis of (3-cyclopropyl-2-fluoro-6-(1H-tetrazol-1-yl)phenyl)methanol. To a mixture of (6-amino-3-cyclopropyl-2-fluorophenyl)methanol (100 mg, 0.55 mmol) in trimethoxymethane (175 mg, 1.65 mmol) was added NaN₃ (107 mg, 1.65 mmol) at 0° C. The reaction mixture was stirred at 0° C. for 0.5 h. Then AcOH (3 mL) was added and the mixture was stirred at 50° C. for 16 h. The pH was adjusted to 8 using sat. aq. NaHCO₃, then extracted with DCM (20 mL×3). The combined organic layers were washed with brine (20 mL), dried over Na₂SO₄, and concentrated in vacuo to give (3-cyclopropyl-2-fluoro-6-(1H-tetrazol-1-yl)phenyl)methanol (80 mg, crude) as a yellow solid. ESI-MS [M+H]+: 235.0.

Synthesis of 1-(2-(chloromethyl)-4-cyclopropyl-3-fluorophenyl)-1H-tetrazole. To a mixture of (3-cyclopropyl-2-fluoro-6-(1H-tetrazol-1-yl)phenyl)methanol (80 mg, crude) in DCM (1 mL) was added SOCl₂ (1 mL). The reaction mixture was stirred at room temperature for 16 h. The mixture was concentrated to give 1-(2-(chloromethyl)-4-cyclopropyl-3-fluorophenyl)-1H-tetrazole (80 mg, crude) as a brown oil which was used in the next step without further purification. ESI-MS [M+H]+: 253.1.

Synthesis of (3-cyclopropyl-2-fluoro-6-(1H-tetrazol-1-yl) phenyl)methanamine. A mixture of 1-(2-(chloromethyl)-3- fluoro-4-methoxyphenyl)-1H-tetrazole (80 mg, crude) and NH$_3$ in IPA (6 mL) was stirred at 50° C. for 16 h. The reaction mixture was concentrated in vacuo to give (3-cyclopropyl-2-fluoro-6-(1H-tetrazol-1-yl)phenyl)methanamine (80 mg, crude) as a yellow solid which was used in the next step without further purification. ESI-MS [M+H]+: 234.1.

Example 169

Synthesis of N-((6-chlorobenzo[b]thiophen-2-yl)methyl)-1-((6-cyclopropylimidazo[1,2-a]pyridin-2-yl)methyl)-1H-1,2,3-triazole-4-carboxamide Scheme 171

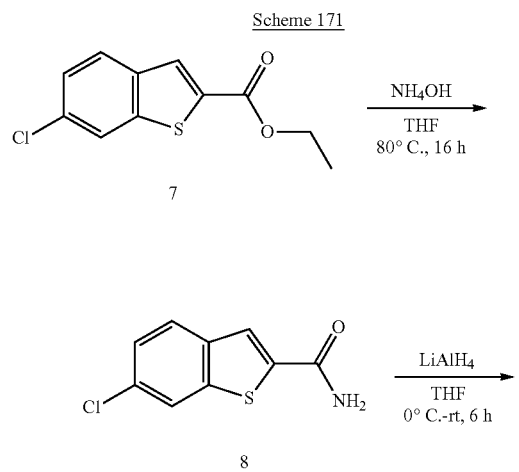

Synthesis of 6-chlorobenzo[b]thiophene-2-carboxamide. A solution of ethyl 6-chlorobenzo[b]thiophene-2-carboxylate (200 mg, 0.83 mmol) and NH$_4$OH (25%, 10 mL) in THF was stirred at 80° C. for 16 h in a sealed tube. The mixture was concentrated in vacuo and triturated with diethyl ether (10 mL) to give 6-chlorobenzo[b]thiophene-2-carboxamide as a brown solid (100 mg, yield: 57%). ESI-MS [M+H]$^+$: 212.1.

Synthesis of (6-chlorobenzo[b]thiophen-2-yl)methanamine. To a solution of 6-chlorobenzo[b]thiophene-2-carboxamide (100 mg, 0.47 mmol) in THF (15 mL) was added LiAlH$_4$ (27 mg, 0.71 mmol) slowly at 0° C. The reaction mixture was stirred at room temperature for 6 h. The reaction was quenched by water (0.1 mL), 10% NaOH (0.1 mL) and water (0.3 mL). The mixture was filtered and the filtrate was concentrated to give (6-chlorobenzo[b]thiophen-2-yl)methanamine as a brown solid (40 mg, crude) which was used in the next step without further purification. ESI-MS [M+H]+: 198.1.

Example 170

Synthesis of (2-fluoro-3-methoxy-6-(1H-1,2,3-triazol-1-yl)phenyl)methanamine

Scheme 172

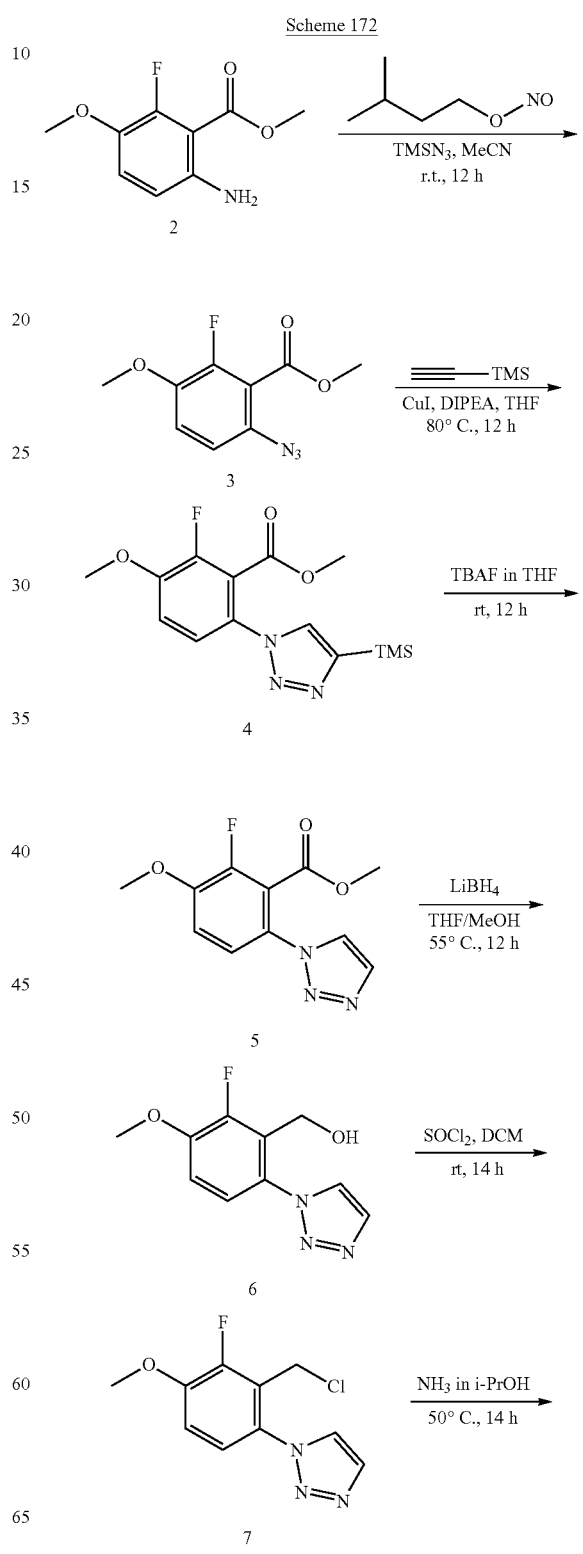

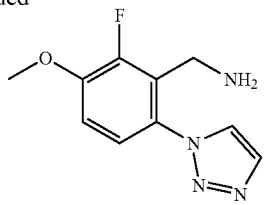

8

Synthesis of methyl 6-azido-2-fluoro-3-methoxybenzoate. A mixture of methyl 6-amino-2-fluoro-3-methoxybenzoate (650 mg, 3.26 mmol) and isopentyl nitrite (566 mg, 4.83 mmol) in MeCN (50 mL) was stirred at 0° C. for 15 min. TMSN₃ (558 mg, 4.85 mmol) was added at 0° C. The reaction mixture was stirred at room temperature for 12 h and then quenched with H₂O (50 mL). The aqueous phase was extracted with EtOAc (50 mL×3). The combined organic layers were washed with brine (30 mL×2), dried over Na₂SO₄, and concentrated in vacuo to give the crude, which was purified by silica gel chromatography (DCM/MeOH=10/1) to give methyl 6-azido-2-fluoro-3-methoxybenzoate as a yellow solid. (210 mg, 29%). ESI-MS [M+H]+: 226.1

Synthesis of methyl 2-fluoro-3-methoxy-6-(4-(trimethylsilyl)-1H-1,2,3-triazol-1-yl)benzoate. A mixture of methyl 6-azido-2-fluoro-3-methoxybenzoate (210 mg, 0.93 mmol), ethynyltrimethylsilane (4.57 g, 46.53 mmol), CuI (1.06 g, 5.58 mmol) and DIPEA (2.4 g, 18.6 mmol) in THF (30 mL) was stirred at 80° C. for 12 h. The reaction was quenched with H₂O (30 mL). The aqueous phase was extracted with EtOAc (50 mL×3). The combined organic layers were washed with brine (30 mL×2), dried over Na₂SO₄, and concentrated in vacuo to give the crude, which was purified by silica gel chromatography (PE/EtOAc=1/1) to give methyl 2-fluoro-3-methoxy-6-(4-(trimethylsilyl)-1H-1,2,3-triazol-1-yl)benzoate as a yellow solid. (220 mg, 73%). ESI-MS [M+H]+: 324.1

Synthesis of methyl 2-fluoro-3-methoxy-6-(1H-1,2,3-triazol-1-yl)benzoate. A mixture of methyl 2-fluoro-3-methoxy-6-(4-(trimethylsilyl)-1H-1,2,3-triazol-1-yl)benzoate (220 mg, 0.68 mmol) and TBAF (3.4 mL, 3.40 mmol) in THF (30 mL) was stirred at room temperature under N₂ for 12 h. The reaction was quenched with H₂O (30 mL). The aqueous phase was extracted with EtOAc (50 mL×3). The combined organic layers were washed with brine (30 mL×2), dried over Na₂SO₄, and concentrated in vacuo to give the crude, which was purified by silica gel chromatography (PE/EtOAc=1/1) to give methyl 2-fluoro-3-methoxy-6-(1H-1,2,3-triazol-1-yl)benzoate as a white solid. (100 mg, 58.5%). ESI-MS [M+H]+: 252.2

Synthesis of (2-fluoro-3-methoxy-6-(1H-1,2,3-triazol-1-yl)phenyl)methanol. A mixture of methyl 2-fluoro-3-methoxy-6-(1H-1,2,3-triazol-1-yl)benzoate (100 mg, 0.40 mmol) and LiBH₄ (132 mg, 6.0 mmol) in THF/MeOH (25 mL/5 mL) was stirred at 55° C. under N₂ for 12 h. The reaction was quenched with H₂O (50 mL). The aqueous phase was extracted with EtOAc (50 mL×3). The combined organic layers were washed with brine (30 mL×2), dried over Na₂SO₄, and concentrated in vacuo to give crude (2-fluoro-3-methoxy-6-(1H-1,2,3-triazol-1-yl)phenyl)methanol (110 mg, crude), which was used to the next step without further purification. ESI-MS [M+H]+: 224.2.

Synthesis of 1-(2-(chloromethyl)-3-fluoro-4-methoxyphenyl)-1H-1,2,3-triazole To a mixture of (2-fluoro-3-methoxy-6-(1H-1,2,3-triazol-1-yl)phenyl)methanol (110 mg, 0.49 mmol) in DCM (20 mL) was added SOCl₂ (2 mL). The reaction mixture was stirred at rt for 14 h. The reaction was concentrated in vacuo to give crude 1-(2-(chloromethyl)-3-fluoro-4-methoxyphenyl)-1H-1,2,3-triazole (120 mg, crude), which was used to the next step directly without further purification. ESI-MS [M+H]+: 242.1

Synthesis of (2-fluoro-3-methoxy-6-(1H-1,2,3-triazol-1-yl)phenyl)methanamine. A mixture of 1-(2-(chloromethyl)-3-fluoro-4-methoxyphenyl)-1H-1,2,3-triazole (120 mg, 0.50 mmol) in NH₃ in isopropyl alcohol (40 mL) was stirred at 50° C. for 14 h in a sealed tube. The reaction mixture was concentrated in vacuo to give crude (2-fluoro-3-methoxy-6-(1H-1,2,3-triazol-1-yl)phenyl)methanamine (120 mg crude), which was used into next step without further purification. ESI-MS [M+H]+: 223.2

Example 171

Synthesis of methyl 5-(2-(aminomethyl)-3 fluoro-4-methoxyphenyl)pyrimidine-2-carboxylate Scheme 173

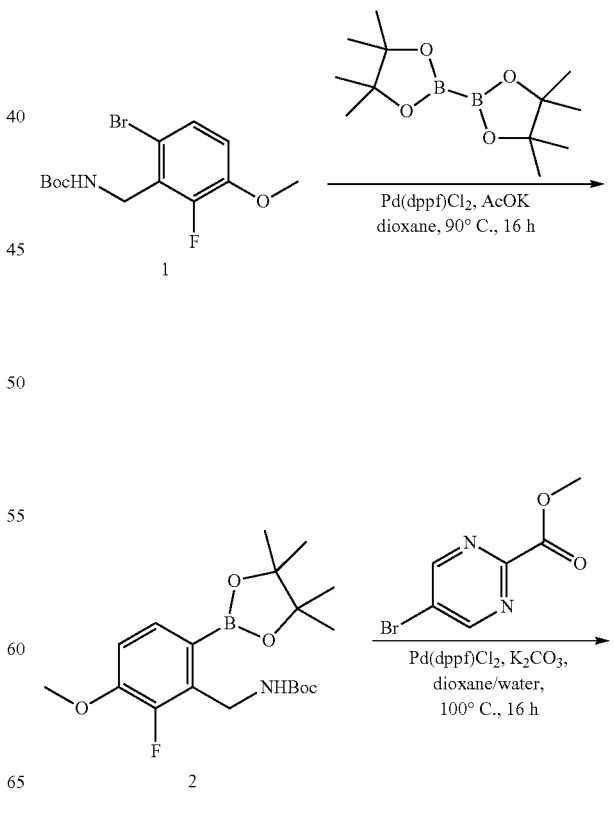

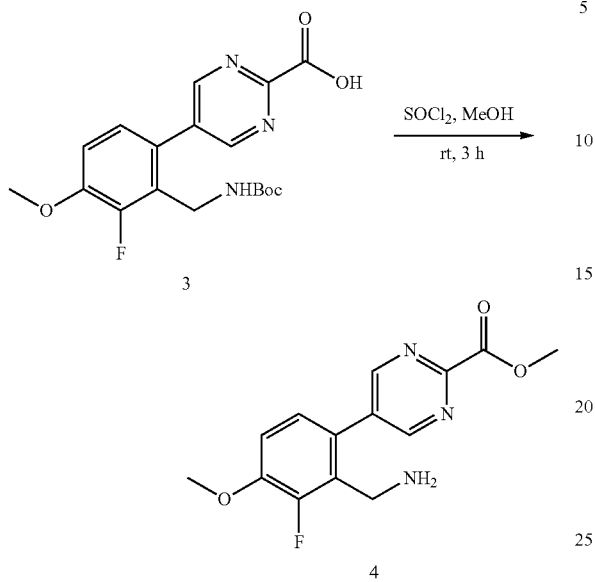

Example 172

Synthesis of (6-(3,4-dimethyl-1H pyrazol-1-yl)-2 fluoro-3-methoxyphenyl)methanamine hydrochloride Scheme 174

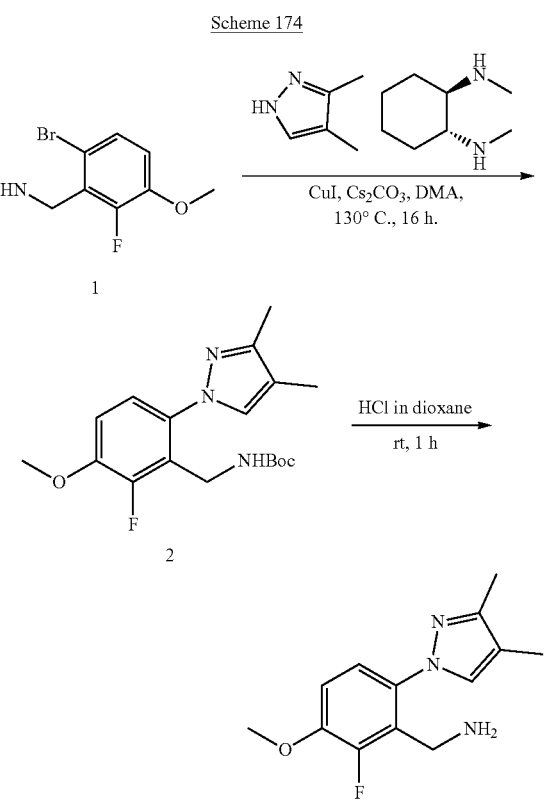

Synthesis of tert-butyl (2-fluoro-3-methoxy-6-(4,4,5,5-tetramethyl-1,3,2-dioxaborolan-2-yl)benzyl)carbamate. A mixture of tert-butyl (6-bromo-2-fluoro-3-methoxybenzyl)carbamate (333 mg, 1.0 mmol), 4,4,4',4',5,5,5',5'-octamethyl-2,2'-bi(1,3,2-dioxaborolane) (381 mg, 1.5 mmol), Pd(dppf)Cl$_2$ (37 mg, 0.05 mmol) and AcOK (294 mg, 3.0 mmol) in dioxane (15.0 mL) was stirred at 90° C. under N$_2$ for 16 h. The reaction mixture was concentrated in vacuo and purified by silica gel chromatography with PE/EtOAc=4/1 to give tert-butyl (2-fluoro-3-methoxy-6-(4,4,5,5-tetramethyl-1,3,2-dioxaborolan-2-yl)benzyl)carbamate (300 mg, 79%) as a colourless oil. ESI-MS [M+H]$^+$: 382.1.

Synthesis of 5-(2-(((tert-butoxycarbonyl)amino)methyl)-3-fluoro-4-methoxyphenyl)pyrimidine-2-carboxylic acid. A mixture of tert-butyl (2-fluoro-3-methoxy-6-(4,4,5,5-tetramethyl-1,3,2-dioxaborolan-2-yl)benzyl)carbamate (300 mg, 0.79 mmol), methyl 5-bromopyrimidine-2-carboxylate (212 mg, 0.98 mmol), Pd(dppf)Cl$_2$ (58.5 mg, 0.08 mmol) and K$_2$CO$_3$ (326 mg, 2.36 mmol) in dioxane/water (10.0 mL/1.0 mL) was stirred at 100° C. under N$_2$ for 16 h. The reaction mixture was concentrated to give the crude, which was purified by silica gel chromatography with DCM/MeOH=10/1 to give 5-(2-(((tert-butoxycarbonyl)amino)methyl)-3-fluoro-4-methoxyphenyl)pyrimidine-2-carboxylic acid (120 mg, 40%) as a yellow oil. ESI-MS [M+H]$^+$: 378.1.

Synthesis of methyl 5-(2-(aminomethyl)-3-fluoro-4-methoxyphenyl)pyrimidine-2-carboxylate. To a mixture of 5-(2-(((tert-butoxycarbonyl)amino)methyl)-3-fluoro-4-methoxyphenyl)pyrimidine-2-carboxylic acid (100 mg, 0.265 mmol) in SOCl$_2$/DCM (0.1 mL/5.0 mL) was stirred at room temperature for 3 h. The reaction mixture was concentrated in vacuo to give methyl 5-(2-(aminomethyl)-3-fluoro-4-methoxyphenyl)pyrimidine-2-carboxylate (80 mg, crude) as a yellow oil, which was used for the next step directly without further purification. ESI-MS [M+H]$^+$: 292.2.

Synthesis of tert-butyl (6-(3,4-dimethyl-1H-pyrazol-1-yl)-2-fluoro-3-methoxybenzyl)carbamate. A mixture of tert-butyl (6-bromo-2-fluoro-3-methoxybenzyl)carbamate (100 mg, 0.3 mmol), 3,4-dimethyl-1H-pyrazole (43 mg, 0.45 mmol), CuI (85.5 mg, 0.45 mmol), (1R,2R)-N1,N2-dimethylcyclohexane-1,2-diamine (64 mg, 0.45 mmol) and Cs$_2$CO$_3$ (196 mg, 0.6 mmol) in DMA (5.0 mL) was stirred at 130° C. under N$_2$ for 16 h. The reaction mixture was diluted with H$_2$O (30 mL) and extracted with EtOAc (30 mL×3). The combined organic layers were washed with brine (30 mL), dried over Na$_2$SO$_4$, and concentrated to give the crude, which was purified by silica gel column chromatography with DCM/MeOH=25/1 to give tert-butyl (6-(3,4-dimethyl-1H-pyrazol-1-yl)-2-fluoro-3-methoxybenzyl)carbamate (60 mg, 57%) as a colorless oil. ESI-MS [M+H]$^+$: 350.1.

Synthesis of (6-(3,4-dimethyl-1H-pyrazol-1-yl)-2-fluoro-3-methoxyphenyl)methanamine. A mixture of tert-butyl (6-(3,4-dimethyl-1H-pyrazol-1-yl)-2-fluoro-3-methoxybenzyl)carbamate (70 mg, 0.2 mmol) in HCl (4M in dioxane, 2.0 mL) was stirred at room temperature for 1 h. The reaction mixture was concentrated in vacuo to give (6-(3,4-dimethyl-1H-pyrazol-1-yl)-2-fluoro-3-methoxyphenyl)methanamine hydrochloride (50 mg, crude) as a yellow solid which was used for the next step directly without further purification. ESI-MS [M+H]$^+$: 250.1.

Example 173

Synthesis of (5-bromo-3-fluoro-2-methoxypyridin-4-yl)methanamine

Scheme 175

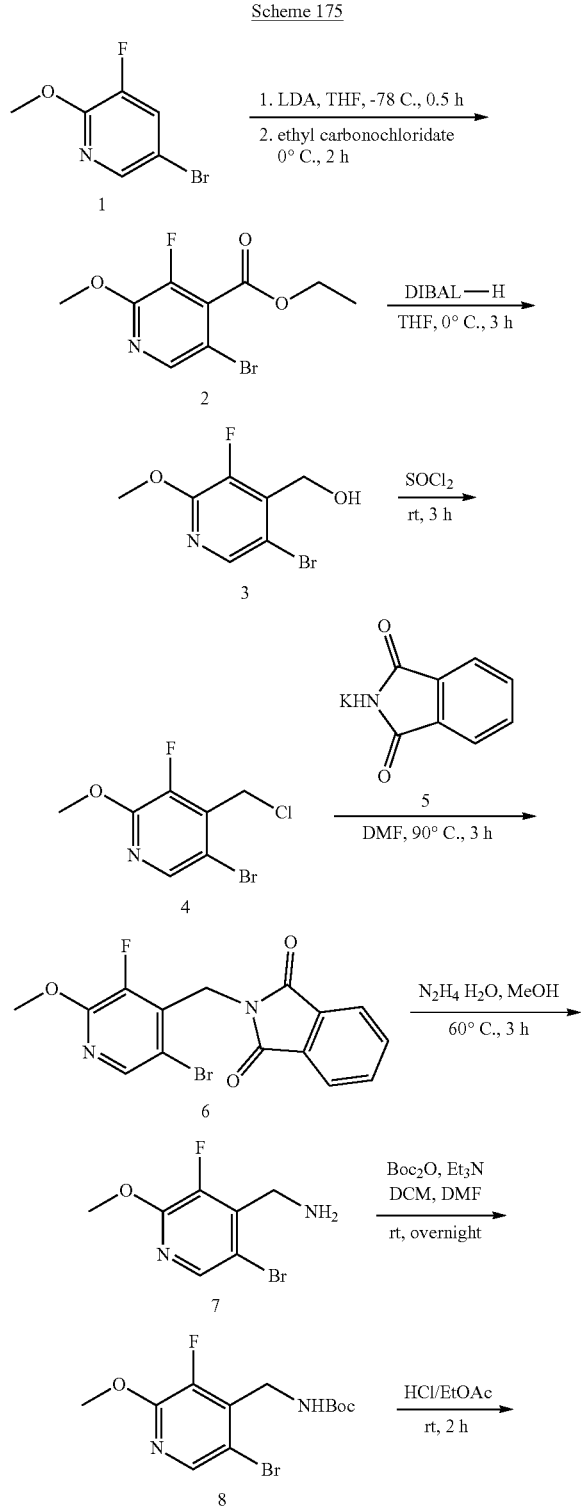

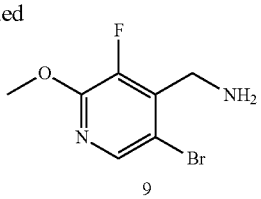

Synthesis of ethyl 5-bromo-3-fluoro-2-methoxyisonicotinate To a solution of 5-bromo-3-fluoro-2-methoxypyridine (1.62 g, 7.86 mmol) in THF (10 mL) was added LDA (5.9 mL, 11.8 mmol) slowly at −78° C. The reaction mixture was stirred at −78° C. for 45 min. Then ethyl carbonochloridate (1.06 g, 9.8 mmol) was added. The reaction mixture was warmed to 0° C. and stirred for another 2 h. The reaction was quenched with saturated aqueous $NH_4Cl$ (20 mL) and extracted by EtOAc (100 mL×2). The combined organic layers were washed with brine (100 mL), dried over $Na_2SO_4$, and concentrated to give the crude, which was purified by silica gel column (PE/EtOAc=10:1) to afford ethyl 5-bromo-3-fluoro-2-methoxyisonicotinate as a colourless oil (1.75 g, 80%). ESI-MS [M+H]$^+$: 277.9.

Synthesis of (5-bromo-3-fluoro-2-methoxypyridin-4-yl)methanol To a solution of ethyl 5-bromo-3-fluoro-2-methoxyisonicotinate (1.5 g, 5.4 mmol) in THF (10 mL) was added DIBAL-H (13.5 mL, 1 M/L, 13.5 mmol) slowly at 0° C. After stirring at 0° C. for 3 h, the reaction was quenched with saturated aqueous $NH_4Cl$ (10 mL) and extracted by EtOAc (100 mL×3). The combined organic layers were washed with brine (50 mL), dried over $Na_2SO_4$, concentrated in vacuo and purified by silica gel column (PE/EtOAc=8:1) to give (5-bromo-3-fluoro-2-methoxypyridin-4-yl)methanol (1.14 g, yield: 90%) as a colourless oil. ESI-MS [M+H]$^+$: 236.0.

Synthesis of 5-bromo-4-(chloromethyl)-3-fluoro-2-methoxypyridine. A solution of (5-bromo-3-fluoro-2-methoxypyridin-4-yl)methanol (1.14 g, 4.83 mmol) in $SOCl_2$ (2 mL) was stirred at rt for 3 h. The reaction mixture was concentrated in vacuo to give 5-bromo-4-(chloromethyl)-3-fluoro-2-methoxypyridine as an oil, which was used to the next reaction without further purification. ESI-MS [M+H]+: 253.9.

Synthesis of 2-((5-bromo-3-fluoro-2-methoxypyridin-4-yl)methyl)isoindoline-1,3-dione A solution of crude 5-bromo-4-(chloromethyl)-3-fluoro-2-methoxypyridine and potassium 1,3-dioxoisoindolin-2-ide (1.07 g, 5.8 mmol) in DMF (10 mL) was stirred at 90° C. for 3 h. The reaction mixture was diluted with $H_2O$ (50 mL) and extracted with EtOAc (100 mL×2). The combined organic layers were washed with brine (50 mL), dried over $Na_2SO_4$, and concentrated in vacuo to give 2-((5-bromo-3-fluoro-2-methoxypyridin-4-yl)methyl)isoindoline-1,3-dione (1.76 g) as a white solid, which was used to the next reaction without further purification. ESI-MS [M+H]+: 364.9.

Synthesis of (5-bromo-3-fluoro-2-methoxypyridin-4-yl)methanamine. To a solution of 2-((5-bromo-3-fluoro-2-methoxypyridin-4-yl)methyl)isoindoline-1,3-dione (1.76 g, 4.82 mmol) in MeOH (15 mL) was added hydrazine monohydrate (5 mL). The reaction mixture was stirred at 60° C. for 3 h, then concentrated in vacuo to give crude (5-bromo-3-fluoro-2-methoxypyridin-4-yl)methanamine which was used to the next reaction without further purification. ESI-MS [M+H]+: 235.0.

Synthesis of tert-butyl ((5-bromo-3-fluoro-2-methoxypyridin-4-yl)methyl)carbamate A solution of crude (5-bromo-3-fluoro-2-methoxypyridin-4-yl)methanamine, di-tert-butyl dicarbonate (2.62 g, 12 mmol) and triethylamine (1.47 g, 14.5 mmol) in DCM (10 mL) and DMF (1 mL) was stirred at rt overnight. The reaction mixture was concentrated in vacuo and purified by column chromatography (PE/EtOAc=10:1) to give tert-butyl ((5-bromo-3-fluoro-2-methoxypyridin-4-yl)methyl)carbamate (1.1 g, yield: 68% over 4 steps) as a white solid. ESI-MS [M+H]+: 335.1.

Synthesis of (5-bromo-3-fluoro-2-methoxypyridin-4-yl) methanamine. A solution of tert-butyl ((5-bromo-3-fluoro-2-methoxypyridin-4-yl)methyl)carbamate (140 mg, 0.42 mmol) in HCl/EtOAc (2 mL) was stirred at rt for 2 h. The reaction mixture was concentrated to give crude (5-bromo-3-fluoro-2-methoxypyridin-4-yl)methanamine, which was used to the next reaction without further purification. ESI-MS [M+H]+: 235.0.

Example 174

Synthesis of (2 fluoro-6-(imidazo[1,2-a]pyridin-2 yl)-3-methoxyphenyl)methanamine Scheme 176

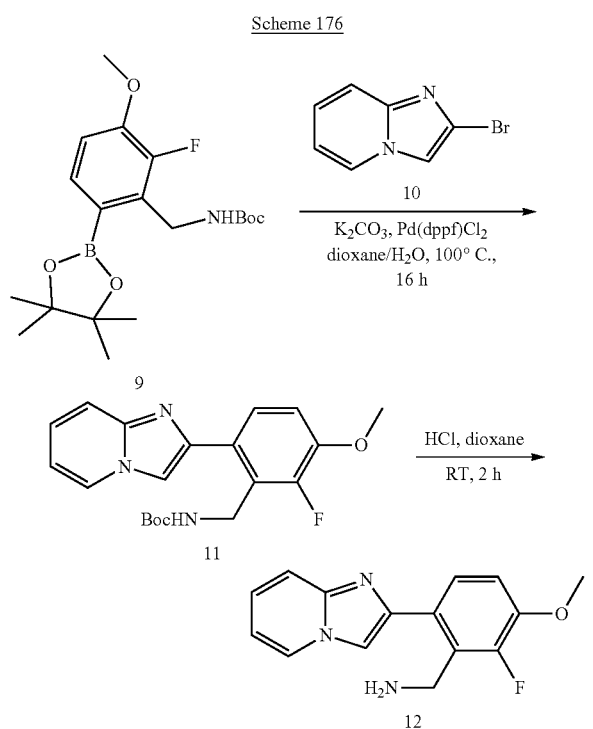

Synthesis of tert-butyl (2-fluoro-6-(imidazo[1,2-a]pyridin-2-yl)-3-methoxybenzyl)carbamate. To a solution of tert-butyl (2-fluoro-3-methoxy-6-(4,4,5,5-tetramethyl-1,3,2-dioxaborolan-2-yl)benzyl)carbamate (320.0 mg, 0.84 mmol) in dioxane/H₂O (10/1 mL), was added 2-bromoimidazo[1,2-a]pyridine (137.20 mg, 0.70 mmol), Pd(dppf)Cl₂ (57.20 mg, 0.07 mmol) and K₂CO₃ (290.00 mg, 2.10 mmol). The reaction mixture was stirred at 100° C. for 16 h, then diluted with EtOAc (100 mL) and washed with water (50 mL×2). The organic layer was dried over Na₂SO₄, concentrated and purified by silica gel chromatography (PE/EtOAc=2/1) to give tert-butyl (2-fluoro-6-(imidazo[1,2-a]pyridin-2-yl)-3-methoxybenzyl)carbamate (130 mg 50.0%). ESI-MS [M+H]+: 372.1

Synthesis of (2 fluoro-6-(imidazo[1,2-a]pyridin-2 yl)-3-methoxyphenyl)methanamine A solution of tert-butyl (2-fluoro-6-(imidazo[1,2-a]pyridin-2-yl)-3-methoxybenzyl) carbamate (130 mg, 0.35 mmol) in HCl in dioxane (10 mL) was stirred at RT for 2 h. The reaction mixture was concentrated in vacuo to give (2-fluoro-6-(imidazo[1,2-a]pyridin-2-yl)-3-methoxyphenyl)methanamine (135.00 mg, crude) as a yellow solid which was used in the next step without purification. ESI-MS [M+H]+: 272.1.

Example 175

Synthesis of (2 fluoro-3-methoxy-6-(1H pyrazol-4 yl)phenyl)methanamine

Scheme 177

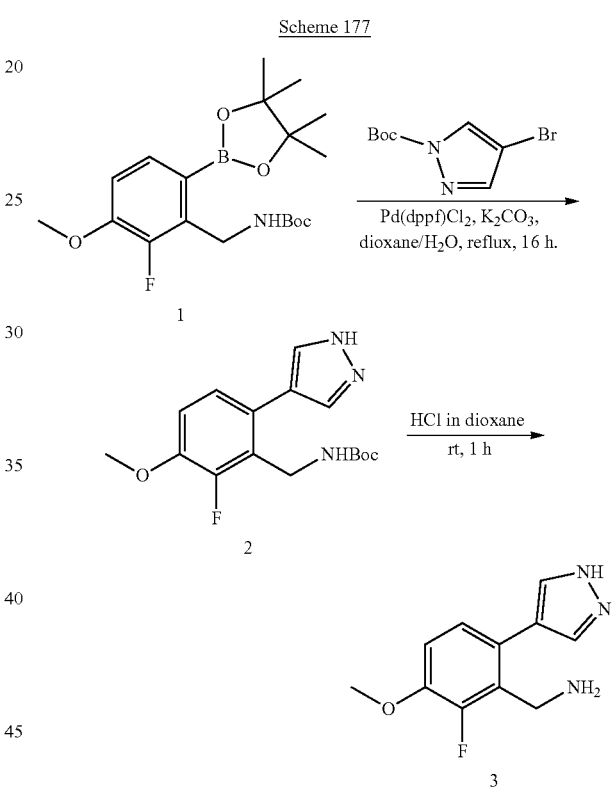

Synthesis of tert-butyl (2-fluoro-3-methoxy-6-(1H-pyrazol-4-yl)benzyl)carbamate. A mixture of tert-butyl (2-fluoro-3-methoxy-6-(4,4,5,5-tetramethyl-1,3,2-dioxaborolan-2-yl)benzyl)carbamate (152 mg, 0.4 mmol), tert-butyl 4-bromo-1H-pyrazole-1-carboxylate (98.4 mg, 0.4 mmol), Pd(dppf)Cl₂ (16.3 mg, 0.02 mmol) and K₂CO₃ (165.6 mg, 1.2 mmol) in dioxane/water (10 mL/1 mL) was stirred at reflux under N₂ for 16 h. The reaction mixture was concentrated in vacuo and purified by silica gel chromatography with DCM/MeOH=10/1 to give tert-butyl (2-fluoro-3-methoxy-6-(1H-pyrazol-4-yl)benzyl)carbamate (100 mg, 78%) as a yellow oil. ESI-MS [M+H]⁺: 322.1.

Synthesis of (2-fluoro-3-methoxy-6-(1H-pyrazol-4-yl) phenyl)methanamine. A mixture of tert-butyl (2-fluoro-3-methoxy-6-(1H-pyrazol-4-yl)benzyl)carbamate (78 mg, 0.245 mmol) in HCl (4M in dioxane, 2.0 mL) was stirred at rt for 1 h. The reaction mixture was concentrated in vacuo to give (2-fluoro-3-methoxy-6-(1H-pyrazol-4-yl)phenyl)

methanamine (60 mg, crude) as a yellow solid which was used for the next step directly without further purification. ESI-MS [M+H]⁺: 222.1.

Example 176

Synthesis of 1-(2 fluoro-3-methoxy-6-(1H-tetrazol-1-yl)phenyl)-N-methylmethanamine

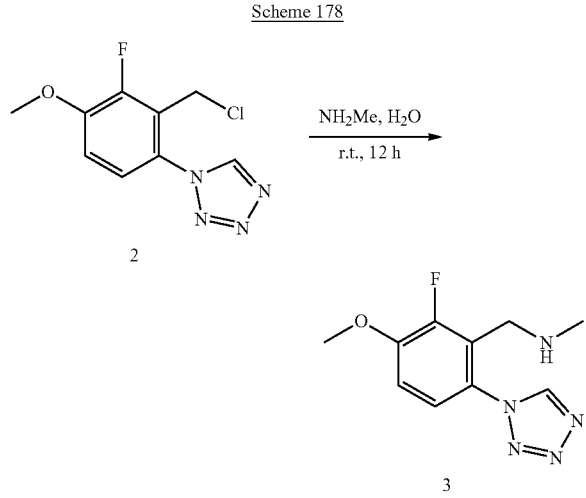

To a solution of 1-(2-(chloromethyl)-3-fluoro-4-methoxyphenyl)-1H-tetrazole (250 mg, 1.03 mmol) in DCM (20 mL) was added NH₂Me (20 mL). The reaction mixture was stirred at room temperature for 12 h. The mixture was concentrated in vacuo to give the crude, which was purified by Prep-TLC (DCM/MeOH=10:1) to give 1-(2-fluoro-3-methoxy-6-(1H-tetrazol-1-yl)phenyl)-N-methylmethanamine as a yellow solid. (150 mg, 61%). ESI-MS [M+H]+: 238.2.

Example 177

Synthesis of (3-chloro-1H-indol-5-yl)methanamine hydrochloride

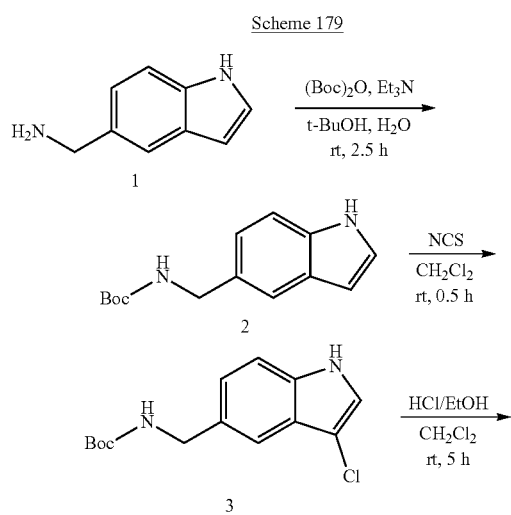

-continued

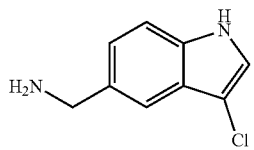

Synthesis of tert-butyl ((1H-indol-5-yl)methyl)carbamate. To a solution of (1H-indol-5-yl)methanamine (300 mg, 2.05 mmol) in t-BuOH (20 mL) was added H₂O (1 mL), Et₃N (214 mg, 2.11 mmol) and (Boc)₂O (784 mg, 3.60 mmol). The reaction mixture was stirred at room temperature for 2.5 h. Then the mixture was concentrated in vacuo. Water (40 mL) was added and the mixture was extracted with EtOAc (50 mL×3). The combined organic layers were concentrated to give the crude product, which was purified by silica gel chromatography (PE/EtOAc=5/1) to give tert-butyl ((1H-indol-5-yl)methyl)carbamate as an orange oil (498 mg, yield: 98%). ESI-MS [M+Na]⁺: 247.1.

Synthesis of tert-butyl ((3-chloro-1H-indol-5-yl)methyl)carbamate. A solution pf tert-butyl ((1H-indol-5-yl)methyl)carbamate (498 mg, 2.02 mmol) and NCS (243 mg, 1.82 mmol) in CH₂Cl₂ (10 ml) was stirred at room temperature for 0.5 h. The reaction was quenched with water (30 mL) and extracted with EtOAc (50 mL×3). The combined organic layers were washed with brine (30 mL), dried over Na₂SO₄ and concentrated to give the crude product, which was purified by silica gel chromatography (PE/EtOAc=5/1) to give tert-butyl ((3-chloro-1H-indol-5-yl)methyl)carbamate (453 mg, 81%) as a colorless oil. ESI-MS [M+Na]⁺: 281.2.

Synthesis of (3-chloro-1H-indol-5-yl)methanamine hydrochloride. A mixture of tert-butyl ((3-chloro-1H-indol-5-yl)methyl)carbamate (453 mg, 1.61 mmol) and HCl/EtOH (1.783 g, 16.1 mmol) in CH₂Cl₂ (30 mL) was stirred at room temperature for 5 h. The reaction mixture was concentrated in vacuo to give (3-chloro-1H-indol-5-yl)methanamine hydrochloride (339 mg, 97%) as a white solid which was used in the next step without further purification. ESI-MS [M+H]⁺: 217.1.

Example 178

Synthesis of (2,6-difluoro-3-methoxyphenyl)methanamine

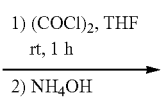

-continued

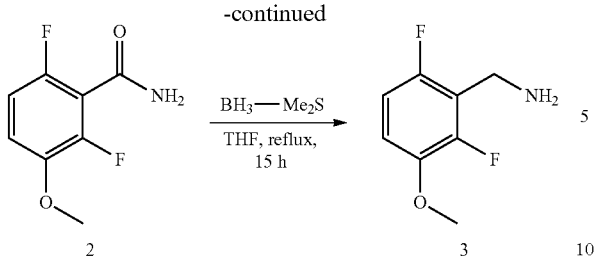

Synthesis of 2,6-difluoro-3-methoxybenzamide. To a solution of 2,6-difluoro-3-methoxybenzoic acid (1 g, 5.3 mmol) and DMF (one drop) in dry THF (10 mL) was added oxalyl chloride (1.26 g, 10.6 mmol) at 0° C. The resulting mixture was stirred at room temperature for 1 h, then concentrated in vacuo. The residue was dissolved in THF (10 mL) and added dropwise to NH$_4$OH (25%, 10 mL) solution. The resulting mixture was stirred at room temperature for 1 h. The organic layer was separated and the aqueous phase was extracted with EtOAc (2×15 mL). The combined organic layers were washed with brine (15 mL), dried over Na$_2$SO$_4$, filtered and concentrated to get crude 2,6-difluoro-3-methoxybenzamide (1 g, crude) as a white solid which was used in the next step directly without further purification. ESI-MS [M+H]$^+$: 188.1. $^1$H NMR (400 MHz, CDCl$_3$) δ 7.06-6.95 (m, 1H), 6.90 (t, J=9.2 Hz, 1H), 5.95 (brs, 2H), 3.89 (s, 3H).

Synthesis of (2,6-difluoro-3-methoxyphenyl)methanamine. To a solution of 2,6-difluoro-3-methoxybenzamide (100 mg, 0.53 mmol) in dry THF was added BH$_3$-Me$_2$S (0.8 mL, 1.59 mmol) at room temperature. The reaction mixture was stirred at reflux under nitrogen atmosphere for 15 h. The reaction was quenched with MeOH (10 mL) and refluxed for another 30 min, and then concentrated in vacuo. The residue was partitioned between DCM (10 mL) and water (10 mL). The organic layer was separated and the aqueous phase was extracted with DCM (2×10 mL). The combined organic layers were washed with brine (10 mL), dried over Na$_2$SO$_4$, filtered and concentrated in vacuo to get (2,6-difluoro-3-methoxyphenyl)methanamine (95 mg, crude) as a light yellow solid. The crude product was used in the next step directly without further purification. ESI-MS [M+H]$^+$: 174.1.

Example 179

Synthesis of (2-fluoro-3-methoxy-6-(pyrazolo[1,5-a]pyridin-2-yl)phenyl)methanamine Scheme 181

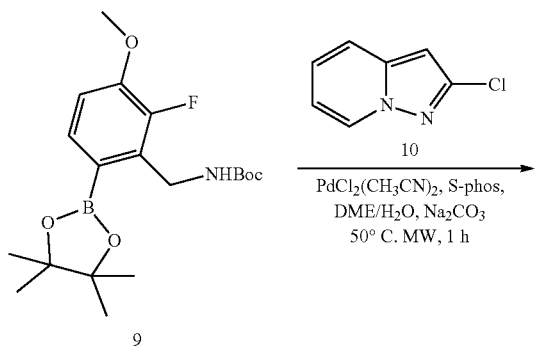

-continued

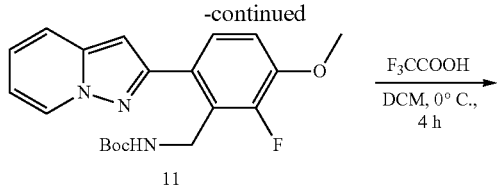

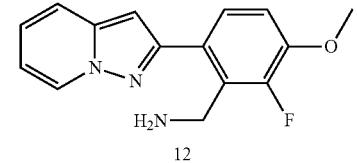

Synthesis of tert-butyl (2-fluoro-3-methoxy-6-(pyrazolo[1,5-a]pyridin-2-yl)benzyl)carbamate. To a solution of tert-butyl (2-fluoro-3-methoxy-6-(4,4,5,5-tetramethyl-1,3,2-dioxaborolan-2-yl)benzyl)carbamate (200.0 mg, 0.52 mmol) in DME/H$_2$O (10/1 mL), was added 2-chloropyrazolo[1,5-a]pyridine (155.04 mg, 1.02 mmol), PdCl$_2$(CH$_3$CN)$_2$ (60.00 mg, 0.23 mmol), S-phos (80.00 mg) and Na$_2$CO$_3$, (165.00 mg, 1.55 mmol). The reaction mixture was stirred at 50° C. under MW for 1 h. The mixture was filtered and the filtrate was extracted with EtOAc (100 mL×2). The combined organic layers were washed with water (50 mL×2), concentrated, and purified by silica gel chromatography (PE/EtOAc=2/1) to give tert-butyl (2-fluoro-3-methoxy-6-(pyrazolo[1,5-a]pyridin-2-yl)benzyl)carbamate (30.0 mg, yield: 15.5%). ESI-MS [M+H]+: 372.1.

Synthesis of (2-fluoro-6-(imidazo[1,2-a]pyridin-2-yl)-3-methoxyphenyl)methanamine. To a solution of tert-butyl (2-fluoro-3-methoxy-6-(pyrazolo[1,5-a]pyridin-2-yl)benzyl)carbamate (30.0 mg, 0.08 mmol) in dry DCM (8 mL) was added TFA (4 mL). The reaction mixture was stirred at 0° C. for 4 h. The reaction was quenched with sat. aq. Na$_2$CO$_3$ (15 mL) and extracted with EtOAc (30 mL×2). The combined organic layers were washed with water (10 mL×2) and concentrated to give (2-fluoro-3-methoxy-6-(pyrazolo[1,5-a]pyridin-2-yl)phenyl)methanamine (8.0 mg, yield: 36.9%) as a yellow solid. ESI-MS [M+H]+: 272.1.

Example 180

Synthesis of (2-fluoro-3-methoxy-6-(3-(trifluoromethyl)-1H-pyrazol-1-yl)phenyl)methanamine Scheme 182

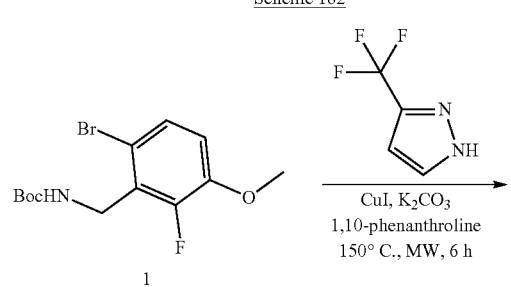

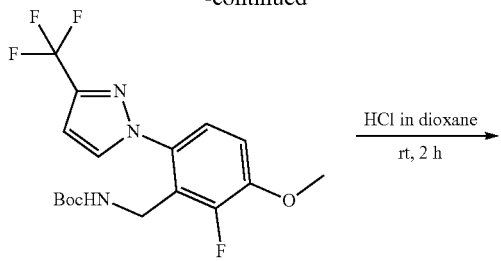

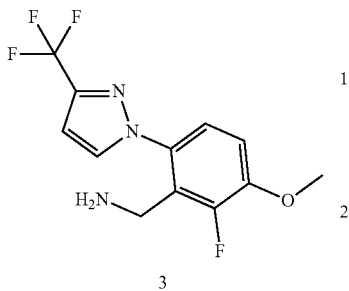

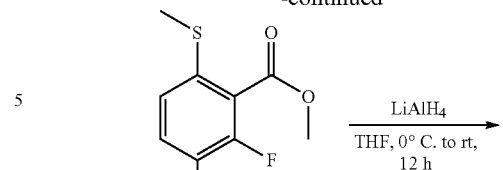

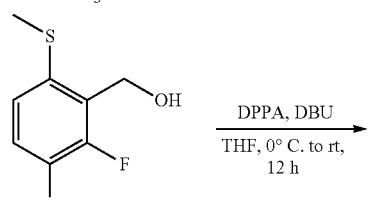

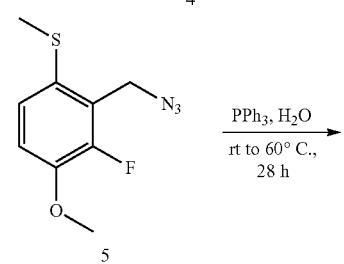 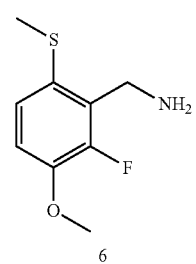

Synthesis of tert-butyl (2-fluoro-3-methoxy-6-(3-(trifluoromethyl)-1H-pyrazol-1-yl)benzyl)carbamate. A mixture of tert-butyl (6-bromo-2-fluoro-3-methoxybenzyl)carbamate (330 mg, 1.0 mmol), 3-(trifluoromethyl)-1H-pyrazole (200 mg, 1.5 mmol), $K_2CO_3$ (350 mg, 2.5 mmol), CuI (10 mg, 0.05 mmol) and 1,10-phenanthroline (180 mg, 0.1 mmol) in dioxane (6 mL) was heated at 150° C. for 6 h under microwave. The mixture was filtered and the filtrate was concentrated. Water (40 mL) was added and the mixture was extracted with EtOAc (50 mL×2). The combined organic layers were washed with brine (20 mL×2), dried over $Na_2SO_4$, concentrated and purified by Prep-HPLC to give tert-butyl (2-fluoro-3-methoxy-6-(3-(trifluoromethyl)-1H-pyrazol-1-yl)benzyl)carbamate (30 mg, yield: 8%) as a white solid. ESI-MS [M+Na]+: 412.1.

Synthesis of (2-fluoro-3-methoxy-6-(3-(trifluoromethyl)-1H-pyrazol-1-yl)phenyl)methanamine. A mixture of tert-butyl (2-fluoro-3-methoxy-6-(3-(trifluoromethyl)-1H-pyrazol-1-yl)benzyl)carbamate (30 mg, 0.08 mmol) and HCl (5 mL, 4M in dioxane) was stirred at rt for 2 h. The reaction mixture was concentrated in vacuo to give (2-fluoro-3-methoxy-6-(3-(trifluoromethyl)-1H-pyrazol-1-yl)phenyl) methanamine (23 mg, crude) as a white solid which was used in the next step without further purification. ESI-MS: [M+H]+: 290.1.

Example 181

Synthesis of (2-fluoro-3-methoxy-6-(methylthio) phenyl)methanamine

Scheme 183

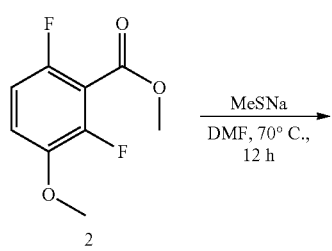

Synthesis of methyl 2-fluoro-3-methoxy-6-(methylthio) benzoate. To a solution methyl 2,6-difluoro-3-methoxybenzoate (2 g, crude) in DMF (20 mL) was added MeSNa (1.48 g, 21.2 mmol) at room temperature. The reaction mixture was stirred at 70° C. for 12 h. The mixture was cooled to room temperature, then poured into water (50 mL). The mixture was extracted with EtOAc (100 ml×2). The combined organic layers were washed with water (50 mL×2), brine (50 mL), dried and concentrated in vacuo to give the crude product, which was purified by silica gel chromatography (PE/EtOAc=5:1 to 3:1) to give methyl 2-fluoro-3-methoxy-6-(methylthio)benzoate (1 g, yield: 41%, two steps) as a yellow oil. ESI-MS [M+Na]+: 253.1.

Synthesis of (2-fluoro-3-methoxy-6-(methylthio)phenyl) methanol. To a solution of methyl 2-fluoro-3-methoxy-6-(methylthio)benzoate (300 mg, 1.3 mmol) in THF (5 mL) was added $LiAlH_4$ (100 mg, 2.6 mmol) at 0° C. slowly. The reaction mixture was stirred at room temperature for 12 h. The mixture was quenched by the addition of saturated ammonium chloride solution (30 mL) and then extracted with EtOAc (30 mL×2). The combined organic layers were washed with brine (30 mL), dried over $Na_2SO_4$, and concentrated to give (2-fluoro-3-methoxy-6-(methylthio)phenyl)methanol (250 mg, crude), which was used in next step without further purification. ESI-MS [M—OH]+: 185.0.

Synthesis of (2-(azidomethyl)-3-fluoro-4-methoxyphenyl)(methyl)sulfane. To a solution of (2-fluoro-3-methoxy-6-(methylthio)phenyl)methanol (250 mg, 1.24 mmol) in THF (5 ml) was added DPPA (410 mg, 1.49 mmol) at 0° C. After 10 min, DBU (415 mg, 2.73 mmol) was added. The reaction mixture was stirred at room temperature for 12 h. The mixture was poured into water (30 mL) and extracted with EtOAc (30 ml×2). The combined organic layers were washed with brine (30 mL), dried and concentrated in vacuo to give (2-(azidomethyl)-3-fluoro-4-methoxyphenyl)

(methyl)sulfane (290 mg, crude) as a brown oil, which was used in next step without further purification. ESI-MS [M—N$_3$]$^+$: 185.1.

Synthesis of (2-fluoro-3-methoxy-6-(methylthio)phenyl) methanamine. To a solution of (2-(azidomethyl)-3-fluoro-4-methoxyphenyl)(methyl)sulfane (290 mg, crude) in THF (4 ml) was added PPh$_3$ (577 mg, 2.2 mmol) and water (1 mL). The reaction mixture was stirred at room temperature for 24 h. Additional water (1 mL) was added and the mixture was stirred at 60° C. for 4 h. A third portion of water (1 mL) was added and the mixture was stirred at 60° C. for a further 12 h. The reaction mixture was poured onto water (20 mL) and adjusted to pH 2 with 1M HCl solution. The mixture was extracted with EtOAc (30 ml) and the aqueous phase was adjusted to pH 8 with NH$_3$—H$_2$O. The aqueous phase was extracted with EtOAc (30 ml×3) and the combined organic layers were washed with brine (30 mL), dried over Na$_2$SO$_4$ and concentrated in vacuo to give (2-fluoro-3-methoxy-6-(methylthio)phenyl)methanamine (240 mg, crude) as a yellow solid. ESI-MS [M+H]$^+$: 202.0.

Example 182

Synthesis of (2-fluoro-3-methoxy-6-(3-(trifluoromethyl)-1H-1,2,4-triazol-1-yl)phenyl)methanamine hydrochloride

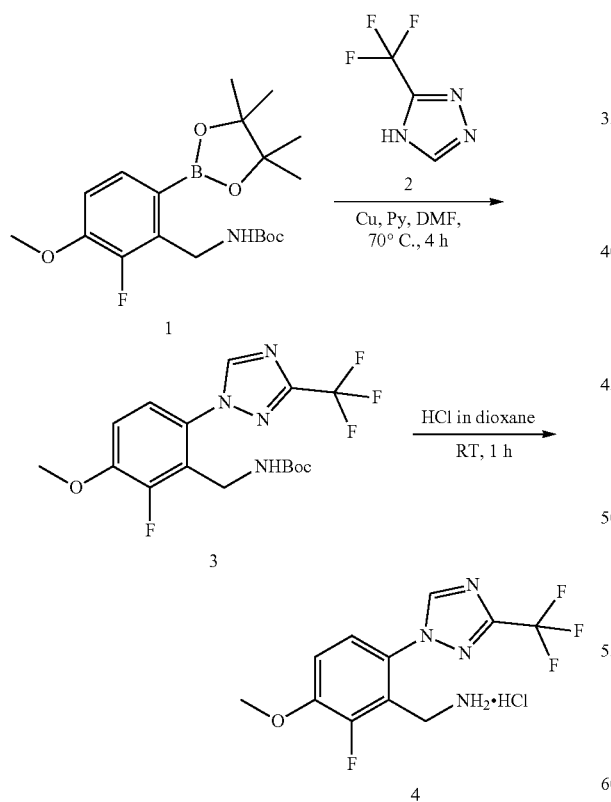

Synthesis of tert-butyl (2-fluoro-3-methoxy-6-(3-(trifluoromethyl)-1H-1,2,4-triazol-1-yl)benzyl)carbamate. A mixture of 3-(trifluoromethyl)-4H-1,2,4-triazole (90 mg, 0.66 mmol), tert-butyl (2-fluoro-3-methoxy-6-(4,4,5,5-tetramethyl-1,3,2-dioxaborolan-2-yl)benzyl)carbamate (250 mg, 0.66 mmol), Cu powder (43 mg, 0.66 mmol) and pyridine (104 mg, 1.32 mmol) in DMF (5.0 mL) was stirred at 70° C. under N$_2$ for 4 h. The reaction mixture was diluted with water (60 mL), and extracted with EtOAc (30 mL×3). The combined organic layers were washed with brine (30 mL), dried over Na$_2$SO$_4$ and concentrated in vacuo. The residue was purified by silica gel chromatography (PE/EtOAc=2/1) to give tert-butyl (2-fluoro-3-methoxy-6-(3-(trifluoromethyl)-1H-1,2,4-triazol-1-yl)benzyl)carbamate (60 mg, 23%) as a yellow oil. ESI-MS [M+H]$^+$: 391.1.

Synthesis of (2-fluoro-3-methoxy-6-(3-(trifluoromethyl)-1H-1,2,4-triazol-1-yl)phenyl)methanamine hydrochloride. A mixture of tert-butyl (2-fluoro-3-methoxy-6-(3-(trifluoromethyl)-1H-1,2,4-triazol-1-yl)benzyl)carbamate (60 mg, 0.15 mmol) in HCl/dioxane (4M, 2.0 mL) was stirred at RT for 1 h. The reaction mixture was concentrated in vacuo to give (2-fluoro-3-methoxy-6-(3-(trifluoromethyl)-1H-1,2,4-triazol-1-yl)phenyl)methanamine hydrochloride (50 mg, crude) as a yellow solid which was used in the next step directly without further purification. ESI-MS [M+H]$^+$: 291.1.

Example 183

Synthesis of (2-fluoro-3-methoxy-6-(1H-1,2,3-triazol-4-yl)phenyl)methanamine hydrochloride

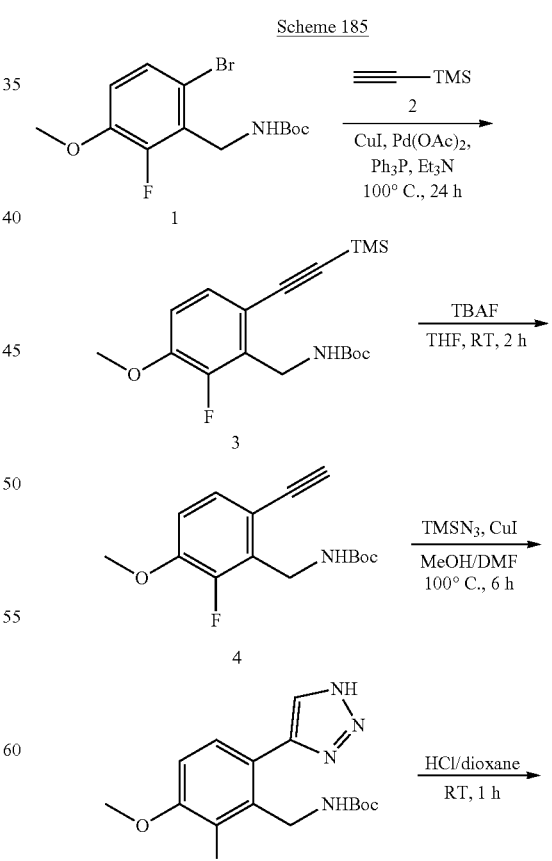

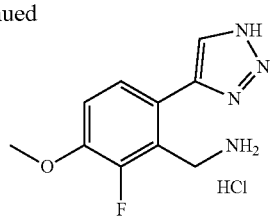

6

Synthesis of tert-butyl (2-fluoro-3-methoxy-6-((trimethylsilyl)ethynyl)benzyl)carbamate. A mixture of tert-butyl (6-bromo-2-fluoro-3-methoxybenzyl)carbamate (666 mg, 2.0 mmol), ethynyltrimethylsilane (980 mg, 10.0 mmol), CuI (76 mg, 0.4 mmol), Pd(OAc)$_2$ (90 mg, 0.4 mmol), Ph$_3$P (105 mg, 0.4 mmol) and Et$_3$N (20 mL) was stirred at 100° C. under N$_2$ for 24 h. The reaction mixture was concentrated in vacuo, then diluted with water (40 mL) and extracted with EtOAc (20 mL×3). The combined organic layers were washed with brine (20 mL), dried over Na$_2$SO$_4$ and concentrated in vacuo. The residue was purified by silica gel chromatography (PE/EtOAc=15/1) to give tert-butyl (2-fluoro-3-methoxy-6-((trimethylsilyl)ethynyl)benzyl)carbamate (500 mg, 71.2%) as a yellow oil. ESI-MS [M+H]$^+$: 352.1.

Synthesis of tert-butyl (6-ethynyl-2-fluoro-3-methoxybenzyl)carbamate. A mixture of tert-butyl (2-fluoro-3-methoxy-6-((trimethylsilyl)ethynyl)benzyl)carbamate (500 mg, 1.42 mmol) and TBAF (2.14 mL, 2.14 mmol) in THF (10 mL) was stirred at RT for 2 h. The reaction mixture was diluted with water (30 mL) and extracted with EtOAc (20 mL×3). The combined organic layers were washed with brine (20 mL), dried over Na$_2$SO$_4$ and concentrated in vacuo. The residue was purified by column chromatography (PE/EtOAc=15/1) to give tert-butyl (6-ethynyl-2-fluoro-3-methoxybenzyl)carbamate (250 mg, 63%) as a yellow solid. ESI-MS [M+H]$^+$: 280.1.

Synthesis of tert-butyl (2-fluoro-3-methoxy-6-(1H-1,2,3-triazol-4-yl)benzyl)carbamate. A mixture of tert-butyl (6-ethynyl-2-fluoro-3-methoxybenzyl)carbamate (279 mg, 1.0 mmol), TMSN$_3$ (230 mg, 2.0 mmol) and CuI (96 mg, 0.5 mmol) in MeOH/DMF (1.0 mL/10.0 mL) was stirred at 100° C. under N$_2$ for 6 h. The reaction mixture was diluted with water (50 mL) and extracted with EtOAc (20 mL×5). The combined organic layers were washed with brine (20 mL), dried over Na$_2$SO$_4$ and concentrated in vacuo. The residue was purified by column chromatography (DCM/MeOH=10/1) to give tert-butyl (2-fluoro-3-methoxy-6-(1H-1,2,3-triazol-4-yl)benzyl)carbamate (80 mg, 25%) as a brown oil. ESI-MS [M+H]$^+$: 323.1.

Synthesis of (2-fluoro-3-methoxy-6-(1H-1,2,3-triazol-4-yl)phenyl)methanamine. A mixture of tert-butyl (2-fluoro-3-methoxy-6-(1H-1,2,3-triazol-4-yl)benzyl)carbamate (64 mg, 0.20 mmol) in HCl/dioxane (4M, 2.0 mL) was stirred at RT for 1 h. The reaction mixture was concentrated in vacuo to give (2-fluoro-3-methoxy-6-(1H-1,2,3-triazol-4-yl)phenyl)methanamine hydrochloride (51.6 mg, crude) as a yellow solid which was used in the next step directly without further purification. ESI-MS [M+H]$^+$: 223.1.

Example 184

Synthesis of 11-(2-fluoro-3-methoxy-6-(1H-tetrazol-1-yl)phenyl)ethan-1-amine

Scheme 186

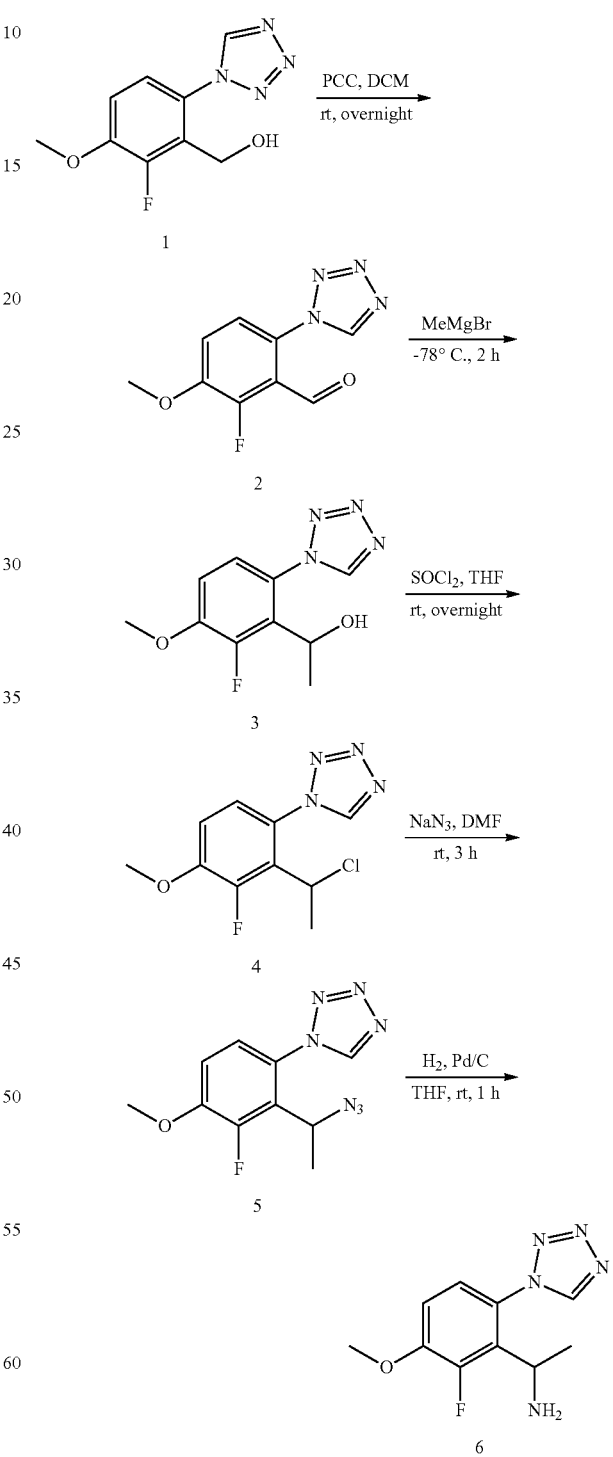

Synthesis of 2-fluoro-3-methoxy-6-(1H-tetrazol-1-yl)benzaldehyde. To a solution of (2-fluoro-3-methoxy-6-(1H- tetrazol-1-yl)phenyl)methanol (440 mg, 1.96 mmol) in DCM (20 mL) was added PCC (1.27 g, 5.9 mmol) slowly at 0° C. The reaction mixture was stirred at room temperature overnight. The mixture was filtered and washed with MeOH. The filtrate was concentrated and purified by silica gel chromatography (EtOAc/PE=3:1) to give 2-fluoro-3-methoxy-6-(1H-tetrazol-1-yl)benzaldehyde (190 mg, yield: 44%) as a white solid. ESI-MS [M+H]$^+$: 223.1.

Synthesis of 1-(2-fluoro-3-methoxy-6-(1H-tetrazol-1-yl)phenyl)ethan-1-ol. Methylmagnesium bromide (3M in THF, 0.3 mL, 0.9 mmol) was added to a solution of 2-fluoro-3-methoxy-6-(1H-tetrazol-1-yl)benzaldehyde (100 mg, 0.45 mmol) at −78° C. under N$_2$. The mixture was stirred at −78° C. for 2 h. The mixture was quenched by adding HCl (3 M in dioxane, 0.3 mL, 0.9 mmol) and EtOAc (5 mL). The mixture was concentrated in vacuo and purified by Prep-TLC (DCM/MeOH=18:1) to give 1-(2-fluoro-3-methoxy-6-(1H-tetrazol-1-yl)phenyl)ethan-1-ol (34 mg, yield: 32%) as a white solid. ESI-MS [M+H]$^+$: 239.2.

Synthesis of 1-(2-(1-chloroethyl)-3-fluoro-4-methoxyphenyl)-1H-tetrazole. SOCl$_2$ (0.5 mL) was added to a solution of 1-(2-fluoro-3-methoxy-6-(1H-tetrazol-1-yl)phenyl)ethan-1-ol (34 mg, 0.143 mmol) in DCM (20 mL) at 0° C. The reaction mixture was stirred at room temperature overnight. The mixture was concentrated in vacuo to give crude 1-(2-(1-chloroethyl)-3-fluoro-4-methoxyphenyl)-1H-tetrazole, which was used in the next step without further purification. ESI-MS [M+H]+: 257.1.

Synthesis of 1-(2-(1-azidoethyl)-3-fluoro-4-methoxyphenyl)-1H-tetrazole. A solution of 1-(2-(1-chloroethyl)-3-fluoro-4-methoxyphenyl)-1H-tetrazole (crude from last step) (36 mg, 0.14 mmol) and NaN$_3$ (19 mg, 0.29 mmol) in DMF (1 mL) was stirred at room temperature for 3 h. Water (15 mL) was added and the mixture was extracted with EtOAc (20 mL×3). The combined organic layers were washed with brine (25 mL), dried over Na$_2$SO$_4$, and concentrated in vacuo to give crude 1-(2-(1-azidoethyl)-3-fluoro-4-methoxyphenyl)-1H-tetrazole (50 mg crude), which was used into the next step without further purification. ESI-MS [M+H]$^+$: 264.1.

Synthesis of 1-(2-fluoro-3-methoxy-6-(1H-tetrazol-1-yl)phenyl)ethan-1-amine. A solution of 1-(2-(1-azidoethyl)-3-fluoro-4-methoxyphenyl)-1H-tetrazole (38 mg, 0.14 mmol) (crude from previous step) and catalytic Pd/C in THE (3 mL) was stirred at room temperature for 1 h under H$_2$. The reaction mixture was filtered and washed with MeOH. The filtrate was concentrated in vacuo and purified by Prep-TLC (DCM:MeOH=30:1) to give 1-(2-fluoro-3-methoxy-6-(1H-tetrazol-1-yl)phenyl)ethan-1-amine (20 mg, yield 59% over 3 steps) as a white solid. ESI-MS [M+H]$^+$: 238.2.

Example 185

Synthesis of 6,7-dihydro-5H-cyclopenta[c]pyridine-1,5-diamine hydrochloride

Scheme 187

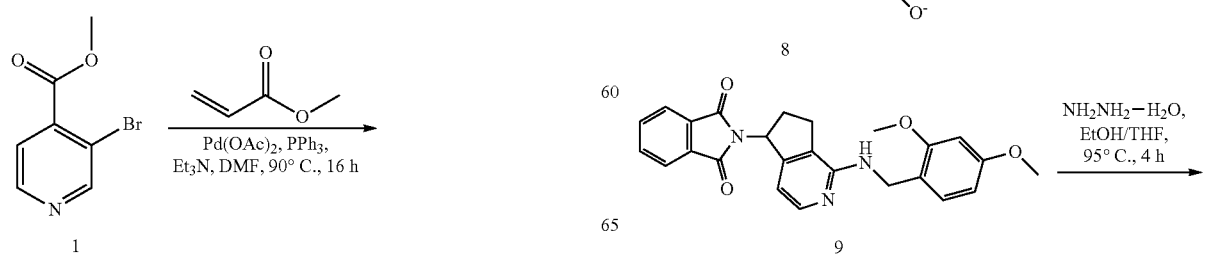

-continued

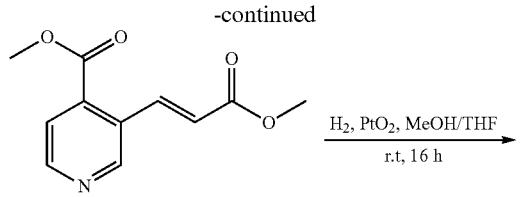

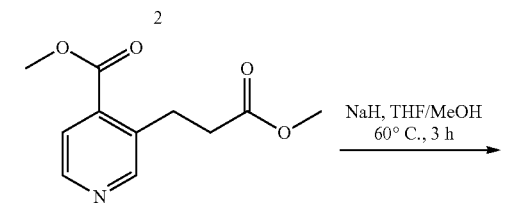

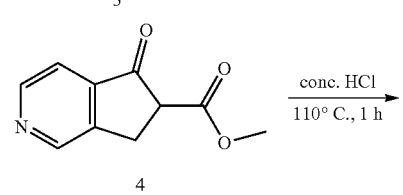

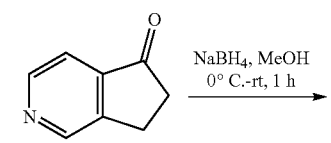

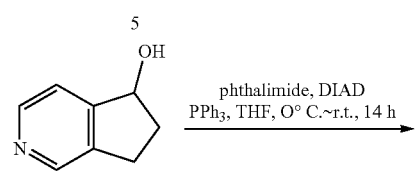

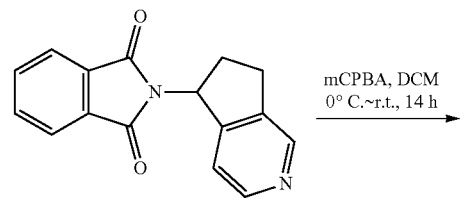

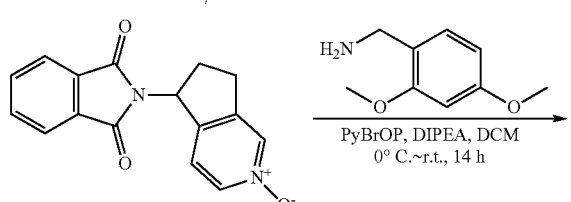

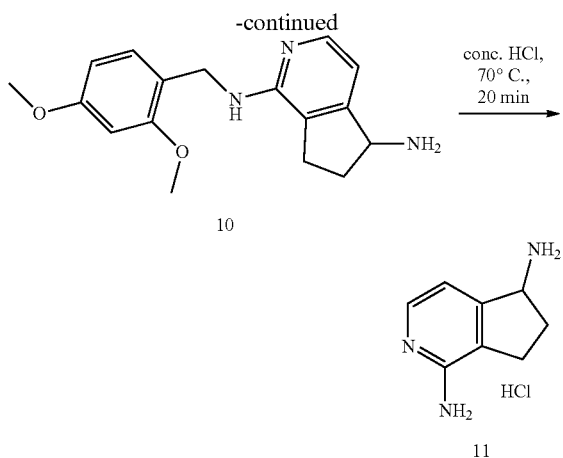

Synthesis of methyl (E)-3-(3-methoxy-3-oxoprop-1-en-1-yl)isonicotinate. A mixture of methyl 3-bromoisonicotinate (21 g, 97.67 mmol), methyl acrylate (84.0 g, 97.67 mol), Pd(OAc)$_2$ (2.18 g, 9.76 mmol), PPh$_3$ (5.12 g, 19.53 mmol) and Et$_3$N (49.3 g, 488.35 mol) in DMF (210 mL) was heated to 90° C. and stirred for 16 h. The reaction mixture was concentrated in vacuo and the residue was dissolved in EtOAc (400 mL) and H$_2$O (300 mL) and filtered. The phases were separated and the aqueous layer was extracted with EtOAc (200 mL×2). The combined organics were washed with water (500 mL×3) and brine (500 mL), dried over Na$_2$SO$_4$, concentrated in vacuo, and purified by silica gel chromatography (EtOAc/PE=1/3) to give methyl (E)-3-(3-methoxy-3-oxoprop-1-en-1-yl)isonicotinate as a yellow solid (12.3 g, yield: 57%). ESI-MS [M+H]$^+$: 222.1.

Synthesis of methyl 3-(3-methoxy-3-oxopropyl)isonicotinate. A mixture of methyl (E)-3-(3-methoxy-3-oxoprop-1-en-1-yl)isonicotinate (12.3 g, 55.6 mmol) and PtO$_2$ (1.26 g, 5.56 mmol) in MeOH (180 mL) and THF (90 mL) was stirred at room temperature for 16 h under H$_2$ (balloon). The reaction mixture was filtered and the filtrate was concentrated in vacuo. The residue was purified by silica gel chromatography (EtOAc/PE=1/3) to give methyl 3-(3-methoxy-3-oxopropyl)isonicotinate as colorless oil (7.5 g, yield: 60%). ESI-MS [M+H]$^+$: 224.1.

Synthesis of methyl 5-oxo-6,7-dihydro-5H-cyclopenta[c]pyridine-6-carboxylate. To a solution of methyl 3-(3-methoxy-3-oxopropyl)isonicotinate (5 g, 22.42 mmol) in THF (120 mL) was added NaH (3.87 g, 60% suspension in paraffin oil, 100.9 mmol) and MeOH (5 mL) at 0° C. The resulting mixture was stirred at 60° C. for 3 h. The mixture was concentrated in vacuo to give crude methyl 5-oxo-6,7-dihydro-5H-cyclopenta[c]pyridine-6-carboxylate (9 g crude), which was used in the next step without further purification. ESI-MS [M+H]$^+$: 192.1.

Synthesis of 6,7-dihydro-5H-cyclopenta[c]pyridin-5-one. To methyl 5-oxo-6,7-dihydro-5H-cyclopenta[c]pyridine-6-carboxylate (9 g crude from previous step) was added conc. HCl (100 mL). The resulting mixture was stirred at 100° C. for 1 h. The reaction was concentrated in vacuo to give the residue, which was adjusted to pH 12 using saturated aqueous NaHCO$_3$ and extracted with EtOAc (150 mL×3). The combined organic layers were washed with brine, dried over Na$_2$SO$_4$, and concentrated in vacuo to give the crude, which was purified by silica gel chromatography (eluent: PE/EtOAc=1/4) to give 6,7-dihydro-5H-cyclopenta[c]pyridin-5-one as a yellow solid. (2.3 g, 77.2% over 2 steps). ESI-MS [M+H]$^+$: 134.2.

Synthesis of 6,7-dihydro-5H-cyclopenta[c]pyridin-5-ol. To a solution of 6,7-dihydro-5H-cyclopenta[c]pyridin-5-one (2.3 g, 17.3 mmol) in MeOH (75 mL) was added NaBH$_4$ (1.95 g, 51.2 mmol) at 0° C. slowly. The reaction was stirred at room temperature for 1 h. The reaction mixture was quenched with H$_2$O (100 mL) and extracted with EtOAc (100 mL×3). The combined organic layers were washed with brine, dried over Na$_2$SO$_4$, and concentrated in vacuo to give the crude, which was purified by silica gel chromatography (eluent: EtOAc/PE=1/1) to give 6,7-dihydro-5H-cyclopenta[c]pyridin-5-ol as a yellow solid. (2 g, 87%). ESI-MS [M+H]$^+$: 136.2.

Synthesis of 2-(6,7-dihydro-5H-cyclopenta[c]pyridin-5-yl)isoindoline-1,3-dione. To a solution of 6,7-dihydro-5H-cyclopenta[c]pyridin-5-ol (2 g, 14.8 mmol) and phthalimide (2.5 g, 17 mmol) in THF (100 mL) at 0° C. was added PPh$_3$ (4.45 g, 17 mmol) and DIAD (3.43 g, 17 mmol). The reaction mixture was stirred at room temperature for 14 h. The reaction was concentrated in vacuo to give the crude, which was purified by silica gel chromatography (eluent: 100% EtOAc) to give 2-(6,7-dihydro-5H-cyclopenta[c]pyridin-5-yl)isoindoline-1,3-dione as a yellow solid (5 g, mixture with Ph$_3$PO). ESI-MS [M+H]$^+$: 265.2.

Synthesis of 5-(1,3-dioxoisoindolin-2-yl)-6,7-dihydro-5H-cyclopenta[c]pyridine 2-oxide. To a solution of 2-(6,7-dihydro-5H-cyclopenta[c]pyridin-5-yl)isoindoline-1,3-dione (5 g, mixture with Ph$_3$PO from previous step) in DCM (100 mL) was added mCPBA (2.83 g, 22.83 mmol) slowly at 0° C. The reaction mixture was stirred at room temperature for 14 h. The reaction was quenched with sat. aq. NaHCO$_3$ and extracted with DCM (150 mL×3). The combined organic layers were washed sequentially with sat. aq. NaHCO$_3$ and brine, dried over Na$_2$SO$_4$, and concentrated in vacuo to give the crude, which was used in the next step without further purification. (6.3 g crude). ESI-MS [M+H]$^+$: 281.1.

Synthesis of 2-(1-((2,4-dimethoxybenzyl)amino)-6,7-dihydro-5H-cyclopenta[c]pyridin-5-yl)isoindoline-1,3-dione. To a solution of 5-(1,3-dioxoisoindolin-2-yl)-6,7-dihydro-5H-cyclopenta[c]pyridine 2-oxide (6.3 g crude) in DCM (120 mL) was added (2,4-dimethoxyphenyl)methanamine (4.9 g, 29.35 mmol), DIPEA (14 mL, 79.03 mmol) and PyBrOP (15.8 g, 33.87 mmol) at 0° C. The reaction mixture was stirred at room temperature for 14 h. H$_2$O (150 mL) was added and the mixture was extracted with DCM (150 mL×3). The combined organic layers were washed with brine, dried over Na$_2$SO$_4$, and concentrated in vacuo to give the crude, which was purified by silica gel chromatography (eluent: PE/EtOAc=1/2) to give 2-(1-((2,4-dimethoxybenzyl)amino)-6,7-dihydro-5H-cyclopenta[c]pyridin-5-yl)isoindoline-1,3-dione (2.32 g, 36.5% over 3 steps). ESI-MS [M+H]$^+$: 430.1.

Synthesis of N$_1$-(2,4-dimethoxybenzyl)-6,7-dihydro-5H-cyclopenta[c]pyridine-1,5-diamine A solution of 2-(1-((2,4-dimethoxybenzyl)amino)-6,7-dihydro-5H-cyclopenta[c]pyridin-5-yl)isoindoline-1,3-dione (2.32 g, 5.4 mmol) and NH$_2$NH$_2$—H$_2$O (6 mL, 80% in H$_2$O) in THF (25 mL) and EtOH (25 mL) was stirred at 95° C. for 4 h. The reaction mixture was concentrated in vacuo to remove solvent. DCM (30 mL) was added to the residue and the suspension was filtered. The filtrate was concentrated in vacuo to give N$_1$-(2,4-dimethoxybenzyl)-6,7-dihydro-5H-cyclopenta[c]pyridine-1,5-diamine (1.14 g, 70.8%). ESI-MS [M+H]$^+$: 300.1.

Synthesis of 6,7-dihydro-5H-cyclopenta[c]pyridine-1,5-diamine hydrochloride. A mixture of N$_1$-(2,4-dimethoxybenzyl)-6,7-dihydro-5H-cyclopenta[c]pyridine-1,5-diamine (1.14 g, 3.8 mmol) in conc. HCl (50 mL) was stirred at 70° C. for 20 min. The reaction mixture was concentrated in vacuo to give the crude, which was triturated with Et$_2$O (100 mL) and filtered to give 6,7-dihydro-5H-cyclopenta[c]pyridine-1,5-diamine hydrochloride as a pink solid (550 mg, 78%). ESI-MS [M+H]$^+$: 150.1.

Example 186

Synthesis of 3-methyl-6,7-dihydro-5H-cyclopenta[c]pyridine-1,5-diamine hydrochloride Scheme 188

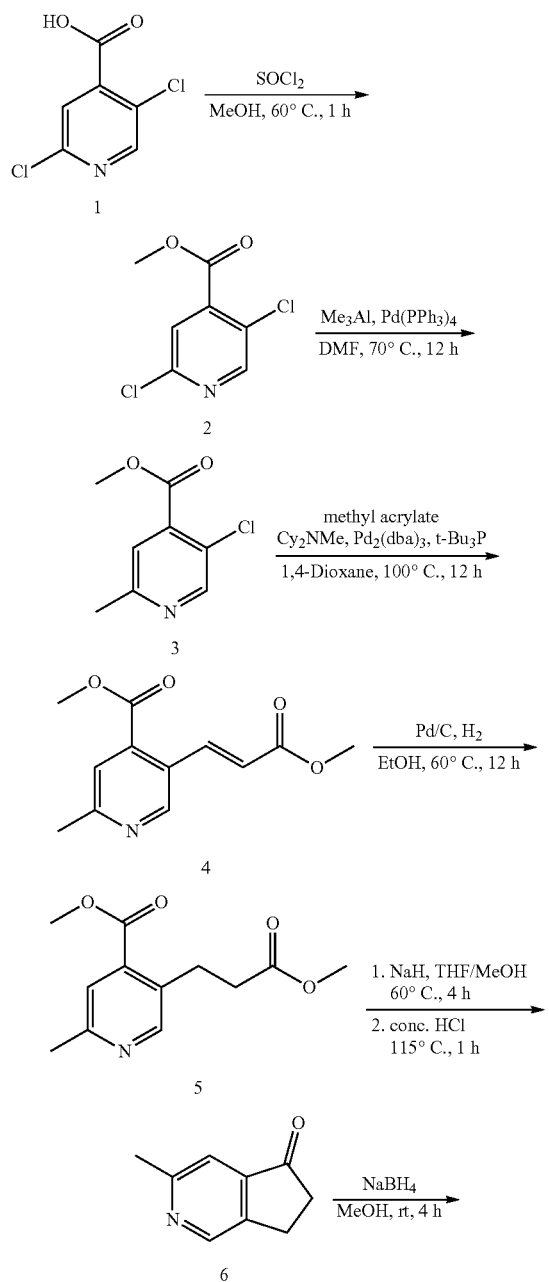

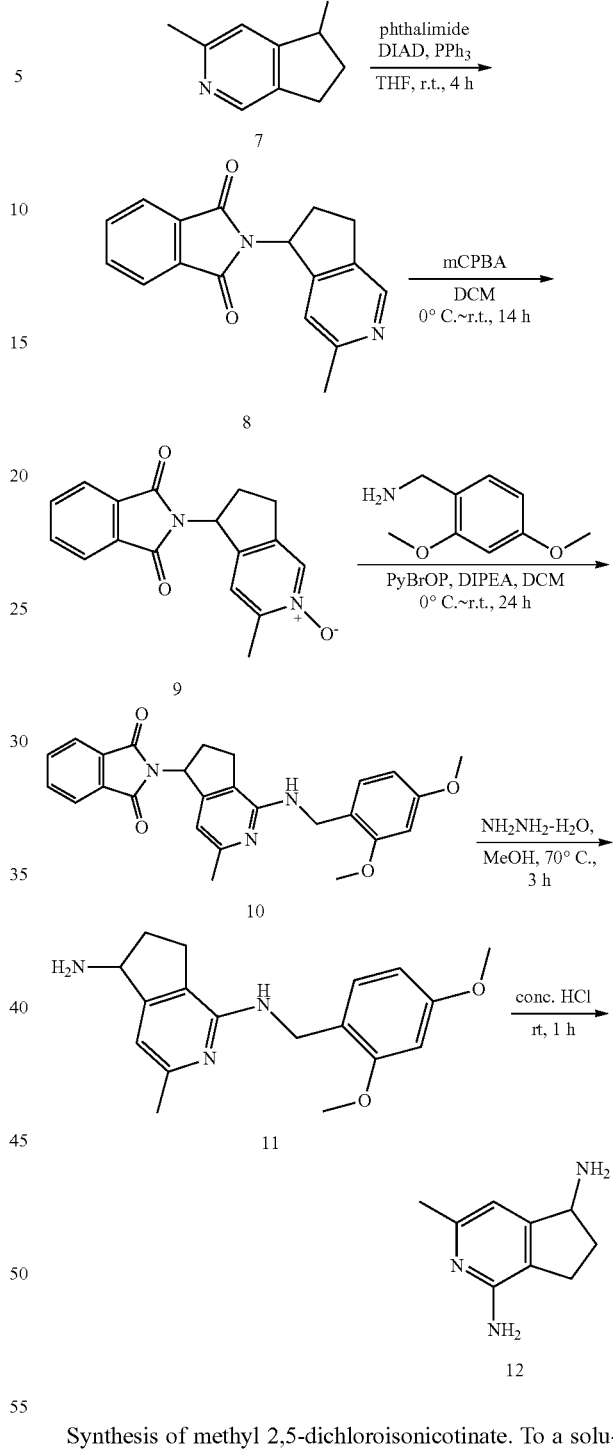

Synthesis of methyl 2,5-dichloroisonicotinate. To a solution of methyl 2,5-dichloroisonicotinic acid (10.0 g, 52.3 mmol) in MeOH (100 mL) was added SOCl$_2$ (18.5 g, 156.9 mmol) at 0° C. slowly. The mixture was stirred at 60° C. for 1 h. Water (100 mL) was added t and the mixture was extracted with EtOAc (100 mL×3). The combined organic layers were dried over Na$_2$SO$_4$ and concentrated to give 2,5-dichloroisonicotinate (10.5 g, yield: 98%) as a yellow oil. ESI-MS [M+H]$^+$: 207.3.

Synthesis of methyl 5-chloro-2-methylisonicotinate. To a solution of methyl 2,5-dichloroisonicotinate (2.3 g, 11.2 mmol) in DMF (20 mL) was added Pd(PPh$_3$)$_4$ (1.9 g, 1.68 mmol) and Me₃Al (1.6 g, 22.4 mmol). The mixture was stirred at 70° C. for 12 h under N₂. Water (100 mL) was added and the mixture was extracted with EtOAc (100 mL×3). The combined organic layers were concentrated in vacuo and purified by silica gel chromatography (EtOAc/PE=3/10) to give methyl 5-chloro-2-methylisonicotinate (1.6 g, yield: 77%) as a yellow oil. ESI-MS [M+H]⁺: 186.1.

Synthesis of methyl (E)-5-(3-methoxy-3-oxoprop-1-en-1-yl)-2-methylisonicotinate. To a solution of methyl 5-chloro-2-methylisonicotinate (900 mg, 4.8 mmol) in dry 1,4-dioxane (10 mL) was added Cy₂NMe (1.9 g, 9.7 mmol), Pd₂(dba)₃ (67 mg, 0.073 mmol), P(t-Bu)₃ (60.6 mg, 0.30 mmol) and methyl acrylate (6.2 g, 72.6 mmol). The reaction mixture was stirred at 100° C. for 12 h under N₂. Water (100 mL) was added and the mixture was extracted with EtOAc (100 mL×3). The combined organic layers were concentrated in vacuo and purified by silica gel chromatography (EtOAc/PE=1/5) to give methyl (E)-5-(3-methoxy-3-oxoprop-1-en-1-yl)-2-methylisonicotinate (200 mg, yield: 18%) as a yellow solid. ESI-MS [M+H]⁺: 236.1.

Synthesis of methyl 5-(3-methoxy-3-oxopropyl)-2-methylisonicotinate. To a solution of methyl (E)-5-(3-methoxy-3-oxoprop-1-en-1-yl)-2-methylisonicotinate (200 mg, 0.85 mmol) in EtOH (4 mL) was added 10% Pd/C (20 mg). The mixture was stirred at 60° C. for 12 h under H₂ atmosphere. The mixture was filtered and filtrate was concentrated in vacuo to give methyl 5-(3-methoxy-3-oxopropyl)-2-methylisonicotinate (180 mg) as a yellow oil which was used in the next step without further purification. ESI-MS [M+H]+: 238.1.

Synthesis of 3-methyl-6,7-dihydro-5H-cyclopenta[c]pyridin-5-one. To a solution of methyl 5-(3-methoxy-3-oxopropyl)-2-methylisonicotinate (1 g, 4.2 mmol) in dry THF (20 mL) was added NaH (756 mg, 18.9 mmol, 60%) and MeOH (63 mg, 0.47 mmol). The reaction mixture was stirred at 60° C. for 4 h. The mixture was then concentrated in vacuo and conc. HCl (10 mL) was added to the residue slowly. Then the mixture was stirred at 115° C. for 1 h. Water (100 mL) was added and the mixture was extracted with EtOAc (100 mL×3). The combined organic layers were concentrated in vacuo and purified by silica gel chromatography (EtOAc) to give 3-methyl-6,7-dihydro-5H-cyclopenta[c]pyridin-5-one (420 mg, yield: 68%) as a yellow solid. ESI-MS [M+H]⁺: 148.1.

Synthesis of 3-methyl-6,7-dihydro-5H-cyclopenta[c]pyridin-5-ol. To a solution of 3-methyl-6,7-dihydro-5H-cyclopenta[c]pyridin-5-one (420 mg, 2.86 mmol) in MeOH (10 mL) was added NaBH₄ (326 mg, 8.57 mmol) slowly. The reaction mixture was stirred at room temperature for 4 h. Water (100 mL) was added and the mixture was extracted with EtOAc (100 mL×3). The combined organic layers were concentrated in vacuo to give 3-methyl-6,7-dihydro-5H-cyclopenta[c]pyridin-5-ol (380 mg, yield: 90%) as a yellow oil which was used in the next step without further purification. ESI-MS [M+H]⁺: 150.1.

Synthesis of 2-(3-methyl-6,7-dihydro-5H-cyclopenta[c]pyridin-5-yl)isoindoline-1,3-dione. To a solution of 3-methyl-6,7-dihydro-5H-cyclopenta[c]pyridin-5-ol (380 mg, 2.55 mmol) in dry THF (20 mL) was added phthalimide (428 mg, 2.91 mmol), PPh₃ (762 mg, 2.91 mmol) and DIAD (588 mg, 2.91 mmol). The reaction mixture was stirred at room temperature for 4 h. The reaction mixture was concentrated in vacuo and purified by silica gel chromatography (EtOAc/PE=1/5) to give 2-(3-methyl-6,7-dihydro-5H-cyclopenta[c]pyridin-5-yl)isoindoline-1,3-dione (1 g) as a gray solid. ESI-MS [M+H]⁺: 279.1.

Synthesis of 5-(1,3-dioxoisoindolin-2-yl)-3-methyl-6,7-dihydro-5H-cyclopenta[c]pyridine 2-oxide. To a solution of 2-(3-methyl-6,7-dihydro-5H-cyclopenta[c]pyridin-5-yl)isoindoline-1,3-dione (1 g) in DCM (10 mL) at 0° C. was added m-CPBA (877 mg, 5.10 mmol). The reaction mixture was stirred at room temperature for 14 h. The mixture was quenched with saturated aqueous Na₂SO₃ solution (20 mL) and extracted with DCM (20 mL×3). The combined organic layers were washed with brine (30 mL), dried over Na₂SO₄, filtered and concentrated in vacuo to give the crude, which was purified by silica gel chromatography (DCM/MeOH=10/1) to give 5-(1,3-dioxoisoindolin-2-yl)-3-methyl-6,7-dihydro-5H-cyclopenta[c]pyridine 2-oxide (200 mg, yield: 26.7% over two steps) as a yellow solid. ESI-MS [M+H]+: 295.1.

Synthesis of 2-(1-((2,4-dimethoxybenzyl)amino)-3-methyl-6,7-dihydro-5H-cyclopenta[c]pyridin-5-yl)isoindoline-1,3-dione. To a solution of 5-(1,3-dioxoisoindolin-2-yl)-3-methyl-6,7-dihydro-5H-cyclopenta[c]pyridine 2-oxide (100 mg, 0.34 mmol) in DCM (5 mL) was added (2,4-dimethoxyphenyl)methanamine (85 mg, 0.51 mmol), PyBrop (285 mg, 0.61 mmol) and DIPEA (153 mg, 1.19 mmol) at 0° C. The reaction mixture was stirred at room temperature for 24 h, then concentrated in vacuo and purified by silica gel chromatography (EtOAc/PE=1/1) to give 2-(1-((2,4-dimethoxybenzyl)amino)-3-methyl-6,7-dihydro-5H-cyclopenta[c]pyridin-5-yl)isoindoline-1,3-dione (130 mg, yield: 86%) as a yellow oil. ESI-MS [M+H]⁺: 444.1.

Synthesis of N₁-(2,4-dimethoxybenzyl)-3-methyl-6,7-dihydro-5H-cyclopenta[c]pyridine-1,5-diamine. To a solution of 2-(1-((2,4-dimethoxybenzyl)amino)-3-methyl-6,7-dihydro-5H-cyclopenta[c]pyridin-5-yl)isoindoline-1,3-dione (130 mg, 0.29 mmol) in MeOH (3 mL) was added NH₂NH₂·H₂O (0.067 mL). The reaction mixture was stirred at 70° C. for 3 h. The mixture was concentrated in vacuo and diluted with EtOAc (20 mL). The mixture was filtered and the filtrate was concentrated in vacuo to give crude N₁-(2,4-dimethoxybenzyl)-3-methyl-6,7-dihydro-5H-cyclopenta[c]pyridine-1,5-diamine (80 mg, crude) as a yellow oil which was used in the next step without further purification. ESI-MS [M+H]⁺: 314.1.

Synthesis of 3-methyl-6,7-dihydro-5H-cyclopenta[c]pyridine-1,5-diamine. A mixture of N₁-(2,4-dimethoxybenzyl)-3-methyl-6,7-dihydro-5H-cyclopenta[c]pyridine-1,5-diamine (150 mg, 0.48 mmol) in conc. HCl (2 mL) was stirred at room temperature for 1 h. The reaction mixture was concentrated in vacuo to give crude 3-methyl-6,7-dihydro-5H-cyclopenta[c]pyridine-1,5-diamine hydrochloride (116 mg, 100%) which was used in the next step without further purification. ESI-MS [M+H]⁺: 164.1.

Example 187

Synthesis of (4-chlorothieno[3,2-c]pyridin-2-yl)methanamine

Scheme 189

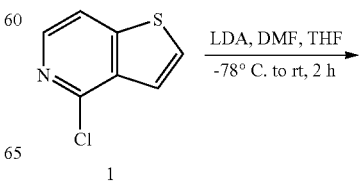

LDA, DMF, THF
-78° C. to rt, 2 h

1

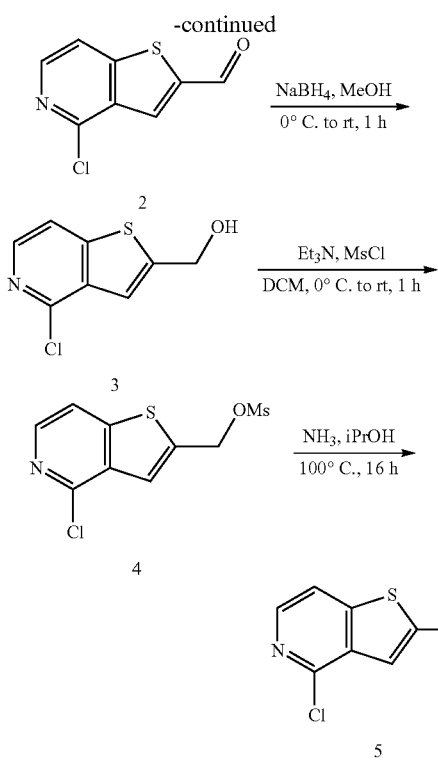

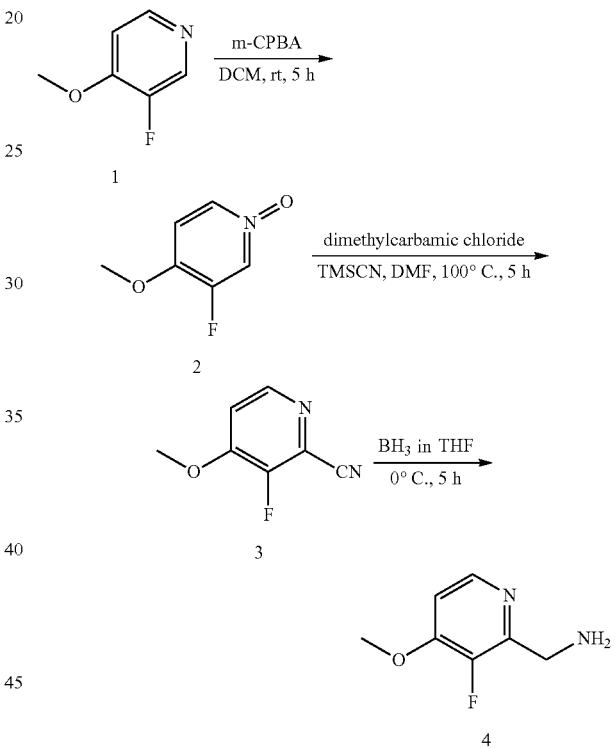

Synthesis of 4-chlorothieno[3,2-c]pyridine-2-carbaldehyde. To a mixture of 4-chlorothieno[3,2-c]pyridine (1 g, 5.89 mmol) in THF (40 mL) was added LDA (3.8 mL, 2M) at 78° C. under $N_2$. The reaction mixture was stirred at −78° C. for 0.5 h. Then DMF (560 mg, 7.66 mmol) was added. The mixture was allowed to warm to room temperature and stirred for 2 h. The reaction mixture was quenched with sat. aq. $NH_4Cl$ solution (100 mL), extracted with EtOAc (50 mL×3), washed with brine (100 mL), dried over $Na_2SO_4$, and concentrated to give crude 4-chlorothieno[3,2-c]pyridine-2-carbaldehyde (1.2 g, crude) which was used in the next step without further purification. ESI-MS [M+H]+: 198.1.

Synthesis of (4-chlorothieno[3,2-c]pyridin-2-yl)methanol. To a mixture of 4-chlorothieno[3,2-c]pyridine-2-carbaldehyde (1.1 g, 5.56 mmol) in MeOH (30 mL) was added $NaBH_4$ (420 mg, 11.1 mmol) at 0° C. The reaction mixture was stirred at room temperature for 1 h. The mixture was quenched with sat. aq. $NH_4Cl$ (100 mL), extracted with EtOAc (50 mL×3), washed with brine (100 mL), dried over $Na_2SO_4$ and concentrated in vacuo to give the crude product. The residue was purified by flash chromatography (MeOH in DCM from 0 to 10%) to give (4-chlorothieno[3,2-c]pyridin-2-yl)methanol (1.0 g, 90% yield) as a light yellow solid. ESI-MS [M+H]+: 200.0.

Synthesis of (4-chlorothieno[3,2-c]pyridin-2-yl)methyl methanesulfonate. To a mixture of (4-chlorothieno[3,2-c]pyridin-2-yl)methanol (100 mg, 0.5 mmol) in DCM (10 mL) was added $Et_3N$ (152 mg, 1.5 mmol) and MsCl (104 mg, 1 mmol) at 0° C. under $N_2$. The reaction mixture was stirred at room temperature for 1 h. The mixture was quenched with sat. aq. $NH_4Cl$ (30 mL), extracted with EtOAc (20 mL×3), washed with brine (30 mL), dried over $Na_2SO_4$ and concentrated to give crude (4-chlorothieno[3,2-c]pyridin-2-yl)methyl methanesulfonate, which was used in the next step without further purification (100 mg, crude). ESI-MS [M+H]+: 278.0.

Synthesis of (4-chlorothieno[3,2-c]pyridin-2-yl)methanamine. A mixture of (4-chlorothieno[3,2-c]pyridin-2-yl)methyl methanesulfonate (100 mg, 0.36 mmol) in $NH_3$ in i-PrOH (6 mL) was stirred at 100° C. for 16 h under $N_2$ in a sealed tube. The reaction mixture was concentrated in vacuo to give crude (4-chlorothieno[3,2-c]pyridin-2-yl)methanamine as a yellow solid which was used in the next step without further purification (150 mg, crude). ESI-MS [M+H]+: 199.1

Example 188

Synthesis of (3 fluoro-4-methoxypyridin-2 yl)methanamine

Scheme 190

Synthesis of 3-fluoro-4-methoxypyridine 1-oxide. To a solution of 3-fluoro-4-methoxypyridine (500 mg, 3.93 mmol) in DCM (10 mL) was added m-CPBA (1.36 g, 7.88 mmol) at 0° C. The reaction mixture was warmed to room temperature and stirred for 5 h. The mixture was adjusted to pH 8-9 using sat. aq. $NaHCO_3$ (120 mL) and extracted with DCM/MeOH (DCM:MeOH=5:1, 80 mL x 3), washed with brine (100 mL×2), dried over $Na_2SO_4$, and concentrated in vacuo to give crude 3-fluoro-4-methoxypyridine 1-oxide (500 mg, crude), which was used in the next step without further purification. ESI-MS: [M+H]+, 144.2.

Synthesis of 3-fluoro-4-methoxypicolinonitrile. A mixture of 3-fluoro-4-methoxypyridine 1-oxide (500 mg, 3.50 mmol), dimethylcarbamic chloride (539 mg, 5.04 mmol) and TMSCN (499 mg, 5.04 mmol) in DMF (10 mL) was stirred at 0° C. for 0.5 h, then heated to 100° C. and stirred at 100° C. for 5 h. Water (100 ml) was added and the mixture was extracted with EtOAc (100 ml×3). The combined organic layers were washed with brine (100 mL×2), dried (Na₂SO₄), and concentrated in vacuo to give the crude which was purified by flash chromatography (PE:EtOAc=5:1) to afford 3-fluoro-4-methoxypicolinonitrile (130 mg, 24.4%) as yellow solid. ESI-MS: [M+H]⁺, 153.2.

Synthesis of (3-fluoro-4-methoxypyridin-2-yl)methanamine. A mixture of 3-fluoro-4-methoxypicolinonitrile (130 mg, 0.855 mol) and BH₃ in THF (9 mL, 9 mmol) was stirred at 0° C. for 5 h. The reaction was quenched with MeOH (10 ml) at 0° C. and concentrated in vacuo to give the crude, which was purified by Prep-TLC (DCM:MeOH=5:1) to afford (3-fluoro-4-methoxypyridin-2-yl)methanamine (45 mg, 33.8%) as a white solid. ESI-MS: [M+H]+, 157.1.

Example 189

Synthesis of (5-chloro-2-(4-chloro-1H-1,2,3-triazol-1-yl)phenyl)methanamine

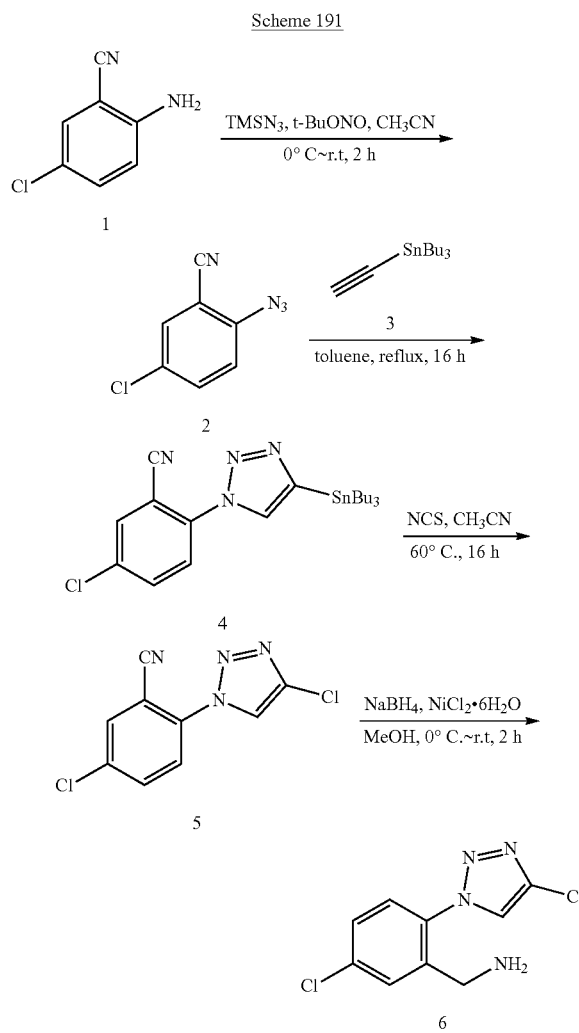

Synthesis of 2-azido-5-chlorobenzonitrile. To a stirred solution of 2-amino-5-chlorobenzonitrile (500 mg, 3.28 mmol) and TMSN₃ (491 mg, 4.26 mmol) in CH₃CN (18 mL) at 0° C. was added a solution of t-BuONO (439 mg, 4.26 mmol) in CH₃CN (2 mL) dropwise. The reaction mixture was stirred at room temperature for 2 h. The mixture was concentrated in vacuo and purified by silica gel chromatography (EtOAc/PE=1/30) to give 2-azido-5-chlorobenzonitrile (570 mg, yield: 97%) as a colorless oil. ESI-MS [M+H]⁺: 179.1.

Synthesis of 5-chloro-2-(4-(tributylstannyl)-1H-1,2,3-triazol-1-yl)benzonitrile. A mixture of 2-azido-5-chlorobenzonitrile (570 mg, 3.19 mmol) and tributyl(ethynyl)stannane (1.21 g, 3.83 mmol) in toluene (15 mL) was stirred at reflux for 16 h. The reaction mixture was concentrated in vacuo and purified by silica gel chromatography (EtOAc/PE=1/20) to give 5-chloro-2-(4-(tributylstannyl)-1H-1,2,3-triazol-1-yl)benzonitrile (1.1 g, yield: 70%) as a colorless oil. ESI-MS [M+H]⁺: 495.2.

Synthesis of 5-chloro-2-(4-chloro-1H-1,2,3-triazol-1-yl)benzonitrile. A mixture of 5-chloro-2-(4-(tributylstannyl)-1H-1,2,3-triazol-1-yl)benzonitrile (1.1 g, 2.23 mmol) and NCS (596 mg, 3.83 mmol) in CH₃CN (15 mL) was stirred at 60° C. for 16 h. The reaction mixture was concentrated in vacuo and purified by silica gel chromatography (EtOAc/PE=1/5) to give 5-chloro-2-(4-chloro-1H-1,2,3-triazol-1-yl)benzonitrile (450 mg, yield: 84.5%) as a yellow solid. ESI-MS [M+H]⁺: 239.1.

Synthesis of (5-chloro-2-(4-chloro-1H-1,2,3-triazol-1-yl)phenyl)methanamine. To a stirred solution of 5-chloro-2-(4-chloro-1H-1,2,3-triazol-1-yl)benzonitrile (450 mg, 1.88 mmol) and NiCl₂·6H₂O in MeOH (15 mL) was added NaBH₄ (214 mg, 5.65 mmol) portionwise at 0° C. The reaction mixture was stirred at room temperature for 2 h, then quenched with saturated aq. NH₄Cl (40 mL) and extracted with EtOAc (40 ml×2). The combined organics were washed with brine (80 mL), dried over Na₂SO₄, concentrated in vacuo and purified by silica gel chromatography (DCM/MeOH=10/1) to give (5-chloro-2-(4-chloro-1H-1,2,3-triazol-1-yl)phenyl)methanamine (170 mg, yield: 37%) as a white solid. ESI-MS [M+H]⁺: 243.0.

Example 190

Synthesis of (6-(4-chloro-1H-1,2,3-triazol-1-yl)-2 fluoro-3-methoxyphenyl)methanamine

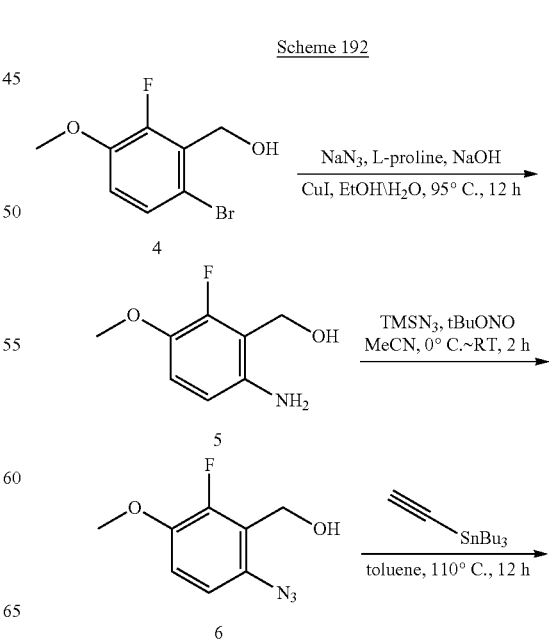

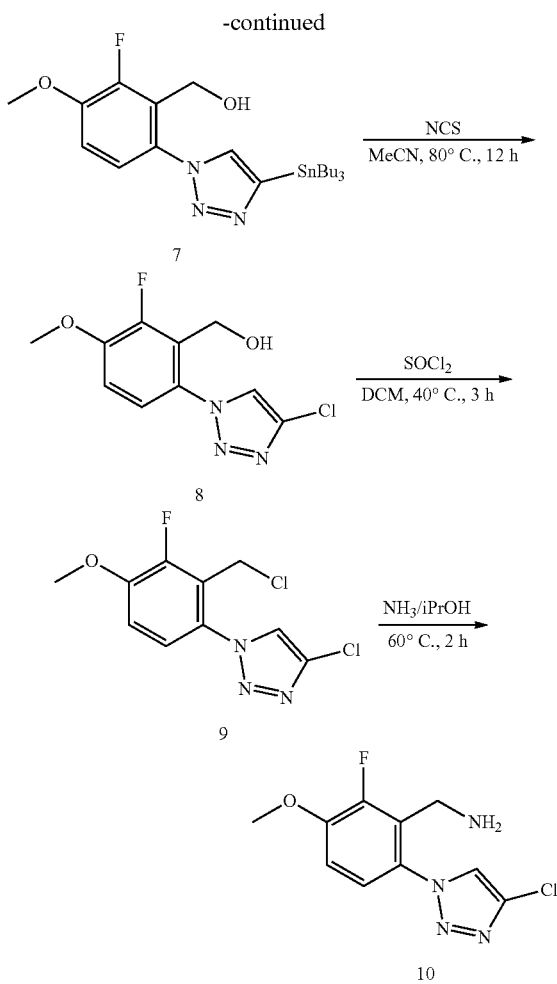

Synthesis of (6-amino-2-fluoro-3-methoxyphenyl)methanol. A mixture of (6-bromo-2-fluoro-3-methoxyphenyl)methanol (2.14 g, 9.15 mmol), NaN₃ (892 mg, 13.72 mmol), L-proline (315.6 mg, 2.74 mmol), NaOH (107.5 mg, 2.74 mmol) and CuI (174 mg, 0.915 mmol) in EtOH (21 mL) and H₂O (6 mL) was stirred at 95° C. for 12 h. Water (40 mL) was added and the mixture was extracted with EtOAc (30 mL×3). The combined organic layers were washed with brine (20 mL), dried over Na₂SO₄, filtered and concentrated in vacuo to give the crude, which was purified by silica gel chromatography (PE/EtOAc=5/1) to give (6-amino-2-fluoro-3-methoxyphenyl)methanol (375 mg, yield: 24%) as a yellow solid. ESI-MS [M+H]+: 172.2.

Synthesis of (6-azido-2-fluoro-3-methoxyphenyl)methanol. To a mixture of (6-amino-2-fluoro-3-methoxyphenyl)methanol (50 mg, 0.29 mmol) and TMSN₃ (43.8 mg, 0.38 mmol) in MeCN (3 mL) was added t-BuONO (39 mg, 0.38 mmol) at 0° C. slowly. The reaction mixture was stirred at room temperature for 2 h, The mixture was concentrated in vacuo and purified by Prep-TLC to give the product (50 mg, yield: 87.5%) as a yellow oil. ESI-MS [M+H]+: 198.2.

Synthesis of (2-fluoro-3-methoxy-6-(4-(tributylstannyl)-1H-1,2,3-triazol-1-yl)phenyl)methanol. A mixture of (6-azido-2-fluoro-3-methoxyphenyl)methanol (300 mg, 1.5 mmol), tributyl(ethynyl)stannane (727 mg, 2.3 mmol) and toluene (10 mL) was stirred at 110° C. for 12 h under N₂. Water (60 mL) was added and the mixture was extracted with EtOAc (50 mL×3). The combined organics were concentrated in vacuo and purified by silica gel chromatography (PE/EtOAc=5/1) to give (2-fluoro-3-methoxy-6-(4-(tributylstannyl)-1H-1,2,3-triazol-1-yl)phenyl)methanol (400 mg, yield: 52.1%) as a yellow oil. ESI-MS [M+H]+: 514.2.

Synthesis of (6-(4-chloro-1H-1,2,3-triazol-1-yl)-2-fluoro-3-methoxyphenyl)methanol. A mixture of (2-fluoro-3-methoxy-6-(4-(tributylstannyl)-1H-1,2,3-triazol-1-yl)phenyl)methanol (450 mg, 0.88 mmol), NCS (468.5 mg, 3.51 mmol) and MeCN (6 mL) was stirred at 80° C. for 12 h. Water (60 mL) was added and the mixture was extracted with EtOAc (50 mL×3). The combined organic layers were washed with brine (20 mL), dried over Na₂SO₄, filtered and concentrated in vacuo to give the crude, which was purified by silica gel chromatography (PE/EtOAc=5/1) to give (6-(4-chloro-1H-1,2,3-triazol-1-yl)-2-fluoro-3-methoxyphenyl)methanol (200 mg, yield: 88%) as a yellow solid. ESI-MS [M+H]+: 258.2.

Synthesis of 4-chloro-1-(2-(chloromethyl)-3-fluoro-4-methoxyphenyl)-1H-1,2,3-triazole. A mixture of (6-(4-chloro-1H-1,2,3-triazol-1-yl)-2-fluoro-3-methoxyphenyl)methanol (400 mg, 1.55 mmol), SOCl₂ (916 mg, 7.76 mmol) and DCM (10 mL) was stirred at 40° C. for 3 h. Water (30 mL) was added and the mixture was extracted with EtOAc (50 mL×3). The combined organic layers were washed with brine (20 mL), dried over Na₂SO₄, filtered and concentrated in vacuo to give crude 4-chloro-1-(2-(chloromethyl)-3-fluoro-4-methoxyphenyl)-1H-1,2,3-triazole (428 mg, crude) as a yellow oil which was used in the next step without further purification. ESI-MS [M+H]+: 276.2.

Synthesis of (6-(4-chloro-1H-1,2,3-triazol-1-yl)-2-fluoro-3-methoxyphenyl)methanamine. A mixture of 4-chloro-1-(2-(chloromethyl)-3-fluoro-4-methoxyphenyl)-1H-1,2,3-triazole (300 mg, 1.09 mmol) and NH₃ in i-PrOH (18 mL) was stirred at 60° C. for 2 h in a sealed tube. The reaction mixture was concentrated in vacuo and purified by Prep-TLC (DCM/MeOH=20/1) to give (6-(4-chloro-1H-1,2,3-triazol-1-yl)-2-fluoro-3-methoxyphenyl)methanamine (120 mg, yield: 43%) as a gray solid. ESI-MS [M+H]+: 257.2.

Example 191

Synthesis of (t)-6-chloro-8,9-dihydro-7H-imidazo[4,5,1-ij]quinolin-9-amine hydrochloride Scheme 193

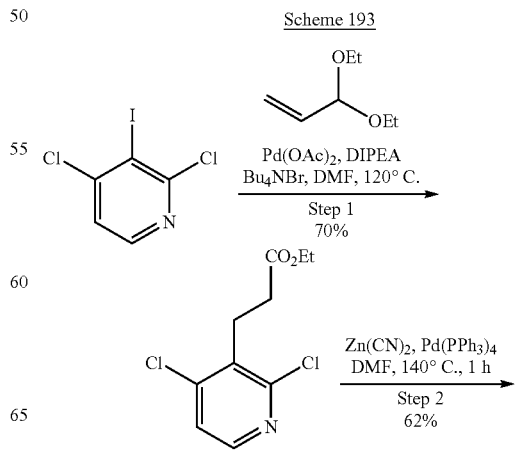

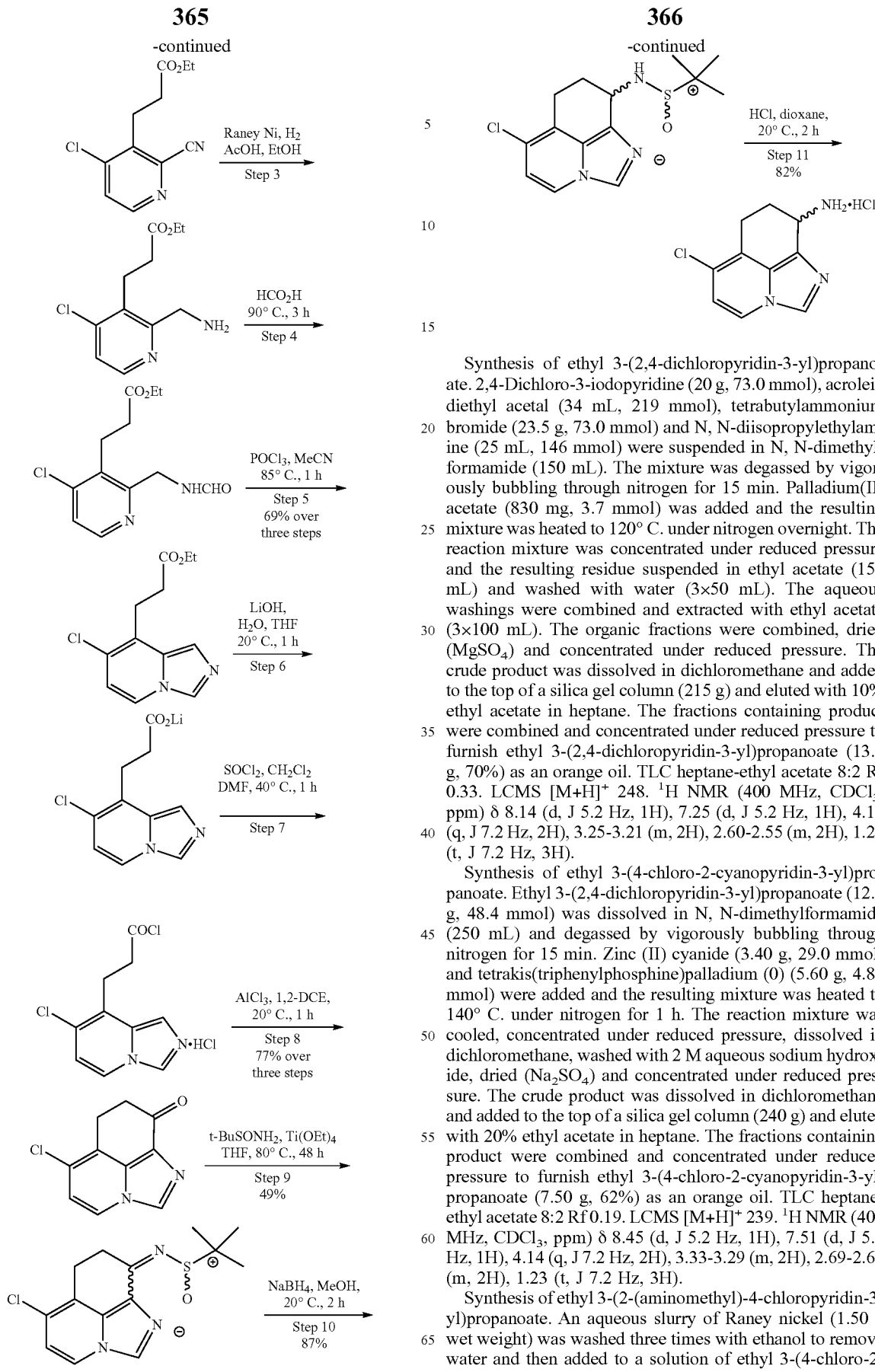

Synthesis of ethyl 3-(2,4-dichloropyridin-3-yl)propanoate. 2,4-Dichloro-3-iodopyridine (20 g, 73.0 mmol), acrolein diethyl acetal (34 mL, 219 mmol), tetrabutylammonium bromide (23.5 g, 73.0 mmol) and N, N-diisopropylethylamine (25 mL, 146 mmol) were suspended in N, N-dimethylformamide (150 mL). The mixture was degassed by vigorously bubbling through nitrogen for 15 min. Palladium(II) acetate (830 mg, 3.7 mmol) was added and the resulting mixture was heated to 120° C. under nitrogen overnight. The reaction mixture was concentrated under reduced pressure and the resulting residue suspended in ethyl acetate (150 mL) and washed with water (3×50 mL). The aqueous washings were combined and extracted with ethyl acetate (3×100 mL). The organic fractions were combined, dried (MgSO$_4$) and concentrated under reduced pressure. The crude product was dissolved in dichloromethane and added to the top of a silica gel column (215 g) and eluted with 10% ethyl acetate in heptane. The fractions containing product were combined and concentrated under reduced pressure to furnish ethyl 3-(2,4-dichloropyridin-3-yl)propanoate (13.0 g, 70%) as an orange oil. TLC heptane-ethyl acetate 8:2 Rf 0.33. LCMS [M+H]$^+$ 248. $^1$H NMR (400 MHz, CDCl$_3$, ppm) δ 8.14 (d, J 5.2 Hz, 1H), 7.25 (d, J 5.2 Hz, 1H), 4.15 (q, J 7.2 Hz, 2H), 3.25-3.21 (m, 2H), 2.60-2.55 (m, 2H), 1.25 (t, J 7.2 Hz, 3H).

Synthesis of ethyl 3-(4-chloro-2-cyanopyridin-3-yl)propanoate. Ethyl 3-(2,4-dichloropyridin-3-yl)propanoate (12.0 g, 48.4 mmol) was dissolved in N, N-dimethylformamide (250 mL) and degassed by vigorously bubbling through nitrogen for 15 min. Zinc (II) cyanide (3.40 g, 29.0 mmol) and tetrakis(triphenylphosphine)palladium (0) (5.60 g, 4.84 mmol) were added and the resulting mixture was heated to 140° C. under nitrogen for 1 h. The reaction mixture was cooled, concentrated under reduced pressure, dissolved in dichloromethane, washed with 2 M aqueous sodium hydroxide, dried (Na$_2$SO$_4$) and concentrated under reduced pressure. The crude product was dissolved in dichloromethane and added to the top of a silica gel column (240 g) and eluted with 20% ethyl acetate in heptane. The fractions containing product were combined and concentrated under reduced pressure to furnish ethyl 3-(4-chloro-2-cyanopyridin-3-yl)propanoate (7.50 g, 62%) as an orange oil. TLC heptane-ethyl acetate 8:2 Rf 0.19. LCMS [M+H]$^+$ 239. $^1$H NMR (400 MHz, CDCl$_3$, ppm) δ 8.45 (d, J 5.2 Hz, 1H), 7.51 (d, J 5.2 Hz, 1H), 4.14 (q, J 7.2 Hz, 2H), 3.33-3.29 (m, 2H), 2.69-2.65 (m, 2H), 1.23 (t, J 7.2 Hz, 3H).

Synthesis of ethyl 3-(2-(aminomethyl)-4-chloropyridin-3-yl)propanoate. An aqueous slurry of Raney nickel (1.50 g wet weight) was washed three times with ethanol to remove water and then added to a solution of ethyl 3-(4-chloro-2-cyanopyridin-3-yl)propanoate (3.34 g, 14.0 mmol) in ethanol (50 mL) and glacial acetic acid (50 mL) in a stainless steel autoclave. The autoclave was charged with hydrogen (2 atm) and stirred at ambient temperature for 24 h. The Raney nickel was filtered off through Dicalite and the solvent was removed under reduced pressure. The residue was azeotroped with formic acid to furnish ethyl 3-(2-(aminomethyl)-4-chloropyridin-3-yl)propanoate formate salt as a purple oil. LCMS [M+H]$^+$ 243.

Synthesis of ethyl 3-(4-chloro-2-(formamidomethyl)pyridin-3-yl)propanoate. Ethyl 3-(2-(aminomethyl)-4-chloropyridin-3-yl)propanoate (30.8 mmol) was suspended in formic acid (100 mL) and heated to 90° C. for 3 h. The reaction mixture was concentrated under reduced pressure and azeotroped with toluene to furnish ethyl 3-(4-chloro-2-(formamidomethyl)pyridin-3-yl)propanoate as an off-white solid that was used without any further purification. LCMS [M+H]$^+$ 271 and [M-CHO+H]$^+$243.

Synthesis of ethyl 3-(7-chloroimidazo[1,5-a]pyridin-8-yl)propanoate. A mixture of ethyl 3-(4-chloro-2-(formamidomethyl)pyridin-3-yl)propanoate (30.8 mmol) and phosphorus oxychloride (7.00 mL, 46.2 mmol) in anhydrous acetonitrile (150 mL) was heated at 85° C. for 1 h under nitrogen. The mixture was cooled, concentrated under reduced pressure and azeotroped with acetonitrile. The residue was suspended in dichloromethane and saturated aqueous sodium hydrogen carbonate (70 mL) added slowly. The layers were separated and the aqueous extracted with dichloromethane (3×50 mL), dried (Na$_2$SO$_4$) and concentrated under reduced pressure. The crude residue was dissolved in dichloromethane and added to the top of a silica gel column (180 g) and eluted with ethyl acetate (4.5 L). The fractions containing product were combined and concentrated under reduced pressure to furnish ethyl 3-(7-chloroimidazo[1,5-a]pyridin-8-yl)propanoate (5.35 g, 69% over three steps) as a brown oil. TLC ethyl acetate Rf 0.17. LCMS [M+H]$^+$ 253. $^1$H NMR (400 MHz, CDCl$_3$, ppm) δ 8.13 (br s, 1H), 7.74 (d, J 7.2 Hz, 1H), 7.48 (br s, 1H), 6.53 (br d, J 7.2 Hz, 1H), 4.12 (q, J 7.2 Hz, 2H), 3.20-3.15 (m, 2H), 2.65-2.61 (m, 2H), 1.22 (t, J 7.6 Hz, 3H).

Synthesis of lithium 3-(7-chloroimidazo[1,5-a]pyridin-8-yl)propanoate. To a solution of ethyl 3-(7-chloroimidazo[1,5-a]pyridin-8-yl)propanoate (1.00 g, 3.96 mmol) in tetrahydrofuran (40 mL) was added water (40 mL) and lithium hydroxide (371 mg, 15.8 mmol).

The resulting mixture was stirred at room temperature for 1 h. The mixture was concentrated under reduced pressure and azeotroped with toluene to furnish lithium 3-(7-chloroimidazo[1,5-a]pyridin-8-yl)propanoate as a light brown solid that was used without any further purification. TLC ethyl acetate Rf 0.09.

Synthesis of 3-(7-chloroimidazo[1,5-a]pyridin-8-yl)propanoyl chloride hydrochloride. To a solution of lithium 3-(7-chloroimidazo[1,5-a]pyridin-8-yl)propanoate (3.96 mmol) in dichloromethane (30 mL) was added thionyl chloride (10 mL) and N, N-dimethylformamide (5 drops). The reaction mixture was heated at 40° C. for 1 h. The reaction mixture was concentrated under reduced pressure, azeotroped with toluene and 1,2-dichloroethane and dried under high vacuum for 3 h to give 3-(7-chloroimidazo[1,5-a]pyridin-8-yl)propanoyl chloride hydrochloride as a bright yellow solid that was used without any further purification. LCMS [M+H]$^+$ 239.

Synthesis of 6-chloro-7,8-dihydro-9H-imidazo[4,5,1-ij]quinolin-9-one. To a suspension of 3-(7-chloroimidazo[1,5-a]pyridin-8-yl)propanoyl chloride hydrochloride (3.96 mmol) in 1,2-dichloroethane (100 mL) was added aluminium trichloride and the resulting mixture was stirred at room temperature for 1 h. The reaction mixture was quenched by the slow addition of saturated aqueous sodium hydrogen carbonate (50 mL). The layers were separated and the aqueous layer was extracted with dichloromethane (3×100 mL). The organic solutions were combined, washed with brine (50 mL), dried (Na$_2$SO$_4$) and concentrated under reduced pressure to furnish 6-chloro-7,8-dihydro-9H-imidazo[4,5,1-u]quinolin-9-one (630 mg, 77% over three steps) as a light brown solid. LCMS [M+H]$^+$ 207, purity 82%. $^1$H NMR (400 MHz, CDCl$_3$, ppm) δ 8.16 (s, 1H), 7.88 (d, J 7.2 Hz, 1H), 6.77 (d, J 7.2 Hz, 1H), 3.30 (t, J 7.2 Hz, 2H), 2.92 (t, J 7.2 Hz, 2H).

Synthesis of E- and Z-(±)-N-(6-chloro-7,8-dihydro-9H-imidazo[4,5,1-ij]quinolin-9-ylidene)-2-methylpropane-2-sulfinamide. 6-Chloro-7,8-dihydro-9H-imidazo[4,5,1-ij]quinolin-9-one (500 mg, 2.42 mmol) and (±)-2-methylpropane-2-sulfinamide (616 mg, 5.08 mmol) were suspended in anhydrous tetrahydrofuran (20 mL). Titanium (IV) ethoxide (1.52 mL, 7.26 mmol) was added and the resulting mixture was heated at 80° C. overnight. Additional 2-methylpropane-2-sulfinamide (150 mg, 1.24 mmol) and titanium (IV) ethoxide (400 µL, 1.91 mmol) were added and the resulting mixture heated at 80° C. overnight.

The mixture was allowed to cool to room temperature saturated aqueous sodium hydrogen carbonate (10 mL) was added. The mixture was filtered through Dicalite and the filter cake was washed with ethyl acetate (200 mL) and saturated aqueous sodium hydrogen carbonate (100 mL). The layers were separated and the aqueous solution was extracted with ethyl acetate (3×50 mL). The organic layers were combined, washed with brine (50 mL), dried (Na$_2$SO$_4$) and concentrated under reduced pressure. The residue was dissolved in the minimum of ethyl acetate and added to the top of a silica gel column (25 g) eluting with 10% methanol in ethyl acetate.

The fractions containing product were combined and concentrated under reduced pressure to furnish a 2:1 mixture of E- and Z-(±)-N-(6-chloro-7,8-dihydro-9H-imidazo[4,5,1-ij]quinolin-9-ylidene)-2-methylpropane-2-sulfinamide (364 mg, 49%)diastereoisomers as a bright yellow solid. In the $^1$H NMR spectrum shown below the diastereoisomers were assigned as major or minor where possible, but their stereochemistry has not been assigned. TLC ethyl acetate-methanol 9:1 Rf 0.22. LCMS [M+H]$^+$ 310, purity 98%. $^1$H NMR (400 MHz, CDCl$_3$, ppm) δ 8.20 (s, 1H$_{minor}$), 8.12 (s 1H$_{major}$), 7.84-7.80 (m, 2H$_{major+minor}$), 6.75 (d, J 6.4 Hz, 1H$_{minor}$), 6.69 (d, J 7.2 Hz, 1H$_{major}$), 3.69-3.61 (m, 2H$_{major\ or\ minor}$), 3.42-3.35 (m, 1H$_{major\ or\ minor}$), 3.24-3.04 (m, 5H$_{major\ or\ minor}$), 1.34-1.30 (m, 18H$_{major+minor}$).

Synthesis of (RS)-N-((RS)-6-chloro-8,9-dihydro-7H-imidazo[4,5,1-ij]quinolin-9-yl)-2-methylpropane-2-sulfinamide. Sodium borohydride (124 mg, 3.29 mmol) was added to a suspension of E- and Z-(±)—N-(6-chloro-7,8-dihydro-9H-imidazo[4,5,1-ij]quinolin-9-ylidene)-2-methylpropane-2-sulfinamide (340 mg, 1.10 mmol) in methanol (8 mL). The resulting mixture was stirred at room temperature for 2 h and concentrated under reduced pressure. The residue was partitioned between ethyl acetate (20 mL) and water (10 mL). The layers were separated and the aqueous layer was extracted with ethyl acetate (2×20 mL). The organic fractions were combined, washed with brine (20 mL), dried (Na$_2$SO$_4$) and concentrated under reduced pressure to furnish a 2:1 mixture of (RS)-N-((RS)-6-chloro-8,9-dihydro-7H-imidazo[4,5,1-ij]quinolin-9-yl)-2-methylpropane-2-sulfinamide (298 mg, 87%)diastereoisomers as a light orange foam that was used without any further purification. In the $^1$H NMR spectrum shown below the diastereoisomers were assigned as major or minor where possible, but their stereochemistry has not been assigned. LCMS [M+H]+ 312. ¹H NMR (400 MHz, CDCl₃, ppm) δ 7.96 (s, 1H$_{minor}$), 7.96 (s, 1H$_{major}$), 7.66 (d, J 7.6 Hz, 2H$_{major+minor}$), 6.50 (d, J 7.6 Hz, 2H$_{major+minor}$), 4.90-4.87 (dt, J 4.5, 10 Hz, 1H$_{major}$), 4.83-4.79 (dt, J 17, 10 Hz, 1H$_{minor}$), 3.72 (s, 1H$_{major}$), 3.44 (d, J 8.8 Hz, 1H$_{minor}$), 2.99-2.90 (m, 4H$_{major+minor}$), 2.39-2.34 (m, 2H$_{minor}$), 2.25 (m, 2H$_{major}$), 1.23 (s, 9H$_{minor}$), 1.21 (s, 9H$_{major}$).

Synthesis of (t)-6-chloro-8,9-dihydro-7H-imidazo[4,5,1-ij]quinolin-9-amine hydrochloride. A solution of hydrogen chloride (4M in dioxane, 1 mL, 4 mmol) was added to a suspension of (RS)-N-((RS)-6-chloro-8,9-dihydro-7H-imidazo[4,5,1-ij]quinolin-9-yl)-2-methylpropane-2-sulfinamide (197 mg, 0.63 mmol) in dioxane (3 mL). The reaction mixture was stirred at room temperature for 2 h, filtered and the precipitate washed with ethyl acetate to furnish (±)-6-chloro-8,9-dihydro-7H-imidazo[4,5,1-ij]quinolin-9-amine hydrochloride (126 mg, 82%) as a light orange solid that was used without any further purification. LCMS [M-NH₂]⁺191. ¹H NMR (400 MHz, CD₃SOCD₃, ppm) δ 8.56 (br s, 3H), 8.28 (d, J 7.2 Hz, 1H), 6.78 (d, J 7.6 Hz, 1H), 4.65 (m, 1H), 3.10-2.93 (m, 2H), 2.35-2.22 (m, 2H).

Example 192

Synthesis of 2-(aminomethyl)-3 fluoro-4-methoxy-N,N-dimethylbenzenesulfonamide

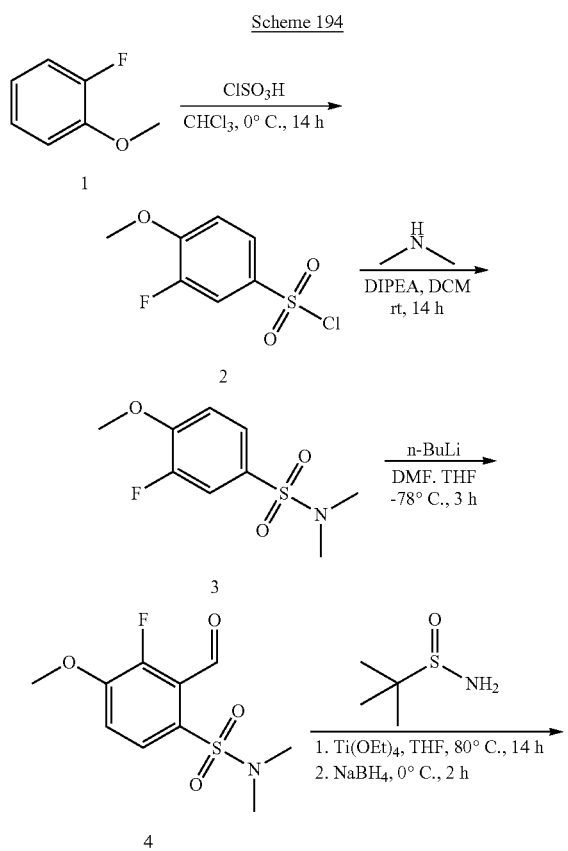

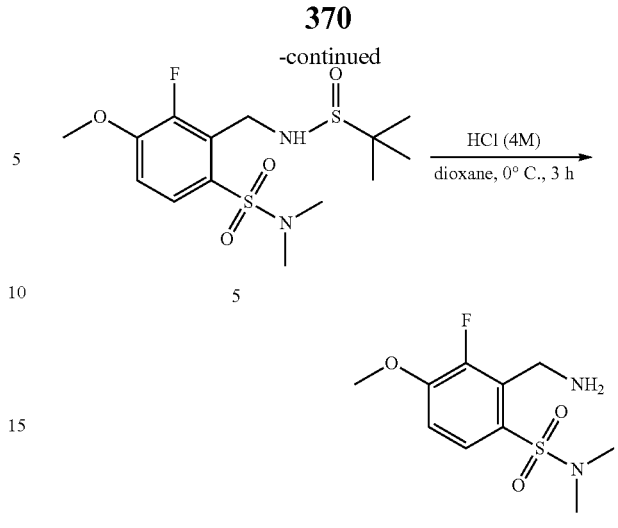

Synthesis of 3-fluoro-4-methoxybenzenesulfonyl chloride. A solution of 1-fluoro-2-methoxybenzene (6.0 g, 47.6 mmol) and sulfurochloridic acid (13.8 g, 119.0 mmol) in CHCl₃ (60 mL) was stirred at 0° C. for 14 h. The reaction mixture was poured into ice water (150 mL) and extracted with DCM (100 mL×3). The combined organic layers were washed with brine, dried over Na₂SO₄, and concentrated in vacuo to give the 3-fluoro-4-methoxybenzenesulfonyl chloride (10 g, crude) as a white solid which was used in the next step without further purification. ESI-MS [M+H]+: 225.2.

Synthesis of 3-fluoro-4-methoxy-N,N-dimethylbenzenesulfonamide, A solution of 3-fluoro-4-methoxybenzenesulfonyl chloride (500 mg, 2.23 mmol), dimethylamine hydrochloride (915 mg, 11.16 mmol) and DIPEA (8.6 mL, 66.9 mmol) in DCM (50 mL) was stirred at room temperature for 14 h. H₂O (100 mL) was added and the mixture was extracted with EtOAc (50 mL×3). The combined organic layers were washed with brine, dried over Na₂SO₄, and concentrated in vacuo to give the crude, which was purified with silica gel chromatography (PE/EtOAc=3/1) to give 3-fluoro-4-methoxy-N,N-dimethylbenzenesulfonamide (500 mg, yield: 96%) as a yellow solid. ESI-MS [M+H]+: 234.2

Synthesis of 3-fluoro-2-formyl-4-methoxy-N,N-dimethylbenzenesulfonamide. To a solution of 3-fluoro-4-methoxy-N,N-dimethylbenzenesulfonamide (200 mg, 0.86 mmol) in THF (10 mL) was added n-BuLi (0.72 mL, 1.72 mmol) at −78° C. slowly under nitrogen. The resulting mixture was stirred at −78° C. for 20 min. Then DMF (125 mg, 1.72 mmol) was added at −78° C. After stirring for 3 h, the reaction was quenched with sat. aqueous NH₄Cl (15 mL) and extracted with EtOAC (15 mL×3). The combined organic layers were washed with brine, dried over Na₂SO₄, and concentrated in vacuo to give 3-fluoro-2-formyl-4-methoxy-N,N-dimethylbenzenesulfonamide (100 mg, yield: 45%). ESI-MS [M+H]⁺: 262.2

Synthesis of 2-(((tert-butylsulfinyl)amino)methyl)-3-fluoro-4-methoxy-N,N-dimethylbenzenesulfonamide. A solution of 3-fluoro-2-formyl-4-methoxy-N,N-dimethylbenzenesulfonamide (140 mg, 0.54 mmol), 2-methylpropane-2-sulfinamide (78 mg, 0.64 mmol) and Ti(OEt)₄ (369 mg, 1.62 mmol) in THF (10 mL) was stirred at 80° C. for 14 h under nitrogen. The reaction mixture was cooled to 0° C. and NaBH₄ (62 mg, 1.62 mmol) was added. The reaction was stirred at 0° C. for 2 h, then quenched with H₂O (20 mL) and extracted with EtOAc (15 mL×3). The combined organic layers were washed with brine, dried over Na$_2$SO$_4$, and concentrated in vacuo to give the crude, which was purified with silica gel chromatography (EtOAc/PE=2/1) to give 2-(((tert-butylsulfinyl)amino)methyl)-3-fluoro-4-methoxy-N,N-dimethylbenzenesulfonamide (120 mg, yield: 61%). ESI-MS [M+H]+: 367.2.

Synthesis of 2-(aminomethyl)-3-fluoro-4-methoxy-N,N-dimethylbenzenesulfonamide. A solution of 2-(((tert-butylsulfinyl)amino)methyl)-3-fluoro-4-methoxy-N,N-dimethylbenzenesulfonamide (120 mg, 0.33 mmol) and HCl (0.33 mL, 1.32 mmol, 4M in dioxane) in dioxane (5 mL) was stirred at 0° C. for 3 h. The reaction mixture was concentrated in vacuo to give 2-(aminomethyl)-3-fluoro-4-methoxy-N,N-dimethylbenzenesulfonamide (100 mg crude), which was used into next step without further purification. ESI-MS [M+H]$^+$: 263.2.

Example 193

Synthesis of (2-fluoro-3-methoxy-6-(morpholinosulfonyl)phenyl)methanamine

Scheme 195

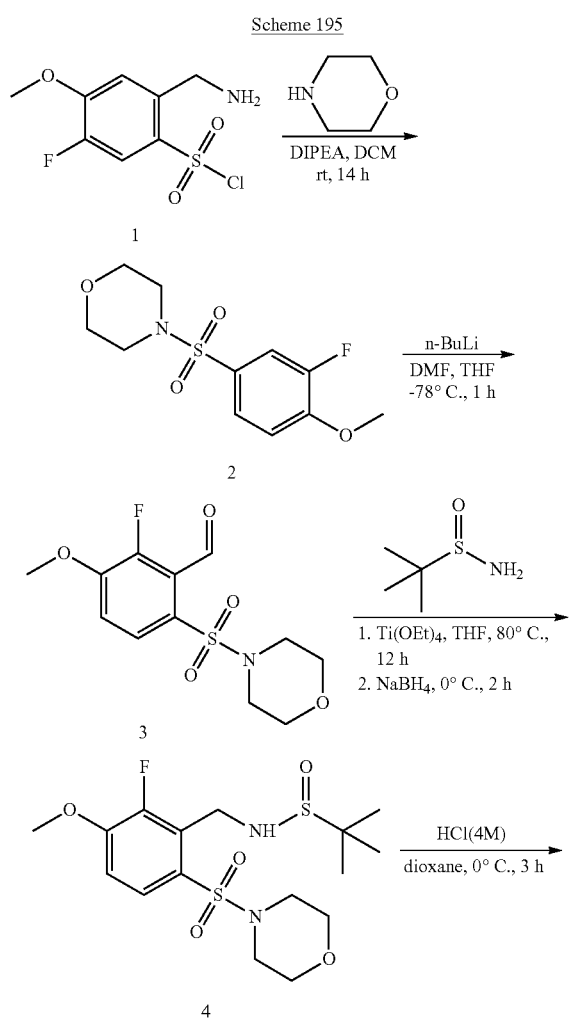

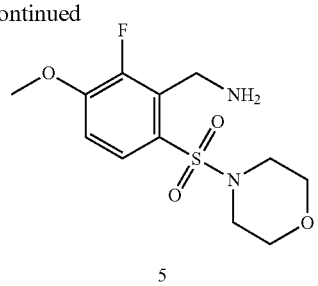

5

Synthesis of 4-((3-fluoro-4-methoxyphenyl)sulfonyl)morpholine. A mixture of 3-fluoro-4-methoxybenzenesulfonyl chloride (700 mg, 3.12 mmol), morpholine (1.08 g, 12.5 mmol) and DIPEA (4.02 g, 31.2 mmol) in DCM (20 mL) was stirred at room temperature for 14 h. H$_2$O (30 mL) was added and the mixture was extracted with EtOAc (20 mL×3). The combined organic layers were washed with brine, dried over Na$_2$SO$_4$, and concentrated in vacuo to give the crude, which was purified with silica gel chromatography (PE/EtOAc=3/1) to give 4-((3-fluoro-4-methoxyphenyl)sulfonyl)morpholine (700 mg, yield: 81.5%) as a yellow solid. ESI-MS [M+H]+: 276.2

Synthesis of ethyl 2-fluoro-3-methoxy-6-(morpholinosulfonyl)benzaldehyde. To a solution of 4-((3-fluoro-4-methoxyphenyl)sulfonyl)morpholine (450 mg, 1.64 mmol) in THF (20 mL) was added n-BuLi (1.37 ml, 3.28 mmol) at −78° C. slowly. The reaction mixture was stirred at −78° C. for 20 min. Then DMF (239 mg, 3.28 mmol) was added at −78° C. After stirring for 1 h, the reaction was quenched with aqueous NH$_4$Cl and extracted with EtOAx (15 mL×3). The combined organic layers were washed with brine, dried over Na$_2$SO$_4$, and concentrated in vacuo to give ethyl 2-fluoro-3-methoxy-6-(morpholinosulfonyl)benzaldehyde (200 mg, yield: 40%), which was used in the next step without further purification. ESI-MS [M+H]$^+$: 304.2.

Synthesis of N-(2-fluoro-3-methoxy-6-(morpholinosulfonyl)benzyl)-2-methylpropane-2-sulfinamide. A solution of 2-fluoro-3-methoxy-6-(morpholinosulfonyl)benzaldehyde (200 mg, 0.66 mmol), 2-methylpropane-2-sulfinamide (96 mg, 0.79 mmol) and Ti(OEt)$_4$ (451 mg, 1.98 mmol) in THF (10 mL) was stirred at 80° C. for 12 h under nitrogen. The reaction mixture was cooled to 0° C. and NaBH$_4$ (75 mg, 1.98 mmol) was added. The reaction was stirred at 0° C. for 2 h. The mixture was quenched with H$_2$O (20 mL) and extracted with EtOAc (15 mL×3). The combined organic layers were washed with brine, dried over Na$_2$SO$_4$, and concentrated in vacuo to give the crude, which was purified by silica gel chromatography (EtOAc/PE=2/1) to give N-(2-fluoro-3-methoxy-6-(morpholinosulfonyl)benzyl)-2-methylpropane-2-sulfinamide (200 mg, yield: 74.2%). ESI-MS [M+H]+: 409.2.

Synthesis of (2-fluoro-3-methoxy-6-(morpholinosulfonyl)phenyl)methanamine. A mixture of ethyl N-(2-fluoro-3-methoxy-6-(morpholinosulfonyl)benzyl)-2-methylpropane-2-sulfinamide (200 mg, 0.49 mmol) and HCl (0.73 mL, 2.94 mmol, 4M in dioxane) in dioxane (5 mL) was stirred at 0° C. for 3 h. The reaction mixture was concentrated in vacuo to give (2-fluoro-3-methoxy-6-(morpholinosulfonyl)phenyl)methanamine (175 mg crude), which was used into next step without further purification. ESI-MS [M+H]$^+$: 305.1.

Example 194
1-((6-cyclopropyl-8-(2-(dimethylamino)ethyl)imidazo[1,2-a]pyridin-2-yl)methyl)-N-((3 fluoro-4-methoxypyridin-2-yl)methyl)-1H-1,2,3-triazole-4-carboxamide (1-138)
Scheme 196
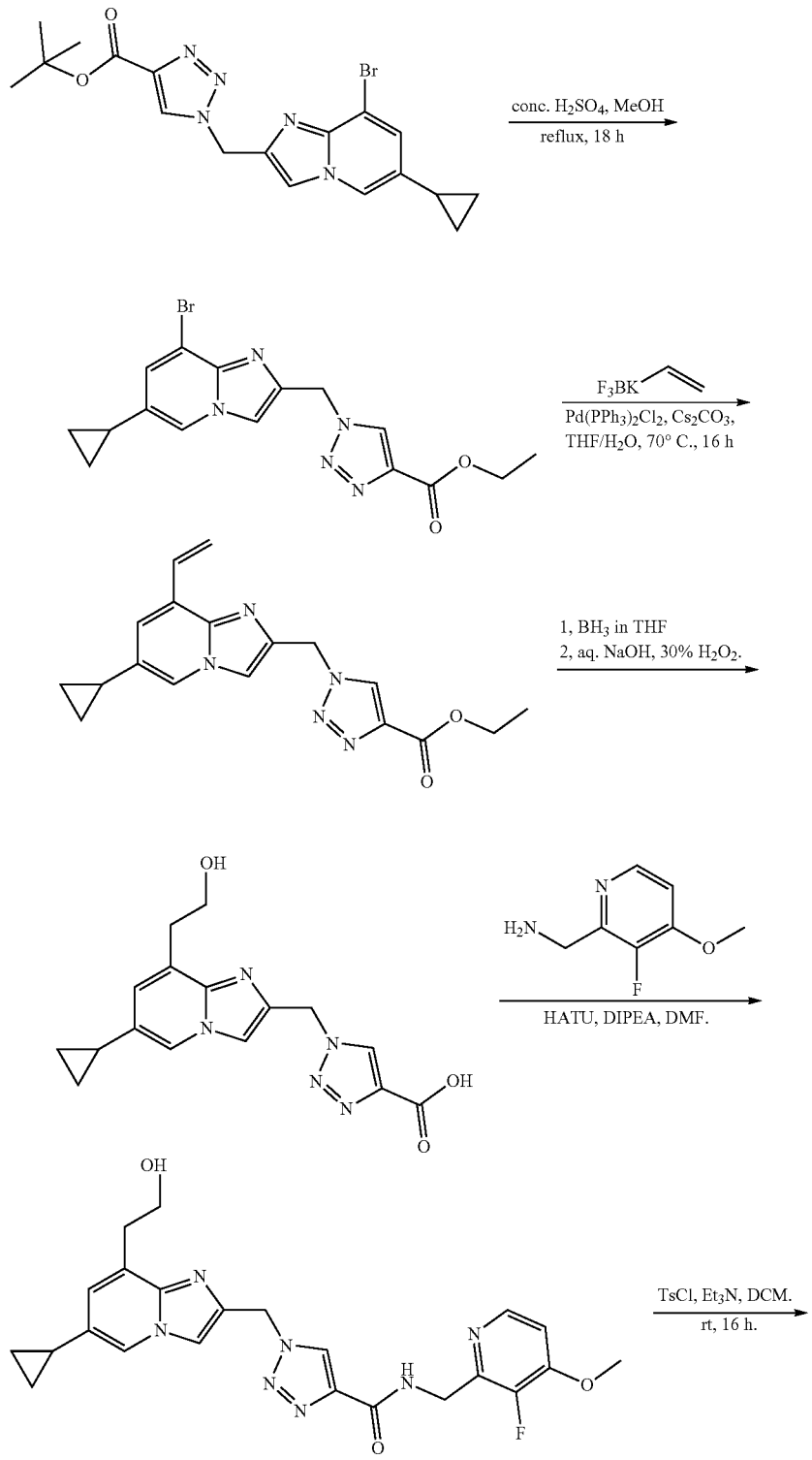

-continued

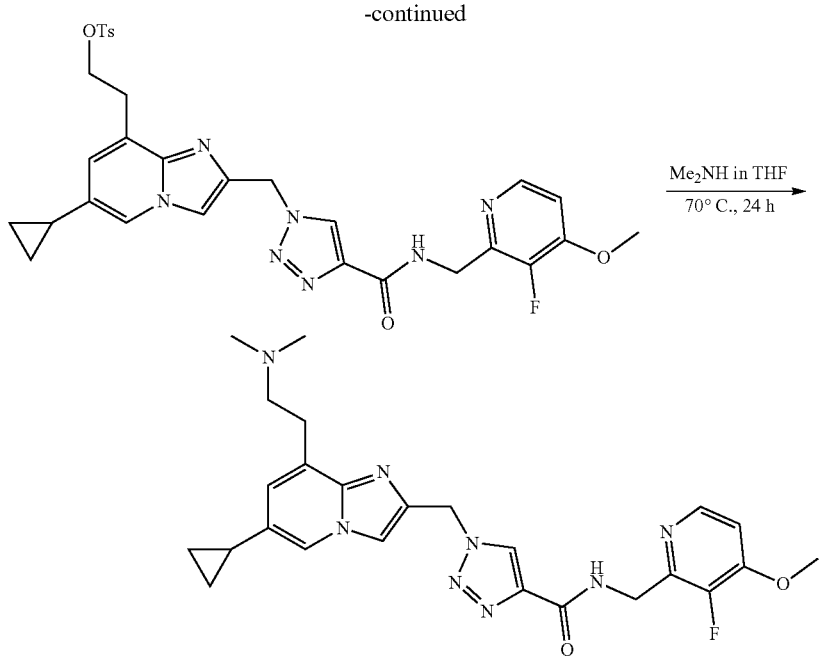

Synthesis of ethyl 1-((8-bromo-6-cyclopropylimidazo[1,2-a]pyridin-2-yl)methyl)-1H-1,2,3-triazole-4-carboxylate. To a stirred solution of tert-butyl 1-((8-bromo-6-cyclopropylimidazo[1,2-a]pyridin-2-yl)methyl)-1H-1,2,3-triazole-4-carboxylate (2.7 g, 6.45 mmol) in MeOH (50 mL) was added conc. $H_2SO_4$ (1 mL) dropwise at room temperature. The mixture was heated to reflux for 18 h, then cooled to room temperature, diluted with water (50 mL), and concentrated in vacuo to remove MeOH. The residue was adjusted to pH=9-10 by addition of sat. aq. $NaHCO_3$. The resulting precipitate was collected by filtration and dried in vacuo to give ethyl 1-((8-bromo-6-cyclopropylimidazo[1,2-a]pyridin-2-yl)methyl)-1H-1,2,3-triazole-4-carboxylate (2.0 g, yield: 82%) as a light brown solid. ESI-MS [M+H]$^+$: 376.0.

Synthesis of ethyl 1-((6-cyclopropyl-8-vinylimidazo[1,2-a]pyridin-2-yl)methyl)-1H-1,2,3-triazole-4-carboxylate. A mixture of ethyl 1-((8-bromo-6-cyclopropylimidazo[1,2-a]pyridin-2-yl)methyl)-1H-1,2,3-triazole-4-carboxylate (220 mg, 0.57 mmol), vinyl trifluoropotassium borate (114 mg, 0.85 mmol), Pd(PPh$_3$)$_2$Cl$_2$ (21 mg, 0.03 mmol) and Cs$_2$CO$_3$ (554 mg, 1.70 mmol) in THF/water (10.0 mL/1.0 mL) was stirred at 70° C. under N$_2$ for 16 h. The mixture was concentrated and purified by silica gel column (DCM/MeOH=20/1) to give ethyl 1-((6-cyclopropyl-8-vinylimidazo[1,2-a]pyridin-2-yl)methyl)-1H-1,2,3-triazole-4-carboxylate (100 mg, 52%) as a yellow solid. ESI-MS [M+H]$^+$: 338.2.

Synthesis of 1-((6-cyclopropyl-8-(2-hydroxyethyl)imidazo[1,2-a]pyridin-2-yl)methyl)-1H-1,2,3-triazole-4-carboxylic acid. To a mixture of methyl 1-((6-cyclopropyl-8-vinylimidazo[1,2-a]pyridin-2-yl) methyl)-1H-1,2,3-triazole-4-carboxylate (100 mg, 0.30 mmol) in THF (5.0 mL) was added a solution of BH$_3$ in THF (1.2 mL, 1.2 mmol) at 0° C. under N$_2$. The mixture was stirred at 0° C. for 2 h. Then a mixture of 2.5 M NaOH (0.48 mL, 1.2 mmol) and H$_2$O$_2$ (0.12 mL, 1.2 mmol) was added. The reaction was stirred at 60° C. for an additional 2 h.

The mixture was diluted with EtOAc (30 mL) and washed with water (30 mL×3). The combined organic layers were dried and concentrated to give the product 1-((6-cyclopropyl-8-(2-hydroxyethyl)imidazo[1,2-a]pyridin-2-yl)methyl)-1H-1,2,3-triazole-4-carboxylic acid (50 mg, crude) as a yellow solid, which was used for the next step directly. ESI-MS [M+H]$^+$: 328.2.

Synthesis of 1-((6-cyclopropyl-8-(2-hydroxyethyl)imidazo[1,2-a]pyridin-2-yl)methyl)-N-((3-fluoro-4-methoxypyridin-2-yl)methyl)-1H-1,2,3-triazole-4-carboxamide. A mixture of 1-((6-cyclopropyl-8-(2-hydroxyethyl)imidazo[1,2-a]pyridin-2-yl)methyl)-1H-1,2,3-triazole-4-carboxylic acid (50 mg, 0.15 mmol), (3-fluoro-4-methoxypyridin-2-yl)methanamine (23.4 mg, 0.15 mmol), HATU (72.2 mg, 0.19 mmol), and DIPEA (58.1 mg, 0.45 mmol) in dry DMF (2.0 mL) was stirred at RT for 3 h. The mixture was concentrated to remove DMF and purified by silica gel chromatography (DCM/MeOH=10/1) to give N-((8-amino-2,4-dimethyl-1,7-naphthyridin-3-yl)methyl)-1-((6-cyclopropylimidazo[1,2-a]pyridin-2-yl)methyl)-1H-pyrazole-4-carboxamide (35 mg, yield: 49%) as a white solid. ESI-MS [M+H]$^+$: 466.1.

Synthesis of 2-(6-cyclopropyl-2-((4-(((3-fluoro-4-methoxypyridin-2-yl)methyl)carbamoyl)-1H-1,2,3-triazol-1-yl)methyl)imidazo[1,2-a]pyridin-8-yl)ethyl 4-methylbenzenesulfonate. To a mixture of 1-((6-cyclopropyl-8-(2-hydroxyethyl)imidazo[1,2-a]pyridin-2-yl)methyl)-N-((3-fluoro-4-methoxypyridin-2-yl)methyl)-1H-1,2,3-triazole-4-carboxamide (35 mg, 0.08 mmol) and Et$_3$N (23.2 mg, 0.23 mmol) in DCM (5 mL) was added TsCl (21 mg, 0.11 mmol) at room temperature. The mixture was stirred at room temperature for 16 h. The mixture was concentrated in vacuo and purified by Prep-TLC (DCM/MeOH=10/1) to give the product 2-(6-cyclopropyl-2-((4-(((3-fluoro-4-methoxypyridin-2-yl)methyl)carbamoyl)-1H-1,2,3-triazol-1-yl)methyl) imidazo[1,2-a]pyridin-8-yl)ethyl 4-methylbenzenesulfonate (30 mg, 61%) as a yellow solid. ESI-MS [M+H]$^+$: 620.2.

Synthesis of 1-((6-cyclopropyl-8-(2-(dimethylamino) ethyl)imidazo[1,2-a]pyridin-2-yl)methyl)-N-((3-fluoro-4-methoxypyridin-2-yl)methyl)-1H-1,2,3-triazole-4-carboxamide. A mixture of 2-(6-cyclopropyl-2-((4-(((3-fluoro-4-methoxypyridin-2-yl)methyl)carbamoyl)-1H-1,2,3-triazol- 1-yl)methyl)imidazo[1,2-a]pyridin-8-yl)ethyl 4-methylbenzenesulfonate (30 mg, 0.05 mmol) in Me₂NH (2.0 M in THF, 3.0 mL) was stirred at 70° C. in a sealed tube for 24 h. The mixture was concentrated and purified by Prep-TLC (DCM/MeOH=10/1) to give the product 1-((6-cyclopropyl-8-(2-(dimethylamino)ethyl)imidazo[1,2-a]pyridin-2-yl)methyl)-N-((3-fluoro-4-methoxypyridin-2-yl)methyl)-1H-1,2,3-triazole-4-carboxamide (10.0 mg, 41%) as a white solid. ESI-MS [M+H]⁺: 493.1. Purity: 93%. ¹H NMR (400 MHz, DMSO) δ 8.78 (t, J=5.6 Hz, 1H), 8.57 (s, 1H), 8.28-8.15 (m, 2H), 7.79 (s, 1H), 7.23-7.14 (m, 1H), 6.89 (s, 1H), 5.75 (s, 2H), 4.64-4.53 (m, 2H), 3.91 (s, 2H), 2.97 (t, J=7.3 Hz, 2H), 2.71-2.61 (m, 3H), 2.20 (s, 6H), 1.92-1.87 (m, 1H), 0.99-0.84 (m, 2H), 0.76-0.55 (m, 2H).

Example 195

1-((6-cyclopropyl-8-(4-methylpiperazin-1-yl)imidazo[1,2-a]pyridin-2-yl)methyl)-N-((3 fluoro-4-methoxypyridin-2-yl)methyl)-1H-1,2,3-triazole-4-carboxamide (I-139)

Scheme 197

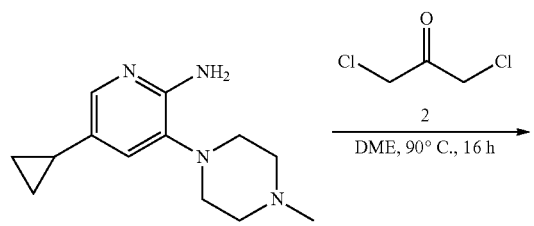

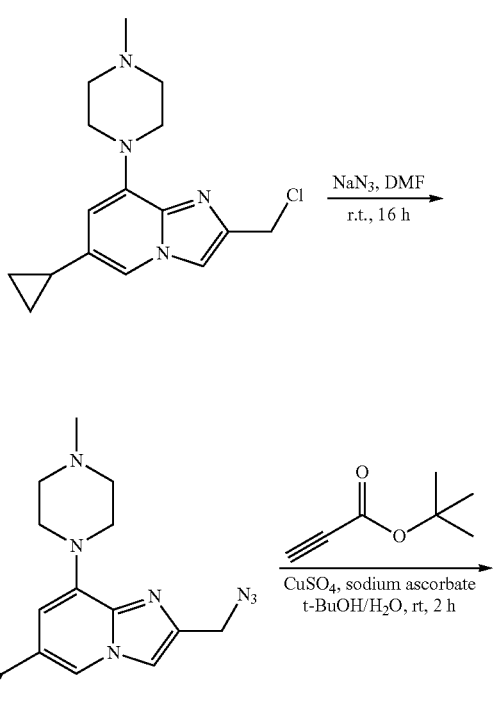

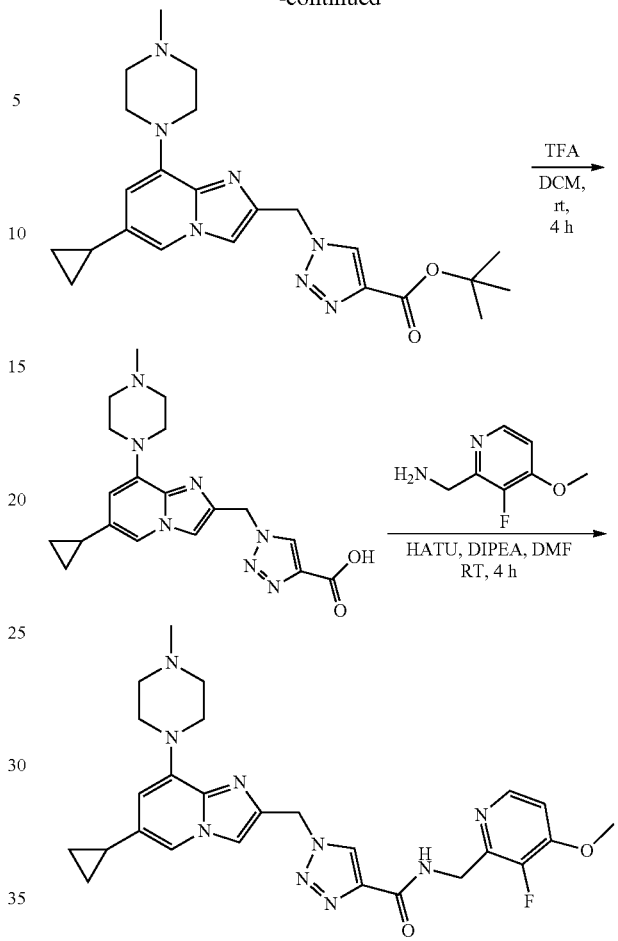

Synthesis of 2-(chloromethyl)-6-cyclopropyl-8-(4-methylpiperazin-1-yl)imidazo[1,2-a]pyridine. To a mixture of 5-cyclopropyl-3-(4-methylpiperazin-1-yl)pyridin-2-amine (460 mg, 1.98 mmol) in DME (25 mL) was added 1,3-dichloropropan-2-one (620 mg, 5 mmol). The reaction was stirred at 90° C. for 16 h. The reaction mixture was concentrated in vacuo to give 2-(chloromethyl)-6-cyclopropyl-8-(4-methylpiperazin-1-yl)imidazo[1,2-a]pyridine (400 mg, yield: 32%, crude) as a yellow solid which was used in next step directly without further purification. ESI-MS [M+H]⁺: 305.1.

Synthesis of 2-(azidomethyl)-6-cyclopropyl-8-(4-methylpiperazin-1-yl)imidazo[1,2-a]pyridine. To a mixture of 2-(chloromethyl)-6-cyclopropyl-8-(4-methylpiperazin-1-yl)imidazo[1,2-a]pyridine (400 mg, 1.3 mmol) in DMF (5 mL) was added NaN₃ (250 mg, 3.9 mmol). The reaction mixture was stirred at room temperature for 16 h. Water (50 mL) was added and the mixture was extracted with EtOAc (30 mL×3). The combined organic layers were washed with brine (30 ml), dried over Na₂SO₄ and concentrated in vacuo. The residue was purified by flash column chromatography (MeOH/DCM from 0 to 10%) to give 2-(azidomethyl)-6-cyclopropyl-8-(4-methylpiperazin-1-yl)imidazo[1,2-a]pyridine (100 mg, yield: 25%) as a yellow solid. ESI-MS [M+H]⁺: 312.1.

Synthesis of tert-butyl 1-((6-cyclopropyl-8-(4-methylpiperazin-1-yl)imidazo[1,2-a]pyridin-2-yl)methyl)-1H-1,2,3-triazole-4-carboxylate. To a mixture of 2-(azidomethyl)-6-cyclopropyl-8-(4-methylpiperazin-1-yl)imidazo[1,2-a]

pyridine (100 mg, 0.32 mmol) in t-BuOH (5 mL) and H₂O (5 mL) was added tert-butyl propiolate (52 mg, 0.42 mmol), CuSO₄ (25 mg, 0.16 mmol) and sodium ascorbate (31 mg, 0.16 mmol). The reaction mixture was stirred at rt for 2 h. Water (30 mL) was added and the mixture was extracted with EtOAc (20 mL×3). The combined organic layers were washed with brine (20 mL), dried over Na₂SO₄, and concentrated in vacuo. The residue was purified by flash column chromatography (MeOH/DCM from 0 to 10%) to give tert-butyl 1-((6-cyclopropyl-8-(4-methylpiperazin-1-yl)imidazo[1,2-a]pyridin-2-yl)methyl)-1H-1,2,3-triazole-4-carboxylate (20 mg, yield: 14%) as a yellow solid. ESI-MS [M+H]⁺: 438.2.

Synthesis of 1-((6-cyclopropyl-8-(4-methylpiperazin-1-yl)imidazo[1,2-a]pyridin-2-yl)methyl)-1H-1,2,3-triazole-4-carboxylic acid. A mixture of tert-butyl 1-((6-cyclopropyl-8-(4-methylpiperazin-1-yl)imidazo[1,2-a]pyridin-2-yl)methyl)-1H-1,2,3-triazole-4-carboxylate (15 mg, 0.034 mmol) in dry DCM (3 mL) and TFA (0.6 mL) was stirred at room temperature for 4 h. The reaction mixture was concentrated in vacuo to give 1-((6-cyclopropyl-8-(4-methylpiperazin-1-yl)imidazo[1,2-a]pyridin-2-yl)methyl)-1H-1,2,3-triazole-4-carboxylic acid (3 mg, yield: 23% crude) as a yellow solid which was used in next step directly without further purification. ESI-MS [M+H]+: 382.1.

Synthesis of 1-((6-cyclopropyl-8-(4-methylpiperazin-1-yl)imidazo[1,2-a]pyridin-2-yl)methyl)-N-((3-fluoro-4-methoxypyridin-2-yl)methyl)-1H-1,2,3-triazole-4-carboxamide. A mixture of 1-((6-cyclopropyl-8-(4-methylpiperazin-1-yl)imidazo[1,2-a]pyridin-2-yl)methyl)-1H-1,2,3-triazole-4-carboxylic acid (40 mg, crude), (3-fluoro-4-methoxypyridin-2-yl)methanamine (19 mg, 0.12 mmol), HATU (20 mg, 0.053 mmol), and DIPEA (68 mg, 0.53 mmol) in DMF (5 mL) was stirred at RT for 4 h. H₂O (15 mL) was added and the mixture was extracted with EtOAc (15 mL×3). The organic layers were concentrated and purified by Prep-TLC (DCM/MeOH=10:1) to give 1-((6-cyclopropyl-8-(4-methylpiperazin-1-yl)imidazo[1,2-a]pyridin-2-yl)methyl)-N-((3-fluoro-4-methoxypyridin-2-yl)methyl)-1H-1,2,3-triazole-4-carboxamide (7.3 mg) as a light yellow solid. ESI-MS [M+H]⁺: 520.2. Purity: 97.39%. ¹H NMR (400 MHz, dmso) δ 8.75 (t, J=5.5 Hz, 1H), 8.52 (s, 1H), 8.19 (d, J=5.5 Hz, 1H), 7.88 (s, 1H), 7.69 (s, 1H), 7.15 (t, J=6.1 Hz, 1H), 6.16 (s, 1H), 5.70 (s, 2H), 4.55 (d, J=4.2 Hz, 2H), 3.89 (s, 3H), 3.43 (s, 4H), 2.49 (s, 4H), 2.22 (s, 3H), 1.85-1.81 (m, 1H), 0.86-0.83 (m, 2H), 0.65-0.62 (m, 2H).

Example 196

1-((6-cyclopropylimidazo[1,2-a]pyridin-2-yl)methyl)-N-(furo[3,2-c]pyridin-6 ylmethyl)-1H-1,2,3-triazole-4-carboxamide (I-140)

Scheme 198

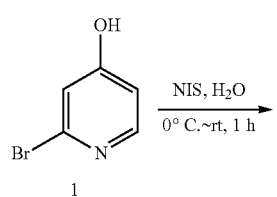

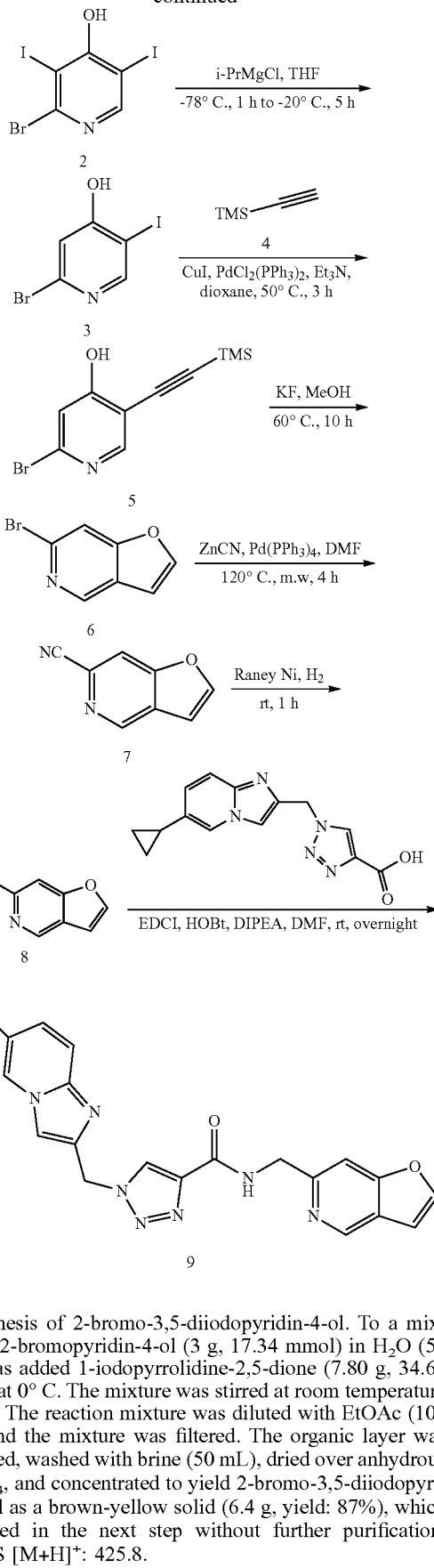

Synthesis of 2-bromo-3,5-diiodopyridin-4-ol. To a mixture of 2-bromopyridin-4-ol (3 g, 17.34 mmol) in H₂O (50 mL) was added 1-iodopyrrolidine-2,5-dione (7.80 g, 34.68 mmol) at 0° C. The mixture was stirred at room temperature for 1 h. The reaction mixture was diluted with EtOAc (100 mL), and the mixture was filtered. The organic layer was separated, washed with brine (50 mL), dried over anhydrous Na₂SO₄, and concentrated to yield 2-bromo-3,5-diiodopyridin-4-ol as a brown-yellow solid (6.4 g, yield: 87%), which was used in the next step without further purification. ESI-MS [M+H]⁺: 425.8.

Synthesis of 2-bromo-5-iodopyridin-4-ol. To a mixture of 2-bromo-3,5-diiodopyridin-4-ol (3.95 g, 9.3 mmol) in THF (30 mL), i-PrMgCl (26 mL, 26.0 mmol, 1.0M in THF) was added slowly at −78° C. The resulting reaction was stirred at −78° C. for 1 h. The mixture reaction was allowed to warm to −20° C. and stirred for another 5 h. The reaction mixture was adjusted to pH 6 using 3 N HCl, and then stirred for 30 min. The mixture was adjusted to pH 8 by adding saturated aqueous NaHCO$_3$. The reaction mixture was extracted with EtOAc (100 mL×3), the combined organics washed with brine (100 mL), and dried over Na$_2$SO$_4$. The organic layers were concentrated and purified by flash chromatography (EtOAc/PE=1:5) to yield a black oily solid (2.2 g, yield: 79%). ESI-MS [M+H]$^+$: 299.9.

Synthesis of 2-bromo-5-(((trimethylsilyl)ethynyl)pyridin-4-ol. To a mixture of 2-bromo-5-iodopyridin-4-ol (2 g, 6.7 mmol) in dioxane (15 mL) was added ethynyltrimethylsilane (722 mg, 7.37 mmol), CuI (254 mg, 1.35 mmol), PdCl$_2$(PPh$_3$)$_2$ (468 mg, 1.36 mmol), and Et$_3$N (2.03 g, 20.08 mmol) at room temperature. The mixture was stirred at 50° C. for 6 h. The reaction mixture was filtered. The filtrate was concentrated and purified by flash chromatography (EtOAc:PE=1:4) to yield a white solid (410 mg, yield: 23%). ESI-MS [M+H]$^+$: 270.0.

Synthesis of 6-bromofuro[3,2-c]pyridine. To a mixture of 2-bromo-5-(((trimethylsilyl)ethynyl)pyridin-4-ol (410 mg, 1.52 mmol) in MeOH (8 mL) was added KF (1.76 g, 30.4 mmol) at room temperature. The mixture was stirred at 50° C. for 6 h. The reaction mixture was filtered and washed with MeOH (50 mL). The filtrate was concentrated to yield a white solid (230 mg, yield: 77%), which was carried forward without further purification. ESI-MS [M+H]$^+$: 198.0.

Synthesis of furo[3,2-c]pyridine-6-carbonitrile. To a mixture of 6-bromofuro[3,2-c]pyridine (220 mg, 1.11 mmol) in DMF (10 mL) was added Zn(CN)$_2$ (772 mg, 6.6 mmol) and Pd(PPh$_3$)$_4$ (258 mg, 0.22 mmol) at room temperature. The mixture was stirred at 140° C. under microwave radiation for 5 h. The reaction mixture was filtered, then the organic layers were concentrated and purified by flash chromatography (PE:EtOAc=5:1) to yield a white solid (80 mg, yield: 50%). ESI-MS [M+H]$^+$: 145.1.

Synthesis of furo[3,2-c]pyridin-6-ylmethanamine. A mixture of furo[3,2-c]pyridine-6-carbonitrile (20 mg, 0.14 mmol) and Raney Ni (10 mg) in MeOH (5 mL) was stirred at room temperature under H$_2$ atmosphere for 1 h. The reaction mixture was filtered and washed with MeOH (20 mL). The filtrate was concentrated to yield furo[3,2-c]pyridin-6-ylmethanamine as a white solid (20 mg, yield: 97%). ESI-MS [M+H]$^+$: 149.2.

Synthesis of 1-((6-cyclopropylimidazo[1,2-a]pyridin-2-yl)methyl)-N-(furo[3,2-c]pyridin-6-ylmethyl)-1H-1,2,3-triazole-4-carboxamide. To a mixture of furo[3,2-c]pyridin-6-ylmethanamine (20 mg, 0.135 mmol) in DMF (5 mL) was added 1-((6-cyclopropylimidazo[1,2-a]pyridin-2-yl)methyl)-1H-1,2,3-triazole-4-carboxylic acid (16.07 mg, 0.06 mmol), EDCI (18.2 mg, 0.1 mmol), HOBT (12.8 mg, 0.1 mmol), and DIPEA (122.5 mg, 0.5 mmol) at room temperature. The mixture was stirred at room temperature overnight. The reaction mixture was poured into water (30 mL) and extracted with EtOAc (30 mL×3). The combined organics were washed with brine (30 mL) and dried over Na$_2$SO$_4$. The organic layers were concentrated and purified by flash chromatography (DCM:MeOH=10:1) to yield 1-((6-cyclopropylimidazo[1,2-a]pyridin-2-yl)methyl)-N-(furo[3,2-c]pyridin-6-ylmethyl)-1H-1,2,3-triazole-4-carboxamide as a white solid (6 mg, yield: 24%). ESI-MS [M+H]$^+$: 414.1. $^1$H NMR (400 MHz, MeOD) δ=8.83 (s, 1H), 8.42 (s, 1H), 8.21 (s, 1H), 7.85 (d, J=2.3, 1H), 7.82 (s, 1H), 7.56 (s, 1H), 7.40 (d, J=9.4, 1H), 7.12-6.99 (m, 1H), 7.02-6.97 (m, 1H), 5.77 (s, 2H), 4.79 (s, 2H), 1.94 (s, 1H), 1.01-0.95 (m, 2H), 0.75-0.69 (m, 2H).

Example 197

1-((6-cyclopropylimidazo[1,2-a]pyridin-2-yl)methyl)-N-((2,3-dihydrofuro[3,2-c]pyridin-6-yl)methyl)-1H-1,2,3-triazole-4-carboxamide (I-141)

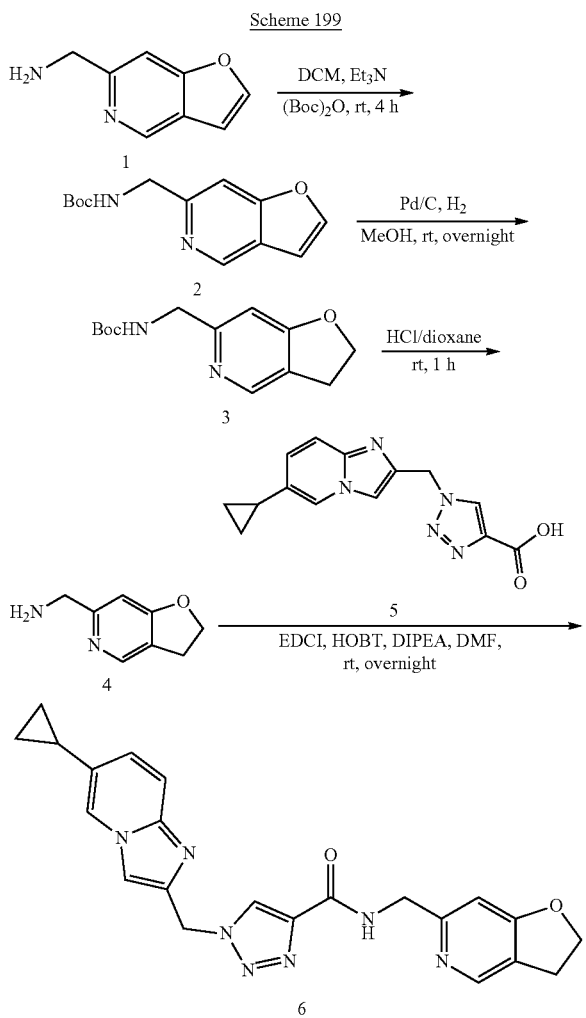

Scheme 199

Synthesis of tert-butyl (furo[3,2-c]pyridin-6-ylmethyl)carbamate. To a solution of furo[3,2-c]pyridin-6-ylmethanamine (30 mg, 0.20 mmol) in DCM (5 mL) was added Et$_3$N (0.3 mL, 1.0 mmol) and (Boc)$_2$O (0.24 mL, 2.0 mmol). The reaction mixture was stirred at room temperature for 4 h, then poured into water (10 mL) and extracted with EtOAc (10 mL×3). The combined organics were washed with brine (10 mL), dried over Na$_2$SO$_4$, concentrated, and purified by flash chromatography (DCM:MeOH=10:1) to yield a white solid (32 mg, yield 65%). ESI-MS [M+H]$^+$:249.2.

Synthesis of tert-butyl ((2,3-dihydrofuro[3,2-c]pyridin-6-yl)methyl)carbamate. A solution of tert-butyl (furo[3,2-c]pyridin-6-ylmethyl)carbamate (32 mg, 0.13 mmol) in MeOH (4 mL) was combined with a solution of Pd/C (15 mg) in MeOH (3 mL) to form a mixture that was stirred at room temperature overnight under an H₂ atmosphere. The reaction mixture was filtered, washed with MeOH (20 mL), and the filtrate concentrated in vacuo to yield tert-butyl ((2,3-dihydrofuro[3,2-c]pyridin-6-yl)methyl)carbamate as a white solid (32 mg, yield 98%). ESI-MS [M+H]⁺: 251.2.

Synthesis of (2,3-dihydrofuro[3,2-c]pyridin-6-yl)methanamine. A mixture of tert-butyl ((2,3-dihydrofuro[3,2-c]pyridin-6-yl)methyl)carbamate (32 mg, 0.13 mmol) in HCl/dioxane (4 mL) was stirred at room temperature for 1 h. The reaction mixture was concentrated in vacuo to yield (2,3-dihydrofuro[3,2-c]pyridin-6-yl)methanamine as a white solid, which was carried forward without further purification (18 mg, yield 92%). ESI-MS [M+H]⁺: 151.2.

Synthesis of 1-((6-cyclopropylimidazo[1,2-a]pyridin-2-yl)methyl)-N-((2,3-dihydrofuro[3,2-c]pyridin-6-yl)methyl)-1H-1,2,3-triazole-4-carboxamide. To a solution of (2,3-dihydrofuro[3,2-c]pyridin-6-yl)methanamine (18 mg, 0.12 mmol) in DMF (7 mL) was added 1-((6-cyclopropylimidazo[1,2-a]pyridin-2-yl)methyl)-1H-1,2,3-triazole-4-carboxylic acid (40.6 mg, 0.14 mmol), EDCI (91.4 mg, 0.48 mmol), HOBT (72 mg, 0.48 mmol), and DIPEA (0.4 mL, 1.2 mmol). The resulting mixture was stirred at room temperature overnight, then poured into water (10 mL), and extracted with EtOAc (10 mL×3). The combined organics were washed with brine (10 mL), dried over Na₂SO₄, and filtered. The organic layers were concentrated in vacuo and purified by flash chromatography (DCM/MeOH=10:1) to yield 1-((6-cyclopropylimidazo[1,2-a]pyridin-2-yl)methyl)-N-((2,3-dihydrofuro[3,2-c]pyridin-6-yl)methyl)-1H-1,2,3-triazole-4-carboxamide as a white solid (20 mg, yield 40%). ESI-MS [M+H]⁺: 416.2. ¹H NMR (400 MHz, MeOD) δ 8.40 (s, 1H), 8.20 (d, J=9.6 Hz, 2H), 7.81 (s, 1H), 7.40 (d, J=9.4 Hz, 1H), 7.12 (dd, J=9.4, 1.7 Hz, 1H), 6.78 (s, 1H), 5.76 (s, 2H), 4.68-4.64 (m, 2H), 4.58 (s, 2H), 3.26-3.22 (m, 2H), 1.98-1.93 (m, 1H), 1.00-0.96 (m, 2H), 0.74-0.70 (m, 2H).

Example 198

N-((4-chloropyridin-2-yl)methyl)-1-((6-cyclopropylimidazo[1,2-a]pyridin-2 yl)methyl)-1H-1,2,3-triazole-4-carboxamide (I-142)

Scheme 200

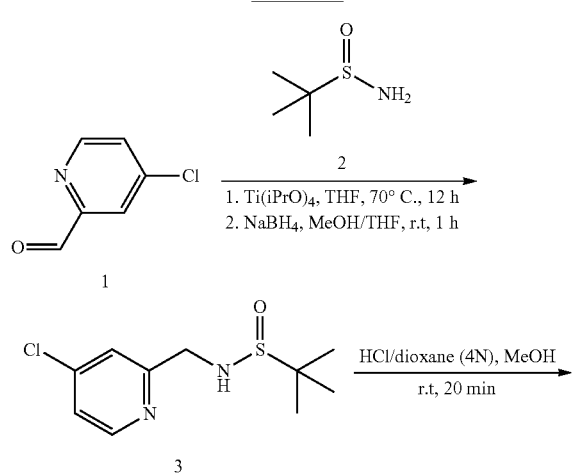

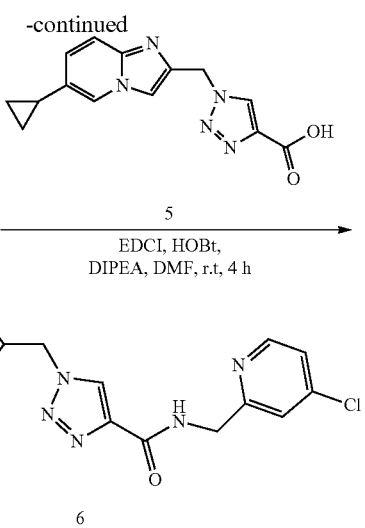

Synthesis of N-((4-chloropyridin-2-yl)methyl)-2-methylpropane-2-sulfinamide. To a stirred solution of 4-chloropicolinaldehyde (995 mg, 7.06 mmol) and 2-methylpropane-2-sulfinamide (1.03 g, 8.48 mmol) in THF (20 mL) was added dropwise Ti(i-PrO)₄ (6.02 g, 21.18 mmol) at room temperature. The resulting mixture was stirred for 12 h at 70° C. The reaction mixture was cooled to 0° C. and MeOH (5 mL) was added, followed by NaBH₄ (801 mg, 21.18 mmol) portionwise. The mixture was stirred for 1 h at room temperature. The reaction mixture was quenched with aqueous NH₄Cl (50 mL) and extracted with EtOAc (50 mL×2). The combined organics were washed with brine (100 mL), dried over Na₂SO₄, concentrated in vacuo, and purified by silica gel chromatography (EtOAc) to yield N-((4-chloropyridin-2-yl)methyl)-2-methylpropane-2-sulfinamide (720 mg, yield: 41%) as a colorless syrup. ESI-MS [M+H]⁺: 247.1.

Synthesis of (4-chloropyridin-2-yl)methanamine hydrochloride. To a stirred solution of N-((4-chloropyridin-2-yl)methyl)-2-methylpropane-2-sulfinamide (650 mg, 2.64 mmol) in MeOH (4 mL) was added HCl/1,4-dioxane (10 mL) dropwise. The resulting mixture was stirred at room temperature for 20 min. The reaction mixture was concentrated and dried in vacuo to give (4-chloropyridin-2-yl)methanamine hydrochloride (470 mg, yield: 100%) as a white solid. ESI-MS [M+H]⁺: 143.2.

Synthesis of N-((4-chloropyridin-2-yl)methyl)-1-((6-cyclopropylimidazo[1,2-a]pyridin-2-yl)methyl)-1H-1,2,3-triazole-4-carboxamide. A mixture of 1-((6-cyclopropylimidazo[1,2-a]pyridin-2-yl)methyl)-1H-1,2,3-triazole-4-carboxylic acid (100 mg, 0.353 mmol), (4-chloropyridin-2-yl)methanamine hydrochloride (63 mg, 0.353 mmol), EDCI (203 mg, 1.06 mmol), HOBT (143 mg, 1.06 mmol), and DIPEA (456 mg, 3.53 mmol) in DMF (5 mL) was stirred at room temperature for 4 h. The reaction mixture was poured into water (40 mL) and extracted with EtOAc (30 ml×2). The combined organics were washed with water (60 mL×3) and brine (60 mL×1), dried over Na₂SO₄, concentrated, and purified by silica gel chromatography (DCM/MeOH=15/1) to yield N-((4-chloropyridin-2-yl)methyl)-1-((6-cyclopropylimidazo[1,2-a]pyridin-2-yl)methyl)-1H-1,2,3-triazole-4-carboxamide (60 mg, yield: 42%) as a white solid. ESI-MS [M+H]⁺: 408.1. Purity: 97%. ¹H NMR (400 MHz, DMSO-d6) δ 9.14 (t, J=6.0 Hz, 1H), 8.61 (s, 1H), 8.49 (d, J=5.3 Hz, 1H), 8.36 (s, 1H), 7.86 (s, 1H), 7.46-7.39 (m, 2H), 7.38 (s, 1H), 7.01 (d, J=9.4 Hz, 1H), 5.75 (s, 2H), 4.55 (d, J=6.0 Hz, 2H), 1.99-1.89 (m, 1H), 0.96-0.88 (m, 2H), 0.70-0.64 (m, 2H).

Example 199

1-((6-cyclopropylimidazo[1,2-a]pyridin-2-yl)methyl)-N-((2,3-dihydro-[1,4]dioxino[2,3-c]pyridin-7-yl)methyl)-1H-1,2,3-triazole-4-carboxamide (I-143)

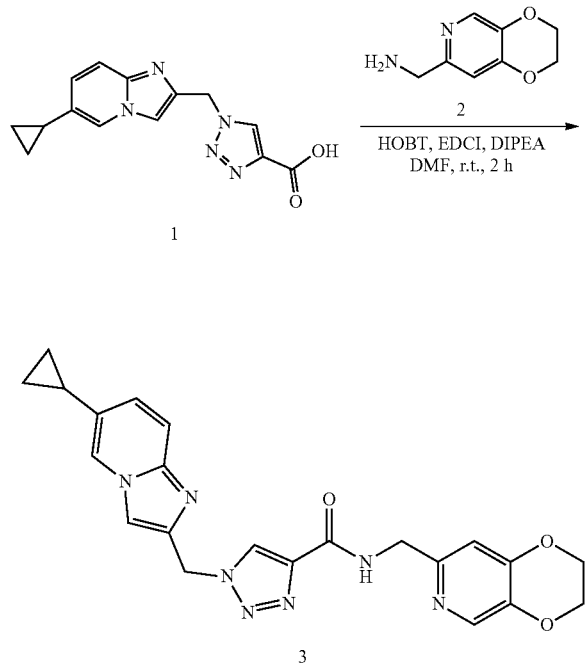

Scheme 201

Synthesis of 1-((6-cyclopropylimidazo[1,2-a]pyridin-2-yl)methyl)-N-((2,3-dihydro-[1,4]dioxino[2,3-c]pyridin-7-yl)methyl)-1H-1,2,3-triazole-4-carboxamide. A mixture of (2,3-dihydro-[1,4]dioxino[2,3-c]pyridin-7-yl)methanamine (50 mg, 0.30 mmol), 1-((6-cyclopropylimidazo[1,2-a]pyridin-2-yl)methyl)-1H-1,2,3-triazole-4-carboxylic acid (85.2 mg, 0.30 mmol), HOBT (61.6 mg, 0.45 mmol), EDCI (86.3 mg, 0.45 mmol), DIPEA (116.1 mg, 0.90 mmol), and DMF (5 mL) was stirred at room temperature for 12 h. Water (20 mL) was added and the mixture was extracted with EtOAc (30 mL×3). The combined organic layers were washed with brine (30 mL), dried over Na₂SO₄, filtered, and concentrated to yield the crude product, which was purified by Prep-TLC (DCM/MeOH=20/1) to afford tert-butyl 7-((1-((6-cyclopropylimidazo[1,2-a]pyridin-2-yl)methyl)-1H-1,2,3-triazole-4-carboxamido)methyl)-2,3-dihydro-4H-pyrido[4,3-b][1,4]oxazine-4-carboxylate (90 mg, yield: 69.6%) as a white solid. ESI-MS [M+H]⁺: 431.2. ¹H NMR (400 MHz, DMSO) 1H NMR (400 MHz, DMSO) δ 8.98 (t, J=6 Hz, 1H), 8.57 (s, 1H), 8.21 (s, 1H), 7.94 (d, J=9.5 Hz, 1H), 7.11 (d, J=9.5 Hz, 1H), 6.79-6.76 (m, 2H), 5.76 (s, 2H), 4.32-4.17 (m, 2H), 4.19 (s, 4H), 2.18-2.12 (m, 1H), 1.13-1.00 (m, 2H), 1.04-0.90 (m, 2H).

Example 200

N-((1H pyrrolo[2,3-c]pyridin-5 yl)methyl)-1-((6-cyclopropylimidazo[1,2-a]pyridin-2-yl)methyl)-1H-1,2,3-triazole-4-carboxamide (I-144)

Scheme 202

Synthesis of 2-bromo-4-methyl-5-nitropyridine. To a solution of 4-methyl-5-nitropyridin-2-ol (1 g, 6.5 mmol) in DCE (10 mL) was added POBr₃ (2.8 g, 9.75 mmol). The mixture was stirred at 90° C. for 3 h. The reaction mixture was extracted with DCM (20 mL×3). The combined organic layers were washed with brine (50 mL), dried over Na₂SO₄, and concentrated in vacuo to give the crude product, which was purified by flash chromatography (eluent: PE/EtOAc=3/1) to afford 2-bromo-4-methyl-5-nitropyridine as a yellow solid (1 g, 71%). ESI-MS [M+H]⁺: 217.1.

Synthesis of 4-methyl-5-nitropicolinonitrile. A mixture of 2-bromo-4-methyl-5-nitropyridine (1 g, 4.63 mmol), $Zn(CN)_2$ (1.1 g, 9.26 mmol), and $Pd(PPh_3)_4$ (535 mg, 0.463 mmol) in DMF (10 mL) was stirred at 95° C. for 3 h. The reaction was quenched with water (50 mL) and extracted with DCM (50 mL×3). The combined organic layers were washed with brine (50 mL), dried over $Na_2SO_4$, and concentrated in vacuo to give the crude product, which was purified by flash chromatography (PE:EtOAc=4:1) to afford 4-methyl-5-nitropicolinonitrile as a yellow solid (450 mg, 60%). ESI-MS [M+H]+: 164.1.

Synthesis of (E)-4-(2-(dimethylamino)vinyl)-5-nitropicolinonitrile. To a solution of 4-methyl-5-nitropicolinonitrile (450 mg, 2.76 mmol) in DMF (5 mL) was added DMF-DMA (427 mg, 3.59 mmol). The reaction mixture was stirred at 90° C. for 2 h. The reaction was concentrated in vacuo to yield the crude product (E)-4-(2-(dimethylamino)vinyl)-5-nitropicolinonitrile as a black solid (650 mg, crude), which was used in the next step without further purification. ESI-MS [M+H]+: 219.1.

Synthesis of (1H-pyrrolo[2,3-c]pyridin-5-yl)methanamine. To a solution of (E)-4-(2-(dimethylamino)vinyl)-5-nitropicolinonitrile (600 mg, 2.75 mmol) in MeOH (10 mL) and 6 M HCl (2 mL) was added Pd/C (500 mg). The mixture was stirred at room temperature for 12 h under $H_2$. The mixture was filtered through celite, washing with MeOH. The filtrate was neutralized with ammonium hydroxide and concentrated in vacuo. The crude product was purified by flash column chromatography (DCM:MeOH: $NH_3 \cdot H_2O$=80:19:1) to afford 1H-pyrrolo[2,3-c]pyridin-5-yl)methanamine as a yellow solid (230 mg, 57%). ESI-MS [M+H]+: 148.2.

Synthesis of N-((1H-pyrrolo[2,3-c]pyridin-5-yl)methyl)-1-((6-cyclopropylimidazo[1,2-a]pyridin-2-yl)methyl)-1H-1,2,3-triazole-4-carboxamide. A mixture of (1H-pyrrolo[2,3-c]pyridin-5-yl)methanamine (60 mg, 0.41 mmol), 1-((6-cyclopropylimidazo[1,2-a]pyridin-2-yl)methyl)-1H-1,2,3-triazole-4-carboxylic acid (115 mg, 0.41 mmol), HOBT (111 mg, 0.82 mmol), EDCI (157 mg, 0.82 mmol), and DIPEA (264 mg, 2.05 mmol) in DMF (5 mL) was stirred at RT for 12 h. The reaction mixture was quenched with $H_2O$ (20 mL), then extracted with EtOAc (30 mL×3). The combined organic layers were washed with brine (50 mL), dried over $Na_2SO_4$, and concentrated in vacuo to yield the crude product, which was purified by Pre-TLC (DCM:MeOH=15:1) to afford N-((1H-pyrrolo[2,3-c]pyridin-5-yl)methyl)-1-((6-cyclopropylimidazo[1,2-a]pyridin-2-yl)methyl)-1H-1,2,3-triazole-4-carboxamide as a white solid (25 mg, 15%). ESI-MS [M+H]+: 413.3. Purity: 100 (214 nm) 100 (254 nm). 1H NMR (400 MHz, DMSO) δ 11.51 (s, 1H), 8.93 (t, J=5.7 Hz, 1H), 8.68 (s, 1H), 8.60 (s, 1H), 8.36 (s, 1H), 7.85 (s, 1H), 7.56 (s, 1H), 7.47-7.37 (m, 2H), 7.02 (d, J=9.4 Hz, 1H), 6.44 (s, 1H), 5.75 (s, 2H), 4.60 (d, J=5.8 Hz, 2H), 1.98-1.87 (m, 1H), 0.96-0.86 (m, 2H), 0.74-0.57 (m, 2H).

Example 201

N-((4-chloropyrimidin-2-yl)methyl)-1-((6-cyclopropylimidazo[1,2-a]pyridin-2 yl)methyl)-1H-1,2,3-triazole-4-carboxamide (I-145)

Scheme 203

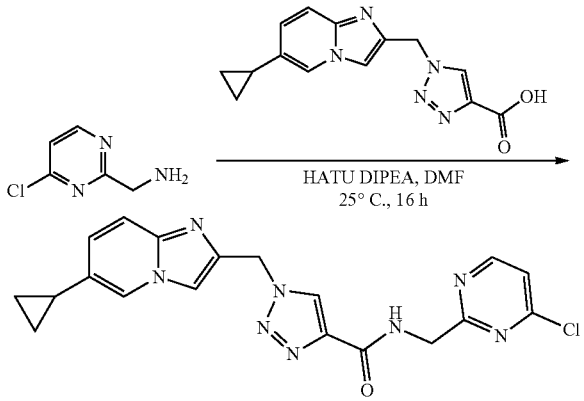

Synthesis of N-((4-chloropyrimidin-2-yl)methyl)-1-((6-cyclopropylimidazo[1,2-a]pyridin-2-yl)methyl)-1H-1,2,3-triazole-4-carboxamide. A mixture of 1-((6-cyclopropylimidazo[1,2-a]pyridin-2-yl)methyl)-1H-1,2,3-triazole-4-carboxylic acid (20 mg, 0.07 mmol), (4-chloropyrimidin-2-yl)methanamine (20 mg, 0.14 mmol), HATU (40 mg, 0.1 mmol), and DIPEA (27 mg, 0.2 mmol) in DMF (6 mL) was stirred at 25° C. for 16 h. The reaction mixture was concentrated to yield the crude product, which was purified by Prep-TLC (DCM/MeOH=10:1) to afford N-((4-chloropyrimidin-2-yl)methyl)-1-((6-cyclopropylimidazo[1,2-a]pyridin-2-yl)methyl)-1H-1,2,3-triazole-4-carboxamide as a white solid (2.0 mg, 7% yield). ESI-MS [M+H]+: 409.1. Purity: 93.34%. 1H NMR (400 MHz, MeOD) S 8.64 (d, J=5.4 Hz, 1H), 8.41 (s, 1H), 8.22 (s, 1H), 7.83 (s, 1H), 7.46-7.40 (m, 2H), 7.12 (d, J=9.4 Hz, 1H), 5.77 (s, 2H), 4.76 (s, 2H), 1.96-1.89 (m, 1H), 0.99-0.96 (m, 2H), 0.74-0.72 (m, 2H).

Example 202

N-((3-chloro-1H pyrrolo[2,3-c]pyridin-5-yl)methyl)-1-((6-cyclopropylimidazo[1,2-a]pyridin-2-yl)methyl)-1H-1,2,3-triazole-4-carboxamide (I-146)

Scheme 204

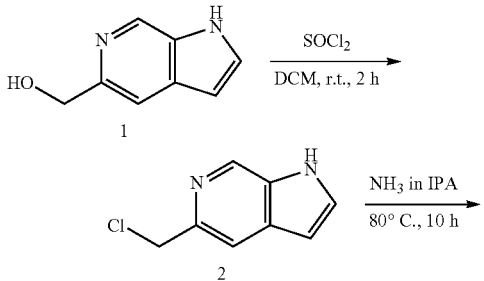

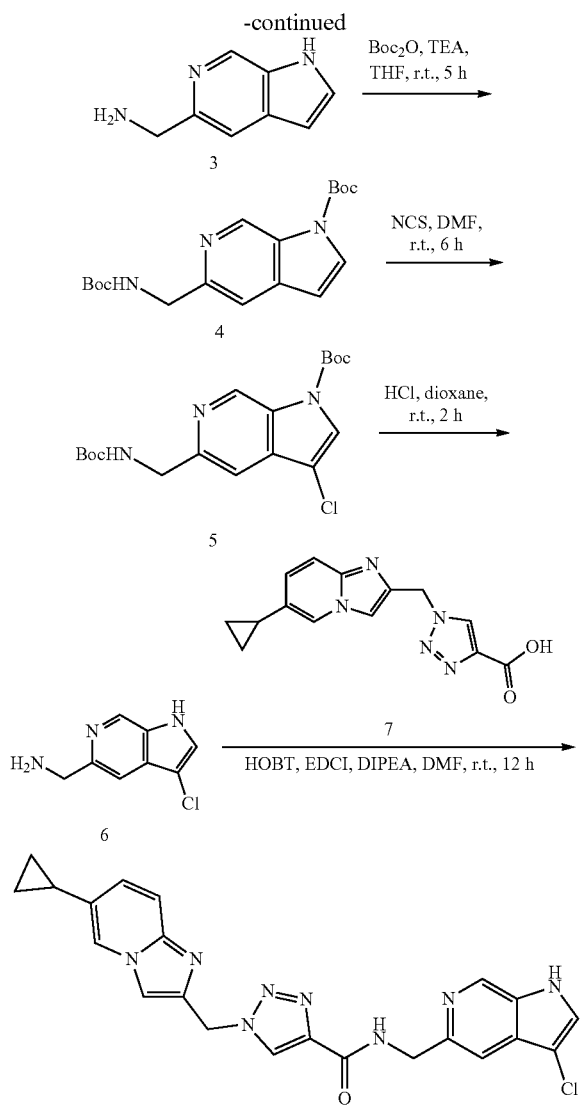

Synthesis of 5-(chloromethyl)-1H-pyrrolo[2,3-c]pyridine. To a solution of (1H-pyrrolo[2,3-c]pyridin-5-yl)methanol (50 mg, 0.34 mmol) in DCM (5 mL) was added SOCl₂ (0.5 mL). The mixture was stirred at room temperature for 2 h. The reaction was concentrated in vacuo to yield the crude product 5-(chloromethyl)-1H-pyrrolo[2,3-c]pyridine (60 mg, crude), which was used to the next step without further purification. ESI-MS [M+H]⁺: 167.1.

Synthesis of (1H-pyrrolo[2,3-c]pyridin-5-yl)methanamine. A mixture of 5-(chloromethyl)-1H-pyrrolo[2,3-c]pyridine (56 mg, 0.34 mmol) and NH₃ in IPA (10 mL) was stirred at 80° C. for 12 h. The reaction mixture was concentrated in vacuo to yield the crude product (1H-pyrrolo[2,3-c]pyridin-5-yl)methanamine (50 mg, crude), which was used to the next step without further purification. ESI-MS [M+H]⁺: 148.1.

Synthesis of tert-butyl 5-(((tert-butoxycarbonyl)amino)methyl)-1H-pyrrolo[2,3-c]pyridine-1-carboxylate. A mixture of (1H-pyrrolo[2,3-c]pyridin-5-yl)methanamine (50 mg, 0.34 mmol), DMAP (4 mg, 0.034 mmol), Boc₂O (222 mg, 1.02 mmol), and TEA (103 mg, 1.02 mmol) in THF (5 mL) was stirred at room temperature for 3 h. The reaction mixture was concentrated in vacuo to yield the crude product, which was purified by Prep-TLC (petroleum ether (PE)/EtOAc=1/1) to afford tert-butyl 5-(((tert-butoxycarbonyl)amino)methyl)-1H-pyrrolo[2,3-c]pyridine-1-carboxylate as a colorless oil (65 mg, 55%). ESI-MS [M+H]⁺: 348.2.

Synthesis of tert-butyl 5-(((tert-butoxycarbonyl)amino)methyl)-3-chloro-1H-pyrrolo[2,3-c]pyridine-1-carboxylate. A mixture of tert-butyl (Z)-((4-(2-((tert-butoxycarbonyl)amino)vinyl)pyridin-2-yl)methyl)carbamate (65 mg, 0.187 mmol) and NCS (27 mg, 0.206 mmol) in DMF (5 mL) was stirred at 50° C. for 12 h. The reaction mixture was quenched with H₂O (20 mL) and extracted with EtOAc (30 mL×3). The combined organic layers were washed with brine (50 mL), dried over Na₂SO₄, and concentrated in vacuo to yield the crude product, which was purified by Prep-TLC (PE:EtOAc=2:1) to afford the product tert-butyl 5-(((tert-butoxycarbonyl)amino)methyl)-3-chloro-1H-pyrrolo[2,3-c]pyridine-1-carboxylate as a colorless oil (50 mg, 70%). ESI-MS [M+H]⁺: 382.2.

Synthesis of (3-chloro-1H-pyrrolo[2,3-c]pyridin-5-yl)methanamine. To a solution of tert-butyl 5-(((tert-butoxycarbonyl)amino)methyl)-3-chloro-1H-pyrrolo[2,3-c]pyridine-1-carboxylate (50 mg, 0.13 mmol) in MeOH (5 mL) was added HCl in dioxane (4 M, 5 mL). The reaction mixture was stirred at room temperature for 3 h. The reaction was concentrated in vacuo to yield the crude product (3-chloro-1H-pyrrolo[2,3-c]pyridin-5-yl)methanamine as a yellow solid (24 mg, crude), which was used in the next step without further purification. ESI-MS [M+H]⁺: 182.2.

Synthesis of N-((3-chloro-1H-pyrrolo[2,3-c]pyridin-5-yl)methyl)-1-((6-cyclopropylimidazo[1,2-a]pyridin-2-yl)methyl)-1H-1,2,3-triazole-4-carboxamide. A mixture of (3-chloro-1H-pyrrolo[2,3-c]pyridin-5-yl)methanamine (24 mg, 0.13 mmol), 1-((6-cyclopropylimidazo[1,2-a]pyridin-2-yl)methyl)-1H-1,2,3-triazole-4-carboxylic acid (37 mg, 0.13 mmol), HOBT (35 mg, 0.26 mmol), EDCI (50 mg, 0.26 mmol), and DIPEA (84 mg, 0.65 mmol) in DMF (5 mL) was stirred at room temperature for 12 h. The reaction mixture was quenched with H₂O (20 mL). The aqueous phase was extracted with EtOAc (30 mL×3). The combined organic layers were washed with brine (50 mL), dried over Na₂SO₄, and concentrated in vacuo to yield the crude product, which was purified by Prep-TLC (DCM:MeOH=15:1) to afford N-((3-chloro-1H-pyrrolo[2,3-c]pyridin-5-yl)methyl)-1-((6-cyclopropylimidazo[1,2-a]pyridin-2-yl)methyl)-1H-1,2,3-triazole-4-carboxamide as a white solid (15 mg, 26%). ESI-MS [M+H]⁺: 447.1. Purity: 99.3%. ¹H NMR (400 MHz, DMSO) δ 9.04 (t, J=6.0 Hz, 1H), 8.74 (s, 1H), 8.61 (s, 1H), 8.36 (s, 1H), 7.86 (s, 1H), 7.76 (s, 1H), 7.42 (d, J=9.3 Hz, 1H), 7.36 (s, 1H), 7.02 (dd, J=9.4, 1.7 Hz, 1H), 5.76 (s, 2H), 4.62 (d, J=6.0 Hz, 2H), 1.99-1.85 (m, 1H), 0.96-0.88 (m, 2H), 0.73-0.66 (m, 2H).

Example 203

(5-(aminomethyl)-2,3-dihydro-1H pyrrolo[2,3-c]pyridin-1-yl)(1-((6-cyclopropylimidazo[1,2-a]pyridin-2 yl)methyl)-1H-1,2,3-triazol-4 yl)methanone
(I-147)

Scheme 205

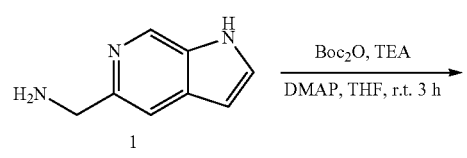

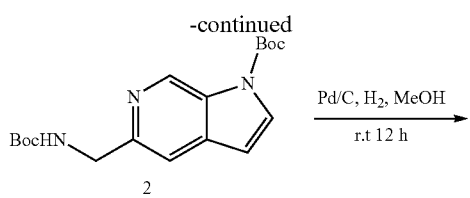

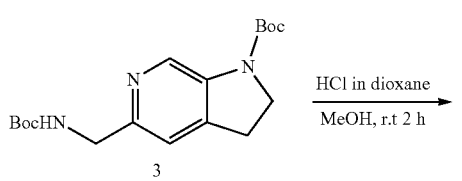

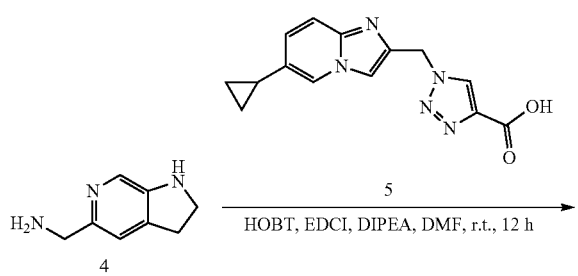

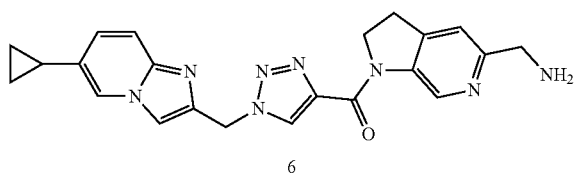

Synthesis of tert-butyl 5-(((tert-butoxycarbonyl)amino)methyl)-1H-pyrrolo[2,3-c]pyridine-1-carboxylate. A mixture of (1H-pyrrolo[2,3-c]pyridin-5-yl)methanamine (70 mg, 0.48 mmol), DMAP (6 mg, 0.048 mmol), Boc₂O (311 mg, 1.43 mmol), and TEA (144 mg, 1.43 mmol) in THF (10 mL) was stirred at RT for 3 h. Water (30 mL) was added and the mixture extracted with EtOAc (20 mL×3). The combined organic layers were washed with brine (20 mL), dried over anhydrous Na₂SO₄, filtered and concentrated. The residue was purified by Prep-TLC (PE/EtOAc=2/1) to afford tert-butyl 5-(((tert-butoxycarbonyl)amino)methyl)-1H-pyrrolo[2,3-c]pyridine-1-carboxylate as a red solid (60 mg, 36%). ESI-MS [M+H]⁺: 348.1.

Synthesis of tert-butyl 5-(((tert-butoxycarbonyl)amino)methyl)-2,3-dihydro-1H-pyrrolo[2,3-c]pyridine-1-carboxylate. To a solution of tert-butyl 5-(((tert-butoxycarbonyl)amino)methyl)-1H-pyrrolo[2,3-c]pyridine-1-carboxylate (60 mg, 0.17 mmol) in MeOH (15 mL) was added Pd/C (30 mg). The reaction mixture was stirred at RT for 12 h under H₂. Water (30 mL) was added and the mixture extracted with EtOAc (20 mL×3). The combined organic layers were washed with brine (30 mL), dried over anhydrous Na₂SO₄, filtered and concentrated. The residue was purified by Prep-TLC (PE/EtOAc=2/1) to yield tert-butyl 5-(((tert-butoxycarbonyl)amino)methyl)-2,3-dihydro-1H-pyrrolo[2,3-c]pyridine-1-carboxylate (55 mg, 93%) as a colorless oil. ESI-MS [M+H]⁺: 350.2.

Synthesis of (2,3-dihydro-1H-pyrrolo[2,3-c]pyridin-5-yl)methanamine. To a solution of tert-butyl 5-(((tert-butoxycarbonyl)amino)methyl)-2,3-dihydro-1H-pyrrolo[2,3-c]pyridine-1-carboxylate (55 mg, 0.157 mmol) in MeOH (5 mL) was added HCl/dioxane (4 M, 5 mL). The reaction mixture was stirred at RT for 2 h. The reaction mixture was concentrated in vacuo to yield the crude product (2,3-dihydro-1H-pyrrolo[2,3-c]pyridin-5-yl)methanamine as a yellow solid (24 mg, crude), which was used in the next step without further purification. ESI-MS [M+H]⁺: 150.1.

Synthesis of (5-(aminomethyl)-2,3-dihydro-1H-pyrrolo[2,3-c]pyridin-1-yl)(1-((6-cyclopropylimidazo[1,2-a]pyridin-2-yl)methyl)-1H-1,2,3-triazol-4-yl)methanone. A mixture of (2,3-dihydro-1H-pyrrolo[2,3-c]pyridin-5-yl)methanamine (24 mg, 0.16 mmol), 1-((6-cyclopropylimidazo[1,2-a]pyridin-2-yl)methyl)-1H-1,2,3-triazole-4-carboxylic acid (45 mg, 0.16 mmol), HOBT (43 mg, 0.32 mmol), EDCI (61 mg, 0.32 mmol), and DIPEA (103 mg, 0.80 mmol) in DMF (5 mL) was stirred at RT for 12 h. Water (60 mL) was added and the reaction mixture was extracted with EtOAc (30 mL×3). The combined organic layers were washed with brine (30 mL), dried over anhydrous Na₂SO₄, filtered and concentrated. The residue was purified by Prep-TLC (DCM:MeOH=10:1) to yield (5-(aminomethyl)-2,3-dihydro-1H-pyrrolo[2,3-c]pyridin-1-yl)(1-((6-cyclopropylimidazo[1,2-a]pyridin-2-yl)methyl)-1H-1,2,3-triazol-4-yl)methanone (18 mg, 27%) as a white solid. ESI-MS [M+H]⁺: 415.2. Purity: 100%. ¹H NMR (400 MHz, DMSO) δ 8.85 (s, 1H), 8.58 (s, 1H), 8.36 (s, 1H), 7.85 (s, 1H), 7.70 (s, 1H), 7.42 (d, J=9.1 Hz, 1H), 7.02 (s, 2H), 5.75 (s, 2H), 5.61 (s, 1H), 4.39 (d, J=4.6 Hz, 2H), 3.44-3.38 (m, 2H), 2.90 (t, J=8.2 Hz, 2H), 1.93 (s, 1H), 0.95-0.89 (m, 2H), 0.68 (s, 2H).

Example 204

1-((6-cyclopropylimidazo[1,2-a]pyridin-2-yl)methyl)-N-((2,3-dihydro-1H-pyrrolo[2,3-c]pyridin-5-yl)methyl)-1H-1,2,3-triazole-4-carboxamide (I-148)

Scheme 206

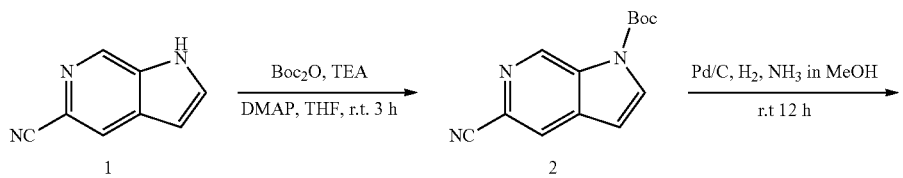

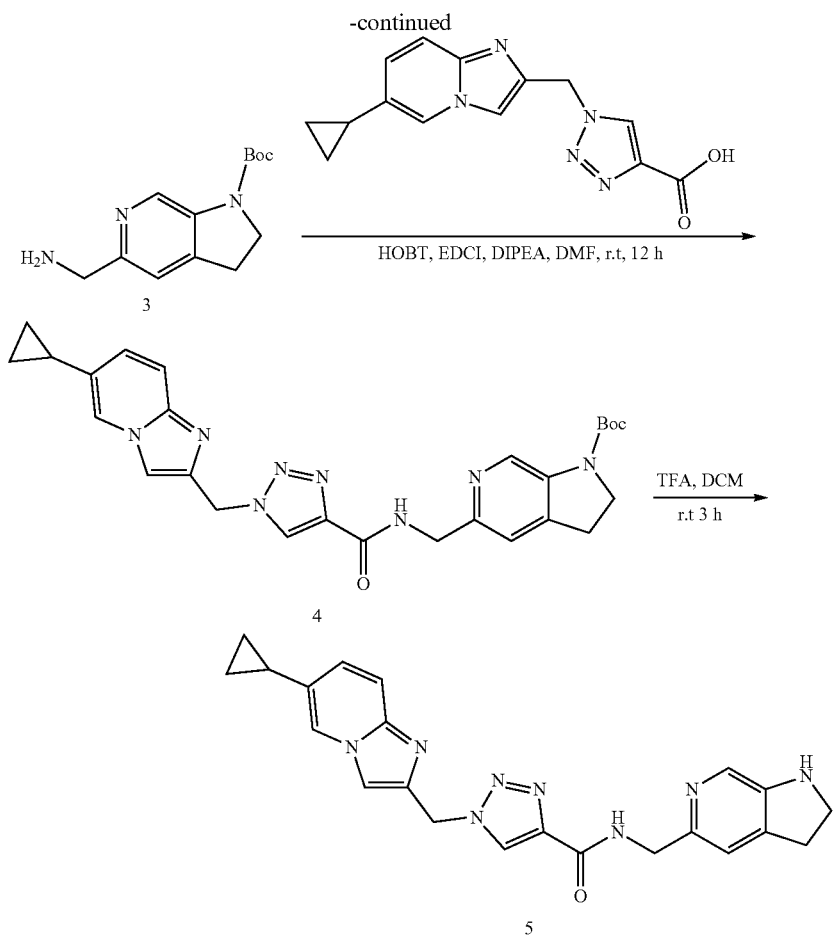

Synthesis of tert-butyl 5-cyano-1H-pyrrolo[2,3-c]pyridine-1-carboxylate. A mixture of 1H-pyrrolo[2,3-c]pyridine-5-carbonitrile (286 mg, 2.0 mmol), DMAP (25 mg, 0.2 mmol), Boc₂O (1.3 g, 6.0 mmol), and TEA (606 mg, 6.0 mmol) in THE (20 mL) was stirred at RT for 3 h. Water (50 mL) was added and the mixture was extracted with EtOAc (30 mL×3). The combined organic layers were washed with brine (30 mL), dried over anhydrous Na₂SO₄, filtered and concentrated. The residue was purified by Prep-TLC (PE/EtOAc=2/1) to yield the product tert-butyl 5-cyano-1H-pyrrolo[2,3-c]pyridine-1-carboxylate as a white solid. (274 mg, 56%). ESI-MS [M+H]⁺: 244.1.

Synthesis of tert-butyl 5-(aminomethyl)-2,3-dihydro-1H-pyrrolo[2,3-c]pyridine-1-carboxylate. To a solution of tert-butyl 5-cyano-1H-pyrrolo[2,3-c]pyridine-1-carboxylate (190 mg, 0.78 mmol) in NH₃/MeOH (20 mL, 7 M) was added Pd/C (100 mg). The reaction mixture was stirred at RT for 12 h under H₂, then filtered and concentrated in vacuo. The residue was purified by Prep-TLC (DCM/MeOH=10/1) to yield tert-butyl 5-(aminomethyl)-2,3-dihydro-1H-pyrrolo[2,3-c]pyridine-1-carboxylate as a colorless oil (30 mg, 15%). ESI-MS [M+H]⁺: 250.2.

Synthesis of tert-butyl 5-((1-((6-cyclopropylimidazo[1,2-a]pyridin-2-yl)methyl)-1H-1,2,3-triazole-4-carboxamido)methyl)-2,3-dihydro-1H-pyrrolo[2,3-c]pyridine-1-carboxylate. A mixture of tert-butyl 5-(aminomethyl)-2,3-dihydro-1H-pyrrolo[2,3-c]pyridine-1-carboxylate (30 mg, 0.12 mmol), 1-((6-cyclopropylimidazo[1,2-a]pyridin-2-yl)methyl)-1H-1,2,3-triazole-4-carboxylic acid (34 mg, 0.12 mmol), HOBT (32 mg, 0.24 mmol), EDCI (46 mg, 0.24 mmol), and DIPEA (77 mg, 0.60 mmol) in DMF (5 mL) was stirred at RT for 12 h. Water (60 mL) was added and the aqueous phase was extracted with EtOAc (30 mL×3). The combined organic layers were washed with brine (30 mL), dried over Na₂SO₄ and concentrated in vacuo. The residue was purified by Prep-TLC (DCM:MeOH=15:1) to yield tert-butyl 5-((1-((6-cyclopropylimidazo[1,2-a]pyridin-2-yl)methyl)-1H-1,2,3-triazole-4-carboxamido)methyl)-2,3-dihydro-1H-pyrrolo[2,3-c]pyridine-1-carboxylate as a white solid (30 mg, 48%). ESI-MS [M+H]⁺: 514.2.

Synthesis of 1-((6-cyclopropylimidazo[1,2-a]pyridin-2-yl)methyl)-N-((2,3-dihydro-1H-pyrrolo[2,3-c]pyridin-5-yl)methyl)-1H-1,2,3-triazole-4-carboxamide. To a solution of tert-butyl 5-((1-((6-cyclopropylimidazo[1,2-a]pyridin-2-yl)methyl)-1H-1,2,3-triazole-4-carboxamido)methyl)-2,3-dihydro-1H-pyrrolo[2,3-c]pyridine-1-carboxylate (30 mg, 0.058 mmol) in DCM (5 mL) was added TFA (1 mL). The reaction mixture was stirred at RT for 5 h. The reaction mixture was concentrated in vacuo and dissolved in a NaHCO₃ solution (20 mL). The mixture was extracted with EtOAc (30 mL×3) and the combined organic layers were washed with brine (30 mL), dried over Na₂SO₄, and concentrated in vacuo. The residue was purified by Prep-HPLC to yield 1-((6-cyclopropylimidazo[1,2-a]pyridin-2-yl)methyl)-N-((2,3-dihydro-1H-pyrrolo[2,3-c]pyridin-5-yl)methyl)-1H-1,2,3-triazole-4-carboxamide as a white solid (9 mg, 37%). ESI-MS [M+H]⁺: 415.2. Purity: 97.51 (214 nm) 97.69 (254 nm). ¹H NMR (400 MHz, DMSO) δ 12.78 (s, 1H), 8.96 (t, J=5.8 Hz, 1H), 8.59 (s, 1H), 8.37 (s, 1H), 8.14 (s, 1H), 7.86 (s, 1H), 7.69 (s, 1H), 7.41 (d, J=9.3 Hz, 1H), 7.13 (s, 1H), 7.05-7.00 (m, 1H), 5.75 (s, 2H), 4.43 (d, J=5.9 Hz, 2H), 3.46 (t, J=8.7 Hz, 2H), 2.97 (t, J=8.6 Hz, 2H), 1.99-1.85 (m, 1H), 0.97-0.87 (m, 2H), 0.73-0.63 (m, 2H).
Example 205
1-((6-cyclopropylimidazo[1,2-a]pyridin-2-yl)methyl)-N-((3,4-dihydro-2H-pyrido[4,3-b][1,4]oxazin-7-yl)methyl)-1H-1,2,3-triazole-4-carboxamide (I-149)
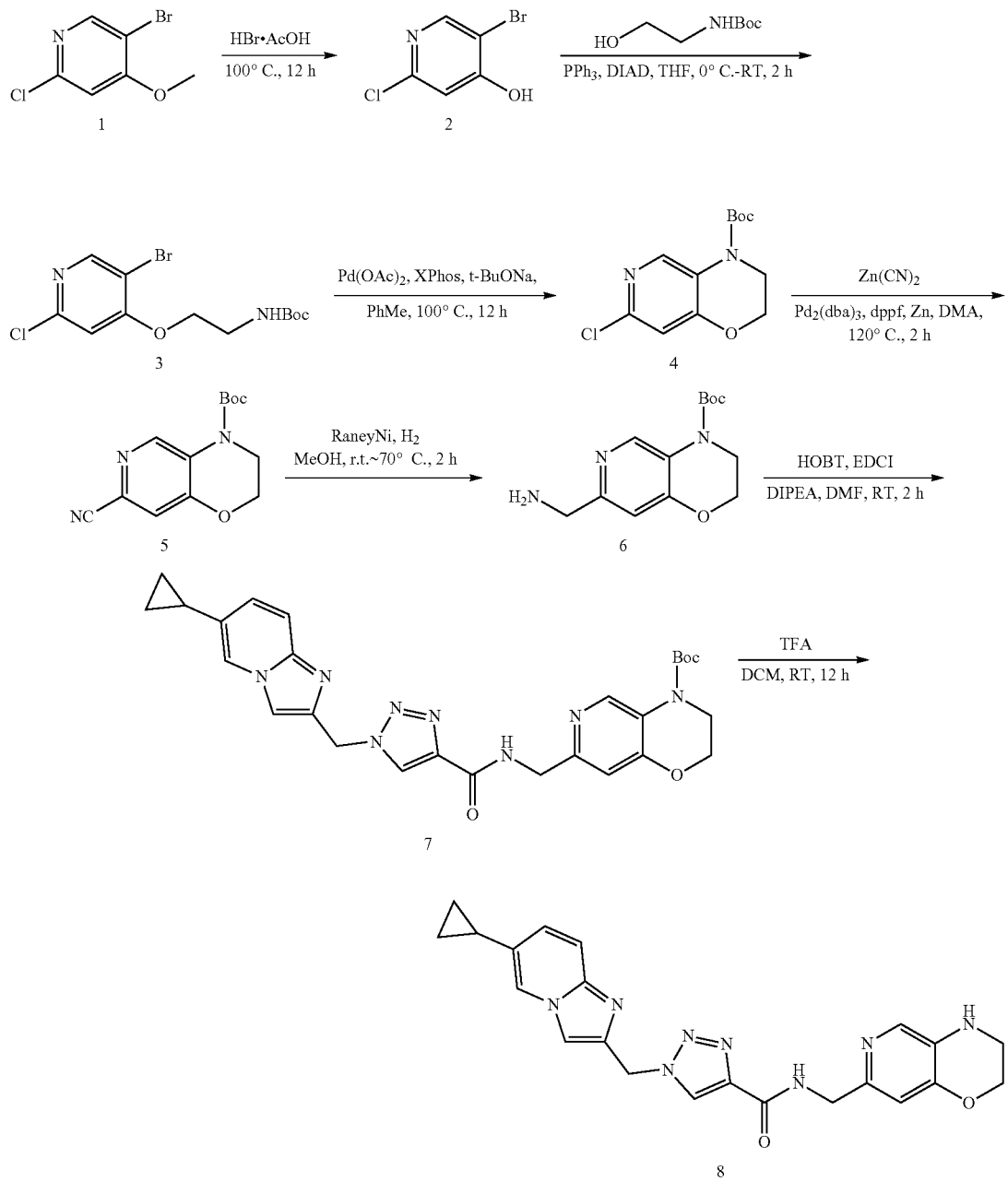

Synthesis of 5-bromo-2-chloropyridin-4-ol. A mixture of 5-bromo-2-chloro-4-methoxypyridine (2 g, 9 mmol), HBr—AcOH (10 mL) and water (2 mL) was stirred at 100° C. for 4 h. Water (100 mL) was added and the mixture was extracted with EtOAc (60 mL×3). The combined organic layers were washed with brine (50 mL), dried over $Na_2SO_4$, filtered, and concentrated in vacuo to yield 5-bromo-2-chloropyridin-4-ol (400 mg, 21.5%) as a yellow solid, which was used in the next step without further purification. ESI-MS [M+H]$^+$: 207.9.

Synthesis of 1-(1-(bromomethyl)cyclopropyl)-3-chlorobenzene. To a solution of 5-bromo-2-chloropyridin-4-ol (1.6 g, 7.73 mmol) in THF (100 mL) was added $PPh_3$ (3.04 g, 11.59 mmol), tert-butyl (2-hydroxyethyl)carbamate (1.88 g, 11.59 mmol) and DIAD (2.30 g, 11.59 mmol) at 0° C. The mixture was stirred at RT for 12 h. Water (100 mL) was added and the mixture was extracted with EtOAc (50 mL×3). The combined organic layers were washed with brine (50 mL), dried over $Na_2SO_4$, filtered and concentrated. The residue was purified by silica gel chromatography (PE/EtOAc=5/1) to give tert-butyl (2-((5-bromo-2-chloropyridin-4-yl)oxy)ethyl)carbamate (1.5 g, 55%) as a yellow oil. ESI-MS [M+H]+: 351.2.

Synthesis of tert-butyl 7-chloro-2,3-dihydro-4H-pyrido[4,3-b][1,4]oxazine-4-carboxylate. The mixture of tert-butyl (2-((5-bromo-2-chloropyridin-4-yl)oxy)ethyl)carbamate (1.4 g, 4 mmol), XPhos (381 mg, 0.8 mmol), t-BuONa (768 mg, 8 mmol), Pd(OAc)$_2$ (135 mg, 0.6 mmol) and PhMe (20 mL) was stirred at 100° C. for 12 h. Water (30 mL) was added and the mixture was extracted with EtOAc (20 mL×3). The combined organic layers were washed with brine (20 mL), dried over $Na_2SO_4$, filtered and concentrated in vacuo to give the crude which was purified by silica gel chromatography (PE/EtOAc=5/1) to give tert-butyl 7-chloro-2,3-dihydro-4H-pyrido[4,3-b][1,4]oxazine-4-carboxylate (400 mg, yield: 37%) as a yellow solid. ESI-MS [M+H]+: 271.2.

Synthesis of tert-butyl 7-cyano-2,3-dihydro-4H-pyrido[4,3-b][1,4]oxazine-4-carboxylate. A mixture of tert-butyl 7-chloro-2,3-dihydro-4H-pyrido[4,3-b][1,4]oxazine-4-carboxylate (270 mg, 1 mmol), Zn(CN)$_2$(128.7 mg, 1.1 mmol), Pd$_2$(dba)$_3$ (57.9 mg, 0.1 mmol), Zn (3.3 mg, 0.05 mmol), dppf (55.4 mg, 0.1 mmol) in DMA (5 mL) was stirred at 120° C. for 2 h. Water (50 mL) was added and the mixture was extracted with EtOAc (30 mL×3). The combined organic layers were washed with brine, dried over $Na_2SO_4$, filtered and concentrated. The residue was purified by silica gel chromatography (PE/EtOAc=5/1) to give tert-butyl 7-cyano-2,3-dihydro-4H-pyrido[4,3-b][1,4]oxazine-4-carboxylate(180 mg, yield: 69%) as a yellow solid. ESI-MS [M+H]+: 262.2.

Synthesis of tert-butyl 7-(aminomethyl)-2,3-dihydro-4H-pyrido[4,3-b][1,4]oxazine-4-carboxylate. The mixture of tert-butyl 7-cyano-2,3-dihydro-4H-pyrido[4,3-b][1,4]oxazine-4-carboxylate (200 mg, 0.77 mmol), 50% Raney Ni (100 mg) and MeOH (5 mL) was stirred at 70° C. for 2 h. The reaction mixture was filtered and concentrated in vacuo to give tert-butyl 7-(aminomethyl)-2,3-dihydro-4H-pyrido[4,3-b][1,4]oxazine-4-carboxylate(210 mg, yield: 100%) as a gray oil which was used in the next step directly. ESI-MS [M+H]+: 266.2.

Synthesis of (1S,2S)-2-(5-chloropyridazin-3-yl)cyclopropane-1-carboxamide. The mixture of tert-butyl 7-(aminomethyl)-2,3-dihydro-4H-pyrido[4,3-b][1,4]oxazine-4-carboxylate (100 mg, 0.38 mmol), 1-((6-cyclopropylimidazo[1,2-a]pyridin-2-yl)methyl)-1H-1,2,3-triazole-4-carboxylic acid (117.5 mg, 0.42 mmol), HOBT (76.9 mg, 0.57 mmol), EDCI (109.3 mg, 0.57 mmol), and DIPEA (147 mg, 0.14 mmol) in DMF (5 mL) was stirred at RT for 12 h. Water (50 mL) was added and the mixture was extracted with EtOAc (30 mL×3). The combined organic layers were washed with brine (30 mL), dried over $Na_2SO_4$, filtered and concentrated in vacuo. The residue was purified by Prep-TLC (DCM/MeOH=20/1) to give tert-butyl 7-((1-((6-cyclopropylimidazo[1,2-a]pyridin-2-yl)methyl)-1H-1,2,3-triazole-4-carboxamido)methyl)-2,3-dihydro-4H-pyrido[4,3-b][1,4]oxazine-4-carboxylate(120 mg, yield: 59.6%) as a white solid. ESI-MS [M+H]+: 531.2.

Synthesis of 1-((6-cyclopropylimidazo[1,2-a]pyridin-2-yl)methyl)-N-((3,4-dihydro-2H-pyrido[4,3-b][1,4]oxazin-7-yl)methyl)-1H-1,2,3-triazole-4-carboxamide. The mixture of tert-butyl 7-((1-((6-cyclopropylimidazo[1,2-a]pyridin-2-yl)methyl)-1H-1,2,3-triazole-4-carboxamido)methyl)-2,3-dihydro-4H-pyrido[4,3-b][1,4]oxazine-4-carboxylate (80 mg, 0.15 mmol) and TFA (1 mL) in DCM (5 mL) was stirred at RT for 12 h. The reaction mixture was concentrated to give the crude, which was purified by Prep-TLC (DCM/MeOH=10/1) to give 1 ((6-cyclopropylimidazo[1,2-a]pyridin-2-yl)methyl)-N-((3,4-dihydro-2H-pyrido[4,3-b][1,4]oxazin-7-yl)methyl)-1H-1,2,3-triazole-4-carboxamide(40 mg, yield: 62%) as a white solid. ESI-MS [M+H]+: 431.2. 1H NMR (400 MHz, DMSO) δ 8.96-8.84 (m, 1H), 8.58 (s, 1H), 8.36 (s, 1H), 7.84 (s, 1H), 7.74 (s, 1H), 7.42 (d, J=9.3 Hz, 1H), 7.05-6.98 (m, 1H), 6.59 (s, 1H), 5.86 (s, 1H), 5.74 (s, 2H), 4.32 (d, J=5.9 Hz, 2H), 4.21-4.15 (m, 2H), 3.3-3.27 (m, 2H), 2.02-1.88 (m, 1H), 0.99-0.87 (m, 2H), 0.86-0.64 (m, 2H).

Example 206

Synthesis of 1-((6-cyclopropylimidazo[1,2-a]pyridin-2 yl)methyl)-N-((3,4-dihydro-2H-pyrano[3,2-c]pyridin-7-yl)methyl)-1H-1,2,3-triazole-4-carboxamide (I-150)

Scheme 208

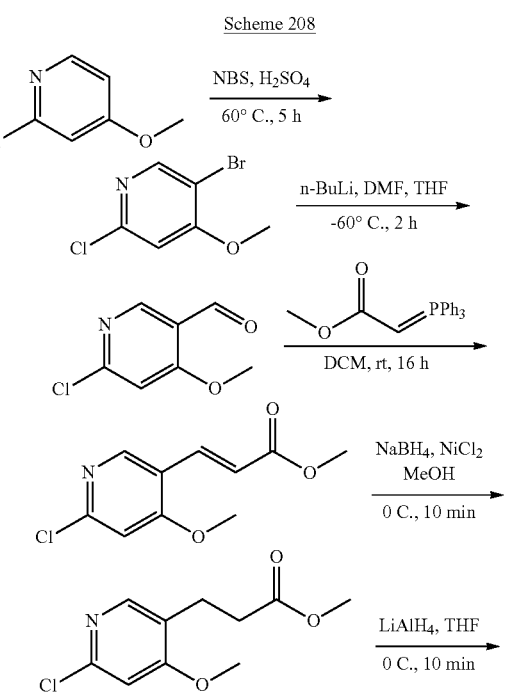

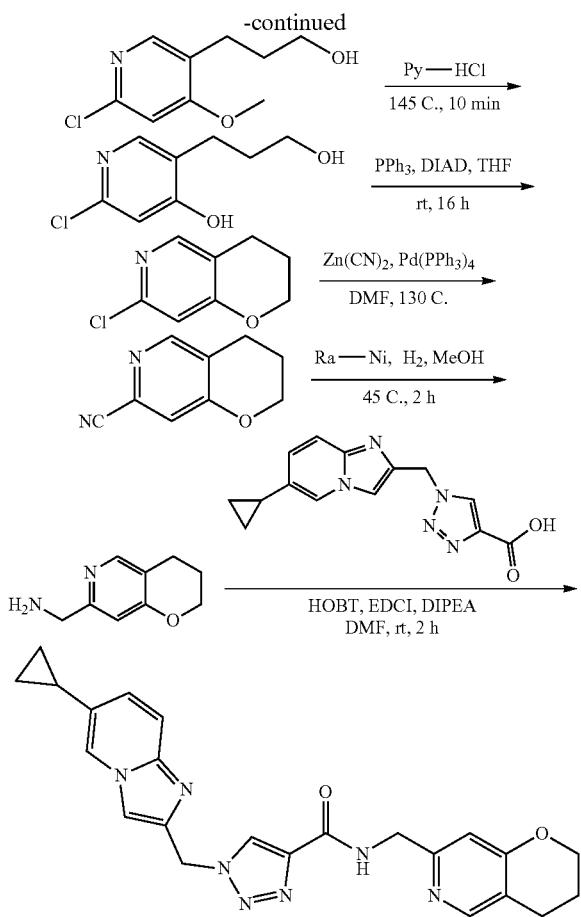

Synthesis of 5-bromo-2-chloro-4-methoxypyridine. To a mixture of 2-chloro-4-methoxypyridine (10 g, 69.9 mmol) in concentrated $H_2SO_4$ (50 mL) was added NBS (13.7 g, 76.9 mmol) at 0° C. The reaction mixture was stirred at 60° C. for 5 h, then cooled to RT, poured into ice-water (500 mL), and extracted with EtOAc (200 mL×3). The combined organic layers were washed with brine (200 mL), dried over anhydrous $Na_2SO_4$, filtered and concentrated. The residue was purified by column chromatography (PE:EtOAc=50:1 to 30:1) to yield 5-bromo-2-chloro-4-methoxypyridine (6.5 g, yield: 42%) as a white solid. ESI-MS [M+H]$^+$: 222.0.

Synthesis of 6-chloro-4-methoxynicotinaldehyde. To a mixture of 5-bromo-2-chloro-4-methoxypyridine (3 g, 13.58 mmol) in THF (30 mL) n-BuLi (2.4 M, 6.8 mL, 16.3 mmol) was added dropwise at −60° C. The reaction mixture was stirred at −60° C. for 5 min, then DMF (1.98 g, 27.1 mmol) was added dropwise at −60° C. The reaction mixture was stirred at −60° C. for an additional 10 min, then a saturated $NH_4Cl$ solution (aq, 10 mL) was added. The mixture was extracted with EtOAc (30 mL×3). The combined organics were concentrated to yield the crude product, which was purified by column chromatography (PE:EtOAc=1:2) to afford 6-chloro-4-methoxynicotinaldehyde (1.5 g, yield: 65%) as a yellow solid. ESI-MS [M+H]$^+$: 172.0.

Synthesis of methyl methyl (E)-3-(6-chloro-4-methoxy-pyridin-3-yl)acrylate. To a mixture of 6-chloro-4-methoxynicotinaldehyde (1.5 g, 8.77 mmol) in DCM (30 mL) was added methyl 2-(triphenyl-15-phosphanylidene)acetate (3 g, 9.2 mmol) at 0° C. The mixture was stirred at 25° C. for 16 h. The reaction mixture was quenched with water (100 mL) and extracted with DCM (50 mL×3). The combined organic layers were washed with brine (50 mL), dried over anhydrous $Na_2SO_4$, filtered and concentrated in vacuo. The residue was purified by column chromatography (PE:EtOAc=1:3) to yield methyl (E)-3-(6-chloro-4-methoxypyridin-3-yl)acrylate (720 mg, yield: 36%) as a yellow solid. ESI-MS [M+H]$^+$: 228.1.

Synthesis of methyl 3-(6-chloro-4-methoxypyridin-3-yl)propanoate. To a mixture of methyl (E)-3-(6-chloro-4-methoxypyridin-3-yl)acrylate (720 mg, 3.17 mmol) in MeOH (10 mL) was added $NiCl_2 \cdot 6H_2O$ (76 mg, 0.032 mmol), followed by $NaBH_4$ (362 mg, 9.51 mmol) at 0° C. The reaction mixture was stirred at 0° C. for 10 min. Water (50 mL) was added and the mixture was extracted with EtOAc (50 mL×3). The combined organic layers were washed with brine (30 mL), dried over anhydrous $Na_2SO_4$, filtered and concentrated to yield methyl 3-(6-chloro-4-methoxypyridin-3-yl)propanoate (600 mg, yield: 83%) as a yellow oil which was used in the next step without further purification. ESI-MS [M+H]$^+$: 230.1.

Synthesis of 3-(6-chloro-4-methoxypyridin-3-yl)propan-1-ol. To a mixture of methyl 3-(6-chloro-4-methoxypyridin-3-yl)propanoate (600 mg, 2.62 mmol) in THF (10 mL) was added $LiAlH_4$ (299 mg, 7.86 mmol) at 0° C. The mixture was stirred at 0° C. for 10 min. Then to the reaction mixture was added water (299 mg), 15% NaOH (aq, 299 mg), and water (897 mg) sequentially, and the mixture was stirred at 0° C. for 30 min. The reaction mixture was filtered and the filtrate concentrated in vacuo to yield the crude product which was purified by column chromatography (PE:EtOAc=1:5) to afford 3-(6-chloro-4-methoxypyridin-3-yl)propan-1-ol (250 mg, yield: 47%) as an oil. ESI-MS [M+H]$^+$: 202.2.

Synthesis of 2-chloro-5-(3-hydroxypropyl)pyridin-4-ol. The mixture of 3-(6-chloro-4-methoxypyridin-3-yl)propan-1-ol (250 mg, 1.24 mmol) and Py-HCl (2.87 g, 24.8 mmol) was heated at 145° C. for 10 min. The reaction mixture was cooled to room temperature, quenched with $NaHCO_3$ solution (20 mL), and extracted with EtOAc (20 mL×3). The combined organic layers were washed with brine (20 mL), dried over anhydrous $Na_2SO_4$, filtered and concentrated in vacuo. The residue was purified by column chromatography (PE:EtOAc=1:5) to afford 2-chloro-5-(3-hydroxypropyl)pyridin-4-ol (130 mg, yield: 56%) as an oil. ESI-MS [M+H]$^+$: 188.1.

Synthesis of 7-chloro-3,4-dihydro-2H-pyrano[3,2-c]pyridine. To a mixture of 2-chloro-5-(3-hydroxypropyl)pyridin-4-ol (130 mg, 0.7 mmol) and $PPh_3$ (263 mg, 1 mmol) in THF (4 mL) was added DIAD (202 mg, 1 mmol) in THF (1 mL) at 0° C. The mixture was stirred at room temperature for 16 h. Water (30 mL) was added and the mixture was extracted with EtOAc (50 mL×3). The combined organic layers were washed with brine (30 mL), dried over anhydrous $Na_2SO_4$, filtered and concentrated. The residue was purified by Prep-TLC (PE:EtOAc=5:1) to yield 7-chloro-3,4-dihydro-2H-pyrano[3,2-c]pyridine (100 mg, yield: 85%) as a yellow solid. ESI-MS [M+H]$^+$: 170.1.

Synthesis of 3,4-dihydro-2H-pyrano[3,2-c]pyridine-7-carbonitrile. To a mixture of 7-chloro-3,4-dihydro-2H-pyrano[3,2-c]pyridine (100 mg, 0.59 mmol) and $Zn(CN)_2$ (137 mg, 1.18 mmol) in DMF (3 mL) was added $Pd(PPh_3)_4$ (136 mg, 0.12 mmol). The reaction mixture was stirred at 130° C. for 4 h under $N_2$, then cooled to RT and filtered. The filtrate was concentrated to yield the crude product which was purified by Prep-TLC (PE:EtOAc=5:1) to afford 3,4-dihydro-2H-pyrano[3,2-c]pyridine-7-carbonitrile (70 mg, yield: 74%) as a yellow solid. ESI-MS [M+H]$^+$: 161.2.

Synthesis of (3,4-dihydro-2H-pyrano[3,2-c]pyridin-7-yl)methanamine. To a mixture of 3,4-dihydro-2H-pyrano[3,2-c]pyridine-7-carbonitrile (70 mg, 0.44 mmol) in MeOH (3 mL) was added Raney Ni (1 g). The mixture was stirred at 45° C. for 2 h under H$_2$, then filtered. The filtrate was concentrated to yield (3,4-dihydro-2H-pyrano[3,2-c]pyridin-7-yl)methanamine (70 mg, yield: 97%) as a yellow oil which was used in the next step without further purification. ESI-MS [M+H]$^+$: 165.2.

Synthesis of 1-((6-cyclopropylimidazo[1,2-a]pyridin-2-yl)methyl)-N-((3,4-dihydro-2H-pyrano[3,2-c]pyridin-7-yl)methyl)-1H-1,2,3-triazole-4-carboxamide. To a mixture of 1-((6-cyclopropylimidazo[1,2-a]pyridin-2-yl)methyl)-1H-1,2,3-triazole-4-carboxylic acid (120 mg, 0.42 mmol) in DMF (5 mL) was added HOBT (85 mg, 0.63 mmol), EDCI (121 mg, 0.63 mmol), DIPEA (163 mg, 1.26 mmol), and (3,4-dihydro-2H-pyrano[3,2-c]pyridin-7-yl)methanamine (70 mg, 0.42 mmol). The mixture was stirred at RT for 3 h. Water (50 mL) was added, and the mixture was extracted with EtOAc (30 mL×3). The combined organic layers were washed with brine (30 mL), dried over anhydrous Na$_2$SO$_4$, filtered and concentrated. The residue was purified by Prep-TLC (DCM:MeOH=10:1) to yield 1-((6-cyclopropylimidazo[1,2-a]pyridin-2-yl)methyl)-N-((3,4-dihydro-2H-pyrano[3,2-c]pyridin-7-yl)methyl)-1H-1,2,3-triazole-4-carboxamide (75 mg, yield: 41%) as a white solid. ESI-MS [M+H]$^+$: 430.2. $^1$H NMR (400 MHz, DMSO) δ 8.78 (t, J=4.9 Hz, 1H), 8.61 (s, 1H), 8.36 (s, 1H), 8.15 (d, J=5.6 Hz, 1H), 7.85 (s, 1H), 7.42 (d, J=9.3 Hz, 1H), 7.04-7.00 (m, 1H), 6.72 (d, J=5.6 Hz, 1H), 5.75 (s, 2H), 4.49 (d, J=4.9 Hz, 2H), 4.22-4.16 (m, 2H), 2.69 (t, J=6.4 Hz, 2H), 2.02-1.90 (m, 3H), 0.96-0.88 (m, 2H), 0.68-0.67 (m, 2H).

Example 207

N-(4-chlorobicyclo[4.2.0]octa-1 (6),2,4-trien-7-yl)-1-((6-cyclopropylimidazo[1,2-a]pyridin-2-yl)methyl)-1H-1,2,3-triazole-4-carboxamide (I-151)

Scheme 209

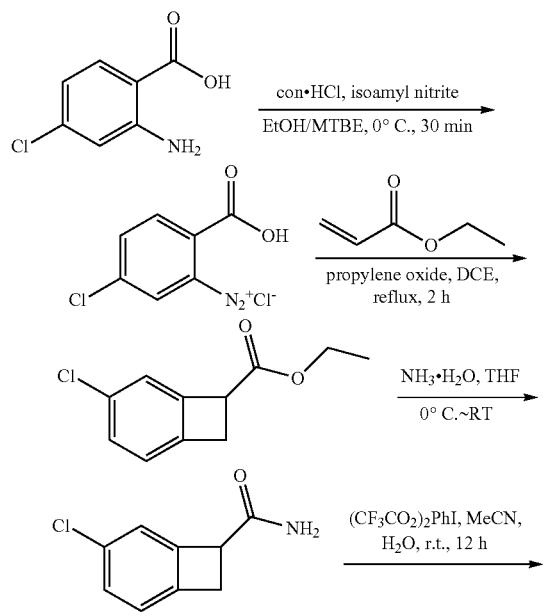

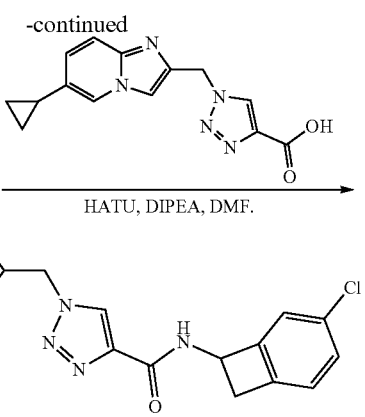

Synthesis of 2-diazonium chloride-4-chlorobenzoic acid. To a mixture of 2-amino-4-chlorobenzoic acid (5.0 g, 29.2 mmol) in a mixture of concentrated HCl, EtOH, and MTBE (5.0 mL/25.0 mL/25.0 mL) was added isoamyl nitrite (5.1 g, 43.8 mmol) at 0° C. under N$_2$. The reaction mixture was stirred at 0° C. for 0.5 h, and then filtered. The filter cake was washed with EtOH and dried to yield 2-diazonium chloride-4-chlorobenzoic acid (4.0 g, crude) as a yellow solid. ESI-MS [M+H]$^+$: 218.2.

Synthesis of ethyl 4-chlorobicyclo[4.2.0]octa-1,3,5-triene-7-carboxylate. A mixture of 2-diazonium chloride-4-chlorobenzoic acid (4.0 g, 18.3 mmol), propylene oxide (1.06 g, 18.3 mmol), and ethyl acrylate (1.83 g, 18.3 mmol) in DCE (50.0 mL) was stirred at 70° C. for 2 h under N$_2$. The mixture was concentrated and purified by silica gel column chromatography (PE/EtOAc=10/1) to give ethyl acrylate (1.2 g, yield: 31%) as light-yellow oil. ESI-MS [M+H]$^+$: 211.1.

Synthesis of 4-chlorobicyclo[4.2.0]octa-1,3,5-trien-7-carboxamide. To a mixture of ethyl 4-chlorobicyclo[4.2.0]octa-1,3,5-triene-7-carboxylate (1.0 g, 4.76 mmol) in THF (20 mL) was added NH$_3$·H$_2$O (5.0 ml) at 0° C. The reaction mixture was stirred at room temperature for 48 h. The mixture was concentrated in vacuo to yield 4-chlorobicyclo[4.2.0]octa-1,3,5-triene-7-carboxamide (700 mg, crude) as a yellow solid. ESI-MS [M+H]$^+$: 182.2.

Synthesis of 4-chlorobicyclo[4.2.0]octa-1,3,5-trien-7-amine. A mixture of 4-chlorobicyclo[4.2.0]octa-1,3,5-triene-7-carboxamide (300 mg, 1.66 mmol) and (CF$_3$CO$_2$)$_2$PhI (1.07 g, 2.49 mmol) in MeCN/H$_2$O (10 mL/2 mL) was stirred at RT for 12 h. The mixture was concentrated and purified by Prep-TLC (DCM/MeOH=10/1) to yield 4-chlorobicyclo[4.2.0]octa-1,3,5-trien-7-amine (100.0 mg, 39%) as a colorless oil. ESI-MS [M+H]$^+$: 154.1.

Synthesis of N-(4-chlorobicyclo[4.2.0]octa-1(6),2,4-trien-7-yl)-1-((6-cyclopropylimidazo[1,2-a]pyridin-2-yl)methyl)-1H-1,2,3-triazole-4-carboxamide. A mixture of 1-((6-cyclopropylimidazo[1,2-a]pyridin-2-yl)methyl)-1H-1,2,3-triazole-4-carboxylic acid (50 mg, 0.18 mmol), 4-chlorobicyclo[4.2.0]octa-1(6),2,4-trien-7-amine (41.3 mg, 0.27 mmol), HATU (102.6 mg, 0.27 mmol), and DIPEA (46.4 mg, 0.36 mmol) in dry DMF (2.0 mL) was stirred at RT for 16 h. The reaction mixture was concentrated to remove DMF and purified by prep-HPLC to yield N-(4-chlorobicyclo[4.2.0]octa-1(6),2,4-trien-7-yl)-1-((6-cyclopropylimidazo[1,2-a]pyridin-2-yl)methyl)-1H-1,2,3-triazole-4-carboxamide (17.6 mg, yield: 23%) as a light yellow solid. ESI-MS [M+H]$^+$: 419.1. Purity: 100%. $^1$H NMR (400 MHz, DMSO) δ 9.23-9.19 (m, 1H), 8.59 (s, 1H), 8.36 (s, 1H), 7.85 (s, 1H), 7.41 (d, J=9.3 Hz, 1H), 7.33-7.24 (m, 2H), 7.21-7.19

(m, 1H), 7.02 (dd, J=9.4, 1.4 Hz, 1H), 5.74 (s, 2H), 5.43-5.39 (m, 1H), 3.56-3.52 (m, J=14.1, 5.1 Hz, 1H), 3.25 (dd, J=14.3, 2.1 Hz, 1H), 1.96-1.90 (m, 1H), 0.95-0.90 (m, 2H), 0.69-0.66 (m, 2H).
Example 208
1-((6-cyclopropyl-8-(4-(2,2,2-trifluoroethyl)piper-azin-1-yl)imidazo[1,2-a]pyridin-2-yl)methyl)-N-((4-(difluoromethoxy)-3 fluoropyridin-2 yl)methyl)-1H-1,2,3-triazole-4-carboxamide (I 152)
Scheme 210
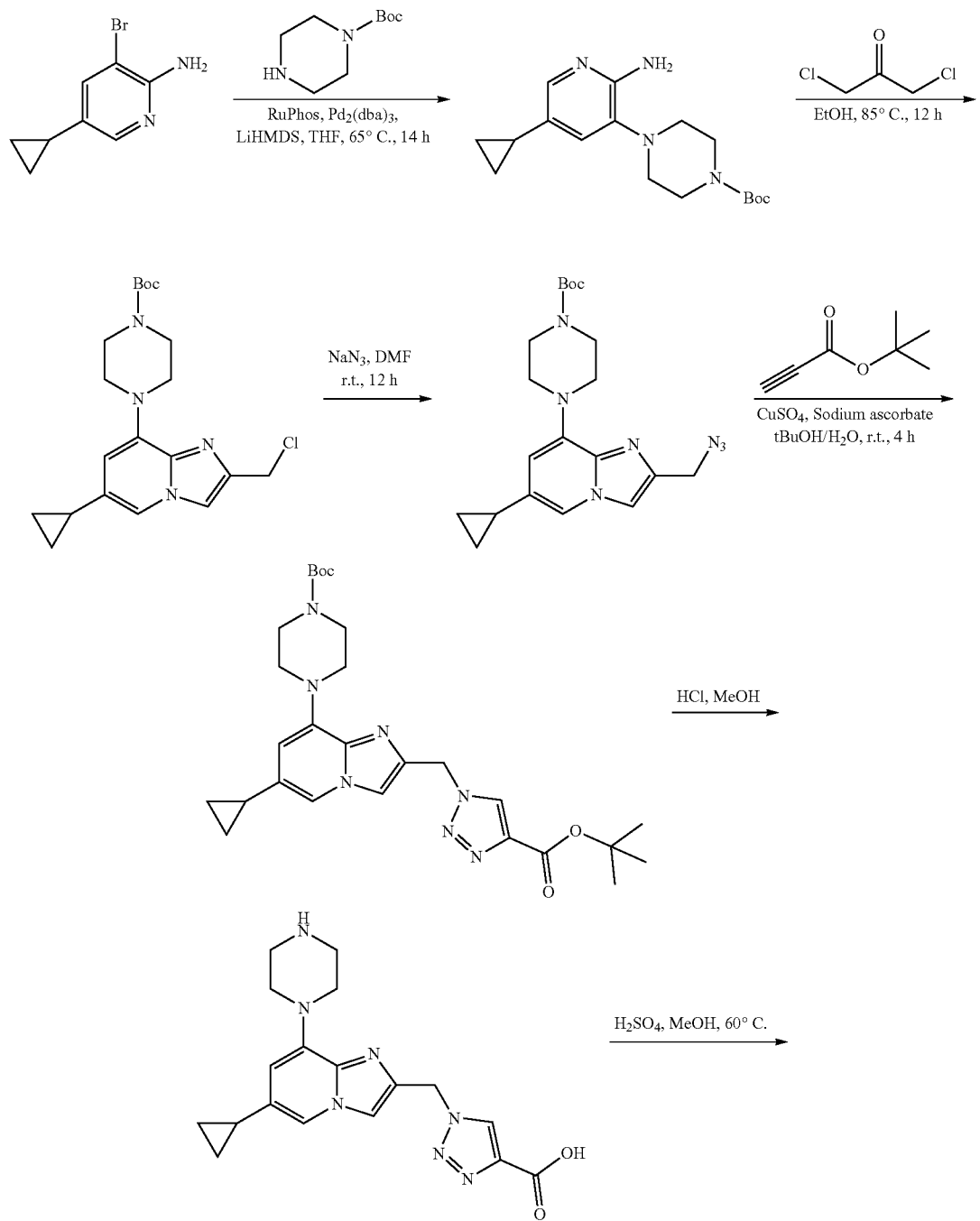

-continued
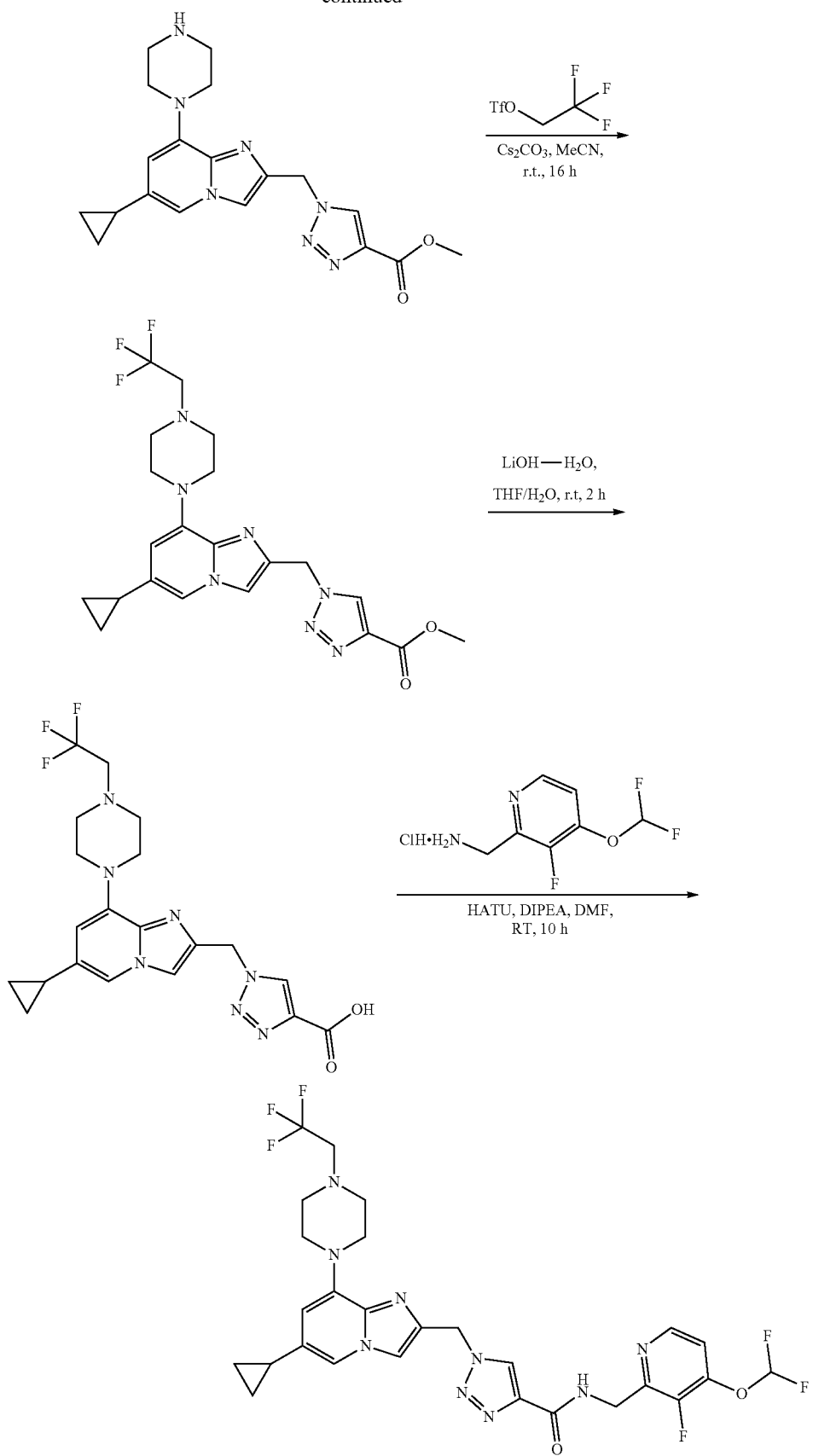

Synthesis of tert-butyl 4-(2-amino-5-cyclopropylpyridin-3-yl)piperazine-1-carboxylate. To a mixture of 3-bromo-5-cyclopropylpyridin-2-amine (3 g, 14.1 mmol), tert-butyl piperazine-1-carboxylate (3.9 g, 21.1 mmol), RuPhos (1.32 g, 2.8 mmol) and $Pd_2(dba)_3$ (1.29 g, 1.41 mmol) in THF (100 mL) was added LiHMDS (1 M in THF) (35.2 mL, 35.2 mmol) dropwise under a $N_2$ atmosphere. The reaction mixture was stirred at 65° C. for 16 h under $N_2$, then quenched with $NH_4Cl$ (80 mL) and extracted with EtOAc (100 mL×3). The combined organic layers were concentrated in vacuo and purified by flash chromatography (PE/EtOAc=0-100%) to yield tert-butyl 4-(2-amino-5-cyclopropylpyridin-3-yl)piperazine-1-carboxylate as a brown solid (4 g, yield: 88%). ESI-MS [M+H]$^+$: 319.2.

Synthesis of tert-butyl 4-(2-(chloromethyl)-6-cyclopropylimidazo[1,2-a]pyridin-8-yl)piperazine-1-carboxylate. A mixture of tert-butyl 4-(2-amino-5-cyclopropylpyridin-3-yl)piperazine-1-carboxylate (3.2 g, 10.06 mmol) and 1,3-dichloropropan-2-one (3.2 ml, 25.40 mmol) in DME (100 mL) was stirred at 85° C. for 12 h under a $N_2$ atmosphere. The reaction mixture was concentrated in vacuo and purified by flash chromatography (DCM/MeO-H=0~10%) to yield tert-butyl 4-(2-(chloromethyl)-6-cyclopropylimidazo[1,2-a]pyridin-8-yl)piperazine-1-carboxylate as a brown solid (2.3 g, yield: 59%). ESI-MS [M+H]$^+$: 391.2.

Synthesis of tert-butyl 4-(2-(azidomethyl)-6-cyclopropylimidazo[1,2-a]pyridin-8-yl)piperazine-1-carboxylate. A mixture of tert-butyl 4-(2-(chloromethyl)-6-cyclopropylimidazo[1,2-a]pyridin-8-yl)piperazine-1-carboxylate (1.2 g, 3.08 mmol) and $NaN_3$ (240 mg, 3.69 mmol) in DMF (10 mL) was stirred at RT for 12 h. $H_2O$ (30 mL) was added to the reaction mixture, and the mixture was extracted with EtOAc (50 mL×3). The combined organic layers were washed with brine (50 mL), dried over $Na_2SO_4$, and concentrated in vacuo to yield tert-butyl 4-(2-(azidomethyl)-6-cyclopropylimidazo[1,2-a]pyridin-8-yl)piperazine-1-carboxylate as a brown solid (1 g, crude), which was used in next step without further purification. ESI-MS [M+H]$^+$: 398.2.

Synthesis of tert-butyl 4-(2-((4-(tert-butoxycarbonyl)-1H-1,2,3-triazol-1-yl)methyl)-6-cyclopropylimidazo[1,2-a]pyridin-8-yl)piperazine-1-carboxylate. A mixture of tert-butyl 4-(2-(azidomethyl)-6-cyclopropylimidazo[1,2-a]pyridin-8-yl)piperazine-1-carboxylate (508 mg, 1.28 mmol), tert-butyl propiolate (212 mg, 1.68 mmol), $CuSO_4$ (111 mg, 0.70 mmol), and sodium ascorbate (153 mg, 0.77 mmol) in t-BuOH/$H_2O$ (8 mL8 mL) was stirred at RT for 4 h under a $N_2$ atmosphere. The reaction mixture was concentrated in vacuo, diluted with $H_2O$ (20 mL), and extracted with DCM/MeOH=10/1 (50 mL×3). The combined organic layers were concentrated in vacuo and purified by Prep-TLC (DCM:MeOH=20:1) to yield tert-butyl 4-(2-((4-(tert-butoxycarbonyl)-1H-1,2,3-triazol-1-yl)methyl)-6-cyclopropylimidazo[1,2-a]pyridin-8-yl)piperazine-1-carboxylate as a yellow solid (400 mg, yield: 59%). ESI-MS [M+H]$^+$: 524.3.

Synthesis of 1-((6-cyclopropyl-8-(piperazin-1-yl)imidazo[1,2-a]pyridin-2-yl)methyl)-1H-1,2,3-triazole-4-carboxylic acid. A mixture of tert-butyl 4-(2-((4-(tert-butoxycarbonyl)-1H-1,2,3-triazol-1-yl)methyl)-6-cyclopropylimidazo[1,2-a]pyridin-8-yl)piperazine-1-carboxylate (523 mg, 1.0 mmol) in HCl (2.0 M in MeOH, 10 mL) was stirred at RT for 16 h. The reaction mixture was concentrated to yield 1-((6-cyclopropyl-8-(piperazin-1-yl)imidazo[1,2-a]pyridin-2-yl)methyl)-1H-1,2,3-triazole-4-carboxylic acid (400 mg, crude) as a yellow solid, which was used for the next step without further purification. ESI-MS [M+H]$^+$: 368.2.

Synthesis of methyl 1-((6-cyclopropyl-8-(piperazin-1-yl)imidazo[1,2-a]pyridin-2-yl)methyl)-1H-1,2,3-triazole-4-carboxylate. A mixture of 1-((6-cyclopropyl-8-(piperazin-1-yl)imidazo[1,2-a]pyridin-2-yl)methyl)-1H-1,2,3-triazole-4-carboxylic acid (367 mg, 1.0 mmol) in a mixture of $H_2SO_4$ and MeOH (1.0 mL/10.0 mL) was stirred at 60° C. for 16 h. The reaction mixture was concentrated to yield methyl 1-((6-cyclopropyl-8-(piperazin-1-yl)imidazo[1,2-a]pyridin-2-yl)methyl)-1H-1,2,3-triazole-4-carboxylate (380 mg, crude) as a yellow solid, which was used for the next step without further purification. ESI-MS [M+H]$^+$: 382.2.

Synthesis of methyl 1-((6-cyclopropyl-8-(4-(2,2,2-trifluoroethyl)piperazin-1-yl)imidazo[1,2-a]pyridin-2-yl)methyl)-1H-1,2,3-triazole-4-carboxylate. A mixture of methyl 1-((6-cyclopropyl-8-(piperazin-1-yl)imidazo[1,2-a]pyridin-2-yl)methyl)-1H-1,2,3-triazole-4-carboxylate (380 mg, 1.0 mmol), 2,2,2-trifluoroethyl trifluoromethanesulfonate (348.0 mg, 1.5 mmol), and $Cs_2CO_3$ (652 mg, 3.0 mmol) in $CH_3CN$ (10 mL) was stirred at RT for 16 h. The reaction mixture was concentrated in vacuo and purified by Prep-TLC (DCM/MeOH=30/1) to yield methyl 1-((6-cyclopropyl-8-(4-(2,2,2-trifluoroethyl)piperazin-1-yl)imidazo[1,2-a]pyridin-2-yl)methyl)-1H-1,2,3-triazole-4-carboxylate (40 mg, 8.6%) as a yellow oil. ESI-MS [M+H]$^+$: 464.2.

Synthesis of 1-((6-cyclopropyl-8-(4-(2,2,2-trifluoroethyl)piperazin-1-yl)imidazo[1,2-a]pyridin-2-yl)methyl)-1H-1,2,3-triazole-4-carboxylic acid. A solution of methyl 1-((6-cyclopropyl-8-(4-(2,2,2-trifluoroethyl)piperazin-1-yl)imidazo[1,2-a]pyridin-2-yl)methyl)-1H-1,2,3-triazole-4-carboxylate (40 mg, 0.086 mmol) and LiOH·$H_2O$ (7.2 mg, 0.172 mmol) in THF/water (5 mL/1 mL) was stirred at RT for 2 h. The pH of the reaction mixture was adjusted to 4 by addition of a 1 M HCl solution. The reaction mixture was concentrated to yield 1-((6-cyclopropyl-8-(4-(2,2,2-trifluoroethyl)piperazin-1-yl)imidazo[1,2-a]pyridin-2-yl)methyl)-1H-1,2,3-triazole-4-carboxylic acid (40 mg, crude) as a yellow oil. ESI-MS [M+H]$^+$: 450.1.

Synthesis of 1-((6-cyclopropyl-8-(4-(2,2,2-trifluoroethyl)piperazin-1-yl)imidazo[1,2-a]pyridin-2-yl)methyl)-N-((4-(difluoromethoxy)-3-fluoropyridin-2-yl)methyl)-1H-1,2,3-triazole-4-carboxamide. A mixture of 1-((6-cyclopropyl-8-(4-(2,2,2-trifluoroethyl)piperazin-1-yl)imidazo[1,2-a]pyridin-2-yl)methyl)-1H-1,2,3-triazole-4-carboxylic acid (40 mg, 0.089 mmol), (4-(difluoromethoxy)-3-fluoropyridin-2-yl)methanamine hydrochloride (30.4 mg, 0.134 mmol), HATU (67.6 mg, 0.178 mmol), and DIPEA (57.4 mg, 0.445 mmol) in dry DMF (2.0 mL) was stirred at RT for 16 h. The mixture was concentrated to remove DMF, and purified by prep-HPLC to yield 1-((6-cyclopropyl-8-(4-(2,2,2-trifluoroethyl)piperazin-1-yl)imidazo[1,2-a]pyridin-2-yl)methyl)-N-((4-(difluoromethoxy)-3-fluoropyridin-2-yl)methyl)-1H-1,2,3-triazole-4-carboxamide (2.1 mg, yield: 3.8%) as a white solid. ESI-MS [M+H]$^+$: 624.1. Purity: 99.3%. $^1$H NMR (400 MHz, DMSO) δ 8.89 (s, 1H), 8.56-8.55 (m, 1H), 8.35-8.34 (m, 2H), 7.92 (s, 1H), 7.74 (d, J=2.5 Hz, 1H), 7.36 (s, 1H), 6.21 (s, 1H), 5.73 (s, 2H), 4.64 (s, 2H), 3.46 (s, 4H), 3.18-3.17 (m, 4H), 2.80 (s, 2H), 2.08 (d, J=2.7 Hz, 1H), 0.89-0.87 (m, 2H), 0.70-0.66 (m, 2H).

Example 209

1-((6-cyclopropyl-8-(4-methylpiperazin-1-yl)imidazo[1,2-a]pyridin-2-yl)methyl)-N-((4-(difluoromethoxy)-3 fluoropyridin-2-yl)methyl)-1H-1,2,3-triazole-4-carboxamide (I-153)

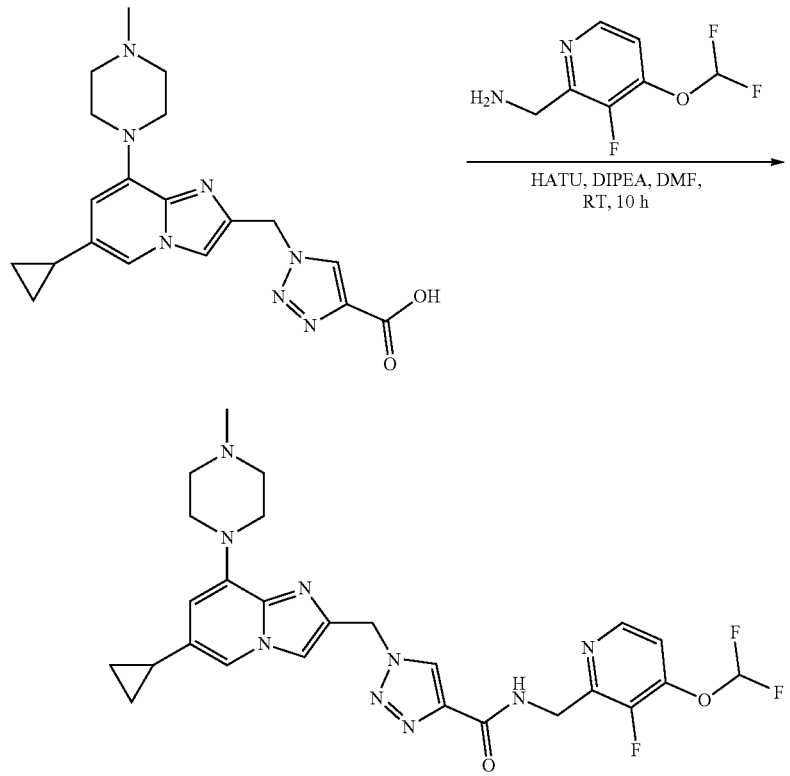

Synthesis of 1-((6-cyclopropyl-8-(4-methylpiperazin-1-yl)imidazo[1,2-a]pyridin-2-yl)methyl)-N-((4-(difluoromethoxy)-3-fluoropyridin-2-yl)methyl)-1H-1,2,3-triazole-4-carboxamide. A mixture of 1-((6-cyclopropyl-8-(4-methylpiperazin-1-yl)imidazo[1,2-a]pyridin-2-yl)methyl)-1H-1,2,3-triazole-4-carboxylic acid (50 mg, 0.13 mmol), HATU (100 mg, 0.26 mmol), and DIPEA (50 mg, 0.39 mmol) in DMF (3 mL) was stirred at RT for 2 h. Then (4-(difluoromethoxy)-3-fluoropyridin-2-yl)methanamine (15.6 mg, 0.081 mmol) was added into the mixture and stirred for another 8 h. The mixture was diluted with EtOAc (30 mL) and washed with brine (10 mL×3). The organic layer was concentrated and purified by Prep-TLC (DCM:MeOH=10:1) to yield 1-((6-cyclopropyl-8-(4-methylpiperazin-1-yl)imidazo[1,2-a]pyridin-2-yl)methyl)-N-((4-(difluoromethoxy)-3-fluoropyridin-2-yl)methyl)-1H-1,2,3-triazole-4-carboxamide as a white solid (35 mg, yield: 48%). ESI-MS [M+H]$^+$: 556.2. Purity: 92.58%. $^1$H NMR (400 MHz, d6-DMSO) δ 8.88 (t, J=5.7 Hz, 1H), 8.53 (s, 1H), 8.32 (d, J=5.5 Hz, 1H), 7.88 (s, 1H), 7.70 (s, 1H), 7.35-7.32 (m, 1H), 6.17-6.16 (m, 1H), 5.70 (s, 2H), 4.62-4.60 (m, 2H), 3.42 (s, 4H), 2.48-2.47 (m, 4H), 2.20 (s, 3H), 1.87-1.80 (m, 1H), 0.87-0.82 (m, 2H), 0.66-0.60 (m, 2H).

Example 210

(R)-1-((6-cyclopropylimidazo[1,2-a]pyridin-2-yl)methyl)-N-(3-methyl-2,4,5,6-tetrahydrocyclopenta[c]pyrazol-6 yl)-1H-1,2,3-triazole-4-carboxamide (I-154)

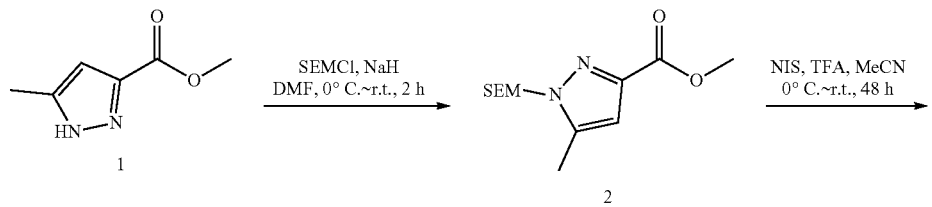

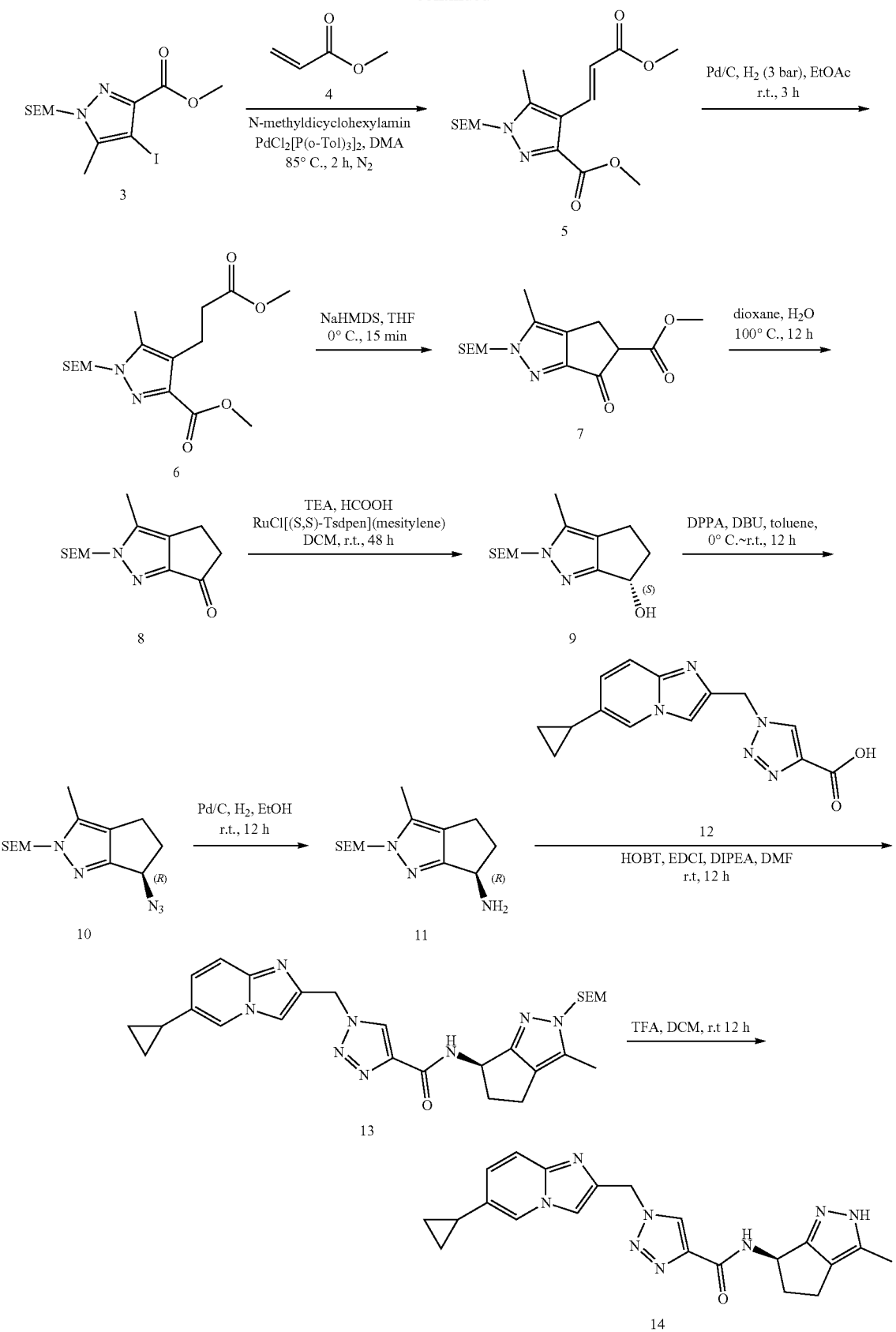

Synthesis of methyl 5-methyl-1-((2-(trimethylsilyl)ethoxy)methyl)-1H-pyrazole-3-carboxylate. NaH (5.2 g, 130 mmol) was added portionwise to DMF (100 mL). The mixture was stirred for 10 min, cooled to 0° C., and treated dropwise with a solution of methyl 5-methyl-1H-pyrazole-3-carboxylate (14 g, 100 mmol) in DMF (100 mL). After stirring for 20 min, SEMCl (21.7 g, 130 mmol) was added dropwise. The reaction mixture was stirred for 2 h, then quenched with $H_2O$ (200 mL) and extracted with EtOAc (200 mL×3). The combined organic layers were washed with brine (200 mL), dried over $Na_2SO_4$, and concentrated in vacuo to yield the crude product, which was purified with flash chromatography (PE:EtOAc=2:1) to afford methyl 5-methyl-1-((2-(trimethylsilyl)ethoxy)methyl)-1H-pyrazole-3-carboxylate as a yellow oil (21.7 g, 80%). ESI-MS [M+H]$^+$: 271.1.

Synthesis of methyl 4-iodo-5-methyl-1-((2-(trimethylsilyl)ethoxy)methyl)-1H-pyrazole-3-carboxylate. To a solution of methyl 5-methyl-1-((2-(trimethylsilyl)ethoxy)methyl)-1H-pyrazole-3-carboxylate (21.7 g, 80 mmol) in MeCN (300 mL) was added TFA (912 mg, 8 mmol) and NIS (21.6 g, 96 mmol). The reaction mixture was stirred at room temperature for 48 h, then quenched with $H_2O$ (300 mL). The aqueous phase was extracted with EtOAc (100 mL×3), the combined organic layers washed with brine (200 mL), dried over $Na_2SO_4$, and concentrated in vacuo to yield the crude product, which was purified with flash chromatography (PE:EtOAc=2:1) to afford methyl 4-iodo-5-methyl-1-((2-(trimethylsilyl)ethoxy)methyl)-1H-pyrazole-3-carboxylate as a colorless oil (16.6 g, 52%). ESI-MS [M+H]$^+$: 397.2.

Synthesis of methyl (E)-4-(3-methoxy-3-oxoprop-1-en-1-yl)-5-methyl-1-((2-(trimethylsilyl)ethoxy)methyl)-1H-pyrazole-3-carboxylate. Methyl 4-iodo-5-methyl-1-((2-(trimethylsilyl)ethoxy)methyl)-1H-pyrazole-3-carboxylate (16.6 g, 41.9 mmol), methyl acrylate (6.3 g. 62.85 mmol), and N-methyldicyclohexylamine (12.2 g, 62.85 mmol) were dissolved in DMA (100 mL) and $H_2O$ (25 mL). The reaction mixture was purged for 10 min with $N_2$, then $PdCl_2[P(o-Tol)_3]_2$ (988 mg, 1.26 mmol) was added and the mixture stirred for 2 h at 85° C. The reaction mixture was diluted with EtOAc (50 mL) and washed with a 1 M solution of $H_3PO_4$ (50 mL, aqueous) and brine (50 mL). After drying over $Na_2SO_4$, the reaction mixture was concentrated in vacuo to yield the crude product, which was purified with flash chromatography (PE:EtOAc=2:1) to afford methyl (E)-4-(3-methoxy-3-oxoprop-1-en-1-yl)-5-methyl-1-((2-(trimethylsilyl)ethoxy)methyl)-1H-pyrazole-3-carboxylate as a yellow oil (13.5 g, 91%). ESI-MS [M+H]$^+$: 355.2.

Synthesis of methyl 4-(3-methoxy-3-oxopropyl)-5-methyl-1-((2-(trimethylsilyl)ethoxy)methyl)-1H-pyrazole-3-carboxylate. Methyl (E)-4-(3-methoxy-3-oxoprop-1-en-1-yl)-5-methyl-1-((2-(trimethylsilyl)ethoxy)methyl)-1H-pyrazole-3-carboxylate (13.5 g, 3.8 mmol) and Pd/C (2.25 g) in EtOAc (100 ml) was stirred at room temperature for 3 h under $H_2$. The reaction mixture was filtered, and the filtrate is concentrated to yield methyl 4-(3-methoxy-3-oxopropyl)-5-methyl-1-((2-(trimethylsilyl)ethoxy)methyl)-1H-pyrazole-3-carboxylate as a colorless oil (15 g, crude). ESI-MS [M+H]$^+$: 357.1.

Synthesis of methyl 3-methyl-6-oxo-2-((2-(trimethylsilyl)ethoxy)methyl)-2,4,5,6-tetrahydrocyclopenta[c]pyrazole-5-carboxylate. Methyl 4-(3-methoxy-3-oxopropyl)-5-methyl-1-((2-(trimethylsilyl)ethoxy)methyl)-1H-pyrazole-3-carboxylate (15 g, 42.1 mmol) in THF (200 mL) was cooled to 0° C., treated with NaHMDS (40.7 mL, 2.0 M in THF), and stirred for 15 min. The reaction mixture was poured into a 1 M solution of $H_3PO_4$ (200 mL, aqueous) under ice-cooling and vigorous stirring. The organic phase was separated, washed with brine (200 mL), and dried with $Na_2SO_4$. The reaction mixture was concentrated in vacuo to yield the crude product, which was purified with flash chromatography (PE:EtOAc=2:1) to afford methyl 3-methyl-6-oxo-2-((2-(trimethylsilyl)ethoxy)methyl)-2,4,5,6-tetrahydrocyclopenta[c]pyrazole-5-carboxylate as a yellow oil (2.8 g, 20%). ESI-MS [M+H]$^+$: 325.2.

Synthesis of 3-methyl-2-((2-(trimethylsilyl)ethoxy)methyl)-4,5-dihydrocyclopenta[c]pyrazol-6(2H)-one. Methyl 3-methyl-6-oxo-2-((2-(trimethylsilyl)ethoxy)methyl)-2,4,5,6-tetrahydrocyclopenta[c]pyrazole-5-carboxylate (2.8 g, 8.6 mmol) in dioxane/$H_2O$ (30 mL/1 mL) was stirred at 100° C. for 12 h. The reaction mixture was concentrated in vacuo to yield the crude product, which was purified with flash chromatography (PE:EtOAc=2:1) to afford 3-methyl-2-((2-(trimethylsilyl)ethoxy)methyl)-4,5-dihydrocyclopenta[c]pyrazol-6(2H)-one as a colorless oil (1.3 g, 57%). ESI-MS [M+H]$^+$: 267.1.

Synthesis of (S)-3-methyl-2-((2-(trimethylsilyl)ethoxy)methyl)-2,4,5,6-tetrahydrocyclopenta[c]pyrazol-6-ol. To a solution of TEA (990 mg, 9.8 mmol) in DCM (20 mL) was added HCOOH (676 mg, 14.7 mmol), followed by 3-methyl-2-((2-(trimethylsilyl)ethoxy)methyl)-4,5-dihydrocyclopenta[c]pyrazol-6(2H)-one (1.3 g. 4.9 mmol). After degassing with $N_2$ for 10 min, RuCl[(S,S)-Tsdpen](mesitylene) and N-methyldicyclohexylamine (156 mg, 0.245 mmol) were added and the reaction mixture was stirred at room temperature for 48 h. Then, the reaction mixture was treated with 1 M $NaHCO_3$ (10 mL, aqueous) under vigorous stirring. The phases were separated, and the aqueous phase extracted with DCM (20 mL×3). The combined organic phases were washed with water (50 mL) and brine (50 mL). After drying over $Na_2SO_4$, the reaction mixture was concentrated in vacuo to yield crude product which was purified with flash chromatography (PE:EtOAc=1:1) to afford (S)-3-methyl-2-((2-(trimethylsilyl)ethoxy)methyl)-2,4,5,6-tetrahydrocyclopenta[c]pyrazol-6-ol as a yellow oil (740 mg, 5%). ESI-MS [M+H]$^+$: 269.1.

Synthesis of (R)-6-azido-3-methyl-2-((2-(trimethylsilyl)ethoxy)methyl)-2,4,5,6-tetrahydrocyclopenta[c]pyrazole. Under $N_2$, DBU (395 mg, 2.6 mmol) was added to a solution of (S)-3-methyl-2-((2-(trimethylsilyl)ethoxy)methyl)-2,4,5,6-tetrahydrocyclopenta[c]pyrazol-6-ol (700 mg, 395 mmol) in toluene (15 mL). The reaction mixture was cooled to 0° C. and DPPA (715 mg, 2.6 mmol) was added dropwise over 5 min. The reaction mixture was stirred at room temperature for 12 h. Then MeOH (1 mL) was added and the reaction mixture stirred for an additional 1 h. The mixture was extracted with EtOAc (20 mL×3). The combined organic phases were washed with brine (50 mL), dried over $Na_2SO_4$, and concentrated in vacuo to yield the crude product. The crude product was chromatographed on $Al_2O_3$ (DCM) to afford (R)-6-azido-3-methyl-2-((2-(trimethylsilyl)ethoxy)methyl)-2,4,5,6-tetrahydrocyclopenta[c]pyrazole as a colorless oil (500 mg, 65%). ESI-MS [M+H]$^+$: 294.1.

Synthesis of (R)-3-methyl-2-((2-(trimethylsilyl)ethoxy)methyl)-2,4,5,6-tetrahydrocyclopenta[c]pyrazol-6-amine. A mixture of (R)-6-azido-3-methyl-2-((2-(trimethylsilyl)ethoxy)methyl)-2,4,5,6-tetrahydrocyclopenta[c]pyrazole (500 mg, 1.71 mmol) and Pd/C (100 mg) in EtOH (25 ml) was stirred at room temperature for 12 h under $H_2$. The reaction mixture was filtered, and the filtrate was concentrated to yield (R)-3-methyl-2-((2-(trimethylsilyl)ethoxy)methyl)-2,4,5,6-tetrahydrocyclopenta[c]pyrazol-6-amine as a colorless oil (450 mg, crude). ESI-MS [M+H]$^+$: 268.1.

415

Synthesis of (R)-1-((6-cyclopropylimidazo[1,2-a]pyridin-2-yl)methyl)-N-(3-methyl-2-((2-(trimethylsilyl)ethoxy)methyl)-2,4,5,6-tetrahydrocyclopenta[c]pyrazol-6-yl)-1H-1,2,3-triazole-4-carboxamide. A mixture of 1-((6-cyclopropylimidazo[1,2-a]pyridin-2-yl)methyl)-1H-1,2,3-triazole-4-carboxylic acid (105 mg, 0.37 mmol), HOBT (125 mg, 0.925 mmol), EDCI (178 mg, 0.925 mmol), and DIPEA (239 mg, 1.85 mmol) in DMF (10 mL) was stirred at room temperature for 10 min. Then (R)-3-methyl-2-((2-(trimethylsilyl)ethoxy)methyl)-2,4,5,6-tetrahydrocyclopenta[c]pyrazol-6-amine (100 mg, 0.37 mmol) was added. The reaction mixture was stirred at room temperature for another 12 h, then quenched with H$_2$O (30 mL). The aqueous phase was extracted with EtOAc (30 mL×3). The combined organic layers were washed with brine (50 mL), dried over Na$_2$SO$_4$, and concentrated in vacuo to yield crude product, which was purified with Prep-TLC (DCM:MeOH=10:1) to afford (R)-1-((6-cyclopropylimidazo[1,2-a]pyridin-2-yl)methyl)-N-(3-methyl-2-((2-(trimethylsilyl)ethoxy)methyl)-2,4,5,6-tetrahydrocyclopenta[c]pyrazol-6-yl)-1H-1,2,3-triazole-4-carboxamide as a white solid (150 mg, 76%). ESI-MS [M+H]$^+$: 533.2.

Synthesis of (R)-1-((6-cyclopropylimidazo[1,2-a]pyridin-2-yl)methyl)-N-(3-methyl-2,4,5,6-tetrahydrocyclopenta[c]pyrazol-6-yl)-1H-1,2,3-triazole-4-carboxamide. To a mixture of (R)-1-((6-cyclopropylimidazo[1,2-a]pyridin-2-yl)methyl)-N-(3-methyl-2-((2-(trimethylsilyl)ethoxy)methyl)-2,4,5,6-tetrahydrocyclopenta[c]pyrazol-6-yl)-1H-1,2,3-triazole-4-carboxamide (150 mg, 0.28 mmol) in DCM (10 mL) was added TFA (5 mL) at 0° C. The reaction mixture was stirred at room temperature for 12 h. The reaction mixture was concentrated, the residue was dissolved in DCM, and the pH adjusted to 7-8 with NH$_3$ in MeOH, then the solvent was evaporated in vacuo. The residue was purified with Prep-TLC (DCM:MeOH=10:1) to yield (R)-1-((6-cyclopropylimidazo[1,2-a]pyridin-2-yl)methyl)-N-(3-methyl-2,4,5,6-tetrahydrocyclopenta[c]pyrazol-6-yl)-1H-1,2,3-triazole-4-carboxamide as a white solid (50 mg, 44.6%). ESI-MS [M+H]$^+$: 403.2. Purity: 99.17 (214 nm) 98.53 (254 nm). $^1$H NMR (400 MHz, DMSO) δ 12.12 (s, 1H), 8.57 (s, 1H), 8.45 (s, 1H), 8.36 (s, 1H), 7.83 (s, 1H), 7.41 (d, J=9.4 Hz, 1H), 7.02 (d, J=9.1 Hz, 1H), 5.73 (s, 2H), 5.28 (d, J=5.8 Hz, 1H), 2.68-2.56 (m, 2H), 2.46-2.36 (m, 2H), 2.14 (s, 3H), 1.98-1.87 (m, 1H), 1.00-0.86 (m, 2H), 0.74-0.61 (m, 2H).

Example 211

(R)-1-((6-cyclopropylimidazo[1,2-a]pyridin-2-yl)methyl)-N-(3-methyl-2,4,5,6-tetrahydrocyclopenta[c]pyrazol-6 yl)-1H pyrazole-4-carboxamide (I-155)

Scheme 213

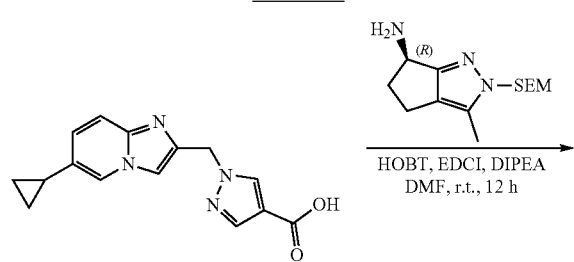

416

-continued

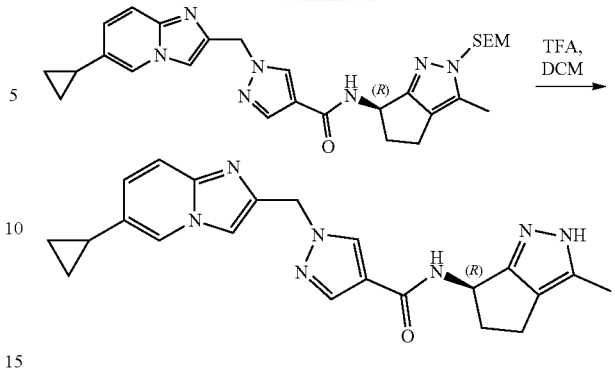

Synthesis of (R)-1-((6-cyclopropylimidazo[1,2-a]pyridin-2-yl)methyl)-N-(3-methyl-2-((2-(trimethylsilyl)ethoxy)methyl)-2,4,5,6-tetrahydrocyclopenta[c]pyrazol-6-yl)-1H-pyrazole-4-carboxamide. To a solution of 1-((6-cyclopropylimidazo[1,2-a]pyridin-2-yl)methyl)-1H-pyrazole-4-carboxylic acid (50 mg, 0.18 mmol) in DMF (5 mL) was added (R)-3-methyl-2-((2-(trimethylsilyl)ethoxy)methyl)-2,4,5,6-tetrahydrocyclopenta[c]pyrazol-6-amine (47 mg, 0.18 mmol), DIPEA (114 mg, 0.89 mmol), HOBT (60 mg, 0.44 mmol), and EDCI (85 mg, 0.44 mmol). The reaction mixture was stirred at room temperature overnight, then diluted with EtOAc (50 mL), washed with brine (15 mL×3), dried over anhydrous Na$_2$SO$_4$, filtered and concentrated in vacuo. The residue was purified by Prep-TLC (DCM:MeOH=10:1) to give (R)-1-((6-cyclopropylimidazo[1,2-a]pyridin-2-yl)methyl)-N-(3-methyl-2-((2-(trimethylsilyl)ethoxy)methyl)-2,4,5,6-tetrahydrocyclopenta[c]pyrazol-6-yl)-1H-pyrazole-4-carboxamide as yellow oil (56 mg, 59% yield). ESI-MS [M+H]$^+$: 532.3.

Synthesis of (R)-1-((6-cyclopropylimidazo[1,2-a]pyridin-2-yl)methyl)-N-(3-methyl-2,4,5,6-tetrahydrocyclopenta[c]pyrazol-6-yl)-1H-pyrazole-4-carboxamide. To a solution of (R)-1-((6-cyclopropylimidazo[1,2-a]pyridin-2-yl)methyl)-N-(3-methyl-2-((2-(trimethylsilyl)ethoxy)methyl)-2,4,5,6-tetrahydrocyclopenta[c]pyrazol-6-yl)-1H-pyrazole-4-carboxamide (56 mg, 0.11 mmol) in DCM (5 mL) was added TFA (0.5 mL). The reaction mixture was stirred at room temperature for 16 h, then concentrated in vacuo. Ice water (20 mL) was added to the residue and the mixture was adjusted to pH ~10 by addition of a saturated solution of NaHCO$_3$(aq.). The reaction mixture was extracted with DCM (2×20 mL). The combined organic layers were dried with anhydrous Na$_2$SO$_4$, filtered and concentrated in vacuo. The residue was purified by Prep-TLC to yield (R)-1-((6-cyclopropylimidazo[1,2-a]pyridin-2-yl)methyl)-N-(3-methyl-2,4,5,6-tetrahydrocyclopenta[c]pyrazol-6-yl)-1H-pyrazole-4-carboxamide (22 mg, 52% yield) as white solid. ESI-MS [M+H]$^+$: 402.2. $^1$H NMR (400 MHz, DMSO) δ 12.18 (s, 1H), 8.40 (s, 1H), 8.33 (d, J=8.2 Hz, 1H), 8.24 (s, 1H), 7.89 (s, 1H), 7.79 (s, 1H), 7.46 (d, J=9.3 Hz, 1H), 7.11 (d, J=9.2 Hz, 1H), 5.43 (s, 2H), 5.28-5.23 (m, 1H), 2.73-2.67 (m, 1H), 2.62-2.54 (m, 2H), 2.45-2.38 (m, 1H), 2.13 (s, 3H), 1.98-1.91 (m, 1H), 0.96-0.91 (m, 2H), 0.71-0.67 (m, 2H).

Example 212

Inhibitory Activity of Exemplary Compounds against Plasma Kallikrein. Example compounds were evaluated for inhibition of the human activated kallikrein enzyme in two formats of an assay employing a fluorogenic peptide substrate. In one assay format, the concentrations of reagents were as follows: 20 mM Tris pH 7.5, 1 mM EDTA, 150 mM sodium chloride, 0.1% PEG-400, 0.1% Triton X-100, 500 pM activated kallikrein enzyme, 300 uM Pro-Phe-Arg-7-amido-4-methylcoumarin substrate. Prior to reaction initiation with substrate, enzyme and inhibitors were preincubated for 30 min at RT. After initiation with substrate, reactions were incubated for 10 min at RT and fluorescence emission at 460 nm from 380 nm excitation measured with a microplate reader. In another assay format, the concentrations of reagents were as follows: 20 mM Tris pH 7.5, 1 mM EDTA, 150 mM sodium chloride, 0.1% PEG-400, 0.1% Triton X-100, 5 pM activated kallikrein enzyme, 300 uM Pro-Phe-Arg-7-amido-4-methylcoumarin substrate. Prior to reaction initiation with substrate, enzyme and inhibitors were preincubated for 30 min at RT. After initiation with substrate, reactions were incubated for 18 h at RT and fluorescence emission at 460 nm from 380 nm excitation measured with a microplate reader.

Table II provides the results of the assay in the format with 500 pM activated kallikrein assay. For the compounds listed in Table II, the $EC_{50}$ values are reported according to the following ranges: A≤1.0 nM; 1.0 nM<B≤10 nM; 10 nM<C≤100 nM; 100 nM<D≤2000 nM; 2000 nM<E≤7100 nM; F>7100 nM.

TABLE II

| Compound | Primary Dose Response Assay: Average EC50 |
|---|---|
| I-1 | A |
| I-2 | B |
| I-3 | C |
| I-4 | B |
| I-5 | C |
| I-6 | F |
| I-7 | C |
| I-8 | B |
| I-9 | C |
| I-10 | A |
| I-11 | F |
| I-12 | B |
| I-13 | B |
| I-14 | B |
| I-15 | D |
| I-16 | A |
| I-17 | A |
| I-18 | D |
| I-19 | E |
| I-20 | E |
| I-21 | E |
| I-22 | A |
| I-23 | A |
| I-24 | E |
| I-25 | A |
| I-26 | A |
| I-27 | A |
| I-28 | A |
| I-29 | B |
| I-30 | D |
| I-31 | B |
| I-32 | B |
| I-33 | E |
| I-34 | F |
| I-35 | F |
| I-36 | F |
| I-37 | F |
| I-38 | F |
| I-39 | C |
| I-40 | C |
| I-41 | E |
| I-42 | F |
| I-43 | F |
| I-44 | F |
| I-45 | B |
| I-46 | D |
| I-47 | F |
| I-48 | B |
| I-49 | C |
| I-50 | F |
| I-51 | D |
| I-52 | A |
| I-53 | D |
| I-54 | A |
| I-55 | A |
| I-56 | F |
| I-57 | B |
| I-58 | E |
| I-59 | F |
| I-60 | F |
| I-61 | A |
| I-62 | B |
| I-63 | D |
| I-64 | C |
| I-65 | C |
| I-66 | D |
| I-67 | B |
| I-68 | A |
| I-69 | A |
| I-70 | C |
| I-71 | A |
| I-72 | D |
| I-73 | C |
| I-74 | B |
| I-75 | B |
| I-76 | A |
| I-77 | F |
| I-78 | C |
| I-79 | C |
| I-80 | D |
| I-81 | A |
| I-82 | E |
| I-83 | C |
| I-84 | D |
| I-85 | A |
| I-86 | B |
| I-87 | C |
| I-88 | B |
| I-89 | A |
| I-90 | A |
| I-91 | A |
| I-92 | A |
| I-93 | A |
| I-94 | A |
| I-95 | B |
| I-96 | B |
| I-97 | C |
| I-98 | D |
| I-99 | A |
| I-100 | D |
| I-101 | B |
| I-102 | C |
| I-103 | A |
| I-104 | B |
| I-105 | A |
| I-106 | A |
| I-107 | A |
| I-108 | B |
| I-109 | A |
| I-110 | B |
| I-111 | A |
| I-112 | A |
| I-113 | A |
| I-114 | D |
| I-115 | A |
| I-116 | A |
| I-117 | F |
| I-118 | A |
| I-119 | B |
| I-120 | C |
| I-121 | D |

TABLE II-continued

| Compound | Primary Dose Response Assay: Average EC50 |
|---|---|
| I-122 | B |
| I-123 | C |
| I-124 | C |
| I-125 | B |
| I-126 | D |
| I-127 | C |
| I-128 | D |
| I-129 | D |
| I-130 | E |
| I-131 | D |
| I-132 | D |
| I-133 | E |
| I-134 | E |
| I-135 | C |
| I-136 | D |
| I-137 | D |
| I-138 | B |
| I-139 | A |
| I-140 | D |
| I-141 | C |
| I-142 | E |
| I-143 | D |
| I-144 | B |
| I-145 | D |
| I-146 | B |
| I-147 | D |
| I-148 | D |
| I-149 | C |
| I-150 | D |
| I-151 | D |
| I-152 | D |
| I-153 | B |
| I-154 | B |
| I-155 | B |

Example 213

Comparative Inhibitory Activity of Various Compounds against Plasma Kallikrein. Table III provides comparative plasma kallikrein inhibition potency in the assay format with 500 pM activated kallikrein assay (described in detail in the preceding example). For the compounds listed in Table III, the $EC_{50}$ values are reported according to the following ranges: A≤1.0 nM; 1.0 nM<B≤10 nM; 10 nM<C≤100 nM; 100 nM<D≤2000 nM; 2000 nM<E≤7100 nM; F>7100 nM.

TABLE III

| Compound | Primary Dose Response Assay: Average EC50 |
|---|---|
| 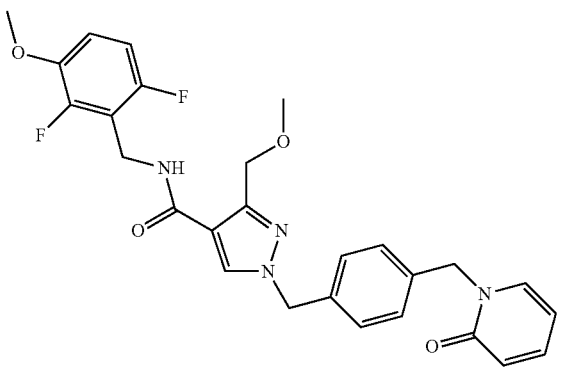 [SMILES: COCc1nn(Cc2ccc(Cn3ccccc3=O)cc2)cc1C(=O)NCc1c(F)ccc(OC)c1F] | C |
| 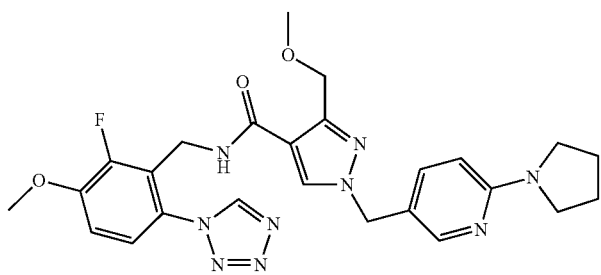 [SMILES: COCc1nn(Cc2ccc(N3CCCC3)nc2)cc1C(=O)NCc1c(-n2cnnn2)ccc(OC)c1F] | B |

TABLE III-continued

| Compound | Primary Dose Response Assay: Average EC50 |
|---|---|
| (structure) | C |
| (structure) | B |
| (structure) | C |
| (structure) | C |

TABLE III-continued
| Compound | Primary Dose Response Assay: Average EC50 |
|---|---|
| 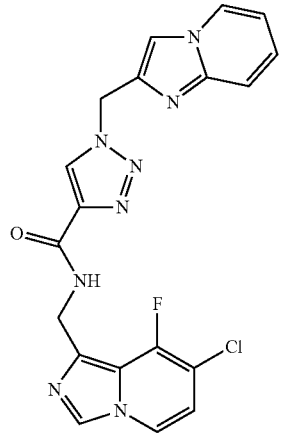 [SMILES: O=C(NCc1ncn2ccc(Cl)c(F)c12)c1cn(Cc2cn3ccccc3n2)nn1] | C |
| 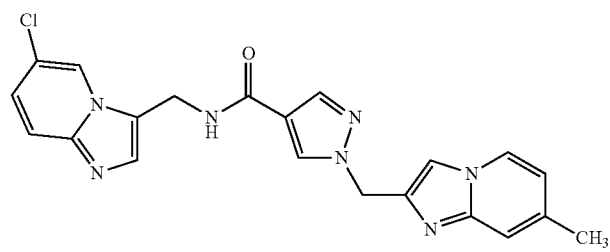 [SMILES: Cc1ccn2cc(Cn3cc(C(=O)NCc4cnc5ccc(Cl)cn45)cn3)nc2c1] | D |
| 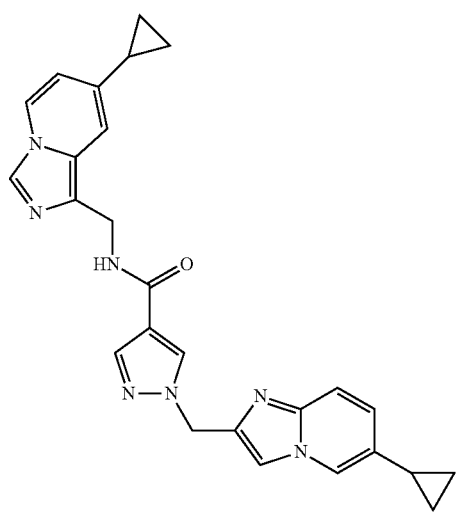 [SMILES: O=C(NCc1ncn2ccc(C3CC3)cc12)c1cnn(Cc2cn3cc(C4CC4)ccc3n2)c1] | D |
| 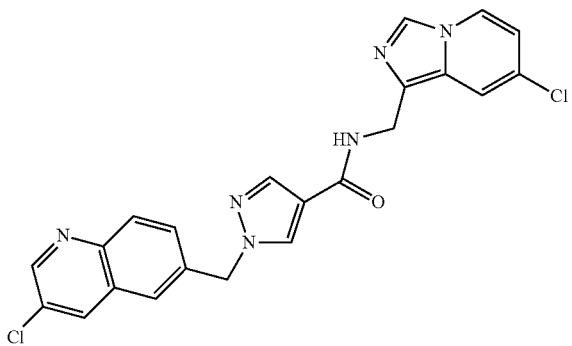 [SMILES: O=C(NCc1ncn2ccc(Cl)cc12)c1cnn(Cc2ccc3ncc(Cl)cc3c2)c1] | C |

TABLE III-continued

| Compound | Primary Dose Response Assay: Average EC50 |
|---|---|
| 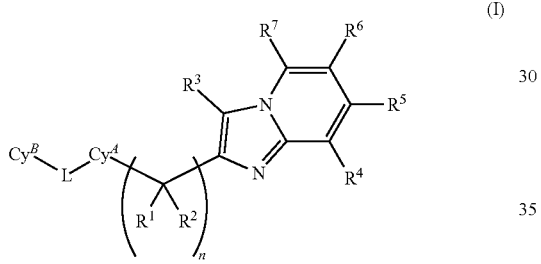 | F |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

What is claimed is:

1. A method of treating a plasma kallikrein-mediated disease or disorder using a compound of Formula (I):

(I)

or a pharmaceutically acceptable salt thereof,
wherein:
$Cy^A$ is selected from a 5-membered monocyclic heteroarylene having 1-4 heteroatoms independently selected from oxygen, nitrogen, and sulfur, and a 7- to 10-membered partially unsaturated bicyclic heterocyclylene having 1-4 heteroatoms selected from oxygen, nitrogen, and sulfur, wherein $Cy^A$ is substituted with 0-4 $R^A$ groups;

each $R^A$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, -N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, and an optionally substituted group selected from $C_{1-6}$ aliphatic, phenyl, a 5- to 6-membered heteroaryl having 1-4 heteroatoms selected from oxygen, nitrogen, and sulfur, a 3- to 7-membered saturated or partially unsaturated monocyclic carbocyclyl, and a 3- to 7-membered saturated or partially unsaturated monocyclic heterocyclyl having 1-2 heteroatoms selected from oxygen, nitrogen, and sulfur;

$Cy^B$ is selected from phenyl, a 5- to 6-membered monocyclic heteroaryl having 1-4 heteroatoms selected from oxygen, nitrogen, and sulfur, a 7- to 10-membered partially unsaturated bicyclic carbocyclyl, a 10-membered bicyclic aryl, a 7- to 10-membered bicyclic heterocyclyl having 1-4 heteroatoms selected from oxygen, nitrogen, and sulfur, a 7- to 10-membered bicyclic heteroaryl having 1-4 heteroatoms selected from oxygen, nitrogen, and sulfur, and a 12-membered tricyclic heterocyclyl having 1-4 heteroatoms selected from oxygen, nitrogen, and sulfur, wherein $Cy^B$ is substituted with 0-5 $R^B$ groups;

each $R^B$ is independently selected from halogen, —CN, oxo, —C(R)=N(R), —C(O)R, —C(O)$_2$R, —C(O)N(R)$_2$, —C(=N(R))N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, and an optionally substituted group selected from $C_{1-6}$ aliphatic, phenyl, a 5- to 6-membered heteroaryl having 1-4 heteroatoms selected from oxygen, nitrogen, and sulfur, a 3- to 7-membered saturated or partially unsaturated monocyclic carbocyclyl, a 3-to 7-membered saturated or partially unsaturated monocyclic heterocyclyl having 1-2 heteroatoms selected from oxygen, nitrogen, and sulfur, a 7- to 10-membered bicyclic heteroaryl having 1-4 heteroatoms selected from oxygen, nitrogen, and sulfur, and an 8- to 10-membered spirocyclic heterocyclyl having 1-3 heteroatoms selected from oxygen, nitrogen, and sulfur;

L is an optionally substituted $C_{1-6}$ hydrocarbon chain, wherein 1 to 3 methylene units are independently replaced with -Cy-, —O—, —NR—, —C(O)—, —C(O)NR—, —NRC(O)—, —S(O)$_2$NR—, —NRS(O)$_2$—, or —S(O)$_2$—;

-Cy- is a 3- to 7-membered saturated or partially unsaturated monocyclic carbocyclylene, a 3- to 7-membered saturated or partially unsaturated monocyclic heterocyclylene having 1-2 heteroatoms selected from oxygen, nitrogen, and sulfur, or a 5- to 6-membered heteroarylene having 1-4 heteroatoms selected from oxygen, nitrogen, and sulfur;

$R^1$ and $R^2$ are independently selected from hydrogen, halogen, —OR, —SR, —N(R)$_2$, and optionally substituted $C_{1-6}$ aliphatic; wherein $R^1$ may be taken together with a monocyclic $Cy^A$ to form an optionally substituted fused 7- to 10-membered saturated or partially unsaturated bicyclic heterocyclylene having 1-4 heteroatoms selected from oxygen, nitrogen, and sulfur;

$R^3$, $R^4$, $R^5$, and $R^7$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, and an optionally substituted group selected from $C_{1-6}$ aliphatic, phenyl, a 5- to 6-membered heteroaryl having 1-4 heteroatoms selected from oxygen, nitrogen, and sulfur, a 3- to 7-membered saturated or partially unsaturated monocyclic carbocyclyl, and a 3- to 7-membered saturated or partially unsaturated monocyclic heterocyclyl having 1-2 heteroatoms selected from oxygen, nitrogen, and sulfur;

$R^6$ is selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, -OC(O)N(R)$_2$, —SR, —S(O)R, —S(O)$_2$R, —S(O)N(R)$_2$, —S(O)$_2$N(R)$_2$, and an optionally substituted group selected from $C_{1-6}$ aliphatic, phenyl, a 5- to 6-membered heteroaryl having 1-4 heteroatoms selected from oxygen, nitrogen, and sulfur, a 3- to 7-membered saturated or partially unsaturated monocyclic carbocyclyl, and a 3- to 7-membered saturated or partially unsaturated monocyclic heterocyclyl having 1-2 heteroatoms selected from oxygen, nitrogen, and sulfur;

each R is independently hydrogen or an optionally substituted group selected from $C_{1-6}$ aliphatic, phenyl, a 5- to 6-membered heteroaryl having 1-4 heteroatoms selected from oxygen, nitrogen, and sulfur, a 3- to 7-membered saturated or partially unsaturated monocyclic carbocyclyl, and a 3- to 7-membered saturated or partially unsaturated monocyclic heterocyclyl having 1-2 heteroatoms selected from oxygen, nitrogen, and sulfur;

or two R groups on the same carbon or nitrogen are taken together with their intervening atoms to form a ring selected from a 3- to 7-membered saturated or partially unsaturated monocyclic ring having 0-2 heteroatoms selected from oxygen, nitrogen, and sulfur, and a 5- to 6-membered heteroaryl having 1-4 heteroatoms selected from oxygen, nitrogen, and sulfur; and n is 0 or 1;

with the proviso that:
(a) at least one of $R^3$, $R^4$, $R^5$, $R^6$ and $R^7$ is $C_{1-6}$ aliphatic or halogen; and
(b) the compound is other than N-[1-[(6-fluoroimidazo[1,2-a]pyridin-2-yl)methyl]-5-methyl-1H-pyrazol-3-yl]-3-pyridinecarboxamide, N-[1-[(6-chloroimidazo[1,2-a]pyridin-2-yl)methyl]-5-methyl-1H-pyrazol-3-yl]-3-pyridinecarboxamide, 3-chloro-4-[[5-[8-chloro-6-(trifluoromethyl)imidazo[1,2-a]pyridin-2-yl]-1,3,4-oxadiazol-2-yl]amino]-benzenepropanoic acid, 2-[(6,8-dichloroimidazo[1,2-a]pyridin-2-yl)methyl]-4-methyl-N-phenyl-5-thiazolecarboxamide, and N-(furan-2-ylmethyl)-N,3,5-trimethyl-1-((6-methylimidazo[1,2-a]pyridin-2-yl)methyl)-1H-pyrazole-4-sulfonamide.

2. The method of claim 1, wherein $Cy^4$ is selected from a 5-membered heteroarylene having 1-4 heteroatoms independently selected from oxygen and nitrogen and an 8-membered partially unsaturated bicyclic heterocyclylene having 2-3 heteroatoms selected from oxygen and nitrogen, wherein $Cy^4$ is substituted with 0-3 $R^4$ groups.

3. The method of claim 1, wherein $Cy^4$ is selected from the group consisting of:

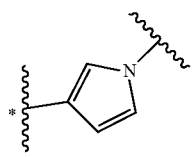
a

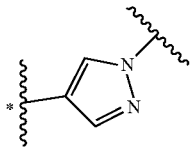
b

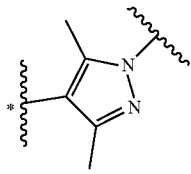
c

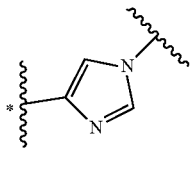
d

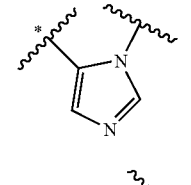
e

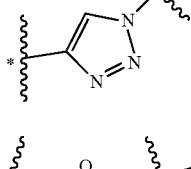
f

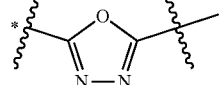
g

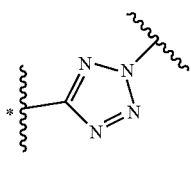
h

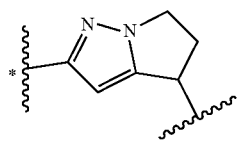
i

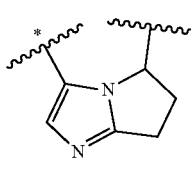
j

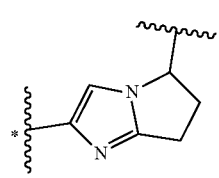
k

-continued

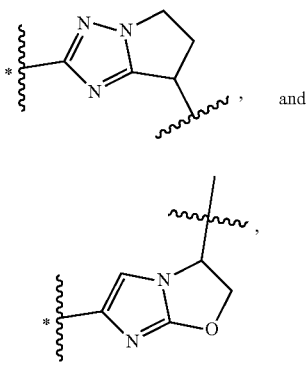

and

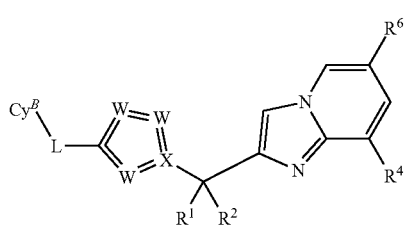

wherein * represents the point of attachment to L.

4. The method of claim 1, wherein $R^3$, $R^5$, and $R^7$ are hydrogen.

5. The method of claim 1, wherein the compound is of Formula (III):

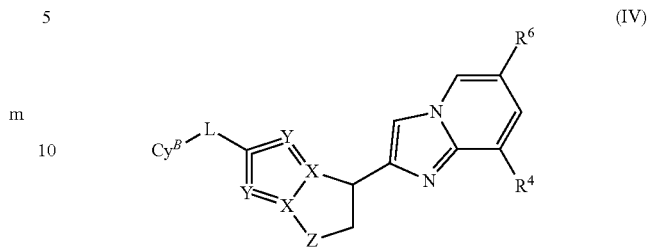

or a pharmaceutically acceptable salt thereof, wherein:

--------- represents a single or double bond;

X is selected from C and N;

each W is independently selected from $CR^A$, CH, N, and O;

$R^4$ is selected from hydrogen, halogen, —CN, —C(O)OR, and an optionally substituted group selected from $C_{1-6}$ aliphatic, a 5- to 6-membered heteroaryl having 1-4 heteroatoms selected from oxygen, nitrogen, and sulfur, and a 3- to 7-membered saturated or partially unsaturated monocyclic heterocyclyl having 1-2 heteroatoms selected from oxygen, nitrogen, and sulfur;

$R^6$ is selected from $C_{1-6}$ aliphatic and halogen; and each R is independently hydrogen or an optionally substituted $C_{1-6}$ aliphatic;

or two R groups on the same carbon or nitrogen are taken together with their intervening atoms to form a ring selected from a 3- to 7-membered saturated or partially unsaturated monocyclic ring having 0-2 heteroatoms selected from oxygen, nitrogen, and sulfur, and a 5- to 6-membered heteroaryl having 1-4 heteroatoms selected from oxygen, nitrogen, and sulfur;

with the proviso that the compound is other than N-(furan-2-ylmethyl)-N,3,5-trimethyl-1-((6-methyl-imidazo[1,2-a]pyridin-2-yl)methyl)-1H-pyrazole-4-sulfonamide.

6. The method of claim 1, wherein the compound is of Formula (IV):

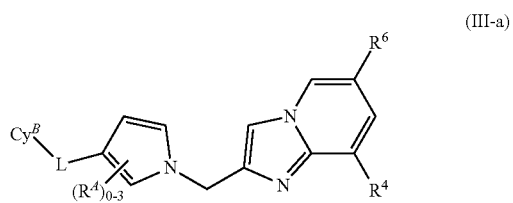

wherein --------- represents a single or double bond;

each X is independently N or C;

each Y is independently $CR^A$, CH, or N;

Z is $CH_2$ or 0;

$R^A$ is selected from an optionally substituted group selected from $C_{1-6}$ aliphatic, a 3- to 7-membered saturated or partially unsaturated monocyclic carbocyclyl, and a 3- to 7-membered saturated or partially unsaturated monocyclic heterocyclyl having 1-2 heteroatoms selected from oxygen, nitrogen, and sulfur;

$R^4$ is selected from hydrogen, halogen, —CN, —C(O)OR, and an optionally substituted group selected from $C_{1-6}$ aliphatic, a 5- to 6-membered heteroaryl having 1-4 heteroatoms selected from oxygen, nitrogen, and sulfur, and a 3- to 7-membered saturated or partially unsaturated monocyclic heterocyclyl having 1-2 heteroatoms selected from oxygen, nitrogen, and sulfur; and $R^6$ is selected from $C_{1-6}$ aliphatic and halogen.

7. The method of claim 1, wherein the compound is of Formula (III-a), Formula (III-b), Formula (III-c), Formula (III-d), Formula (III-e), Formula (III-f), Formula (III-g), Formula (IV-a), Formula (IV-b), Formula (IV-c), or Formula (IV-d):

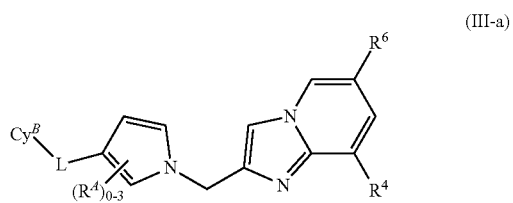

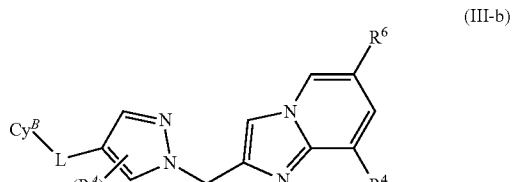

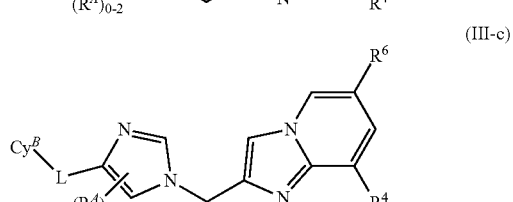

431
-continued

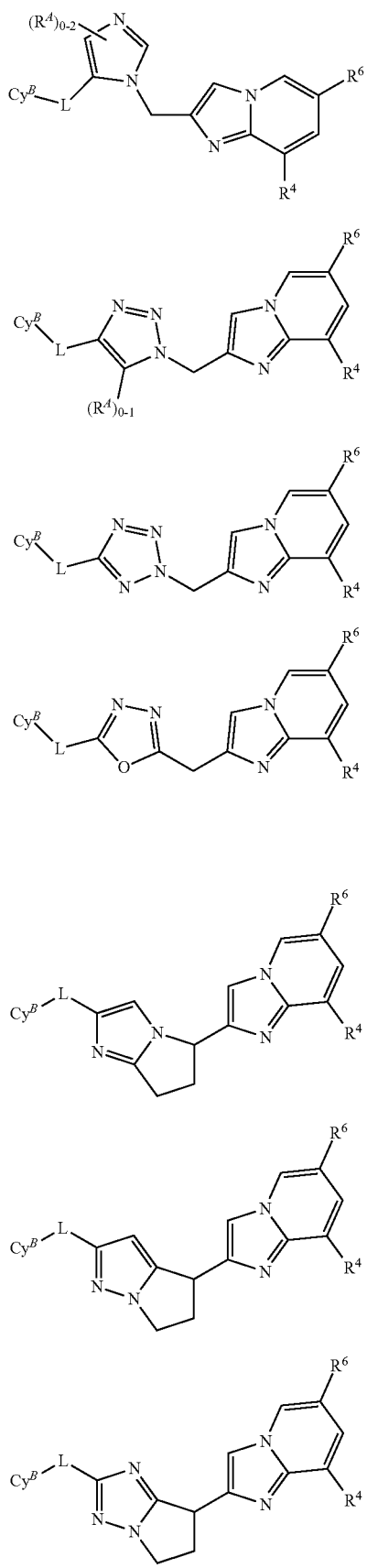

(III-d)
(III-e)
(III-f)
(III-g)
(IV-a)
(IV-b)
(IV-c)

432
-continued

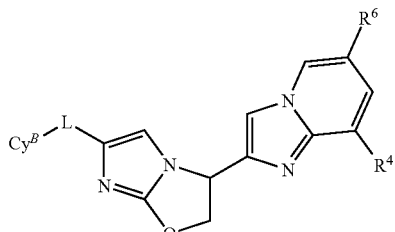

(IV-d)

or a pharmaceutically acceptable salt thereof,
wherein:
$R^A$ is an optionally substituted group selected from $C_{1-6}$ aliphatic, a 3- to 7-membered saturated or partially unsaturated monocyclic carbocyclyl, and a 3- to 7-membered saturated or partially unsaturated monocyclic heterocyclyl having 1-2 heteroatoms selected from oxygen, nitrogen, and sulfur;

$R^4$ is selected from hydrogen, halogen, —CN, —C(O)OR, or an optionally substituted group selected from $C_{1-6}$ aliphatic, a 5- to 6-membered heteroaryl having 1-4 heteroatoms selected from oxygen, nitrogen, and sulfur, and a 3- to 7-membered saturated or partially unsaturated monocyclic heterocyclyl having 1-2 heteroatoms selected from oxygen, nitrogen, and sulfur; and $R^6$ is selected from $C_{1-6}$ aliphatic and halogen;
with the proviso that the compound is other than N-(furan-2-ylmethyl)-N,3,5-trimethyl-1-((6-methyl-imidazo[1,2-a]pyridin-2-yl)methyl)-1H-pyrazole-4-sulfonamide.

8. The method of claim 1, wherein L is selected from —NR-#, —C(R)$_2$NR-#, —C(R)$_2$NRC(R)$_2$-#, —NRC(O)-#, —C(R)$_2$NRC(O)-#, —C(R)$_2$C(R)$_2$NRC(O)-#, —C(O)NRC(R)$_2$- #, —C(R)$_2$C(O)NR-#, —C(R)$_2$C(O)NRC(R)$_2$- #, —NRC(O)NR-#, —C(R)$_2$OC(O)NR-#, —OC(R)$_2$C(R)$_2$NRC(O)-#, —OC(R)$_2$C(R)$_2$NRS(O)$_2$-#, —S(O)$_2$NRC(R)$_2$-#, —C(R)$_2$NRS(O)$_2$-#, and —C(R)$_2$C(R)$_2$NRS(O)$_2$-#, wherein each R is independently hydrogen or optionally substituted $C_{1-6}$ aliphatic and #represents the point of attachment to $Cy^A$.

9. The method of claim 1, wherein L is selected from —NRC(O)— #and —C(R)$_2$NRC(O)-#, wherein each R is independently selected from hydrogen and optionally substituted $C_{1-6}$ aliphatic and #represents the point of attachment to $Cy^A$.

10. The method of claim 1, wherein the compound is of Formula (II):

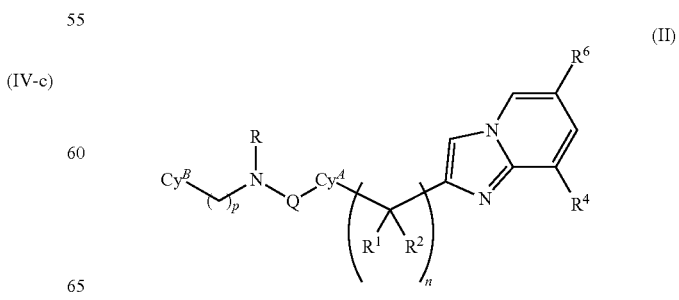

(II)

or a pharmaceutically acceptable salt thereof,
wherein:
Cy$^A$ is selected from a 5-membered monocyclic heteroarylene having 1-4 heteroatoms independently selected from oxygen, nitrogen, and sulfur, and a 7- to 10-membered partially unsaturated bicyclic heterocyclylene having 1-4 heteroatoms selected from oxygen, nitrogen, and sulfur, wherein Cy$^A$ is substituted with 0-4 R$^A$ groups;
R$^A$ is an optionally substituted group selected from C$_{1-6}$ aliphatic, a 3- to 7-membered saturated or partially unsaturated monocyclic carbocyclyl, and a 3- to 7-membered saturated or partially unsaturated monocyclic heterocyclyl having 1-2 heteroatoms selected from oxygen, nitrogen, and sulfur;
Q is selected from —C(R)$_2$—, —C(O)—, and —S(O)$_2$—;
Cy$^B$ is selected from phenyl, a 5- to 6-membered monocyclic heteroaryl having 1-4 heteroatoms selected from oxygen, nitrogen, and sulfur, a 7- to 10-membered partially unsaturated bicyclic carbocyclyl, a 10-membered bicyclic aryl, a 7- to 10-membered bicyclic heterocyclyl having 1-4 heteroatoms selected from oxygen, nitrogen, and sulfur, a 7- to 10-membered bicyclic heteroaryl having 1-4 heteroatoms selected from oxygen, nitrogen, and sulfur, and a 12-membered tricyclic heterocyclyl having 1-4 heteroatoms selected from oxygen, nitrogen, and sulfur, wherein Cy$^B$ is substituted with 0-5 R$^B$ groups;
R$^B$ is selected from halogen, —CN, —OR, —N(R)$_2$, —N(R)CN, —C(=N(R))N(R)$_2$, —S(O)R, —S(O)$_2$R, —S(O)$_2$N(R)$_2$, and an optionally substituted group selected from C$_{1-6}$ aliphatic, phenyl, a 5- to 6-membered heteroaryl having 1-4 heteroatoms selected from oxygen, nitrogen, and sulfur, a 3-to 7-membered saturated or partially unsaturated monocyclic carbocyclyl, a 3- to 7-membered saturated or partially unsaturated monocyclic heterocyclyl having 1-2 heteroatoms selected from oxygen, nitrogen, and sulfur, a 7- to 10-membered bicyclic heteroaryl having 1-4 heteroatoms selected from oxygen, nitrogen, and sulfur, and 8- to 10-membered spirocyclic heterocyclyl having 1-3 heteroatoms selected from oxygen, nitrogen, and sulfur, wherein each R is independently hydrogen or optionally substituted C$_{1-6}$ aliphatic;
R$^1$ and R$^2$ are independently selected from hydrogen, halogen, —OR, —SR, —N(R)$_2$, and optionally substituted C$_{1-6}$ aliphatic; wherein R$^1$ may be taken together with a monocyclic Cy$^A$ to form an optionally substituted fused 7- to 10-membered saturated or partially unsaturated bicyclic heterocyclylene having 1-4 heteroatoms selected from oxygen, nitrogen, and sulfur;
R$^4$ is selected from hydrogen, halogen, —CN, —C(O)OR, or an optionally substituted group selected from C$_{1-6}$ aliphatic, 5- to 6-membered heteroaryl having 1-4 heteroatoms selected from oxygen, nitrogen, and sulfur, and 3- to 7-membered saturated or partially unsaturated monocyclic heterocyclyl having 1-2 heteroatoms selected from oxygen, nitrogen, and sulfur;
R$^6$ is selected from C$_{1-6}$ aliphatic and halogen;
each R is independently hydrogen or an optionally substituted group selected from C$_{1-6}$ aliphatic;
or two R groups on the same carbon or nitrogen are taken together with their intervening atoms to form a ring selected from a 3- to 7-membered saturated or partially unsaturated monocyclic ring having 0-2 heteroatoms selected from oxygen, nitrogen, and sulfur, and a 5- to 6-membered heteroaryl having 1-4 heteroatoms selected from oxygen, nitrogen, and sulfur;

n is 0 or 1; and p is 0, 1, or 2;

with the proviso that the compound is other than N-(furan-2-ylmethyl)-N,3,5-trimethyl-1-((6-methylimidazo[1,2-a]pyridin-2-yl)methyl)-1H-pyrazole-4-sulfonamide and 2-[(6,8-dichloroimidazo[1,2-a]pyridin-2-yl)methyl]-4-methyl-N-phenyl-5-thiazolecarboxamide.

11. The method of claim 10, wherein Cy$^A$ is selected from the group consisting of:

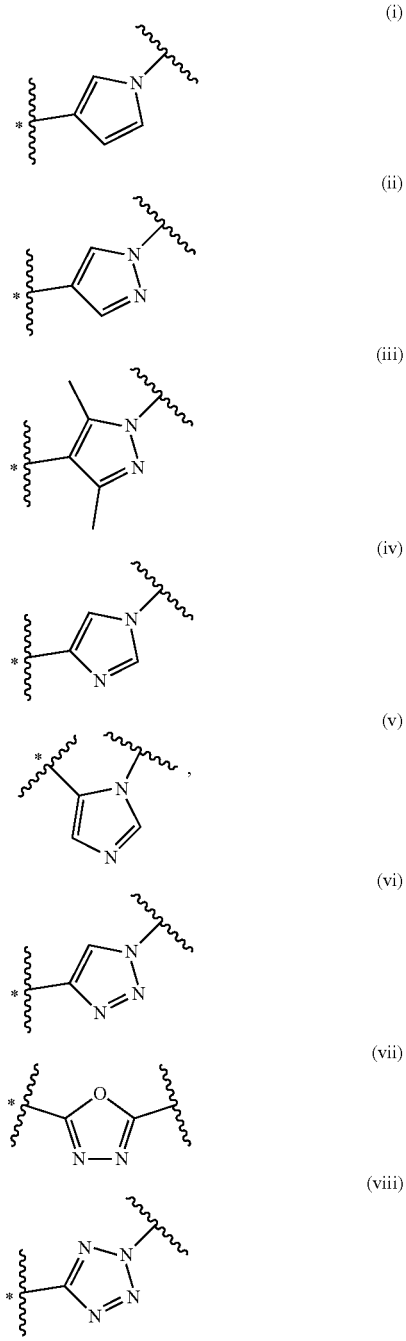

435

-continued

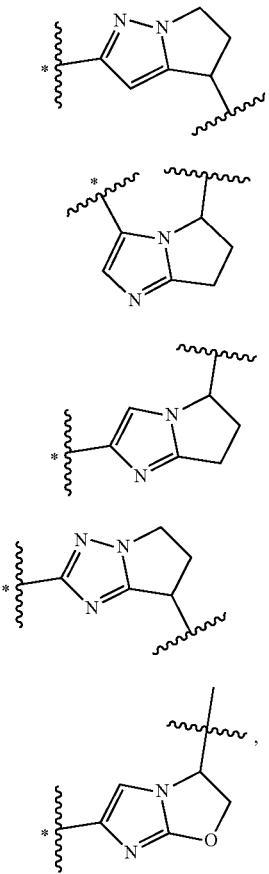

(ix)

(x)

(xi)

(xii) and (xiii)

, wherein * represents the point of attachment to L.

12. The method of claim 1, wherein the compound is of Formula (III-a-i), Formula (III-b-i), Formula (III-c-i), Formula (III-d-i), Formula (III-e-i), Formula (III-f-i), or Formula (III-g-i):

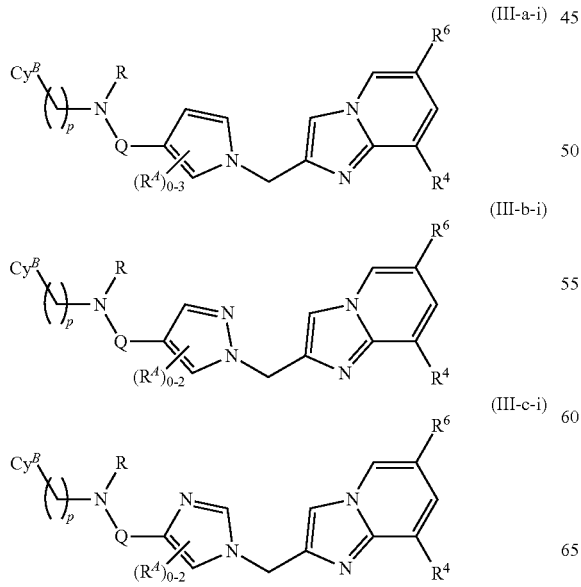

436

-continued

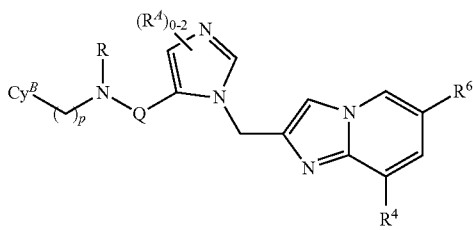

(III-d-i)

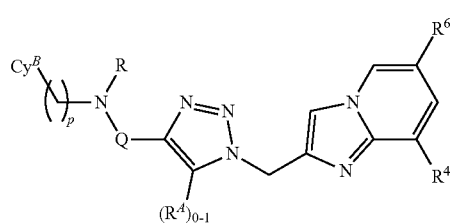

(III-e-i)

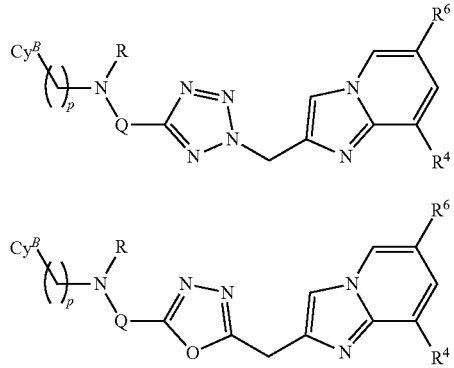

(III-f-i)

(III-g-i)

or a pharmaceutically acceptable salt thereof, wherein:

Q is selected from —C(R)$_2$—, —C(O)—, and —S(O)$_2$—;

$R^A$ is an optionally substituted group selected from C$_{1-6}$ aliphatic, a 3- to 7-membered saturated or partially unsaturated monocyclic carbocyclyl, and a 3- to 7-membered saturated or partially unsaturated monocyclic heterocyclyl having 1-2 heteroatoms selected from oxygen, nitrogen, and sulfur;

$R^4$ is selected from hydrogen, halogen, —CN, —C(O)OR, and an optionally substituted group selected from C$_{1-6}$ aliphatic, a 5- to 6-membered heteroaryl having 1-4 heteroatoms selected from oxygen, nitrogen, and sulfur, and a 3- to 7-membered saturated or partially unsaturated monocyclic heterocyclyl having 1-2 heteroatoms selected from oxygen, nitrogen, and sulfur;

$R^6$ is selected from C$_{1-6}$ aliphatic and halogen; and p is 0, 1, or 2;

with the proviso that the compound is other than N-(furan-2-ylmethyl)-N,3,5-trimethyl-1-((6-methylimidazo[1,2-a]pyridin-2-yl)methyl)-1H-pyrazole-4-sulfonamide.

13. The method of claim 1, wherein the compound is of Formula (IV-a-i), Formula (IV-b-i), Formula (IV-c-i), or Formula (IV-d-i):

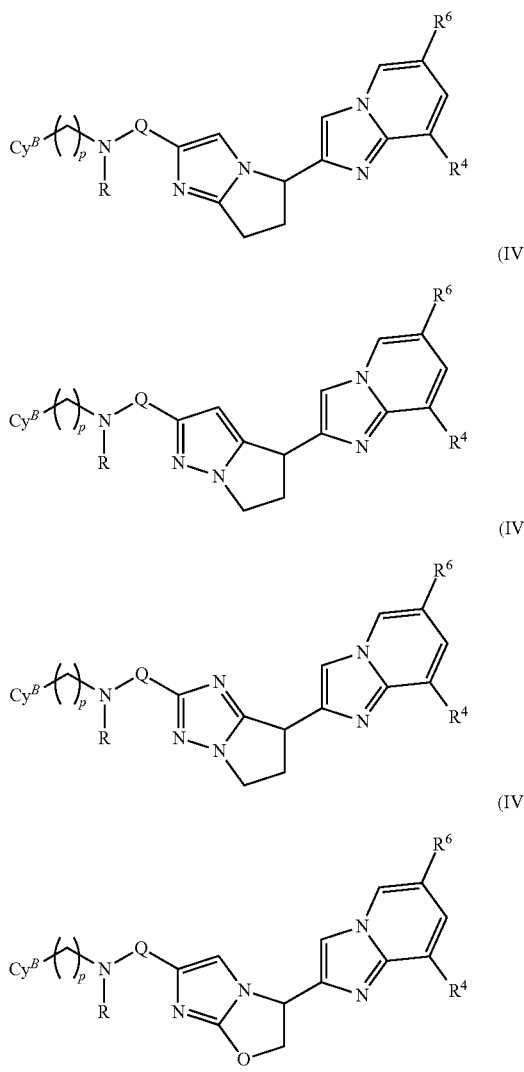

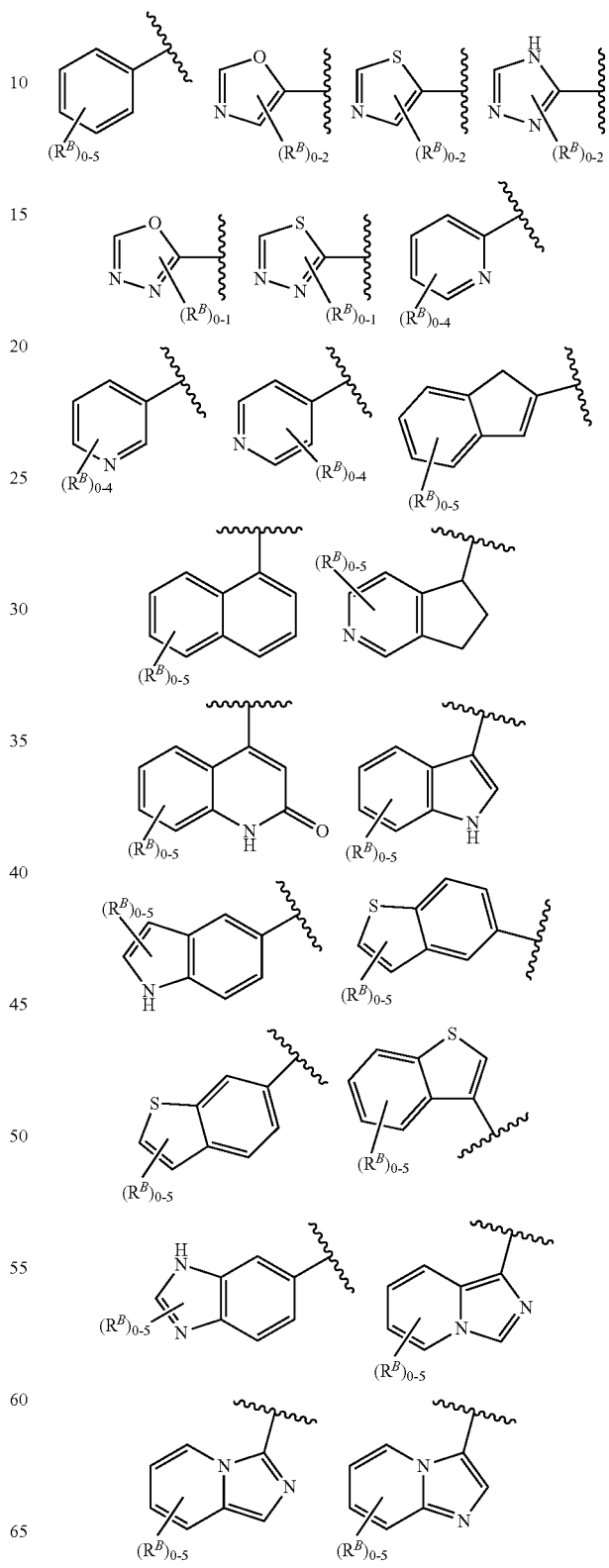

or a pharmaceutically acceptable salt thereof, wherein:

Q is selected from —C(R)$_2$—, —C(O)—, and —S(O)$_2$—;
p is 0, 1, or 2;
R$^4$ is selected from hydrogen, halogen, —CN, —C(O)OR, or an optionally substituted group selected from C$_{1-6}$ aliphatic, a 5- to 6-membered heteroaryl having 1-4 heteroatoms selected from oxygen, nitrogen, and sulfur, and a 3- to 7-membered saturated or partially unsaturated monocyclic heterocyclyl having 1-2 heteroatoms selected from oxygen, nitrogen, and sulfur; and
R$^6$ is selected from C$_{1-6}$ aliphatic and halogen.

14. The method of claim 1, wherein Cy$^B$ is selected from phenyl, a 5- to 6-membered monocyclic heteroaryl having 1-4 heteroatoms selected from oxygen, nitrogen, and sulfur, a 7- to 10-membered partially unsaturated bicyclic carbocyclyl, a 10-membered bicyclic aryl, a 7- to 10-membered bicyclic heterocyclyl having 1-4 heteroatoms selected from oxygen, nitrogen, and sulfur, a 7- to 10-membered bicyclic heteroaryl having 1-4 heteroatoms selected from oxygen, nitrogen, and sulfur, and a 12-membered tricyclic heterocyclyl having 1-4 heteroatoms selected from oxygen, nitrogen, and sulfur, wherein Cy$^B$ is substituted with 0-5 R$^B$ groups.

15. The method of claim 14, wherein Cy$^B$ is selected from the group consisting of:

-continued
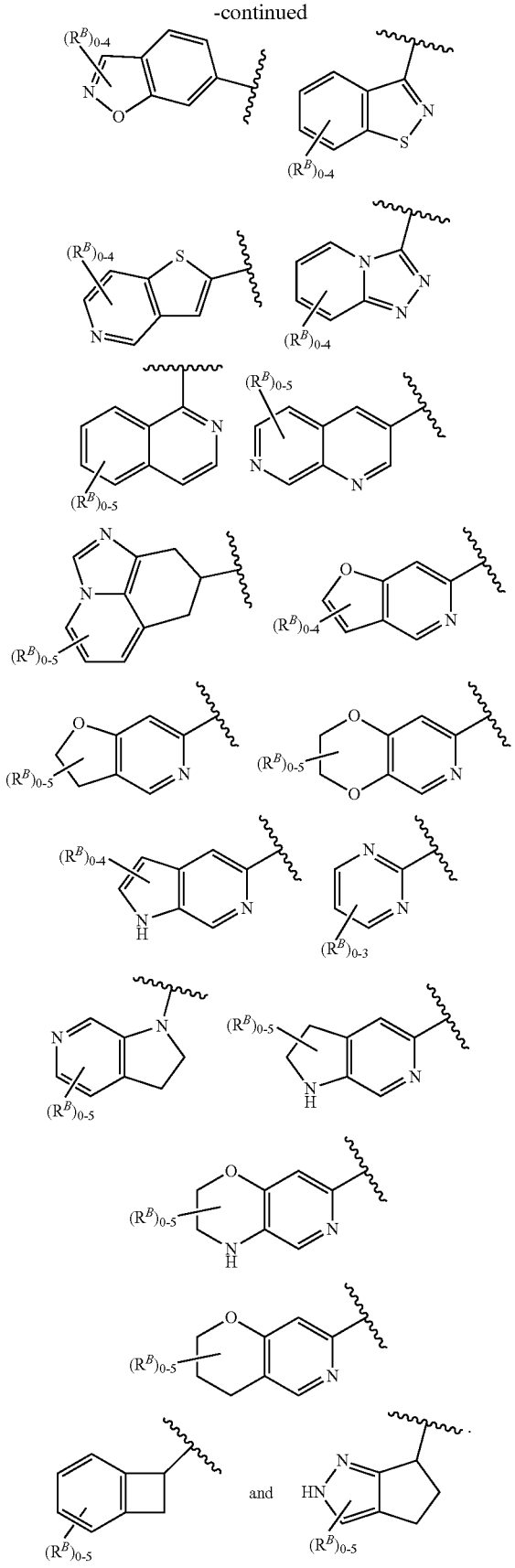
16. The method of claim 1, wherein $R^6$ is $C_{1-6}$ cycloalkyl.
17. The method of claim 1, wherein $R^6$ is cyclopropyl.
18. The method of claim 1, wherein the compound is selected from:
I-1
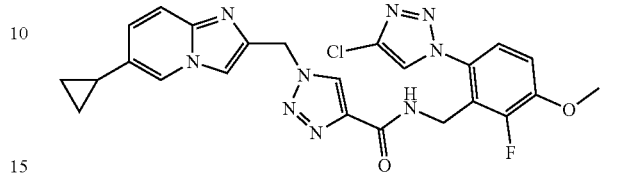
I-2
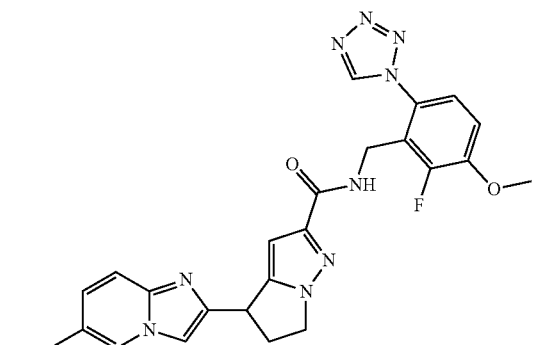
I-3
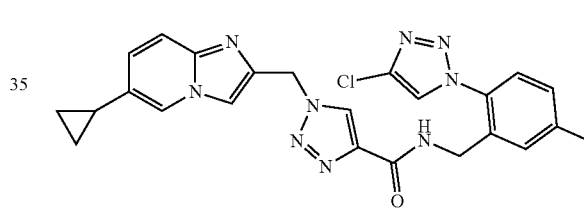
I-4
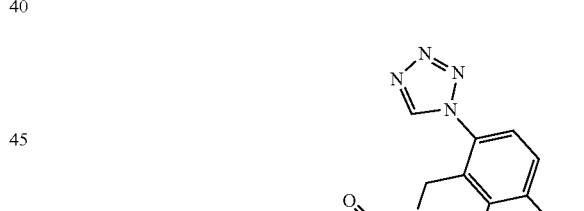
I-5
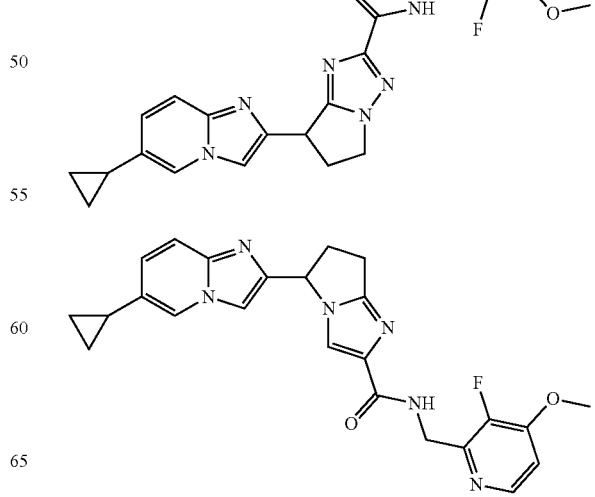

441
-continued
442
-continued
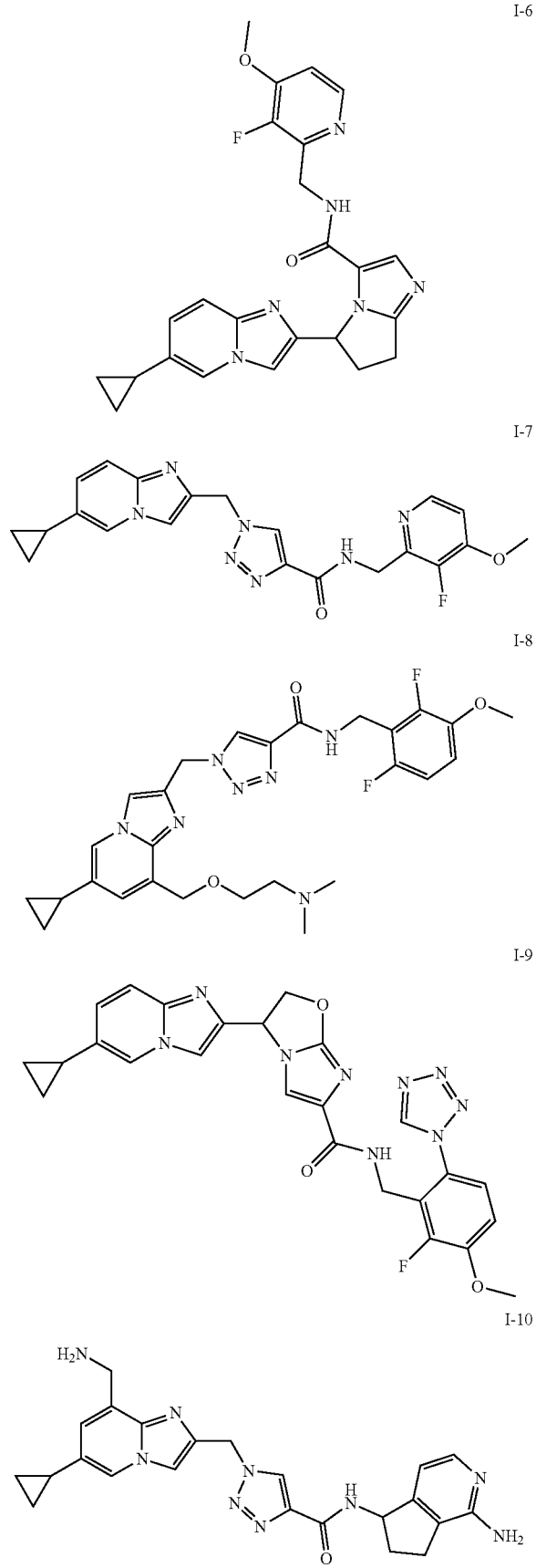
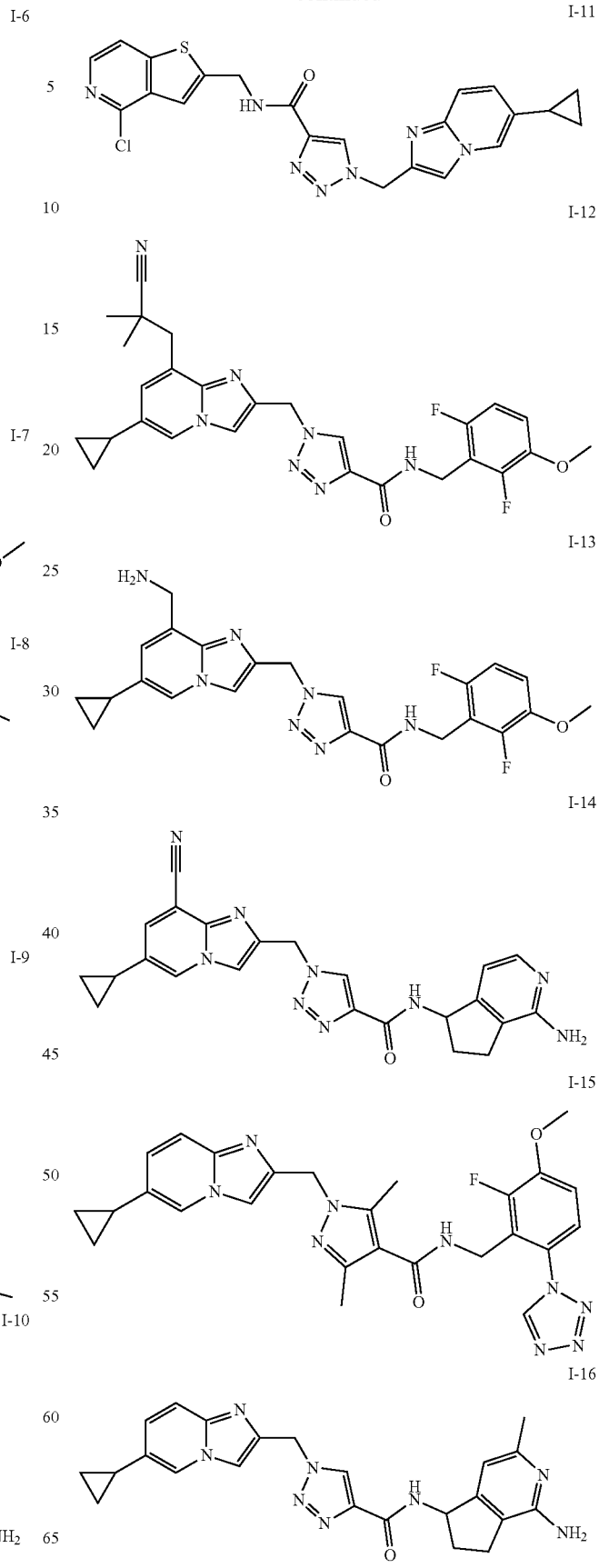

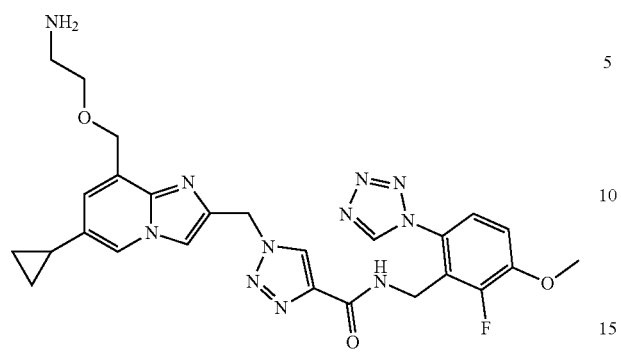
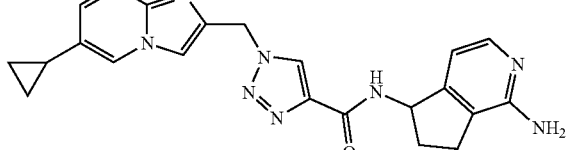
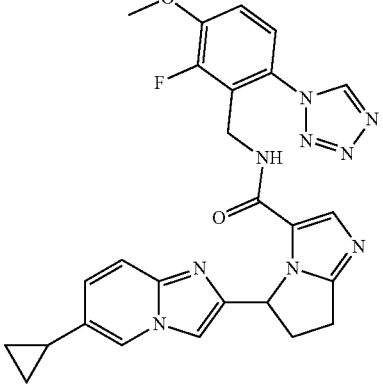
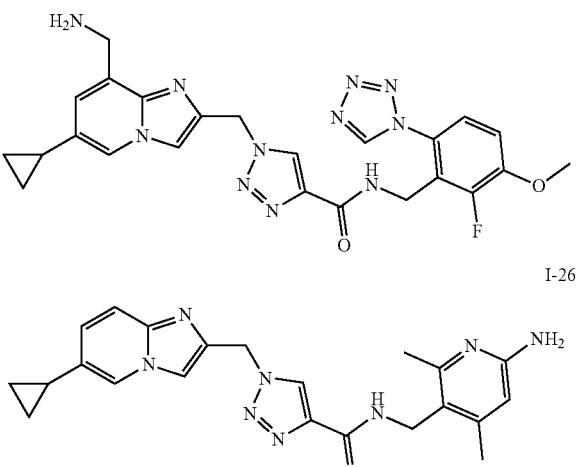
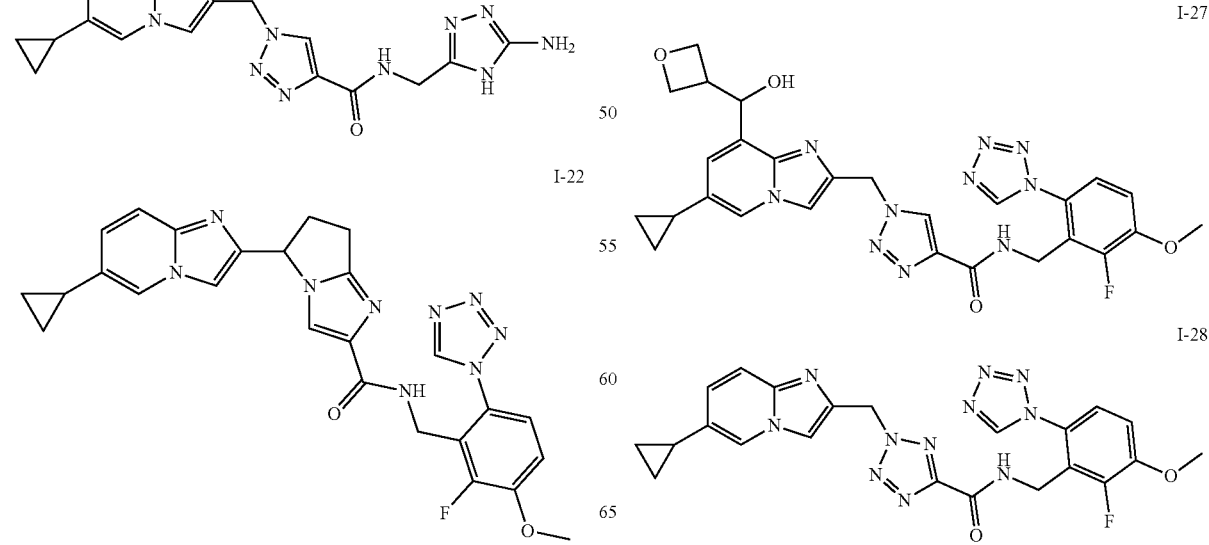

I-29
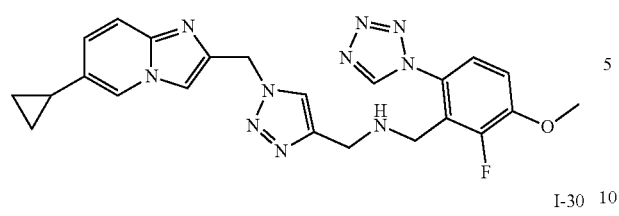
I-30
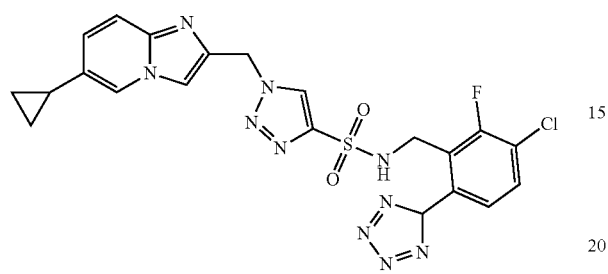
I-31
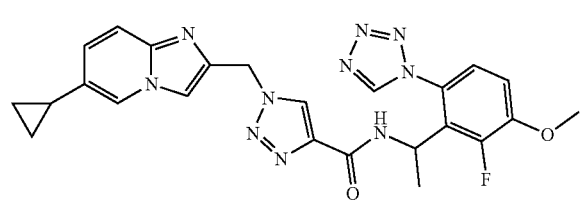
I-32
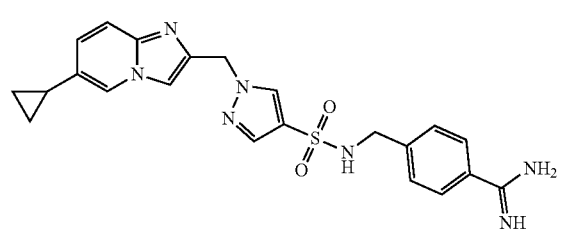
I-33
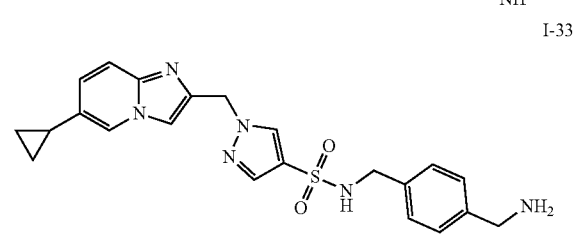
I-34
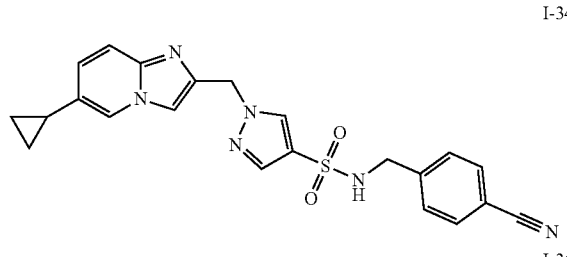
I-35
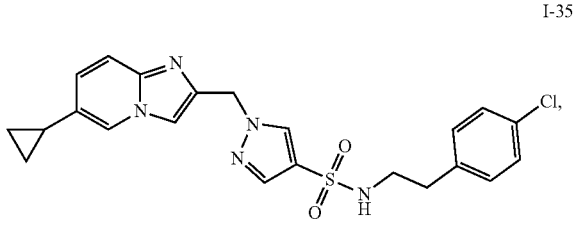
I-36
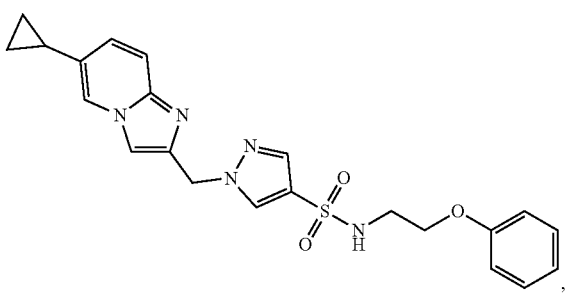
I-37
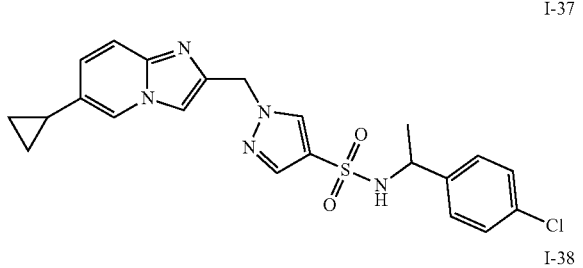
I-38
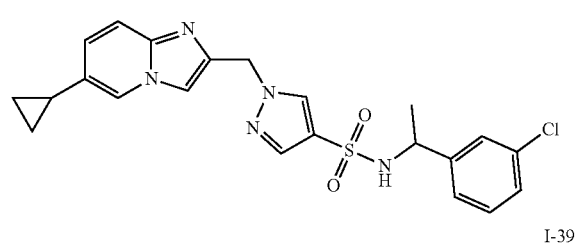
I-39
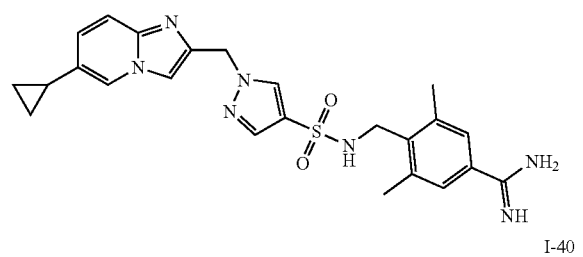
I-40
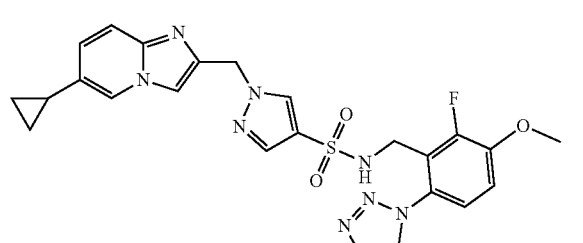
I-41
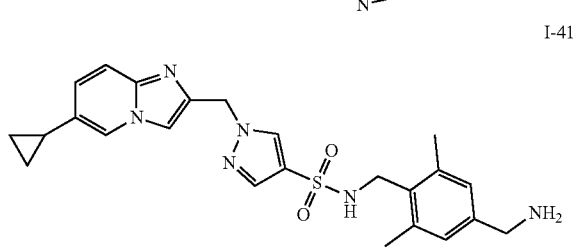

447
-continued
I-42
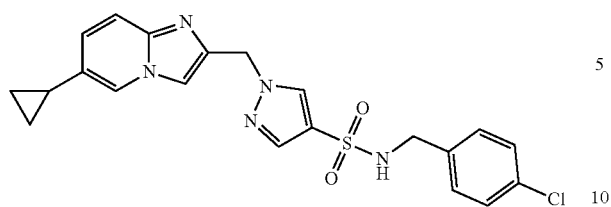
I-43
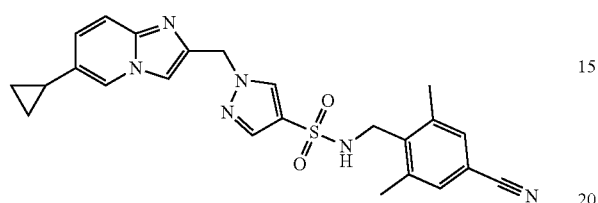
I-44
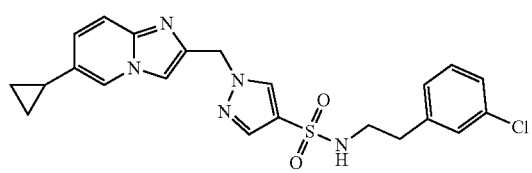
I-45
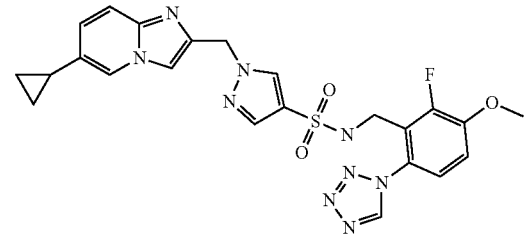
I-46
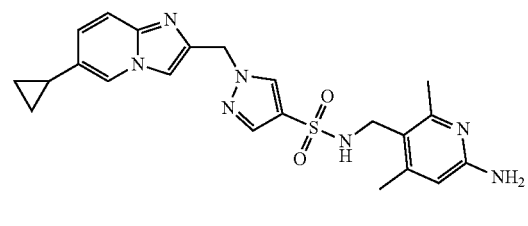
I-47
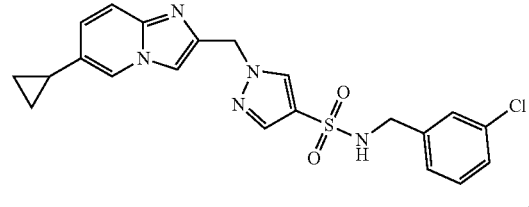
I-48
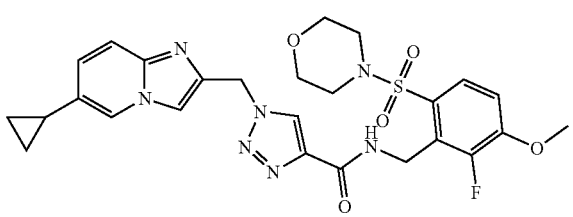
448
-continued
I-49
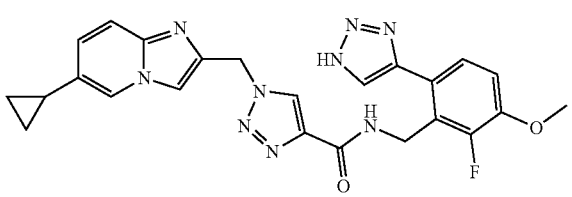
I-50
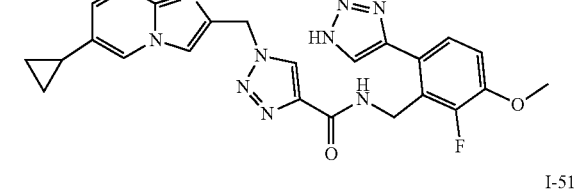
I-51
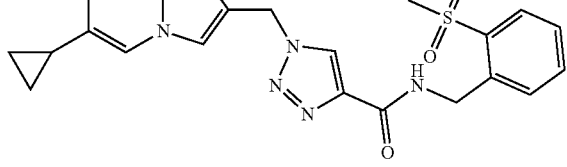
I-52
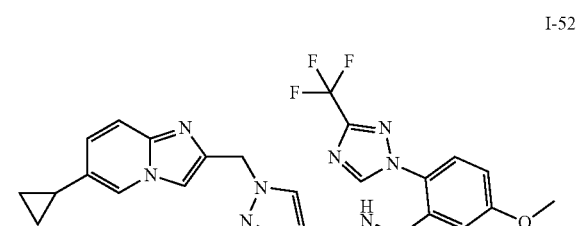
I-53
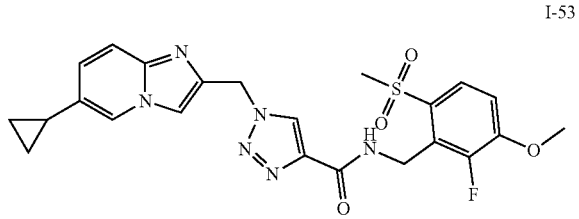
I-54
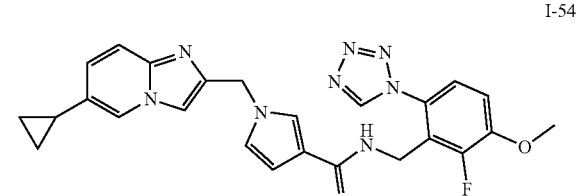
I-55
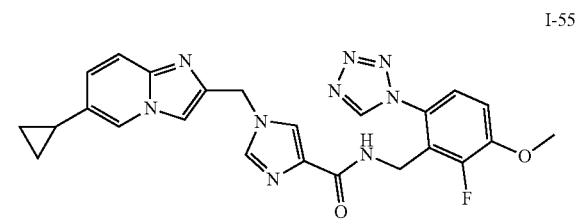

I-56
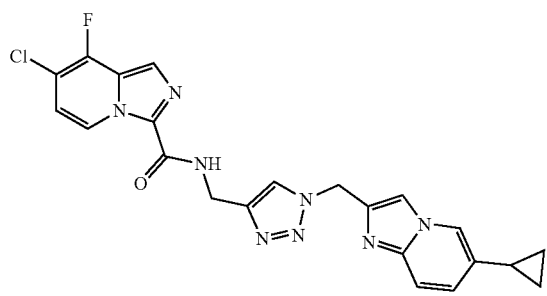
I-57
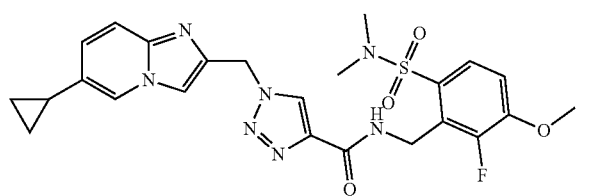
I-58
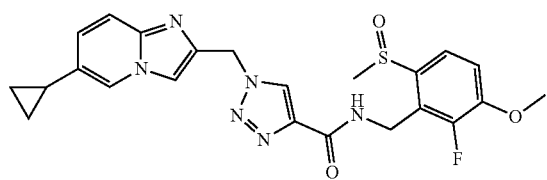
I-59
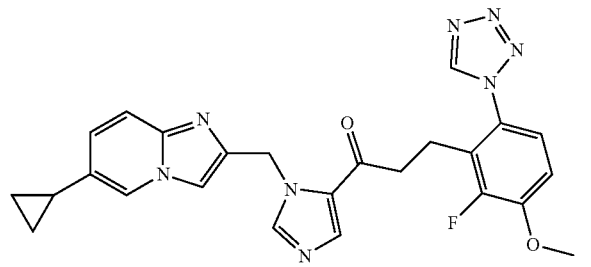
I-60
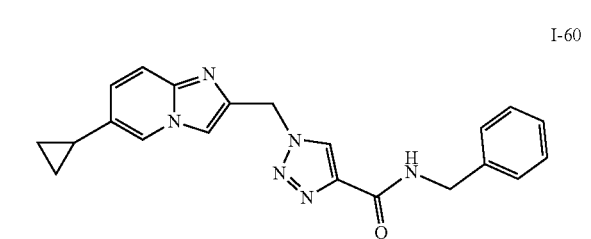
I-61
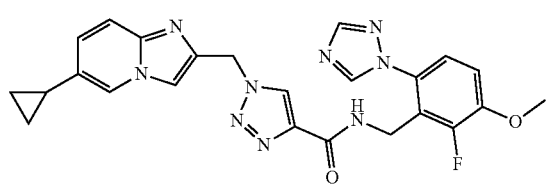
I-62
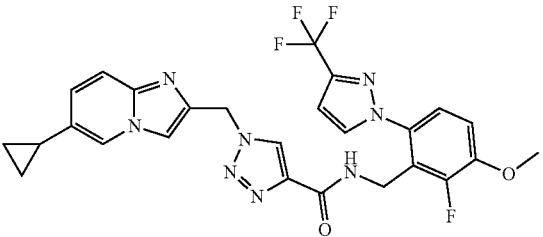
I-63
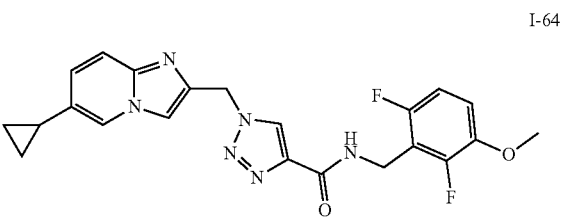
I-64
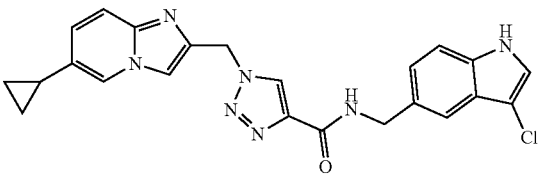
I-65
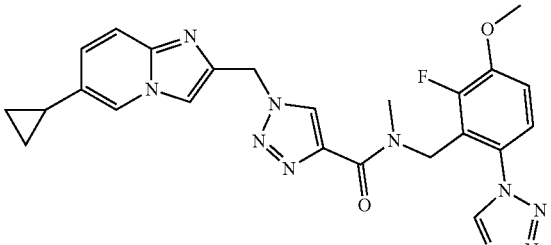
I-66
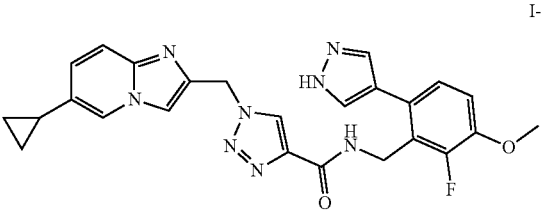
I-67

I-68
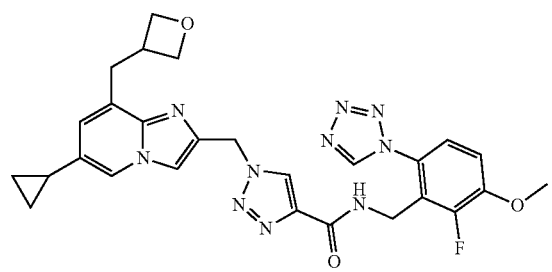
I-69
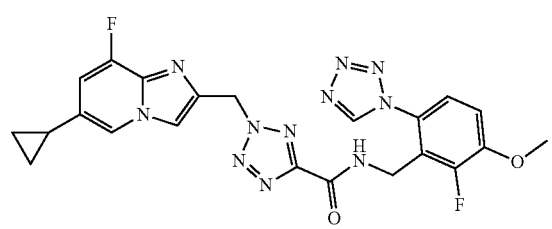
I-70
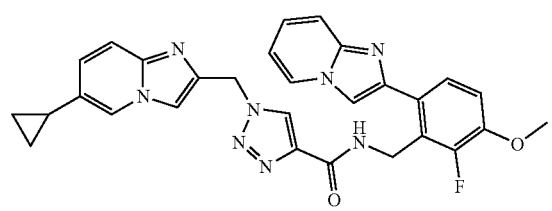
I-71
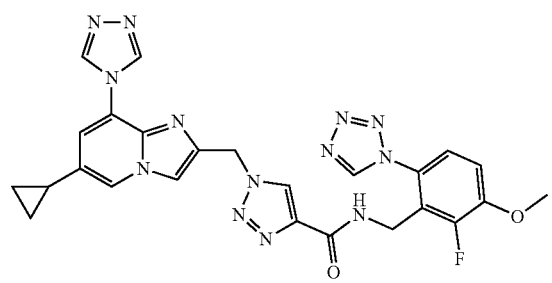
I-72
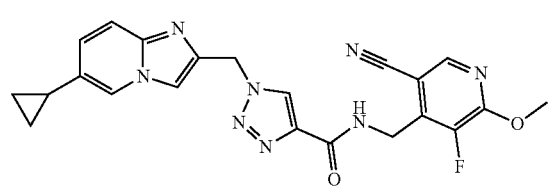
I-73
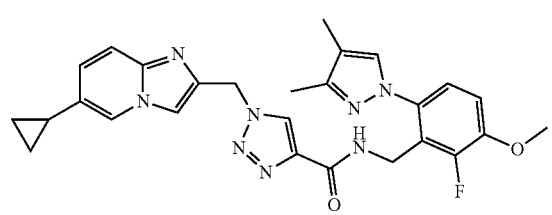
I-74
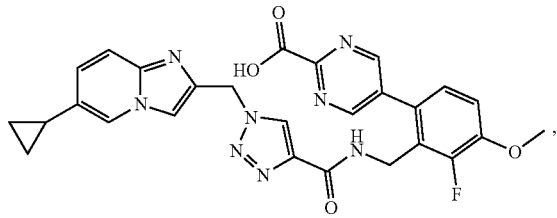
I-75
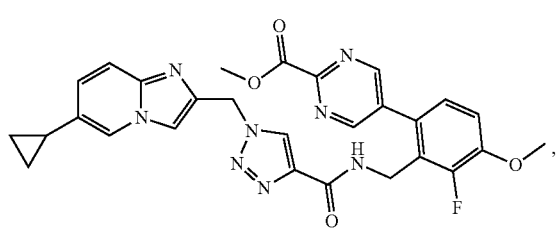
I-76
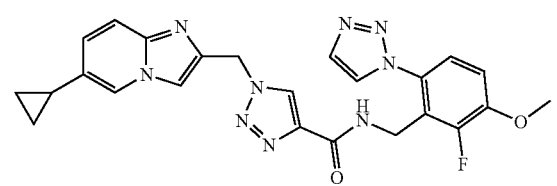
I-77
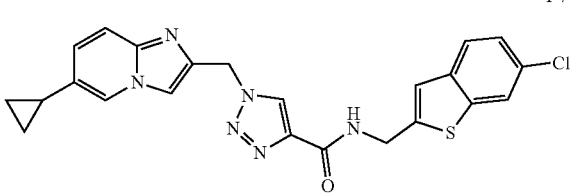
I-78
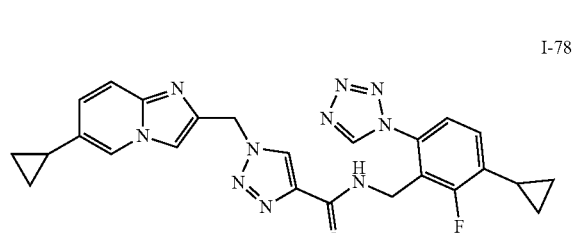
I-79
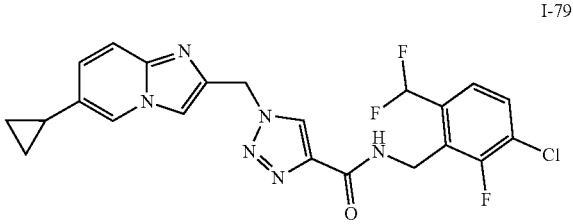
I-80
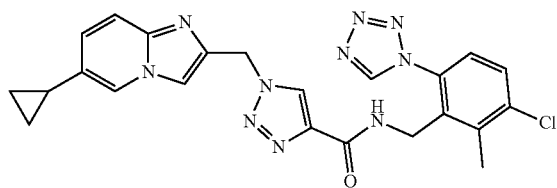

I-81
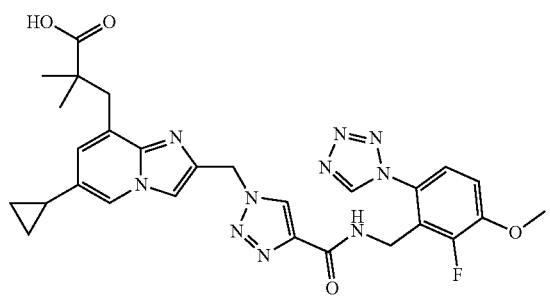
I-82
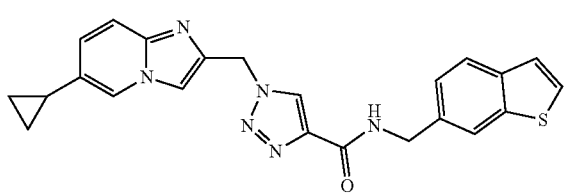
I-83
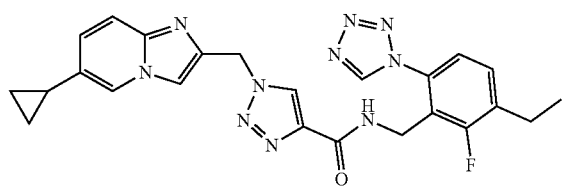
I-84
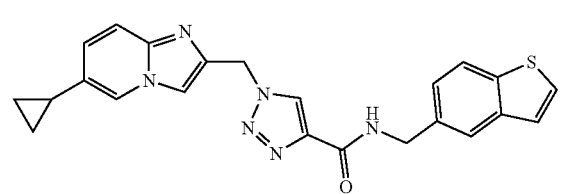
I-85
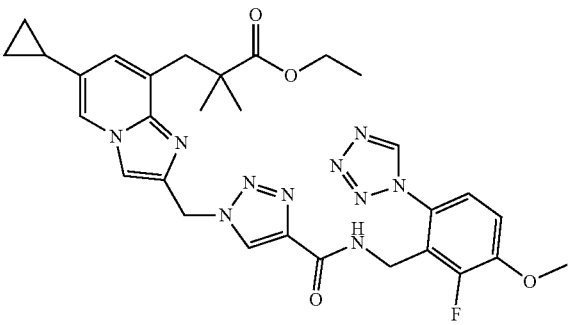
I-86
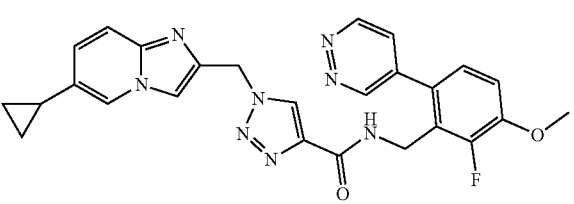
I-87
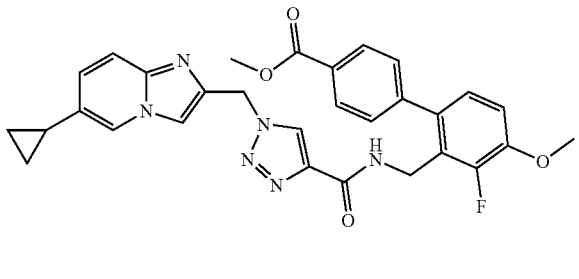
I-88
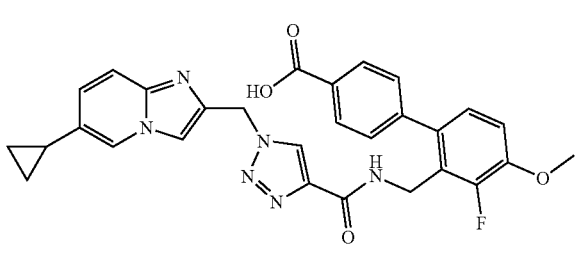
I-89
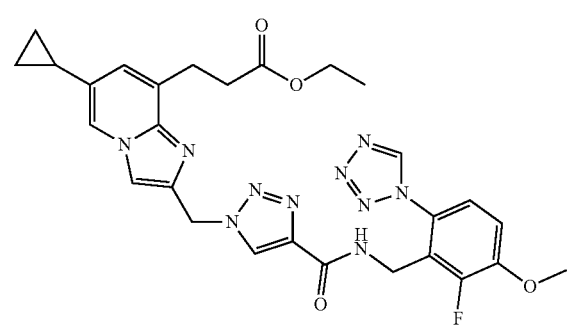
I-90
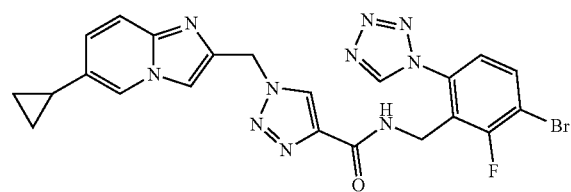
I-91
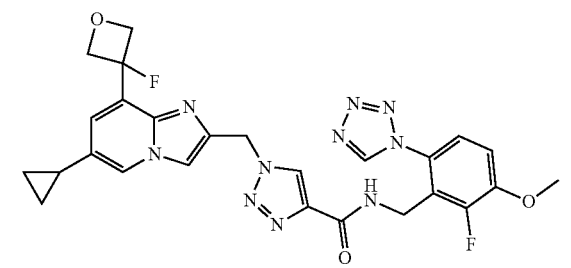

I-92
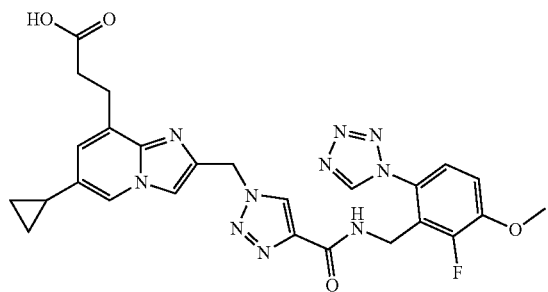
I-93
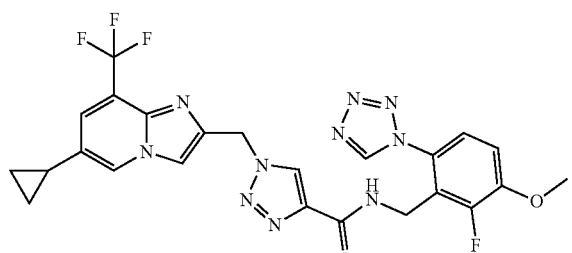
I-94
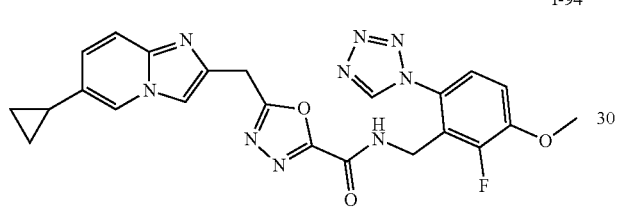
I-95
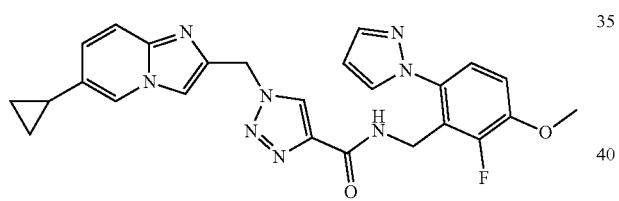
I-96
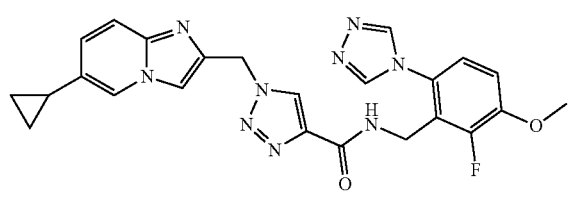
I-97
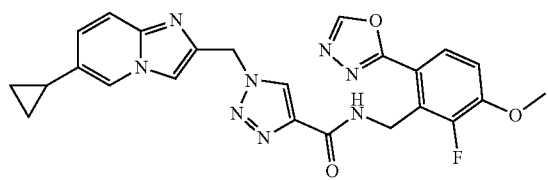
I-98
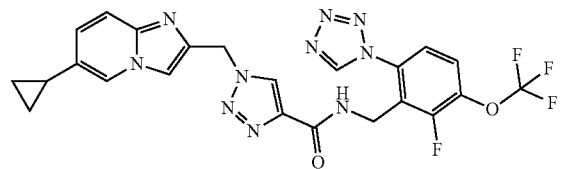
I-99
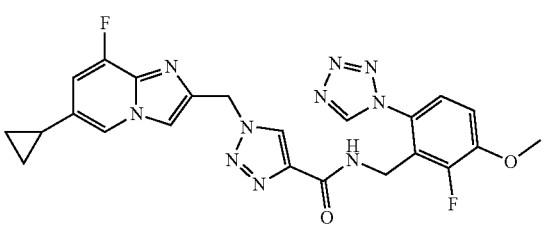
I-100
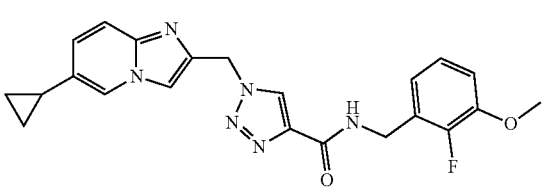
I-101
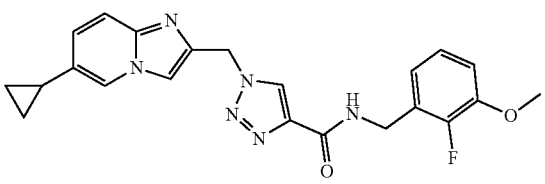
I-102
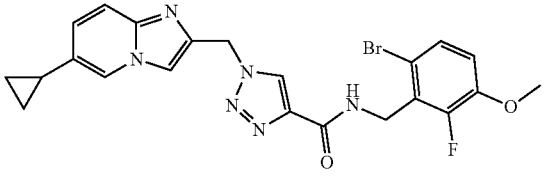
I-103
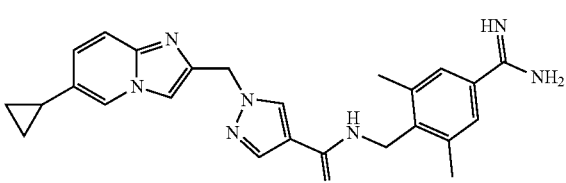
I-104
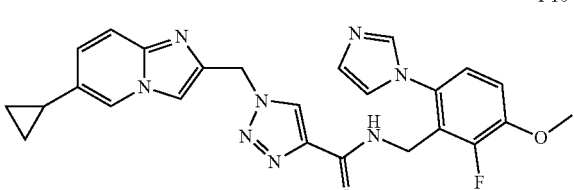
I-105
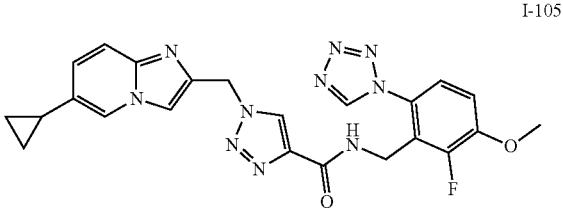

I-106
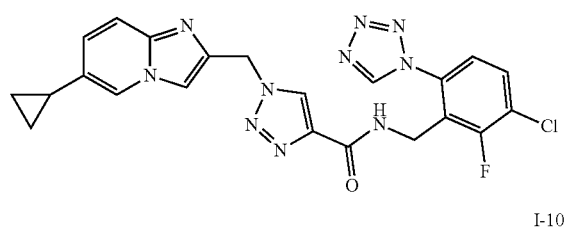
I-107
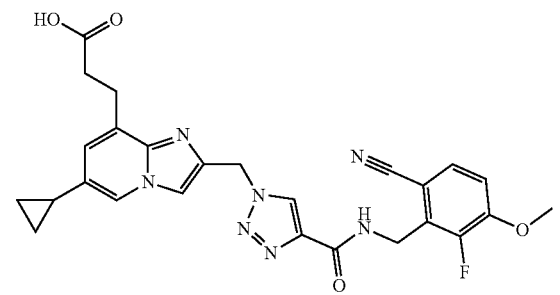
I-108
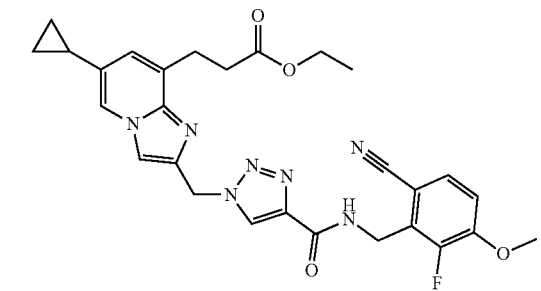
I-109
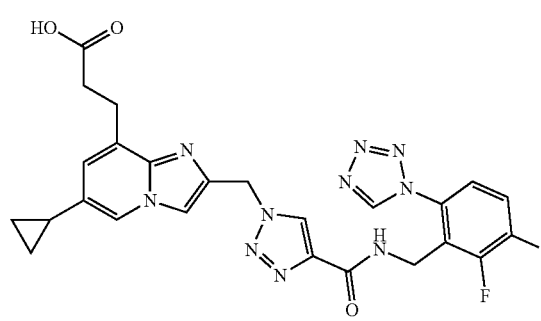
I-110
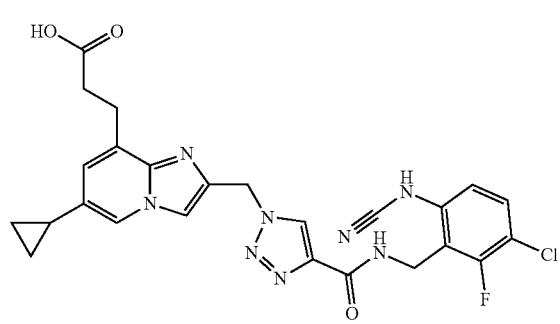
I-111
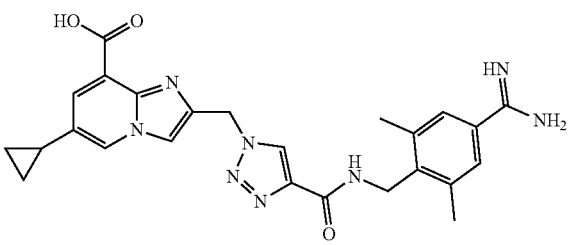
I-112
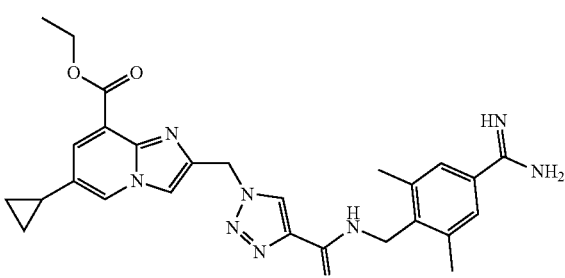
I-113
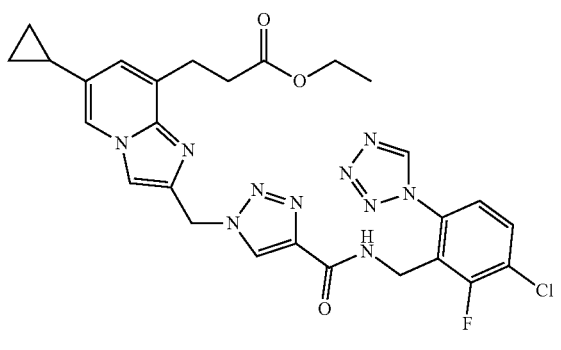
I-114
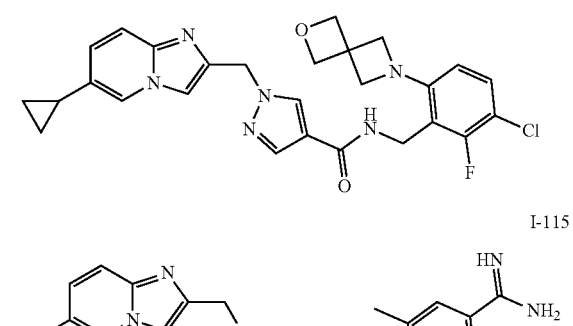
I-115
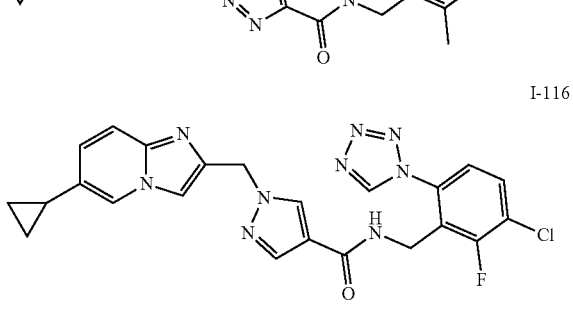
I-116

| | |
|---|---|
| I-117 | I-122 |
| I-118 | I-123 |
| I-119 | I-124 |
| I-120 | I-125 |
| I-121 | I-126 |
| | I-127 |

I-128
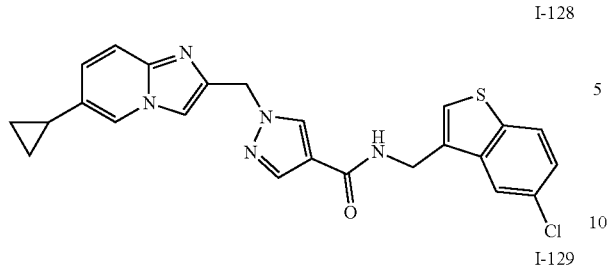
I-129
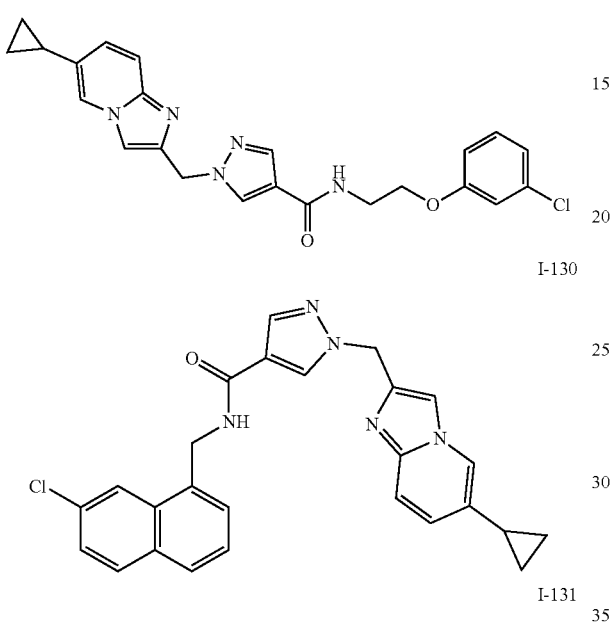
I-130
I-131
I-132
I-133
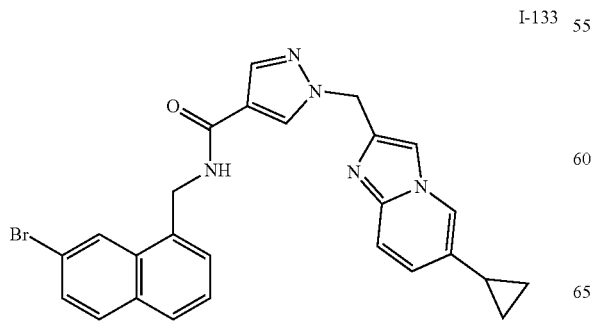
I-134
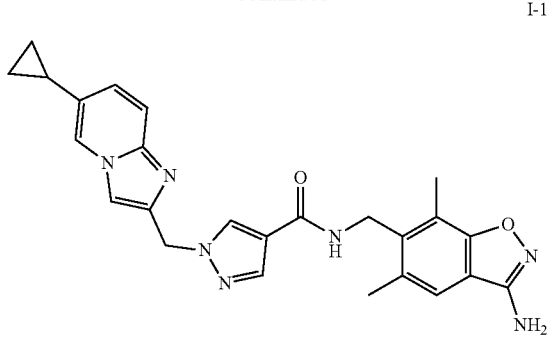
I-135
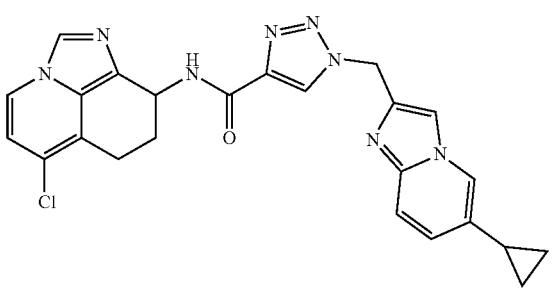
I-136
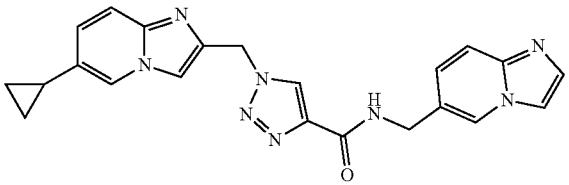
I-137
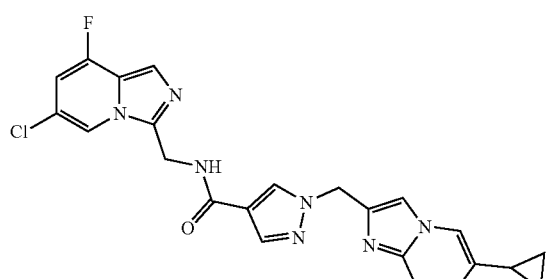
I-138
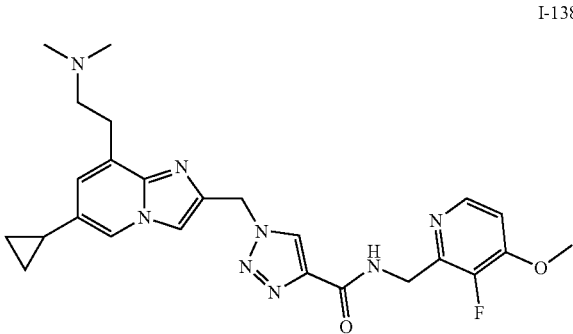

I-139
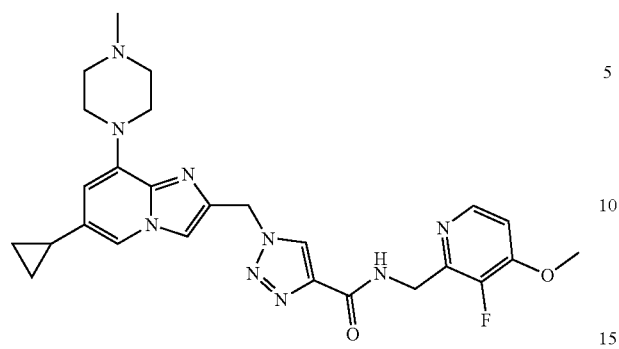
I-140
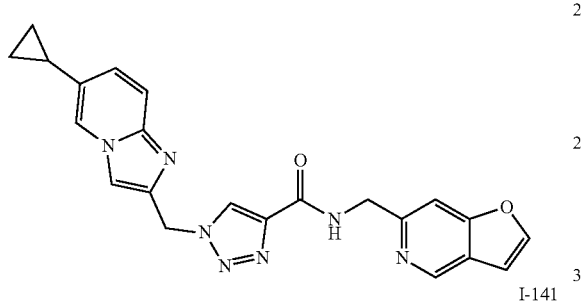
I-141
I-142
I-143
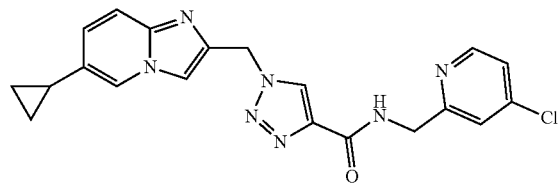
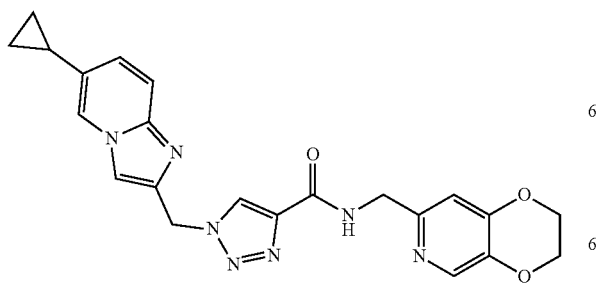
I-144
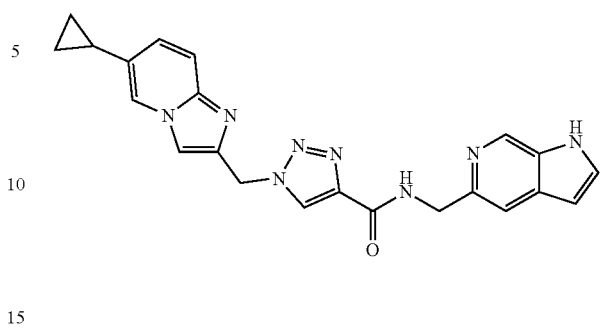
I-145
I-146
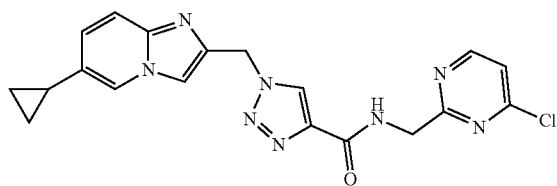
I-147
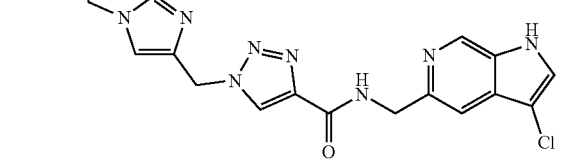
I-148
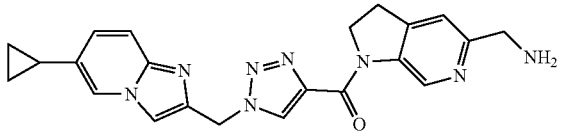
I-149
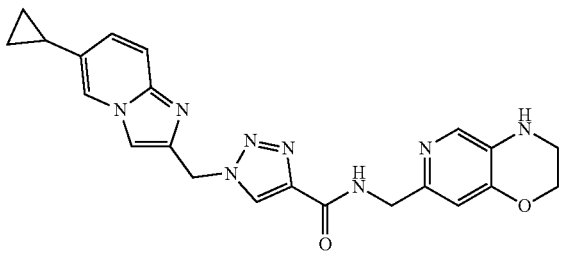

I-150
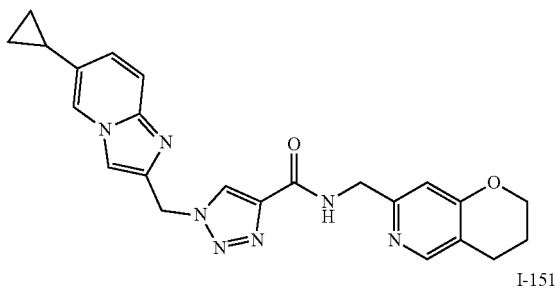
I-153
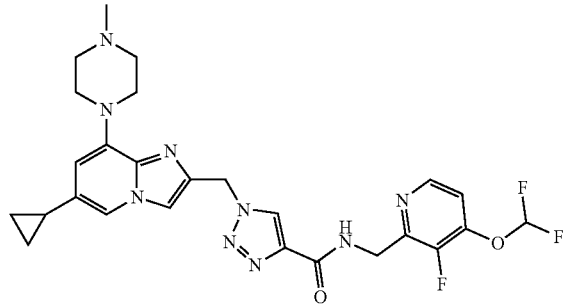
I-151
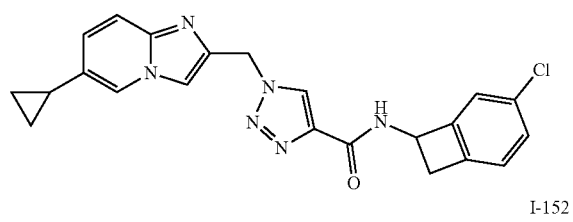
I-154
I-152
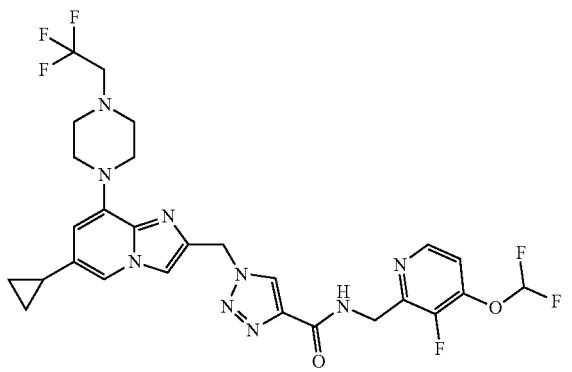
I-155
or a pharmaceutically acceptable salt thereof.
19. The method of claim 1, wherein the plasma kallikrein-mediated disease or disorder is hereditary angioedema or diabetic macular edema.
* * * * *